United States Patent
Lin et al.

(10) Patent No.: US 10,280,150 B2
(45) Date of Patent: *May 7, 2019

(54) QUINOLINONE PYRIMIDINES COMPOSITIONS AS MUTANT-ISOCITRATE DEHYDROGENASE INHIBITORS

(71) Applicant: FORMA TM2, Inc., Watertown, MA (US)

(72) Inventors: Jian Lin, Acton, MA (US); Anna Ericsson, Shrewsbury, MA (US); Ann-Marie Campbell, Monroe, CT (US); Gary Gustafson, Ridgefield, CT (US); Zhongguo Wang, Lexington, MA (US); R. Bruce Diebold, Waltham, MA (US); Susan Ashwell, Carlisle, MA (US); David R. Lancia, Jr., Boston, MA (US); Justin Andrew Caravella, Cambridge, MA (US); Wei Lu, Newton, MA (US)

(73) Assignee: FORMA TM2, INC., Watertown, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/712,446

(22) Filed: Sep. 22, 2017

(65) Prior Publication Data

US 2018/0134682 A1 May 17, 2018

Related U.S. Application Data

(63) Continuation of application No. 14/858,165, filed on Sep. 18, 2015, now Pat. No. 9,815,817.

(60) Provisional application No. 62/053,010, filed on Sep. 19, 2014.

(51) Int. Cl.
| | |
|---|---|
| *C07D 401/12* | (2006.01) |
| *A61K 31/506* | (2006.01) |
| *C07D 405/14* | (2006.01) |
| *C07D 401/14* | (2006.01) |
| *C07D 417/14* | (2006.01) |
| *C07D 413/14* | (2006.01) |
| *C07D 471/04* | (2006.01) |
| *C07D 409/14* | (2006.01) |
| *C07D 403/12* | (2006.01) |

(52) U.S. Cl.
CPC ........ *C07D 401/12* (2013.01); *C07D 401/14* (2013.01); *C07D 403/12* (2013.01); *C07D 405/14* (2013.01); *C07D 409/14* (2013.01); *C07D 413/14* (2013.01); *C07D 417/14* (2013.01); *C07D 471/04* (2013.01)

(58) Field of Classification Search
None
See application file for complete search history.

(56) References Cited

U.S. PATENT DOCUMENTS

| | | | |
|---|---|---|---|
| 5,262,564 A | 11/1993 | Kun et al. | |
| 9,073,941 B2 | 7/2015 | Wong et al. | |
| 9,624,175 B2 | 4/2017 | Lin et al. | |
| 9,624,216 B2 | 4/2017 | Lin et al. | |
| 9,771,349 B2 | 9/2017 | Lin et al. | |
| 9,615,817 B2 | 11/2017 | Lin et al. | |
| 10,005,734 B2 | 6/2018 | Lin et al. | |
| 2014/0235620 A1 | 8/2014 | Caferro et al. | |
| 2016/0083349 A1 | 3/2016 | Lin et al. | |
| 2016/0083365 A1 | 3/2016 | Lin et al. | |
| 2016/0083366 A1 | 3/2016 | Lin et al. | |
| 2016/0083367 A1 | 3/2016 | Lin et al. | |
| 2016/0311774 A1 | 10/2016 | Lin et al. | |
| 2016/0311818 A1 | 10/2016 | Lin et al. | |
| 2017/0174658 A1 | 6/2017 | Lin et al. | |
| 2018/0086733 A1 | 3/2018 | Lin et al. | |
| 2018/0118732 A1 | 5/2018 | Lin et al. | |

(Continued)

FOREIGN PATENT DOCUMENTS

| | | |
|---|---|---|
| RU | 2284325 C2 | 9/2006 |
| WO | WO-2006/054912 A1 | 5/2006 |
| WO | WO-2007/117778 A2 | 10/2007 |

(Continued)

OTHER PUBLICATIONS

Badr, M.Z.A. et al., Reaction of Quinoxaline Derivatives with Nucleophilic Reagents, , Bull Chem Soc Jpn, 56(1): 326-330 (1983).

(Continued)

*Primary Examiner* — Michael Barker
(74) *Attorney, Agent, or Firm* — Choate, Hall & Stewart LLP; John P. Rearick; Christopher K. Haley

(57) ABSTRACT

The invention relates to inhibitors of mutant isocitrate dehydrogenase (mt-IDH) proteins with neomorphic activity useful in the treatment of cell-proliferation disorders and cancers, having the Formula:

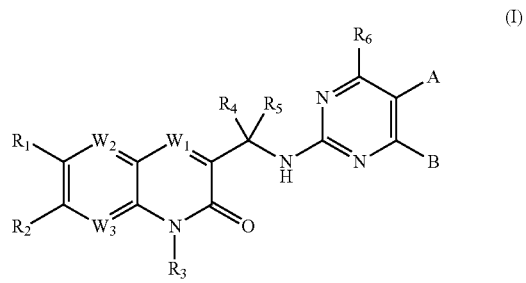

where A, B, $W_1$, $W_2$, $W_3$, and $R_1$-$R_6$ are described herein.

2 Claims, 4 Drawing Sheets

(56) References Cited

U.S. PATENT DOCUMENTS

| | | | |
|---|---|---|---|
| 2018/0141910 A1 | 5/2018 | Lin et al. | |
| 2018/0312487 A1 | 11/2018 | Lin et al. | |

FOREIGN PATENT DOCUMENTS

| | | |
|---|---|---|
| WO | WO-2008/069242 A1 | 6/2008 |
| WO | WO-2011/072174 A1 | 6/2011 |
| WO | WO-2012/129562 A2 | 9/2012 |
| WO | WO-2012/171506 A1 | 12/2012 |
| WO | WO-2013/102431 A1 | 7/2013 |
| WO | WO-2014/141153 A1 | 9/2014 |
| WO | WO-2015/003146 A1 | 1/2015 |
| WO | WO-2016/044781 A1 | 3/2016 |
| WO | WO-2016/044782 A1 | 3/2016 |
| WO | WO-2016/044787 A1 | 3/2016 |
| WO | WO-2016/044789 A1 | 3/2016 |
| WO | WO-2016/106331 A1 | 6/2016 |
| WO | WO-2016/108045 A2 | 7/2016 |
| WO | WO-2016/171755 A1 | 10/2016 |
| WO | WO-2016/171756 A1 | 10/2016 |
| WO | WO-2017/019429 A1 | 2/2017 |
| WO | WO-2017/146795 A1 | 8/2017 |
| WO | WO-2017/213910 A1 | 12/2017 |
| WO | WO-2017/223202 A1 | 12/2017 |
| WO | WO-2018/111707 A1 | 6/2018 |

OTHER PUBLICATIONS

Balss, J. et al., Analysis of the IDH1 codon 132 mutation in brain tumors, Acta Neuropathol., 116: 597-602 (2008).
Dang, L. et al., Cancer-associated IDH1 mutations produce 2-hydroxyglutarate, Nature, 462: 739-744 (2009).
Dang, L. et al., IDH mutations in glioma and acute myeloid leukemia, Trends Mol. Med., 16(9): 387-397 (2010).
Dinardo, C.D. et al., Serum 2-hydroxyglutarate levels predict isocitrate dehydrogenase mutations and clinical outcome in acute myeloid leukemia, Blood, 121(24): 4917-1924 (2013).
Fatima, S., Molecular docking and 3D-QSAR studies on inhibitors of DNA damage signaling enzyme human PARP-1, J Receptors and Signal Transduction, 32(4) 214-224 (2012).
Gaal, J. et al., Isocitrate Dehydrogenase Mutations Are Rare in Pheochromocytomas and Paragangliomas, J. Clin. Endocrinol. Metab., 95(3): 1274-1278 (2010).
Gross, S. et al., Cancer-associated metabolite 2-hydroxyglutarate accumulates in acute myelogenous leukemia with isocitrate dehydrogenase 1 and 2 mutations, J. Exp. Med., 207(2): 339-344 (2010).
Hayden, J.T. et al., Frequent IDH1 mutations in supratentorial primitive neuroectodermal tumors (sPNET) of adults but not children, Cell Cycle, 8(11): 1806-1807 (2009).
International Search Report for PCT/US2015/051044, 4 pages (dated Nov. 23, 2015).
International Search Report for PCT/US2015/051046, 3 pages (dated Oct. 30, 2015).
International Search Report for PCT/US2015/051053, 4 pages (dated Oct. 28, 2015).
International Search Report for PCT/US2015/051055, 3 pages (dated Nov. 13, 2015).
International Search Report for PCT/US2015/051056, 4 pages (dated Nov. 20, 2015).
International Search Report for PCT/US2015/051059, 3 pages (dated Oct. 30, 2015).
Kombarov, R.V. et al., CA Accession No. 138:368869, abstract only of Chem of Het Compounds, 38(9): 1154-1155 (2002).
Losman, J.-A. et al., (R)-2-Hydroxyglutarate is Sufficient to Promote Leukemogenesis and its Effects are Reversible, Science, 339(6127): 1-9 (2013).
Mohamed, E.A. et al., CA Accession No. 122:160601, abstract only of Indian J Chem, Sect B: Org Chem Inc Med Chem, 34B(1): 21-26 (1995).
Morshed, M.N. et al., Computational approach to the identification of novel Aurora-A inhibitors, Bioorg & Med Chem, 19: 907-916 (2011).
Schrader, F.C. et al., Novel Type II Fatty Acid Biosynthesis (FAS II) Inhibitors as Multistage Antimalarial Agents, Chem Med Chem, 8: 442-461 (2013).
Sellner, L. et al. Increased levels of 2-hydroxyglutarate in AML patients with IDH1-R132H and IDH2-R140Q mutations, Eur. J. Haematol., 85: 457-459 (2010).
Shibata, T. et al., Mutant IDH1 Confers an in Vivo Growth in a Melanoma Cell Line with BRAF Mutation, Am. J. Pathol., 178(3): 1395-1402 (2011).
Tintori, C. et al., Identification of Hck Inhibitors as Hits for the Development of Antileukemia and Anti-HIV Agents, Chem Med Chem, 8: 1353-1360 (2013).
Wang, F. et. al., Targeted Inhibition of Mutant IDH2 in Leukemia Cells Induces Cellular Differentiation, Science, 340: 622-626 (2013).
Wang, P. et al., Mutations in Isocitrate Dehydrogenase 1 and 2 Occur Frequently in Intrahepatic Cholangiocarcinomas and Share Hypermetylation Targets with Glioblastomas, Oncogene, 32(25): 3091-3100 (2013).
Ward, P.S. et al., The common feature of leukemia-associated IDH1 and IDH2 mutations is a neomorphic enzymatic activity that converts α-ketoglutarate to 2-hydroxyglutarate, Cancer Cell, 17(3): 225-234 (2010).
Zhao, S. et. al., Glioma-Derived Mutations in IDH1 Dominantly Inhibit IDH1 Catalytic Activity and Induce HIF-1α, Science, 324(5924): 261-265 (2009).
Cui, Z. et al., Structure and properties of N-heterocycle-containing benzotriazoles as UV absorbers, Journal of Molecular Structure, 1054: 94-99 (2013).
Database Caplus (Online) Chemical Abstracts Service, Columbus, Ohio, US; retrieved from STN Database accession No. 1987: 407040 abstract, Prostakov, N.S. et al., Synthesis of substituted 2-pyridones and 4-aza-3-fluorenones, Khimiya Geterotsiklicheskikh Soedinenii, 7: 939-942 (1986).
Database Registry (Online) Chemical Abstracts Service, Columbus, Ohio, US; Database accession No. 1434379-53-9 (Jun. 5, 2013).
Database Registry (Online) Chemical Abstracts Service, Columbus, Ohio, US; Database accession No. 1497653-96-9 (Dec. 18, 2013).
Database Registry (Online) Chemical Abstracts Service, Columbus, Ohio, US; Database accession No. 1567357-55-4 (Mar. 12, 2014).
Database Registry (Online) Chemical Abstracts Service, Columbus, Ohio, US; Database accession No. 1567456-94-3 (Mar. 12, 2014).
Forma Therapeutics, Discovery and Optimization of a Novel Series of Inhibitors of mt-IDH1, 7th Annual Advances in Chemical Sciences Symposium, Presentation, 21 slides (May 4, 2018).
Prostakov, N.S. et al., Chemistry of Heterocyclic Compounds, CHCCAL, 22(7): 685-810 (1986).
Zheng, B. et al., Crystallographic Investigation and Selective Inhibition of Mutant Isocitrate Dehydrogenase, ACS Medicinal Chemistry Letters, 4(6): 542-546 (2013).
U.S. Appl. No. 15/712,446, filed Sep. 22, 2017, Lin et al.
U.S. Appl. No. 15/964,844, filed Apr. 27, 2018, Lin et al.
U.S. Appl. No. 15/964,812, filed Apr. 27, 2018, Lin et al.
U.S. Appl. No. 15/977,512, filed May 11, 2018, Lin et al.

Compound I-46

QUINOLINONE PYRIMIDINES COMPOSITIONS AS MUTANT-ISOCITRATE DEHYDROGENASE INHIBITORS

CROSS-REFERENCE TO RELATED APPLICATIONS

This application is a continuation of U.S. Pat. No. 9,815,817, filed Sep. 18, 2015, which claims the benefit of priority of U.S. Provisional Application No. 62/053,010, filed Sep. 19, 2014, all of which is incorporated herein by reference in its entirety.

FIELD OF INVENTION

The present invention is directed to inhibitors of mutant isocitrate dehydrogenase (mt-IDH) proteins with neomorphic activity useful in the treatment of diseases or disorders associated with such mutant IDH proteins including cell-proliferation disorders and cancers. Specifically, the invention is concerned with compounds and compositions inhibiting mt-IDH, methods of treating diseases or disorders associated with mt-IDH, and methods of synthesis of these compounds.

BACKGROUND OF THE INVENTION

Isocitrate dehydrogenases (IDHs) are enzymes that participate in the citric acid cycle (cellular metabolism). They catalyze the oxidative decarboxylation of isocitrate to 2-oxoglutarate (i.e., α-ketoglutarate, α-KG). There are three isoforms within the IDH family. IDH-1, expressed in the cytoplasm and peroxisome, IDH-2, localized in the mitochondria, both utilize NADP$^+$ as the cofactor and exist as homodimers. IDH-3 is localized in mitochondrial matrix and utilizes NAD$^+$ as a cofactor and exists as tetramer. Mutations in IDH-1 (cytosolic) and IDH-2 (mitochondrial) have been identified in various diseases or disorders including glioma, glioblastoma multiforme, paraganglioma, supratentorial primordial neuroectodermal tumors, acute myeloid leukemia (AML), prostate cancer, thyroid cancer, colon cancer, chondrosarcoma, cholangiocarcinoma, peripheral T-cell lymphoma, and melanoma (L. Deng et al., *Trends Mol. Med.*, 2010, 16, 387; T. Shibata et al., *Am. J. Pathol.*, 201 1, 178 (3), 1395; Gaal et al., *J. Clin. Endocrinol. Metab.* 2010; Hayden et al., *Cell Cycle*, 2009; Balss et al., *Acta Neuropathol.*, 2008). The mutations have been found at or near key residues in the active site: G97D, R100, R132, H133Q, and A134D for IDH1, and R140 and R172 for IDH2. (See L. Deng et al., *Nature*, 2009, 462, 739; L. Sellner et al., *Eur. J. Haematol.*, 2011, 85, 457).

Mutant forms of IDH-1 and IDH-2 have been shown to lose wild type activity, and instead exhibit a neomorphic activity (also known as a gain of function activity), of reducing alpha-ketoglutarate to 2-hydroxyglutarate (2-HG). (See P. S. Ward et al., *Cancer Cell*, 2010, 17, 225; Zhao et. al., *Science* 324, 261 (2009); Dang et. al *Nature* 462, 739 (2009)). In general, production of 2-HG is enantiospecific, resulting in generation of the D-enantiomer (also known as the R enantiomer or R-2-HG). Normal cells have low basal levels of 2-HG, whereas cells harboring mutations in IDH1 or IDH2 show significantly elevated levels of 2-HG. High levels of 2-HG have also been detected in tumors harboring the mutations. For example, high levels of 2-HG have been detected in the plasma of patients with mutant IDH containing AML. (See S. Gross et al., *J. Exp. Med.*, 2010, 207 (2), 339). High levels of 2-HG have been shown to block α-KG dependent DNA and histone demethylases, and ultimately to result in improper dedifferentiation of hematopoietic progenitor cells in AML patients (Wang et. al., *Science* 340, 622 (2013); Losman et al., Science 339, 1621 (2013)).

Furthermore, patients with Oilier Disease and Mafucci Syndrome (two rare disorders that predispose to cartilaginous tumors) have been shown to be somatically mosaic for IDH1 and 2 mutations and exhibit high levels of D-2-HG. (See Amary et al., *Nature Genetics*, 2011 and Pansuriya et al., *Nature Genetics*, 2011).

The inhibition of mt-IDHs and their neomorphic activity with small molecule inhibitors therefore has the potential to be a treatment for cancers and other disorders of cellular proliferation.

SUMMARY OF THE INVENTION

A first aspect of the invention relates to compounds of Formula (I):

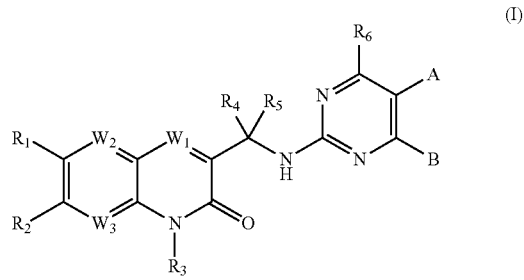

and pharmaceutically acceptable salts, enantiomers, hydrates, solvates, prodrugs, isomers, and tautomers thereof, wherein:

each $W_1$ and $W_2$ are independently CH, CF, or N;
$W_3$ is, $CR_2$, or N;
A is selected from the group consisting of H, D, halogen, CN, —CHO, —COOH, —COOR, —C(O)NH$_2$, —C(O)NHR, —S(O)Me, —S(O)$_2$Me,

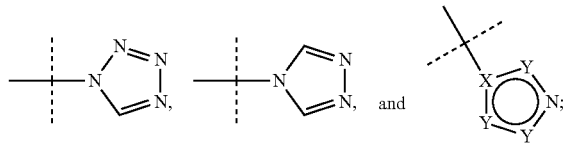

B is selected from the group consisting of:
H, D, OH, NH$_2$, —NR$_7$R$_8$, CN, C$_1$-C$_6$ alkyl, C$_3$-C$_8$ cycloalkyl, substituted aryl, C$_1$-C$_6$ alkoxy, substituted heteroaryl, —(CH$_2$)$_n$C(O)NHR, —C(O)NH$_2$, —(CH$_2$)$_n$NHR'C(O)R, —SR, —(CHR')$_n$S(O)R, —(CHR')$_n$S(O)$_2$R, —COOR,

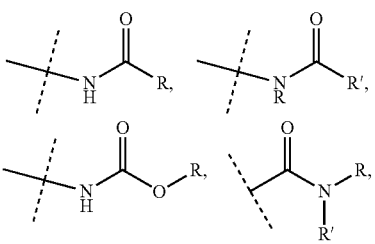

-continued

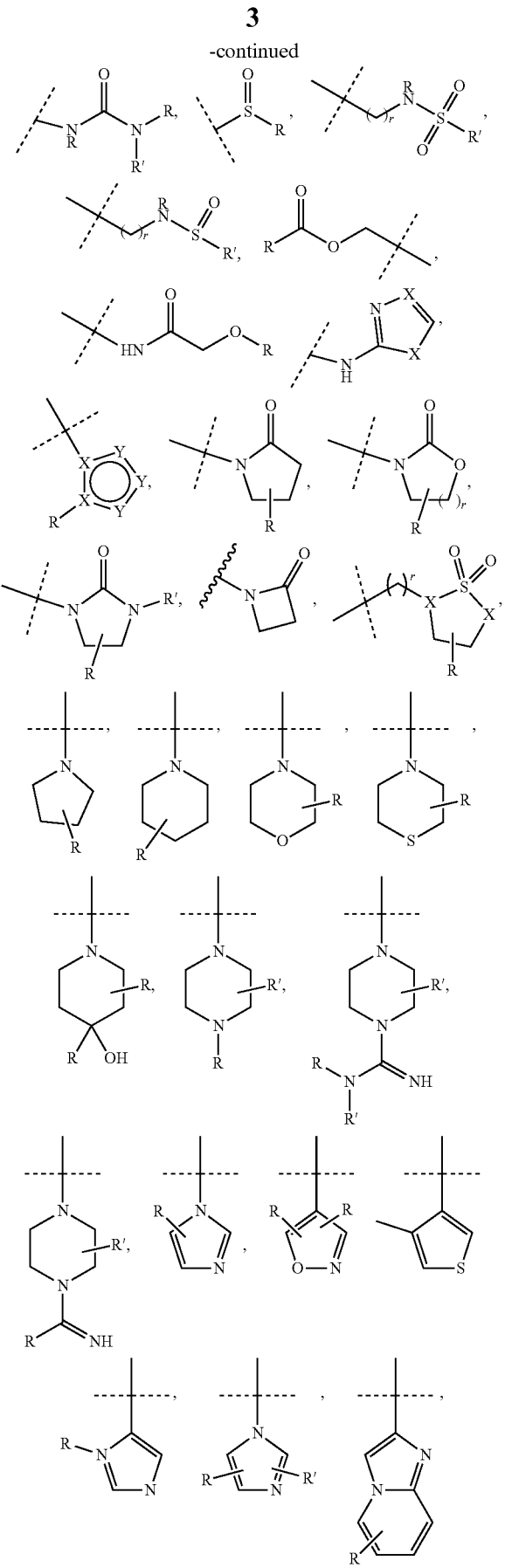

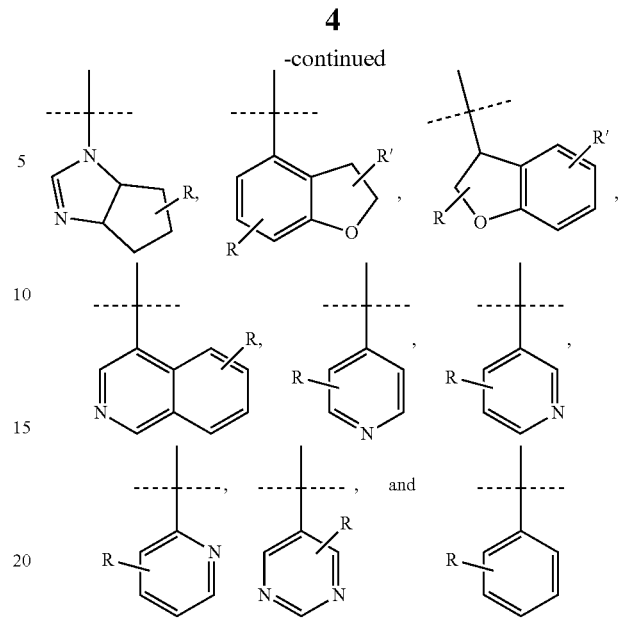

wherein X and Y are independently in each occurrence C, N, NR, S, and O, provided that the ring containing X and Y cannot have more than 4 N or NR atoms or more than one S or O atoms;

R and R' at each occurrence are independently selected from the group consisting of H, halogen, —C(O)$C_1$-$C_3$ alkyl, —C(O)O$C_1$-$C_3$ alkyl, $CF_3$, $C_1$-$C_6$ alkyl, $C_1$-$C_6$ alkoxy, $C_2$-$C_6$ alkenyl, $C_2$-$C_6$ alkynyl, $C_3$-$C_8$ cycloalkyl, $C_3$-$C_8$ cycloalkylalkyl, $C_3$-$C_8$ heterocyclyl, aryl, and heteroaryl, wherein each R or R' is optionally further substituted with one or more substituents independently selected from the group consisting of OH, halogen, $C_1$-$C_6$ alkoxy, $NH_2$, CN, $C_3$-$C_8$ cycloalkyl, $C_3$-$C_8$ heterocyclyl, aryl, and heteroaryl;

$R_1$ is independently H, OH, CN, halogen, $CF_3$, $CHF_2$, $C_1$-$C_6$ alkyl, $C_1$-$C_6$ alkoxy, $C_2$-$C_6$ alkenyl, $C_2$-$C_6$ alkynyl, $C_3$-$C_8$ cycloalkyl, $C_3$-$C_8$ heterocyclyl, aryl, or heteroaryl, wherein each $C_1$-$C_6$ alkyl, $C_2$-$C_6$ alkenyl, $C_2$-$C_6$ alkynyl, $C_3$-$C_8$ cycloalkyl, $C_3$-$C_8$ heterocyclyl, aryl, and heteroaryl is optionally substituted with one or more substituents independently selected from the group consisting of halogen, OH, $NH_2$, CN, $C_1$-$C_6$ alkyl, and $C_1$-$C_6$ alkoxy;

$R_2$ is independently H, OH, CN, halogen, $CF_3$, $CHF_2$, benzyl, $C_1$-$C_6$ alkyl, $C_1$-$C_6$ alkoxy, $NH_2$, $NHR_7$, —N($R_7$)($R_8$), NHC(O)$R_7$, NHS(O)$R_7$, NHS(O)$_2R_7$, NHC(O)O$R_7$, NHC(O)NH$R_7$, —S(O)$_2$NH$R_7$, NHC(O)N($R_8$)$R_7$, OCH$_2R_7$, OCHRR', CHRR', or OCHR'$R_7$, wherein $C_1$-$C_6$ alkyl and $C_1$-$C_6$ alkoxy are optionally substituted with one or more substituents independently selected from the group consisting of $C_1$-$C_6$ alkyl, $C_1$-$C_6$ alkoxy, $C_2$-$C_6$ alkenyl, $C_2$-$C_6$ alkynyl, $C_3$-$C_8$ cycloalkyl, $C_3$-$C_8$ heterocyclyl, aryl, and heteroaryl;

$R_3$ is H, $C_1$-$C_6$ alkyl, or —OH;

$R_4$ and $R_5$ are independently H, $C_1$-$C_3$ alkyl, $CH_2OH$, or $C_1$-$C_3$ alkyl substituted with one or more halogen, or $R_4$ and $R_5$ when combined can form a $C_3$-$C_6$ cycloalkyl or $C_3$-$C_6$ heterocyclyl;

$R_6$ is H, halogen, $CF_3$, $CHF_2$, $C_1$-$C_6$ alkyl, $C_1$-$C_6$ alkoxy, $C_2$-$C_6$ alkenyl, $C_2$-$C_6$ alkynyl, or $C_3$-$C_8$ cycloalkyl;

$R_7$ and $R_8$ are independently H, $C_1$-$C_6$ alkyl, $C_1$-$C_6$ alkoxy, $C_2$-$C_6$ alkenyl, $C_2$-$C_6$ alkynyl, $C_3$-$C_8$ cycloalkyl, $C_3$-$C_8$ heterocyclyl, aryl, or heteroaryl; or when combined $R_7$ and $R_8$ can form a $C_3$-$C_8$ heterocyclyl or heteroaryl ring;

n is 0, 1, or 2; and
r is 0, 1, or 2;
with the proviso that when $R_1$ is H and $R_2$ is F, then B is

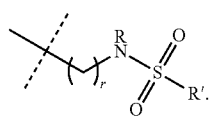

Another aspect of the invention relates to a method of treating a disease or disorder associated with mutant isocitrate dehydrogenase. The method comprises administering to a patient in need of a treatment for diseases or disorders associated with mutant isocitrate dehydrogenase an effective amount of a compound of Formula (I).

Another aspect of the invention is directed to a method inhibiting mutant isocitrate dehydrogenase. The method involves administering to a patient in need thereof an effective amount of a compound of Formula (I).

Another aspect of the invention relates to method of reducing 2-hydroxyglutarate. The method comprises administering to a patient in need thereof an effective amount of a compound of Formula (I).

Another aspect of the invention is directed to pharmaceutical compositions comprising a compound of Formula (I) and a pharmaceutically acceptable carrier. The pharmaceutical acceptable carrier may further include an excipient, diluent, or surfactant.

The present invention further provides methods of treating cell proliferative diseases and cancers including, without limitation, glioma, glioblastoma multiforme, paraganglioma, supratentorial primordial neuroectodermal tumors, acute myeloid leukemia (AML), prostate cancer, thyroid cancer, colon cancer, chondrosarcoma, cholangiocarcinoma, peripheral T-cell lymphoma, melanoma, intrahepatic cholangiocarcinoma (IHCC), myelodysplastic syndrome (MDS), myeloproliferative disease (MPD), and other solid tumors, comprising administering to a patient suffering from at least one of said diseases or cancers a compound of Formula (I). The inhibitors of the present invention may target mutated IDH1 at residue 97, 100 or 132, for example G97D, R100Q, R132H, R132C, R132S, R132G, R132L, and R132V. The inhibitors of the present invention may target mutated IDH2 at residue 140 or 172, for example R172K, R172M, R172S, R172G, and R172W.

Another aspect of the invention provides for a compound of Formula (I), or a pharmaceutically acceptable salt thereof, in combination with another therapeutic agent.

BRIEF DESCRIPTION OF THE DRAWINGS OF THE INVENTION

DETAILED DESCRIPTION OF THE INVENTION

Figure 1:
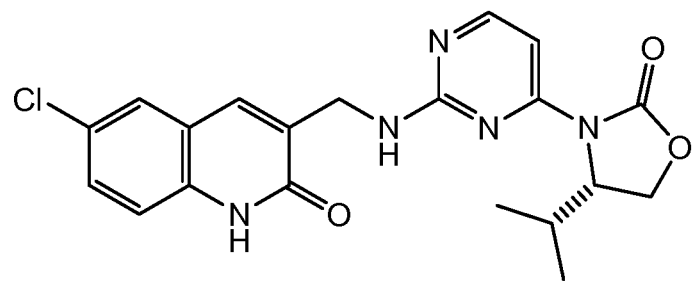
FIG. 1 illustrates the structure of compound I-46
Figure 2:
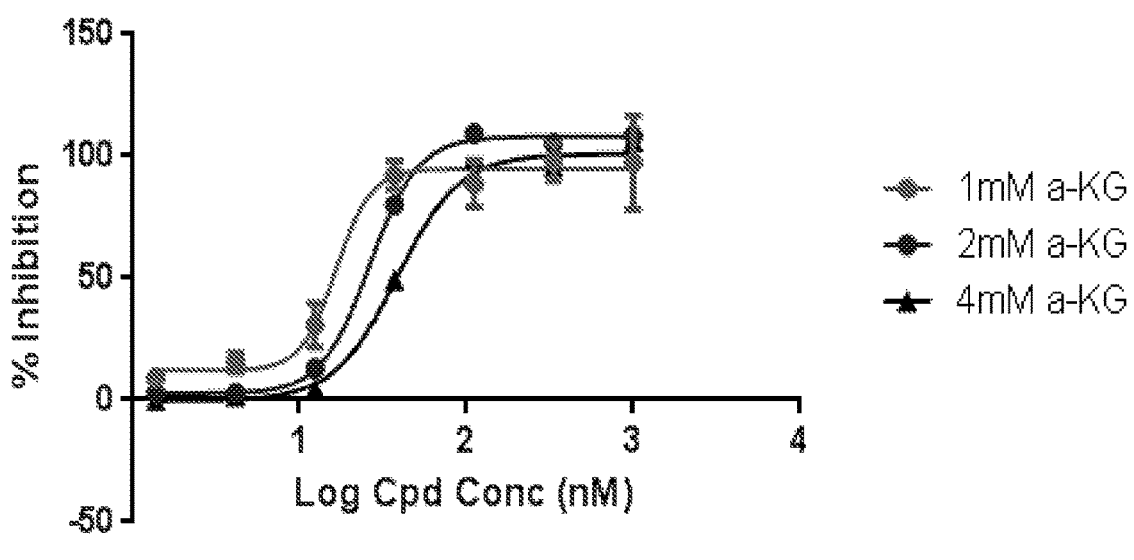
FIG. 2 illustrates a graph showing α-KG competition for the representative compound I-46 at varying concentrations of α-KG.
Figure 3:
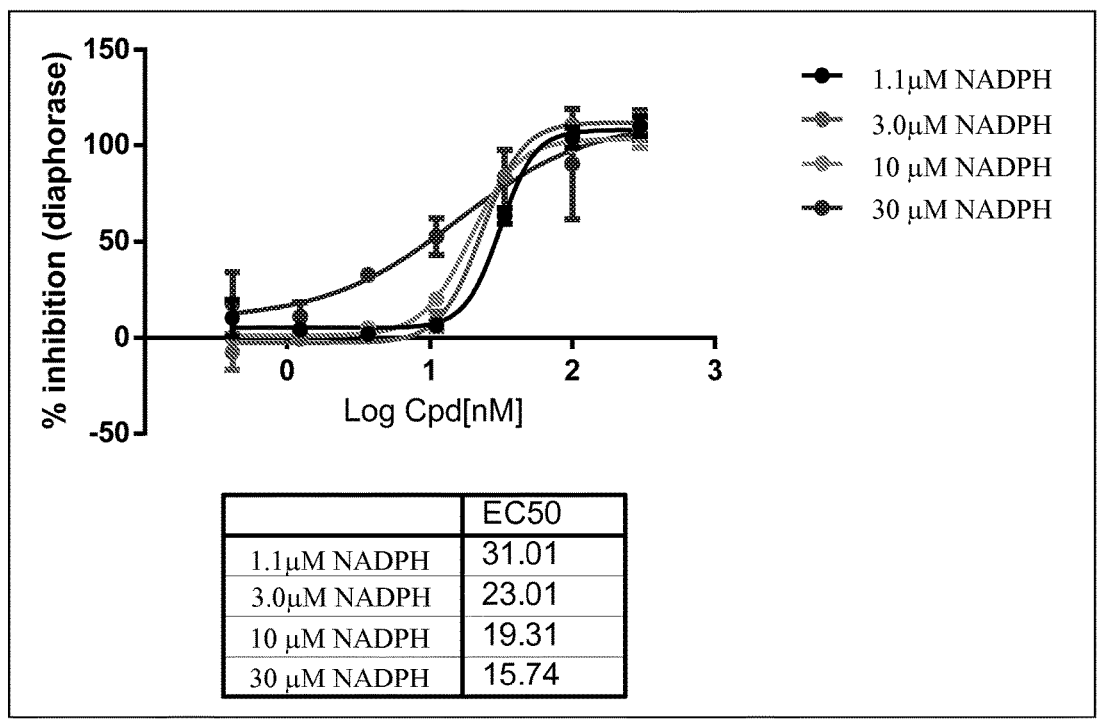
FIG. 3 illustrates a graph showing NADPH competition for the representative compound I-46 at varying concentrations of NADPH.
Figure 4:
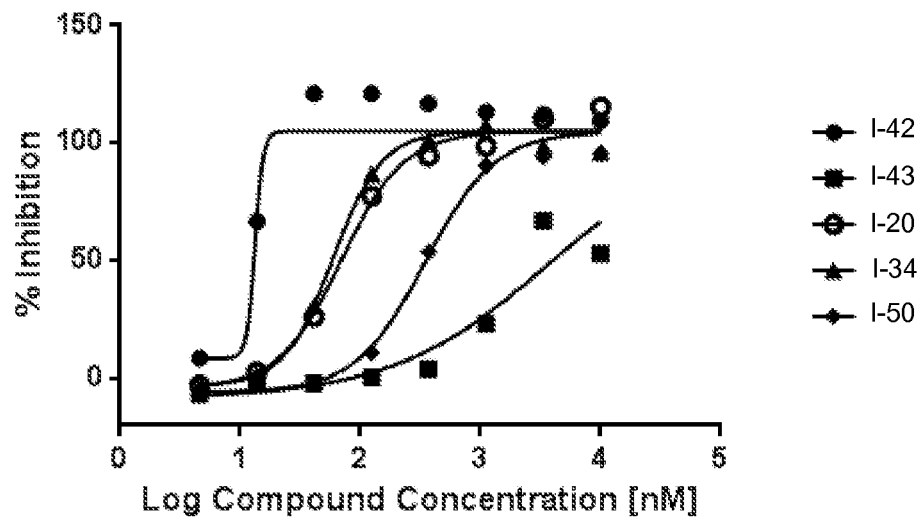
FIG. 4 illustrates a graph showing the potency of various IDH1 inhibitors of the present invention in IDH1-R132H enzymatic assay.

IDH1 or IDH2 mutations are a genetically validated target in many solid and hematologic cancers, but there are currently no targeted therapies available for patients in need of treatment for specific conditions associated with mt-IDH activity. Non-mutant IDH (e.g., wild-type) catalyze the oxidative decarboxylation of isocitrate to α-ketoglutarate thereby reducing NAD$^+$ (NADP$^+$) to NADH (NADPH) (WO 2013/102431 to Cianchetta et al., hereby incorporated by reference in its entirety). Mutations of IDH present in certain cancer cells result in a new ability of the enzyme to catalyze the NADPH-dependent reduction of α-ketoglutarate R(−)-2-hydroxyglutarate (2HG). 2HG is not formed by wild-type IDH. The production of 2HG contributes to the formation and progression of cancer (Dang, L et al., Nature, 2009, 462:739-44, hereby incorporated by reference in its entirety). The present invention provides inhibitors of mt-IDH, and prophylactic measures to reduce the formation and progression of 2HG in cells.

In a first aspect of the invention, are described the compounds of Formula (I):

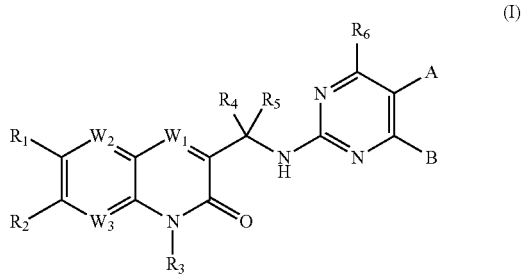

and pharmaceutically acceptable salts, enantiomers, hydrates, solvates, prodrugs, isomers, and tautomers thereof, where A, B, $W_1$, $W_2$, $W_3$, $R_1$-$R_6$ are described as above.

The details of the invention are set forth in the accompanying description below. Although methods and materials similar or equivalent to those described herein can be used in the practice or testing of the present invention, illustrative methods and materials are now described. Other features, objects, and advantages of the invention will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this invention belongs. All patents and publications cited in this specification are incorporated herein by reference in their entireties.

Definitions

The articles "a" and "an" are used in this disclosure to refer to one or more than one (i.e., to at least one) of the grammatical object of the article. By way of example, "an element" means one element or more than one element.

The term "and/or" is used in this disclosure to mean either "and" or "or" unless indicated otherwise.

The term "optionally substituted" is understood to mean that a given chemical moiety (e.g. an alkyl group) can (but is not required to) be bonded other substituents (e.g. heteroatoms). For instance, an alkyl group that is optionally substituted can be a fully saturated alkyl chain (i.e. a pure hydrocarbon). Alternatively, the same optionally substituted alkyl group can have substituents different from hydrogen. For instance, it can, at any point along the chain be bounded to a halogen atom, a hydroxyl group, or any other substituent described herein. Thus the term "optionally substituted"

means that a given chemical moiety has the potential to contain other functional groups, but does not necessarily have any further functional groups. Suitable substituents used in the optional substitution of the described groups include, without limitation, halogen, oxo, CN, —COOH, —CH$_2$CN, —O—C$_1$-C$_6$alkyl, C$_1$-C$_6$alkyl, —OC$_1$-C$_6$alkenyl, —OC$_1$-C$_6$alkynyl, —C$_1$-C$_6$alkenyl, —C$_1$-C$_6$alkynyl, —OH, —OP(O)(OH)$_2$, —OC(O)C$_1$-C$_6$alkyl, —C(O)C$_1$-C$_6$alkyl, —OC(O)OC$_1$-C$_6$alkyl, NH$_2$, NH(C$_1$-C$_6$alkyl), N(C$_1$-C$_6$alkyl)$_2$, —NHC(O)C$_1$-C$_6$alkyl, —C(O)NHC$_1$-C$_6$alkyl, —S(O)$_2$—C$_1$-C$_6$alkyl, —S(O)NHC$_1$-C$_6$alkyl, and S(O)N(C$_1$-C$_6$alkyl)$_2$ Unless otherwise specifically defined, the term "aryl" refers to cyclic, aromatic hydrocarbon groups that have 1 to 2 aromatic rings, including monocyclic or bicyclic groups such as phenyl, biphenyl or naphthyl. Where containing two aromatic rings (bicyclic, etc.), the aromatic rings of the aryl group may be joined at a single point (e.g., biphenyl), or fused (e.g., naphthyl). The aryl group may be optionally substituted by one or more substituents, e.g., 1 to 5 substituents, at any point of attachment. Exemplary substituents include, but are not limited to, —H, -halogen, —O—C$_1$-C$_6$alkyl, C$_1$-C$_6$alkyl, —OC$_1$-C$_6$alkenyl, —OC$_1$-C$_6$alkynyl, —C$_1$-C$_6$alkenyl, —C$_1$-C$_6$alkynyl, —OH, —OP(O)(OH)$_2$, —OC(O)C$_1$-C$_6$alkyl, —C(O)C$_1$-C$_6$alkyl, —OC(O)OC$_1$-C$_6$alkyl, NH$_2$, NH(C$_1$-C$_6$alkyl), N(C$_1$-C$_6$alkyl)$_2$, —S(O)$_2$—C$_1$-C$_6$alkyl, —S(O)NHC$_1$-C$_6$alkyl, and S(O)N(C$_1$-C$_6$alkyl)$_2$. The substituents can themselves be optionally substituted. Furthermore when containing two fused rings the aryl groups herein defined may have an unsaturated or partially saturated ring fused with a fully saturated ring. Exemplary ring systems of these aryl groups include indanyl, indenyl, tetrahydronaphthalenyl, and tetrahydrobenzoannulenyl.

Unless otherwise specifically defined, "heteroaryl" means a monovalent monocyclic aromatic radical of 5 to 10 ring atoms or a polycyclic aromatic radical, containing one or more ring heteroatoms selected from N, O, or S, the remaining ring atoms being C. Heteroaryl as herein defined also means a bicyclic heteroaromatic group wherein the heteroatom is selected from N, O, or S. The aromatic radical is optionally substituted independently with one or more substituents described herein. Examples include, but are not limited to, furyl, thienyl, pyrrolyl, pyridyl, pyrazolyl, pyrimidinyl, imidazolyl, pyrazinyl, indolyl, thiophen-2-yl, quinolyl, benzopyranyl, thiazolyl, and derivatives thereof. Furthermore when containing two fused rings the aryl groups herein defined may have an unsaturated or partially saturated ring fused with a fully saturated ring. Exemplary ring systems of these heteroaryl groups include indolinyl, indolinonyl, dihydrobenzothiophenyl, dihydrobenzofuran, chromanyl, thiochromanyl, tetrahydroquinolinyl, dihydrobenzothiazine, and dihydrobenzoxanyl.

Halogen or "halo" refers to fluorine, chlorine, bromine, or iodine.

Alkyl refers to a straight or branched chain saturated hydrocarbon containing 1-12 carbon atoms. Examples of a C$_1$-C$_6$ alkyl group include, but are not limited to, methyl, ethyl, propyl, butyl, pentyl, hexyl, isopropyl, isobutyl, sec-butyl, tert-butyl, isopentyl, neopentyl, and isohexyl.

"Alkoxy" refers to a straight or branched chain saturated hydrocarbon containing 1-12 carbon atoms containing a terminal "O" in the chain. Examples of alkoxy groups include without limitation, methoxy, ethoxy, propoxy, butoxy, t-butoxy, or pentoxy groups.

"Alkenyl" refers to a straight or branched chain unsaturated hydrocarbon containing 2-12 carbon atoms. The "alkenyl" group contains at least one double bond in the chain.

Examples of alkenyl groups include ethenyl, propenyl, n-butenyl, iso-butenyl, pentenyl, or hexenyl.

"Alkynyl" refers to a straight or branched chain unsaturated hydrocarbon containing 2-12 carbon atoms. The "alkynyl" group contains at least one triple bond in the chain. Examples of alkenyl groups include ethynyl, propargyl, n-butynyl, iso-butynyl, pentynyl, or hexynyl.

"Cycloalkyl" means monocyclic saturated carbon rings containing 3-18 carbon atoms. Examples of cycloalkyl groups include, without limitations, cyclopropyl, cyclobutyl, cyclopentyl, cyclohexyl, cycloheptanyl, cyclooctanyl, norboranyl, norborenyl, bicyclo[2.2.2]octanyl, or bicyclo[2.2.2]octenyl.

"Cycloalkylalkyl" means monocyclic saturated carbon rings containing 3-18 carbon atoms further substituted with C$_1$-C$_6$ alkyl groups. In general cycloalkylalkyl groups herein described display the following formula

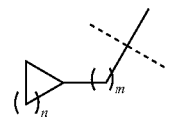

where m is an integer from 1 to 6 and n is an integer from 1 to 16.

"Heterocyclyl" or "heterocycloalkyl" monocyclic rings containing carbon and heteroatoms taken from oxygen, nitrogen, or sulfur and wherein there is not delocalized π electrons (aromaticity) shared among the ring carbon or heteroatoms; heterocyclyl rings include, but are not limited to, oxetanyl, azetadinyl, tetrahydrofuranyl, pyrrolidinyl, oxazolinyl, oxazolidinyl, thiazolinyl, thiazolidinyl, pyranyl, thiopyranyl, tetrahydropyranyl, dioxalinyl, piperidinyl, morpholinyl, thiomorpholinyl, thiomorpholinyl S-oxide, thiomorpholinyl S-dioxide, piperazinyl, azepinyl, oxepinyl, diazepinyl, tropanyl, and homotropanyl.

The term "solvate" refers to a complex of variable stoichiometry formed by a solute and solvent. Such solvents for the purpose of the invention may not interfere with the biological activity of the solute. Examples of suitable solvents include, but are not limited to, water, MeOH, EtOH, and AcOH. Solvates wherein water is the solvent molecule are typically referred to as hydrates. Hydrates include compositions containing stoichiometric amounts of water, as well as compositions containing variable amounts of water.

The term "isomer" refers to compounds that have the same composition and molecular weight but differ in physical and/or chemical properties. The structural difference may be in constitution (geometric isomers) or in the ability to rotate the plane of polarized light (stereoisomers). With regard to stereoisomers, the compounds of Formula (I) may have one or more asymmetric carbon atom and may occur as racemates, racemic mixtures and as individual enantiomers or diastereomers.

The disclosure also includes pharmaceutical compositions comprising an effective amount of a disclosed compound and a pharmaceutically acceptable carrier. Representative "pharmaceutically acceptable salts" include, e.g., water-soluble and water-insoluble salts, such as the acetate, amsonate (4,4-diaminostilbene-2,2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fiunarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, magnesium, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosalicylate, suramate, tannate, tartrate, teoclate, tosylate, triethiodide, and valerate salts.

A "patient" or "subject" is a mammal, e.g., a human, mouse, rat, guinea pig, dog, cat, horse, cow, pig, or non-human primate, such as a monkey, chimpanzee, baboon or rhesus.

An "effective amount" when used in connection with a compound is an amount effective for treating or preventing a disease in a subject as described herein.

The term "carrier", as used in this disclosure, encompasses carriers, excipients, and diluents and means a material, composition or vehicle, such as a liquid or solid filler, diluent, excipient, solvent or encapsulating material, involved in carrying or transporting a pharmaceutical agent from one organ, or portion of the body, to another organ, or portion of the body of a subject.

The term "treating" with regard to a subject, refers to improving at least one symptom of the subject's disorder. Treating includes curing, improving, or at least partially ameliorating the disorder.

The term "disorder" is used in this disclosure to mean, and is used interchangeably with, the terms disease, condition, or illness, unless otherwise indicated.

The term "administer", "administering", or "administration" as used in this disclosure refers to either directly administering a disclosed compound or pharmaceutically acceptable salt of the disclosed compound or a composition to a subject, or administering a prodrug derivative or analog of the compound or pharmaceutically acceptable salt of the compound or composition to the subject, which can form an equivalent amount of active compound within the subject's body.

The term "prodrug," as used in this disclosure, means a compound which is convertible in vivo by metabolic means (e.g., by hydrolysis) to a disclosed compound.

In one embodiment, A is CN. In this embodiment, B may further be $C_1$-$C_6$ alkoxy or $C_1$-$C_6$ alkyl. In another embodiment, B may also be methoxy.

In another embodiment, B may be

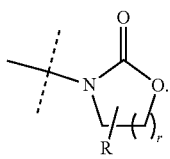

In this embodiment of Formula (I), A may also be H or F.

In another embodiment, B is

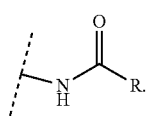

In this embodiment, A may also be H or F.

In another embodiment, B may be

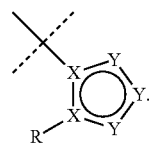

In this embodiment, A may also be H or F.

Yet another embodiment relates to compounds of Formula (I) where B is

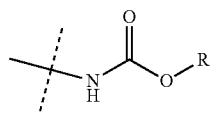

This embodiment also optionally provides for compounds of Formula (I) where A is H or F.

In another embodiment, B is

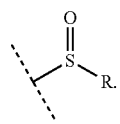

In this embodiment A may also be CN. This embodiment may further provide for compounds of Formula (I) where A is H or F.

In another embodiment, B is

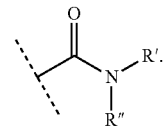

In this embodiment, A may also further be H or F.

In other embodiments, A is H or F.

Other embodiments relate to compounds of Formula (I) where B is

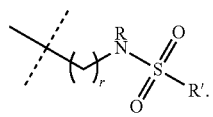

In these embodiments, r may be 0 or 1, and R and R' may independently be $C_1$-$C_6$ alkyl, $C_1$-$C_6$ alkoxy, $C_2$-$C_6$ alkenyl, $C_2$-$C_6$ alkynyl, $C_3$-$C_8$ cycloalkyl, $C_3$-$C_8$ cycloalkylalkyl, $C_3$-$C_8$ heterocyclyl, aryl, or heteroaryl. In these embodiments, A may further be H or F, r may be 0 or 1, and R and R' may independently be $C_1$-$C_6$ alkyl, $C_1$-$C_6$ alkoxy, $C_2$-$C_6$ alkenyl, $C_2$-$C_6$ alkynyl, $C_3$-$C_8$ cycloalkyl, $C_3$-$C_8$ cycloalkylalkyl, $C_3$-$C_8$ heterocyclyl, aryl, or heteroaryl. In these embodiments of the compounds of Formula (I), R' may also be aryl or heteroaryl, In other embodiments of this invention, R' may also be methyl, ethyl, isopropyl, or isobutyl. In one or more other embodiments, R' may be phenyl. In some embodiments of the invention, A is H or F and R' is methyl, ethyl, isopropyl, or isobutyl.

In other embodiments, A is also H or F and R' is phenyl.

In other embodiments, A is H or F and B is $C_1$-$C_6$ alkoxy or $C_1$-$C_6$ alkyl. In another embodiment, A is H or F and B is methoxy.

Another embodiment of the invention pertains to compounds of Formula (I) where $R_4$ and $R_5$ are H.

In another embodiment, $R_4$ is H and $R_5$ is methyl.

In yet another embodiment, $R_4$ is H and $R_5$ is (S)-methyl.

In another embodiment, $R_4$ and $R_5$ are halogen. In yet another embodiment $R_4$ and $R_5$ are fluorine.

In another embodiment, $R_4$ is F and $R_5$ is methyl.

In another embodiment, $R_4$ and $R_5$ can combine to form a $C_3$-$C_5$ cycloalkyl.

In one embodiment, $W_1$, $W_2$, and $W_3$ are CH.

In another embodiment, $W_1$, $W_2$, or $W_3$ is N.

In another embodiment, $R_1$ can be halogen. In another embodiment, $R_1$ is chloro.

In one embodiment, $R_2$ can be H, halogen, or $C_1$-$C_6$ alkyl. In another embodiment, $R_2$ can also be $C_1$-$C_6$ alkoxy substituted with heteroaryl or $C_3$-$C_8$ heterocyclyl.

In one embodiment, illustrative compounds of the invention include:

N-(2-{[(1S)-1-(6-chloro-2-oxo-1,2-dihydroquinolin-3-yl)ethyl]amino}pyrimidin-4-yl)-N-(2,2-dimethylpropyl)methanesulfonamide;

N-(2-{[(1S)-1-(6-chloro-2-oxo-1,2-dihydroquinolin-3-yl)ethyl]amino}pyrimidin-4-yl)-N-(cyclopropylmethyl)methanesulfonamide;

N-(2-{[(1S)-1-(6-chloro-2-oxo-1,2-dihydroquinolin-3-yl)ethyl]amino}pyrimidin-4-yl)-N-(oxan-3-yl)methanesulfonamide;

N-(2-{[(1S)-1-(6-chloro-2-oxo-1,2-dihydroquinolin-3-yl)ethyl]amino}pyrimidin-4-yl)-N-(propan-2-yl)pyridine-3-sulfonamide;

N-(2-{[(1S)-1-(6-chloro-2-oxo-1,2-dihydroquinolin-3-yl)ethyl]amino}pyrimidin-4-yl)-2-methyl-N-(propan-2-yl)propane-1-sulfonamide;

N-[(2-{[(1S)-1-(6-chloro-2-oxo-1,2-dihydroquinolin-3-yl)ethyl]amino}pyrimidin-4-yl)methyl]-N-cyclopropylmethanesulfonamide;

3-[(1S)-1-{[4-(tert-butylamino)pyrimidin-2-yl]amino}ethyl]-6-chloro-1,2-dihydroquinolin-2-one;

N-(2-{[(1S)-1-(6-chloro-2-oxo-1,2-dihydroquinolin-3-yl)ethyl]amino}pyrimidin-4-yl)-N-(2-methylpropyl)methanesulfonamide;

6-chloro-3-[(1S)-1-{[4-(cyclopropylamino)pyrimidin-2-yl]amino}ethyl]-1,2-dihydroquinolin-2-one;

N-(2-{[(1S)-1-(6-chloro-2-oxo-1,2-dihydroquinolin-3-yl)ethyl]amino}pyrimidin-4-yl)-N-(propan-2-yl)methanesulfonamide;

N-(2-{[(1S)-1-(6-chloro-2-oxo-1,2-dihydroquinolin-3-yl)ethyl]amino}pyrimidin-4-yl)-1-cyclopropyl-N-(propan-2-yl)methanesulfonamide;

2-(2-{[(1S)-1-(6-chloro-2-oxo-1,2-dihydroquinolin-3-yl)ethyl]amino}pyrimidin-4-yl)-1$\lambda^6$,2-thiazolidine-1,1-dione;

N-(2-{[(1S)-1-(6-chloro-2-oxo-1,2-dihydroquinolin-3-yl)ethyl]amino}pyrimidin-4-yl)-N-(2,2,2-trifluoroethyl)methanesulfonamide;

N-(2-{[(1S)-1-(6-chloro-2-oxo-1,2-dihydroquinolin-3-yl)ethyl]amino}pyrimidin-4-yl)-N-cyclopropylmethanesulfonamide;

N-(2-{[(1S)-1-(6-chloro-2-oxo-1,2-dihydroquinolin-3-yl)ethyl]amino}pyrimidin-4-yl)-N,2-dimethylpropane-1-sulfonamide;

N-(2-{[(1S)-1-(6-chloro-2-oxo-1,2-dihydroquinolin-3-yl)ethyl]amino}pyrimidin-4-yl)-N-[2-(oxan-4-yl)ethyl]methanesulfonamide;

N-(2-{[(1S)-1-(6-chloro-2-oxo-1,2-dihydroquinolin-3-yl)ethyl]amino}pyrimidin-4-yl)methanesulfonamide;

N-(2-{[(1S)-1-(6-chloro-2-oxo-1,2-dihydroquinolin-3-yl)ethyl]amino}pyrimidin-4-yl)-2-methylpropane-1-sulfonamide;

N-(2-{[(1S)-1-(6-chloro-2-oxo-1,2-dihydroquinolin-3-yl)ethyl]amino}pyrimidin-4-yl)-N-(2-hydroxy-2-methylpropyl)methanesulfonamide;

N-(2-{[1-(6-chloro-2-oxo-1,2-dihydroquinolin-3-yl)ethyl]amino}pyrimidin-4-yl)-N-(propan-2-yl)methanesulfonamide;

N-(2-{[(1S)-1-(6-chloro-2-oxo-1,2-dihydroquinolin-3-yl)ethyl]amino}pyrimidin-4-yl)-3-methyl-2-oxo-N-(propan-2-yl)-2,3-dihydro-1,3-benzoxazole-6-sulfonamide;

methyl-N-(2-{[(1S)-1-(6-chloro-2-oxo-1,2-dihydroquinolin-3-yl)ethyl]amino}pyrimidin-4-yl)carbamate;

propan-2-yl-N-(2-{[(1S)-1-(6-chloro-2-oxo-1,2-dihydroquinolin-3-yl)ethyl]amino}pyrimidin-4-yl)carbamate;

N-(2-{[(1S)-1-(6-chloro-2-oxo-1,2-dihydroquinolin-3-yl)ethyl]amino}pyrimidin-4-yl)-N-cyclopropyl-3-methylbutanamide;

N-(2-{[(1S)-1-(6-chloro-2-oxo-1,2-dihydroquinolin-3-yl)ethyl]amino}pyrimidin-4-yl)acetamide;

N-(2-{[(1S)-1-(6-chloro-2-oxo-1,2-dihydroquinolin-3-yl)ethyl]amino}pyrimidin-4-yl)-N-(2,2-dimethylpropyl)acetamide;

N-(2-{[(1S)-1-(6-chloro-2-oxo-1,2-dihydroquinolin-3-yl)ethyl]amino}pyrimidin-4-yl)-2-(oxan-4-yl)acetamide;

N-(2-{[(1S)-1-(6-chloro-2-oxo-1,2-dihydroquinolin-3-yl)ethyl]amino}pyrimidin-4-yl)-N-cyclopropylacetamide;

N-(2-{[(1S)-1-(6-chloro-2-oxo-1,2-dihydroquinolin-3-yl)ethyl]amino}pyrimidin-4-yl)cyclopropanecarboxamide;

N-tert-butyl-N-(2-{[(1S)-1-(6-chloro-2-oxo-1,2-dihydroquinolin-3-yl)ethyl]amino}pyrimidin-4-yl)acetamide;

N-(2-{[(1S)-1-(6-chloro-2-oxo-1,2-dihydroquinolin-3-yl)ethyl]amino}pyrimidin-4-yl)-3-methylbutanamide;

N-(2-{[(1S)-1-(6-chloro-2-oxo-1,2-dihydroquinolin-3-yl)ethyl]amino}pyrimidin-4-yl)-2-methoxyacetamide;

N-(2-{[(1S)-1-(6-chloro-2-oxo-1,2-dihydroquinolin-3-yl)ethyl]amino}pyrimidin-4-yl)propanamide;

N-(2-{[1-(6-chloro-2-oxo-1,2-dihydroquinolin-3-yl)ethyl]amino}pyrimidin-4-yl)-N-(2-methylpropyl)acetamide;

N-(2-{[(1S)-1-(6-chloro-2-oxo-1,2-dihydroquinolin-3-yl)ethyl]amino}pyrimidin-4-yl)-N-(2-methylpropyl)cyclopropanecarboxamide;

2-{[(1S)-1-(6-chloro-2-oxo-1,2-dihydroquinolin-3-yl)ethyl]amino}-4-methoxypyrimidine-5-carbonitrile;

4-amino-2-{[(1S)-1-(6-chloro-2-oxo-1,2-dihydroquinolin-3-yl)ethyl]amino}pyrimidine-5-carbonitrile;

2-{[(1S)-1-(6-chloro-2-oxo-1,2-dihydroquinolin-3-yl)ethyl]amino}-4-(methylamino)pyrimidine-5-carbonitrile;

2-{[(1S)-1-(6-chloro-2-oxo-1,2-dihydroquinolin-3-yl)ethyl]amino}-4-methylpyrimidine-5-carbonitrile;

2-{[(1S)-1-(6-chloro-2-oxo-1,2-dihydroquinolin-3-yl)ethyl]amino}-4-cyclopropylpyrimidine-5-carbonitrile;

2-{[(1S)-1-(6-chloro-1-methyl-2-oxo-1,2-dihydroquinolin-3-yl)ethyl]amino}-4-methoxypyrimidine-5-carbonitrile;

6-chloro-3-[(1S)-1-({4-[(4S)-2-oxo-4-(propan-2-yl)-1,3-oxazolidin-3-yl]pyrimidin-2-yl}amino)ethyl]-1,2-dihydroquinolin-2-one;

6-chloro-3-[(1R)-1-({4-[(4S)-2-oxo-4-(propan-2-yl)-1,3-oxazolidin-3-yl]pyrimidin-2-yl}amino)ethyl]-1,2-dihydroquinolin-2-one;
6-chloro-3-[(1S)-1-{[4-(2-oxo-1,3-oxazolidin-3-yl)pyrimidin-2-yl]amino}ethyl]-1,2-dihydroquinolin-2-one;
6-chloro-3-[(1R)-1-{[4-(2-oxo-1,3-oxazolidin-3-yl)pyrimidin-2-yl]amino}ethyl]-1,2-dihydroquinolin-2-one;
6-chloro-3-[({4-[(4S)-2-oxo-4-(propan-2-yl)-1,3-oxazolidin-3-yl]pyrimidin-2-yl}amino)methyl]-1,2-dihydroquinolin-2-one;
6-chloro-3-({[4-(2-oxo-1,3-oxazolidin-3-yl)pyrimidin-2-yl]amino}methyl)-1,2-dihydroquinolin-2-one;
6-chloro-3-(1-{[4-(2-oxo-1,3-oxazolidin-3-yl)pyrimidin-2-yl]amino}ethyl)-1,2-dihydroquinolin-2-one;
3-(1-{[4-(2-oxo-1,3-oxazolidin-3-yl)pyrimidin-2-yl]amino}ethyl)-1,2-dihydroquinolin-2-one;
6-chloro-3-({[4-(2-oxopyrrolidin-1-yl)pyrimidin-2-yl]amino}methyl)-1,2-dihydroquinolin-2-one;
6-chloro-3-[(1S)-1-{[4-(2-methyl-1H-pyrrol-1-yl)pyrimidin-2-yl]amino}ethyl]-1,2-dihydroquinolin-2-one;
6-chloro-3-[(1S)-1-{[4-(1H-pyrrol-1-yl)pyrimidin-2-yl]amino}ethyl]-1,2-dihydroquinolin-2-one;
6-chloro-3-[(1S)-1-{[4-(4,5-dimethyl-1H-imidazol-1-yl)pyrimidin-2-yl]amino}ethyl]-1,2-dihydroquinolin-2-one;
6-chloro-3-[(1S)-1-{[4-(1H-imidazol-1-yl)pyrimidin-2-yl]amino}ethyl]-1,2-dihydroquinolin-2-one;
6-chloro-3-[(1S)-1-[(4-{1H,4H,5H,6H-cyclopenta[d]imidazol-1-yl}pyrimidin-2-yl)amino]ethyl]-1,2-dihydroquinolin-2-one;
6-chloro-3-[(1S)-1-{[4-(2-methyl-1H-imidazol-1-yl)pyrimidin-2-yl]amino}ethyl]-1,2-dihydroquinolin-2-one;
6-chloro-3-[(1S)-1-{[4-(4-methyl-1H-imidazol-1-yl)pyrimidin-2-yl]amino}ethyl]-1,2-dihydroquinolin-2-one;
6-chloro-3-[(1S)-1-{[4-(5-methyl-1,2-oxazol-4-yl)pyrimidin-2-yl]amino}ethyl]-1,2-dihydroquinolin-2-one;
6-chloro-3-[(1S)-1-{[4-(5-methyl-1H-1,2,3,4-tetrazol-1-yl)pyrimidin-2-yl]amino}ethyl]-1,2-dihydroquinolin-2-one;
6-chloro-3-[(1S)-1-({4-[1-(2,2,2-trifluoroethyl)-1H-imidazol-5-yl]pyrimidin-2-yl}amino)ethyl]-1,2-dihydroquinolin-2-one;
6-chloro-3-[(1S)-1-({4-[1-(cyclopropylmethyl)-1H-imidazol-5-yl]pyrimidin-2-yl}amino)ethyl]-1,2-dihydroquinolin-2-one;
6-chloro-3-[(1S)-1-{[4-(pyrimidin-5-yl)pyrimidin-2-yl]amino}ethyl]-1,2-dihydroquinolin-2-one;
6-chloro-3-[(1S)-1-[(4-{imidazo[1,2-a]pyridin-3-yl}pyrimidin-2-yl)amino]ethyl]-1,2-dihydroquinolin-2-one;
6-chloro-3-[(1S)-1-({4-[1-(propan-2-yl)-1H-imidazol-5-yl]pyrimidin-2-yl}amino)ethyl]-1,2-dihydroquinolin-2-one;
6-chloro-3-[(1S)-1-({4-[2-(trifluoromethyl)-1H-pyrrol-1-yl]pyrimidin-2-yl}amino)ethyl]-1,2-dihydroquinolin-2-one;
6-chloro-3-[(1S)-1-{[4-(1-methyl-1H-1,2,3-triazol-5-yl)pyrimidin-2-yl]amino}ethyl]-1,2-dihydroquinolin-2-one;
6-chloro-3-[(1S)-1-{[4-(1-methyl-1H-pyrazol-5-yl)pyrimidin-2-yl]amino}ethyl]-1,2-dihydroquinolin-2-one;
3-[(1S)-1-{[4-(1-benzyl-1H-imidazol-5-yl)pyrimidin-2-yl]amino}ethyl]-6-chloro-1,2-dihydroquinolin-2-one;
6-chloro-3-[(1S)-1-{[4-(dimethyl-1,2-oxazol-4-yl)pyrimidin-2-yl]amino}ethyl]-1,2-dihydroquinolin-2-one;
6-chloro-3-[(1S)-1-{[4-(1,2-oxazol-4-yl)pyrimidin-2-yl]amino}ethyl]-1,2-dihydroquinolin-2-one;
6-chloro-3-[(1S)-1-{[4-(1-methyl-1H-imidazol-5-yl)pyrimidin-2-yl]amino}ethyl]-1,2-dihydroquinolin-2-one;
3-[(1S)-1-{[4-(2-acetylphenyl)pyrimidin-2-yl]amino}ethyl]-6-chloro-1,2-dihydroquinolin-2-one;
N-[2-(2-{[(1S)-1-(6-chloro-2-oxo-1,2-dihydroquinolin-3-yl)ethyl]amino}pyrimidin-4-yl)phenyl]acetamide;
6-chloro-3-[(1S)-1-{[4-(1,5-dimethyl-1H-pyrazol-4-yl)pyrimidin-2-yl]amino}ethyl]-1,2-dihydroquinolin-2-one;
6-chloro-3-[(1S)-1-({4-[1-(propan-2-yl)-1H-pyrazol-5-yl]pyrimidin-2-yl}amino)ethyl]-1,2-dihydroquinolin-2-one;
6-chloro-3-[(1S)-1-{[4-(1,3-dimethyl-1H-pyrazol-5-yl)pyrimidin-2-yl]amino}ethyl]-1,2-dihydroquinolin-2-one;
6-chloro-3-[(1S)-1-{[4-(1,3-dimethyl-1H-pyrazol-4-yl)pyrimidin-2-yl]amino}ethyl]-1,2-dihydroquinolin-2-one;
6-chloro-3-[(1S)-1-{[4-(dimethyl-1,3-thiazol-5-yl)pyrimidin-2-yl]amino}ethyl]-1,2-dihydroquinolin-2-one;
6-chloro-3-[(1S)-1-({4-[1-(oxan-2-yl)-1H-pyrazol-5-yl]pyrimidin-2-yl}amino)ethyl]-1,2-dihydroquinolin-2-one;
6-chloro-3-[(1S)-1-{[4-(4-methylthiophen-3-yl)pyrimidin-2-yl]amino}ethyl]-1,2-dihydroquinolin-2-one;
6-chloro-3-[(1S)-1-{[4-(1-methyl-1H-pyrrol-2-yl)pyrimidin-2-yl]amino}ethyl]-1,2-dihydroquinolin-2-one;
6-chloro-3-[(1S)-1-{[4-(3,5-dimethyl-1H-pyrazol-4-yl)pyrimidin-2-yl]amino}ethyl]-1,2-dihydroquinolin-2-one;
6-chloro-3-[(1S)-1-{[4-(5-methyl-1H-pyrazol-4-yl)pyrimidin-2-yl]amino}ethyl]-1,2-dihydroquinolin-2-one;
6-chloro-3-[(1S)-1-{[4-(trimethyl-1H-pyrazol-4-yl)pyrimidin-2-yl]amino}ethyl]-1,2-dihydroquinolin-2-one;
6-chloro-3-[(1S)-1-({4-[1-(2-methylpropyl)-1H-pyrazol-5-yl]pyrimidin-2-yl}amino)ethyl]-1,2-dihydroquinolin-2-one;
6-chloro-3-[(1S)-1-({4-[3-(trifluoromethyl)-1H-pyrazol-4-yl]pyrimidin-2-yl}amino)ethyl]-1,2-dihydroquinolin-2-one;
6-chloro-3-[(1S)-1-{[4-(1H-pyrazol-5-yl)pyrimidin-2-yl]amino}ethyl]-1,2-dihydroquinolin-2-one;
6-chloro-3-[(1S)-1-{[4-(1,2-thiazol-4-yl)pyrimidin-2-yl]amino}ethyl]-1,2-dihydroquinolin-2-one;
3-[(1S)-1-{[4-(1-benzofuran-3-yl)pyrimidin-2-yl]amino}ethyl]-6-chloro-1,2-dihydroquinolin-2-one;
6-chloro-3-[(1S)-1-{[4-(2-methylpyridin-3-yl)pyrimidin-2-yl]amino}ethyl]-1,2-dihydroquinolin-2-one;
6-chloro-3-[(1S)-1-{[4-(1-methyl-1H-pyrazol-4-yl)pyrimidin-2-yl]amino}ethyl]-1,2-dihydroquinolin-2-one;
6-chloro-3-[(1S)-1-{[4-(isoquinolin-4-yl)pyrimidin-2-yl]amino}ethyl]-1,2-dihydroquinolin-2-one;
6-chloro-3-[(1S)-1-{[4-(2-methoxypyridin-3-yl)pyrimidin-2-yl]amino}ethyl]-1,2-dihydroquinolin-2-one;
6-chloro-3-[(1S)-1-{[4-(pyridin-3-yl)pyrimidin-2-yl]amino}ethyl]-1,2-dihydroquinolin-2-one;
6-chloro-3-[(1S)-1-{[4-(pyridin-4-yl)pyrimidin-2-yl]amino}ethyl]-1,2-dihydroquinolin-2-one;
6-chloro-3-[(1S)-1-{[4-(3-methylpyridin-4-yl)pyrimidin-2-yl]amino}ethyl]-1,2-dihydroquinolin-2-one;
6-chloro-3-[(1S)-1-{[4-(3-methoxypyridin-4-yl)pyrimidin-2-yl]amino}ethyl]-1,2-dihydroquinolin-2-one;
6-chloro-3-[(1S)-1-{[4-(2,3-dihydro-1-benzofuran-7-yl)pyrimidin-2-yl]amino}ethyl]-1,2-dihydroquinolin-2-one;
6-chloro-3-[(1S)-1-{[4-(4-methoxypyridin-3-yl)pyrimidin-2-yl]amino}ethyl]-1,2-dihydroquinolin-2-one;
6-chloro-3-[(1S)-1-({4-[2-(methoxymethyl)phenyl]pyrimidin-2-yl}amino)ethyl]-1,2-dihydroquinolin-2-one;
6-chloro-3-[(1S)-1-[(4-phenylpyrimidin-2-yl)amino]ethyl]-1,2-dihydroquinolin-2-one;
6-chloro-3-[(1S)-1-{[4-(2-methoxyphenyl)pyrimidin-2-yl]amino}ethyl]-1,2-dihydroquinolin-2-one;
3-[(1S)-1-[(5-bromo-4-methylpyrimidin-2-yl)amino]ethyl]-6-chloro-1,2-dihydroquinolin-2-one;
6-chloro-3-[(1S)-1-({4-[(3 S)-3-(propan-2-yl)morpholin-4-yl]pyrimidin-2-yl}amino)ethyl]-1,2-dihydroquinolin-2-one;

6-chloro-3-[(1S)-1-[(4-methanesulfonylpyrimidin-2-yl)amino]ethyl]-1,2-dihydroquinolin-2-one;
6-chloro-3-[(1S)-1-({4-[(R)-2-methylpropanesulfinyl]pyrimidin-2-yl}amino)ethyl]-1,2-dihydroquinolin-2-one;
6-chloro-3-[(1S)-1-({4-[(2-methylpropyl)sulfanyl]pyrimidin-2-yl}amino)ethyl]-1,2-dihydroquinolin-2-one;
6-chloro-3-[(1S)-1-{[4-(2-methylpropanesulfonyl)pyrimidin-2-yl]amino}ethyl]-1,2-dihydroquinolin-2-one;
6-chloro-3-[(1S)-1-({4-[(S)-2-methylpropanesulfinyl]pyrimidin-2-yl}amino)ethyl]-1,2-dihydroquinolin-2-one;
3-[(1S)-1-{[4-(benzyl sulfanyl)pyrimidin-2-yl]amino}ethyl]-6-chloro-1,2-dihydroquinolin-2-one;
6-chloro-3-[(1S)-1-[(4-methanesulfinylpyrimidin-2-yl)amino]ethyl]-1,2-dihydroquinolin-2-one;
6-chloro-3-[(1S)-1-({4-[(R)-methanesulfinyl]pyrimidin-2-yl}amino)ethyl]-1,2-dihydroquinolin-2-one;
6-chloro-3-[(1S)-1-({4-[(S)-methanesulfinyl]pyrimidin-2-yl}amino)ethyl]-1,2-dihydroquinolin-2-one;
2-{[(1S)-1-(6-chloro-2-oxo-1,2-dihydroquinolin-3-yl)ethyl]amino}pyrimidine-4-carboxamide;
2-{[(1S)-1-(6-chloro-2-oxo-1,2-dihydroquinolin-3-yl)ethyl]amino}-N-methylpyrimidine-4-carboxamide;
2-{[(1S)-1-(6-chloro-2-oxo-1,2-dihydroquinolin-3-yl)ethyl]amino}-N-(2-methylpropyl)pyrimidine-4-carboxamide;
2-{[(1S)-1-(6-chloro-2-oxo-1,2-dihydroquinolin-3-yl)ethyl]amino}-N-(propan-2-yl)pyrimidine-4-carboxamide;
6-chloro-3-[(1S)-1-{[4-(1-methanesulfonyl-3-methylbutyl)pyrimidin-2-yl]amino}ethyl]-1,2-dihydroquinolin-2-one;
2-[(2-{[(1S)-1-(6-chloro-2-oxo-1,2-dihydroquinolin-3-yl)ethyl]amino}pyrimidin-4-yl)methyl]-1$\lambda^6$,2-thiazolidine-1,1-dione;
2-(2-{[(1S)-1-(6-chloro-2-oxo-1,2-dihydroquinolin-3-yl)ethyl]amino}pyrimidin-4-yl)-1$\lambda^6$-thiolane-1,1-dione;
6-chloro-3-[(1S)-1-({4-[(2-methylpropanesulfonyl)methyl]pyrimidin-2-yl}amino)ethyl]-1,2-dihydroquinolin-2-one;
6-chloro-3-[(1S)-1-({4-[(oxolan-3-yl)amino]pyrimidin-2-yl}amino)ethyl]-1,2-dihydroquinolin-2-one;
6-chloro-3-[(1S)-1-{[4-(2-oxoimidazolidin-1-yl)pyrimidin-2-yl]amino}ethyl]-1,2-dihydroquinolin-2-one;
6-chloro-3-[(1S)-1-{[4-(3-methyl-2-oxoimidazolidin-1-yl)pyrimidin-2-yl]amino}ethyl]-1,2-dihydroquinolin-2-one;
1-(2-{[(1S)-1-(6-chloro-2-oxo-1,2-dihydroquinolin-3-yl)ethyl]amino}pyrimidin-4-yl)-1,3,3-trimethylurea;
1-(2-{[(1S)-1-(6-chloro-2-oxo-1,2-dihydroquinolin-3-yl)ethyl]amino}pyrimidin-4-yl)-3,3-dimethylurea;
6-chloro-3-[(1S)-1-({4-[(1,3-oxazol-2-yl)amino]pyrimidin-2-yl}amino)ethyl]-1,2-dihydroquinolin-2-one;
6-chloro-3-[(1S)-1-({4-[(2-methylpropyl)(1,3-oxazol-2-yl)amino]pyrimidin-2-yl}amino)ethyl]-1,2-dihydroquinolin-2-one;
methyl-2-{[(1S)-1-(6-chloro-2-oxo-1,2-dihydroquinolin-3-yl)ethyl]amino}pyrimidine-4-carboxylate;
2-(2-{[(1S)-1-(6-chloro-2-oxo-1,2-dihydroquinolin-3-yl)ethyl]amino}pyrimidin-4-yl)acetamide;
2-(2-{[(1S)-1-(6-chloro-2-oxo-1,2-dihydroquinolin-3-yl)ethyl]amino}pyrimidin-4-yl)-N-methylacetamide;
N-[(2-{[(1S)-1-(6-chloro-2-oxo-1,2-dihydroquinolin-3-yl)ethyl]amino}pyrimidin-4-yl)methyl]methanesulfonamide;
6-chloro-3-[(1S)-1-{[4-(methanesulfonylmethyl)pyrimidin-2-yl]amino}ethyl]-1,2-dihydroquinolin-2-one;
methyl-2-(2-{[(1S)-1-(6-chloro-2-oxo-1,2-dihydroquinolin-3-yl)ethyl]amino}pyrimidin-4-yl)-2-methanesulfonylacetate;
6-chloro-3-[(1S)-1-{[4-(1-methanesulfonylethyl)pyrimidin-2-yl]amino}ethyl]-1,2-dihydroquinolin-2-one;
6-chloro-3-[(1S)-1-{[4-(1-methanesulfonylcyclopropyl)pyrimidin-2-yl]amino}ethyl]-1,2-dihydroquinolin-2-one;
N-[(2-{[(1S)-1-(6-chloro-2-oxo-1,2-dihydroquinolin-3-yl)ethyl]amino}pyrimidin-4-yl)methyl]-N-cyclopropylacetamide;
6-chloro-3-[(1S)-1-{[4-(2-oxopyrrolidin-1-yl)pyrimidin-2-yl]amino}ethyl]-1,2-dihydroquinolin-2-one;
3-[(1S)-1-[(4-aminopyrimidin-2-yl)amino]ethyl]-6-chloro-1,2-dihydroquinolin-2-one
6-chloro-3-[(1R)-1-{[4-(2-oxo-1,3-oxazinan-3-yl)pyrimidin-2-yl]amino}ethyl]-1,2-dihydroquinolin-2-one;
2-{[(1R)-1-(6-chloro-7-fluoro-2-oxo-1,2-dihydroquinolin-3-yl)ethyl]amino}-4-methoxypyrimidine-5-carbonitrile;
2-{[1-(6-chloro-7-fluoro-2-oxo-1,2-dihydroquinolin-3-yl)ethyl]amino}-4-methoxypyrimidine-5-carbonitrile;
2-{[(1S)-1-(6-chloro-7-methoxy-2-oxo-1,2-dihydroquinolin-3-yl)ethyl]amino}-4-methoxypyrimidine-5-carbonitrile;
2-{[(1R)-1-(6-chloro-7-methoxy-2-oxo-1,2-dihydroquinolin-3-yl)ethyl]amino}-4-methoxypyrimidine-5-carbonitrile;
2-{[1-(6-chloro-7-methoxy-2-oxo-1,2-dihydroquinolin-3-yl)ethyl]amino}-4-methoxypyrimidine-5-carbonitrile;
6-chloro-7-methoxy-3-(1-{[4-(2-oxo-1,3-oxazolidin-3-yl)pyrimidin-2-yl]amino}ethyl)-1,2-dihydroquinolin-2-one;
6-chloro-7-methoxy-3-[(1S)-1-{[4-(2-oxo-1,3-oxazolidin-3-yl)pyrimidin-2-yl]amino}ethyl]-1,2-dihydroquinolin-2-one;
6-chloro-7-methoxy-3-[(1R)-1-{[4-(2-oxo-1,3-oxazolidin-3-yl)pyrimidin-2-yl]amino}ethyl]-1,2-dihydroquinolin-2-one;
N-[2-({1-[6-chloro-2-oxo-7-(pyridin-2-ylmethoxy)-1,2-dihydroquinolin-3-yl]ethyl}amino)pyrimidin-4-yl]acetamide;
2-({1-[6-chloro-2-oxo-7-(pyridin-2-ylmethoxy)-1,2-dihydroquinolin-3-yl]ethyl}amino)-4-methoxypyrimidine-5-carbonitrile;
2-{[(1S)-1-[6-chloro-2-oxo-7-(pyridin-2-ylmethoxy)-1,2-dihydroquinolin-3-yl]ethyl]amino}-4-methoxypyrimidine-5-carbonitrile;
2-{[(1S)-1-[6-chloro-2-oxo-7-(pyridin-2-ylmethoxy)-1,2-dihydroquinolin-3-yl]ethyl]amino}-4-hydroxypyrimidine-5-carbonitrile;
2-{[(1S)-1-[6-chloro-2-oxo-7-(pyridin-2-ylmethoxy)-1,2-dihydroquinolin-3-yl]ethyl]amino}-4-methylpyrimidine-5-carbonitrile;
methyl-N-(2-{[(1S)-1-[6-chloro-2-oxo-7-(pyridin-2-ylmethoxy)-1,2-dihydroquinolin-3-yl]ethyl]amino}pyrimidin-4-yl)carbamate;
2-{[(1S)-1-(6-chloro-2-oxo-1,2-dihydro-1,8-naphthyridin-3-yl)ethyl]amino}-4-methoxypyrimidine-5-carbonitrile;
2-{[(1S)-1-(7-chloro-3-oxo-3,4-dihydroquinoxalin-2-yl)ethyl]amino}-4-methoxypyrimidine-5-carbonitrile;
2-{[(1R)-1-(7-chloro-3-oxo-3,4-dihydroquinoxalin-2-yl)ethyl]amino}-4-methoxypyrimidine-5-carbonitrile;
2-{[(1S)-1-{6-chloro-2-oxo-7-[(1R)-1-(pyridin-2-yl)ethoxy]-1,2-dihydroquinolin-3-yl}ethyl]amino}-4-methoxypyrimidine-5-carbonitrile;
2-{[(1S)-1-[6-chloro-7-(cyclopropylmethoxy)-2-oxo-1,2-dihydroquinolin-3-yl]ethyl]amino}-4-methoxypyrimidine-5-carbonitrile;
N-(2-{[(1S)-1-(6-chloro-8-fluoro-2-oxo-1,2-dihydroquinolin-3-yl)ethyl]amino}pyrimidin-4-yl)acetamide;
2-{[(1S)-1-(6-chloro-8-fluoro-2-oxo-1,2-dihydroquinolin-3-yl)ethyl]amino}-4-methoxypyrimidine-5-carbonitrile;
2-{[(1S)-1-(7-bromo-6-chloro-2-oxo-1,2-dihydroquinolin-3-yl)ethyl]amino}-4-methoxypyrimidine-5-carbonitrile;

6-chloro-3-{[(4,6-dimethoxypyrimidin-2-yl)amino]
methyl}-1,2-dihydroquinolin-2-one N-(2-{[(2-oxo-1,2-dihydroquinolin-3-yl)methyl]
amino}pyrimidin-4-yl)-N-(propan-2-yl)methanesulfonamide;

N-(2-{[(7-fluoro-2-oxo-1,2-dihydroquinolin-3-yl)methyl]
amino}pyrimidin-4-yl)-N-(propan-2-yl)methanesulfonamide;

N-(2-{[(6-methyl-2-oxo-1,2-dihydroquinolin-3-yl)methyl]
amino}pyrimidin-4-yl)-N-(propan-2-yl)methanesulfonamide;

N-[2-({[2-oxo-6-(propan-2-yl)-1,2-dihydroquinolin-3-yl]
methyl)}amino)pyrimidin-4-yl]-N-(propan-2-yl)methanesulfonamide;

6-chloro-3-(1-{[4-(2-oxo-1,3-oxazolidin-3-yl)pyrimidin-2-yl]amino}cyclopropyl)-1,2-dihydroquinolin-2-one;

2-{[1-(6-chloro-2-oxo-1,2-dihydroquinolin-3-yl)cyclopropyl]amino}-4-methoxypyrimidine-5-carbonitrile;

6-chloro-3-(2-{[4-(2-oxo-1,3-oxazolidin-3-yl)pyrimidin-2-yl]amino}propan-2-yl)-1,2-dihydroquinolin-2-one;

6-chloro-3-(2-fluoro-1-{[4-(2-oxo-1,3-oxazolidin-3-yl)pyrimidin-2-yl]amino}ethyl)-1,2-dihydroquinolin-2-one;

2-[(1-{6-chloro-7-[(3,3-difluorocyclobutyl)methoxy]-2-oxo-1,2-dihydroquinolin-3-yl}ethyl)amino]-4-methoxypyrimidine-5-carbonitrile;

6-chloro-1-methyl-3-[(1S)-1-({4-[1-(propan-2-yl)-1H-imidazol-5-yl]pyrimidin-2-yl}amino)ethyl]-1,2-dihydroquinolin-2-one;

2-{[(1R)-1-(6-chloro-2-oxo-1,2-dihydroquinolin-3-yl)ethyl]amino}-4-methoxypyrimidine-5-carbonitrile;

2-{[(1S)-1-[6-chloro-2-oxo-7-(propan-2-yloxy)-1,2-dihydroquinolin-3-yl]ethyl]amino}-4-methoxypyrimidine-5-carbonitrile;

2-{[(1S)-1-(6-chloro-7-cyclopropyl-2-oxo-1,2-dihydroquinolin-3-yl)ethyl]amino}-4-methoxypyrimidine-5-carbonitrile;

4-methoxy-2-{[(1S)-1-(2-oxo-1,2-dihydro-1,5-naphthyridin-3-yl)ethyl]amino}pyrimidine-5-carbonitrile;

2-{[(1S)-1-(6-chloro-2-oxo-1,2-dihydroquinolin-3-yl)ethyl]amino}-4-hydroxypyrimidine-5-carbonitrile;

N-(2-{[(1S)-1-(6-chloro-7-fluoro-2-oxo-1,2-dihydroquinolin-3-yl)ethyl]amino}pyrimidin-4-yl)acetamide;

N-(2-{[(1S)-1-(6-chloro-7-fluoro-2-oxo-1,2-dihydroquinolin-3-yl)ethyl]amino}pyrimidin-4-yl)cyclopropanecarboxamide;

2-{[(1S)-1-(6-chloro-7-fluoro-2-oxo-1,2-dihydroquinolin-3-yl)ethyl]amino}-4-methoxypyrimidine-5-carbonitrile;

N-(2-{[(1S)-1-(6-chloro-2-oxo-1,2-dihydro-1,8-naphthyridin-3-yl)ethyl]amino}pyrimidin-4-yl)acetamide;

6-chloro-3-[(1S)-1-{[4-(5-cyclopropyl-1H-1,2,3,4-tetrazol-1-yl)pyrimidin-2-yl]amino}ethyl]-1,2-dihydroquinolin-2-one; and 6-chloro-3-[(1S)-1-{[4-(5-cyclopropyl-1H-1,2,3,4-tetrazol-1-yl)pyrimidin-2-yl]amino}ethyl]-1,2-dihydro-1,8-naphthyridin-2-one.

In another embodiment, illustrative compounds of the invention include:

6-chloro-3-[(1S)-1-{[4-methoxy-5-(1H-1,2,3,4-tetrazol-1-yl)pyrimidin-2-yl]amino}ethyl]-1,2-dihydroquinolin-2-one;

6-chloro-3-[(1S)-1-{[4-(2-oxo-1,3-oxazolidin-3-yl)pyrimidin-2-yl]amino}ethyl]-7-(pyridin-2-ylmethoxy)-1,2-dihydroquinolin-2-one;

2-{[(1S)-1-[6-chloro-2-oxo-7-(pyridin-2-ylmethoxy)-1,2-dihydroquinolin-3-yl]ethyl]amino}pyrimidine-4-carboxamide;

6-chloro-3-[(1S)-1-{[4-(5-methyl-1H-1,2,3,4-tetrazol-1-yl)pyrimidin-2-yl]amino}ethyl]-7-(pyridin-2-ylmethoxy)-1,2-dihydroquinolin-2-one;

N-(2-{[(1S)-1-[6-chloro-2-oxo-7-(pyridin-2-ylmethoxy)-1,2-dihydroquinolin-3-yl]ethyl]amino}pyrimidin-4-yl)cyclopropanecarboxamide;

N-(2-{[(1S)-1-[6-chloro-2-oxo-7-(pyridin-2-ylmethoxy)-1,2-dihydroquinolin-3-yl]ethyl]amino}pyrimidin-4-yl)propanamide;

N-(2-{[(1S)-1-[6-chloro-2-oxo-7-(pyridin-2-ylmethoxy)-1,2-dihydroquinolin-3-yl]ethyl]amino}pyrimidin-4-yl)acetamide;

6-chloro-3-[(1S)-1-{[4-(1H-imidazol-1-yl)pyrimidin-2-yl]amino}ethyl]-7-(pyridin-2-ylmethoxy)-1,2-dihydroquinolin-2-one;

6-chloro-3-[(1S)-1-{[4-(1,2-oxazol-4-yl)pyrimidin-2-yl]amino}ethyl]-7-(pyridin-2-ylmethoxy)-1,2-dihydroquinolin-2-one;

6-chloro-3-[(1S)-1-{[4-(4-methylthiophen-3-yl)pyrimidin-2-yl]amino}ethyl]-7-(pyridin-2-ylmethoxy)-1,2-dihydroquinolin-2-one;

3-[(1S)-1-{[4-(1-benzyl-1H-imidazol-5-yl)pyrimidin-2-yl]amino}ethyl]-6-chloro-7-(pyridin-2-ylmethoxy)-1,2-dihydroquinolin-2-one;

6-chloro-3-[(1S)-1-{[4-(1-methyl-1H-imidazol-5-yl)pyrimidin-2-yl]amino}ethyl]-7-(pyridin-2-ylmethoxy)-1,2-dihydroquinolin-2-one;

6-chloro-3-[(1S)-1-{[4-(3-methylpyridin-4-yl)pyrimidin-2-yl]amino}ethyl]-7-(pyridin-2-ylmethoxy)-1,2-dihydroquinolin-2-one;

N-(2-{[(1S)-1-[6-chloro-2-oxo-7-(pyridin-2-ylmethoxy)-1,2-dihydroquinolin-3-yl]ethyl]amino}pyrimidin-4-yl)-N-(2-methylpropyl)methanesulfonamide;

6-chloro-3-[(1S)-1-{[4-methoxy-5-(1H-1,2,3,4-tetrazol-1-yl)pyrimidin-2-yl]amino}ethyl]-7-(pyridin-2-ylmethoxy)-1,2-dihydroquinolin-2-one;

2-{[(1S)-1-(6-chloro-7-methoxy-2-oxo-1,2-dihydroquinolin-3-yl)ethyl]amino}-4-methylpyrimidine-5-carbonitrile;

methyl-N-(2-{[(1S)-1-(6-chloro-7-methoxy-2-oxo-1,2-dihydroquinolin-3-yl)ethyl]amino}pyrimidin-4-yl)carbamate;

2-{[(1S)-1-(6-chloro-7-methoxy-2-oxo-1,2-dihydroquinolin-3-yl)ethyl]amino}pyrimidine-4-carboxamide;

6-chloro-7-methoxy-3-[(1S)-1-{[4-(5-methyl-1H-1,2,3,4-tetrazol-1-yl)pyrimidin-2-yl]amino}ethyl]-1,2-dihydroquinolin-2-one;

N-(2-{[(1S)-1-(6-chloro-7-methoxy-2-oxo-1,2-dihydroquinolin-3-yl)ethyl]amino}pyrimidin-4-yl)cyclopropanecarboxamide;

N-(2-{[(1S)-1-(6-chloro-7-methoxy-2-oxo-1,2-dihydroquinolin-3-yl)ethyl]amino}pyrimidin-4-yl)propanamide;

N-(2-{[(1S)-1-(6-chloro-7-methoxy-2-oxo-1,2-dihydroquinolin-3-yl)ethyl]amino}pyrimidin-4-yl)acetamide;

6-chloro-3-[(1S)-1-{[4-(1H-imidazol-1-yl)pyrimidin-2-yl]amino}ethyl]-7-methoxy-1,2-dihydroquinolin-2-one;

6-chloro-7-methoxy-3-[(1S)-1-{[4-(1,2-oxazol-4-yl)pyrimidin-2-yl]amino}ethyl]-1,2-dihydroquinolin-2-one;

6-chloro-7-methoxy-3-[(1S)-1-{[4-(4-methylthiophen-3-yl)pyrimidin-2-yl]amino}ethyl]-1,2-dihydroquinolin-2-one;

3-[(1S)-1-{[4-(1-benzyl-1H-imidazol-5-yl)pyrimidin-2-yl]amino}ethyl]-6-chloro-7-methoxy-1,2-dihydroquinolin-2-one;

6-chloro-7-methoxy-3-[(1S)-1-{[4-(1-methyl-1H-imidazol-5-yl)pyrimidin-2-yl]amino}ethyl]-1,2-dihydroquinolin-2-one;

6-chloro-7-methoxy-3-[(1S)-1-{[4-(3-methylpyridin-4-yl)pyrimidin-2-yl]amino}ethyl]-1,2-dihydroquinolin-2-one;

N-(2-{[(1S)-1-(6-chloro-7-methoxy-2-oxo-1,2-dihydroquinolin-3-yl)ethyl]amino}pyrimidin-4-yl)-N-(2-methylpropyl)methanesulfonamide;

6-chloro-7-methoxy-3-[(1S)-1-{[4-methoxy-5-(1H-1,2,3,4-tetrazol-1-yl)pyrimidin-2-yl]amino}ethyl]-1,2-dihydroquinolin-2-one;

2-{[(1S)-1-[6-chloro-2-oxo-7-(propan-2-yloxy)-1,2-dihydroquinolin-3-yl]ethyl]amino}-4-methylpyrimidine-5-carbonitrile;

5-{[(1S)-1-[6-chloro-2-oxo-7-(propan-2-yloxy)-1,2-dihydroquinolin-3-yl]ethyl]amino}-1-methyl-6-oxo-1,6-dihydropyridine-2-carbonitrile;

6-chloro-3-[(1S)-1-{[4-(2-oxo-1,3-oxazolidin-3-yl)pyrimidin-2-yl]amino}ethyl]-7-(propan-2-yloxy)-1,2-dihydroquinolin-2-one;

methyl-N-(2-{[(1S)-1-[6-chloro-2-oxo-7-(propan-2-yloxy)-1,2-dihydroquinolin-3-yl]ethyl]amino}pyrimidin-4-yl)carbamate;

2-{[(1S)-1-[6-chloro-2-oxo-7-(propan-2-yloxy)-1,2-dihydroquinolin-3-yl]ethyl]amino}pyrimidine-4-carboxamide;

6-chloro-3-[(1S)-1-{[4-(5-methyl-1H-1,2,3,4-tetrazol-1-yl)pyrimidin-2-yl]amino}ethyl]-7-(propan-2-yloxy)-1,2-dihydroquinolin-2-one;

N-(2-{[(1S)-1-[6-chloro-2-oxo-7-(propan-2-yloxy)-1,2-dihydroquinolin-3-yl]ethyl]amino}pyrimidin-4-yl)cyclopropanecarboxamide;

N-(2-{[(1S)-1-[6-chloro-2-oxo-7-(propan-2-yloxy)-1,2-dihydroquinolin-3-yl]ethyl]amino}pyrimidin-4-yl)propanamide;

N-(2-{[(1S)-1-[6-chloro-2-oxo-7-(propan-2-yloxy)-1,2-dihydroquinolin-3-yl]ethyl]amino}pyrimidin-4-yl)acetamide;

6-chloro-3-[(1S)-1-{[4-(1H-imidazol-1-yl)pyrimidin-2-yl]amino}ethyl]-7-(propan-2-yloxy)-1,2-dihydroquinolin-2-one;

6-chloro-3-[(1S)-1-{[4-(1,2-oxazol-4-yl)pyrimidin-2-yl]amino}ethyl]-7-(propan-2-yloxy)-1,2-dihydroquinolin-2-one;

6-chloro-3-[(1S)-1-{[4-(4-methylthiophen-3-yl)pyrimidin-2-yl]amino}ethyl]-7-(propan-2-yloxy)-1,2-dihydroquinolin-2-one;

3-[(1S)-1-{[4-(1-benzyl-1H-imidazol-5-yl)pyrimidin-2-yl]amino}ethyl]-6-chloro-7-(propan-2-yloxy)-1,2-dihydroquinolin-2-one;

6-chloro-3-[(1S)-1-{[4-(1-methyl-1H-imidazol-5-yl)pyrimidin-2-yl]amino}ethyl]-7-(propan-2-yloxy)-1,2-dihydroquinolin-2-one;

6-chloro-3-[(1S)-1-{[4-(3-methylpyridin-4-yl)pyrimidin-2-yl]amino}ethyl]-7-(propan-2-yloxy)-1,2-dihydroquinolin-2-one;

N-(2-{[(1S)-1-[6-chloro-2-oxo-7-(propan-2-yloxy)-1,2-dihydroquinolin-3-yl]ethyl]amino}pyrimidin-4-yl)-N-(2-methylpropyl)methanesulfonamide;

6-chloro-3-[(1S)-1-{[4-methoxy-5-(1H-1,2,3,4-tetrazol-1-yl)pyrimidin-2-yl]amino}ethyl]-7-(propan-2-yloxy)-1,2-dihydroquinolin-2-one;

2-{[(1S)-1-[6-chloro-7-(cyclopropylmethoxy)-2-oxo-1,2-dihydroquinolin-3-yl]ethyl]amino}-4-methylpyrimidine-5-carbonitrile;

6-chloro-7-(cyclopropylmethoxy)-3-[(1S)-1-{[4-(2-oxo-1,3-oxazolidin-3-yl)pyrimidin-2-yl]amino}ethyl]-1,2-dihydroquinolin-2-one;

methyl-N-(2-{[(1S)-1-[6-chloro-7-(cyclopropylmethoxy)-2-oxo-1,2-dihydroquinolin-3-yl]ethyl]amino}pyrimidin-4-yl)carbamate;

2-{[(1S)-1-[6-chloro-7-(cyclopropylmethoxy)-2-oxo-1,2-dihydroquinolin-3-yl]ethyl]amino}pyrimidine-4-carboxamide;

6-chloro-7-(cyclopropylmethoxy)-3-[(1S)-1-{[4-(5-methyl-1H-1,2,3,4-tetrazol-1-yl)pyrimidin-2-yl]amino}ethyl]-1,2-dihydroquinolin-2-one;

N-(2-{[(1S)-1-[6-chloro-7-(cyclopropylmethoxy)-2-oxo-1,2-dihydroquinolin-3-yl]ethyl]amino}pyrimidin-4-yl)cyclopropanecarboxamide;

N-(2-{[(1S)-1-[6-chloro-7-(cyclopropylmethoxy)-2-oxo-1,2-dihydroquinolin-3-yl]ethyl]amino}pyrimidin-4-yl)propanamide;

N-(2-{[(1S)-1-[6-chloro-7-(cyclopropylmethoxy)-2-oxo-1,2-dihydroquinolin-3-yl]ethyl]amino}pyrimidin-4-yl)acetamide;

6-chloro-7-(cyclopropylmethoxy)-3-[(1S)-1-{[4-(1H-imidazol-1-yl)pyrimidin-2-yl]amino}ethyl]-1,2-dihydroquinolin-2-one;

6-chloro-7-(cyclopropylmethoxy)-3-[(1S)-1-{[4-(1,2-oxazol-4-yl)pyrimidin-2-yl]amino}ethyl]-1,2-dihydroquinolin-2-one;

6-chloro-7-(cyclopropylmethoxy)-3-[(1S)-1-{[4-(4-methylthiophen-3-yl)pyrimidin-2-yl]amino}ethyl]-1,2-dihydroquinolin-2-one;

3-[(1S)-1-{[4-(1-benzyl-1H-imidazol-5-yl)pyrimidin-2-yl]amino}ethyl]-6-chloro-7-(cyclopropylmethoxy)-1,2-dihydroquinolin-2-one;

6-chloro-7-(cyclopropylmethoxy)-3-[(1S)-1-{[4-(1-methyl-1H-imidazol-5-yl)pyrimidin-2-yl]amino}ethyl]-1,2-dihydroquinolin-2-one;

6-chloro-7-(cyclopropylmethoxy)-3-[(1S)-1-{[4-(3-methylpyridin-4-yl)pyrimidin-2-yl]amino}ethyl]-1,2-dihydroquinolin-2-one;

N-(2-{[(1S)-1-[6-chloro-7-(cyclopropylmethoxy)-2-oxo-1,2-dihydroquinolin-3-yl]ethyl]amino}pyrimidin-4-yl)-N-(2-methylpropyl)methanesulfonamide;

6-chloro-7-(cyclopropylmethoxy)-3-[(1S)-1-{[4-methoxy-5-(1H-1,2,3,4-tetrazol-1-yl)pyrimidin-2-yl]amino}ethyl]-1,2-dihydroquinolin-2-one;

2-{[(1S)-1-(6-chloro-7-fluoro-2-oxo-1,2-dihydroquinolin-3-yl)ethyl]amino}-4-methoxypyrimidine-5-carbonitrile;

2-{[(1S)-1-(6-chloro-7-fluoro-2-oxo-1,2-dihydroquinolin-3-yl)ethyl]amino}-4-methylpyrimidine-5-carbonitrile;

6-chloro-7-fluoro-3-[(1S)-1-{[4-(2-oxo-1,3-oxazolidin-3-yl)pyrimidin-2-yl]amino}ethyl]-1,2-dihydroquinolin-2-one;

methyl-N-(2-{[(1S)-1-(6-chloro-7-fluoro-2-oxo-1,2-dihydroquinolin-3-yl)ethyl]amino}pyrimidin-4-yl)carbamate;

2-{[(1S)-1-(6-chloro-7-fluoro-2-oxo-1,2-dihydroquinolin-3-yl)ethyl]amino}pyrimidine-4-carboxamide;

6-chloro-7-fluoro-3-[(1S)-1-{[4-(5-methyl-1H-1,2,3,4-tetrazol-1-yl)pyrimidin-2-yl]amino}ethyl]-1,2-dihydroquinolin-2-one;

N-(2-{[(1S)-1-(6-chloro-7-fluoro-2-oxo-1,2-dihydroquinolin-3-yl)ethyl]amino}pyrimidin-4-yl)cyclopropanecarboxamide;

N-(2-{[(1S)-1-(6-chloro-7-fluoro-2-oxo-1,2-dihydroquinolin-3-yl)ethyl]amino}pyrimidin-4-yl)propanamide;

N-(2-{[(1S)-1-(6-chloro-7-fluoro-2-oxo-1,2-dihydroquinolin-3-yl)ethyl]amino}pyrimidin-4-yl)acetamide;

6-chloro-7-fluoro-3-[(1S)-1-{[4-(1H-imidazol-1-yl)pyrimidin-2-yl]amino}ethyl]-1,2-dihydroquinolin-2-one;

6-chloro-7-fluoro-3-[(1S)-1-{[4-(1,2-oxazol-4-yl)pyrimidin-2-yl]amino}ethyl]-1,2-dihydroquinolin-2-one;

6-chloro-7-fluoro-3-[(1S)-1-{[4-(4-methylthiophen-3-yl)pyrimidin-2-yl]amino}ethyl]-1,2-dihydroquinolin-2-one;

3-[(1S)-1-{[4-(1-benzyl-1H-imidazol-5-yl)pyrimidin-2-yl]amino}ethyl]-6-chloro-7-fluoro-1,2-dihydroquinolin-2-one;

6-chloro-7-fluoro-3-[(1S)-1-{[4-(1-methyl-1H-imidazol-5-yl)pyrimidin-2-yl]amino}ethyl]-1,2-dihydroquinolin-2-one;

6-chloro-7-fluoro-3-[(1S)-1-{[4-(3-methylpyridin-4-yl)pyrimidin-2-yl]amino}ethyl]-1,2-dihydroquinolin-2-one;

N-(2-{[(1S)-1-(6-chloro-7-fluoro-2-oxo-1,2-dihydroquinolin-3-yl)ethyl]amino}pyrimidin-4-yl)-N-(2-methylpropyl)methanesulfonamide;

6-chloro-7-fluoro-3-[(1S)-1-{[4-methoxy-5-(1H-1,2,3,4-tetrazol-1-yl)pyrimidin-2-yl]amino}ethyl]-1,2-dihydroquinolin-2-one;

2-{[(1S)-1-(6-chloro-8-fluoro-2-oxo-1,2-dihydroquinolin-3-yl)ethyl]amino}-4-methylpyrimidine-5-carbonitrile;

5-{[(1S)-1-(6-chloro-8-fluoro-2-oxo-1,2-dihydroquinolin-3-yl)ethyl]amino}-1-methyl-6-oxo-1,6-dihydropyridine-2-carbonitrile;

6-chloro-8-fluoro-3-[(1S)-1-{[4-(2-oxo-1,3-oxazolidin-3-yl)pyrimidin-2-yl]amino}ethyl]-1,2-dihydroquinolin-2-one;

Methyl-N-(2-{[(1S)-1-(6-chloro-8-fluoro-2-oxo-1,2-dihydroquinolin-3-yl)ethyl]amino}pyrimidin-4-yl)carbamate;

2-{[(1S)-1-(6-chloro-8-fluoro-2-oxo-1,2-dihydroquinolin-3-yl)ethyl]amino}pyrimidine-4-carboxamide;

6-chloro-8-fluoro-3-[(1S)-1-{[4-(5-methyl-1H-1,2,3,4-tetrazol-1-yl)pyrimidin-2-yl]amino}ethyl]-1,2-dihydroquinolin-2-one;

N-(2-{[(1S)-1-(6-chloro-8-fluoro-2-oxo-1,2-dihydroquinolin-3-yl)ethyl]amino}pyrimidin-4-yl)cyclopropanecarboxamide;

N-(2-{[(1S)-1-(6-chloro-8-fluoro-2-oxo-1,2-dihydroquinolin-3-yl)ethyl]amino}pyrimidin-4-yl)propanamide;

6-chloro-8-fluoro-3-[(1S)-1-{[4-(1H-imidazol-1-yl)pyrimidin-2-yl]amino}ethyl]-1,2-dihydroquinolin-2-one;

6-chloro-8-fluoro-3-[(1S)-1-{[4-(1,2-oxazol-4-yl)pyrimidin-2-yl]amino}ethyl]-1,2-dihydroquinolin-2-one;

6-chloro-8-fluoro-3-[(1S)-1-{[4-(4-methylthiophen-3-yl)pyrimidin-2-yl]amino}ethyl]-1,2-dihydroquinolin-2-one;

3-[(1S)-1-{[4-(1-benzyl-1H-imidazol-5-yl)pyrimidin-2-yl]amino}ethyl]-6-chloro-8-fluoro-1,2-dihydroquinolin-2-one;

6-chloro-8-fluoro-3-[(1S)-1-{[4-(1-methyl-1H-imidazol-5-yl)pyrimidin-2-yl]amino}ethyl]-1,2-dihydroquinolin-2-one;

6-chloro-8-fluoro-3-[(1S)-1-{[4-(3-methylpyridin-4-yl)pyrimidin-2-yl]amino}ethyl]-1,2-dihydroquinolin-2-one;

N-(2-{[(1S)-1-(6-chloro-8-fluoro-2-oxo-1,2-dihydroquinolin-3-yl)ethyl]amino}pyrimidin-4-yl)-N-(2-methylpropyl)methanesulfonamide;

6-chloro-8-fluoro-3-[(1S)-1-{[4-methoxy-5-(1H-1,2,3,4-tetrazol-1-yl)pyrimidin-2-yl]amino}ethyl]-1,2-dihydroquinolin-2-one;

2-{[(1S)-1-(6-chloro-2-oxo-1,2-dihydro-1,8-naphthyridin-3-yl)ethyl]amino}-4-methylpyrimidine-5-carbonitrile;

5-{[(1S)-1-(6-chloro-2-oxo-1,2-dihydro-1,8-naphthyridin-3-yl)ethyl]amino}-1-methyl-6-oxo-1,6-dihydropyridine-2-carbonitrile;

6-chloro-3-[(1S)-1-{[4-(2-oxo-1,3-oxazolidin-3-yl)pyrimidin-2-yl]amino}ethyl]-1,2-dihydro-1,8-naphthyridin-2-one;

methyl-N-(2-{[(1S)-1-(6-chloro-2-oxo-1,2-dihydro-1,8-naphthyridin-3-yl)ethyl]amino}pyrimidin-4-yl)carbamate;

2-{[(1S)-1-(6-chloro-2-oxo-1,2-dihydro-1,8-naphthyridin-3-yl)ethyl]amino}pyrimidine-4-carboxamide;

6-chloro-3-[(1S)-1-{[4-(5-methyl-1H-1,2,3,4-tetrazol-1-yl)pyrimidin-2-yl]amino}ethyl]-1,2-dihydro-1,8-naphthyridin-2-one;

N-(2-{[(1S)-1-(6-chloro-2-oxo-1,2-dihydro-1,8-naphthyridin-3-yl)ethyl]amino}pyrimidin-4-yl)cyclopropanecarboxamide;

N-(2-{[(1S)-1-(6-chloro-2-oxo-1,2-dihydro-1,8-naphthyridin-3-yl)ethyl]amino}pyrimidin-4-yl)propanamide;

N-(2-{[(1S)-1-(6-chloro-2-oxo-1,2-dihydro-1,8-naphthyridin-3-yl)ethyl]amino}pyrimidin-4-yl)acetamide;

6-chloro-3-[(1S)-1-{[4-(1H-imidazol-1-yl)pyrimidin-2-yl]amino}ethyl]-1,2-dihydro-1,8-naphthyridin-2-one;

6-chloro-3-[(1S)-1-{[4-(1,2-oxazol-4-yl)pyrimidin-2-yl]amino}ethyl]-1,2-dihydro-1,8-naphthyridin-2-one;

6-chloro-3-[(1S)-1-{[4-(4-methylthiophen-3-yl)pyrimidin-2-yl]amino}ethyl]-1,2-dihydro-1,8-naphthyridin-2-one;

3-[(1S)-1-{[4-(1-benzyl-1H-imidazol-5-yl)pyrimidin-2-yl]amino}ethyl]-6-chloro-1,2-dihydro-1,8-naphthyridin-2-one;

6-chloro-3-[(1S)-1-{[4-(1-methyl-1H-imidazol-5-yl)pyrimidin-2-yl]amino}ethyl]-1,2-dihydro-1,8-naphthyridin-2-one;

6-chloro-3-[(1S)-1-{[4-(3-methylpyridin-4-yl)pyrimidin-2-yl]amino}ethyl]-1,2-dihydro-1,8-naphthyridin-2-one;

N-(2-{[(1S)-1-(6-chloro-2-oxo-1,2-dihydro-1,8-naphthyridin-3-yl)ethyl]amino}pyrimidin-4-yl)-N-(2-methylpropyl)methanesulfonamide;

6-chloro-3-[(1S)-1-{[4-methoxy-5-(1H-1,2,3,4-tetrazol-1-yl)pyrimidin-2-yl]amino}ethyl]-1,2-dihydro-1,8-naphthyridin-2-one;

2-{[(1S)-1-(7-chloro-3-oxo-3,4-dihydroquinoxalin-2-yl)ethyl]amino}-4-methylpyrimidine-5-carbonitrile;

6-chloro-3-[(1S)-1-{[4-(2-oxo-1,3-oxazolidin-3-yl)pyrimidin-2-yl]amino}ethyl]-1,2-dihydroquinoxalin-2-one;

methyl-N-(2-{[(1S)-1-(7-chloro-3-oxo-3,4-dihydroquinoxalin-2-yl)ethyl]amino}pyrimidin-4-yl)carbamate;

2-{[(1S)-1-(7-chloro-3-oxo-3,4-dihydroquinoxalin-2-yl)ethyl]amino}pyrimidine-4-carboxamide;

6-chloro-3-[(1S)-1-{[4-(5-methyl-1H-1,2,3,4-tetrazol-1-yl)pyrimidin-2-yl]amino}ethyl]-1,2-dihydroquinoxalin-2-one;

N-(2-{[(1S)-1-(7-chloro-3-oxo-3,4-dihydroquinoxalin-2-yl)ethyl]amino}pyrimidin-4-yl)cyclopropanecarboxamide;

N-(2-{[(1S)-1-(7-chloro-3-oxo-3,4-dihydroquinoxalin-2-yl)ethyl]amino}pyrimidin-4-yl)propanamide;

N-(2-{[(1S)-1-(7-chloro-3-oxo-3,4-dihydroquinoxalin-2-yl)ethyl]amino}pyrimidin-4-yl)acetamide;

6-chloro-3-[(1S)-1-{[4-(1H-imidazol-1-yl)pyrimidin-2-yl]amino}ethyl]-1,2-dihydroquinoxalin-2-one;

6-chloro-3-[(1S)-1-{[4-(1,2-oxazol-4-yl)pyrimidin-2-yl]amino}ethyl]-1,2-dihydroquinoxalin-2-one;

6-chloro-3-[(1S)-1-{[4-(4-methylthiophen-3-yl)pyrimidin-2-yl]amino}ethyl]-1,2-dihydroquinoxalin-2-one;

3-[(1S)-1-{[4-(1-benzyl-1H-imidazol-5-yl)pyrimidin-2-yl]amino}ethyl]-6-chloro-1,2-dihydroquinoxalin-2-one;

6-chloro-3-[(1S)-1-{[4-(1-methyl-1H-imidazol-5-yl)pyrimidin-2-yl]amino}ethyl]-1,2-dihydroquinoxalin-2-one;

6-chloro-3-[(1S)-1-{[4-(3-methylpyridin-4-yl)pyrimidin-2-yl]amino}ethyl]-1,2-dihydroquinoxalin-2-one;

N-(2-{[(1S)-1-(7-chloro-3-oxo-3,4-dihydroquinoxalin-2-yl)ethyl]amino}pyrimidin-4-yl)-N-(2-methylpropyl)methanesulfonamide;

6-chloro-3-[(1S)-1-{[4-methoxy-5-(1H-1,2,3,4-tetrazol-1-yl)pyrimidin-2-yl]amino}ethyl]-1,2-dihydroquinoxalin-2-one;
2-{[(1S)-1-(6-chloro-5-fluoro-2-oxo-1,2-dihydroquinolin-3-yl)ethyl]amino}-4-methoxypyrimidine-5-carbonitrile;
2-{[(1S)-1-(6-chloro-1-hydroxy-2-oxo-1,2-dihydroquinolin-3-yl)ethyl]amino}-4-methoxypyrimidine-5-carbonitrile;
2-{[(1S)-1-{6-chloro-2-oxo-7-[(1R)-1-(pyridin-2-yl)ethoxy]-1,2-dihydroquinolin-3-yl}ethyl]amino}-4-methylpyrimidine-5-carbonitrile;
N-(2-{[(1S)-1-{6-chloro-2-oxo-7-[(1R)-1-(pyridin-2-yl)ethoxy]-1,2-dihydroquinolin-3-yl}ethyl]amino}pyrimidin-4-yl)acetamide;
4-methoxy-2-{[(1S)-1-(6-methyl-2-oxo-1,2-dihydro-1,5-naphthyridin-3-yl)ethyl]amino}pyrimidine-5-carbonitrile;
N-(2-{[(1S)-1-(2-oxo-1,2-dihydro-1,5-naphthyridin-3-yl)ethyl]amino}pyrimidin-4-yl)acetamide; and
N-(2-{[(1S)-1-(6-methyl-2-oxo-1,2-dihydro-1,5-naphthyridin-3-yl)ethyl]amino}pyrimidin-4-yl)acetamide.

In another embodiment of the invention, the compounds of Formula (I) are enantiomers. In some embodiments the compounds are the (S)-enantiomer. In other embodiments the compounds are the (R)-enantiomer. In yet other embodiments, the compounds of Formula (I) may be (+) or (−) enantiomers.

It should be understood that all isomeric forms are included within the present invention, including mixtures thereof. If the compound contains a double bond, the substituent may be in the E or Z configuration. If the compound contains a disubstituted cycloalkyl, the cycloalkyl substituent may have a cis- or trans configuration. All tautomeric forms are also intended to be included.

Method of Synthesizing the Compounds

The compounds of the present invention may be made by a variety of methods, including standard chemistry. Suitable synthetic routes are depicted in the Schemes given below.

The compounds of Formula (I) may be prepared by methods known in the art of organic synthesis as set forth in part by the following synthetic schemes. In the schemes described below, it is well understood that protecting groups for sensitive or reactive groups are employed where necessary in accordance with general principles or chemistry. Protecting groups are manipulated according to standard methods of organic synthesis (T. W. Greene and P. G. M. Wuts, "Protective Groups in Organic Synthesis", Third edition, Wiley, New York 1999). These groups are removed at a convenient stage of the compound synthesis using methods that are readily apparent to those skilled in the art. The selection processes, as well as the reaction conditions and order of their execution, shall be consistent with the preparation of compounds of Formula (I).

Those skilled in the art will recognize if a stereocenter exists in the compounds of Formula (I). Accordingly, the present invention includes both possible stereoisomers (unless specified in the synthesis) and includes not only racemic compounds but the individual enantiomers and/or diastereomers as well. When a compound is desired as a single enantiomer or diastereomer, it may be obtained by stereospecific synthesis or by resolution of the final product or any convenient intermediate. Resolution of the final product, an intermediate, or a starting material may be affected by any suitable method known in the art. See, for example, "Stereochemistry of Organic Compounds" by E. L. Eliel, S. H. Wilen, and L. N. Mander (Wiley-Interscience, 1994).

The compounds described herein may be made from commercially available starting materials or synthesized using known organic, inorganic, and/or enzymatic processes.

Preparation of Compounds

The compounds of the present invention can be prepared in a number of ways well known to those skilled in the art of organic synthesis. By way of example, compounds of the present invention can be synthesized using the methods described below, together with synthetic methods known in the art of synthetic organic chemistry, or variations thereon as appreciated by those skilled in the art. Preferred methods include but are not limited to those methods described below. Compounds of the present invention can be synthesized by following the steps outlined in General Schemes 1 and 2, which comprise different sequences of assembling intermediates II, III, and IV. Starting materials are either commercially available or made by known procedures in the reported literature or as illustrated.

Scheme 1

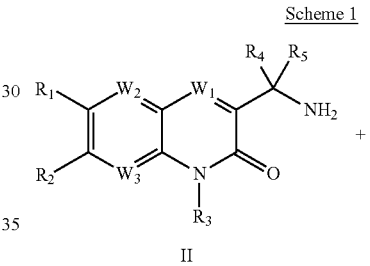

II

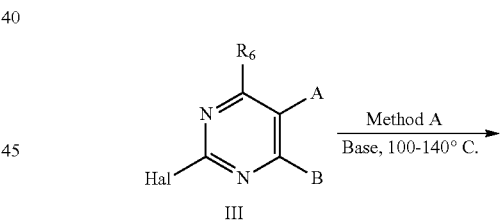

III

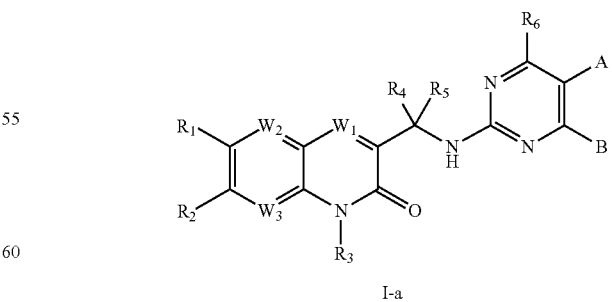

I-a

Hal = Cl, F, Br
Base = DIEA
Cs₂CO₃
K₂CO₃

Scheme 2

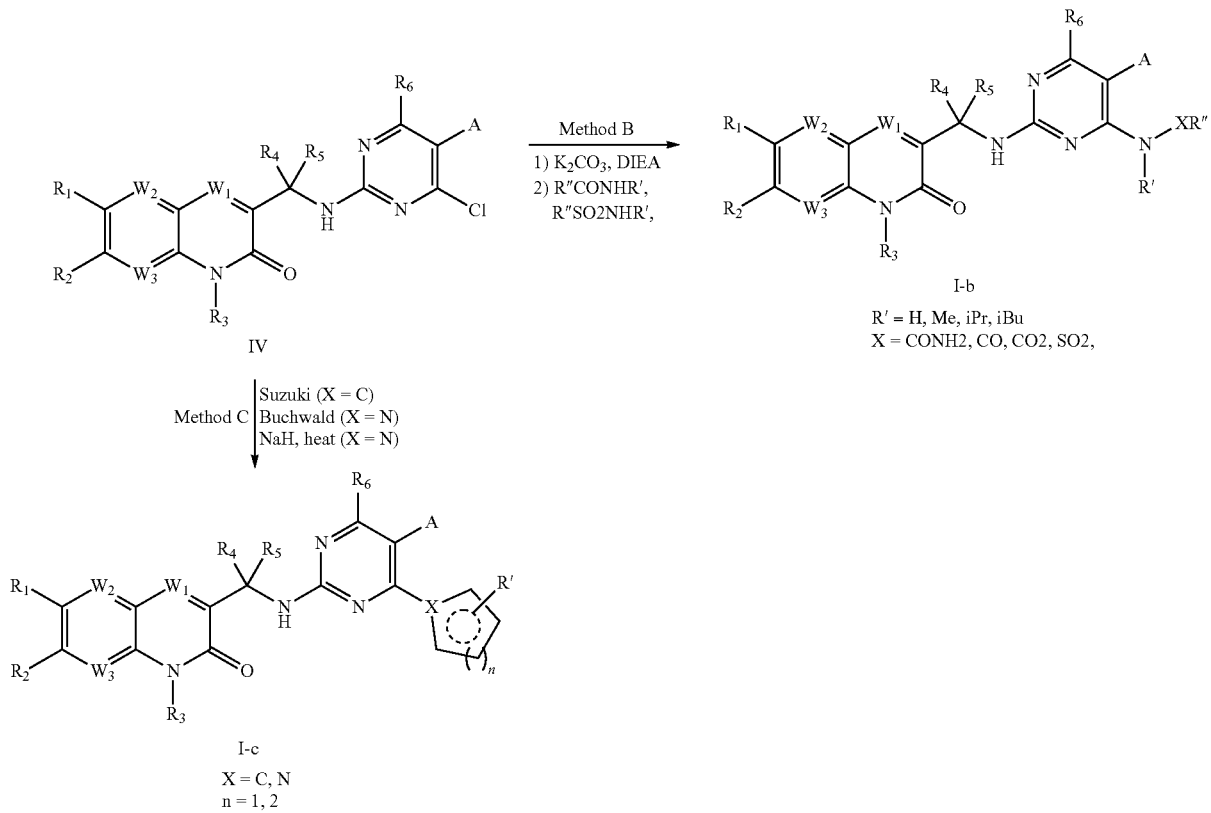

wherein A, B, $R^1$ - $R^6$ and W are defined as in Formula (I).

The general way of preparing target molecules Ia and Ib by using intermediates II, III, and IV is outlined in Scheme 1 and Scheme 2. Displacement of pyrimidine halides (III) with intermediates amine (II) under standard nucleophilic substitution conditions using base such as N,N-diisopropylethylamine, and/or potassium carbonate, cesium carbonate in solvent DMSO or DMF gives the compounds of Formula (I). Displacement of pyrimidine halides (IV) with 2° amine, amide or sulfonamide in presence of base such as $K_2CO_3$, or $Cs_2CO_3$ combined with organic base such as DIEA or TEA under elevated temperature also yield the compound of Formula (I). Coupling of pyrimidine halides (IV) with aryl-, heterocyclic boronic acid/ester in presence of palladium catalyst under elevated temperature yield the compound of Formula (I). A mixture of enantiomers, diastereomers, cis/trans isomers resulted from the process can be separated into their single components by chiral salt technique, chromatography using normal phase, reverse phase or chiral column, depending on the nature of the separation.

It should be understood that in the description and formulae shown above, the various groups A, B, $W_1$, $W_2$, $W_3$, $R_1$-$R_6$ and other variables are as defined above, except where otherwise indicated. Furthermore, for synthetic purposes, the compounds of Schemes 1 and 2 are mere representative with elected radicals to illustrate the general synthetic methodology of the compound of Formula (I) as defined herein.

Methods of Using the Disclosed Compounds

Another aspect of the invention relates to a method of treating a disease or disorder associated with mutant isocitrate dehydrogenase. The method involves administering to a patient in need of a treatment for diseases or disorders associated with mutant isocitrate dehydrogenase an effective amount of the compositions and compounds of Formula (I).

Another aspect of the invention is directed to a method of inhibiting mutant isocitrate dehydrogenase. The method involves administering to a patient in need thereof an effective amount of a compound of Formula (I).

Examples of a mutant IDH protein having a neomorphic activity are mutant IDH1 and mutant IDH2. A neomorphic activity associated with mutant IDH1 and mutant IDH2 is the ability to produce 2-hydroxyglutarate (2-HG neomorphic activity), specifically R-2-HG (R-2-HG neomorphic activity). Mutations in IDH 1 associated with 2-HG neomorphic activity, specifically R-2-HG neomorphic activity, include mutations at residues 97, 100, and 132, e.g. G97D, R100Q, R132H, R132C, R132S, R132G, R132L, and R132V. Mutations in IDH2 associated with 2-HG neoactivity, specifically R-2-HG neomorphic activity, include mutations at residues 140 and 172, e.g. R140Q, R140G, R172K, R172M, R172S, R172G, and R172W.

Another aspect of the invention relates to method of reducing 2-hydroxyglutarate. The method comprises administering to a patient in need thereof an effective amount of a compound of Formula (I).

One therapeutic use of the compounds or compositions of the present invention which inhibit mt-IDH is to provide treatment to patients or subjects suffering from cell proliferative diseases and cancers including, without limitation, glioma, glioblastoma multiforme, paraganglioma, supratentorial primordial neuroectodermal tumors, acute myeloid leukemia (AML), prostate cancer, thyroid cancer, colon cancer, chondrosarcoma, cholangiocarcinoma, peripheral T-cell lymphoma, melanoma, intrahepatic cholangiocarcinoma (IHCC), myelodysplastic syndrome (MDS), myeloproliferative disease (MPD), and other solid tumors. Targeted treatments for these cancers and cell proliferative diseases are not currently available to patients suffering from these conditions. Therefore, there is a need for new therapeutic agents selective to these conditions.

The disclosed compounds of the invention can be administered in effective amounts to treat or prevent a disorder and/or prevent the development thereof in subjects.

Administration of the disclosed compounds can be accomplished via any mode of administration for therapeutic agents. These modes include systemic or local administration such as oral, nasal, parenteral, transdermal, subcutaneous, vaginal, buccal, rectal or topical administration modes.

Depending on the intended mode of administration, the disclosed compositions can be in solid, semi-solid or liquid dosage form, such as, for example, injectables, tablets, suppositories, pills, time-release capsules, elixirs, tinctures, emulsions, syrups, powders, liquids, suspensions, or the like, sometimes in unit dosages and consistent with conventional pharmaceutical practices. Likewise, they can also be administered in intravenous (both bolus and infusion), intraperitoneal, subcutaneous or intramuscular form, and all using forms well known to those skilled in the pharmaceutical arts.

Illustrative pharmaceutical compositions are tablets and gelatin capsules comprising a Compound of the Invention and a pharmaceutically acceptable carrier, such as a) a diluent, e.g., purified water, triglyceride oils, such as hydrogenated or partially hydrogenated vegetable oil, or mixtures thereof, corn oil, olive oil, sunflower oil, safflower oil, fish oils, such as EPA or DHA, or their esters or triglycerides or mixtures thereof, omega-3 fatty acids or derivatives thereof, lactose, dextrose, sucrose, mannitol, sorbitol, cellulose, sodium, saccharin, glucose and/or glycine; b) a lubricant, e.g., silica, talcum, stearic acid, its magnesium or calcium salt, sodium oleate, sodium stearate, magnesium stearate, sodium benzoate, sodium acetate, sodium chloride and/or polyethylene glycol; for tablets also; c) a binder, e.g., magnesium aluminum silicate, starch paste, gelatin, tragacanth, methylcellulose, sodium carboxymethylcellulose, magnesium carbonate, natural sugars such as glucose or beta-lactose, corn sweeteners, natural and synthetic gums such as acacia, tragacanth or sodium alginate, waxes and/or polyvinylpyrrolidone, if desired; d) a disintegrant, e.g., starches, agar, methyl cellulose, bentonite, xanthan gum, algic acid or its sodium salt, or effervescent mixtures; e) absorbent, colorant, flavorant and sweetener; f) an emulsifier or dispersing agent, such as Tween 80, Labrasol, HPMC, DOSS, caproyl 909, labrafac, labrafil, peceol, transcutol, capmul MCM, capmul PG-12, captex 355, gelucire, vitamin E TGPS or other acceptable emulsifier; and/or g) an agent that enhances absorption of the compound such as cyclodextrin, hydroxypropyl-cyclodextrin, PEG400, PEG200.

Liquid, particularly injectable, compositions can, for example, be prepared by dissolution, dispersion, etc. For example, the disclosed compound is dissolved in or mixed with a pharmaceutically acceptable solvent such as, for example, water, saline, aqueous dextrose, glycerol, ethanol, and the like, to thereby form an injectable isotonic solution or suspension. Proteins such as albumin, chylomicron particles, or serum proteins can be used to solubilize the disclosed compounds.

The disclosed compounds can be also formulated as a suppository that can be prepared from fatty emulsions or suspensions; using polyalkylene glycols such as propylene glycol, as the carrier.

The disclosed compounds can also be administered in the form of liposome delivery systems, such as small unilamellar vesicles, large unilamellar vesicles and multilamellar vesicles. Liposomes can be formed from a variety of phospholipids, containing cholesterol, stearylamine or phosphatidylcholines. In some embodiments, a film of lipid components is hydrated with an aqueous solution of drug to a form lipid layer encapsulating the drug, as described in U.S. Pat. No. 5,262,564.

Disclosed compounds can also be delivered by the use of monoclonal antibodies as individual carriers to which the disclosed compounds are coupled. The disclosed compounds can also be coupled with soluble polymers as targetable drug carriers. Such polymers can include polyvinylpyrrolidone, pyran copolymer, polyhydroxypropylmethacrylamide-phenol, polyhydroxyethylaspanami dephenol, or polyethyleneoxidepolylysine substituted with palmitoyl residues. Furthermore, the Disclosed compounds can be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels. In one embodiment, disclosed compounds are not covalently bound to a polymer, e.g., a polycarboxylic acid polymer, or a polyacrylate.

Parental injectable administration is generally used for subcutaneous, intramuscular or intravenous injections and infusions. Injectables can be prepared in conventional forms, either as liquid solutions or suspensions or solid forms suitable for dissolving in liquid prior to injection.

Another aspect of the invention is directed to pharmaceutical compositions comprising a compound of Formula (I) and a pharmaceutically acceptable carrier. The pharmaceutical acceptable carrier may further include an excipient, diluent, or surfactant.

Compositions can be prepared according to conventional mixing, granulating or coating methods, respectively, and the present pharmaceutical compositions can contain from about 0.1% to about 99%, from about 5% to about 90%, or from about 1% to about 20% of the disclosed compound by weight or volume.

The dosage regimen utilizing the disclosed compound is selected in accordance with a variety of factors including type, species, age, weight, sex and medical condition of the patient; the severity of the condition to be treated; the route of administration; the renal or hepatic function of the patient; and the particular disclosed compound employed. A physician or veterinarian of ordinary skill in the art can readily determine and prescribe the effective amount of the drug required to prevent, counter or arrest the progress of the condition.

Effective dosage amounts of the disclosed compounds, when used for the indicated effects, range from about 0.5 mg to about 5000 mg of the disclosed compound as needed to treat the condition. Compositions for in vivo or in vitro use can contain about 0.5, 5, 20, 50, 75, 100, 150, 250, 500, 750, 1000, 1250, 2500, 3500, or 5000 mg of the disclosed compound, or, in a range of from one amount to another amount in the list of doses. In one embodiment, the compositions are in the form of a tablet that can be scored.

EXAMPLES

The disclosure is further illustrated by the following examples and synthesis schemes, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

Analytical Methods, Materials, and Instrumentation

Unless otherwise noted, reagents and solvents were used as received from commercial suppliers. Proton nuclear magnetic resonance (NMR) spectra were obtained on either Bruker or Varian spectrometers at 300 MHz. Spectra are given in ppm (δ) and coupling constants, J, are reported in Hertz. Tetramethylsilane (TMS) was used as an internal standard. Mass spectra were collected using a Waters ZQ Single Quad Mass Spectrometer (ion trap electrospray ionization (ESI)). High performance liquid chromatograph (HPLC) analyses were obtained using a XBridge Phenyl or C18 column (5 µm, 50×4.6 mm, 150×4.6 mm or 250×4.6 mm) with UV detection (Waters 996 PDA) at 254 nm or 223 nm using a standard solvent gradient program (Method 1-4).

LCMS Method 1 (ESI, 4 Min Method):

| Instruments: | |
|---|---|
| HPLC: Waters HT2790 Alliance | MS: Waters ZQ Single Quad Mass Spectrometer |
| UV: Waters 996 PDA | |
| Conditions: | |
| Mobile phase A | 95% water/5% methanol with 0.1% Formic Acid |
| Mobile phase B (B) | 95% methanol/5% water with 0.1% Formic Acid |
| Column | XBridge Phenyl or C18, 5 µm 4.6 × 50 mm |
| Column temperature | Ambient |
| LC gradient | Linear 5-95% B in 2.5 min, hold 95% B to 3.5 min |
| LC Flow rate | 3 mL/min |
| UV wavelength | 220 nm and 254 nm |
| Ionization Mode | Electrospray Ionization; positive/negative |

LCMS Method 2 (ESI, 10 Min Method):

| Instruments: | |
|---|---|
| HPLC: Waters HT2790 Alliance | MS: Waters ZQ Single Quad Mass Spectrometer |
| UV: Waters 996 PDA | |
| Conditions: | |
| Mobile phase A (A) | 95% water/5% methanol with 0.1% Formic Acid |
| Mobile phase B (B) | 95% methanol/5% water with 0.1% Formic Acid |
| Column | XBridge C18, 5 µm 4.6 × 150 mm |
| Column temperature | Ambient |
| LC gradient | Linear 5-95% B in 5.5 min, hold 95% B to 7.5 min |
| LC Flow rate | 1.2 mL/min |
| UV wavelength | 220 nm and 254 nm |
| Ionization Mode | Electrospray Ionization; positive/negative |

LCMS Method 3: (APCI, 20 Min)

| Instruments and conditions: | | |
|---|---|---|
| HPLC-Agilent 1100 series. | | |
| Column: Agela Technologies Durashell C18, 3 µm, 4.6 × 50 mm,). | | |
| Mobile Phase A: ACN + 0.1% TFA. | | |
| Mobile Phase B: Water + 0.1% TFA. | | |
| Gradient: | Time (min) | % B |
| | 00 | 95 |
| | 15 | 05 |
| | 18 | 05 |
| | 20 | 95 |

Flow Rate: 1 mL/min.
Column Temperature: Ambient.
Detector: 254 nm.

LCMS Method 4 (ESI, 2.5 Main Method):

| Instruments and conditions: | |
|---|---|
| HPLC: Waters Acquity Binary Solvent Manager | MS: Waters ZQ Mass Detector |
| UV: Waters Acquity PDA | |
| Mobile phase A (A) | 95% water/5% acetonitrile with 0.1% formic acid in 10 mM ammonium formate |
| Mobile phase B (B) | 95% acetonitrile/5% water with 0.09% formic acid |
| Column | Waters Acquity UPLC BEH C18, 1.7 µm, 2.1 × 50 mm |
| Column temperature | 35° C. |
| LC gradient | 5-100% B in 2.0 min, hold 100% B to 2.2 min |
| LC Flow rate | 0.6 mL/min |
| UV wavelength | 220 nm and 254 nm |
| Ionization Mode | Electrospray Ionization; positive/negative |

Abbreviations Used in the Following Examples and Elsewhere Herein are $Ac_2O$ acetic anhydride
ACN Acetonitrile
BOP ammonium 4-(3-(pyridin-3-ylmethyl)ureido)benzenesulfinate
$CDCl_3$ deuterated chloroform
$Cs_2CO_3$ cesium carbonate
$CuSO_4$ copper sulfate
δ chemical shift
DCM dichloromethane or methylene chloride
DCE 1,2-dichloroethane
DEAD diethyl azodicarboxylate
DIAD diisopropyl azodicarboxylate
DIEA N,N-diisopropylethylamine
DMA N,N-dimethylacetamide
DME dimethoxyethane
DMF N,N-dimethylformamide
DMP Dess-Martin Periodinane
DMSO dimethylsulfoxide
DMSO-$d_6$ deuterated dimethylsulfoxide
dppf 1,1'-Bis(diphenylphosphino)ferrocene EDCI  N-(3-dimethylaminopropyl)-N'-ethylcarbodiimide hydrochloride
EDTA ethylenediaminetetraacetic acid
ee enantiomeric excess
EtOAc ethyl acetate
EtOH ethanol
¹H NMR proton nuclear magnetic resonance
HOAc acetic acid
HATU 2-(3H-[1,2,3]triazolo[4,5-b]pyridin-3-yl)-1,1,3,3-tetramethylisouronium hexafluorophosphate
HCl hydrochloric acid
HOBT 1H-benzo[d][1,2,3]triazol-1-ol hydrate
HPLC high pressure liquid chromatography
Hz hertz
IPA isopropyl alcohol
KOAc potassium acetate
K₂CO₃ potassium carbonate
LAH lithium aluminum hydride
LCMS liquid chromatography/mass spectrometry
(M+1) mass+1
m-CPBA m-chloroperbenzoic acid
MeOH methanol
MeMgBr methyl magnesium bromide
MS mass spectrometry
NaBH₄ sodium borohydride
Na₂SO₄ sodium sulfate
Pd(dppf)Cl₂ [1,1'-Bis(diphenylphosphino)ferrocene]dichloropalladium(II)
Palladium tetrakis Tetrakis(triphenylphosphine)palladium (0)
Rt retention time
TBDMS-Cl Tert-butyl dimethylsilyl chloride
TEA triethylamine
THF tetrahydrofuran
TLC thin layer chromatography
Xantphos 4,5-Bis(diphenylphosphino)-9,9-dimethylxanthene Example 1—Intermediate II-1: (S)-3-(1-aminoethyl)-6-chloroquinolin-2(1H)-one hydrochloride

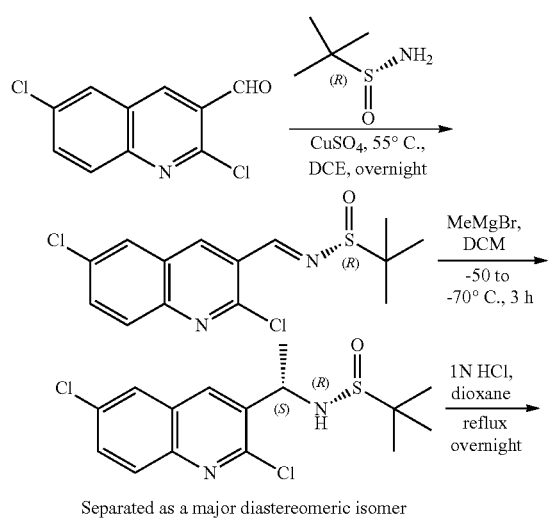

Separated as a major diastereomeric isomer

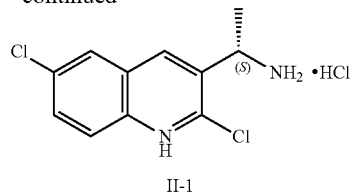

Step-1: (R,E)-N-((2,6-dichloroquinolin-3-yl)methylene)-2-methylpropane-2-sulfinamide

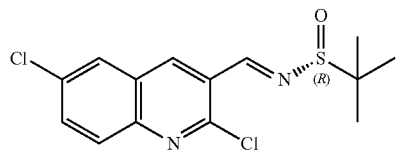

To a mixture of 2,6-dichloroquinoline-3-carbaldehyde (15.0 g, 66.37 mmol) and (R)-2-methylpropane-2-sulfinamide (8.85 g, 73.14 mmol) in 1,2-dichloroethane (150 mL) was added CuSO₄ (16.0 g, 100.25 mmol). The resulting mixture was heated to 55° C. and stirred at 55° C. overnight. After TLC and MS showed complete disappearance of starting materials, the mixture was cooled to room temperature and filtered through a pad of Celite®. The pad of celite was then rinsed with CH₂Cl₂. The filtrate was evaporated to dryness in vacuo and purified by SiO₂ column chromatography (0 to 25% hexanes/EtOAc) to afford the title compound, (R,E)-N-((2,6-dichloroquinolin-3-yl)methylene)-2-methylpropane-2-sulfinamide, as a yellow solid (17.7 g, 81% yield).

Step-2: (R)—N—((S)-1-(2,6-dichloroquinolin-3-yl)ethyl)-2-methylpropane-2-sulfinamide

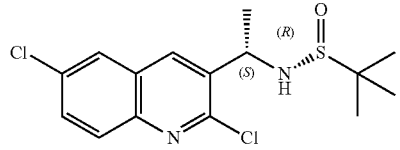

To a solution of (R,E)-N-((2,6-dichloroquinolin-3-yl)methylene)-2-methylpropane-2-sulfinamide (8.85 g, 26.88 mmol) in anhydrous CH₂Cl₂ (200 mL) at −60° C. was added dropwise MeMgBr (3M solution in diethyl ether, 13.5 mL, 40.54 mmol). The resulting reaction mixture was stirred at about −60 to −50° C. for 3 hours and then stirred at −20° C. overnight under an atmosphere of N₂. After TLC and MS showed complete disappearance of starting materials, saturated NH₄Cl (163 ml) was added at −20° C. and the resulting mixture was stirred for 10 minutes. The aqueous phase was extracted with CH₂Cl₂ (100 mL×3), dried over anhydrous Na₂SO₄, filtered, and evaporated. The residue was purified by column chromatography on an ISCO® chromatography system (SiO₂: Gold column; gradient; hexanes to 100% EtOAc) to provide the title compound, (R)—N—((S)-1-(2,6-dichloroquinolin-3-yl)ethyl)-2-methylpropane-2-sulfinamide, as a yellow solid (5.8 g, 63% yield).

Step-3: (S)-3-(1-aminoethyl)-6-chloroquinolin-2(1H)-one hydrochloride (II-1)

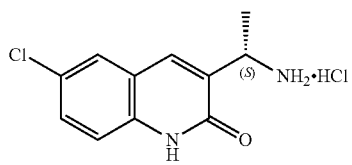

A mixture of (R)—N—((S)-1-(2,6-dichloroquinolin-3-yl)ethyl)-2-methylpropane-2-sulfinamide (6.6 g, 19.13 mmol) in 1,4-dioxane (41 mL) and 1N HCl (41 mL) was heated at reflux overnight. The solvents were evaporated in vacuo and the resulting residue was dissolved in hot water and lyophilized. The crude product was triturated with diethyl ether to afford the title compound II-1 as a yellow solid (9.0 g, ee: 98.4%). $^1$H NMR (300 MHz, DMSO-d$_6$): δ ppm 12.4 (br s, 1H), 8.32 (br s, 2H), 8.07 (s, 1H), 7.85 (d, J=2.2 Hz, 1H), 7.63 (dd, J=8.8 Hz, J$_2$=2.5 Hz, 1H), 7.40 (d, J=8.8 Hz, 1H), 4.40-4.45 (m, 1H), 1.53 (d, J=8.5 Hz, 3H). LCMS (Method 3): Rt 3.42 min, m/z 223.1 [M+H]$^+$.

Example 2—Intermediate II-2: (R)-3-(1-aminoethyl)-6-chloroquinolin-2(1H)-one hydrochloride

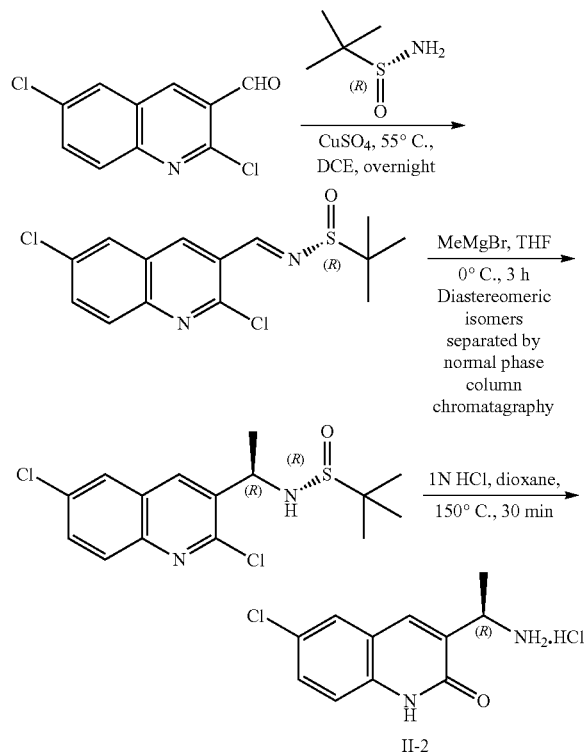

Step-1: (R)—N-((2,6-dichloroquinolin-3-yl)methylene)-2-methylpropane-2-sulfinamide To a mixture of 2,6-dichloroquinoline-3-carbaldehyde (500 mg, 2.21 mmol) and (R)-2-methylpropane-2-sulfinamide (295 g, 2.43 mmol) in 1,2-dichloroethane (15 mL) was added CuSO$_4$ (530 mg, 3.31 mmol). The resulting mixture was heated to 55° C. and stirred at 55° C. for 18 hours. Once TLC and MS showed complete disappearance of starting materials, the reaction mixture was cooled to room temperature and filtered through a pad of Celite®. The pad of celite was then rinsed with CH$_2$Cl$_2$. The filtrate was evaporated to dryness in vacuo and purified by column chromatography on an ISCO® chromatography system (SiO$_2$; hexanes to 60% EtOAc/hexanes) to afford the title compound, (R)—N-((2,6-dichloroquinolin-3-yl)methylene)-2-methylpropane-2-sulfinamide, as a yellow solid (510 mg, 70% yield).

Step-2: (R)—N—((R)-1-(2,6-dichloroquinolin-3-yl)ethyl)-2-methylpropane-2-sulfinamide To a solution of (R)—N-((2,6-dichloroquinolin-3-yl)methylene)-2-methylpropane-2-sulfinamide (505 mg, 1.534 mmol) in anhydrous THF (8 mL) at 0° C. was added dropwise MeMgBr (3M solution in diethyl ether, 0.56 mL, 1.687 mmol). The mixture was stirred at 0° C. for 3 hours under an atmosphere of N$_2$. After TLC and MS showed complete disappearance of starting materials, saturated NH$_4$Cl (5 mL) was added at 0° C. and the resulting mixture was stirred for 10 minutes. The aqueous phase was extracted with EtOAc (10 mL×3), dried over anhydrous Na$_2$SO$_4$, filtered, and evaporated. The residue was purified by column chromatography on an ISCO® chromatography system (SiO$_2$; hexanes to 80% EtOAc/hexanes) to afford the title compound as the R,R isomer as a pale yellow solid (200 mg, 38%) and the R,S isomer as a pale yellow solid (93 mg, 18% yield).

Step-3: (R)-3-(1-aminoethyl)-6-chloroquinolin-2(1H)-one hydrochloride (II-2)

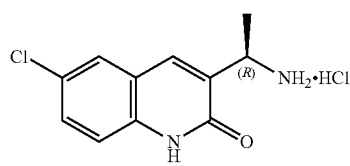

A mixture of (R)—N—((R)-1-(2,6-dichloroquinolin-3-yl)ethyl)-2-methylpropane-2-sulfinamide (190 mg, 0.55 mmol) in 1,4-dioxane (2 mL) and 1N HCl (1.1 mL, 1.1 mmol) was heated to 150° C. for 30 minutes in a microwave reactor. The solvents were evaporated and the residue was dissolved in hot water and lyophilized to afford the title compound II-2 as a yellow solid (148 mg, quantitative yield). $^1$H NMR (300 MHz, DMSO-d$_6$): δ ppm 12.35 (br s, 1H), 8.28 (br s, 2H), 8.05 (s, 1H), 7.86 (d, J=2.2 Hz, 1H), 7.63 (dd, J=8.8 Hz, J$_2$=2.5 Hz, 1H), 7.40 (d, J=8.8 Hz, 1H), 4.40-4.45 (m, 1H), 1.53 (d, J=8.5 Hz, 3H). LCMS (Method 3): Rt 3.40 min, m/z 223.1 [M+H]$^+$.

Example 3—an Alternative Approach to Intermediate II-1

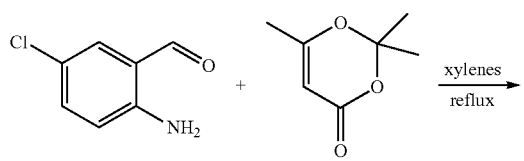

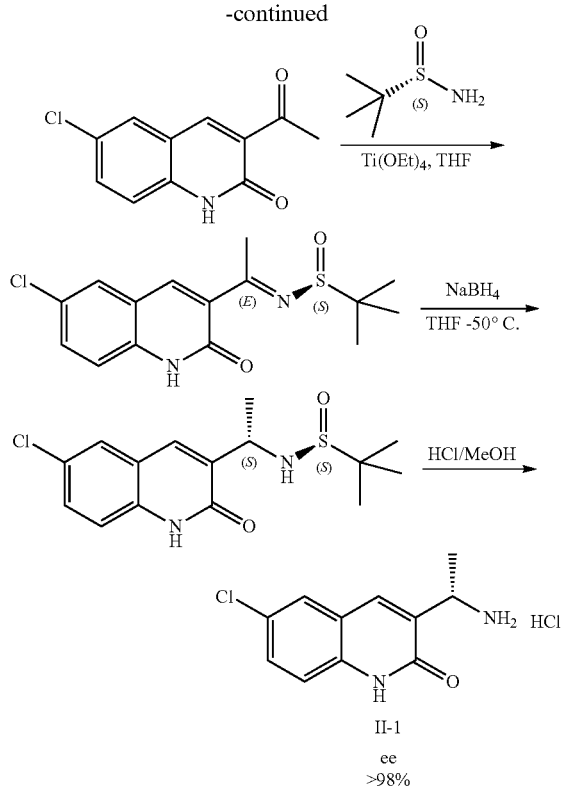

Step-1: 3-acetyl-6-chloroquinolin-2(1H)-one

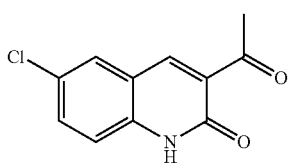

A mixture of 2-amino-5-chlorobenzaldehyde (0.5 g, 3.21 mmol) and 2,2,6-trimethyl-4H-1,3-dioxin-4-one (0.594 g, 4.18 mmol) in xylenes (10 mL) under an atmosphere of nitrogen was heated to reflux for 3 hours and then cooled to room temperature. The reaction mixture was filtered and washed with xylenes twice to afford the title compound, 3-acetyl-6-chloroquinolin-2(1H)-one (330 mg, 46.3%). $^1$H NMR (300 MHz, DMSO-$d_6$): δ ppm 12.22 (br, 1H), 8.41 (s, 2H), 8.00 (s, 1H), 7.63 (d, J=8.8 Hz, 1H), 7.32 (dd, J=8.8 Hz, $J_2$=2.5 Hz, 1H), 2.58 (s, 3H). LCMS (Method 1): m/z 222.94 [M+H]$^+$.

Step-2: ((S)—N—((S)-1-(6-chloro-2-oxo-1,2-dihydroquinolin-3-yl)ethyl)-2-methyl propane-2-sulfinamide

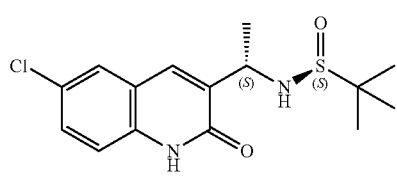

A mixture of tetraethoxytitanium (144 mg, 0.632 mmol), (S)-2-methylpropane-2-sulfinamide (38.3 mg, 0.316 mmol), and 3-acetyl-6-chloroquinolin-2(1H)-one (70 mg, 0.316 mmol) in THF (20 mL) was heated to 80° C. overnight and then cooled to room temperature. To this mixture was added NaBH$_4$ (59.7 mg, 1.579 mmol) at −50° C. The mixture was then slowly warmed up to room temperature overnight. MeOH (2 mL) was added to quench excess NaBH$_4$ and was followed by the addition of water. The resulting mixture was filtered to remove solids and the aqueous phase was extracted with EtOAc twice, dried over Na$_2$SO$_4$ and concentrated. The residue was purified on a Biotage® chromatography system using a 25 g SiO$_2$ column with gradient elution (20% to 100% EtOAc/Hexanes, then 0-5% MeOH/DCM) to afford (S)—N—((S)-1-(2,6-dichloroquinolin-3-yl) ethyl)-2-methylpropane-2-sulfinamide (39 mg, 38% yield). $^1$H NMR (300 MHz, DMSO-$d_6$): δ ppm 12.05 (br, 1H), 7.95 (s, 1H), 7.84 (s, 1H), 7.38 (d, J=8.8 Hz, 1H), 5.76 (d, J=8.06 Hz, 1H), 5.37 (m, 1H), 4.55 (m, 1H), 1.44 (d, J=6.82 Hz, 3H), 1.18 (s, 9H). LCMS (Method 1): Rt 2.22 min; m/z 327.96 [M+H]$^+$.

Step-3: (S)-3-(1-aminoethyl)-6-chloroquinolin-2(1H)-one hydrochloride (II-1)

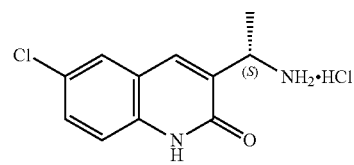

To a solution of ((S)—N—((S)-1-(6-chloro-2-oxo-1,2-dihydroquinolin-3-yl)ethyl)-2-methyl propane-2-sulfinamide (150 mg, 0.459 mmol) in MeOH (5 mL) was added HCl (2 mL, 8.0 mmol, 4M in 1,4-dioxane). The mixture was stirred at room temperature overnight. To this mixture was added 6 mL of ethyl ether and the resulting precipitate was collected by filtration, washed with ethyl ether (2×), and then dried to afford (S)-3-(1-aminoethyl)-6-chloroquinolin-2(1H)-one hydrochloride (50 mg, 42% yield). $^1$H NMR (300 MHz, DMSO-$d_6$): δ ppm 12.4 (br s, 1H), 8.32 (br s, 2H), 8.07 (s, 1H), 7.85 (d, J=2.2 Hz, 1H), 7.63 (dd, J=8.8 Hz, $J_2$=2.5 Hz, 1H), 7.40 (d, J=8.8 Hz, 1H), 4.40-4.45 (m, 1H), 1.53 (d, J=8.5 Hz, 3H). LCMS (Method 1): Rt 1.22 min, m/z 223.1 [M+H]$^+$.

Example 4—Alternate Approach (R)-3-(1-aminoethyl)-6-chloroquinolin-2(1H)-one hydrochloride (II-2)

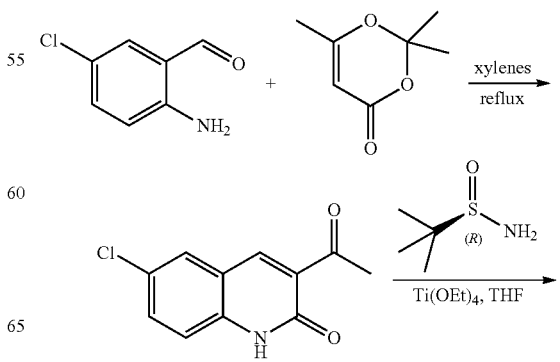

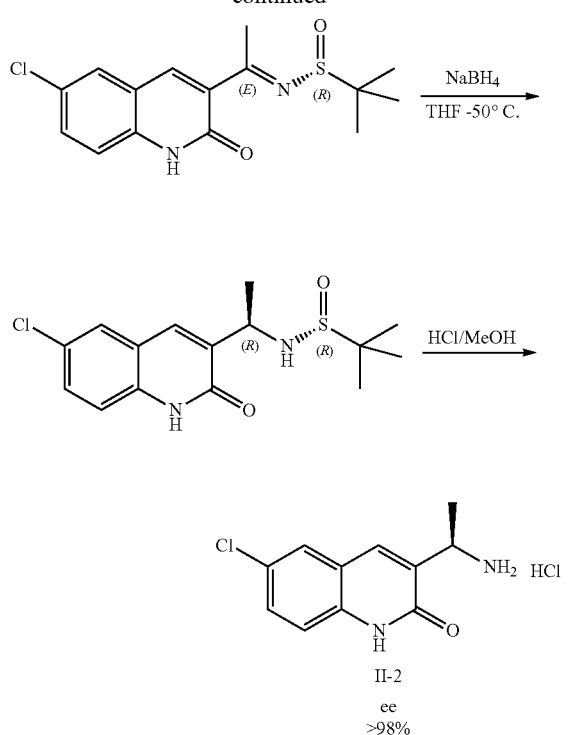

II-2
ee >98%

Step-1: ((R)—N—((R)-1-(6-chloro-2-oxo-1,2-dihydroquinolin-3-yl)ethyl)-2-methyl propane-2-sulfinamide

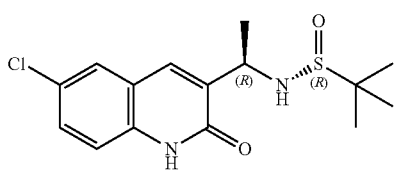

A mixture of tetraethoxytitanium (412 mg, 1.805 mmol) (R)-2-methylpropane-2-sulfinamide (131 mg, 1.083 mmol) and 3-acetyl-6-chloroquinolin-2(1H)-one (160 mg, 0.722 mmol) in THF (20 mL) was heated to 80° C. overnight, and then cooled to room temperature. To this mixture was added NaBH$_4$ (137 mg, 3.61 mmol) −50° C. The mixture was then slowly warmed up to room temperature overnight. MeOH (2 mL) was added to quench excess NaBH$_4$ and was followed by the addition of water. The resulting mixture was filtered to remove solids and the aqueous phase was extracted with EtOAc twice, dried over Na$_2$SO$_4$ and concentrated. The residue was purified on a Biotage® chromatography system using a 25 g SiO$_2$ column with gradient elution (20 to 100% EtOAc/Hexanes, then 0-5% MeOH/DCM) to afford ((R)—N—((R)-1-(6-chloro-2-oxo-1,2-dihydroquinolin-3-yl) ethyl)-2-methyl propane-2-sulfinamide (157 mg, 66% yield). $^1$H NMR (300 MHz, CDCl$_3$): δ ppm 11.31 (br, 1H), 7.35 (s, 1H), 7.07-7.22 (m, 2H), 5.86 (d, J=9.3 Hz, 1H), 5.37 (m, 1H), 4.55 (m, 1H), 1.56 (d, J=6.94 Hz, 3H), 1.32 (s, 9H). LCMS (Method 1): Rt 2.20 min, m/z 327.96 [M+H]$^+$.

Step-2: (R)-3-(1-aminoethyl)-6-chloroquinolin-2 (1H)-one hydrochloride (II-2)

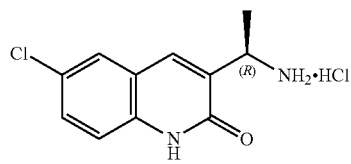

To a solution of (R)—N—((R)-1-(6-chloro-2-oxo-1,2-dihydroquinolin-3-yl)ethyl)-2-methylpropane-2-sulfinamide (150 mg, 0.459 mmol) in MeOH (5 mL) was added HCl (2 mL, 8.00 mmol, 4M in 1,4-dioxane). The mixture was stirred at room temperature overnight. To this mixture was added 6 mL of ethyl ether and the resulting precipitate was collected by filtration, washed with ethyl ether (2×), and then dried to afford (R)-3-(1-aminoethyl)-6-chloroquinolin-2(1H)-one hydrochloride (80 mg, 67% yield). $^1$H NMR (300 MHz, DMSO-d$_6$): δ ppm 12.32 (br s, 1H), 8.34 (br, 2H), 8.06 (s, 1H), 7.81 (s, 1H), 7.58 (d, J=8.82 Hz, 1H), 7.31 (d, J=8.83 Hz, 1H), 4.40-4.45 (m, 1H), 1.53 (d, J=6.81 Hz, 3H). LCMS (Method 1): Rt 1.20 min, m/z 223.1 [M+H]$^+$.

Example 5—Intermediate II-3: (S)-3-(1-aminoethyl)-6-chloro-7-fluoroquinolin-2(1H)-one

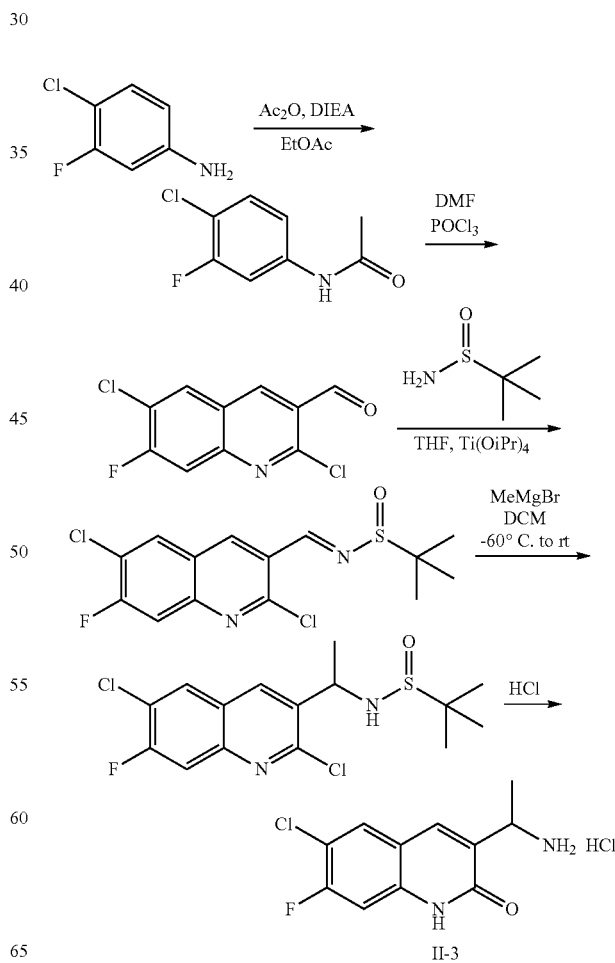

Step-1: N-(4-chloro-3-fluorophenyl)acetamide

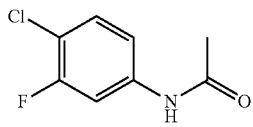

To a solution of 4-chloro-3-fluoroaniline (10.00 g, 68.7 mmol) and DIEA (13.2 mL, 76 mmol) in EtOAc (200 mL) was added Ac$_2$O (7.1 mL, 75 mmol) dropwise. The solution was stirred at room temperature overnight. Once LCMS indicated the reaction had gone to completion, the solution was washed with water (2×100 mL) and brine (100 mL), dried (Na$_2$SO$_4$), filtered, and evaporated under reduced pressure to provide the product as a white solid. LCMS and $^1$H NMR are consistent with N-(4-chloro-3-fluorophenyl)acetamide (12.39 g, 66.0 mmol, 96% yield) $^1$H NMR (300 MHz, DMSO-d$_6$): δ ppm 10.26 (s, 1H), 7.77 (dd, J=12.17, 2.20 Hz, 1H), 7.49 (dd, J=8.60, 8.60 Hz, 1H), 7.30 (dd, J=8.79, 2.35 Hz, 1H), 2.06 (s, 3H). LCMS (Method 1): m/z 188 [M+H]$^+$.

Step-2: 2,6-dichloro-7-fluoroquinoline-3-carbaldehyde

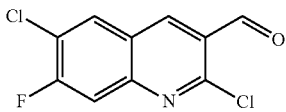 [SMILES: O=Cc1cc2cc(Cl)c(F)cc2nc1Cl]

A tube was capped with a septum and placed under an atmosphere of nitrogen. DMF (9.5 mL, 123 mmol) was added by syringe and then cooled on an ice bath. POCl$_3$ (37 mL, 397 mmol) was added dropwise by syringe (over 25 minutes). The red solution was allowed to warm to room temperature (over 20 minutes), then the septum was removed and the mixture was treated with N-(4-chloro-3-fluorophenyl)acetamide (7.00 g, 37.3 mmol). The tube was then sealed and the solution was stirred at 80° C. overnight. The solution was pipetted onto ice, resulting in formation of a yellow precipitate. The precipitate was collected on a Buchner funnel and washed with water (500 mL), during which most of the precipitate dissolved. The filter cake was dried to provide 427.6 mg of the title compound as a pale yellow solid. LCMS and $^1$H NMR are consistent with impure 2,6-dichloro-7-fluoroquinoline-3-carbaldehyde (427.6 mg, 1.752 mmol, 4.70% yield). The material was used as is. $^1$H NMR (300 MHz, DMSO-d$_6$): δ ppm 10.36 (s, 1H), 8.99 (s, 1H), 8.67 (d, J=8.21 Hz, 1H), 8.13 (d, J=10.26 Hz, 1H), 5.76 (s, 1H). LCMS (Method 1): m/z 244 [M+H]$^+$.

Step-3: N-((2,6-dichloro-7-fluoroquinolin-3-yl)methylene)-2-methylpropane-2-sulfinamide

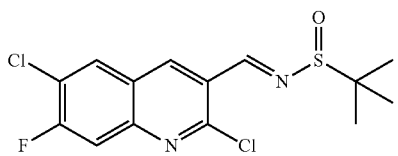 [SMILES: CC(C)(C)S(=O)/N=C/c1cc2cc(Cl)c(F)cc2nc1Cl]

A mixture of 2,6-dichloro-7-fluoroquinoline-3-carbaldehyde (424.4 mg, 1.739 mmol) and 2-methylpropane-2-sulfinamide (253.8 mg, 2.094 mmol) was placed under an atmosphere of nitrogen. THF (4 mL) and titanium (IV) isopropoxide (Ti(O$^i$Pr)$_4$) (1.00 mL, 3.41 mmol) were then added by syringe and the resulting suspension was stirred at room temperature for 48 hours. Once LCMS indicated the reaction had gone cleanly to completion. The reaction was quenched by dropwise addition of aqueous saturated NH$_4$Cl (2 mL). The mixture was triturated with EtOAc (100 mL), and the solid was collected on a Buchner funnel, and was washed with EtOAc (50 mL). The filtrate was washed with brine (50 mL), dried (Na$_2$SO$_4$), filtered, and evaporated under reduced pressure to provide 574.3 mg of the title compound as a yellow solid. LCMS and $^1$H NMR are consistent with (E)-N-((2,6-dichloro-7-fluoroquinolin-3-yl)methylene)-2-methylpropane-2-sulfinamide (574.3 mg, 1.654 mmol, 95% yield). $^1$H NMR (300 MHz, DMSO-d$_6$): δ ppm 9.13 (s, 1H), 8.87 (s, 1H), 8.67 (d, J=8.21 Hz, 1H), 8.11 (d, J=10.26 Hz, 1H), 1.25 (s, 9H). LCMS (Method 1): m/z 347 [M+H]$^+$.

Step-4: N-(1-(2,6-dichloro-7-fluoroquinolin-3-yl)ethyl)-2-methylpropane-2-sulfinamide

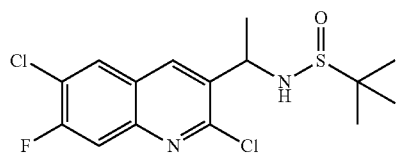 [SMILES: CC(NS(=O)C(C)(C)C)c1cc2cc(Cl)c(F)cc2nc1Cl]

N-((2,6-dichloro-7-fluoroquinolin-3-yl)methylene)-2-methylpropane-2-sulfinamide (573.6 mg, 1.652 mmol) was placed in a 100 mL round-bottom flask under an atmosphere of nitrogen. DCM (14 mL) was added and the resulting suspension was cooled in a dry ice/chloroform bath (to approx. −60° C.). Methyl magnesium bromide (MeMgBr) (3M in ethyl ether, 0.83 mL, 2.490 mmol) was then added dropwise. The reaction was stirred at −60° C. for several hours, and then at −20° C. overnight. The mixture was placed in an ice bath and treated dropwise with water (7 mL). The mixture was diluted with water (150 mL) and extracted with EtOAc (3×50 mL). Silica gel was added to the combined extracts and the sample was evaporated under reduced pressure. The sample was purified by column chromatography on a Biotage® MPLC chromatography system (eluted with 0 to 100% EtOAc in hexanes and with isocratic elution when peaks eluted) to provide 226.3 mg of the title compound as a yellowish solid. LCMS and $^1$H NMR are consistent with N-(1-(2,6-dichloro-7-fluoroquinolin-3-yl)ethyl)-2-methylpropane-2-sulfinamide (226.3 mg, 0.623 mmol, 25.02% yield). $^1$H NMR indicates a single diastereomer. $^1$H NMR (300 MHz, DMSO-d$_6$): δ ppm 8.52 (s, 1H), 8.47 (d, J=7.92 Hz, 1H), 8.01 (d, J=10.26 Hz, 1H), 5.66 (d, J=6.16 Hz, 1H), 4.83 (q, J=6.60 Hz, 1H), 1.60 (d, J=6.74 Hz, 3H), 1.13 (s, 9H). LCMS (Method 1): m/z 363 [M+H]$^+$.

Step-5: 3-(1-aminoethyl)-6-chloro-7-fluoroquinolin-2(1H)-one hydrochloride (II-3)

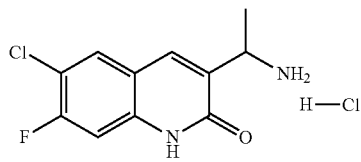

A sample of N-(1-(2,6-dichloro-7-fluoroquinolin-3-yl)ethyl)-2-methylpropane-2-sulfinamide (226.3 mg, 0.623 mmol) was mixed with 1,4-dioxane (3.5 mL) and 3.6% HCl (aqueous, 3.5 mL) and stirred at 95° C. overnight; the material quickly went into solution upon heating. Once LCMS showed the reaction had gone to completion, the solution was evaporated under reduced pressure. The residue was dissolved in MeOH (~10 mL), treated with heptane (~15 mL), and evaporated again under reduced pressure. The resulting residue was then triturated with Et$_2$O, collected on a Hirsch funnel, and washed with Et$_2$O (20 mL) to provide 179.8 mg of the title compound as a yellow solid. LCMS and $^1$H NMR are consistent with 3-(1-aminoethyl)-6-chloro-7-fluoroquinolin-2(1H)-one hydrochloride (179.8 mg, 0.649 mmol, 104% yield). $^1$H NMR (300 MHz, Methanol-d$_4$): δ ppm 8.02 (s, 1H), 7.92 (d, J=7.62 Hz, 1H), 7.23 (d, J=9.97 Hz, 1H), 4.53 (q, J=6.84 Hz, 1H), 1.68 (d, J=6.74 Hz, 3H). LCMS (Method 1): m/z 241 [M+H]$^+$.

Example 6—Intermediate II-3b: (R)-3-(1-aminoethyl)-6-chloro-7-fluoroquinolin-2(1H)-one

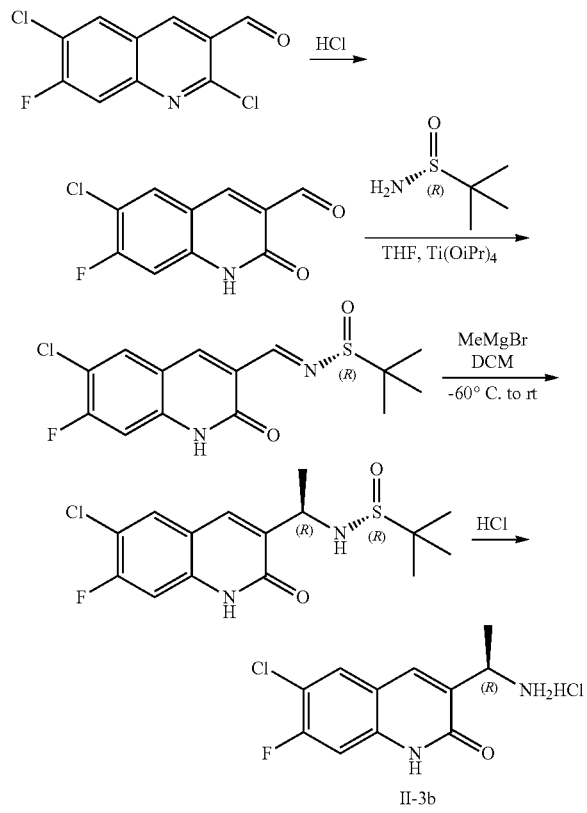

Step-1: 6-chloro-7-fluoro-2-oxo-1,2-dihydroquinoline-3-carbaldehyde 2,6-dichloro-7-fluoroquinoline-3-carbaldehyde (2.56 g, 10.49 mmol) was heated at reflux in concentrated HCl (12M, 100 mL) overnight, during which the material did not appear to go into solution. The mixture was allowed to cool, and then was poured into water (750 mL). The slurry was filtered on a Buchner funnel, washed with water (750 mL), and dried to provide impure 6-chloro-7-fluoro-2-oxo-1,2-dihydroquinoline-3-carbaldehyde (2.1991 g, 9.75 mmol, 93% yield) as a reddish brown solid. The material was suitable for use as is. $^1$H NMR (300 MHz, DMSO-d$_6$): δ ppm 12.41 (s, 1H), 10.20 (s, 1H), 8.49 (s, 1H), 8.28 (d, J=7.92 Hz, 1H), 7.25 (d, J=10.26 Hz, 1H). LCMS: m/z+226 [M+H]$^+$.

Step-2: (R,E)-N-((6-chloro-7-fluoro-2-oxo-1,2-dihydroquinolin-3-yl)methylene)-2-methylpropane-2-sulfinamide

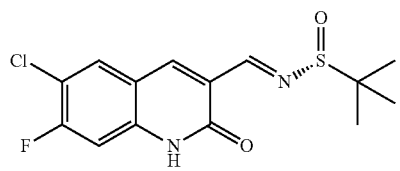 [SMILES: CC(C)(C)[S@@](=O)/N=C/c1cc2cc(Cl)c(F)cc2[nH]c1=O]

A mixture of 6-chloro-7-fluoro-2-oxo-1,2-dihydroquinoline-3-carbaldehyde (2.20 g, 9.75 mmol) and (R)-2-methylpropane-2-sulfinamide (1.42 g, 11.72 mmol) was placed in a 50 mL round bottom flask under an atmosphere of nitrogen. THF (20 mL) and titanium (IV) isopropoxide (Ti(O$^i$Pr)$_4$) (5.8 mL, 19.79 mmol) were added by syringe and the resulting suspension was stirred at room temperature for one day, during which the mixture turned dark. The reaction mixture was quenched by dropwise addition of saturated aqueous NH$_4$Cl, resulting in precipitation. The mixture was triturated with EtOAc (400 mL) and filtered on a Buchner funnel. The filter cake was then sonicated in 300 mL EtOAc for 15 minutes. The mixture was filtered on a Buchner funnel, and the filtrates from the two filtrations were combined. The combined filtrate solution was washed with brine (200 mL), dried (Na$_2$SO$_4$), filtered, and evaporated under reduced pressure to provide (R,E)-N-((6-chloro-7-fluoro-2-oxo-1,2-dihydroquinolin-3-yl)methylene)-2-methylpropane-2-sulfinamide (3.22 g, 9.79 mmol, 100% yield) as an orange solid. $^1$H NMR (300 MHz, DMSO-d$_6$): δ ppm 12.40 (br s, 1H), 8.75 (br s, 1H), 8.65 (s, 1H), 8.27 (d, J=8.21 Hz, 1H), 7.25 (d, J=10.26 Hz, 1H), 1.20 (s, 9H). LCMS: m/z 329 [M+H]$^+$.

Step-3: (R)—N—((R)-1-(6-chloro-7-fluoro-2-oxo-1,2-dihydroquinolin-3-yl)ethyl)-2-methylpropane-2-sulfinamide

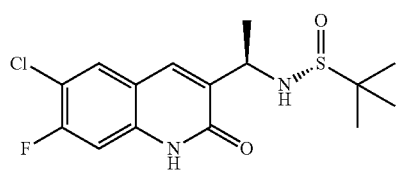 [SMILES: C[C@@H](N[S@](=O)C(C)(C)C)c1cc2cc(Cl)c(F)cc2[nH]c1=O]

(R,E)-N-((6-chloro-7-fluoro-2-oxo-1,2-dihydroquinolin-3-yl)methylene)-2-methylpropane-2-sulfinamide (3.22 g, 9.79 mmol) was placed in a 500 mL round-bottom flask under an atmosphere of nitrogen. DCM (100 mL) was added and the resulting suspension was cooled on a dry ice/chloroform bath (to approximately −60° C.). Methyl magnesium bromide (MeMgBr) (3M in ether, 10 mL, 30.0 mmol) was added dropwise. The reaction mixture was stirred at −60° C. for several hours, and then allowed to warm to room temperature overnight, resulting in a red solution. The solution was then cooled on an ice bath, treated dropwise with water (40 mL) and concentrated under reduced pressure. The resulting slurry was diluted with water (300 mL) and washed with EtOAc. The resulting emulsion was allowed to separate overnight. The layers were separated, and silica gel was added to the organic layer. Most of the solvent was evaporated under reduced pressure. MeOH and heptane were added and the mixture was evaporated under reduced pressure to dryness. The material was purified by column chromatography on a Biotage® MPLC chromatography system (using 50 g silica gel column; eluted with 0 to 50% EtOAc in hexanes, with isocratic elution when peaks eluted) to provide (R)—N—((R)-1-(6-chloro-7-fluoro-2-oxo-1,2-dihydroquinolin-3-yl)ethyl)-2-methylpropane-2-sulfinamide (774.3 mg, 2.245 mmol, 23% yield) as a greenish solid. $^1$H NMR shows a single diastereomer. $^1$H NMR (300 MHz, DMSO-$d_6$): δ ppm 12.03 (s, 1H), 7.98 (d, J=7.92 Hz, 1H), 7.89 (s, 1H), 7.22 (d, J=10.26 Hz, 1H), 5.67 (d, J=7.92 Hz, 1H), 4.41-4.55 (m, 1H), 1.37 (d, J=6.74 Hz, 3H), 1.12 (s, 9H). LCMS: m/z+345 [M+H]$^+$.

Step 4: (R)-3-(1-aminoethyl)-6-chloro-7-fluoroquinolin-2(1H)-one hydrochloride (II-3b)

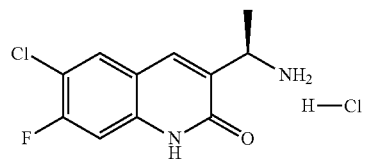

A solution of (R)—N—((R)-1-(6-chloro-7-fluoro-2-oxo-1,2-dihydroquinolin-3-yl)ethyl)-2-methylpropane-2-sulfinamide (773 mg, 2.242 mmol) in MeOH (20 mL) was cooled on an ice bath and treated dropwise with 4M HCl in dioxane (12 mL), during which the material went into solution. The reaction was stirred 25 minutes, during which time precipitate formed. The solvents were evaporated under reduced pressure at room temperature. The residue was triturated with ethyl ether (50 mL), and then the solid was collected on a Hirsch funnel and washed with more ethyl ether (50 mL) to provide (R)-3-(1-aminoethyl)-6-chloro-7-fluoroquinolin-2(1H)-one hydrochloride (613.5 mg, 2.214 mmol, 99% yield) as a yellow solid. $^1$H NMR (300 MHz, Methanol-$d_4$): δ ppm 7.99 (s, 1H), 7.90 (d, J=7.62 Hz, 1H), 7.22 (d, J=9.67 Hz, 1H), 4.51 (q, J=6.64 Hz, 1H), 1.66 (d, J=7.04 Hz, 3H). LCMS: m/z+241 [M+H]$^+$.

Example 7—Intermediate II-4:3-(1-aminoethyl)-6-chloro-7-methoxyquinolin-2(1H)-one

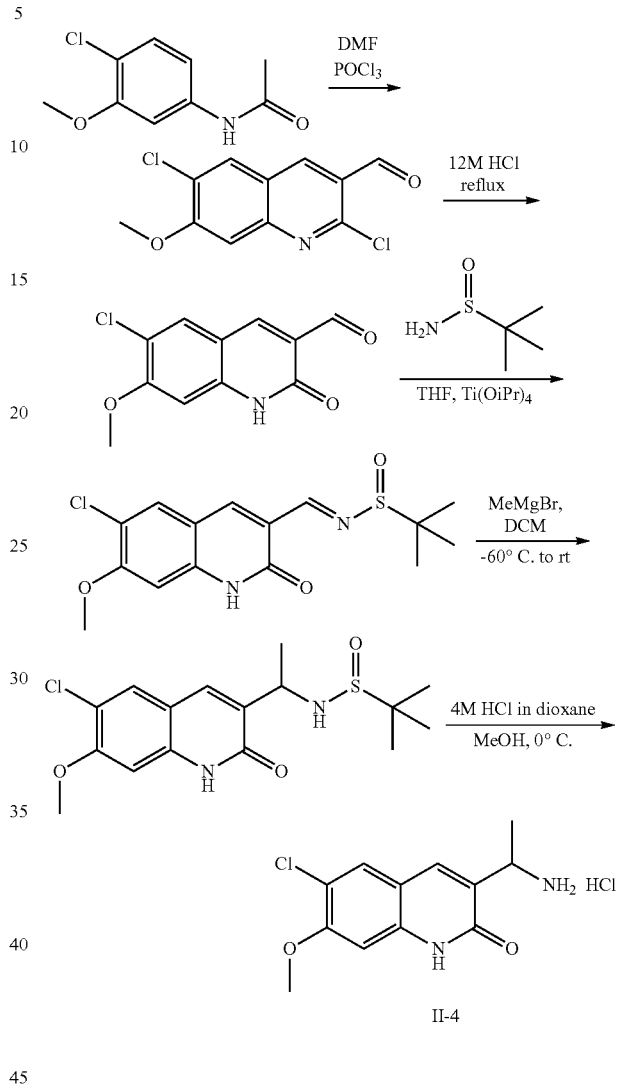

Step 1: 2,6-dichloro-7-methoxyquinoline-3-carbaldehyde

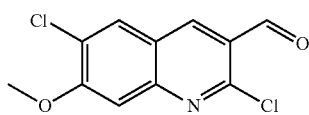 [SMILES: COc1cc2nc(Cl)c(C=O)cc2cc1Cl]

A tube was capped with a septum and placed under an atmosphere of nitrogen. DMF (6.4 mL, 83 mmol) was added by syringe and then cooled on an ice bath. POCl$_3$ (25 mL, 268 mmol) was added dropwise by syringe (over 20 minutes). The red solution was allowed to warm to room temperature (over 20 minutes), and then the septum was removed, and the mixture was treated with N-(4-chloro-3-methoxyphenyl)acetamide (5 g, 25.05 mmol). The tube was sealed and the solution was stirred at 80° C. overnight. The solution was then pipetted onto ice, resulting in formation of a yellow precipitate. The precipitate was collected on a Buchner funnel, washed with water (1200 mL), and dried to provide 5.06 g of the title compound as a pale yellow solid. LCMS and ¹H NMR are consistent with 2,6-dichloro-7-methoxyquinoline-3-carbaldehyde (5.06 g, 19.76 mmol, 79% yield). ¹H NMR (300 MHz, DMSO-d₆): δ ppm 10.33 (s, 1H), 8.87 (s, 1H), 8.47 (s, 1H), 7.64 (s, 1H), 4.08 (s, 3H). LCMS (Method 1): m/z 256 [M+H]⁺.

Step-2: 6-chloro-7-methoxy-2-oxo-1,2-dihydroquinoline-3-carbaldehyde

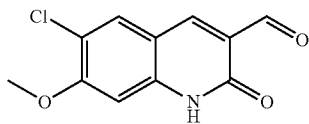 [SMILES: COc1cc2[nH]c(=O)c(C=O)cc2cc1Cl]

2,6-Dichloro-7-methoxyquinoline-3-carbaldehyde (5.06 g, 19.76 mmol) was heated at reflux in concentrated HCl (12M, 185 mL) overnight. The material went into solution during heating and then a solid precipitated during the course of the reaction. The mixture was allowed to cool and then was poured into water (1500 mL) resulting in further precipitation. The slurry was filtered on a Buchner funnel, washed with water (1500 mL), and dried to provide 4.04 g of the title compound as a yellowish-brown solid. LCMS and ¹H NMR are consistent with 6-chloro-7-methoxy-2-oxo-1,2-dihydroquinoline-3-carbaldehyde (4.04 g, 17.00 mmol, 86% yield). ¹H NMR (300 MHz, DMSO-d₆): δ ppm 12.22 (s, 1H), 10.16-10.18 (m, 1H), 8.43 (s, 1H), 8.08 (s, 1H), 6.95 (s, 1H), 3.94 (s, 3H). LCMS (Method 1): m/z 238 [M+H]⁺.

Step-3: N-((6-chloro-7-methoxy-2-oxo-1,2-dihydroquinolin-3-yl)methylene)-2-methylpropane-2-sulfinamide

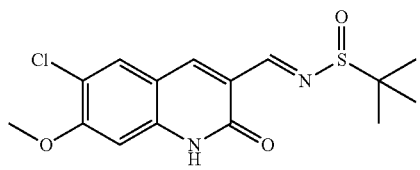 [SMILES: COc1cc2[nH]c(=O)c(/C=N/S(=O)C(C)(C)C)cc2cc1Cl]

A mixture of 6-chloro-7-methoxy-2-oxo-1,2-dihydroquinoline-3-carbaldehyde (2.00 g, 8.42 mmol) and 2-methylpropane-2-sulfinamide (1.22 g, 10.07 mmol) was placed under an atmosphere of nitrogen. THF (20 mL) and titanium (IV) isopropoxide (Ti(OⁱPr)₄) (5.0 mL, 17.06 mmol) were added by syringe and the resulting suspension was stirred at room temperature overnight. Once LCMS indicated the reaction had gone to completion, the reaction was quenched by dropwise addition of aqueous saturated NH₄Cl (10 mL). The mixture was triturated with EtOAc (450 mL), then filtered through Celite® 545, and the Celite® was washed further with EtOAc (200 mL). The filter cake was then sonicated in EtOAc (450 mL) for 15 minutes, and then filtered on a Buchner funnel. The two filtrates were combined, washed with brine (200 mL), dried (Na₂SO₄), filtered, and evaporated under reduced pressure to provide 1.01 g of the title compound as a yellow solid. LCMS and ¹H NMR are consistent with (E)-N-((6-chloro-7-methoxy-2-oxo-1,2-dihydroquinolin-3-yl)methylene)-2-methylpropane-2-sulfinamide (1.01 g, 2.96 mmol, 35.2% yield). ¹H NMR (300 MHz, DMSO-d₆): δ ppm 12.21 (s, 1H), 8.74 (s, 1H), 8.59 (s, 1H), 8.08 (s, 1H), 6.97 (s, 1H), 3.94 (s, 3H), 1.19 (s, 9H). LCMS (Method 1): m/z 341 [M+H]⁺.

Step-4: N-(1-(6-chloro-7-methoxy-2-oxo-1,2-dihydroquinolin-3-yl)ethyl)-2-methylpropane-2-sulfinamide

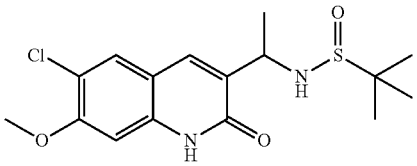 [SMILES: COc1cc2[nH]c(=O)c(C(C)NS(=O)C(C)(C)C)cc2cc1Cl]

N-(((6-chloro-7-methoxy-2-oxo-1,2-dihydroquinolin-3-yl)methylene)-2-methylpropane-2-sulfinamide (265 mg, 0.778 mmol) was placed in a 50 mL round-bottom flask under an atmosphere of nitrogen. DCM (7 mL) was added, and the suspension was cooled on a dry ice/chloroform bath (to approx. −60° C.). Methylmagnesium bromide (MeMgBr) (3M in ether, 0.80 mL, 2.40 mmol) was added dropwise. The reaction mixture was stirred at −60° C. for several hours, and then allowed to warm to room temperature overnight, resulting in an orange solution. Once LCMS indicated the reaction had gone to completion, the suspension was cooled on an ice bath and treated dropwise with water (3 mL). The resulting mixture was diluted with water (75 mL) and extracted with EtOAc (75 mL+20 mL). Silica gel was added and the EtOAc was evaporated under reduced pressure to provide a wet globular mass. Heptane and MeOH were added and the mixture was evaporated under reduced pressure to provide a powder. The material was purified by column chromatography on a Biotage® MPLC chromatography system (eluted with 0 to 4.2% MeOH in DCM, with isocratic elution when peaks eluted). The product fractions provided 152.7 mg of the title compound as a blue-green brittle foam. LCMS and ¹H NMR are consistent with N-(1-(6-chloro-7-methoxy-2-oxo-1,2-dihydroquinolin-3-yl)ethyl)-2-methylpropane-2-sulfinamide (152.7 mg, 0.428 mmol, 55% yield). LCMS (Method 1): m/z 357 [M+H]⁺.

Step-5: 3-(1-aminoethyl)-6-chloro-7-methoxyquinolin-2(1H)-one hydrochloride (II-4)

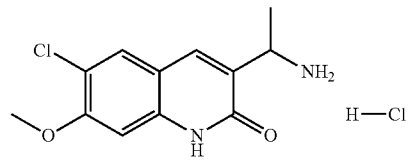 [SMILES: COc1cc2[nH]c(=O)c(C(C)N)cc2cc1Cl ; Cl]

A solution of N-(1-(6-chloro-7-methoxy-2-oxo-1,2-dihydroquinolin-3-yl)ethyl)-2-methyl propane-2-sulfinamide (149.6 mg, 0.419 mmol) in MeOH (3.8 mL) was cooled on an ice bath and treated dropwise with 4M HCl in 1,4-dioxane (2.2 mL). The reaction was stirred for 25 minutes, during which time a small amount of precipitate formed. The solvents were evaporated under reduced pressure at room temperature. The residue was triturated with 10 mL of ethyl ether, and then collected on a Hirsch funnel, and washed with more ethyl ether to provide 115.6 mg of the title compound as a pale green solid. LCMS and $^1$H NMR are consistent with 3-(1-aminoethyl)-6-chloro-7-methoxyquinolin-2(1H)-one hydrochloride (115.6 mg, 0.400 mmol, 95% yield). $^1$H NMR (300 MHz, Methanol-$d_4$): δ ppm 7.95 (s, 1H), 7.77 (s, 1H), 6.97 (s, 1H), 4.51 (q, J=6.84 Hz, 1H), 3.98 (s, 3H), 1.68 (d, J=7.04 Hz, 3H). LCMS (Method 1): m/z 253 [M+H]$^+$.

Example 8—Intermediate II-4a: (S)-3-(1-aminoethyl)-6-chloro-7-methoxyquinolin-2(1H)-one A mixture of 6-chloro-7-methoxy-2-oxo-1,2-dihydroquinoline-3-carbaldehyde (1.00 g, 4.21 mmol) and (R)-2-methylpropane-2-sulfinamide (0.61 g, 5.03 mmol) was placed in a 50 mL round bottom flask under an atmosphere of nitrogen. THF (10 mL) and titanium (IV) isopropoxide (Ti(O$^i$Pr)$_4$) (2.5 mL, 8.53 mmol) were added by syringe, and the suspension was stirred at room temperature overnight. Once LCMS indicated the reaction had gone to completion,

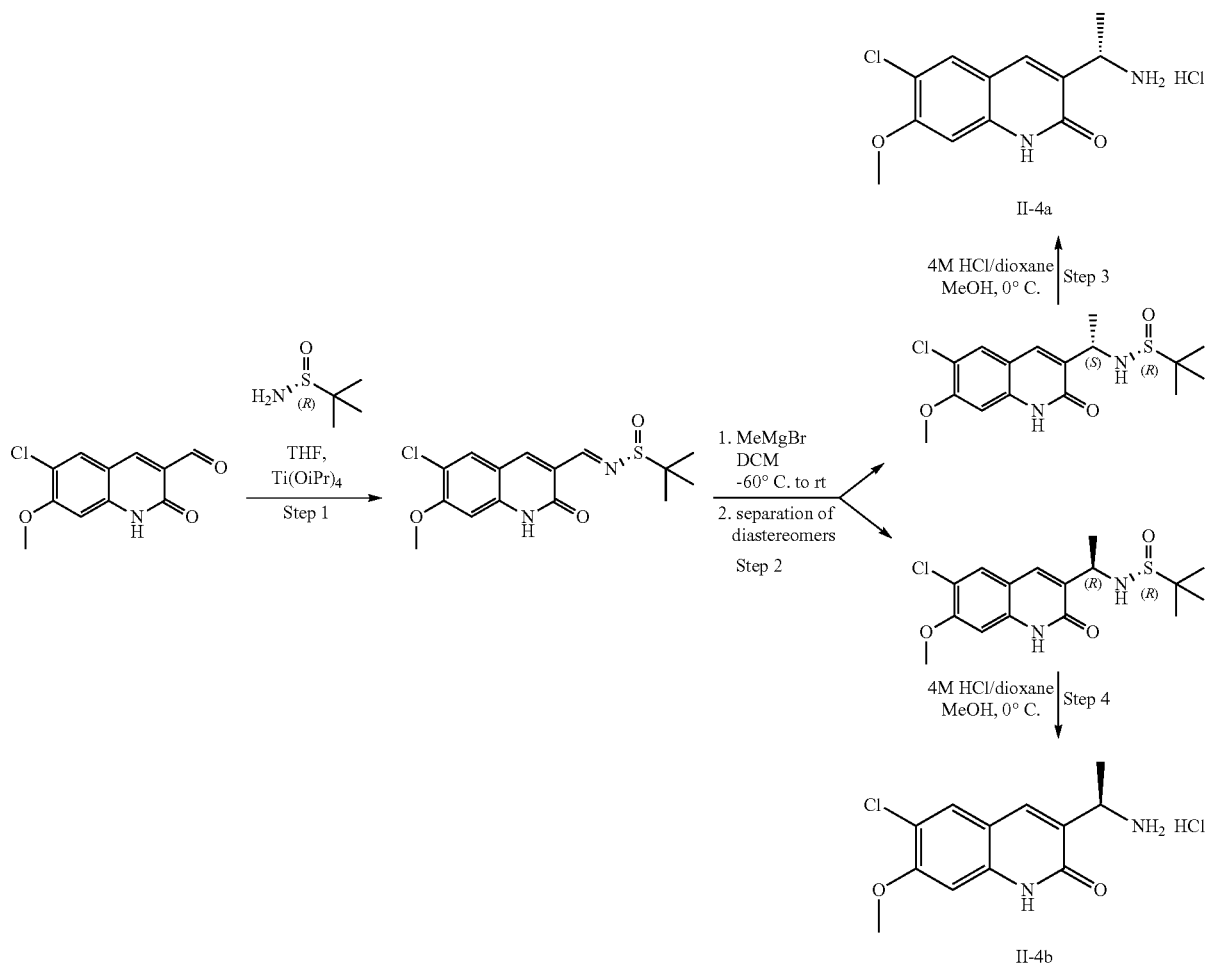

Step-1: (R,E)-N-((6-chloro-7-methoxy-2-oxo-1,2-dihydroquinolin-3-yl)methylene)-2-methylpropane-2-sulfinamide

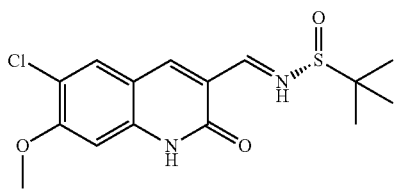 [SMILES: COc1cc2[nH]c(=O)c(/C=N/[S@](=O)C(C)(C)C)cc2cc1Cl]

the reaction was quenched by dropwise addition of saturated aqueous NH$_4$Cl (5 mL). The mixture was triturated with EtOAc (200 mL), filtered on a Buchner funnel, and the filter cake was washed with EtOAc (50 mL). The filter cake was then sonicated in EtOAc (200 mL) for 15 minutes and then filtered on a Buchner funnel. The two filtrates were combined, washed with brine (100 mL), dried (Na$_2$SO$_4$), filtered, and evaporated under reduced pressure to provide impure (R,E)-N-((6-chloro-7-methoxy-2-oxo-1,2-dihydroquinolin-3-yl)methylene)-2-methyl propane-2-sulfinamide (776.0 mg, 2.277 mmol, 54.1% yield) as a yellow solid. The sample was used as is. LCMS: m/z 341 [M+H]$^+$.

Step-2: (R)—N-(1-(6-chloro-7-methoxy-2-oxo-1,2-dihydroquinolin-3-yl)ethyl)-2-methylpropane-2-sulfinamide

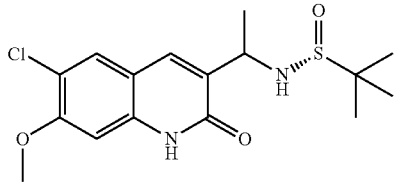 [SMILES: COc1cc2[nH]c(=O)c(C(C)N[S@](=O)C(C)(C)C)cc2cc1Cl]

(R,E)-N-((6-chloro-7-methoxy-2-oxo-1,2-dihydroquinolin-3-yl)methylene)-2-methylpropane-2-sulfinamide (774 mg, 2.271 mmol) was placed in a 100 mL round-bottom flask under an atmosphere of nitrogen. DCM (20 mL) was added, and the suspension was cooled on a dry ice/chloroform bath (to approximately −60° C.). Methylmagnesium bromide (MeMgBr) (3M in ethyl ether, 2.25 mL, 6.75 mmol) was added dropwise. The reaction mixture was stirred at −60° C. for several hours, and then allowed to warm to room temperature overnight, resulting in an orange solution. The solution was cooled on an ice bath and treated dropwise with water (10 mL). The resulting mixture was diluted with water (250 mL) and extracted with EtOAc (250 mL+2×100 mL); some water remained mixed with the EtOAc layer. Silica gel was added, and the solvent was evaporated under reduced pressure. The material was purified by column chromatography on a Biotage® MPLC chromatography system (silica gel column, eluted with 0 to 5% MeOH in DCM, with isocratic elution when peaks eluted) to provide (R)—N-(1-(6-chloro-7-methoxy-2-oxo-1,2-dihydroquinolin-3-yl)ethyl)-2-methylpropane-2-sulfinamide (488 mg) as a blue-green solid mixture of diastereomers. The diastereomers were separated by column chromatography (CHIRALPAK IA, 2×25 cm, 5 μm; 75:25 hexanes-IPA) to provide:

(R)—N—((S)-1-(6-chloro-7-methoxy-2-oxo-1,2-dihydroquinolin-3-yl)ethyl)-2-methylpropane-2-sulfinamide (221.6 mg, 0.621 mmol, 27% yield). $^1$H NMR (300 MHz, DMSO-$d_6$): δ ppm 11.82 (s, 1H), 7.75-7.81 (m, 2H), 6.95 (s, 1H), 5.29 (d, J=6.45 Hz, 1H), 4.53 (quin, J=6.74 Hz, 1H), 3.88 (s, 3H), 1.43 (d, J=6.74 Hz, 3H), 1.12 (s, 9H). LCMS: Rt 2.52 min, m/z 355 [M−1]$^−$.

(R)—N—((R)-1-(6-chloro-7-methoxy-2-oxo-1,2-dihydroquinolin-3-yl)ethyl)-2-methylpropane-2-sulfinamide (142.3 mg, 0.399 mmol, 18% yield). $^1$H NMR (300 MHz, DMSO-$d_6$): δ ppm 11.81 (br s, 1H), 7.81 (s, 1H), 7.77 (s, 1H), 6.96 (s, 1H), 5.64 (d, J=7.92 Hz, 1H), 4.45 (quin, J=7.11 Hz, 1H), 3.89 (s, 3H), 1.36 (d, J=6.74 Hz, 3H), 1.11 (s, 9H). LCMS: Rt 1.87 min, m/z 355 [M−1]$^−$.

Step-3: (S)-3-(1-aminoethyl)-6-chloro-7-methoxyquinolin-2(1H)-one hydrochloride, (II-4a)

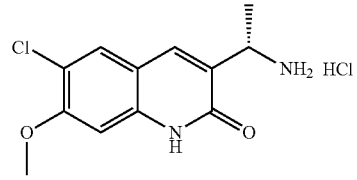 [SMILES: COc1cc2[nH]c(=O)c([C@H](C)N)cc2cc1Cl ; Cl]

A suspension of (R)—N—((S)-1-(6-chloro-7-methoxy-2-oxo-1,2-dihydroquinolin-3-yl)ethyl)-2-methylpropane-2-sulfinamide (219.7 mg, 0.616 mmol) in MeOH (5.5 mL) was cooled on an ice bath and treated dropwise with 4M HCl in 1,4-dioxane (3.3 mL). The material went into solution during the acid addition. The reaction was stirred 25 minutes during which time a small amount of precipitate formed. The solvents were evaporated under reduced pressure at room temperature. The residue was triturated with 30 mL ethyl ether, and then collected on a Hirsch funnel and washed with more ethyl ether (10 mL) to provide (S)-3-(1-aminoethyl)-6-chloro-7-methoxyquinolin-2(1H)-one hydrochloride (175.4 mg, 0.607 mmol, 99% yield) as a pale greenish solid. $^1$H NMR (300 MHz, Methanol-$d_4$): δ ppm 7.93 (s, 1H), 7.75 (s, 1H), 6.95 (s, 1H), 4.49 (q, J=6.74 Hz, 1H), 3.96 (s, 3H), 1.65 (d, J=6.74 Hz, 3H). LCMS: m/z+253 [M+H]$^+$.

Step-4: (R)-3-(1-aminoethyl)-6-chloro-7-methoxyquinolin-2(1H)-one hydrochloride II-4b

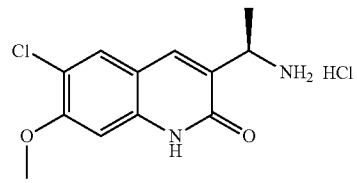 [SMILES: COc1cc2[nH]c(=O)c([C@@H](C)N)cc2cc1Cl ; Cl]

A solution of (R)—N—((R)-1-(6-chloro-7-methoxy-2-oxo-1,2-dihydroquinolin-3-yl)ethyl)-2-methylpropane-2-sulfinamide (140.5 mg, 0.394 mmol) in MeOH (3.4 mL) was cooled on an ice bath and treated dropwise with 4M HCl in 1,4-dioxane (2.1 mL). The reaction was stirred 25 minutes, during which time a small amount of precipitate formed. The solvents were evaporated under reduced pressure at room temperature. The residue was triturated with 20 mL ethyl ether, and then collected on a Hirsch funnel and washed with more ethyl ether (20 mL) to provide (R)-3-(1-aminoethyl)-6-chloro-7-methoxyquinolin-2(1H)-one hydrochloride (101.3 mg, 0.350 mmol, 89% yield) as a pale greenish solid. $^1$H NMR (300 MHz, Methanol-$d_4$): δ ppm 7.92 (s, 1H), 7.75 (s, 1H), 6.95 (s, 1H), 4.48 (q, J=6.84 Hz, 1H), 3.96 (s, 3H), 1.65 (d, J=6.74 Hz, 3H). LCMS: m/z 253 [M+H]$^+$.

Below is an alternative method used to prepare Intermediate II-4a.

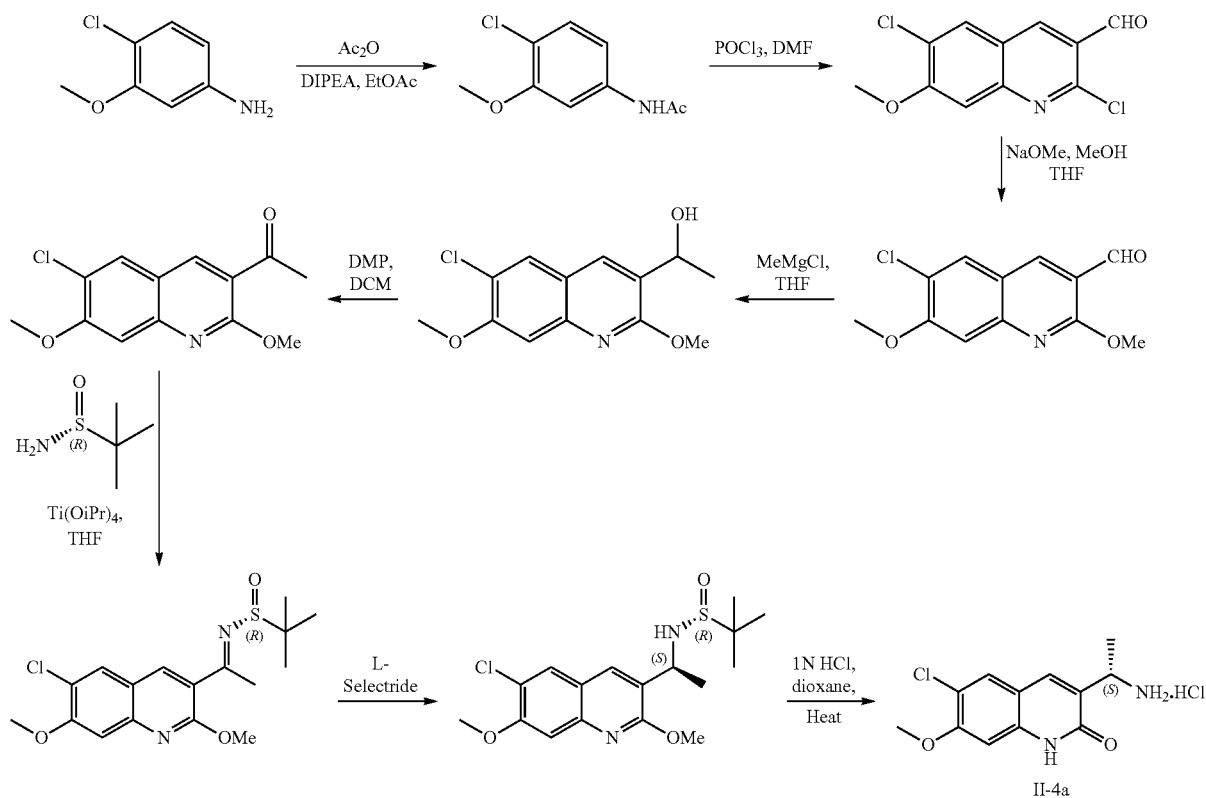
Example 9—Intermediate II-5:3-(1-aminoethyl)-6-chloro-7-(pyridin-2-ylmethoxy)quinolin-2(1H)-one
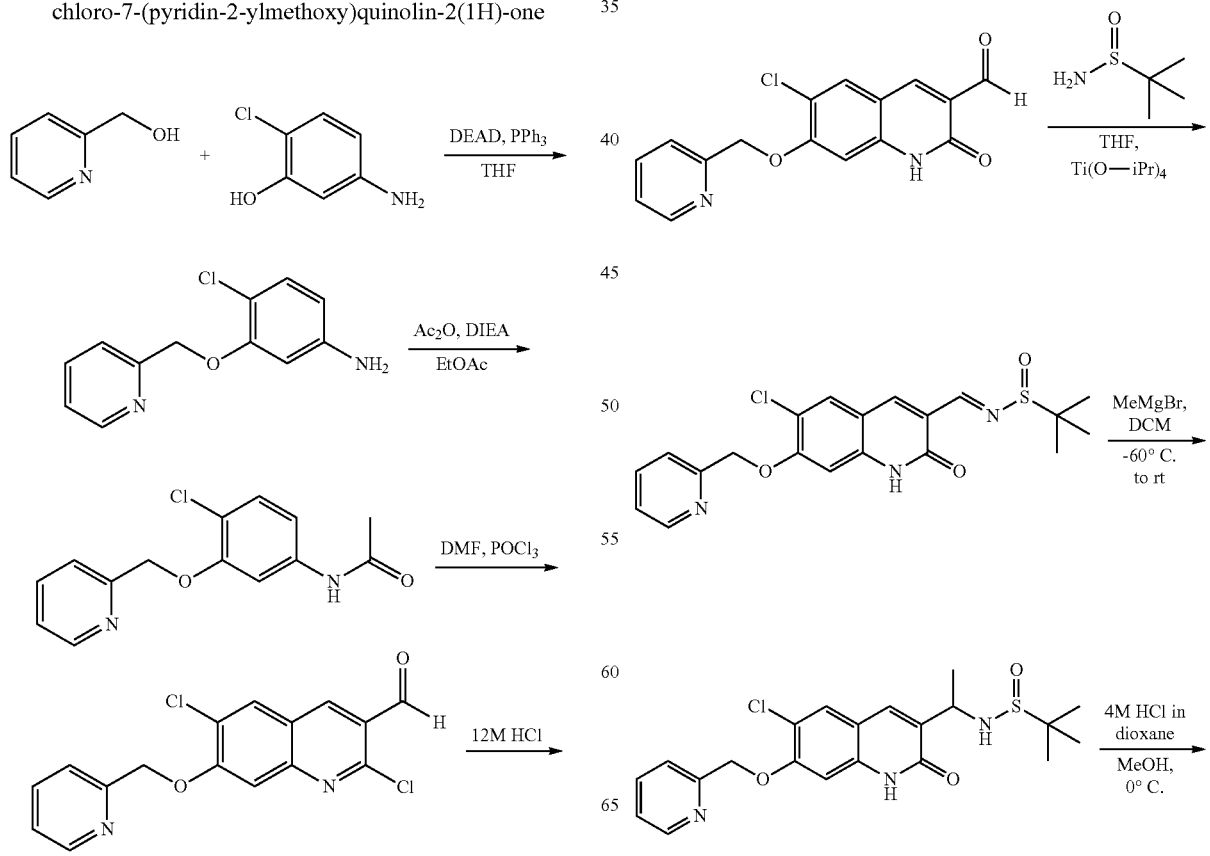

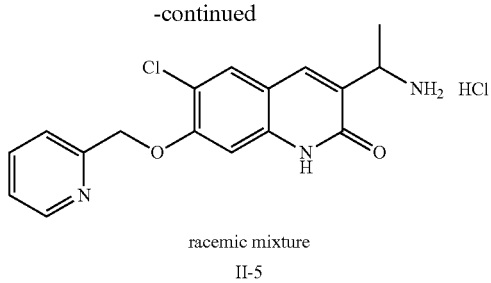

racemic mixture
II-5

Step-1: 4-chloro-3-(pyridin-2-ylmethoxy)aniline

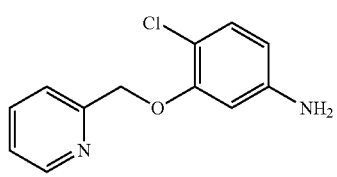 [SMILES: Nc1ccc(Cl)c(OCc2ccccn2)c1]

A solution of 5-amino-2-chlorophenol (2.00 g, 13.93 mmol) pyridin-2-ylmethanol (1.4 mL, 14.51 mmol), and triphenylphosphine (4.30 g, 16.39 mmol) in THF (250 mL) was placed under an atmosphere of nitrogen and treated with DEAD (2.6 mL, 16.42 mmol) The solution was stirred at room temperature overnight. Once LCMS indicated the reaction had gone to completion, the solution was treated with silica gel and evaporated under reduced pressure. The material was purified by column chromatography on a Biotage® MPLC chromatography system (using a 340 g silica gel column, eluted with 0 to 100% EtOAc in hexanes, then 2.3% MeOH in EtOAc) to provide the title compound as a light brown solid. LCMS and $^1$H NMR are consistent with 4-chloro-3-(pyridin-2-ylmethoxy)aniline (2.29 g, 9.76 mmol, 70.0% yield) with residual triphenylphosphine oxide. The crude was used in the next step without further purification. $^1$H NMR (300 MHz, DMSO-d$_6$): δ ppm 8.55-8.62 (m, 1H), 7.86 (ddd, J=7.77, 7.77, 1.76 Hz, 1H), 7.52 (d, J=7.92 Hz, 1H), 7.35 (dd, J=6.89, 5.42 Hz, 1H), 7.02 (d, J=8.50 Hz, 1H), 6.37 (d, J=2.35 Hz, 1H), 6.15 (dd, J=8.50, 2.35 Hz, 1H), 5.28 (s, 2H), 5.14 (s, 2H). LCMS (Method 1, ESI): m/z 235 [M+H]$^+$.

Step-2: N-(4-chloro-3-(pyridin-2-ylmethoxy)phenyl)acetamide

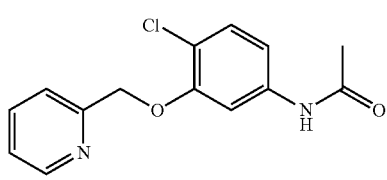 [SMILES: CC(=O)Nc1ccc(Cl)c(OCc2ccccn2)c1]

A solution of 4-chloro-3-(pyridin-2-ylmethoxy)aniline (5.22 g, 22.24 mmol) and DIEA (4.30 mL, 24.62 mmol) in EtOAc (125 mL) was treated with Ac$_2$O (2.30 mL, 24.38 mmol) The solution was stirred at room temperature overnight, after which a thick white precipitate formed. EtOAc (300 mL) was added and the mixture was shaken until most of the precipitate dissolved. The organic layer was then washed with water and brine (125 mL each), dried (Na$_2$SO$_4$) and filtered. Silica gel was added, and the mixture was evaporated under reduced pressure. The residue was purified by column chromatography on a Biotage® MPLC chromatography system (using a 100 g silica gel column, eluted with 0 to 5% MeOH in DCM) to provide 3.23 g of the title compound as a white solid. LCMS and $^1$H NMR are consistent with N-(4-chloro-3-(pyridin-2-ylmethoxy)phenyl)acetamide (3.23 g, 11.67 mmol, 52.5% yield). $^1$H NMR (300 MHz, DMSO-d$_6$): δ ppm 10.06 (s, 1H), 8.56-8.62 (m, 1H), 7.87 (ddd, J=7.80, 7.80, 1.80 Hz, 1H), 7.53 (d, J=7.62 Hz, 1H), 7.49 (d, J=2.05 Hz, 1H), 7.33-7.40 (m, 2H), 7.22 (dd, J=8.65, 2.20 Hz, 1H), 5.21 (s, 2H), 2.02 (s, 3H). LCMS (Method 1): m/z 277 [M+H]$^+$.

Step-3: 2,6-dichloro-7-(pyridin-2-ylmethoxy)quinoline-3-carbaldehyde

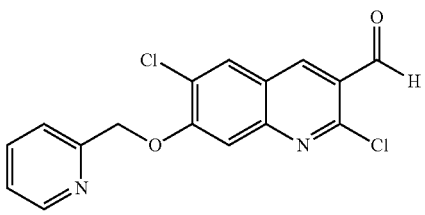 [SMILES: O=Cc1cc2cc(Cl)c(OCc3ccccn3)cc2nc1Cl]

A tube was capped with a septum and placed under an atmosphere of nitrogen. DMF (2.9 mL, 37.5 mmol) was added by syringe and then cooled on an ice bath. POCl$_3$ (11.4 mL, 122 mmol) was added dropwise by syringe (over 20 minutes). The solution was allowed to warm to room temperature (over 15 minutes) and the septum was removed. The mixture was treated with N-(4-chloro-3-(pyridin-2-ylmethoxy)phenyl)acetamide (3.16 g, 11.42 mmol). The tube was again sealed and the solution was stirred at 80° C. overnight. The solution was then pipetted onto ice, resulting in the formation of a yellow precipitate. The precipitate was collected on a Buchner funnel, washed with water (500 mL), and dried to provide 2.88 g of the title compound as a pale yellow solid. LCMS and $^1$H NMR are consistent with 2,6-dichloro-7-(pyridin-2-ylmethoxy)quinoline-3-carbaldehyde (2.88 g, 8.64 mmol, 76% yield). $^1$H NMR (300 MHz, DMSO-d$_6$): δ ppm 10.34 (s, 1H), 8.89 (s, 1H), 8.66 (br d, J=4.10 Hz, 1H), 8.52 (s, 1H), 7.92-8.01 (m, 1H), 7.75 (s, 1H), 7.69 (br d, J=7.62 Hz, 1H), 7.41-7.50 (m, 1H), 5.55 (s, 2H). LCMS (Method 1): m/z 333 [M+H]$^+$.

Step-4: 6-chloro-2-oxo-7-(pyridin-2-ylmethoxy)-1,2-dihydroquinoline-3-carbaldehyde

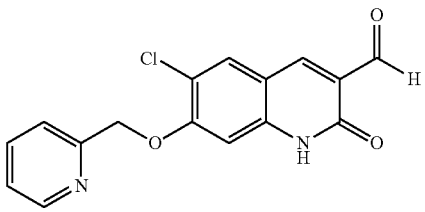 [SMILES: O=Cc1cc2cc(Cl)c(OCc3ccccn3)cc2[nH]c1=O]

A solution of 2,6-dichloro-7-(pyridin-2-ylmethoxy)quinoline-3-carbaldehyde (2.88 g, 8.64 mmol) in concentrated HCl (81 mL) was stirred at reflux (bath temperature 100° C.) for one day, during which time the solution turned orange. The solution was diluted with water (900 mL), resulting in the formation of a yellow precipitate. The precipitate was collected on a Buchner funnel, washed with water (750 mL), and dried under vacuum at 60° C. to provide 2.27 g of the title compound as a yellow solid. LCMS and $^1$H NMR are consistent with 6-chloro-2-oxo-7-(pyridin-2-ylmethoxy)-1,2-dihydroquinoline-3-carbaldehyde (2.27 g, 7.21 mmol, 83% yield). $^1$H NMR (300 MHz, DMSO-$d_6$): δ ppm 12.20 (s, 1H), 10.16-10.19 (m, 1H), 8.60-8.64 (m, 1H), 8.44 (s, 1H), 8.14 (s, 1H), 7.90 (ddd, J=7.60, 7.60, 1.80 Hz, 1H), 7.57 (d, J=7.62 Hz, 1H), 7.36-7.43 (m, 1H), 7.05 (s, 1H), 5.37 (s, 2H). LCMS (Method 1): m/z 315 [M+H]$^+$.

Step-5: (E)-N-((6-chloro-2-oxo-7-(pyridin-2-ylmethoxy)-1,2-dihydroquinolin-3-yl)methylene)-2-methylpropane-2-sulfinamide

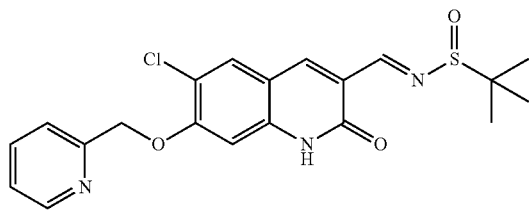 [SMILES: CC(C)(C)S(=O)/N=C/c1cc2cc(Cl)c(OCc3ccccn3)cc2[nH]c1=O]

A mixture of 6-chloro-2-oxo-7-(pyridin-2-ylmethoxy)-1,2-dihydroquinoline-3-carbaldehyde (2.27 g, 7.21 mmol) and 2-methylpropane-2-sulfinamide (1.05 g, 8.66 mmol) was placed in a 25 mL round bottom flask under an atmosphere of nitrogen. THF (9 mL) and titanium (IV) isopropoxide (Ti(O$^i$Pr)$_4$) (4.3 mL, 14.68 mmol) were added by syringe and the suspension was stirred at room temperature for one day. Once LCMS indicated the reaction had gone to completion, the material was triturated with EtOAc (400 mL), then filtered through Celite® 545, and the filter cake was washed with EtOAc (100 mL). The filter cake was sonicated in EtOAc (400 mL) for fifteen minutes and then filtered on a Buchner funnel. The two filtrates were combined and washed with brine (250 mL). The aqueous layer was back-extracted with EtOAc (200 mL+100 mL). The three combined organic layers were dried (Na$_2$SO$_4$), filtered, and evaporated under reduced pressure to provide 1.44 g of the title compound as a yellow solid. LCMS and $^1$H NMR are consistent with (E)-N-((6-chloro-2-oxo-7-(pyridin-2-ylmethoxy)-1,2-dihydroquinolin-3-yl)methylene)-2-methylpropane-2-sulfinamide (1.44 g, 3.45 mmol, 47.8% yield). $^1$H NMR (300 MHz, DMSO-$d_6$): δ ppm 12.20 (s, 1H), 8.74 (s, 1H), 8.62 (d, J=4.10 Hz, 1H), 8.60 (s, 1H), 8.13 (s, 1H), 7.90 (ddd, J=7.80, 7.80, 1.80 Hz, 1H), 7.58 (d, J=7.92 Hz, 1H), 7.40 (dd, J=7.18, 4.54 Hz, 1H), 7.06 (s, 1H), 5.36 (s, 2H), 1.19 (s, 9H). LCMS (Method 1): m/z 418 [M+H]$^+$.

Step-6: N-(1-(6-chloro-2-oxo-7-(pyridin-2-ylmethoxy)-1,2-dihydroquinolin-3-yl)ethyl)-2-methylpropane-2-sulfinamide

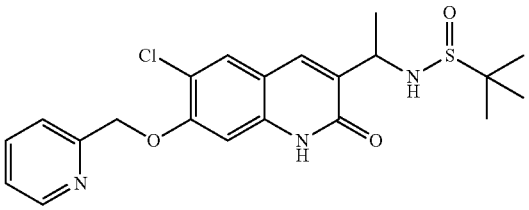 [SMILES: CC(NS(=O)C(C)(C)C)c1cc2cc(Cl)c(OCc3ccccn3)cc2[nH]c1=O]

(E)-N-((6-chloro-2-oxo-7-(pyridin-2-ylmethoxy)-1,2-dihydroquinolin-3-yl)methylene)-2-methyl propane-2-sulfinamide (1.44 g, 3.45 mmol) was placed in a 250 mL round-bottom flask under an atmosphere of nitrogen. DCM (27 mL) was added and the suspension was cooled on a dry ice/chloroform bath (to approx. −60° C.). Methylmagnesium bromide (MeMgBr) (3M in ether, 3.50 mL, 10.50 mmol) was added dropwise. The cold bath was allowed to warm to room temperature overnight resulting in an orange suspension. Once LCMS indicated the reaction had gone to completion, the suspension was cooled on an ice bath and treated dropwise with water (10 mL) resulting in emulsification. The emulsion was diluted with EtOAc (400 mL) and washed with water (400 mL). Silica gel was added to the organic layer and the solvent was evaporated under reduced pressure. The material was purified by column chromatography on a Biotage® MPLC chromatography system (eluted with 0 to 6% MeOH in DCM with isocratic elution when peaks eluted) to provide 1.17 g of the title compound as a yellow brittle foam. LCMS and $^1$H NMR are consistent with N-(1-(6-chloro-2-oxo-7-(pyridin-2-ylmethoxy)-1,2-dihydroquinolin-3-yl)ethyl)-2-methylpropane-2-sulfinamide (1.17 g, 2.70 mmol, 78% yield). NMR indicated a mixture of diastereomers. LCMS (Method 1): m/z 434 [M+H]$^+$.

Step-7: 3-(1-aminoethyl)-6-chloro-7-(pyridin-2-ylmethoxy)quinolin-2(1H)-one hydrochloride (II-5)

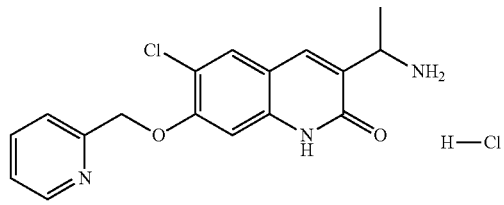 [SMILES: CC(N)c1cc2cc(Cl)c(OCc3ccccn3)cc2[nH]c1=O ; Cl]

A solution of N-(1-(6-chloro-2-oxo-7-(pyridin-2-ylmethoxy)-1,2-dihydroquinolin-3-yl)ethyl)-2-methylpropane-2-sulfinamide (167.3 mg, 0.386 mmol) in MeOH (3.5 mL) was cooled on an ice bath and treated dropwise with 4M HCl in 1,4-dioxane (2 mL). The reaction was stirred for 20 minutes and within five minutes a precipitate began to form. The solvents were evaporated under reduced pressure at room temperature. The residue was triturated with 10 mL of ethyl ether, collected on a Hirsch funnel and washed with more ethyl ether to provide 145.8 mg of the title compound as a pale yellow solid. LCMS and $^1$H NMR are consistent with 3-(1-aminoethyl)-6-chloro-7-(pyridin-2-ylmethoxy)quinolin-2(1H)-one hydrochloride (145.8 mg, 0.398 mmol, 103% yield). $^1$H NMR (300 MHz, Methanol-$d_4$): δ ppm 8.91-8.95 (m, 1H), 8.68 (ddd, J=7.90, 7.90, 1.50 Hz, 1H), 8.29 (d, J=7.62 Hz, 1H), 8.04-8.11 (m, 1H), 8.00 (s, 1H), 7.90 (s, 1H), 7.17 (s, 1H), 5.66 (s, 2H), 4.53 (q, J=6.84 Hz, 1H), 1.69 (d, J=6.74 Hz, 3H). LCMS (Method 1): m/z 352 [M+Na]$^+$.

Example 10—Intermediate II-5a: (S)-3-(1-aminoethyl)-6-chloro-7-(pyridin-2-ylmethoxy)quinolin-2(1H)-one

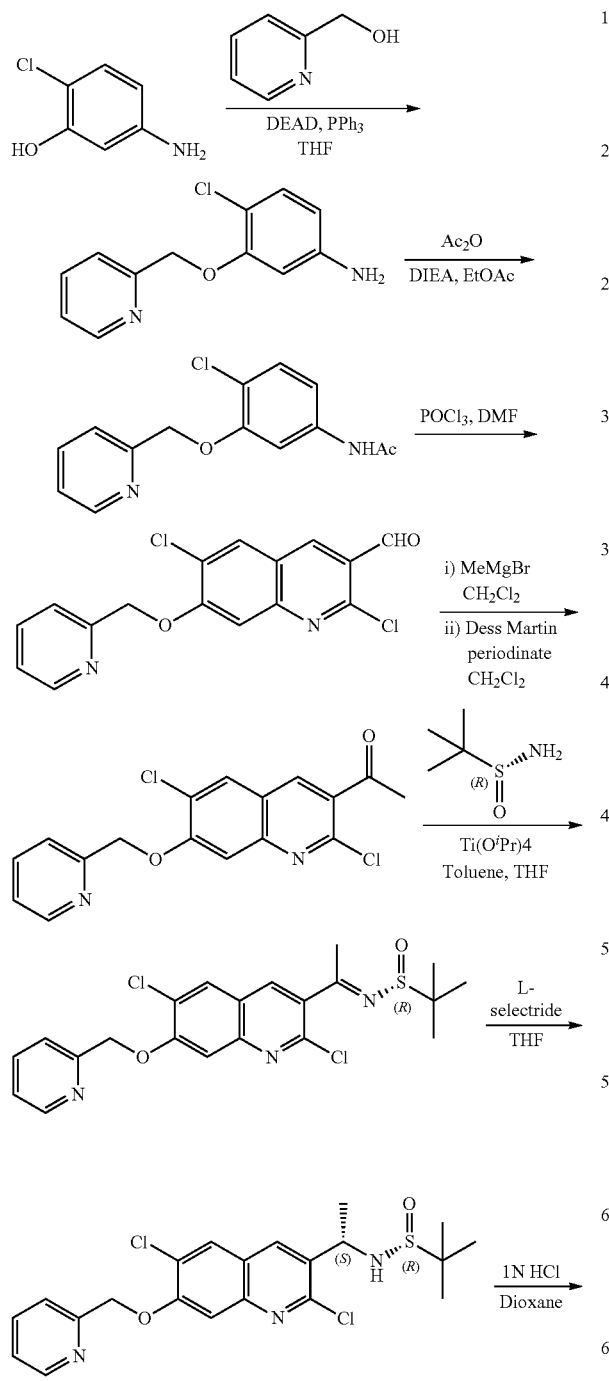

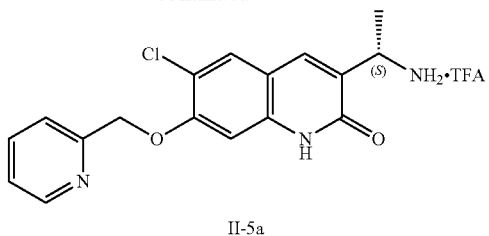

Step-1: 4-Chloro-3-(pyridin-2-ylmethoxy)aniline

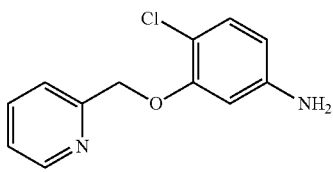 [SMILES: Nc1ccc(Cl)c(OCc2ccccn2)c1]

To a mixture of 5-amino-2-chlorophenol (10 g, 69.63 mmol), pyridin-2-ylmethanol (7.98 g, 73.13 mmol) and triphenylphosphine (21.5 g, 82.07 mmol) in THF (1.1 L) was added slowly diethylazadicarboxylate (DEAD) (13 mL, 82.07 mmol) at room temperature. The resulting mixture was stirred at room temperature for 24 hours. Upon completion of reaction, SiO$_2$ was added and solvents were evaporated to dryness. The crude product was purified by SiO$_2$ column chromatography eluted with 0-100% EtOAc-hexanes and then with 2% MeOH in EtOAc to afford the title compound (11.8 g, 72%) as an off-white solid. Note: The 4H NMR showed a small amount of triphenylphosphine oxide impurity. This material was used in the next step without further purification.

Step-2: N-(4-Chloro-3-(pyridin-2-ylmethoxy)phenyl)acetamide

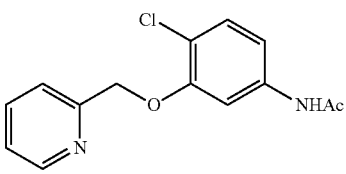 [SMILES: CC(=O)Nc1ccc(Cl)c(OCc2ccccn2)c1]

To a mixture of 4-chloro-3-(pyridin-2-ylmethoxy)aniline (11.8 g, 50.27 mmol) and diisopropylethylamine (DIEA) (9.93 mL, 57.81 mmol) in ethyl acetate (250 mL) was added acetic anhydride (Ac$_2$O) (5.22 mL, 55.3 mmol). The resulting mixture was stirred overnight at ambient temperature. The mixture was diluted with EtOAc (1 L), and washed with water (200 mL). The organic layer was dried over anhydrous Na$_2$SO$_4$, filtered, and evaporated to dryness. The resulting residue was triturated with hexanes-dichloromethane to afford the title compound as white solid (11.62 g, 84% yield).

Step-3: 2,6-Dichloro-7-(pyridin-2-ylmethoxy)quinoline-3-carbaldehyde

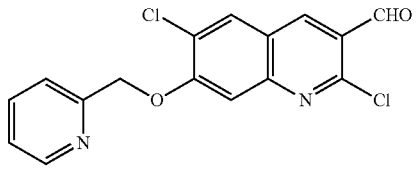 [SMILES: O=Cc1cc2cc(Cl)c(OCc3ccccn3)cc2nc1Cl]

Dimethylformamide (4 mL, 51.6 mmol) was placed in a 150 mL sealed tube and cooled to 0° C. To the DMF was added phosphorous oxychloride (POCl₃) (15.6 mL, 168 mmol) dropwise over 30-40 minutes. The resulting mixture was warmed to room temperature and N-(4-chloro-3-(pyridin-2-ylmethoxy)phenyl)acetamide (4.34 g, 15.68 mmol) was added. The reaction mixture was heated at 80° C. overnight. The mixture was then cooled to room temperature and carefully quenched with ice. The solution turned red and a yellow precipitate was formed, filtered, washed with water and dried over P₂O₅ overnight to afford the title compound as yellow solid (3.53 g, 68% yield).

Step-4: 1-(2,6-Dichloro-7-(pyridin-2-ylmethoxy)quinolin-3-yl)ethanone

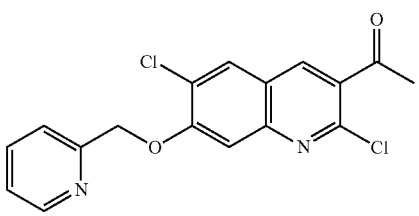 [SMILES: CC(=O)c1cc2cc(Cl)c(OCc3ccccn3)cc2nc1Cl]

To a solution of 2,6-dichloro-7-(pyridin-2-ylmethoxy)quinoline-3-carbaldehyde (1.0 g, 3.0 mmol) in CH₂Cl₂ (40 mL) was added dropwise methyl magnesium bromide (MeMgBr) (3 M solution in diethyl ether, 1.5 mL, 4.50 mmol) at 0° C. The resulting mixture was then stirred at ambient temperature for 1.5 hours. Upon completion of reaction, the mixture was slowly quenched with water (3 mL) and extracted with CH₂Cl₂ (50 mL). The organic layer was separated and dried over anhydrous Na₂SO₄. The solvents were evaporated to dryness. The resulting residue was dissolved in CH₂Cl₂ (25 mL) and treated with Dess-Martin Periodinate (2.54 g, 6.00 mmol). The mixture was stirred at ambient temperature overnight. The mixture was then quenched with an aqueous co-solution of 20% NaHCO₃ and 20% Na₂S₂O₃ (10 mL) and stirred for 5 minutes at room temperature. The solution was extracted with CH₂Cl₂ (40 mL), dried over anhydrous Na₂SO₄, filtered and evaporated. The resulting residue was purified by column chromatography on an ISCO® chromatography system (SiO₂ column: eluted with CH₂C₂ iMeOH 0 to 10%) to afford the title compound (800 mg, 79%).

Step-5: (R,E)-N-(1-(2,6-dichloro-7-(pyridin-2-ylmethoxy)quinolin-3-yl)etlylidene)-2-methylpropane-2-sulfinamide

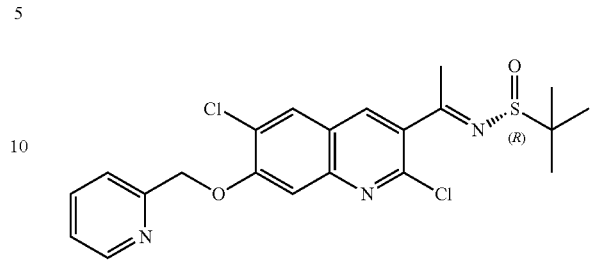

To a mixture of 1-(2,6-dichloro-7-(pyridin-2-ylmethoxy)quinolin-3-yl)ethanone (2.18 g, 6.56 mmol) and (R)-2-methylpropane-2-sulfinamide (1.19 g, 9.84 mmol) in THF:Toluene (40 mL:180 mL), was added titanium (IV) isopropoxide (Ti(O$^i$Pr)₄) (3.96 mL, 13.30 mmol). The resulting mixture was refluxed with a Dean-Stark apparatus for 7 hours. The mixture was then cooled to room temperature, quenched with water, and diluted with EtOAc (300 mL). The organic layer was washed with water (100 mL), dried over anhydrous Na₂SO₄, filtered and evaporated to dryness. The resulting residue was purified by column chromatography on an ISCO® chromatography system (SiO₂ column: eluted with Hex/EtOAc 0 to 100%) to afford the title compound as yellow solid (1.4 g, 50% yield). The starting material ketone was also recovered (250 mg, 11% yield).

Step-6: (R)—N—((S)-1-(2,6-dichloro-7-(pyridin-2-ylmethoxy)quinolin-3-yl)ethyl)-2-methyl propane-2-sulfinamide

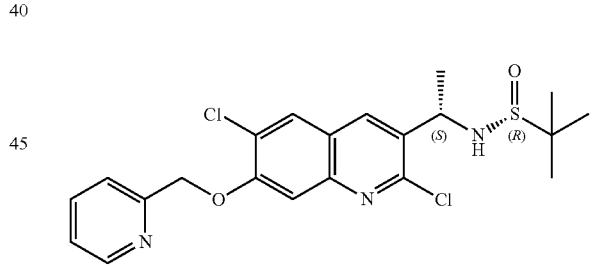

To a solution of (R,E)-N-(1-(2,6-dichloro-7-(pyridin-2-ylmethoxy)quinolin-3-yl)ethylidene)-2-methyl propane-2-sulfinamide (900 mg, 1.99 mmol) in THF (25 mL) at −40 to −50° C. was added L-selectride (1M in THF, 1.98 mL, 2.59 mmol) dropwise. The resulting mixture was stirred at −40 to −50° C. for 2 hours. Upon completion of reaction, the mixture was quenched with ice at −50° C., extracted with EtOAc (100 mL), dried, and evaporated. The resulting residue was purified by column chromatography on an ISCO® chromatography system (SiO₂ column: Hex/EtOAc 0 to 100%) followed by trituration with hexanes-methylene chloride to afford the title compound (266 mg, 30% yield).

Step-7: (S)-3-(1-Aminoethyl)-6-chloro-7-(pyridin-2-ylmethoxy)quinolin-2(1H)-one TFA Salt (II-5a)

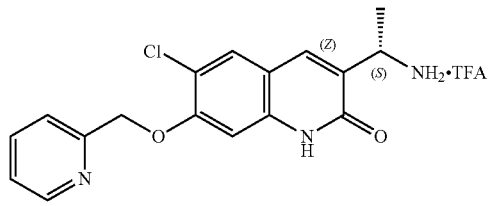

To a mixture of (R)—N—((S)-1-(2,6-dichloro-7-(pyridin-2-ylmethoxy)quinolin-3-yl)ethyl)-2-methylpropane-2-sulfinamide (1.1 g, 2.43 mmol) in 1,4-dioxane (6.6 mL), was added aqueous 1N HCl (6.6 mL) at room temperature. The resulting mixture was heated to 120° C. overnight. After TLC and MS showed completion of reaction, the solvents were removed on a rotary evaporator and lyophilized to provide yellow solid. The crude solid was purified by reverse phase chromatography on an ISCO® chromatography system (C18 column: eluted with $H_2O$/MeCN/0.1% $CF_3CO_2H$ 0 to 100%) and the fractions were monitored by LCMS. The pure fractions were combined and lyophilized to afford the title compound II-5a (920 mg, 86% yield) as the TFA salt. $^1$H NMR (300 MHz, DMSO-$d_6$): δ 12.17 (br s, 1H), 8.62 (d, J=4.95 Hz, 1H), 8.09 (br s, 2H), 7.96-7.85 (m, 3H), 7.59 (d, J=7.9 Hz, 1H), 7.42-7.37 (m, 1H), 7.08 (d, J=2.5 Hz, 1H), 5.33 (s, 2H), 4.39-4.38 (m, 1H), 1.51 (d, J=6.8 Hz, 3H). LCMS (method 3): Rt 3.3 min, m/z 329.1 [M+H]$^+$.

Example 11—Intermediate II-6: (S)-3-(1-aminoethyl)-6-chloro-1,8-naphthyridin-2(1H)-one

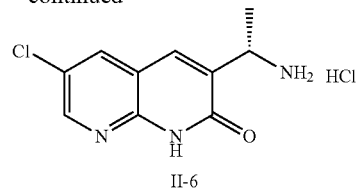

II-6

Step-1: 3-acetyl-6-chloro-1,8-naphthyridin-2(1H)-one

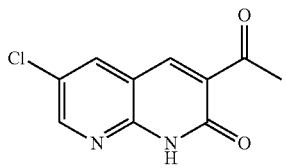

A mixture of 2-amino-5-chloronicotinaldehyde (1 g, 6.39 mmol) and 2,2,6-trimethyl-4H-1,3-dioxin-4-one (1.362 g, 9.58 mmol) in xylenes (10 mL) was heated to reflux for 3 hours, and then cooled to room temperature, filtered, and washed with xylenes twice to afford 914 mg of 3-acetyl-6-chloro-1,8-naphthyridin-2(1H)-one (64.3% yield). $^1$H NMR (300 MHz, DMSO-$d_6$): δ 12.68 (br, 1H), 8.63 (s, 1H), 8.49 (s, 1H), 8.39 (s, 1H), 2.48 (s, 3H). LCMS (Method 1): Rt 1.60 min, m/z 223.03 [M+H]$^+$.

Step-2: (S)—N—((S)-1-(2,6-dichloroquinolin-3-yl)ethyl)-2-methylpropane-2-sulfinamide

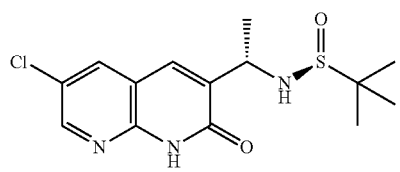 [SMILES: C[C@H](N[S@@](=O)C(C)(C)C)c1cc2cc(Cl)cnc2[nH]c1=O]

A mixture of tetraethoxytitanium (512 mg, 2.25 mmol), (R)-2-methylpropane-2-sulfinamide (163 mg, 1.35 mmol) and 3-acetyl-6-chloro-1,8-naphthyridin-2(1H)-one (200 mg, 0.898 mmol) in THF (15 mL) was heated to 80° C. overnight, and then cooled to room temperature. To this mixture was added NaBH$_4$ (170 mg, 4.49 mmol) and the mixture was slowly warmed up to room temperature overnight. MeOH was then added to quench any excess NaBH$_4$, followed by the addition of water. The mixture was filtered to remove solids, then extracted with EtOAc twice, dried over Na$_2$SO$_4$, and concentrated. The residue was purified on a Biotage® chromatography system using a 25 g SiO$_2$ column eluted on a gradient (first 20% to 100% EtOAc/Hexanes, then 0-5% MeOH/DCM) to afford (S)—N—((S)-1-(2,6-dichloroquinolin-3-yl)ethyl)-2-methylpropane-2-sulfinamide (123 mg, 42% yield). $^1$H NMR (300 MHz, DMSO-$d_6$): δ 8.40 (s, 1H), 7.74 (s, 1H), 7.75 (s, 1H), 7.24 (s, 1H), 5.24 (d, J=9.45 Hz, 1H), 4.42 (m, 3H), 1.54 (d, J=6.93 Hz, 3H), 1.20 (s, 9H). LCMS (Method 1): Rt 2.07 min, m/z 328.98 [M+H]$^+$.

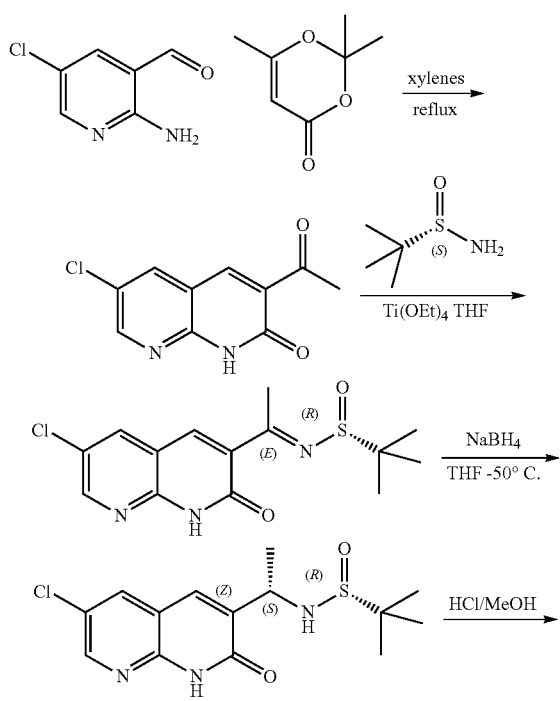

Step-3: (S)-3-(1-aminoethyl)-6-chloro-1,8-naphthyridin-2(1H)-one (II-6)

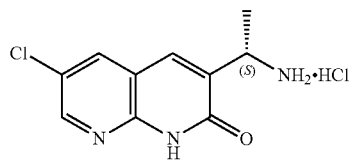

To a solution of ((S)—N—((S)-1-(6-chloro-2-oxo-1,2-dihydro-1,8-naphthyridin-3-yl)ethyl)-2-methylpropane-2-sulfinamide (123 mg, 0.375 mmol) in MeOH (5 mL) was added HCl (2 mL, 8.00 mmol, 4M in 1,4-dioxane). The mixture was then stirred at room temperature overnight. To this mixture was added 6 mL of ethyl ether and the resulting precipitate was filtered, washed with ethyl ether (2×), dried and concentrated to afford (S)-3-(1-aminoethyl)-6-chloro-1,8-naphthyridin-2(1H)-one, HCl (96 mg, 98% yield). $^1$H NMR (300 MHz, DMSO-$d_6$): δ 12.75 (br s, 1H), 8.60-8.35 (s, 1H), 8.26 (br, 1H) 8.07 (s, 1H), 4.40-4.50 (m, 1H), 1.51 (d, J=6.78 Hz, 3H). LCMS (Method 1): Rt 0.87 min, m/z 224.99 [M+H]$^+$.

Example 12—Intermediate II-7a: (R)-3-(1-aminoethyl)-6-chloroquinoxalin-2(1H)-one

Step-1: Ethyl 3-((4-chloro-2-nitrophenyl)amino)-3-oxopropanoate

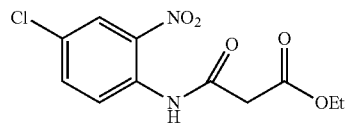 [SMILES: CCOC(=O)CC(=O)Nc1ccc(Cl)cc1[N+](=O)[O-]]

To a solution of 4-chloro-2-nitroaniline (42.3 g, 245 mmol) in CH$_2$Cl$_2$ (1 L) was added ethyl 3-chloro-3-oxopropanoate (48 g, 319 mmol) dropwise and the reaction mixture was stirred at room temperature overnight. The solvent was removed under vacuum and the resulting residue was dissolved in a minimum amount of MTBE (200 mL) and hexanes (800 mL) which was slowly added. Any product that precipitated out from solution was filtered and the filtrate was concentrated and purified by column chromatography ISCO® chromatography system with hexanes/ethyl acetate gradient elution to afford additional desired product. The title compound was obtained in 98% yield (69.85 g).

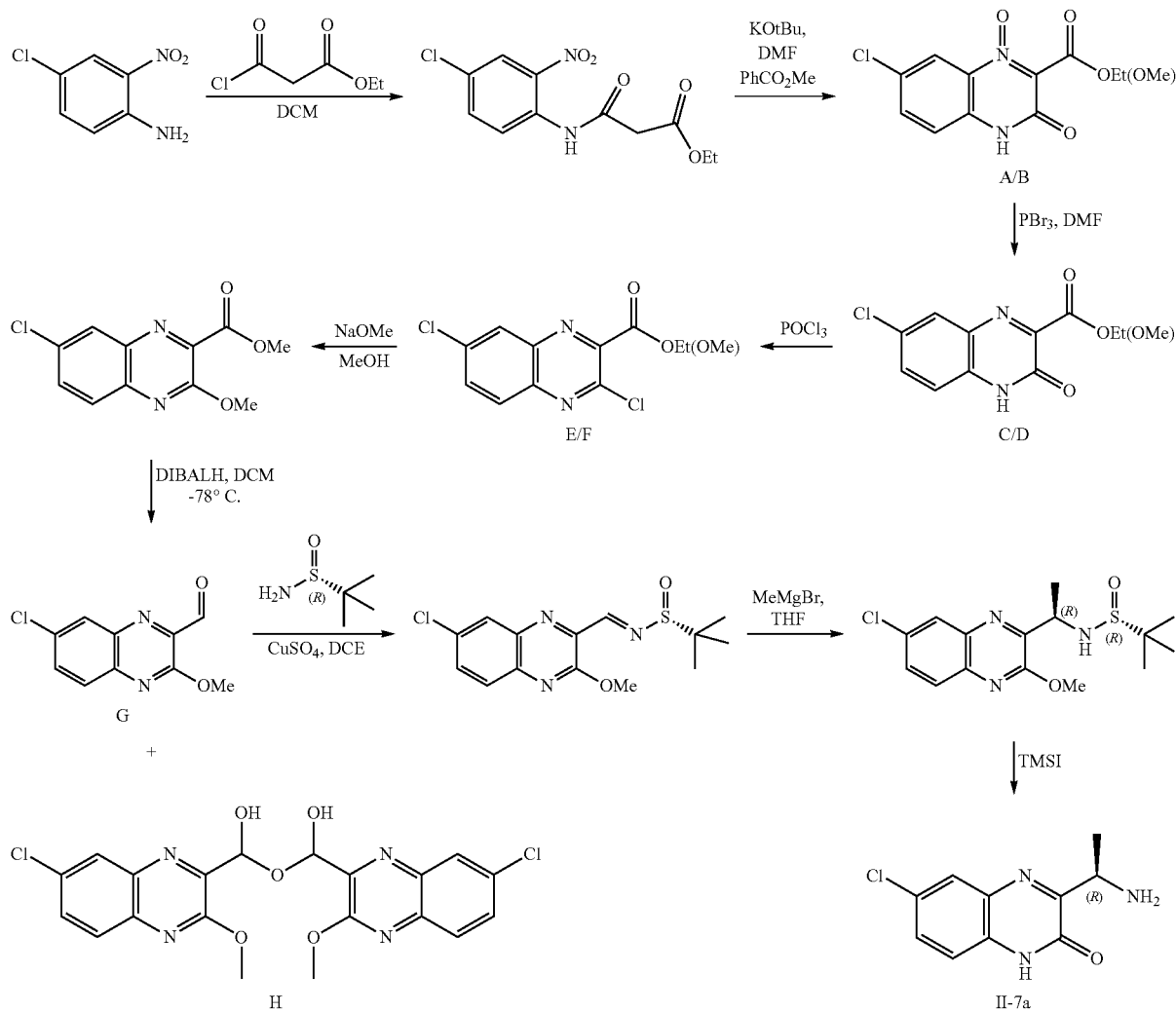

Step-2: 7-Chloro-2-(ethoxycarbonyl)-3-oxo-3,4-dihydroquinoxaline 1-oxide (A) and 7-Chloro-2-(methoxycarbonyl)-3-oxo-3,4-dihydroquinoxaline 1-oxide (B)

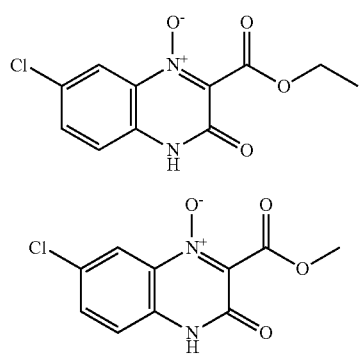

To a solution of ethyl 3-((4-chloro-2-nitrophenyl)amino)-3-oxopropanoate (68 g, 238 mmol) and methyl benzoate (150 mL) in anhydrous DMF (500 mL) at 0° C. was added dropwise KO$^t$Bu (1M solution in THF, 500 mL, 500 mmol). The reaction mixture was stirred at 0° C. for 4 hours and then quenched with saturated NH$_4$Cl aqueous solution. The mixture was extracted with CH$_2$Cl$_2$ (300 mL×3). The combined organic layers were dried (Na$_2$SO$_4$), concentrated, and purified by SiO$_2$ flash chromatography and eluted with CH$_2$Cl$_2$/MeOH to afford a mixture of A/B (42.54 g, 67% yield, A/B ratio 1:2) as a solid. This was used in the next step without further purification.

Step 3: Ethyl 7-chloro-3-oxo-3,4-dihydroquinoxaline-2-carboxylate (D) and methyl 7-chloro-3-oxo-3,4-dihydroquinoxaline-2-carboxylate (C)

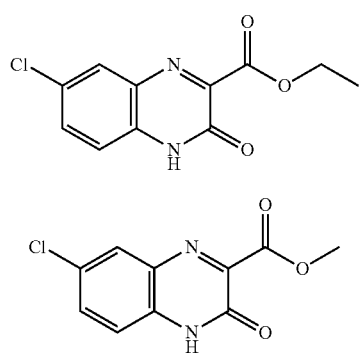

To a mixture of compounds A and B (42.54 g, 159 mmol) in DMF (200 mL) was added PBr$_3$ (85.9 g, 318 mmol) dropwise at room temperature. The reaction mixture was stirred at room temperature for 3 hours and was then quenched with ice water and extracted with CH$_2$Cl$_2$ (200 mL×3). The combined organic layers were dried (Na$_2$SO$_4$), concentrated, and purified by flash chromatography using CH$_2$Cl$_2$/MeOH (9:1) as eluent to afford C/D (36.6 g, 91% yield) as a solid. This was used in the next step without further purification.

Step-4: Ethyl 3,7-dichloroquinoxaline-2-carboxylate (E) and methyl 3,7-dichloro quinoxaline-2-carboxylate (F)

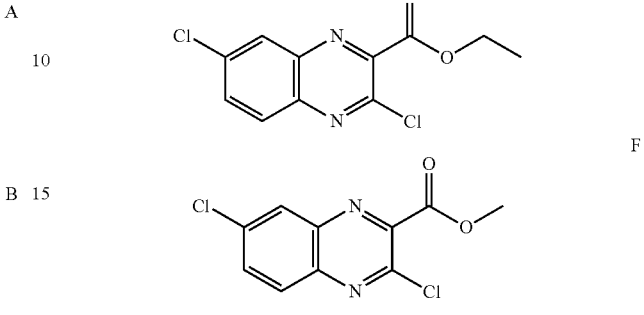

To a mixture of compounds C/D (36.6 g, 145 mmol) in a 1 L flask was added POCl$_3$ (150 mL) in one portion and the resulting mixture was refluxed for 3 hours. The mixture was then cooled to room temperature and carefully quenched with aqueous NaHCO$_3$ solution. The mixture was extracted with CH$_2$Cl$_2$ (200 mL×3). The combined organic layer was dried (Na$_2$SO$_4$), concentrated, and purified by SiO$_2$ flash chromatography using hexane/ethyl acetate (9:1) as eluent to afford E/F (23.7 g, 61% yield) as a solid. This mixture was used in the next step without further purification.

Step-5: Methyl 7-chloro-3-methoxyquinoxaline-2-carboxylate

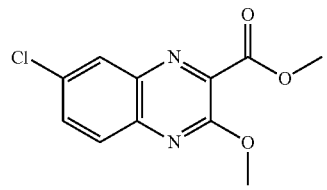 [SMILES: COC(=O)c1nc2cc(Cl)ccc2nc1OC]

To a mixture of compounds E/F (22.11 g, 81.9 mmol) in THF/MeOH (9:1, 300 mL) was added NaOMe (0.5 M, 360 mL) dropwise at 0° C. The resulting mixture was stirred at room temperature for 3 hours and quenched with solid NH$_4$Cl (20 g). The solvent was removed under vacuum and water was added (200 mL). The mixture was extracted with CH$_2$Cl$_2$ (150 mL×3) and the combined organic layers were dried (Na$_2$SO$_4$), concentrated, and purified by SiO$_2$ flash chromatography using hexanes/ethyl acetate (9:1) as eluent to afford the title compound (19.1 g, 88% yield) as a solid.

Step-6: 7-Chloro-3-methoxyquinoxaline-2-carbaldehyde (G) and oxybis((7-chloro-3-methoxyquinoxalin-2-yl)methanol) (H)

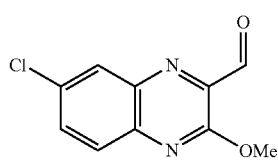

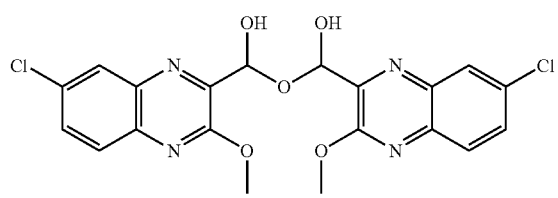

To methyl 7-chloro-3-methoxyquinoxaline-2-carboxylate (5.3 g, 20 mmol) in CH$_2$Cl$_2$ (250 mL) was added diisobutylaluminum hydride (1 M, 30 mL) drop-wise at −78° C. The resulting mixture was stirred at −78° C. for 3 hours and was then quenched with MeOH (at −78° C., 20 mL). After stirring for 0.5 hours, the mixture was warmed to room temperature and potassium sodium L-tartrate aqueous solution (100 mL) was added. The organic layer was then separated, and the aqueous layer was extracted with CH$_2$Cl$_2$ (50 mL×3). The combined organic layers were dried (Na$_2$SO$_4$), concentrated, and purified by SiO$_2$ flash chromatography using hexanes/ethyl acetate (1:1) as eluent to afford G (1.02 g, 23% yield) and H (2.24 g, 50% yield). The structure of H was assigned based on MS and $^1$H NMR.

Step-7: (R,E)-N-((7-chloro-3-methoxyqinoxalin-2-yl)methylene)-2-methylpropane-2-sulfinamide

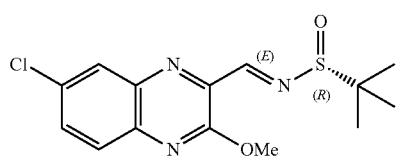

To compound H (2.24 g, 5.1 mmol) in DCE (300 mL) at room temperature was added (R)-2-methylpropane-2-sulfinamide (2.44 g, 20.1 mmol) and CuSO$_4$ (4.85 g, 30.3 mmol). The reaction was heated to 60° C. and stirred for 4 hours. The reaction mixture was then cooled to room temperature and quenched with 50 mL of saturated aqueous NaHCO$_3$ solution. After stirring for 10 minutes, the reaction mixture was filtered through a pad of Celite®. The filtrate was extracted with CH$_2$Cl$_2$ (50 mL×3), dried (Na$_2$SO$_4$), concentrated, and purified by column chromatography on an ISCO® chromatography system using hexanes/ethyl acetate as eluent to afford the title compound (2.21 g, 67% yield).

Step-8: (R)—N—((R)-1-(7-chloro-3-methoxyquinoxalin-2-yl)ethyl)-2-methylpropane-2-sulfinamide

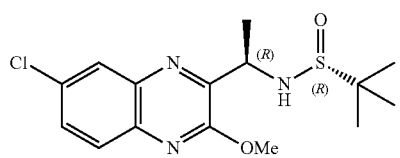

To (R,E)-N-((7-chloro-3-methoxyquinoxalin-2-yl)methylene)-2-methylpropane-2-sulfinamide (2.21 g, 6.8 mmol) in CH$_2$Cl$_2$ (150 mL) was added methyl magnesium chloride (MeMgCl) (3M in THF, 3.4 mL) dropwise at −78° C. The resulting mixture was stirred at −78° C. for 2 hours and was then quenched with aqueous NH$_4$Cl solution (20 mL). After stirring for 10 minutes, the organic layer was separated, and the aqueous layer was extracted with CH$_2$Cl$_2$ (25 mL×3). The combined organic layers were dried (Na$_2$SO$_4$), concentrated, and purified by column chromatography on an ISCO® chromatography system using hexanes/ethyl acetate as eluent to afford the title compound (1.18 g, 51% yield).

Step-9: (R)-3-(1-aminoethyl)-6-chloroquinoxalin-2(1H)-one (II-7a)

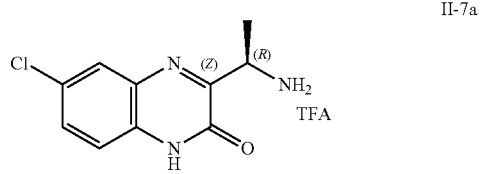

To the compound (R)—N—((R)-1-(7-chloro-3-methoxyquinoxalin-2-yl)ethyl)-2-methylpropane-2-sulfinamide (1.29 g, 3.46 mmol) in CH$_3$CN (100 mL) was added iodotrimethylsilane (3.46 g, 17.3 mmol) dropwise at 0° C. The mixture was then refluxed for 2 hours, cooled to room temperature, and quenched with MeOH (10 mL). The solvent was removed under vacuum, and the residue was purified by reverse C-18 chromatography on an ISCO® chromatography system using water (0.1% TFA)/CH$_3$CN (0.1% TFA) as eluent to afford the compound II-7a (1.22 g, 95% yield) as a TFA salt.

Example 13—Intermediate II-7b: (S)-3-(1-aminoethyl)-6-chloroquinoxalin-2(1H)-one

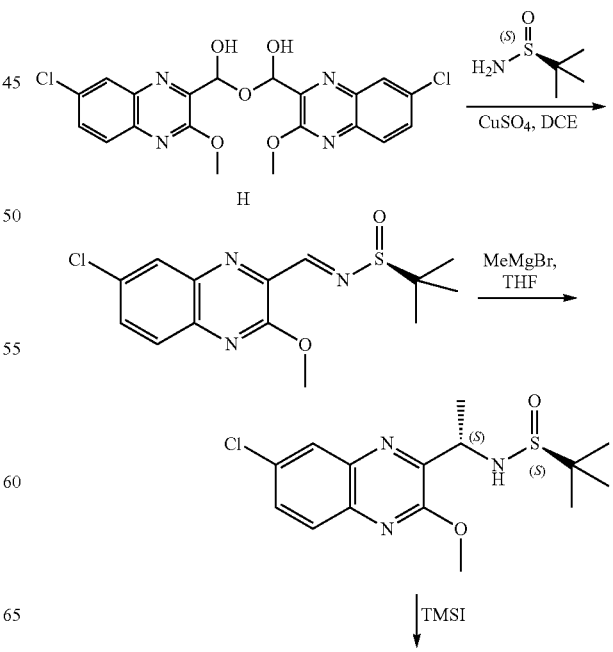

-continued

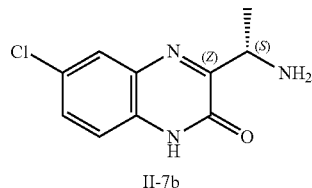

II-7b

Step-1: (S,E)-N-((7-chloro-3-methoxyquinoxalin-2-yl)methylene)-2-methylpropane-2-sulfinamide

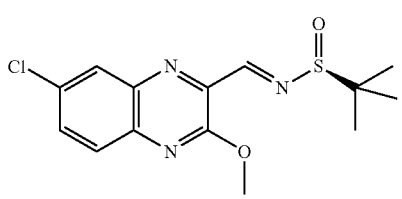 [SMILES: COc1nc2ccc(Cl)cc2nc1/C=N/[S@@](=O)C(C)(C)C]

To compound H (2.31 g, 5.2 mmol) in DCE (300 mL) at room temperature was added (S)-2-methylpropane-2-sulfinamide (2.52 g, 20.8 mmol) and CuSO$_4$ (5.0 g, 31.2 mmol). The resulting reaction mixture was heated to 60° C. and stirred for 4 hours. The reaction mixture was then cooled to room temperature and quenched with 50 mL of saturated aqueous NaHCO$_3$ solution. After stirring for 10 minutes, the mixture was filtered through a pad of Celite®. The filtrate was extracted with CH$_2$Cl$_2$ (50 mL×3), dried (Na$_2$SO$_4$), concentrated, and purified by column chromatography on an ISCO® chromatography system using hexanes/ethyl acetate as eluent to afford the title compound (2.62 g, 78% yield).

Step-2: (S)—N—((S)-1-(7-chloro-3-methoxyquinoxalin-2-yl)ethiyl)-2-methylpropane-2-sulfinamide

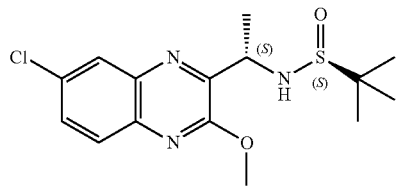

To compound (S,E)-N-((7-chloro-3-methoxyquinoxalin-2-yl)methylene)-2-methylpropane-2-sulfinamide (2.62 g, 8.0 mmol) in CH$_2$Cl$_2$ (150 mL) was added methyl magnesium chloride (MeMgCl) (3M in THF, 4.0 mL) dropwise at −78° C. The resulting mixture was stirred at −78° C. for 2 hours and was then quenched with aqueous NH$_4$Cl solution (20 mL). After stirring for 10 minutes, the organic layer was separated, and the aqueous layer was extracted with CH$_2$Cl$_2$ (25 mL×3). The combined organic layers were dried (Na$_2$SO$_4$), concentrated, and purified by column chromatography on an ISCO® chromatography system using hexanes/ethyl acetate as eluent to afford the title compound (1.69 g, 62%).

Step-14: (S)-3-(1-aminoethyl)-6-chloroquinxaioxalin-2(1H)-one (II-7b)

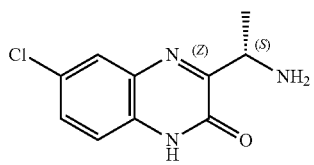

To the compound (S)—N—((S)-1-(7-chloro-3-methoxyquinoxalin-2-yl)ethyl)-2-methylpropane-2-sulfinamide (350 mg, 1.03 mmol) in CH$_3$CN (40 mL) was added iodotrimethylsilane (1.03 g, 5.15 mmol) dropwise at 0° C. The mixture was then refluxed for 2 hours. After it was cooled to room temperature, the reaction was quenched with MeOH (2 mL). The solvent was removed under vacuum, and the residue was purified by reverse C-18 chromatography on an ISCO® chromatography system using water (0.1% TFA)/CH$_3$CN (0.1% TFA) as eluent to afford the title compound (267 mg, 79% yield) as a TFA salt.

Example 14—Intermediate II-8: (3-((S)-1-aminoethyl)-6-chloro-7-((R)-1-(pyridin-2-yl)ethoxy)quinolin-2(1H)-one

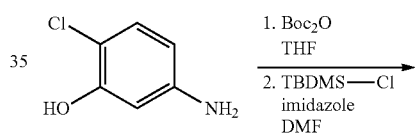

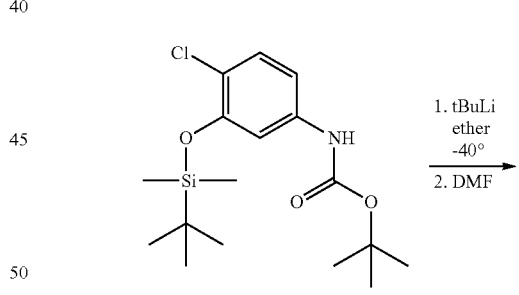

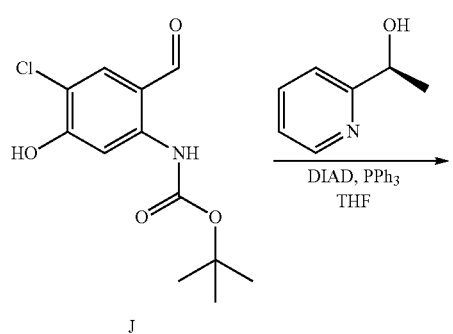

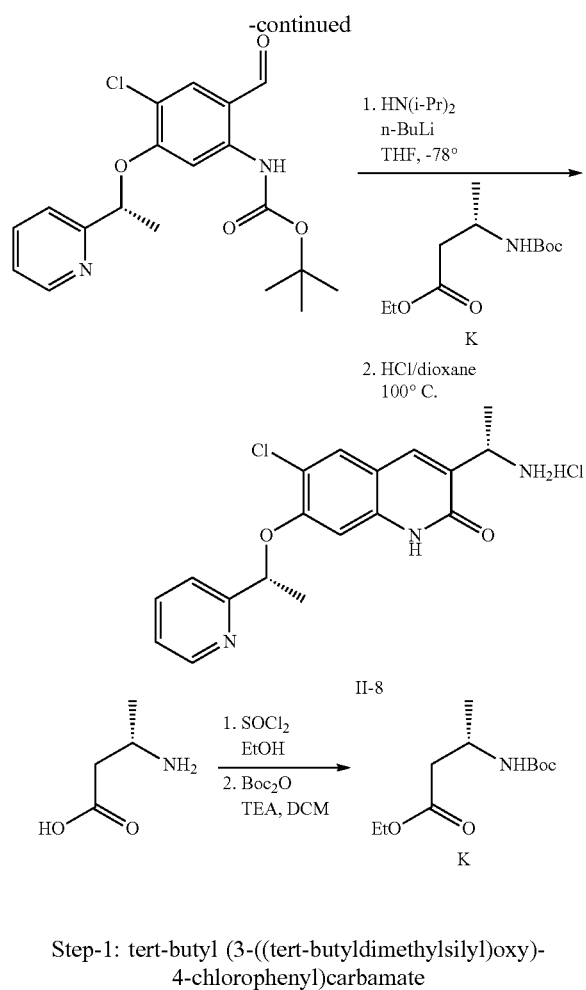

Step-1: tert-butyl (3-((tert-butyldimethylsilyl)oxy)-4-chlorophenyl)carbamate A solution of 5-amino-2-chlorophenol (10.00 g, 69.7 mmol) in THF (350 mL) was treated with di-tert-butyl dicarbonate (20 mL, 86 mmol) and stirred at reflux overnight. The solvent was evaporated under reduced pressure to provide a brown oil. The oil was then dissolved in EtOAc (300 mL), washed with water, saturated aqueous NaHCO₃, and brine (300 mL each), dried (Na₂SO₄), filtered, and evaporated under reduced pressure to provide 21.01 g of impure tert-butyl (4-chloro-3-hydroxyphenyl)carbamate as a brown oil (LCMS: m/z 244 [M+H]⁺). This material was dissolved in DMF (130 mL) and cooled on an ice bath. Imidazole (11.74 g, 172 mmol) was then added slowly (over ~10 minutes). A solution of TBDMS-Cl (14.98 g, 99 mmol) in DMF (45 mL) was added (over ~2 minutes). The ice bath was removed and the solution was stirred at room temperature overnight. Once LCMS indicated the reaction had gone to completion, the solution was diluted with EtOAc (1 L) and washed with water (2×600 mL), half-saturated aqueous NaHCO₃ (600 mL), half-saturated aqueous NH₄Cl (600 mL), saturated NaHCO₃ (600 mL), and brine (600 mL). The organic layer was dried (MgSO₄), filtered, and evaporated under reduced pressure to provide 28.00 g of a brown solid. The sample was dissolved in EtOAc, silica gel (33 g) was added, and the solvent was evaporated under reduced pressure. The material was divided into two batches, each of which was purified by column chromatography on a Biotage® MPLC chromatography system using a 330 g silica gel column eluted with 0 to 5% EtOAc in hexanes and with isocratic elution at 4.5% or 5% EtOAc when the product eluted. The product fractions were collected and provided 21.76 g of tert-butyl (3-((tert-butyldimethylsilyl)oxy)-4-chlorophenyl)carbamate (21.76 g, 60.8 mmol, 88% yield) as a peach-colored solid. ¹H NMR (300 MHz, DMSO-d₆): δ ppm 9.43 (s, 1H), 7.23-7.28 (m, 1H), 7.22 (d, J=2.35 Hz, 1H), 7.09-7.16 (m, 1H), 1.46 (s, 9H), 0.99 (s, 9H), 0.21 (s, 6H). LCMS (Method 1): m/z 358 [M+H]⁺.

Step-2: tert-butyl (4-chloro-2-formyl-5-hydroxyphenyl)carbamate (J)

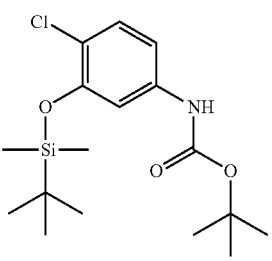 [SMILES: CC(C)(C)OC(=O)Nc1ccc(Cl)c(O[Si](C)(C)C(C)(C)C)c1]

An oven-dried 3-necked 500 mL round bottom flask was charged with tert-butyl (3-((tert-butyldimethyl silyl)oxy)-4-chlorophenyl)carbamate (10 g, 27.9 mmol). An oven-dried addition funnel was attached, and the system was flushed with nitrogen. Ethyl ether (113 mL) was added by syringe. The resulting yellow solution was cooled on an acetonitrile/dry ice bath (to approximately −40° C.). t-BuLi (1.7 M in pentane, 40 mL, 68.0 mmol) was then added to the addition funnel by cannula. The t-BuLi solution was added dropwise to the ether solution (over ~10 minutes), during which time the ether solution gradually became cloudy with a precipitate. The mixture was stirred at about −40° C. for 2.5 hours, and then DMF (11 mL) was added dropwise by syringe (over ~10 minutes), during which time the solids went back into solution. The acetonitrile/dry ice bath was replaced with an ice bath, and the yellow solution was stirred at 0° C. for 1.75 hours. The reaction was then quenched by dropwise addition of water (25 mL), resulting in formation of an orange precipitate. The ice bath was removed and the sample was diluted with water (125 mL), resulting in dissolution of the precipitate. The mixture was shaken, and the layers were separated. The aqueous layer was acidified to pH ~4-5 with AcOH. The resulting precipitate was extracted with EtOAc (200 mL), washed with water (2×100 mL), dried (Na₂SO₄), filtered, and evaporated under reduced pressure to provide tert-butyl (4-chloro-2-formyl-5-hydroxyphenyl)carbamate as a yellow solid (4.79 g, 17.63 mmol, 63% yield). ¹H NMR (300 MHz, DMSO-d₆): δ ppm 11.72 (s, 1H), 10.50 (s, 1H), 9.68 (br s, 1H), 7.99 (s, 1H), 7.88-7.91 (m, 1H), 1.48 (s, 9H). LCMS (Method 1): m/z 216 (M-56, loss of t-Bu).

Step-3: (R)-tert-butyl (4-chloro-2-formyl-5-(1-(pyridin-2-yl)ethoxy)phenyl)carbamate

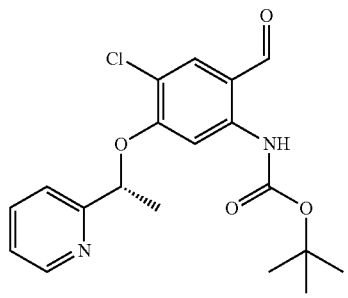 [SMILES: C[C@@H](Oc1cc(NC(=O)OC(C)(C)C)c(C=O)cc1Cl)c1ccccn1]

A mixture of (S)-1-(pyridin-2-yl)ethanol (454.3 mg, 3.69 mmol), tert-butyl (4-chloro-2-formyl-5-hydroxyphenyl)carbamate (1 g, 3.68 mmol) and triphenylphosphine (1.158 g, 4.42 mmol) was placed in a 100 mL round bottom flask under an atmosphere of nitrogen. THF (40 mL) was added by syringe. The resulting yellow solution was cooled on an ice bath and then DIAD (0.86 mL, 4.42 mmol) was added dropwise. The ice bath was removed and the solution was stirred at room temperature overnight. Once LCMS indicated the reaction had gone to completion, silica gel was added and the solvent was evaporated under reduced pressure. The sample was purified by column chromatography on a Biotage® MPLC chromatography system (using a 50 g silica gel column eluted with 0 to 13% EtOAc in hexanes) to provide 473.7 mg of a white solid. LCMS and NMR are consistent with (R)-tert-butyl (4-chloro-2-formyl-5-(1-(pyridin-2-yl)ethoxy)phenyl)carbamate contaminated with phenolic starting material (~5:1 product to starting material by NMR). The material was used for next step without further purification. $^1$H NMR (300 MHz, DMSO-$d_6$): δ ppm 10.42 (s, 1H), 9.73 (s, 1H), 8.54-8.60 (m, 1H), 7.98 (s, 1H), 7.92 (s, 1H), 7.82 (ddd, J=7.80, 7.80, 1.80 Hz, 1H), 7.44 (br d, J=7.90 Hz, 1H), 7.30-7.36 (m, 1H), 5.64 (q, J=6.35 Hz, 1H), 1.67 (d, J=6.45 Hz, 3H), 1.46 (s, 9H). LCMS (Method 1): m/z 377 [M+H]$^+$.

Step-4: (S)-ethyl 3-((tert-butoxycarbonyl)amino)butanoate (K)

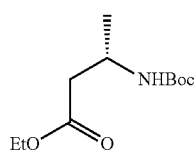 [SMILES: CCOC(=O)C[C@H](C)NC(=O)OC(C)(C)C]

A suspension of (S)-3-aminobutanoic acid (6.25 g, 60.6 mmol) in EtOH (27.5 mL) was cooled on an ice bath. Thionyl chloride (7.5 mL, 103 mmol) was then added dropwise over 40 minutes, during which time the amino acid went into solution. The ice bath was allowed to melt, and the solution was stirred at room temperature overnight. The mixture was evaporated under reduced pressure, and the residue was mixed with more EtOH (60 mL) and again evaporated under reduced pressure to provide an oil. The oil was dissolved in DCM (55 mL) and cooled on an ice bath. TEA (25 mL, 179 mmol) was added dropwise over 15 minutes with stirring, resulting in a milky mixture. Di-tert-butyl dicarbonate (17 mL, 73.2 mmol) was then added. The ice bath was allowed to melt, and the mixture was stirred at room temperature for five days. The resulting mixture was filtered through Celite® 545 on a Buchner funnel, and the filter cake was washed with DCM (50 mL). The filtrate was washed with saturated aqueous citric acid (20 mL) and water (2×100 mL), dried (MgSO$_4$), filtered, and evaporated under reduced pressure to provide the title compound as a clear oil. $^1$H NMR is consistent with (S)-ethyl 3-((tert-butoxycarbonyl)amino)butanoate (13.47 g, 58.2 mmol, 96% yield). $^1$H NMR (300 MHz, CDCl$_3$): δ ppm 4.95 (br s, 1H), 4.15 (q, J=7.13, 2H), 3.98-4.10 (m, 1H), 2.40-2.57 (m, 2H), 1.44 (s, 9H), 1.27 (t, J=7.18, 3H), 1.22 (d, J=6.74, Hz, 3H).

Step-5 & 6: 3-((S)-1-aminoethyl)-6-chloro-7-((R)-1-(pyridin-2-yl)ethoxy)quinolin-2(1H)-one hydrochloride (II-8)

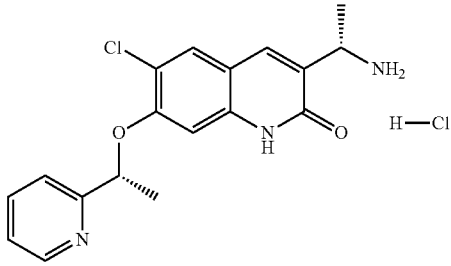

An oven-dried 25 mL round bottom flask and stir bar were placed under an atmosphere of nitrogen. THF (2.25 mL) and diisopropylamine (0.27 mL, 1.894 mmol) were then added by syringe. The solution was cooled using a dry ice/acetone bath (−78° C.) and n-BuLi (1.6 M in hexane, 1.15 mL, 1.84 mmol) was added dropwise over 5 minutes. After stirring for 10 minutes, a solution of (S)-ethyl 3-((tert-butoxycarbonyl)amino)butanoate K (115.3 mg, 0.499 mmol) in THF (0.5 mL) was added dropwise (over 5 minutes). The solution was stirred for 75 minutes at −78° C. and then a solution of (R)-tert-butyl (4-chloro-2-formyl-5-(1-(pyridin-2-yl)ethoxy)phenyl)carbamate (188.7 mg, 0.501 mmol) in THF (1.0 mL) was added dropwise by syringe. The reaction solution became yellow when the aldehyde was added. The reaction was stirred at −78° C. for 13 minutes and then quenched by the addition of saturated aqueous NH$_4$Cl solution (2.5 mL). The mixture was partitioned between EtOAc and water (10 mL each). The organic layer was dried (MgSO$_4$), filtered, and evaporated under reduced pressure to provide an impure mixture of isomers of (3S)-ethyl 3-((tert-butoxycarbonyl)amino)-2-((2-((tert-butoxycarbonyl)amino)-5-chloro-4-((R)-1-(pyridin-2-yl)ethoxy)phenyl)(hydroxy)methyl) butanoate as a yellow oil (344.8 mg; LCMS: m/z+608 [M+H]$^+$). The crude material (334 mg) was dissolved in 1,4-dioxane (5 mL), treated with 12M aqueous HCl (0.125 mL), and stirred at 110° C. for 90 minutes, during which time a red material precipitated. The mixture was allowed to cool and the supernatant was decanted and discarded. Heptane (~4 mL) was added to the red precipitate remaining in the round bottom and then evaporated under reduced pressure to provide 161.8 mg of a red solid. The material was triturated with $^i$PrOH (5 mL) and the resulting precipitate was collected on a Hirsch funnel and washed with $^i$PrOH (1 mL) and ethyl ether (~20 mL) to provide 3-((S)-1-aminoethyl)-6-chloro-7-((R)-1-(pyridin-2-yl)ethoxy)quinolin-2(1H)-one hydrochloride (104.2 mg, 0.274 mmol, 55% yield) as a red solid, impure but suitable for use as it is. $^1$H NMR (300 MHz, Methanol-$d_4$): δ ppm 8.81-8.87

(m, 1H), 8.55-8.64 (m, 1H), 8.18 (d, J=7.92 Hz, 1H), 7.96-8.04 (m, 1H), 7.95 (s, 1H), 7.85 (s, 1H), 6.99 (s, 1H), 5.98 (q, J=6.84 Hz, 1H), 4.48 (q, J=6.84 Hz, 1H), 1.86 (d, J=6.45 Hz, 3H), 1.64 (d, J=6.74 Hz, 3H). LCMS (Method 1): m/z 344 [M+H]$^+$.

Example 15—Intermediate II-9: (S)-3-(1-aminoethyl)-6-chloro-7-(cyclopropylmethoxy) quinolin-2(1H)one

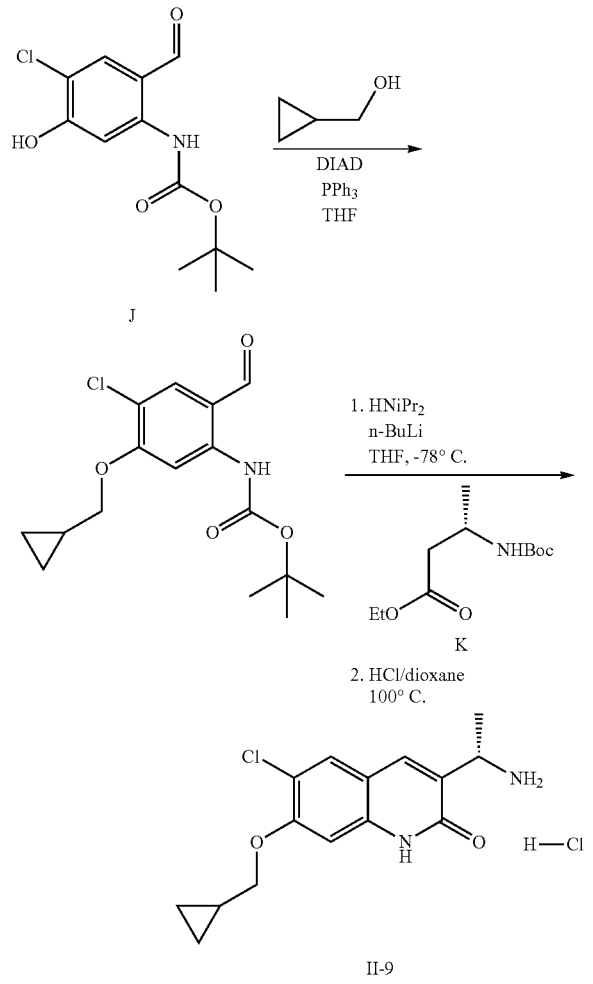

Step-1: tert-butyl (4-chloro-5-(cyclopropylmethoxy)-2-formylphenyl)carbamate.

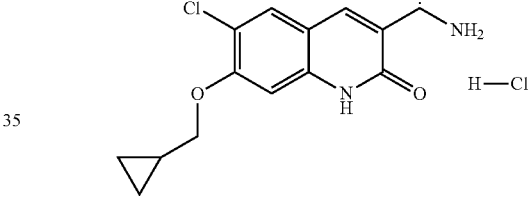

A mixture of cyclopropylmethanol (0.145 mL, 1.838 mmol), tert-butyl (4-chloro-2-formyl-5-hydroxyphenyl)carbamate J (499.4 mg, 1.838 mmol) and triphenylphosphine (579.4 mg, 2.209 mmol) was placed in a 100 mL round bottom flask under an atmosphere of nitrogen and THF (20 mL) was then added by syringe. The resulting orange solution was cooled on an ice bath and DIAD (0.43 mL, 2.184 mmol) was added dropwise. The ice bath was removed and the solution was stirred at room temperature for 48 hours. Once LCMS indicated the reaction had gone to completion, silica gel was added and the solvent was evaporated under reduced pressure. The sample was purified by column chromatography on a Biotage® MPLC chromatography system using a 25 g silica gel column eluted with 0 to 3% EtOAc in hexanes to provide tert-butyl (4-chloro-5-(cyclopropylmethoxy)-2-formylphenyl)carbamate (410.6 mg, 1.260 mmol, 68.6% yield) as a yellowish solid. $^1$H NMR (300 MHz, DMSO-d$_6$): δ ppm 10.57 (s, 1H), 9.75 (s, 1H), 7.95-8.00 (m, 2H), 4.02 (d, J=7.04 Hz, 2H), 1.49 (s, 9H), 1.23-1.31 (m, 1H), 0.57-0.66 (m, 2H), 0.38-0.46 (m, 2H). LCMS (Method 1): m/z 270 (loss of t-Bu).

Step-2 & 3: (S)-3-(1-aminoethyl)-6-chloro-7-(cyclopropylmethoxy)quinolin-2(1H)-one hydrochloride (II-9)

An oven-dried 25 mL round bottom flask and stir bar were placed under an atmosphere of nitrogen and THF (5.6 mL) and diisopropylamine (0.53 mL, 3.72 mmol) were added by syringe. The solution was cooled on a dry ice/acetone bath (to −78° C.) and n-BuLi (1.6 M in hexane, 2.35 mL, 3.76 mmol) was added dropwise over a 5 minute period. After stirring for 15 minutes, a solution of (S)-ethyl 3-((tert-butoxycarbonyl)amino)butanoate K (286 mg, 1.238 mmol) in THF (1.25 mL) was added dropwise (over 5 minutes). The solution was stirred for 80 minutes at −78° C. and a solution of tert-butyl (4-chloro-5-(cyclopropylmethoxy)-2-formylphenyl)carbamate (403.2 mg, 1.238 mmol) in THF (2.5 mL) was added dropwise by syringe. The reaction solution became yellow when the aldehyde was added. The reaction was stirred at −78° C. for 12 minutes and then quenched by addition of saturated aqueous NH$_4$Cl solution (6 mL). The mixture was partitioned between EtOAc and water (25 mL each) and the organic layer was dried (MgSO$_4$), filtered, and evaporated under reduced pressure to provide 724.5 g of a yellowish oil. The material was dissolved in 1,4-dioxane (12.5 mL), treated with 12M HCl (aqueous; 0.32 mL), and stirred at 110° C. for 70 minutes during which time the solution became thick with a pink precipitate. The sample was allowed to cool and the solvent was evaporated under reduced pressure to provide 1.13 g of a fibrous red solid. The material was triturated with i-PrOH (15 mL) and the resulting precipitate was collected on a Buchner funnel and washed with i-PrOH (20 mL) and ethyl ether (~60 mL) to provide (S)-3-(1-aminoethyl)-6-chloro-7-(cyclopropylmethoxy)quinolin-2(1H)-one hydrochloride (146.1 mg, 0.444 mmol, 36% yield) as a papery white solid. $^1$H NMR (300 MHz, DMSO-$d_6$): δ ppm 12.13 (br s, 1H), 8.21 (br s, 3H), 7.98 (s, 1H), 7.86 (s, 1H), 6.98 (s, 1H), 4.32-4.46 (m, 1H), 3.96 (d, J=6.40 Hz, 2H), 1.51 (d, J=6.70 Hz, 3H), 1.21-1.35 (m, 1H), 0.55-0.68 (m, 2H), 0.35-0.46 (m, 2H). LCMS (Method 1): m/z 293 [M+H]$^+$.

Example 16—Intermediate II-10: 3-(1-Aminoethyl)-6-chloro-7-((3,3-difluorocyclobutyl) methoxy)quinolin-2(1H)-one

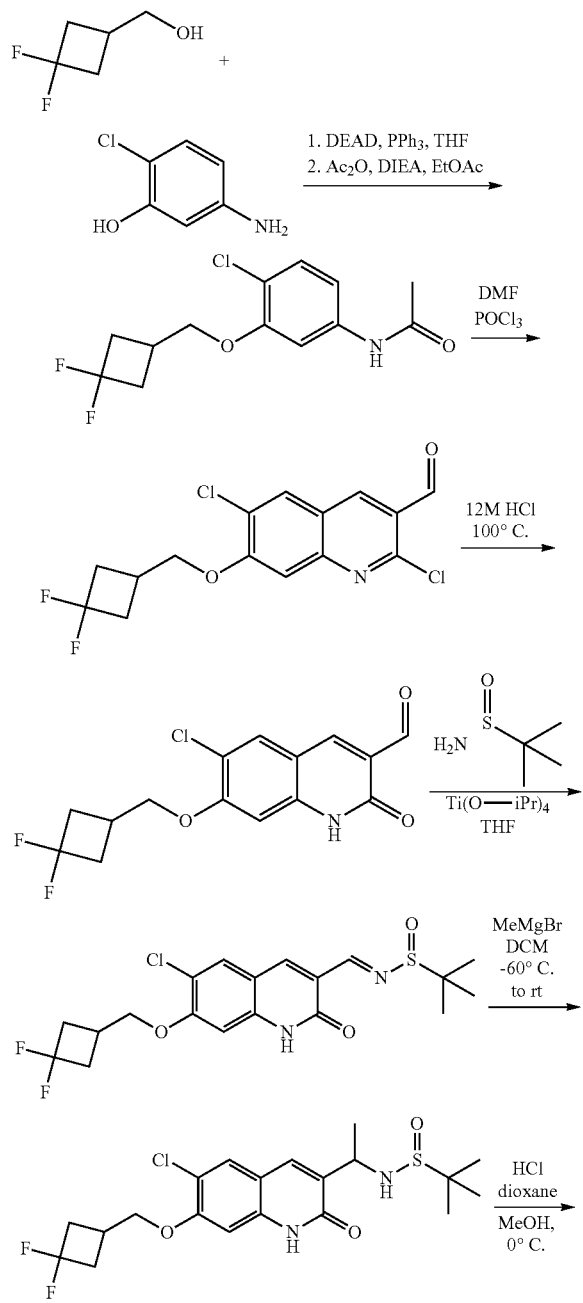

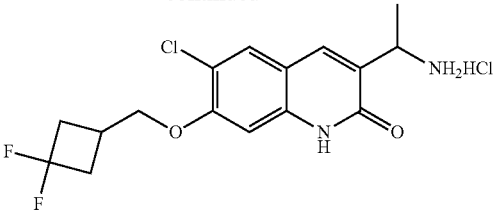

Step-1: N-(4-Chloro-3-((3,3-difluorocyclobutyl)methoxy)phenyl)acetamide

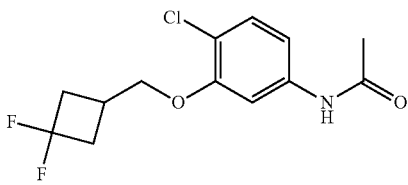 [SMILES: CC(=O)Nc1ccc(Cl)c(OCC2CC(F)(F)C2)c1]

A solution of 5-amino-2-chlorophenol (3 g, 20.90 mmol) (3,3-difluorocyclobutyl) methanol (2.66 g, 21.78 mmol) in THF (375 mL) was placed under an atmosphere of nitrogen and treated with DEAD (3.90 mL, 24.63 mmol). The solution was stirred at room temperature for 48 hours. Once LCMS indicated adequate progression of the reaction, the silica gel was added to the solution and evaporated under reduced pressure. The material was purified by column chromatography on a Biotage® MPLC chromatography system (using a 340 g silica gel column eluted with 0 to 100% EtOAc in hexanes with isocratic elution when peaks eluted) to provide 3.89 g of the title compound as a brown liquid. LCMS was consistent with impure 4-chloro-3-((3,3-difluorocyclobutyl)methoxy)aniline (m/z 248 [M+H]$^+$). The sample was dissolved in EtOAc (80 mL) and treated with DIEA (3.00 mL, 17.18 mmol) and Ac$_2$O (1.60 mL, 16.96 mmol). The solution was stirred at room temperature overnight. The solution was then washed with water and brine (50 mL each), dried (Na$_2$SO$_4$), filtered, and evaporated under reduced pressure. The residue was purified by column chromatography on a Biotage® MPLC chromatography system (using a 50 g silica gel column, eluted with 0 to 50% EtOAc in hexanes with isocratic elution when peaks eluted) to provide 3.16 g of the title compound as a light brown oil, which slowly crystallized on standing. LCMS and $^1$H NMR are consistent with N-(4-chloro-3-((3,3-difluorocyclobutyl)methoxy)phenyl)acetamide (3.16 g, 10.91 mmol, 52% yield). In the NMR one proton is obscured by the solvent signal. $^1$H NMR (300 MHz, DMSO-$d_6$): δ ppm 11.91 (s, 1H), 8.54-8.67 (m, 1H), 7.80-7.95 (m, 2H), 7.68 (s, 1H), 7.56 (d, J=7.30 Hz, 1H), 7.34-7.44 (m, 1H), 7.29 (d, J=9.10 Hz, 1H), 7.13-7.22 (m, 1H), 7.03 (s, 1H), 6.31 (br s, 1H), 6.22 (d, J=7.90 Hz, 1H), 5.30 (s, 2H), 4.10-4.26 (m, 2H), 3.78 (s, 3H). LCMS (Method 1): m/z 290 [M+H]$^+$.

Step-2: 2,6-Dichloro-7-((3,3-difluorocyclobutyl)methoxy)quinoline-3-carbaldehyde

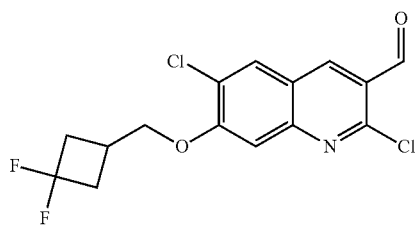 [SMILES: O=Cc1cc2cc(Cl)c(OCC3CC(F)(F)C3)cc2nc1Cl]

A tube was capped with a septum and placed under an atmosphere of nitrogen. DMF (2.15 mL, 27.8 mmol) was then added by syringe and the resulting reaction mixture was cooled on an ice bath. POCl₃ (8.40 mL, 90 mmol) was added dropwise by syringe (10 minutes) during which time a white material precipitated. The solution was then allowed to warm to room temperature over 10 minutes and the mixture was treated with N-(4-chloro-3-((3,3-difluorocyclobutyl)methoxy)phenyl)acetamide (2.44 g, 8.42 mmol). The mixture was stirred at 80° C. for two days. The resulting thick red solution was pipetted onto ice, resulting in a yellow precipitate. The precipitate was collected on a Buchner funnel, washed with water (~500 mL), and dried to provide 2.38 g of the title compound as a pale yellow solid. LCMS and ¹H NMR are consistent with 2,6-dichloro-7-((3,3-difluorocyclobutyl)methoxy)quinoline-3-carbaldehyde (2.38 g, 6.88 mmol, 82% yield). ¹H NMR (300 MHz, DMSO-d₆): δ ppm 10.31-10.36 (m, 1H), 8.88 (s, 1H), 8.48 (s, 1H), 7.65 (s, 1H), 4.37 (d, J=4.69 Hz, 2H), 2.53-2.84 (m, 5H). LCMS (Method 1): m/z 346 [M+H]⁺.

Step-3: 6-Chloro-7-((3,3-difluorocyclobutyl)methoxy)-2-oxo-1,2-dihydroquinoline-3-carbaldehyde

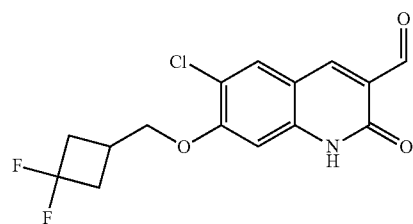 [SMILES: O=Cc1cc2cc(Cl)c(OCC3CC(F)(F)C3)cc2[nH]c1=O]

A solution of 2,6-dichloro-7-((3,3-difluorocyclobutyl)methoxy)quinoline-3-carbaldehyde (2.66 g, 7.68 mmol) in concentrated HCl (75 mL) was stirred at 100° C. for one day during which time a red crust formed on the surface of the flask. The mixture was diluted with water (800 mL), resulting in formation of a red precipitate. The mixture was allowed to stand at room temperature for 4 days. The precipitate was then collected on a Buchner funnel, washed with water (1 L), and dried under vacuum at 50° C. to provide 2.16 g of the title compound as a red solid. LCMS and ¹H NMR are consistent with 6-chloro-7-((3,3-difluorocyclobutyl)methoxy)-2-oxo-1,2-dihydroquinoline-3-carbaldehyde (2.16 g, 6.59 mmol, 86% yield). ¹H NMR (300 MHz, DMSO-d₆): δ ppm 12.21 (s, 1H), 10.16-10.18 (m, 1H), 8.43 (s, 1H), 8.09 (s, 1H), 6.94 (s, 1H), 4.20 (d, J=4.10 Hz, 2H), 2.54-2.80 (m, 5H). LCMS (Method 1): m/z+328 [M+H]⁺.

Step-4: (E)-N-((6-Chloro-7-((3,3-difluorocyclobutyl)methoxy)-2-oxo-1,2-dihydroquinolin-3-yl)methylene)-2-methylpropane-2-sulfinamide

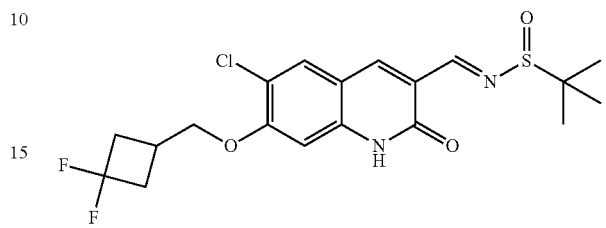

A mixture of 6-chloro-7-((3,3-difluorocyclobutyl)methoxy)-2-oxo-1,2-dihydroquinoline-3-carbaldehyde (499.6 mg, 1.525 mmol) and 2-methylpropane-2-sulfinamide (222.1 mg, 1.832 mmol) was placed in a 25 mL round bottom flask under an atmosphere of nitrogen. THF (3.0 mL) and titanium (IV) isopropoxide (Ti(O$^i$Pr)₄) (0.90 mL, 3.07 mmol) were added by syringe, and the suspension was stirred at room temperature overnight. Once LCMS indicated near completion of reaction, the reaction was quenched by dropwise addition of saturated aqueous NH₄Cl solution (2 mL). The material was then triturated with EtOAc (100 mL) and the resulting precipitate was filtered through Celite®. The filter cake was washed with EtOAc (50 mL), sonicated in EtOAc for 15 minutes and filtered using a Buchner funnel. The filtrates were combined and washed with brine (100 mL), dried (Na₂SO₄), filtered, and evaporated under reduced pressure to provide 413 mg of the title compound as a yellow solid. LCMS and ¹H NMR are consistent with (E)-N-((6-chloro-7-((3,3-difluorocyclobutyl)methoxy)-2-oxo-1,2-dihydroquinolin-3-yl)methylene)-2-methylpropane-2-sulfinamide (413 mg, 0.958 mmol, 62.9% yield). ¹H NMR (300 MHz, DMSO-d₆): δ ppm 12.21 (s, 1H), 8.74 (s, 1H), 8.59 (s, 1H), 8.09 (s, 1H), 6.95 (s, 1H), 4.19 (d, J=4.40 Hz, 2H), 2.55-2.79 (m, 5H), 1.19 (s, 9H). LCMS (Method 1): m/z 431 [M+H]⁺.

Step-5: N-(1-(6-Chloro-7-((3,3-difluorocyclobutyl)methoxy)-2-oxo-1,2-dihydroquinolin-3-yl)ethyl)-2-methylpropane-2-sulfinamide

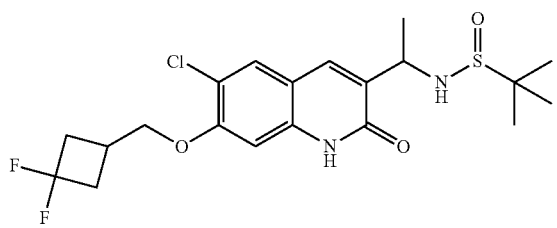 [SMILES: CC(NS(=O)C(C)(C)C)c1cc2cc(Cl)c(OCC3CC(F)(F)C3)cc2[nH]c1=O]

(E)-N-((6-Chloro-7-((3,3-difluorocyclobutyl)methoxy)-2-oxo-1,2-dihydroquinolin-3-yl) methylene)-2-methylpropane-2-sulfinamide (411.3 mg, 0.955 mmol) was placed in a 100 mL round-bottom flask under an atmosphere of nitrogen. DCM (7.6 mL) was added, and the suspension was cooled on a dry ice/chloroform bath (to approx. −60° C.).

Methylmagnesium bromide (MeMgBr, 3M in ether) (0.95 mL, 2.85 mmol) was added dropwise. The cold bath was then allowed to warm to room temperature overnight, resulting in an orange solution. Once LCMS indicated reaction completion, the solution was cooled on an ice bath and treated dropwise with water (5 mL), resulting in precipitation. The mixture was diluted with EtOAc (100 mL) and washed with water (100 mL). Silica gel was added to the organic layer and the solvent was evaporated under reduced pressure. The material was purified by column chromatography on a Biotage® MPLC chromatography system (eluted with 0 to 5% MeOH in DCM with isocratic elution at 3.2% MeOH) to provide 345.5 mg of the title compound as a brown brittle foam. LCMS and $^1$H NMR are consistent with N-(1-(6-chloro-7-((3,3-difluorocyclobutyl)methoxy)-2-oxo-1,2-dihydroquinolin-3-yl)ethyl)-2-methylpropane-2-sulfinamide (345.5 mg, 0.773 mmol, 81% yield). NMR shows a ~1:1 mixture of diastereomers. LCMS (Method 1): m/z 447 [M+H]$^+$.

Step-6: 3-(1-Aminoethyl)-6-chloro-7-((3,3-difluorocyclobutyl)methoxy)quinolin-2(1H)-one hydrochloride (II-10)

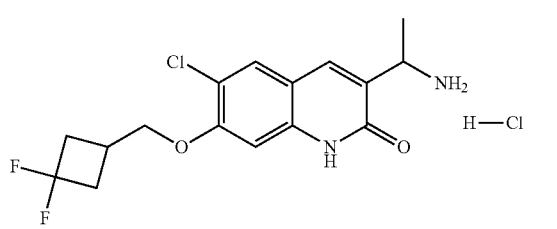

A solution of N-(1-(6-chloro-7-((3,3-difluorocyclobutyl)methoxy)-2-oxo-1,2-dihydroquinolin-3-yl)ethyl)-2-methylpropane-2-sulfinamide (342.7 mg, 0.767 mmol) in MeOH (7.0 mL) was cooled on an ice bath and treated dropwise with 4M HCl in 1,4-dioxane (4 mL). The solution was then stirred for 25 minutes. The solvents were evaporated under reduced pressure at room temperature. The residue was triturated with 20 mL ethyl ether and the resulting precipitate was collected on a Hirsch funnel and washed with more ethyl ether to provide 271.4 mg of a pink solid. LCMS and $^1$H NMR are consistent with 3-(1-aminoethyl)-6-chloro-7-((3,3-difluorocyclobutyl)methoxy)quinolin-2(1H)-one hydrochloride (271.4 mg, 0.716 mmol, 93% yield). $^1$H NMR (300 MHz, Methanol-d$_4$): δ ppm 7.95 (s, 1H), 7.79 (s, 1H), 6.96 (s, 1H), 4.48-4.55 (m, 1H), 4.20 (d, J=4.10 Hz, 2H), 2.56-2.79 (m, 5H), 1.68 (d, J=7.04 Hz, 3H). LCMS (Method 1): m/z 343 [M+H]$^+$.

Example 17—Intermediate II-11: (S)-3-(1-Aminoethyl)-6-chloro-8-fluoroquinolin-2(1H)-one

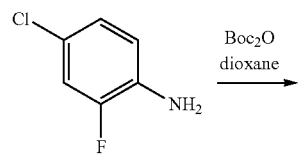

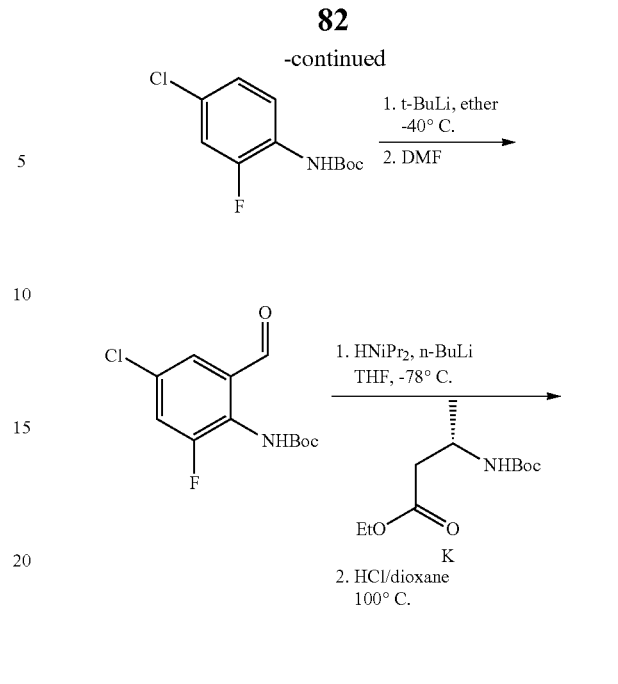

Step-1: tert-Butyl (4-chloro-2-fluorophenyl)carbamate

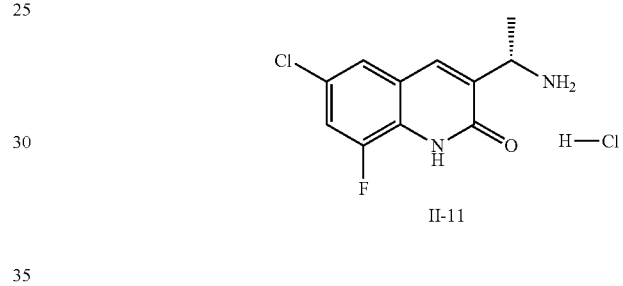

A solution of 4-chloro-2-fluoroaniline (2 g, 13.74 mmol) and di-tert-butyl dicarbonate (6.4 mL, 27.6 mmol) in 1,4-dioxane (50 mL) was stirred at reflux for 2 days. The solvent was then evaporated. The resulting oil was diluted with MeOH, water, and aqueous ammonium hydroxide solution (10 mL each) and vigorously stirred for 45 minutes. The organic lower layer was separated. The organic material was diluted with EtOAc (50 mL), and washed with water (50 mL), 3.6% aqueous HCl solution (2×50 mL), saturated aqueous NaHCO$_3$ solution (50 mL), and then again with water (2×50 mL). The organic layer was dried (MgSO$_4$), filtered, and evaporated under reduced pressure to provide tert-butyl (4-chloro-2-fluorophenyl)carbamate (3.0011 g, 12.22 mmol, 89% yield) as a reddish liquid that solidified on standing. $^1$H NMR (300 MHz, DMSO-d$_6$): δ ppm 9.12 (s, 1H), 7.63 (t, J=8.65 Hz, 1H), 7.42 (dd, J=10.85, 2.35 Hz, 1H), 7.18-7.24 (m, 1H), 1.45 (s, 9H). LCMS (Method 1): m/z 246 [M+H]$^+$.

Step-2: tert-Butyl (4-chloro-2-fluoro-6-formylphenyl)carbamate

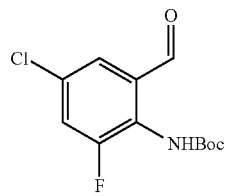 [SMILES: CC(C)(C)OC(=O)Nc1c(F)cc(Cl)cc1C=O]

An oven-dried 3-necked 500 mL round bottom flask was fitted with an oven-dried addition funnel and placed under an atmosphere of nitrogen. tert-Butyl (4-chloro-2-fluorophenyl)carbamate (5.44 g, 22.14 mmol) and ethyl ether (91 mL) were added by syringe. The clear solution was cooled on an acetonitrile/dry ice bath (to approximately −40° C.). tert-Butyllithium (1.7M in pentane, 33 mL, 22.14 mmol) was added to the addition funnel by cannula. The t-BuLi solution was added dropwise to the ether solution (over ~10 minutes), during which time the ether solution began to turn orange. The solution was stirred at about −40° C. for 2 hours, during which time it progressively became more orange. DMF (8.7 mL, 112 mmol) was added dropwise (over ~10 minutes), resulting in precipitation of a yellow solid. The MeCN/dry ice bath was replaced with an ice bath and the mixture was stirred for an additional 2 hours. The reaction was then quenched by dropwise addition of water (20 mL), resulting in a brown mixture and the ice bath was removed. The mixture was diluted with EtOAc (100 mL), washed with water (2×100 mL), dried (Na$_2$SO$_4$), filtered, and evaporated under reduced pressure to provide 5.45 g of an oily black solid. The material was triturated with hexanes (50 mL), collected on a Buchner funnel and washed with more hexanes to provide 2.73 g tert-butyl (4-chloro-2-fluoro-6-formylphenyl)carbamate as a yellow powder. The filtrate was evaporated under reduced pressure, the residue was triturated in hexanes (~15 mL), and the resulting yellow solid was collected on a Hirsch funnel to provide a second crop of the title compound (0.66 g). A total of 3.39 g (12.4 mmol, 56% yield) of tert-butyl (4-chloro-2-fluoro-6-formylphenyl)carbamate was recovered. $^1$H NMR (300 MHz, DMSO-d$_6$): δ ppm 9.93 (d, J=0.88 Hz, 1H), 9.47 (s, 1H), 7.81-7.90 (m, 1H), 7.55-7.61 (m, 1H), 1.44 (s, 9H). LCMS (Method 1): m/z 296 [M+Na].

Steps-3 & 4: (S)-3-(1-Aminoethyl)-6-chloro-8-fluoroquinolin-2(1H)-one hydrochloride (II-11)

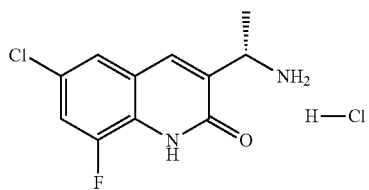

An oven-dried 200 mL round bottom flask and stir bar were placed under an atmosphere of nitrogen. THF (17 mL) and diisopropylamine (1.59 mL, 11.16 mmol) were added by syringe. The resulting solution was cooled on a dry ice/acetone bath (to approximately −78° C.) and then n-butyllithium (1.6M in hexane, 7.1 mL, 11.36 mmol) was added dropwise over a 5 minute period. After stirring for 15 minutes, a solution of (S)-ethyl 3-((tert-butoxycarbonyl)amino)butanoate K (860.7 mg, 3.72 mmol) in THF (3.75 mL) was added dropwise over 5 minutes. The solution was stirred for 80 minutes at −78° C., and a solution of tert-butyl (4-chloro-2-fluoro-6-formylphenyl)carbamate (1016.4 mg, 3.71 mmol) in THF (7.5 mL) was then added dropwise by syringe. The reaction was stirred at −78° C. for another 22 minutes and then quenched by addition of saturated aqueous NH$_4$Cl solution (17 mL). The mixture was partitioned between EtOAc and water (100 mL each). The organic layer was dried (MgSO$_4$), filtered, and evaporated under reduced pressure to provide 1.88 g of the title compound as an orange gum. The material was dissolved in 1,4-dioxane (38 mL), treated with 12M aqueous HCl (0.96 mL), and stirred at 110° C. for 50 minutes. The sample was then allowed to cool. The solvent was evaporated under reduced pressure to provide 1.24 g of a red solid. The material was triturated in IPA (25 mL), collected on a Hirsch funnel and washed sequentially with IPA (5 mL) and ethyl ether (~20 mL) to provide (S)-3-(1-aminoethyl)-6-chloro-8-fluoroquinolin-2(1H)-one hydrochloride (370.4 mg, 1.337 mmol, 36% yield) as a red solid. $^1$H NMR (300 MHz, DMSO-d$_6$): δ ppm 12.41 (s, 1H), 8.33 (br s, 3H), 8.10 (s, 1H), 7.67-7.76 (m, 2H), 4.38-4.53 (m, 1H), 1.52 (d, J=7.04 Hz, 3H). LCMS (Method 1): m/z 241 [M+H]$^+$.

Example 18—Intermediate II-12: (S)-3-(1-aminoethyl)-7-bromo-6-chloroquinolin-2(1H)-one

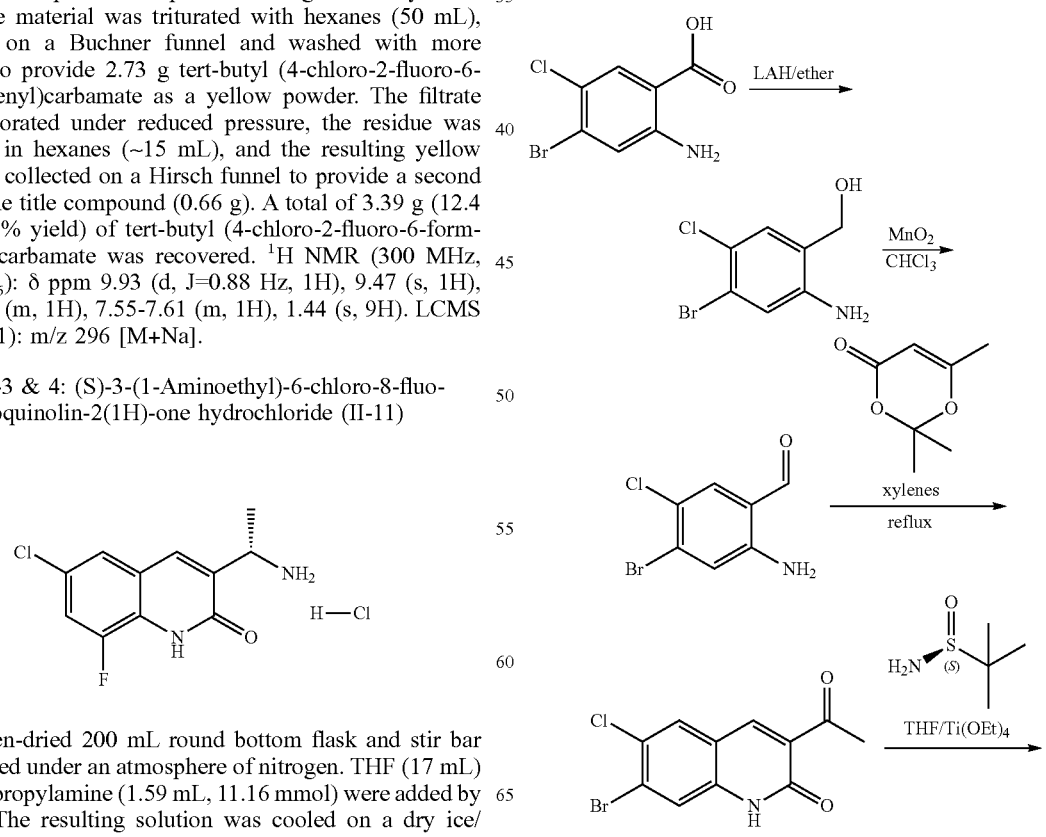

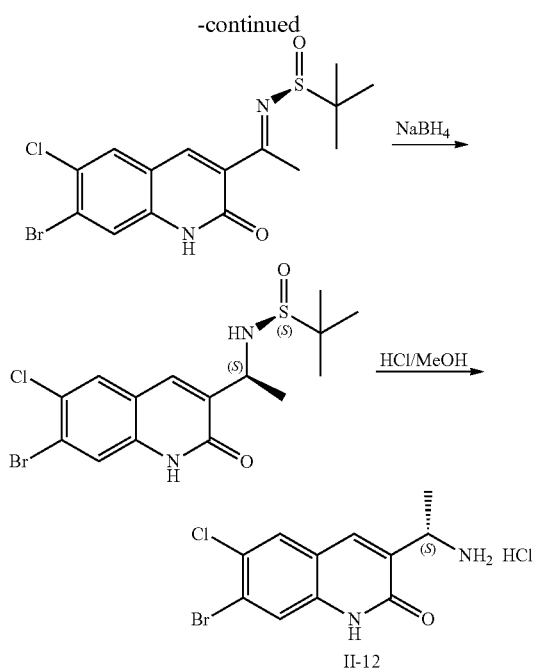

Step-1:
(2-Amino-4-bromo-5-chlorophenyl)methanol

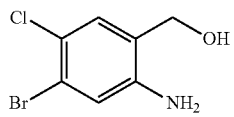 [SMILES: Nc1cc(Br)c(Cl)cc1CO]

A suspension of 2-amino-4-bromo-5-chlorobenzoic acid (4.97 g, 19.84 mmol) in dry ethyl ether (20 mL) was added dropwise to an ice cooled solution of lithium aluminum hydride (20 mmol) in dry ethyl ether (100 mL). The mixture was stirred at room temperature for 2 hours. Water (10 mL) was then added dropwise followed by aqueous sodium hydroxide solution (1M, 20 mL). After stirring at room temperature for one hour, the mixture was filtered. Solids were rinsed with EtOAc twice. The organic layer was separated, dried over sodium sulfate, and concentrated under reduced pressure to afford 4.03 g of crude (2-amino-4-bromo-5-chlorophenyl)methanol (86% yield). $^1$H NMR (300 MHz, CDCl$_3$): δ ppm 7.13 (s, 1H), 6.94 (br, 1H) 4.61 (s, 2H), 4.24 (br, 2H). LCMS (Method 1): Rt 1.92 min, m/z 237.87 [M+H]$^+$.

Step 2: 2-Amino-4-bromo-5-chlorobenzaldehyde

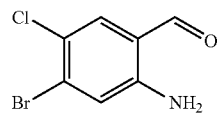

A mixture of manganese dioxide (14.81 g, 170 mmol) and (2-amino-4-bromo-5-chlorophenyl)methanol (4.03 g, 17.04 mmol) in CHCl$_3$ (500 mL) was stirred at room temperature over 2 days. The mixture was filtered, and the filtrate was collected and concentrated to afford 3.6 g of crude 2-amino-4-bromo-5-chlorobenzaldehyde (90% yield). $^1$H NMR (300 MHz, CDCl$_3$): δ ppm 9.77 (s, 1H), 7.52 (br, 1H) 6.98 (s, 2H), 6.12 (br, 2H). LCMS (Method 1): Rt 2.21 min, m/z 235.89 [M+H]$^+$.

Step 3:
3-Acetyl-7-bromo-6-chloroquinolin-2(1H)-one

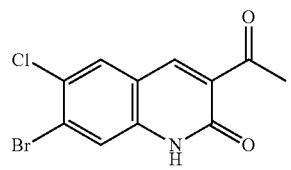 [SMILES: CC(=O)c1cc2cc(Cl)c(Br)cc2[nH]c1=O]

A mixture of 2-amino-4-bromo-5-chlorobenzaldehyde (1.08 g, 4.61 mmol) and 2,2,6-trimethyl-4H-1,3-dioxin-4-one (1.310 g, 9.21 mmol) in xylenes (30 mL) was heated to reflux overnight. The reaction was cooled to room temperature and filtered. Solids were washed with xylenes, and the filtrate was dried and concentrated. The crude material was purified by chromatography on a Biotage® chromatography system on a 25 g SiO$_2$ column and eluted with 0-70% EtOAc/DCM to afford 140 mg of 3-acetyl-7-bromo-6-chloroquinolin-2(1H)-one (52.4% yield). $^1$H NMR (300 MHz, CDCl$_3$): δ ppm 12.23 (s, 1H), 8.40 (br, 1H) 8.20 (s, 1H), 7.65 (s, 1H), 2.58 (s, 3H). LCMS (Method 1): Rt 2.31 min, m/z 301.87 [M+H]$^+$.

Step-4 & 5: (S)—N—((S)-1-(7-Bromo-6-chloro-2-oxo-1,2-dihydroquinolin-3-yl)ethyl)-2-methyl propane-2-sulfinamide

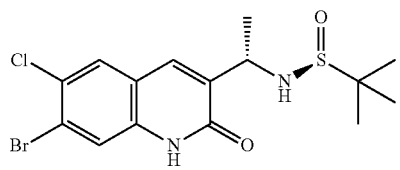 [SMILES: C[C@H](N[S@@](=O)C(C)(C)C)c1cc2cc(Cl)c(Br)cc2[nH]c1=O]

A mixture of tetraethoxytitanium (380 mg, 1.664 mmol) (S)-2-methylpropane-2-sulfinamide (121 mg, 0.998 mmol), and 3-acetyl-7-bromo-6-chloroquinolin-2(1H)-one (200 mg, 0.665 mmol) in THF (15 mL) was heated to 80° C. overnight and then cooled to room temperature. To this mixture was added NaBH$_4$ (126 mg, 3.33 mmol) at −60° C. The mixture was stirred and slowly warmed up to room temperature overnight. MeOH (2 mL) was added to quench excess NaBH$_4$ followed by addition of water. The mixture was filtered to remove solids and then extracted with EtOAc twice. The combined organic layers were dried over Na$_2$SO$_4$ and concentrated. The residue was purified on a Biotage® chromatography system using a 25 g column with gradient elution (first 20 to 100% EtOAc/Hexanes, then 0-5% MeOH/DCM) to afford 137 mg of (S)—N—((S)-1-(7-bromo-6-chloro-2-oxo-1,2-dihydroquinolin-3-yl)ethyl)-2-methylpropane-2-sulfinamide (50.7% yield). $^1$H NMR (300 MHz, CDCl$_3$): δ ppm 11.22 (s, 1H), 7.34 (s, 1H), 7.28 (s, 1H), 7.26 (s, 1H), 7.22 (s, 1H), 6.08 (d, J=9.87 Hz, 1H), 4.29

(m, 1H), 1.55 (d, J=6.96 Hz, 3H). 1.35 (s, 9H). LCMS (Method 1): Rt 2.40 min, m/z 406.80 [M+H]+.

Step-6: (S)-3-(1-Aminoethyl)-7-bromo-6-chloroquinolin-2(1H)-one (II-12)

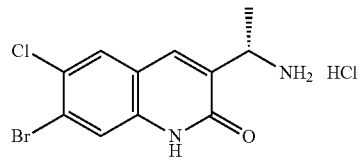 [SMILES: C[C@H](N)c1cc2cc(Cl)c(Br)cc2[nH]c1=O ; Cl]

To a solution of ((S)—N—((S)-1-(7-bromo-6-chloro-2-oxo-1,2-dihydroquinolin-3-yl)ethyl)-2-methylpropane-2-sulfinamide (137 mg, 0.338 mmol) in MeOH (5 mL) was added HCl (2 mL, 4M in 1,4-dioxane, 8.00 mmol). The mixture was stirred at room temperature overnight was and then diluted with 6 mL of ethyl ether. The solids were collected by filtration, washed with ethyl ether 2 times, and dried to afford 90 mg of (S)-3-(1-aminoethyl)-7-bromo-6-chloroquinolin-2(1H)-one as the hydrochloride salt (79% yield). $^1$H NMR (300 MHz, DMSO-$d_6$): δ ppm 12.34 (br, 1H), 8.22 (br, 1H), 8.04 (s, 1H), 8.02 (s, 1H), 7.69 (s, 1H), 4.40 (m, 1H), 1.49 (d, J=6.81 Hz, 3H). LCMS (Method 1): Rt 1.60 min, m/z 302.89 [M+H]+.

Example 19—Intermediate IV-1: (S)-6-Chloro-3-(1-((4-chloropyrimidin-2-yl)amino)ethyl)quinolin-2(1H)-one

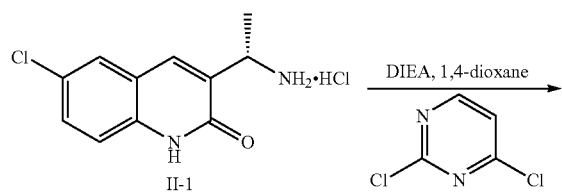

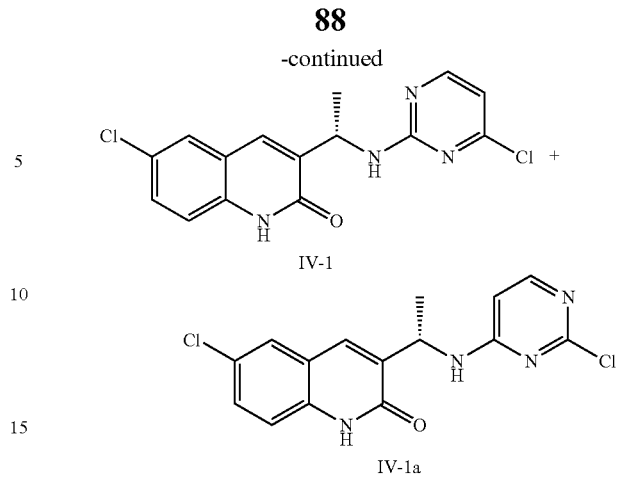

To a suspension of 2,4-dichloropyrimidine (908.8 mg, 6.1 mmol) in 1,4-dioxane (40 mL) was added compound II-1 (1 g, ~3.05 mmol) and DIEA (1.59 mL, 9.15 mmol). The mixture was heated to reflux overnight. EtOAc (200 mL) and water/brine (15 mL/15 mL) were then added. The organic layer was separated, and the aqueous layer was extracted with EtOAc (50 mL). The combined organic layers were washed with brine (30 mL), dried over $Na_2SO_4$, filtered, and evaporated in vacuo. The residue was purified by column chromatography on silica gel (eluted with 0-100% EtOAc/hexane) twice to give the title compound (136 mg, 13% yield) as a yellow solid. $^1$H NMR (300 MHz, DMSO-$d_6$): δ ppm 12.0 (br s, 1H), 8.27-8.10 (m, 2H), 7.76 (d, J=2.4 Hz, 1H), 7.74 (s, 1H), 7.48 (dd, J=2.1, 8.7 Hz, 1H), 7.30 (d, J=8.7 Hz, 1H), 6.69 (d, J=5.1 Hz, 1H), 5.13 (p, J=6.9 Hz, 1H), 1.39 (d, J=6.9 Hz, 3H); m.p.=158.9-160.8° C.; LCMS (method 3): Rt 5.19 min, m/z 335.0, 337.0 [M+H]+.

The fractions containing the other isomer (S)-6-chloro-3-(1-((2-chloropyrimidin-4-yl)amino) ethyl)quinolin-2(1H)-one (IV-1a) were combined, concentrated, and purified by column chromatography on silica gel (0-100% EtOAc/hexane) twice to afford IV-1a (286 mg, 28% yield) as a light yellow solid. $^1$H NMR (300 MHz, DMSO-$d_6$, 70° C.): δ ppm 7.93 (d, J=5.7 Hz, 1H), 7.76 (s, 1H), 7.72 (d, J=2.4 Hz, 1H), 7.48 (dd, J=2.4, 8.7 Hz, 1H), 7.33 (d, J=9.0 Hz, 1H), 6.51 (br s, 1H), 5.13 (br s, 1H), 1.44 (d, J=6.9 Hz, 3H); m.p.=182.1-187.0° C.; LCMS (method 3): Rt 4.40 min, m/z 335.0, 337.0 [M+H]+.

TABLE 1

The Intermediates listed in Table 1 were prepared using either the methods described above or methods similar to those described for the preparation of intermediates II-1 to IV-1.

| Intermediate No. | Chemical names | Structure |
|---|---|---|
| II-1 | (S)-3-(1-aminoethyl)-6-chloroquinolin-2(1H)-one | 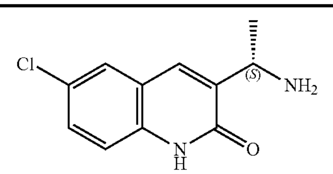 |
| II-2 | (R)-3-(1-aminoethyl)-6-chloroquinolin-2(1H)-one | 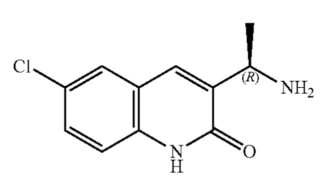 |

TABLE 1-continued

The Intermediates listed in Table 1 were prepared using either the methods described above or methods similar to those described for the preparation of intermediates II-1 to IV-1.

| Intermediate No. | Chemical names | Structure |
|---|---|---|
| II-3 | 3-(1-aminoethyl)-6-chloro-7-fluoroquinolin-2(1H)-one | 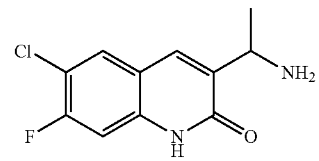 [SMILES: CC(N)c1cc2cc(Cl)c(F)cc2[nH]c1=O] |
| II-3a | (S)-3-(1-aminoethyl)-6-chloro-7-fluoroquinolin-2(1H)-one | 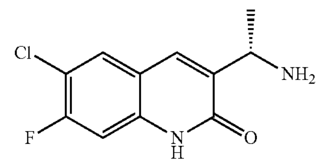 [SMILES: C[C@H](N)c1cc2cc(Cl)c(F)cc2[nH]c1=O] |
| II-3b | (R)-3-(1-aminoethyl)-6-chloro-7-fluoroquinolin-2(1H)-one | 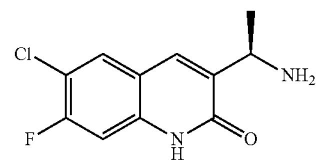 [SMILES: C[C@@H](N)c1cc2cc(Cl)c(F)cc2[nH]c1=O] |
| II-4 | 3-(1-aminoethyl)-6-chloro-7-methoxyquinolin-2(1H)-one | 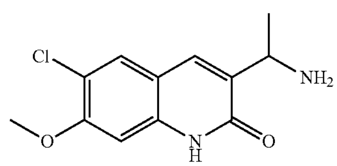 [SMILES: COc1cc2[nH]c(=O)c(C(C)N)cc2cc1Cl] |
| II-4a | (S)-3-(1-aminoethyl)-6-chloro-7-methoxyquinolin-2(1H)-one | 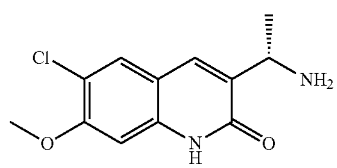 [SMILES: COc1cc2[nH]c(=O)c([C@H](C)N)cc2cc1Cl] |
| II-4b | (R)-3-(1-aminoethyl)-6-chloro-7-methoxyquinolin-2(1H)-one | 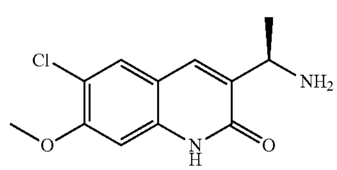 [SMILES: COc1cc2[nH]c(=O)c([C@@H](C)N)cc2cc1Cl] |
| II-5 | 3-(1-aminoethyl)-6-chloro-7-(pyridin-2-ylmethoxy)quinolin-2(1H)-one | 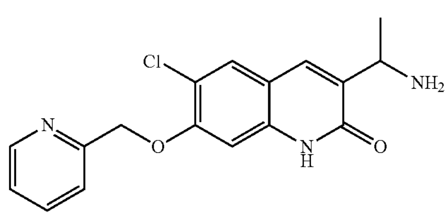 [SMILES: CC(N)c1cc2cc(Cl)c(OCc3ccccn3)cc2[nH]c1=O] |
| II-5a | (S)-3-(1-aminoethyl)-6-chloro-7-(pyridin-2-ylmethoxy)quinolin-2(1H)-one | 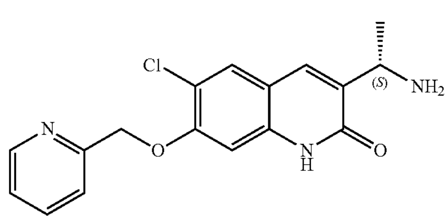 |

TABLE 1-continued

The Intermediates listed in Table 1 were prepared using either the methods described above or methods similar to those described for the preparation of intermediates II-1 to IV-1.

| Intermediate No. | Chemical names | Structure |
|---|---|---|
| II-6 | (S)-3-(1-aminoethyl)-6-chloro-1,8-naphthyridin-2(1H)-one | 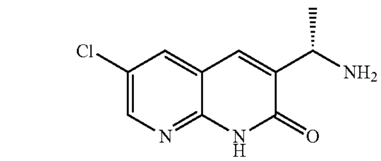 |
| II-7a | (R)-3-(1-aminoethyl)-6-chloroquinoxalin-2(1H)-one | 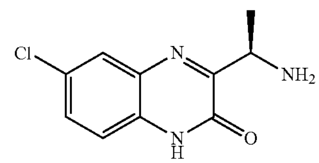 |
| II-7b | (S)-3-(1-aminoethyl)-6-chloroquinoxalin-2(1H)-one | 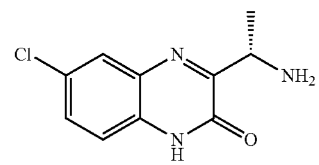 |
| II-8 | (3-((S)-1-aminoethyl)-6-chloro-7-((R)-1-(pyridin-2-yl)ethoxy)quinolin-2(1H)-one | 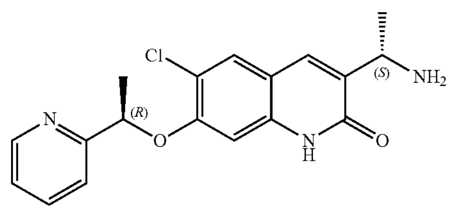 |
| II-9 | (S)-3-(1-aminoethyl)-6-chloro-7-(cyclopropylmethoxy)quinolin-2(1H)-one | 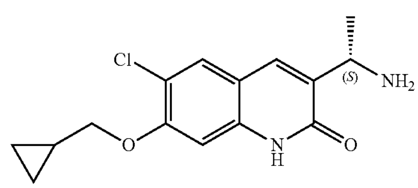 |
| II-10 | (S)-3-(1-aminoethyl)-6-chloro-7-((3,3-difluorocyclobutyl)methoxy)quinolin-2(1H)-one | 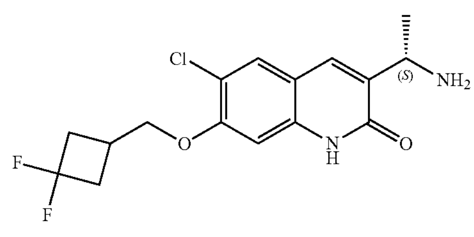 |
| II-11 | (S)-3-(1-aminoethyl)-6-chloro-8-fluoroquinolin-2(1H)-one | 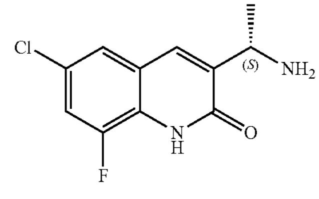 |
| II-12 | (S)-3-(1-aminoethyl)-7-bromo-6-chloroquinolin-2(1H)-one | 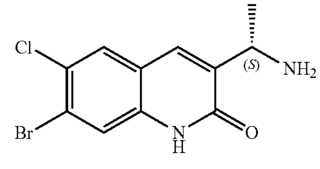 |

TABLE 1-continued

The Intermediates listed in Table 1 were prepared using either the methods described above or methods similar to those described for the preparation of intermediates II-1 to IV-1.

| Intermediate No. | Chemical names | Structure |
|---|---|---|
| II-13 | (S)-3-(1-aminoethyl)-6-chloro-7-isopropoxy quinolin-2(1H)-one | 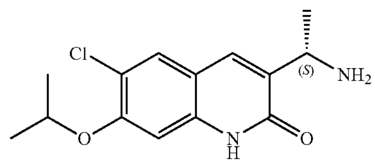 |
| IV-1 | (S)-6-chloro-3-(1-((4-chloropyrimidin-2-yl)amino)ethyl)quinolin-2(1H)-one | 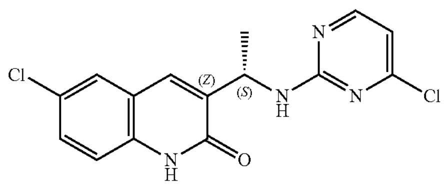 |

Note:
All amines are hydrochloride salts

Example 20—Intermediate III-1: N-(2-Chloropyrimidin-4-yl)-N-isopropyl methanesulfonamide

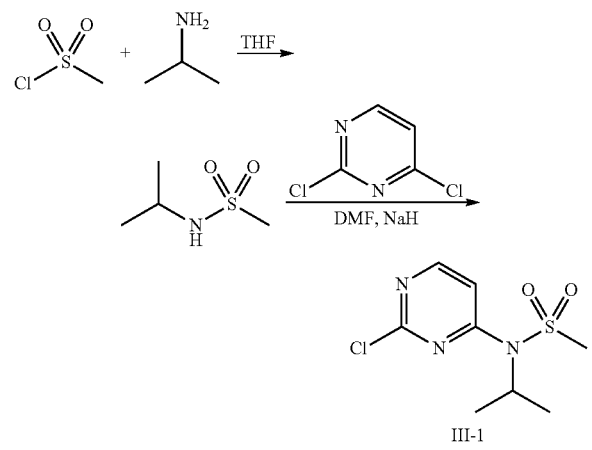

Step-1: N-isopropylmethanesulfonamide

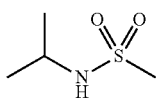

To a solution of propan-2-amine (11.8 g, 17 mL, 0.2 mol) in THF (500 mL) was added methanesulfonyl chloride (11.5 g, 7.8 mL, 0.1 mol) dropwise at 0° C. The reaction mixture was warmed to room temperature and stirred for 5 hours. The solid was removed by filtration, and the filtrate was concentrated and purified by silica gel chromatography on an ISCO® chromatography system and eluted with a gradient (hexanes to ethyl acetate) to afford the title compound (12.9 g, 94% yield).

Step-2: N-(2-Chloropyrimidin-4-yl)-N-isopropyl-methanesulfonamide (III-1)

To a suspension of N-isopropylmethanesulfonamide (10.94 g, 79.8 mmol) in DMF (100 mL) was added 60% sodium hydride (NaH) in oil (3.5 g, 87.8 mmol) portionwise. The mixture was stirred for 30 minutes, and then 2,4-dichloropyrimidine (13 g, 87.8 mmol) was added portionwise. The reaction mixture was stirred at room temperature for 4 hours, quenched with aqueous NH$_4$Cl solution, and extracted with ethyl acetate (100 mL×3). The combined organic layers were washed with water (20 mL×3), dried (Na$_2$SO$_4$), concentrated and purified by silica gel chromatography on an ISCO® chromatography system and eluted with hexanes/EtOAc to afford the target compound III-1 (5.44 g, 80% yield). $^1$H NMR (300 MHz, CDCl$_3$): δ ppm 8.46 (d J=5.76 Hz, 1H), 7.26 (d J=5.76 Hz, 1H), 4.73 (m, 1H), 3.23 (s, 3H), 1.53 (s, 3H), 1.51 (s, 3H). LCMS (Method 3): Rt 5.09 min, mz 250.0 [M+H]$^+$.

Example 21—Intermediate III-3:N-(2-chloropyrimidin-4-yl)-1-cyclopropyl-N-isopropylmethanesulfonamide

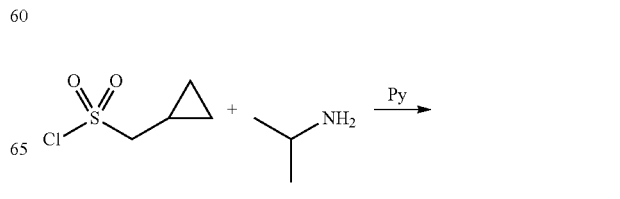

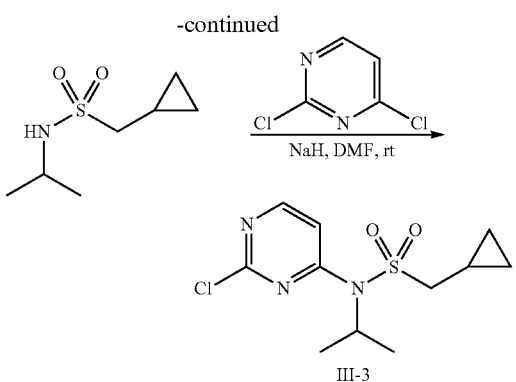

Step-1: 1-Cyclopropyl-N-isopropylmethanesulfonamide

To a solution of propan-2-amine (0.80 g, 4.5 mmol) and TEA (1.3 g, 13.5 mmol) in DCM (20 mL), was added cyclopropylmethanesulfonyl chloride (0.7 g, 4.5 mmol) at 0° C. The reaction mixture was stirred at room temperature overnight. All solvents were then evaporated And the resulting mixture was purified by silica gel chromatography on an ISCO® chromatography system and eluted with 0-100% EtOAc in Hexanes to afford the title compound as an oil (0.64 g, 75% yield). $^1$H NMR (300 MHz, CDCl$_3$) δ ppm 4.24 (d, J=7.4 Hz, 1H), 3.65-3.62 (m, 1H), 2.9-2.91 (d, J=7.1 Hz, 2H), 1.24-1.23 (d, J=4.1 Hz, 6H), 1.22-1.13 (m, 1H), 0.69-0.67 (m, 2H), 0.38-0.36 (m, 2H).

Step-2: N-(2-Chloropyrimidin-4-yl)-1-cyclopropyl-N-isopropylmethanesulfonamide (III-3)

1-Cyclopropyl-N-isopropylmethanesulfonamide (613 mg, 3.4 mmol) was dissolved in DMF (10 mL) and cooled to 0° C. To this cold solution was added 60% NaH in oil (182 mg, 4.6 mmol). The reaction mixture was stirred for 10 minutes before the addition of 2,4-dichloropyrimidine (678 mg, 4.6 mmol). The mixture was then allowed to warm to room temperature and was stirred overnight. Aqueous NH$_4$Cl solution (15 mL) was added and the resulting mixture was extracted with EtOAc (3×30 mL). The combined organic layers were washed with brine (15 mL), dried over Na$_2$SO$_4$, filtered, and evaporated in vacuo. The residue was purified by column chromatography on silica gel (0-65% EtOAc/hexane) to provide a mixture (262 mg) of the title compound and unreacted starting material, which was further purified by reverse phase column chromatography on a C18 bonded silica gel column (0-100% acetonitrile/water, 0.1% TFA) to afford the pure title compound III-3 (198 mg, 22% yield) as a light yellow oil. $^1$H NMR (300 MHz, CDCl$_3$): δ ppm 8.41 (d, J=5.7 Hz, 1H), 7.31 (d, J=5.7 Hz, 1H), 4.77 (d, J=6.9 Hz, 1H), 3.29 (d, J=7.5 Hz, 2H), 1.54 (d, J=6.9 Hz, 6H), 1.13 (m, 1H), 0.71 (m, 2H), 0.41 (m, 2H); LCMS (method 3): Rt 5.44 min, m/z 290.1, 292.0 [M+H]$^+$.

Example 22—Intermediate III-4: N-(2-Chloropyrimidin-4-yl)acetamide

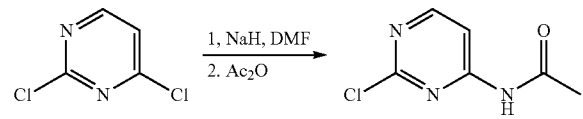

To a solution of 4-amino-2-chloropyrimidine (2.90 g, 22.4 mmol) in DMF (40 mL) was added 60% NaH in oil (1.07 g, 26.9 mmol) at 0° C. After stirring for 20 minutes, acetic anhydride (4.2 mL, 44.8 mmol) was added. The mixture was stirred at room temperature overnight. Once LCMS and TLC showed reaction completion, the reaction mixture was quenched by the addition of water and extracted with EtOAc. The organic layer was washed with water and brine dried (Na$_2$SO$_4$) and concentrated. The crude material was recrystallized from Hexanes/EtOAc to afford the product III-4 as white crystals (2.40 g, 62% yield). $^1$H NMR (300 MHz, DMSO-d$_6$): δ ppm 11.29 (s, 1H), 8.57 (d, J=5.8 Hz, 1H), 8.03 (d, J=5.8 Hz, 1H), 2.13 (s, 3H). LCMS: m/z 172.0, 174.0 [M+H].

Example 23—Intermediate III-5: (S)-3-(2-chloropyrimidin-4-yl)-4-isopropyloxazolidin-2-one

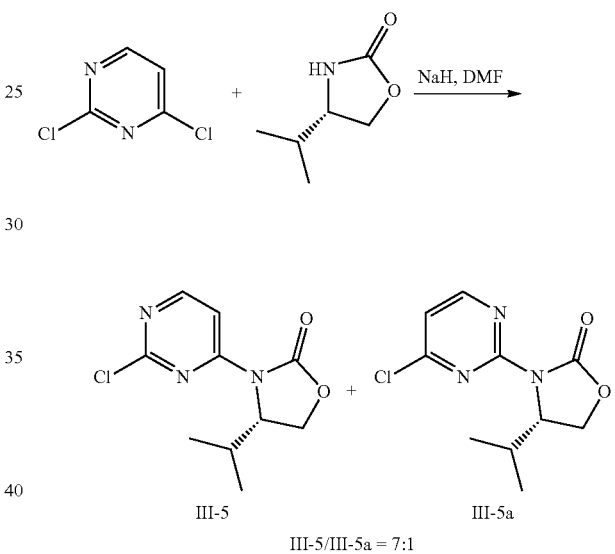

III-5/III-5a = 7:1

A solution of (S)-4-phenyloxazolidin-2-one (3.0 g, 23.2 mmol) and 2,4-dichloropyrimidine (4.10 g, 27.5 mmol) in DMF (40 mL) was treated with NaH (60% in oil, 0.97 g, 24.3 mmol). The resulting mixture (yellow to red cloudy solution) was stirred at room temperature overnight. The reaction mixture was then diluted with EtOAc (200 mL), washed with saturated aqueous NH$_4$Cl (75 mL) and brine (2×100 mL), dried over Na$_2$SO$_4$, filtered and concentrated. The residue was purified by column chromatography on an ISCO® chromatography system (on a SiO$_2$ column: eluted with 0 to 50% Hexanes/EtOAc gradient) to obtain the desired product III-5 as white solid (3.91 g, 70% yield) along with the other isomer III-5a (0.59 g, 11%). III-5: H NMR (300 MHz, CDCl$_3$): δ ppm 8.46 (d, J=6.0 Hz, 1H), 8.18 (d, J=6.0 Hz, 1H), 4.80-4.75 (m, 1H), 4.42-4.34 (m, 2H), 2.66-2.54 (m, 1H), 0.99 (d, J=7.1 Hz, 3H), 0.87 (d, J=7.1 Hz, 3H). LCMS (method 3): Rt 11.62 min, m/z 242.1 [M+H]$^+$. III-5a: $^1$H NMR (300 MHz, CDCl$_3$): δ ppm 8.57 (d, J=5.2 Hz, 1H), 7.07 (d, J=5.2 Hz, 1H), 4.75-4.65 (in, 1H), 4.40-4.29 (m, 2H), 2.60-2.47 (m, 1H), 0.96 (d, J=6.9 Hz, 3H), 0.90 (d, J=6.9 Hz, 3H). LCMS (method 3): Rt 9.90 min, m/z 242.1 [M+H]$^+$.

Example 24—Intermediate III-6:3-(2-Chloropyrimidin-4-yl)oxazolidin-2-one

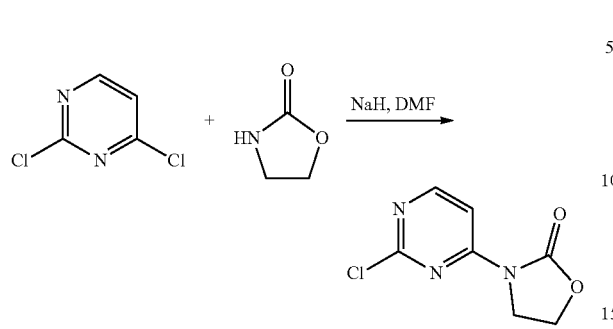

To a solution of 2,4-dichloropyrimidine (5.00 g, 33.5 mmol) and oxazolidin-2-one 2 (3.51 g, 40.3 mmol) in DMF (80 mL), 60% NaH in oil (1.48 g, 36.9 mmol) was added at 0° C. The mixture was stirred at room temperature overnight. The reaction mixture was then quenched with saturated aqueous ammonium chloride solution and extracted with EtOAc. The organic layer was washed with water, brine, and dried over sodium sulfate and concentrated. The resulting residue was purified by column chromatography on an ISCO® chromatography system (on a $SiO_2$ column: eluted with 0-30% DCM/EtOAc) to afford the title compound as white solid (4.09 g, 61% yield) with the other isomer (0.35 g, 5% yield), $^1$H NMR (300 MHz, $CDCl_3$): δ ppm 8.46 (d, J=5.8 Hz, 1H), 8.15 (d, J 5.7 Hz, 1H), 4.55 (t, J=6.9 Hz, 2H), 4.27 (t, J=6.9 Hz, 2H). LCMS: m/z=200.0, 202.0 [M+H]$^+$.

Example 25—Intermediate III-7:2-Chloro-4-(2-methyl-1H-pyrrol-1-yl)pyrimidine

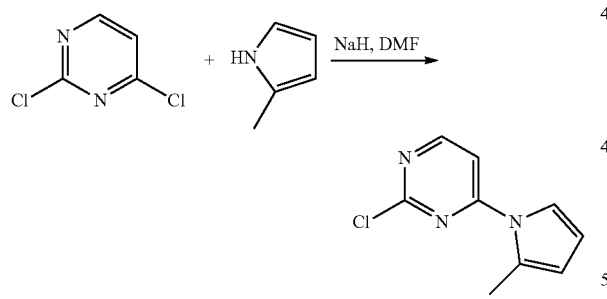

2,4-Dichloropyrimidine (2.0 g, 13.4 mmol) and 2-methyl-1H-pyrrole (1.3 g, 16.1 mmol) were dissolved in DMF (40 mL). The solution was cooled to 0° C. and 60% NaH in oil (590 mg, 14.74 mmol) was added. The mixture was stirred at 0° C. for 15 minutes and allowed to warm up to room temperature. After stirring overnight, ethyl acetate (60 mL) was added. The mixture was washed with water (2×30 mL), brine (30 mL), dried over anhydrous $Na_2SO_4$, filtered, and evaporated. The residue was purified by column chromatography on silica gel (0-30% EtOAc/hexane) to afford the title compound III-7 as an off-white solid (1.12 g, 43% yield). $^1$H NMR (300 MHz, DMSO-$d_6$): δ ppm 8.71 (d, J=5.7 Hz, 1H), 7.73 (d, J=5.7 Hz, 1H), 7.47 (m, 1H), 6.24 (t, J=3.2 Hz, 1H), 6.11 (m, 1H), 2.50 (s, 3H). LCMS (method 3): Rt 5.823 min, m/z 194.1 [M+H]$^+$.

Example 26—Intermediate III-8:2-Chloro-4-(1-methyl-1H-imidazol-5-yl)pyrimidine

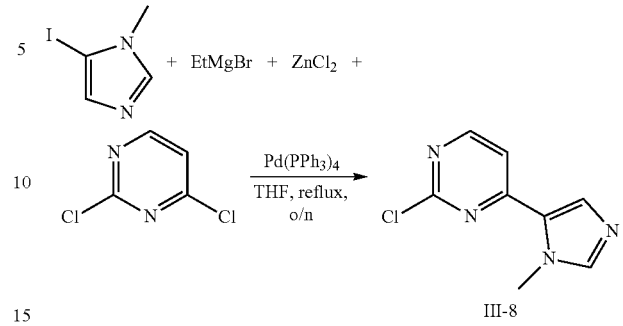

To a suspension of 5-iodo-1-methyl-1H-imidazole (2.08 g, 10 mmol) in anhydrous tetrahydrofuran (30 mL) was added ethyl magnesium bromide (EtMgBr) (3M in THF, 4.3 mL, 13 mmol) slowly at room temperature under $N_2$. The mixture was stirred for 90 minutes. $ZnCl_2$ (0.5 M in THF, 26 mL, 13 mmol) was then added slowly, and the mixture was stirred for another 90 minutes. 2,4-Dichloropyrimidine (1.48 g, 10 mmol) and Pd(PPh$_3$)$_4$ (0.58 g, 0.5 mmol) were then added under $N_2$. The resulting reaction mixture was then refluxed overnight. After removal of solvent under reduced pressure, EtOAc (50 mL) was added to the residue. The mixture was then washed with saturated EDTA aqueous solution (30 mL) and brine (30 mL), dried ($Na_2SO_4$) and concentrated in vacuo. The residue was first purified by column chromatography on an ISCO® chromatography system (silica gel column, eluted with MeOH/dichloromethane 0-10%) and then recrystallized from EtOAc/hexanes to afford the title compound III-8 as a white solid (462 mg, 24% yield). m.p. 228-229° C. $^1$H NMR (300 MHz, $CDCl_3$): δ ppm 8.64 (d, J=5.2 Hz, 1H), 8.15 (br s, 1H), 7.93 (s, 1H), 7.51 (d, J=5.2 Hz, 1H), 4.15 (s, 3H). LCMS (method 1): 98% pure @ 254 nm, Rt=2.93 min, m/z=195, 197 [M+H]$^+$.

Example 27—Intermediate III-9: 2-Chloro-4-(1-isopropyl-1H-imidazol-5-yl)pyrimidine

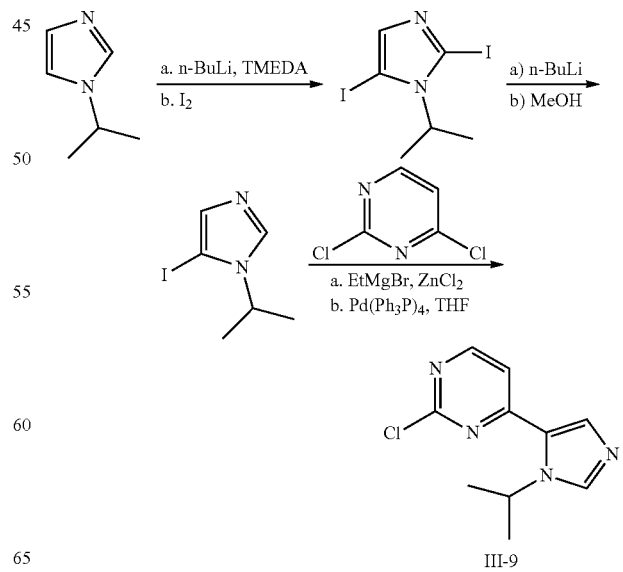

Step-1: 2,5-Diiodo-1-isopropyl-1H-imidazole

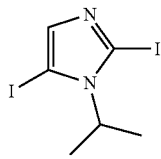

1-Isopropylimidazole (6.0 mL, 52.8 mmol) was added over 20 min to a well-stirred solution of TMEDA (20.2 mL, 135 mmol) and n-BuLi (52.8 mL, 2.5 M in hexane, 132 mmol) in anhydrous pentane (55 mL) under an atmosphere of nitrogen at −20° C. The stirred cloudy yellow heterogeneous mixture was warmed to 20° C. for 1 hour and then diluted with anhydrous THF (50 mL) and cooled to −65° C. A solution of iodine (34.8 g, 137 mmol) in anhydrous THF (180 mL) was added over 90 minutes. The stirred reaction mixture was allowed to warm to room temperature overnight. The reaction was then quenched by the addition of ethyl acetate (10 mL) followed by water, dichloromethane (250 mL), and saturated sodium sulfite solution. The organic layer was separated, washed with saturated sodium sulfite solution and brine, dried over $MgSO_4$, filtered and evaporated to yield the title compound as a golden-brown solid which was further purified on an ISCO® chromatography system ($SiO_2$ column: EtOAc in Hexane, 0 to 100%) to afford the pure product as light yellow solid (10.8 g, 57% yield). $^1$H NMR (300 MHz, $CDCl_3$): δ ppm 7.13 (s, 1H), 4.75 (septet, J=6.9 Hz, 1H), 1.60 (d, J=6.9 Hz, 6H). m/z=362.9 [M+H].

Step-2: 5-Iodo-1-isopropyl-1H-limidazole

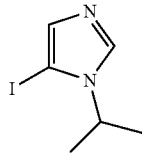

To a solution of 2,5-diiodo-1-isopropyl-1H-imidazole (10.8 g, 29.8 mmol) under an atmosphere of nitrogen in dry THF (320 mL) cooled to −70° C. in an acetone-dry ice bath, n-BuLi solution (12.9 mL, 2.5 M in hexane, 32.2 mmol) was added dropwise over 25 minutes. After the addition, the mixture was stirred at the same temperature for another 45 minutes and then quenched by adding methanol (10.5 mL) and diluted with dichloromethane (500 mL). The organic layer was separated, washed with brine (80 mL×2), and dried over $MgSO_4$. Filtration and concentration under vacuum provided a yellow brown solid which was purified on an ISCO® chromatography system ($SiO_2$ column: EtOAc in Hexanes, 0 to 100%) to afford pure title compound as off-white solid (6.1 g, 86% yield). $^1$H NMR (300 MHz, $CDCl_3$): δ ppm 7.68 (s, 1H), 7.10 (s, 1H), 4.35 (septet, J=6.9 Hz, 1H), 1.48 (d, J=6.9 Hz, 6H). m/z=237.0 [M+H].

Step-3: 2-Chloro-4-(1-isopropyl-1H-imidazol-5-yl) pyrimidine TFA Salt (III-9)

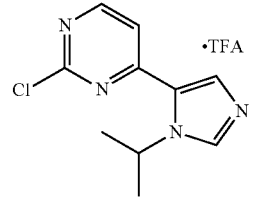

To a solution of 5-iodo-1-isopropyl-1H-limidazole (4.9 g, 20.8 mmol) in dry THF (60 mL) at room temperature and under an atmosphere of nitrogen was added ethyl magnesium bromide (EtMgBr) (8.33 mL, 3 M in diethyl ether, 25 mmol) dropwise over 10 minutes. After the addition, the mixture was stirred at room temperature for 90 minutes. Zinc chloride (50 mL, 0.5 M in THF, 25 mol) was then added dropwise over 5 minutes, and the reaction mixture was stirred at room temperature for another 90 minutes. 2,4-Dichloropyrimidine (3.1 g, 20.8 mmol) and $Pd(PPh_3)_4$ (1.25 g, 1.08 mmol) were added the resulting mixture was purged with nitrogen for 20 minutes and heated to reflux overnight. The reaction solution was warmed to room temperature and diluted with dichloromethane (500 mL). Saturated EDTA aqueous solution (200 mL) was added, and after stirring for 10 minutes, the organic layer was separated and dried over $Na_2SO_4$. Filtration and concentration under vacuum provided a yellow oil which was further purified on an ISCO® chromatography system (reverse phase C18 $SiO_2$ column eluted with 0.1% TFA in $CH_3CN$/0.1% TFA in $H_2O$, 0 to 30%) to yield the title compound III-9 as the TFA salt as colorless oil which solidified to a white solid on standing (4.1 g, 59% yield). $^1$H NMR (300 MHz, $CDCl_3$): δ ppm 9.60 (s, br, 1H), 8.76 (d, J=5.2 Hz, 1H), 8.05 (s, 1H), 7.59 (d, J=5.2 Hz, 1H), 7.25 (s, 1H), 4.72 (septet, J=6.6 Hz, 1H), 1.48 (d, J=6.6 Hz, 6H). LCMS (method 3 LCMS): Rt 3.40 min, m/z 223.1/225.1 [M+H]$^+$.

TABLE 2

The Intermediates listed in Table 2 were prepared using either the methods described above or using methods similar to those described for the preparation of intermediates III-1 to III-9.

| Intermediate No. | Chemical names | Structure |
|---|---|---|
| III-1 | N-(2-chloropyrimidin-4-yl)-N-isopropylmethane sulfonamide | 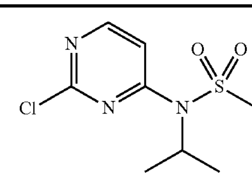 |

TABLE 2-continued

The Intermediates listed in Table 2 were prepared using either the methods described above or using methods similar to those described for the preparation of intermediates III-1 to III-9.

| Intermediate No. | Chemical names | Structure |
|---|---|---|
| III-2 | N-(2-chloropyrimidin-4-yl)-N-(cyclopropylmethyl)methanesulfonamide | 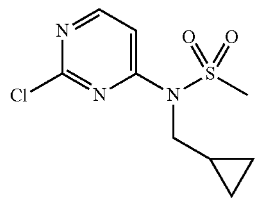 [SMILES: CS(=O)(=O)N(CC1CC1)c1ccnc(Cl)n1] |
| III-3 | N-(2-chloropyrimidin-4-yl)-1-cyclopropyl-N-isopropylmethanesulfonamide | 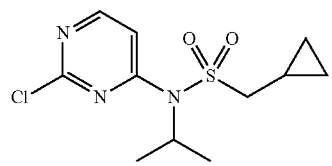 [SMILES: CC(C)N(c1ccnc(Cl)n1)S(=O)(=O)CC1CC1] |
| III-4 | (N)-(2-chloropyrimidin-4-yl)-A-isopropylmethane sulfonamide | 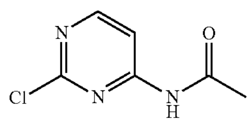 |
| III-5 | (S)-3-(2-chloropyrimidin-4-yl)-4-isopropyloxazolidin-2-one | 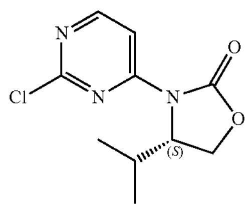 |
| III-6 | 3-(2-chloropyrimidin-4-yl)oxazolidin-2-one | 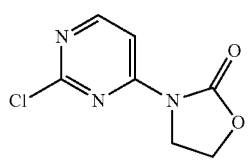 [SMILES: O=C1OCCN1c1ccnc(Cl)n1] |
| III-7 | 2-chloro-4-(2-methyl-1H-pyrrol-1-yl)pyrimidine | 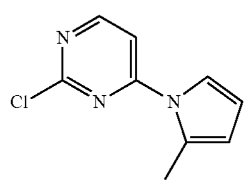 |
| III-8 | 2-chloro-4-(1-methyl-1H-imidazol-5-yl)pyrimidine | 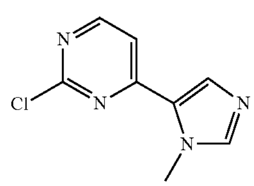 |
| III-9 | 2-chloro-4-(1-isopropyl-1H-imidazol-5-yl)pyrimidine | 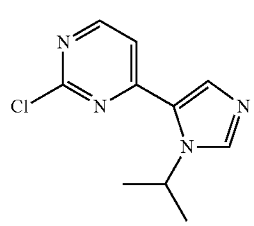 |

TABLE 2-continued

The Intermediates listed in Table 2 were prepared using either the methods described above or using methods similar to those described for the preparation of intermediates III-1 to III-9.

| Intermediate No. | Chemical names | Structure |
|---|---|---|
| III-10 | N-(2-chloropyrimidin-4-yl)cyclopropanecarboxamide | 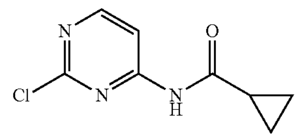 [SMILES: O=C(Nc1ccnc(Cl)n1)C1CC1] |

Example 28—(S)—N-((2-((1-(6-Chloro-2-oxo-1,2-dihydroquinolin-3-yl)ethyl) amino)pyrimidin-4-yl)-N-neopentylmethanesulfonamide (I-1)

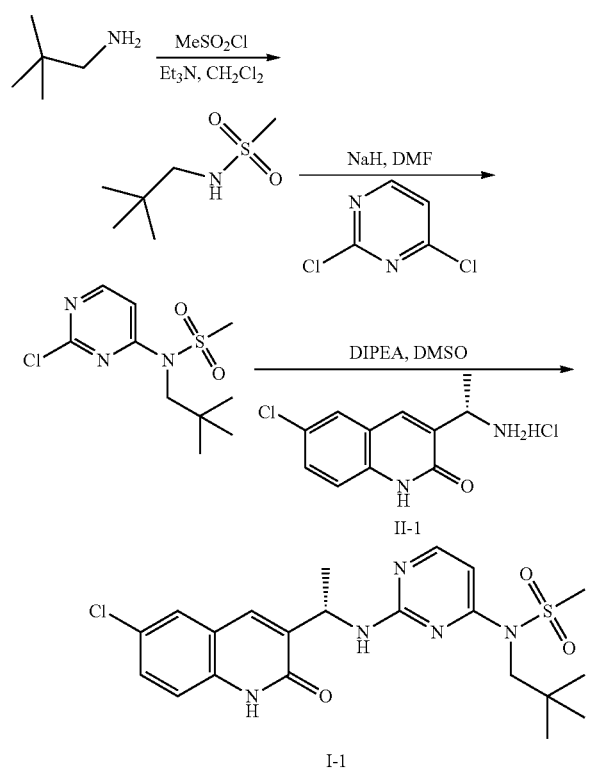

Step-1: N-Neopentylmethanesulfonamide

To a solution of neopentylamine (3.00 g, 34.4 mmol) and triethylamine (9.6 mL, 68.8 mmol) in dichloromethane (50 mL) was slowly added methylsulfonyl chloride (3.2 mL, 41.3 mmol) at 0° C. The mixture was then warmed to room temperature and stirred overnight. After diluting with water and extracting with dichloromethane, the organic layer was washed with brine, dried over magnesium sulfate and concentrated to obtain the title compound as white solid (5.25 g, 92% yield) which was used without further purification in the next step. $^1$H NMR (300 MHz, CDCl$_3$): δ ppm 4.38 (in, 1H), 2.95 (s, 3H), 288 (d, J=6.6 Hz, 2H), 0.94 (s, 9H).

Step-2: N-(2-Chloropyrimidin-4-yl)-N-neopentylmethanesulfonamide

To a solution of N-neopentylmethanesulfonamide (1.65 g, 10 mmol) and 2,4-dichloropyrimidine (1.79 g, 12 mmol) in DMF (30 mL) was added 60% NaH in oil (440 mg, 11 mmol). The mixture was stirred at room temperature overnight. Reaction mixture was then quenched with water and extracted with EtOAc. The organic layer was washed with water and brine, dried over sodium sulfate, and concentrated. The resulting residue was purified on an ISCO® chromatography system (SiO$_2$ column: eluting with hexanes/EtOAc gradient; 0-60% EtOAc) to afford the title compound as pale yellow oil (1.68 g, 60% yield). $^1$H NMR (300 MHz, CDCl$_3$): δ ppm 8.49 (d, J=5.7 Hz, 1H), 7.55 (d, J=5.7 Hz, 1H), 3.98 (s, 2H), 3.02 (s, 3H), 0.89 (s, 9H).

Step-3: (S)—N-(2-((1-(6-Chloro-2-oxo-1,2-dihydroquinolin-3-yl)ethyl)amino)pyrimidin-4-yl)-N-neopentylmethanesulfonamide (I-1)

In a sealed tube, a mixture of N-(2-chloropyrimidin-4-yl)-N-neopentyl methanesulfonamide (278 mg, 1.0 mmol), (S)-3-(1-aminoethyl)-6-chloroquinolin-2(1H)-one hydrochloride (II-1) (130 mg, 0.5 mmol) and diisopropylethylamine (0.26 mL, 1.5 mmol) in DMSO/1,4-dioxane (2 mL/0.5 mL) was heated to 130° C. for 2 hours. Once MS and TLC showed completion of reaction, the reaction mixture was cooled to room temperature, and diluted with EtOAc and water. The layers were separated and the organic layer was washed with brine, dried over sodium sulfate, and concentrated. The resulting residue was purified on an ISCO® chromatography system (SiO$_2$ column: eluted with a hexanes/EtOAc gradient; 20% to 100% EtOAc) to afford I-1 as white solid (102 mg, 44% yield). $^1$H NMR (300 MHz, CDCl$_3$): δ ppm 10.33 (br s, 1H), 8.20 (d, J=5.2 Hz, 1H), 7.66 (s, 1H), 7.49 (d, J=2.2 Hz, 1H), 7.42 (dd, J=8.5 Hz, 2.2 Hz, 1H), 7.18 (d, J=8.5 Hz, 1H), 6.81 (d, J=5.5 Hz, 1H), 6.07-6.02 (m, 1H), 5.27 (m, 1H), 3.85-3.70 (m, 2H), 2.90 (s, 3H), 1.61 (d, J=6.9 Hz, 3H), 0.73 (s, 9H). LCMS (Method 3): Rt 4.68 min, m/z 464.1, 466.1 [M+H]$^+$.

Example 29—(S)—N-(2-((1-(6-Chloro-2-oxo-1,2-dihydroquinolin-3-yl)ethyl)amino) pyrimidin-4-yl)-N-(cyclopropylmethyl)methanesulfonamide TFA Salt (I-2)

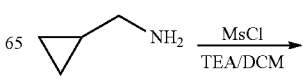

-continued

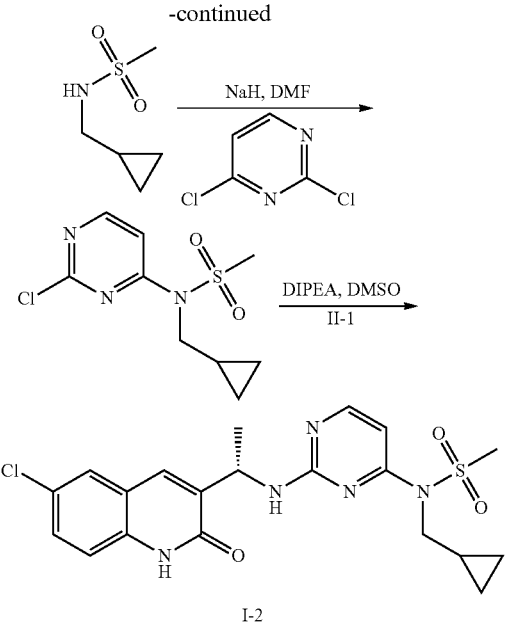

I-2

Step-1: N-(cyclopropylmethyl)methanesulfonamide

To a solution of cyclopropyl methanamine (2.1 g, 20 mmol) and TEA (5.0 mL) in DCM (20 mL) was added methanesulfonyl chloride (1.4 g, 12 mmol) at 0° C. The reaction mixture was then allowed to stir at room temperature overnight. To the reaction mixture was added DCM (20 mL), and the solution was washed with 1N HCl aqueous solution and brine, dried over MgSO$_4$, and filtered. The filtrate was concentrated and dried to obtain the title compound (1.1 g, 57% yield). The product was used in the next step without further purification.

Step-2: N-(2-Chloropyrimidin-4-yl)-N-(cyclopropylmethyl)methanesulfonamide

To a solution of N-(cyclopropylmethyl)methanesulfonamide (247 mg, 1.66 mmol) in DMF (6 mL) at 0° C. was added 60% NaH in oil (86.3 mg, 2.16 mmol). The mixture was stirred for 10 minutes, and 2,4-dichloropyrimidine (321.5 mg, 2.16 mmol) was then added. The resulting mixture was allowed to warm to room temperature and was then stirred overnight. Aqueous NH$_4$Cl solution (10 mL) was added and the mixture was extracted with EtOAc (3×25 mL). The combined organic layers were washed with brine (10 mL), dried over Na$_2$SO$_4$, filtered, and evaporated in vacuo. The residue was purified by column chromatography on silica gel (eluted with 0-65% EtOAc/hexane) to afford the title compound (327 mg, 75% yield) as a light brown oil. $^1$H NMR (300 MHz, CDCl$_3$): δ ppm 8.42 (d, J=5.7 Hz, 1H), 7.42 (d, J=5.7 Hz, 1H), 3.97 (d, J=6.9 Hz, 2H), 3.26 (s, 3H), 1.24 (m, 1H), 0.57 (m, 2H), 0.46 (m, 2H); LCMS (method 3): Rt 4.98 min, m/z 262.0, 264.0 [M+H]$^+$.

Step-3: (S)—N-(2-((1-(6-Chloro-2-oxo-1,2-dihydroquinolin-3-yl)ethyl)amino)pyrimidin-4-yl)-N-(cyclopropylmethyl)methanesulfonamide TFA Salt (I-2)

A solution of N-(2-chloropyrimidin-4-yl)-N-(cyclopropylmethyl)methanesulfonamide (120.4 mg, 0.46 mmol), (S)-3-(1-aminoethyl)-6-chloroquinolin-2(1H)-one hydrochloride (91 mg, 0.35 mmol), and DIEA (183 μL, 1.05 mmol) in DMSO (4 mL) was heated in a sealed tube at 130° C. for 5 hours. The reaction was then cooled to room temperature, and EtOAc (100 mL) was added. The organic mixture was washed with water (3×10 mL), brine (15 mL), dried over Na$_2$SO$_4$, filtered, and evaporated in vacuo. The residue was purified by column chromatography on silica gel (eluted with 10-100% EtOAc/hexane, 1% Et$_3$N) followed by reverse phase column chromatography on C18 bonded silica gel (eluted with 0-100% acetonitrile/water, 0.1% TFA) to afford the title compound 2 (28 mg, 14% yield) as a white solid. $^1$H NMR (300 MHz, DMSO-d$_6$, 80° C.): δ ppm 8.18 (d, J=6.3 Hz, 1H), 7.78 (s, 1H), 7.68 (d, J=2.1 Hz, 1H), 7.46 (dd, J=2.7, 8.7 Hz, 1H), 7.33 (d, J=8.7 Hz, 1H), 6.77 (d, J=6.3 Hz, 1H), 5.17 (m, 1H), 3.85 (dd, J=6.9, 14.7 Hz, 1H), 3.69 (m, 1H), 3.34 (s, 3H), 1.48 (d, J=6.9 Hz, 3H), 1.05 (m, 1H), 0.40-0.19 (m, 4H); m.p.=120.0-127.0° C.; LCMS (method 3): Rt=4.39 min, m/z=448.1, 450.1 [M+H]$^+$.

Example 30—N-(2-(((S)-1-(6-chloro-2-oxo-1,2-dihydroquinolin-3-yl)ethyl)amino)pyrimidin-4-yl)-N-(tetrahydro-2H-pyran-3-yl)methanesulfonamide (I-3)

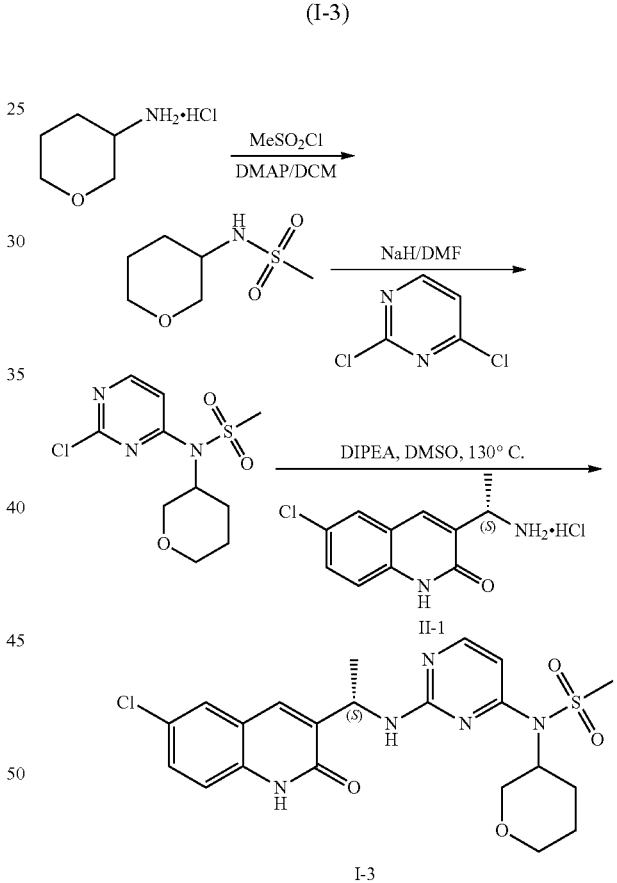

I-3

Step-1: N-(tetrahydro-2H-pyran-3-yl)methanesulfonamide

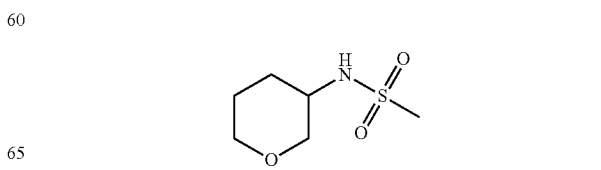

To a solution of tetrahydro-2H-pyran-3-amine hydrochloride (2.0 g, 14.5 mmol) and N,N-dimethylpyridin-4-amine (3.6 g, 29.5 mmol) in anhydrous dichloromethane (50 mL) cooled in an ice-water bath was added MeSO₂Cl (1.25 mL, 16.1 mmol) dropwise. White precipitate formed immediately. The mixture was allowed to warm to room temperature and was stirred overnight. The mixture was then diluted with dichloromethane, washed with water (1×), citric acid (10%, 2×), water (1×), dried (Na₂SO₄), and concentrated in vacuo. The title compound was obtained as a white solid (1.88 g, 72% yield). m.p. 64-66° C. $^1$H NMR (300 MHz, CDCl₃): δ ppm 4.61 (br s, 1H), 3.82 (d, J=9.0 Hz, 1H), 3.4-3.7 (m, 4H), 2.99 (s, 3H), 1.5-2.0 (m, 4H). LCMS: m/z 180 [M+H]⁺.

Step-2: N-(2-chloropyrimidin-4-yl)-N-(tetrahydro-2H-pyran-3-yl)methanesulfonamide

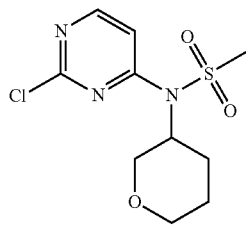 [SMILES: CS(=O)(=O)N(c1ccnc(Cl)n1)C1CCCOC1]

To a solution of N-(tetrahydro-2H-pyran-3-yl)methanesulfonamide (1.63 g, 9.09 mmol) in dimethylformamide (50 mL) cooled in an ice-water bath was added 60% NaH in oil (0.55 g, 13.7 mmol) portionwise under a nitrogen atmosphere. The reaction mixture was stirred at room temperature for 15 minutes and then cooled in an ice-water bath. 2,4-Dichloropyrimidine (1.69 g, 11.3 mmol) was then added in one portion. The reaction mixture was allowed to warm up to room temperature and was stirred for 3 days. After removal of N,N-dimethylformamide under reduced pressure, the residue was partitioned between EtOAc and saturated NH₄Cl aqueous solution. The organic layer was separated, washed with NaHCO₃ (aqueous) and brine, dried (Na₂SO₄) and concentrated in vacuo. The residue was purified by column chromatography on an ISCO® chromatography system (80 g silica gel column, eluted with EtOAc/hexanes 0-100%) to afford the title compound 2 as an off-white solid (1.04 g, 39% yield). m.p. 107-109° C. $^1$H NMR (300 MHz, CDCl₃): δ ppm 8.50 (d, J=5.7 Hz, 1H), 7.30 (d, J=5.5 Hz, 1H), 4.41 (m, 1H), 4.0 (m, 2H), 3.9 (m, 1H), 3.3 (m, 1H), 3.23 (s, 3H), 2.28 (m, 1H), 2.02 (m, 1H), 1.74-1.86 (m, 2H). LCMS (method 3): >96% pure @ 254 nm, Rt 4.62 min, m/z 292, 294 [M+H]⁺.

Step-3: N-(2-(((S)-1-(6-chloro-2-oxo-1,2-dihydroquinolin-3-yl)ethyl)amino)pyrimidin-4-yl)-N-(tetrahydro-2H-pyran-3-yl)methanesulfonamide (I-3)

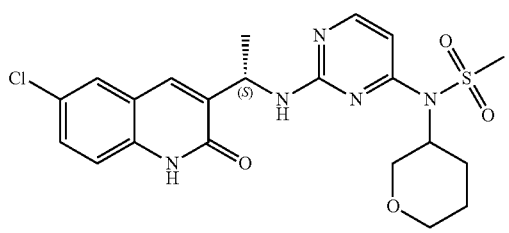

A mixture of N-(2-chloropyrimidin-4-yl)-N-(tetrahydro-2H-pyran-3-yl)methanesulfonamide (225 mg, 0.77 mmol), (S)-3-(1-aminoethyl)-6-chloroquinolin-2(1H)-one hydrochloride II-1 (100 mg, 0.39 mmol) and N,N-diisopropylethylamine (0.2 mL, 1.15 mmol) in anhydrous dimethyl sulfoxide (5 mL) was heated to 130° C. and stirred for 4.5 hours under an atmosphere of nitrogen. After cooling to room temperature, the mixture was diluted with EtOAc, washed with water (3×), dried (Na₂SO₄) and concentrated in vacuo. The residue was purified by column chromatography on an ISCO® chromatography system (20 g silica gel column, eluted with EtOAc/hexanes 0-100%) to afford the title compound 3 as a pale yellow solid (50 mg, 27% yield). m.p. 163-166° C. $^1$H NMR (300 MHz, CDCl₃): δ ppm 11.38 (s, 1H), 8.23 (dd, J=5.2, 1.6 Hz, 1H), 7.69 (s, 1H), 7.52 (m, 1H), 7.41 (dd, J=8.5, 2.2 Hz, 1H), 7.24 (d, J=8.8 Hz, 1 H), 6.52 (t, J=4.5 Hz, 1H), 6.10 (d, J=7.2 Hz, 1H), 5.25 (m, 1H), 3.6-4.3 (m, 5H), 3.11 (m, 4H), 1.94 (m, 2H), 1.6 (m, 5H). LCMS (method 3): 100% pure @ 254 nm, Rt 4.33 min, m/z 478, 480 [M+H]⁺.

Example 31—(S)—N-(2-((1-(6-Chloro-2-oxo-1,2-dihydroquinolin-3-yl)ethyl)amino)pyrimidin-4-yl)-N-isopropylpyridine-3-sulfonamide (I-4)

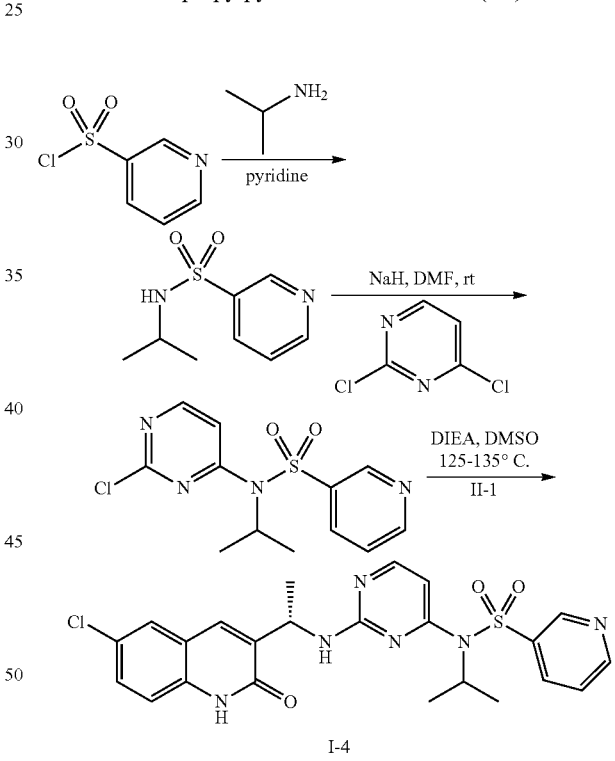

Step-1: N-isopropylpyridine-3-sulfonamide

To pyridine (10 mL) was added pyridine-3-sulfonyl chloride (3.0 g, 16.9 mmol) at 0° C. Propan-2-amine (3.0 g, 50.8 mmol) was then added and the reaction mixture was allowed to stir at room temperature overnight. The reaction mixture was poured into cold water and extracted with ethyl acetate. The combined organic phase was washed with brine, dried over MgSO₄, filtered and concentrated. The resulting residue was purified by column chromatography on an ISCO® chromatography system (120 g SiO₂ column, eluted with 0-10% MeOH in CH₂Cl₂), to afford the title compound (2.3 g, 67% yield). $^1$H NMR (300 MHz, DMSO-$d_6$): δ ppm 8.96 (d, J=1.6 Hz, 1H), 8.80-8.78 (dd, J=4.9 Hz, 1.0 Hz, 1H), 8.19-8.16 (dt, J=8.1 Hz, 0.8 Hz, 1H), 7.86 (s, 1H), 7.65-7.60 (q, J=4.9 Hz, 1H), 3.32-3.28 (m, 1H), 0.95 (d, J=6.5 Hz, 6H).

Step-2: N-(2-Chloropyrimidin-4-yl)-N-isopropylpyridine-3-sulfonamide

To a solution of N-isopropylpyridine-3-sulfonamide (440 mg, 2.2 mmol) in DMF (8 mL) cooled to 0° C. was added 60% NaH in oil (132 mg, 3.3 mmol). The mixture was stirred for 15 minutes, and 2,4-dichloropyrimidine (426 mg, 2.9 mmol) was then added. The mixture was allowed to warm to room temperature and was stirred overnight. MS of the reaction mixture indicated that the reaction had not gone to completion. The reaction mixture was then warmed to 38° C. and stirred for 3.5 hours. The mixture was then heated to 55° C. for 2 hours, and then cooled to room temperature and stirred overnight. An aqueous NH$_4$Cl solution (10 mL) and water (5 mL) were added. The mixture was extracted with EtOAc (3×30 mL) and the combined organic layers were washed with brine (10 mL), dried over Na$_2$SO$_4$, filtered, and evaporated in vacuo. The resulting residue was purified by column chromatography on silica gel (eluted with 0-95% EtOAc/hexane) to afford the title compound (368 mg, 54% yield) as a light brown solid. $^1$H NMR (300 MHz, CDCl$_3$): δ ppm 9.13 (d, J=2.1 Hz, 1H), 8.83 (dd, J=1.8, 5.1 Hz, 1H), 8.47 (d, J=5.7 Hz, 1H); m.p.=88.2-89.5° C.; LCMS (method 3): Rt 4.99 min, m/z 313.0, 315.0 [M+H]$^+$.

Step-3: (S)—N-(2-((1-(6-Chloro-2-oxo-1,2-dihydroquinolin-3-yl)ethyl)amino)pyrimidin-4-yl)-N-isopropylpyridine-3-sulfonamide TFA Salt (I-4)

A solution of N-(2-chloropyrimidin-4-yl)-N-isopropylpyridine-3-sulfonamide (59.5 mg, 0.19 mmol), (S)-3-(1-aminoethyl)-6-chloroquinolin-2(1H)-one hydrochloride II-1 (116.6 mg, 0.45 mmol), and DIEA (209 µL, 1.2 mmol) in DMSO (3 mL) was heated in a sealed tube at 130° C. for 4 hours. The reaction was cooled to room temperature, and EtOAc (70 mL) was added. The organic mixture was washed with water (2×10 mL), brine (10 mL), dried over Na$_2$SO$_4$, filtered, and evaporated in vacuo. The resulting residue was purified by column chromatography on silica gel (eluted with 0-10% MeOH/CH$_2$Cl$_2$) followed by reverse phase column chromatography on C18 bonded silica gel (eluted with 0-100% acetonitrile/water, 0.1% TFA) to afford the title compound 4 (47 mg, 41% yield) as a light yellow solid. $^1$H NMR (300 MHz, DMSO-$d_6$, 80° C.): δ ppm 8.97 (d, J=1.5 Hz, 1H), 8.78 (d, J=4.5 Hz, 1H), 8.25 (d, J=5.7 Hz, 2H), 7.65 (m, 2H), 7.58 (m, 1H), 7.45 (m, 1H), 7.31 (d, J=9.0 Hz, 1H), 6.55 (d, J=5.1 Hz, 1H), 5.02 (m, 1H), 4.41 (m, 1H), 1.41 (d, J=6.6 Hz, 3H), 1.13 (m, 6H); m.p.=94.0-100.0° C.; LCMS (method 3): Rt 4.55 min, m/z 499.1, 501.1 [M+H]$^+$.

Example 32—(S)—N-(2-(1-(6-Chloro-2-oxo-1,2-dihydroquinolin-3-yl)ethylamino)pyrimidin-4-yl)-N-isopropyl-2-methylpropane-1-sulfonamide (I-5)

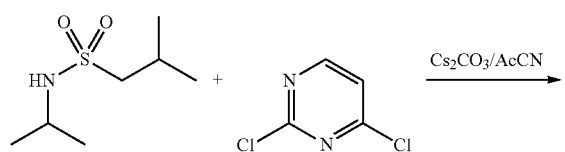

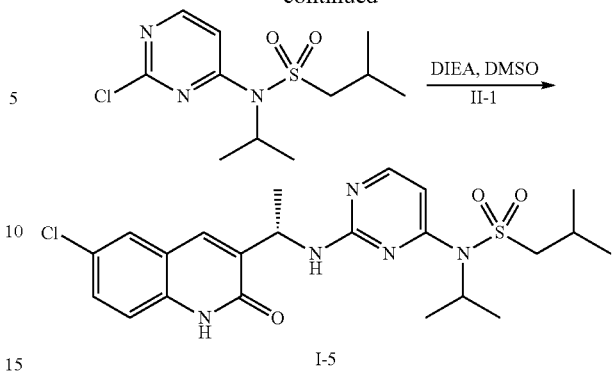

Step-1: N-(2-chloropyrimidin-4-yl)-N-isopropyl-2-methylpropane-1-sulfonamide

To a solution of N-isopropyl-2-methylpropane-1-sulfonamide (0.2 g, 1.116 mmol) and 2,4-dichloropyrimidine (0.166 g, 1.116 mmol) in acetonitrile (3 mL) was added cesium carbonate (0.454 g, 1.394 mmol). The reaction mixture was stirred at 50° C. for 16 hours. LCMS showed ~50% conversion. Additional cesium carbonate (0.454 g, 1.394 mmol) was then added and the reaction mixture was stirred at 50° C. until the reaction was complete. Water (10 mL) was added to the reaction mixture, and the aqueous phase was extracted with DCM (3×10 mL). The combined organic phases were dried over MgSO$_4$, and the volatiles were removed under reduced pressure. The crude oil was purified on SiO$_2$ (25 g SNAP® column, 0% EtOAc/hexanes for 5 minutes then 0-30% EtOAc/hexanes for 30 minutes then 30-60% EtOAc/hexanes for 5 minutes). The desired product N-(2-chloropyrimidin-4-yl)-N-isopropyl-2-methylpropane-1-sulfonamide (0.09 g, 0.308 mmol, 27.6% yield) was isolated and used in the next step without further purification.

Step-2: (S)—N-(2-(1-(6-Chloro-2-oxo-1,2-dihydroquinolin-3-yl)ethylamino)pyrimidin-4-yl)-N-isopropyl-2-methylpropane-1-sulfonamide (I-5)

A solution of (S)-3-(1-aminoethyl)-6-chloroquinolin-2 (1H)-one hydrochloride II-1 (0.044 g, 0.171 mmol), N-(2-chloropyrimidin-4-yl)-N-isopropyl-2-methylpropane-1-sulfonamide (0.05 g, 0.171 mmol), and DIEA (0.180 mL, 1.028 mmol) in DMSO (1.224 mL) was heated to 120° C. for 16 hours. Water (15 mL) was added, and the resulting precipitate was filtered off and washed with water (2×5 mL). The filtrate was dried under reduced pressure and purified on a Gilson reverse phase HPLC (20 mL/min, 10 min gradient 15-85% ACN, 0.01% HCO$_2$H on an XTerra Prep MS C18 OBD 5 M, 19×100 mm column) to afford (S)—N-(2-(1-(6-chloro-2-oxo-1,2-dihydroquinolin-3-yl)ethylamino)pyrimidin-4-yl)-N-isopropyl-2-methylpropane-1-sulfonamide (0.004 g, 8.37 µmol, 4.88% yield). $^1$H NMR (300 MHz, DMSO-$d_6$): δ ppm 11.94 (s, 1H), 8.21 (br s, 1H), 7.61-7.82 (m, 3H), 7.45 (br d, J=8.50 Hz, 1H), 7.26 (d, J=8.79 Hz, 1H), 6.45 (d, J=5.86 Hz, 1H), 4.87-5.07 (m, 1H), 4.17-4.30 (m, 1H), 3.02-3.20 (m, 2H), 2.00-2.15 (m, 1H), 1.35-1.44 (m, 3H), 0.77-1.17 (m, 12H).

Example 33—(S)—N-((2-((1-(6-Chloro-2-oxo-1,2-dihydroquinolin-3-yl)ethyl)amino)pyrimidin-4-yl)methyl)-N-cyclopropylmethanesulfonamide (I-6)

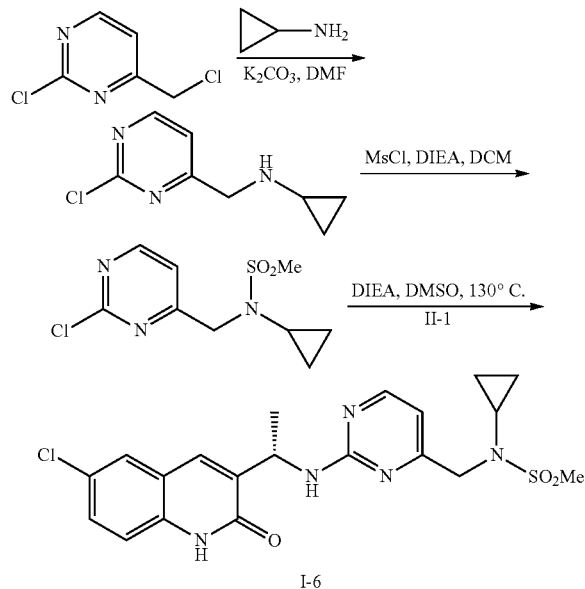

Step-1:
N-((2-chloropyrimidin-4-yl)methyl)cyclopropanamine

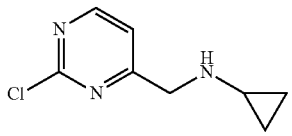 [SMILES: Clc1nccc(CNC2CC2)n1]

A mixture of 2-chloro-4-(chloromethyl)pyrimidine (500 mg, 3.07 mmol, 1 equivalent) and K$_2$CO$_3$ (506 mg, 3.66 mmol, 1.2 equivalents) in 4.5 mL of DMF was treated with cyclopropylamine (173 mg, 3.03 mmol, 1 equivalent) and stirred at room temperature. After 5 hours, the reaction mixture was poured into water and extracted with EtOAc (×2). After washing with brine and drying over Na$_2$SO$_4$, the extracts were chromatographed on a 15 g silica gel column (eluted with EtOAc/hexanes, 65/35) to provide the title compound (235 mg, 41% yield) as a thick gold liquid.

Step-2: N-((2-Chloropyrimidin-4-yl)methyl)-N-cyclopropylmethanesulfonamide

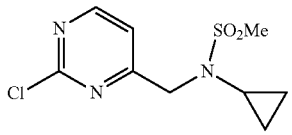 [SMILES: CS(=O)(=O)N(Cc1ccnc(Cl)n1)C1CC1]

A solution of N-((2-chloropyrimidin-4-yl)methyl)cyclopropanamine (208 mg, 1.13 mmol, 1 equivalent) in 4 mL of DCM at 0° C. was treated with DIEA (225 mg, 1.74 mmol, 1.5 equivalents) followed by methanesulfonyl chloride (145 mg, 1.27 mmol, 1.1 equivalents). After stirring for 2 hours at room temperature, the reaction mixture was poured into water and extracted with EtOAc (×2). After washing with brine and drying over Na$_2$SO$_4$, the extracts were chromatographed on 7-8 g silica gel column and eluted with hexane/EtOAc (1/1) to provide the title compound (228 mg, 77% yield) as a pale yellow waxy solid.

Step-3: (S)—N-((2-((1-(6-Chloro-2-oxo-1,2-dihydroquinolin-3-yl)ethyl)amino)pyrimidin-4-yl)methyl)-N-cyclopropylmethanesulfonamide (I-6)

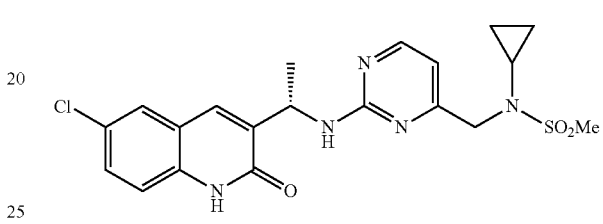

A mixture of N-((2-chloropyrimidin-4-yl)methyl)-N-cyclopropylmethanesulfonamide (228 mg, 0.87 mmol, 1.5 equivalents), (S)-3-(1-aminoethyl)-6-chloroquinoolin-2(1)-one hydrochloride II-1 (154 mg, 0.59 mmol, 1 equivalent) and DIEA (155 mg, 1.2 mmol, 2 equivalents) in 2 mL of DMSO was heated in a sealed tube at 130° C. for 1.5 hours. The reaction was then poured into water and extracted with EtOAc (×2). After washing with brine and drying over Na$_2$SO$_4$, the extracts were chromatographed on a 15 g silica gel column and eluted with 0-3% DCM/EtOH (97/3) gradient and the pure fractions were collected and lyophilized from CH$_3$CN/water to provide 18 mg (9.5% yield) of compound 6 as a pale yellow solid. $^1$H NMR (300 MHz, CDCl$_3$): δ ppm 11.57 (br s, 1H), 8.23 (d, J=4.95 Hz, 1H), 7.70 (s, 1H), 7.50 (d, J=2.19 Hz, 1H), 7.41 (dd, J=2.19, 8.79 Hz, 1H), 7.24 (d, J=8.52 Hz, 1H), 6.56 (d, J=5.22 Hz, 1H), 6.05 (br d, J=7.95 Hz, 1H), 5.30 (m, 1H), 4.30 (s, 2H), 2.93 (br s, 3H), 2.55 (m, 1H), 1.59 (d, 3H), 0.80 (m, 2H), 0.63 (m, 2H). LCMS (Method 3), Rt 4.39 min., m/z 448 [M+H]$^+$.

Example 34—(S)-3-(1-((4-tert-Butylamino)-pyrimidin-2-yl)amino)ethyl)-6-chloroquinolin-2(1H)-one (I-7)

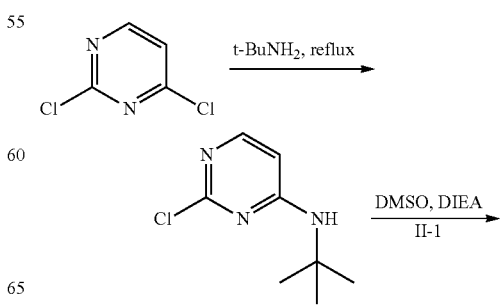

-continued

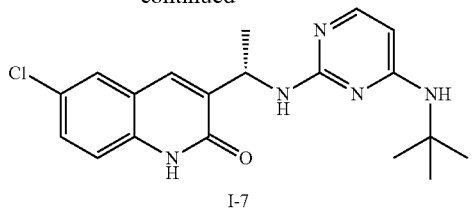

I-7

Step-1: N-(tert-Butyl)-2-chloropyrimidin-4-amine

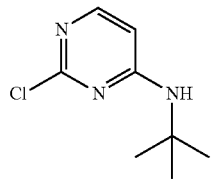

2,4-Dichloropyrimidine (3.10 g, 21.4 mmol) was refluxed in 32 mL of tert-BuNH$_2$ for 3 hours, then was cooled to room temperature and concentrated to dryness under reduced pressure. The crude was purified by column chromatography on an ISCO® chromatography system using a 120 g normal phase column (SiO$_2$) and eluted with a gradient (EtOAc in CH$_2$Cl$_2$) to afford 2.5 g (63% yield) of the title compound. The more polar spot (lower R$_f$) on the SiO$_2$-TLC plate is N-(tert-butyl)-4-chloropyrimidin-2-amine.

Step-2: (S)-3-(1-((4-tert-butylamino)-pyrimidin-2-yl)amino)ethyl)-6-chloroquinolin-2(1H)-one (I-7)

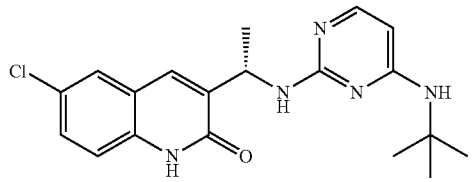 [SMILES: C[C@H](Nc1nccc(NC(C)(C)C)n1)c1cc2cc(Cl)ccc2[nH]c1=O]

To a sealed tube under an atmosphere of nitrogen, was added N-(tert-butyl)-4-chloropyrimidin-2-amine (472 mg, 2.5 mmol), (S)-3-(1-aminoethyl)-6-chloroquinolin-2(1H)-one hydrochloride I-1 (440 mg, 1.7 mmol) and DIEA (0.4 mL) in 4 mL of anhydrous DMSO. The reaction mixture was stirred at 140° C. for 5 hours, then cooled to a room temperature, concentrated to dryness under reduced pressure and purified twice by column chromatography on an ISCO® chromatography system using a 40 g "gold" column and eluting with an EtOAc/CH$_2$Cl$_2$ gradient followed by a MeOH/EtOAc gradient to afford 205 mg (32% yield) of the title compound 7. $^1$H NMR (300 MHz, CDCl$_3$): δ ppm 11.79 (br s, 1H), 7.74 (d, J=6.0 Hz, 1H), 7.71 (s, 1H), 7.48 (d, J=2.2 Hz, 1H), 7.38 (dd, J=8.8, 2.2 Hz, 1H), 7.23-7.28 (m, 2H), 7.75 (br d, J=5.8 Hz, 1H), 5.63 (d, J=6.0 Hz, 1H), 5.20-5.35 (q, 1H), 4.72 (br s, 1H), 1.57 (d, J=6.9 Hz, 3H), 1.25 (s, 9H). LCMS (Method 3): Rt 4.40 min, m/z 372.2.1/374.2 (Cl1-pattern) [M+H]$^+$. m.p.=182-183° C.

Example 35—(S)—N-(2-(1-(6-Chloro-2-oxo-1,2-dihydroquinolin-3-yl)ethylamino)pyrimidin-4-yl)-N-isobutylmethanesulfonamide (I-8)

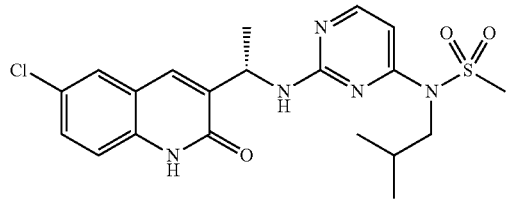 [SMILES: CC(C)CN(c1ccnc(N[C@@H](C)c2cc3cc(Cl)ccc3[nH]c2=O)n1)S(C)(=O)=O]

A mixture of (S)-3-(1-aminoethyl)-6-chloroquinolin-2(1H)-one hydrochloride II-1 (50.1 mg, 0.193 mmol) and N-(2-chloropyrimidin-4-yl)-N-isobutylmethanesulfonamide (52.7 mg, 0.200 mmol) was dissolved in DMSO (1.4 mL) and DIEA (0.10 mL, 0.573 mmol). The solution was stirred at 110° C. overnight. Once LCMS indicated near completion of reaction, the mixture was diluted with water (30 mL) and extracted with EtOAc (2×20 mL). The combined extracts were dried (Na$_2$SO$_4$) and filtered. Silica gel was then added and the solvent was evaporated under reduced pressure. The material was purified by column chromatography on a Biotage® MPLC chromatography system (10 g silica gel column, eluted with 0-85% EtOAc in hexanes and isocratic elution at 72% EtOAc) to provide 33.4 mg of the title compound 8 as a yellow solid. LCMS is consistent with (S)—N-(2-(1-(6-chloro-2-oxo-1,2-dihydroquinolin-3-yl)ethylamino)pyrimidin-4-yl)-N-isobutylmethane sulfonamide (33.4 mg, 0.070 mmol, 36.2% yield). LCMS (Method 1): Rt 1.35 min, m/z 450.23 [M+H]$^+$.

Example 36—(S)-6-Chloro-3-(1-((4-(cyclopropylamino)pyrimidin-2-yl)amino)ethyl)quinolin-2(1H)-one TFA Salt (I-9)

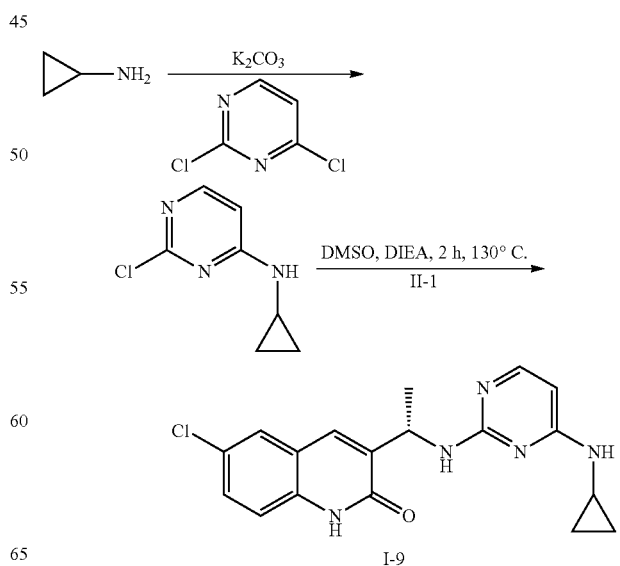

Step-1: 2-Chloro-N-cyclopropylpyrimidin-4-amine

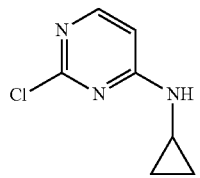 [SMILES: Clc1nccc(NC2CC2)n1]

A mixture of 2,4-dichloropyrimidine (1.98 g, 13.3 mmol, 1 equivalent) and K₂CO₃ (2.2 g, 16 mmol, 1 equivalent) in 20 mL DMF was treated with cyclopropylamine (0.76 g, 13.3 mmol, 1 equivalent) and stirred overnight at room temperature. The reaction mixture was then poured into 125 mL of water, and the resulting precipitate was collected providing the title compound (0.57 g, 25% yield) as a white solid. Concentration of the mother liquor provided a second crop of the title compound (0.41 g, 18% yield).

Step-2: (S)-6-chloro-3-(1-((4-(cyclopropylamino)pyrimidin-2-yl)amino)ethyl)quinolin-2(1H)-one TFA Salt (I-9)

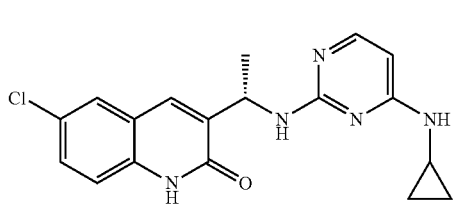 [SMILES: C[C@H](Nc1nccc(NC2CC2)n1)c1cc2cc(Cl)ccc2[nH]c1=O]

A mixture of 2-chloro-N-cyclopropylpyrimidin-4-amine (210 mg, 1.2 mmol, 1.2 equivalents), (S)-3-(l-aminoethyl)-6-chloroquinolin-2(1H)-one hydrochloride II-1 (260 mg, 1.0 mmol, 1 equivalent) and DIEA (252 mg, 1.0 mmol, 2 equivalents) in 2 mL of DMSO was heated in a sealed tube at 130° C. for 2 hours. The reaction was then poured into water, and the resulting precipitate was collected, rinsed with water, and dried to provide 127 mg of the crude product. Purification by reverse phase chromatography (13 g Redisep C18) on an ISCO® chromatography system using a H₂O/0.1% TFA: ACN/0.1% TFA gradient followed by lyophilization of the pure fractions afforded 68 mg of compound I-9 as a TFA salt. ¹H-NMR (300 MHz, d₆-DMSO, 90° C.): δ ppm 11.87 (br s, 1H), 8.75 (br s, 1H), 8.40 (br s, 1H), 7.83 (s, 1H) 7.74 (d, 1H), 7.72 (br s, 1H) 7.49 (m, 1H), 7.35 (m, 1H), 6.10 (br s, 1H), 5.22 (m, 1H), 2.86 (br m, 1H), 1.53 (d, 3H), 0.79 (br m, 2H), 0.56 (br m, 1H), 0.47 (br m, 1H).). LC/MS (Method 3): Rt 5.2 min., m/z 356 [M+H]⁺.

Example 37—(S)—N-(2-(1-(6-Chloro-2-oxo-1,2-dihydroquinolin-3-yl)ethylamino)pyrimidin-4-yl)-N-isopropylmethanesulfonamide (I-10)

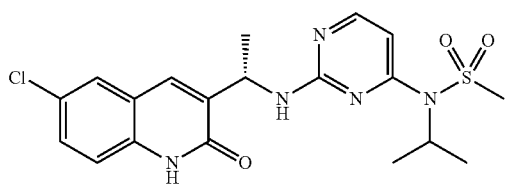 [SMILES: CC(C)N(c1ccnc(N[C@@H](C)c2cc3cc(Cl)ccc3[nH]c2=O)n1)S(C)(=O)=O]

A mixture of (S)-3-(1-aminoethyl)-6-chloroquinolin-2(1H)-one hydrochloride (49.4 mg, 0.191 mmol) and N-(2-chloropyrimidin-4-yl)-N-isopropylmethanesulfonamide (59.7 mg, 0.239 mmol) was dissolved in DMSO (1.4 mL) and DIEA (0.10 mL, 0.573 mmol). The solution was stirred at 110° C. for one day. Once LCMS indicated near completion of reaction, the sample was diluted with water (30 mL) and extracted with EtOAc (2×20 mL). The combined extracts were dried (Na₂SO₄) and filtered. Silica gel was then added and the solvent was evaporated under reduced pressure. The material was purified by column chromatography on a Biotage® MPLC chromatography system (10 g silica gel column, eluted with 0-85% EtOAc in hexanes and with isocratic elution when peaks eluted) to provide 38.5 mg of the title compound as a yellow solid. LCMS is consistent with (S)—N-(2-(1-(6-chloro-2-oxo-1,2-dihydroquinolin-3-yl)ethylamino) pyrimidin-4-yl)-N-isopropyl methanesulfonamide (38.5 mg, 0.085 mmol, 44.6% yield) LCMS (Method 1): Rt 1.24 min; m/z: 436.1938 [M+H]⁺.

Example 38—(S)—N-(2-((1-(6-Chloro-2-oxo-1,2-dihydroquinolin-3-yl)ethyl)amino)pyrimidin-4-yl)-1-cyclopropyl-N-isopropylmethanesulfonamide TFA Salt (I-11)

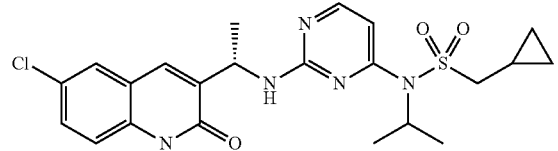

A solution of N-(2-chloropyrimidin-4-yl)-1-cyclopropyl-N-isopropylmethane sulfonamide III-3 (137 mg, 0.47 mmol), (S)-3-(1-aminoethyl)-6-chloroquinolin-2(1H)-one hydrochloride II-1 (158.3 mg, 0.61 mmol), and DIEA (246 µL, 1.41 mmol) in DMSO (3 mL) was heated in a sealed tube at 130° C. for 5 hours. The reaction was cooled to room temperature, and EtOAc (80 mL) was added. The organic layer was washed with water (3×10 mL), brine (15 mL), dried over Na₂SO₄, filtered, and evaporated in vacuo. The resulting residue was purified by column chromatography on silica gel (gradient elution from 10-100% EtOAc/hexane, 1% Et₃N) followed by reverse phase column chromatography on C18 bonded silica gel (gradient elution from 0-100% acetonitrile/water, 0.1% TFA) to afford the title compound (44 mg, 16% yield) as a white solid. ¹H NMR (300 MHz, DMSO-d₆, 80° C.): δ ppm 8.18 (d, J=5.7 Hz, 1H), 7.73 (s, 1H), 7.66 (d, J=2.4 Hz, 1H), 7.45 (dd, J=2.1, 8.7 Hz, 1H), 7.32 (d, J=8.7 Hz, 1H), 6.59 (d, J=6.0 Hz, 1H), 5.07 (m, 1H), 4.46 (p, J=7.2 Hz, 1H), 1.46 (d, J=6.9 Hz, 3H), 1.27 (m, 6H), 0.97 (m, 1H), 0.51 (m, 2H), 0.31 (m, 2H); m.p.=87.5-92.0° C.; LCMS (Method 3): Rt 4.65 min, m/z 476.1, 478.1 [M+H]⁺.

Example 39—(S)-6-Chloro-3-(1-((4-(1,1-dioxido-isothiazolidin-2-yl)pyrimidin-2-yl)amino)ethyl)quinolin-2(1H)-one (I-12)

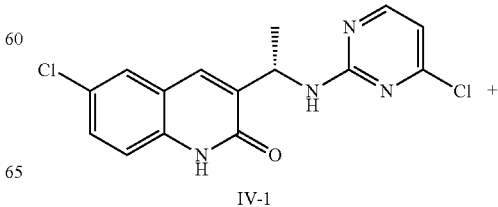

IV-1

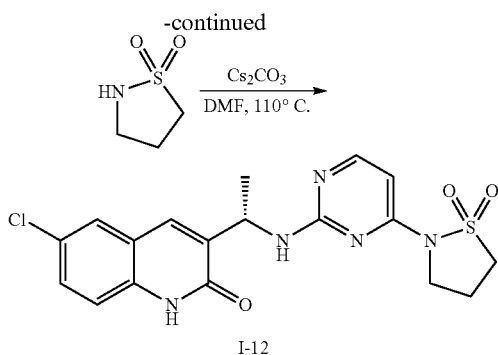

Into a 4 mL vial was added isothiazolidine 1,1-dioxide (9.04 mg, 0.075 mmol) and (S)-6-chloro-3-(1-(4-chloropyrimidin-2-ylamino)ethyl)quinolin-2(1H)-one IV-1 (25 mg, 0.075 mmol) in DMF (250 μL). To this solution was added Cs₂CO₃ (48.6 mg, 0.149 mmol) and DIEA (26.1 μL, 0.149 mmol) and the reaction mixture was stirred at 110° C. for 1.5 hours. The mixture was then diluted with EtOAc and washed with brine (×2). The organic extract was dried over Na₂SO₄, filtered, and concentrated under reduced pressure to provide the crude product. This crude material was purified by column chromatography on a Biotage® chromatography system (eluted with 0-100% EtOAc in hexanes) to afford the title compound (5.2 mg, 17% yield). ¹H NMR (300 MHz, CDCl₃): δ ppm 8.03 (br s, 1H), 7.93 (br s, 1H), 7.61 (br s, 1H), 7.41 (br d, J 8.50 Hz, 2H), 6.70 (br s, 1H), 5.42 (br s, 1H), 4.03 (br s, 1H), 3.83 (br s, 1H), 3.46 (m, 2H), 3.38 (m, 2H), 1.55-1.71 (m, 3H). LCMS (Method 1): Rt 2.02 min, m/z 419.89[M+H]⁺.

TABLE 3

The examples listed in Table 3 were prepared using methods similar to those described for the preparation of Examples 28-39 (I-1-I-12).

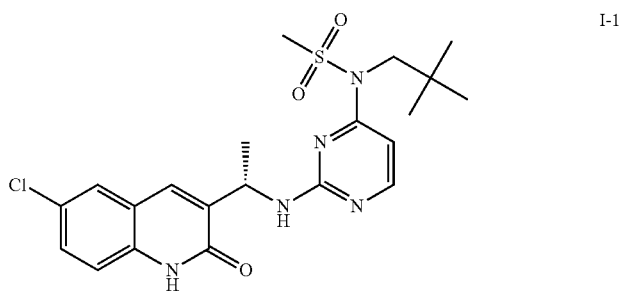

I-1

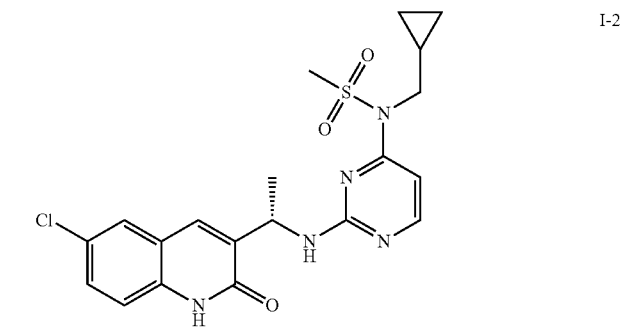

I-2

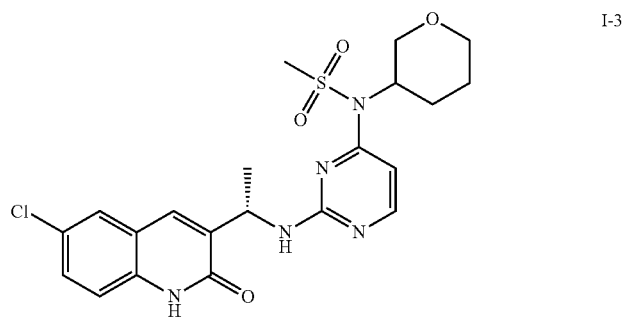

I-3

TABLE 3-continued
The examples listed in Table 3 were prepared using methods similar to those described for the preparation of Examples 28-39 (I-1-I-12).
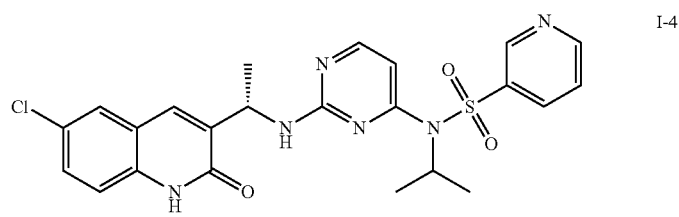 I-4
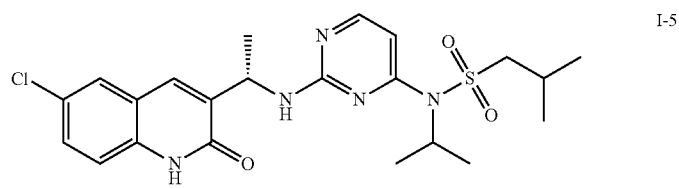 I-5
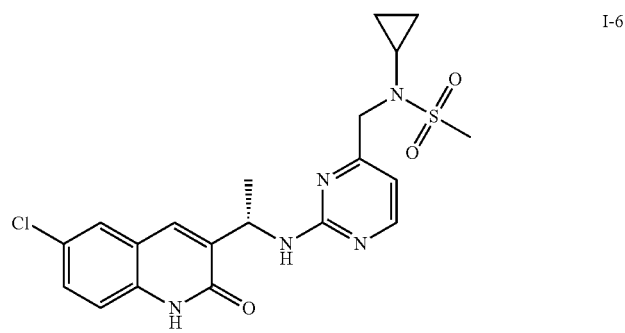 I-6
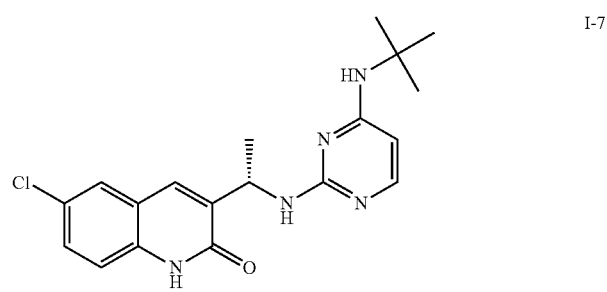 I-7
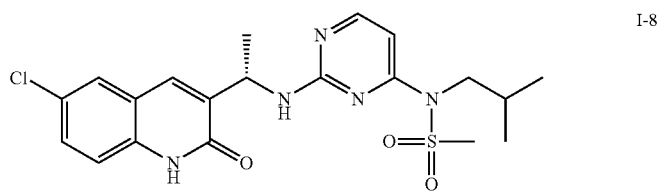 I-8
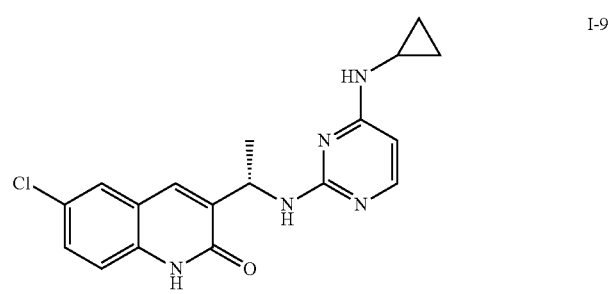 I-9

TABLE 3-continued
The examples listed in Table 3 were prepared using methods similar to those described for the preparation of Examples 28-39 (I-1-I-12).
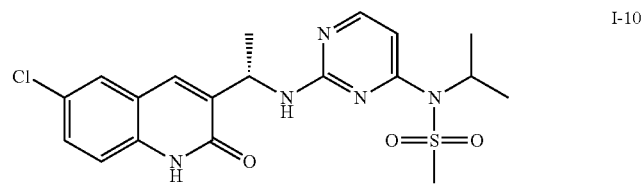
I-10
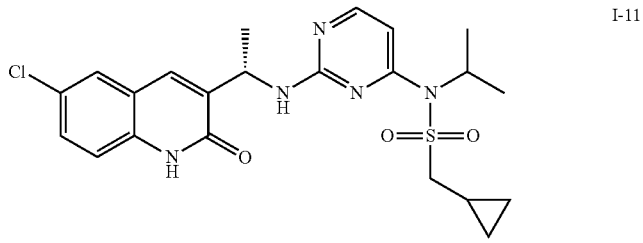
I-11
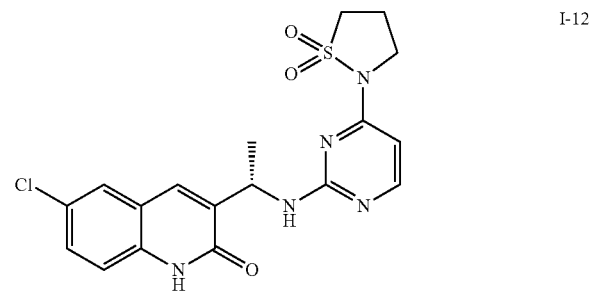
I-12
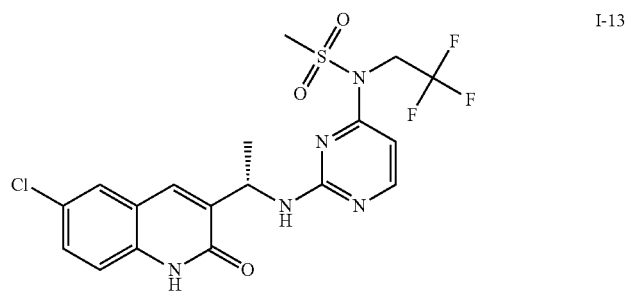
I-13
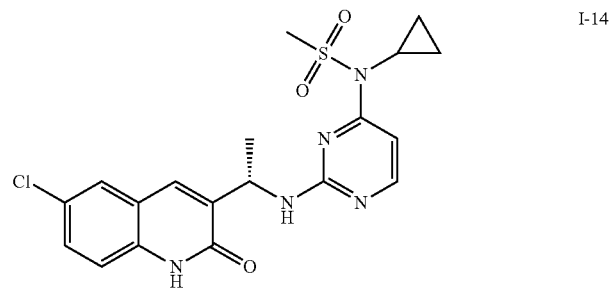
I-14
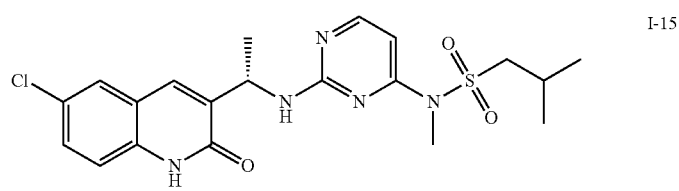
I-15

TABLE 3-continued
The examples listed in Table 3 were prepared using methods similar to those described for the preparation of Examples 28-39 (I-1-I-12).
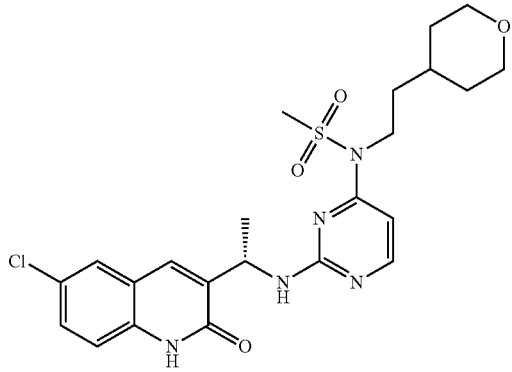 [SMILES: C[C@H](Nc1nccc(N(CCC2CCOCC2)S(C)(=O)=O)n1)c1cc2cc(Cl)ccc2[nH]c1=O]
I-16
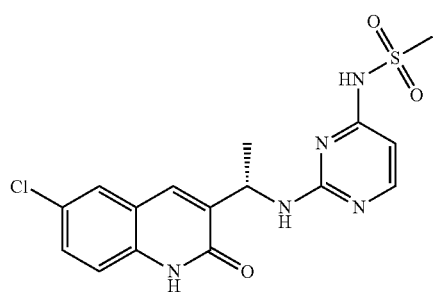 [SMILES: C[C@H](Nc1nccc(NS(C)(=O)=O)n1)c1cc2cc(Cl)ccc2[nH]c1=O]
I-17
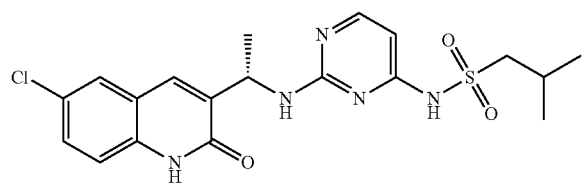 [SMILES: CC(C)CS(=O)(=O)Nc1ccnc(N[C@@H](C)c2cc3cc(Cl)ccc3[nH]c2=O)n1]
I-18
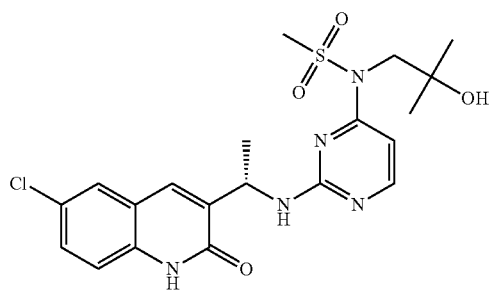 [SMILES: C[C@H](Nc1nccc(N(CC(C)(C)O)S(C)(=O)=O)n1)c1cc2cc(Cl)ccc2[nH]c1=O]
I-19
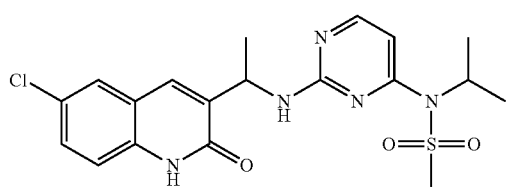 [SMILES: CC(Nc1nccc(N(C(C)C)S(C)(=O)=O)n1)c1cc2cc(Cl)ccc2[nH]c1=O]
I-20

TABLE 3-continued

The examples listed in Table 3 were prepared using methods similar to those described for the preparation of Examples 28-39 (I-1-I-12).

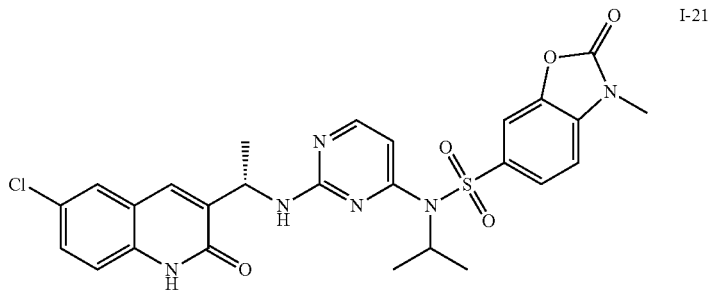

I-21

TABLE 4

LCMS signal and NMR chemical shifts of each compound listed in Table 3.

| Cmpds No | LCMS[a] | ¹H NMR (300 MHz) δ ppm |
|---|---|---|
| I-1 | m/z: 464.09 [M + H]⁺ Rt (min): 1.45 | ¹H NMR (300 MHz, CDCl₃): δ ppm 10.33 (br s, 1 H), 8.20 (d, J = 5.2 Hz, 1 H), 7.66 (s, 1 H), 7.49 (d, J = 2.2 Hz, 1 H), 7.42 (dd, J = 8.5, 2.2 Hz, 1 H), 7.18 (d, J = 8.5 Hz, 1 H), 6.81 (d, J = 5.5 Hz, 1 H), 6.07-6.02 (m, 1 H), 5.27 (m, 1 H), 3.85-3.70 (m, 2 H), 2.90 (s, 3 H), 1.61 (d, J = 6.9 Hz, 3 H), 0.73 (s, 9 H). |
| I-2 | m/z: 448.18 [M + H]⁺ Rt (min): 1.28 | 1H NMR (300 MHz, DMSO- d₆, 80° C.): δ ppm 8.18 (d, J = 6.3 Hz, 1 H), 7.78 (s, 1 H), 7.68 (d, J = 2.1 Hz, 1 H), 7.46 (dd, J = 2.7, 8.7 Hz, 1 H), 7.33 (d, J = 8.7 Hz, 1 H), 6.77 (d, J = 6.3 Hz, 1 H), 5.17 (m, 1 H), 3.85 (dd, J = 6.9, 14.7 Hz, 1 H), 3.69 (m, 1 H), 3.34 (s, 3 H), 1.48 (d, J = 6.9 Hz, 3 H), 1.05 (m, 1 H), 0.40-0.19 (m, 4 H). |
| I-3 | m/z: 478.25 [M + H]⁺ Rt (min): 1.14 | ¹H NMR (300 MHz, CDCl₃): δ ppm 11.38 (s, 1 H), 8.23 (dd, J = 5.2, 1.6 Hz, 1 H), 7.69 (s, 1 H), 7.52 (m, 1 H), 7.41 (dd, J = 8.5, 2.2 Hz, 1 H), 7.24 (d, J = 8.8 Hz, 1 H), 6.52 (t, J = 4.5 Hz, 1 H), 6.10 (d, J = 7.2 Hz, 1 H), 5.25 (m, 1 H), 3.6~4.3 (m, 5 H), 3.11 (m, 4 H), 1.94 (m, 2 H), 1.6 (m, 5 H). |
| I-4 | m/z: 499.24 [M + H]⁺ Rt (min): 1.33 | ¹H NMR (300 MHz, DMSO-d₆, 80° C.): δ ppm 8.97 (d, J = 1.5 Hz, 1 H), 8.78 (d, J = 4.5 Hz, 1 H), 8.25 (d, J = 5.7 Hz, 2 H), 7.65 (m, 2 H), 7.58 (m, 1 H), 7.45 (m, 1 H), 7.31 (d, J = 9.0 Hz, 1 H), 6.55 (d, J = 5.1 Hz, 1 H), 5.02 (m, 1 H), 4.41 (p, J = 6.9 Hz, 1 H), 1.41 (d, J = 6.6 Hz, 3 H), 1.13 (m, 6 H). |
| I-5 | m/z: 478.19 [M + H]⁺ Rt (min): 1.51 | ¹H NMR (300 MHz, DMSO- d₆): δ ppm 11.94 (s, 1 H), 8.21 (br s, 1 H), 7.61-7.82 (m, 3 H), 7.45 (br d, J = 8.50 Hz, 1 H), 7.26 (d, J = 8.79 Hz, 1 H), 6.45 (d, J = 5.86 Hz, 1 H), 4.87-5.07 (m, 1 H), 4.17-4.30 (m, 1 H), 3.02-3.20 (m, 2 H), 2.00-2.15 (m, 1 H), 1.35-1.44 (m, 3 H), 0.77-1.17 (m, 12 H). |
| I-6 | m/z: 448.10 [M + H]⁺ Rt (min): 1.21 | ¹H-NMR(300 MHz, CDCl₃): δ ppm 11.57 (br s, 1 H), 8.23 (d, J = 4.95 Hz, 1 H), 7.70 (s, 1 H), 7.50 (d, J = 2.19 Hz, 1 H), 7.41 (dd, J = 2.19, 8.79 Hz, 1 H), 7.24 (d, J = 8.52 Hz, 1 H), 6.56 (d, J = 5.22 Hz, 1 H), 6.05 (br d, J = 7.95 Hz, 1 H), 5.30 (m, 1 H), 4.30 (s, 2 H), 2.93 (br s, 3 H), 2.55 (m, 1 H), 1.59 (d, 3 H), 0.80 (m, 2 H), 0.63 (m, 2 H). |
| I-7 | m/z: 372.16 [M + H]⁺ Rt (min): 1.05 | ¹H NMR (300 MHz, CDCl₃): δ ppm 11.79 (br s, 1 H), 7.74 (d, J = 6.0 Hz, 1 H), 7.71 (s, 1 H), 7.48 (d, J = 2.2 Hz, 1 H), 7.38 (dd, J = 8.8, 2.2 Hz, 1 H), 7.23-7.28 (m, 2 H), 7.75 (br d, J = 5.8 Hz, 1 H), 5.63 (d, J = 6.0 Hz, 1 H), 5.20-5.35 (q, 1 H), 4.72 (br s, 1 H), 1.57 (d, J = 6.9 Hz, 3 H), 1.25 (s, 9 H). |
| I-8 | m/z: 450.23 [M + H]⁺ Rt (min): 1.35 | |
| I-9 | m/z: 356.11 [M + H]⁺ Rt (min): 0.97 | ¹H-NMR(300 MHz, d₆-DMSO, 90° C.): δ ppm 11.87 (br s, 1 H), 8.75 (br s, 1 H), 8.40 (br s, 1 H), 7.83 (s, 1 H), 7.74 (d, 1 H), 7.72 (br s, 1 H), 7.49 (m, 1 H), 7.35 (m, 1 H), 6.10 (br s, 1 H), 5.22 (m, 1 H), 2.86 (m, 1 H), 1.53 (d, 3 H), 0.79 (m, 2 H), 0.56 (m, 1 H), 0.47 (m, 1 H).). |
| I-10 | m/z: 436.19 [M + H]⁺ Rt (min): 1.24 | |
| I-11 | m/z: 476.26 [M + H]⁺ Rt (min): 1.4 | ¹H NMR (300 MHz, DMSO- d₆, 80° C.): δ ppm 8.18 (d, J = 5.7 Hz, 1 H), 7.73 (s, 1 H), 7.66 (d, J = 2.4 Hz, 1 H), 7.45 (dd, J = 2.1, 8.7 Hz, 1 H), 7.32 (d, J = 8.7 Hz, 1 H), 6.59 (d, J = 6.0 Hz, 1 H), 5.07 (m, 1 H), 4.46 (p, J = 7.2 Hz, 1 H), 1.46 (d, J = 6.9 Hz, 3 H), 1.27 (m, 6 H), 0.97 (m, 1 H), 0.51 (m, 2 H), 0.31 (m, 2 H). |
| I-12 | m/z: 420.08 [M + H]⁺ Rt (min): 0.98 | ¹H NMR (300 MHz, CDCl₃): δ ppm 8.03 (br s, 1 H), 7.93 (br s, 1 H), 7.61 (br s, 1 H), 7.41 (br d, J = 8.50 Hz, 2 H), 6.70 (br s, 1 H), 5.42 (br s, 1 H), 4.03 (br s, 1 H), 3.83 (br s, 1 H), 3.46 (m, 2 H), 3.38 (m, 2 H), 1.55-1.71 (m, 3 H). |
| I-13 | m/z: 476.08 [M + H]⁺ Rt (min): 1.32 | |

TABLE 4-continued

LCMS signal and NMR chemical shifts of each compound listed in Table 3.

| Cmpds No | LCMS[a] | $^1$H NMR (300 MHz) δ ppm |
|---|---|---|
| I-14 | m/z: 434.10 [M + H]$^+$ Rt (min): 1.15 | |
| I-15 | m/z: 450.16 [M + H]$^+$ Rt (min): 1.35 | |
| I-16 | m/z: 506.22 [M + H]$^+$ Rt (min): 1.2 | $^1$H NMR (300 MHz, CDCl$_3$): δ ppm 11.16 (br s, 1 H), 8.18-8.27 (m, 1 H), 7.78 (s, 1 H), 7.52-7.57 (m, 1 H), 7.40-7.47 (m, 1 H), 7.31-7.39 (m, 1 H), 6.67 (br d, J = 5.86 Hz, 1 H), 5.31-5.40 (m, 1 H), 5.31 (s, 1 H), 3.85-4.01 (m, 4 H), 3.50 (s, 1 H), 3.27-3.41 (m, 2 H), 3.24 (s, 2 H), 2.05 (s, 3 H), 1.67 (br d, J = 6.74 Hz, 3 H), 1.56 (br s, 4 H). |
| I-17 | m/z: 394.10 [M + H]$^+$ Rt (min): 0.85 | |
| I-18 | m/z: 436.13 [M + H]$^+$ Rt (min): 1.06 | $^1$H NMR (300 MHz, CDCl$_3$): δ ppm 11.86 (br s, 1 H), 8.25 (br s, 1 H), 7.93 (d, J = 6.16 Hz, 1 H), 7.82 (s, 1 H), 7.57 (s, 1 H), 7.52 (d, J = 8.79 Hz, 1 H), 7.24 (s, 1 H), 6.99 (br s, 1 H), 6.71 (d, J = 5.87 Hz, 1 H) 5.43 (m, 1 H), 2.97 (m, 2 H), 2.34 (m, 1 H), 1.74 (d, J = 7.04 Hz, 3 H), 1.07 (d, J = 6.45 Hz, 6 H) |
| I-19 | m/z: 465.96 [M + H]$^+$ Rt (min): 0.97 | $^1$H NMR (300 MHz, CDCl$_3$): δ ppm 11.22 (br s, 1 H), 7.90 (d, J = 5.86 Hz, 1 H), 7.68 (s, 1 H), 7.45 (s, 1 H), 7.35 (d, J = 8.51 Hz, 1 H), 7.17 (s, 1 H), 5.85 (d, J = 5.87 Hz, 1 H), 5.20 (m, 1 H) 3.32 (d, J = 6.45 Hz, 2 H), 2.84 (s, 3 H), 1.52 (d, J = 6.75 Hz, 3 H), 1.32-1.42 (m, 6 H) |
| I-20 | m/z: 436.18 [M + H]$^+$ Rt (min): 1.23 | |
| I-21 | m/z: 569.25 [M + H]$^+$ Rt (min): 1.42 | |

[a]LCMS (method 4);

Example 40—(S)-Methyl (2-((1-(6-chloro-2-oxo-1,2-dihydroquinolin-3-yl)ethyl)amino) pyrimidin-4-yl) carbamate (I-22)

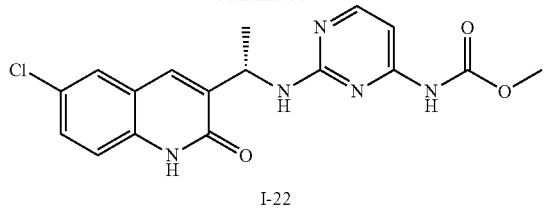

I-22

Step-1: Methyl (2-chloropyrimidin-4-yl)carbamate

To a solution of methyl carbamate (0.252 g, 3.36 mmol) in DMF (6.71 mL) at 0° C. was added 60% NaH (0.322 g, 6.71 mmol). The reaction mixture was stirred at room temperature for 30 minutes, then 2,4-dichloropyrimidine (0.5 g, 3.36 mmol) was added. The reaction mixture was stirred at room temperature for 1 hour. Water (20 mL) was added, and the aqueous phase was extracted with EtOAc (3×30 mL). The combined organic extracts were washed with brine (30 mL) and dried over MgSO$_4$. The volatiles were removed under reduced pressure. The residue was taken up in DCM (2 mL), and a precipitate was filtered off. Methyl (2-chloropyrimidin-4-yl)carbamate (0.153 g, 0.816 mmol, 24.30% yield) was isolated and used in the next step without further purification.

Step-2: (S)-Methyl (2-((1-(6-chloro-2-oxo-1,2-dihydroquinolin-3-yl)ethyl)amino)pyrimidin-4-yl) carbamate A solution of (S)-3-(1-aminoethyl)-6-chloroquinolin-2 (1H)-one hydrochloride (0.207 g, 0.800 mmol), methyl (2-chloropyrimidin-4-yl)carbamate (0.15 g, 0.800 mmol) and DIEA (0.838 mL, 4.80 mmol) in DMSO (2.67 mL) was heated to 130° C. for 5 hours. Water (25 mL) was then added, and the resulting precipitate was removed by filtration and dried under reduced pressure. The crude material was purified by column chromatography on SiO$_2$ (25 g SNAP® column, eluted with 0% MeOH/DCM for 5 minutes, 0-10% MeOH/DCM for 25 minutes and 10% MeOH/DCM for 10 minutes) to provide (S)-methyl (2-((1-(6-chloro-2-oxo-1,2-dihydroquinolin-3-yl)ethyl)amino) pyrimidin-4-yl)carbamate (0.0017 g, 4.55 μmol, 0.569% yield). $^1$H NMR (300 MHz, DMSO-d$_6$): δ ppm 11.94 (s, 1H), 10.09 (s, 1H), 8.08 (br d, J=5.86 Hz, 1H), 7.69-7.74 (m, 2H), 7.46 (dd, J=8.94, 2.49 Hz, 1H), 7.27 (d, J=9.09 Hz, 1H), 7.00 (d, J=5.57 Hz, 1H), 5.08-5.19 (m, 1H), 3.63 (s, 3H), 1.37 (d, J=6.74 Hz, 3H).

Example 41—(S)-Isopropyl (2-((1-(6-chloro-2-oxo-1,2-dihydroquinolin-3-yl)ethyl)amino) pyrimidin-4-yl)carbamate (I-23)

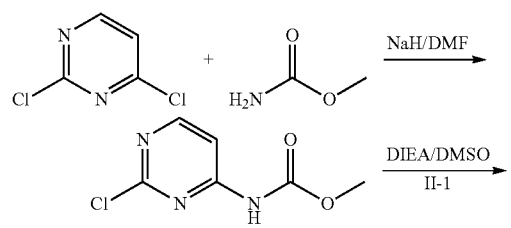

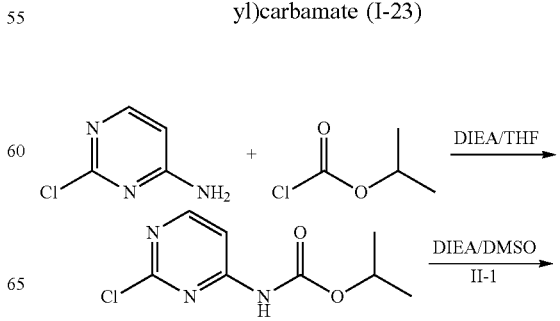

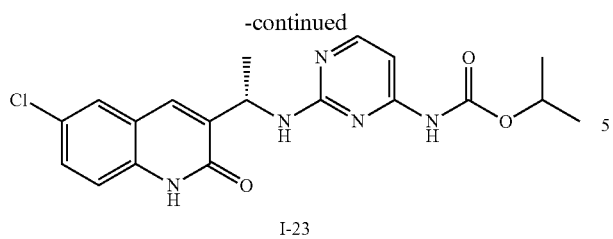

I-23

Step-1: Isopropyl (2-chloropyrimidin-4-yl)carbamate

To a suspension of 2-chloropyrimidin-4-amine (0.250 g, 1.930 mmol) in THF (4 mL) at room temperature were added DIEA (0.337 mL, 1.930 mmol) and isopropyl carbonochloridate (0.236 g, 1.930 mmol). The reaction was stirred at room temperature for 7 hours then additional DIEA (0.337 mL, 1.930 mmol) and isopropyl carbonochloridate (0.236 g, 1.930 mmol) were added. The reaction mixture was stirred at room temperature for 60 hours. Water (5 mL) was added, and a precipitate was filtered off. The filtrate was diluted with EtOAc (10 mL) and then washed with water (3×15 mL). The combined organic phases were dried over MgSO$_4$, and the volatiles were removed under reduced pressure. The crude material was purified by chromatography on SiO$_2$ (25 g SNAP® column eluted with 0% EtOAc/hexanes for 5 minutes then 0-30% EtOAc/hexanes for 15 minutes then 30% EtOAc/hexanes for 15 minutes). Isopropyl (2-chloropyrimidin-4-yl)carbamate was isolated as a white solid and was used in the next step without further purification.

Step-2: (S)-Isopropyl (2-((1-(6-chloro-2-oxo-1,2-dihydroquinolin-3-yl)ethyl)amino) pyrimidin-4-yl)carbamate A solution of (S)-3-(1-aminoethyl)-6-chloroquinolin-2(1H)-one hydrochloride II-1 (0.060 g, 0.232 mmol), isopropyl (2-chloropyrimidin-4-yl)carbamate (0.05 g, 0.232 mmol) and DIEA (0.243 mL, 1.391 mmol) in DMSO (1.546 mL) was heated to 120° C. for 16 hours. Water (25 mL) was then added, and the resulting precipitate was filtered off and dried under reduced pressure. The crude material was purified by column chromatography on SiO$_2$ (25 g SNAP® column, eluted with 0% MeOH/DCM for 5 minutes, 0-10% MeOH/DCM for 25 minutes, and 10% MeOH/DCM for 10 minutes). The product-containing fractions were concentrated under reduced pressure to afford (S)-isopropyl (2-((1-(6-chloro-2-oxo-1,2-dihydroquinolin-3-yl)ethyl)amino) pyrimidin-4-yl)carbamate (0.0098 g, 0.024 mmol, 10.52% yield). LCMS (Method 4): Rt 1.42 min; m/z: 402.05 [M+H]$^+$.

Example 42—(S)—N-(2-((1-(6-Chloro-2-oxo-1,2-dihydroquinolin-3-yl)ethyl)amino) pyrimidin-4-yl)-N-cyclopropyl-3-methylbutanamide (I-24)

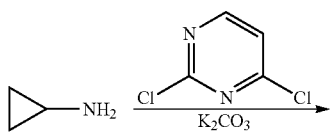

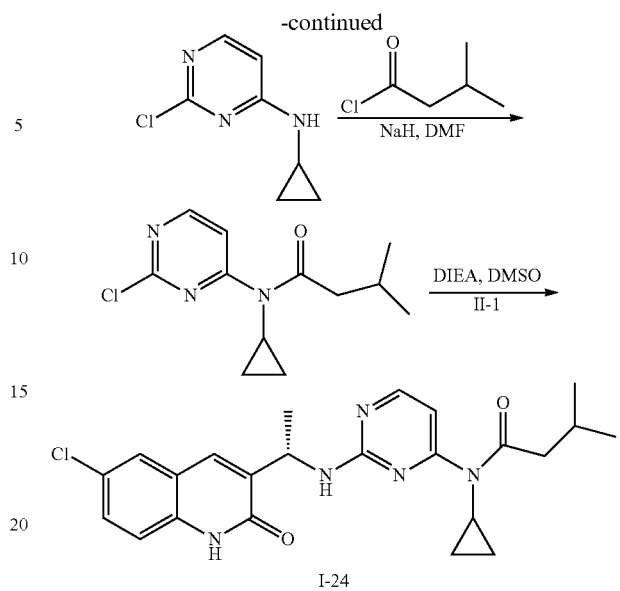

I-24

Step-1: 2-Chloro-N-cyclopropylpyrimidin-4-amine

A mixture of 2,4-dichloropyrimidine (1.98 g, 13.3 mmol, 1 equivalent) and K$_2$CO$_3$ (2.2 g, 16 mmol, 1 equivalent) in 20 mL of DMF was treated with cyclopropylamine (0.76 g, 13.3 mmol, 1 equivalent) and stirred overnight at room temperature. The reaction mixture was then poured into 125 mL of water, and the resulting precipitate was collected to afford the title compound (0.57 g, 25% yield) as a white solid. Concentration of the mother liquor provided an additional 0.41 g (18% yield) of the desired product.

Step-2: N-(2-Chloropyrimidin-4-yl)-N-cyclopropyl-3-methylbutanamide

In a dried 3-neck round bottom flask, a solution of 2-chloro-N-cyclopropylpyrimidin-4-amine (254 mg, 1.5 mmol, 1 equivalent) in 3 mL of DMF was cooled to 0° C. and then treated portionwise with NaH (60 wt % in oil, 72 mg, 1.8 mmol, 1.2 equivalents). After stirring at room temperature for 15 minutes, the solution was cooled to 0° C., and 3-methylbutyryl chloride (196 mg, 1.65 mmol, 1.1 equivalents) was added. The reaction was stirred overnight at room temperature and then quenched with water and an aqueous solution of NaHCO$_3$. Extraction with EtOAc (2×) followed by flash silica gel chromatography with hexane/EtOAc (85/15) provided the title compound (168 mg, 44% yield) as a colorless resin.

Step-3: (S)—N-(2-((1-(6-Chloro-2-oxo-1,2-dihydroquinolin-3-yl)ethyl)amino)pyrimidin-4-yl)-N-cyclopropyl-3-methylbutanamide TFA Salt (I-24)

A mixture of N-(2-chloropyrimidin-4-yl)-N-cyclopropyl-3-methylbutanamide (168 mg, 0.66 mmol, 1.2 equivalents), (S)-3-(1-aminoethyl)-6-chloroquinolin-2(1H)-one hydrochloride II-1 (142 mg, 0.55 mmol, 1 equivalent) and DIEA (141 mg, 1.1 mmol, 2 equivalents) in 1.1 mL of DMSO was heated in a sealed tube at 130° C. for 2.5 hours. The reaction mixture was then poured into water and extracted twice with EtOAc. The combined extracts were dried over Na$_2$SO$_4$ and purified by reverse phase chromatography (40 g Redisep C18) on an ISCO® chromatography system using a H₂O/0.1% TFA:ACN/0.1% TFA gradient. An additional reverse phase chromatography (12 g RediSep C18) purification afforded the title compound (13.3 mg) as the TFA salt. ¹H-NMR (300 MHz, CDCl₃): δ ppm 10.55 (br s, 1H), 7.79 (m, 2H), 7.57 (br s, 1H), 7.41 (br dd, 1H), 7.31 (br d, 1H), 7.18 (br d, 1H), 5.55 (m, 1H), 2.80 (m, 1H), 2.64 (t, 2H), 2.16 (m, 1H), 1.62 (d, 3H), 1.24 (m, 1H), 1.02 (m, 1H), 0.92 (dd, 6H), 0.62 (m, 1H), 0.48 (m, 1H). LCMS (Method 3): Rt 6.2 min; m/z 440 [M+H]⁺.

Example 43—(S)—N-(2-((1-(6-Chloro-2-oxo-1,2-dihydroquinolin-3-yl)ethyl)amino) pyrimidin-4-yl)acetamide (I-25)

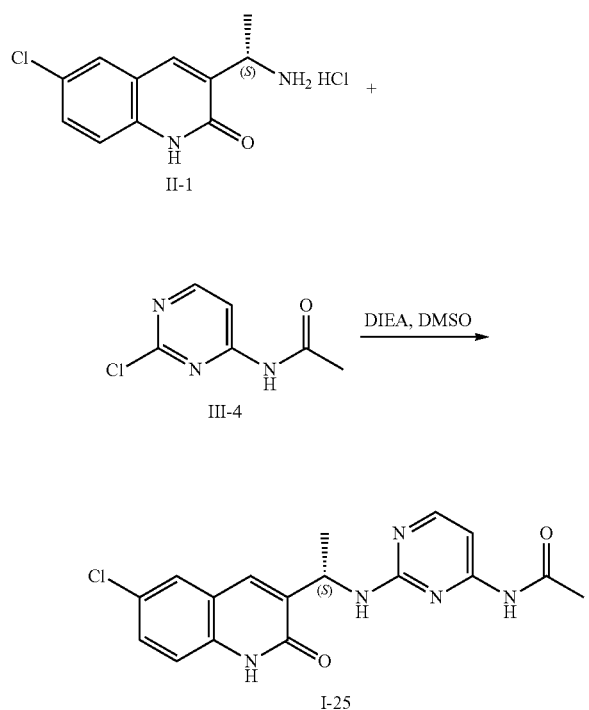

A solution of N-(2-chloropyrimidin-4-yl)acetamide III-4 (172 mg, 1.0 mmol), (S)-3-(1-aminoethyl)-6-chloroquinolin-2(1H)-one hydrochloride II-1 (130 mg, 0.50 mmol) and diisopropylethylamine (0.23 mL, 1.5 mmol) in DMSO (2.0 mL) was heated in a sealed tube at 130° C. for 90 minutes. Once the color of the reaction mixture turned brown from bright yellow, the mixture cooled to room temperature and diluted with EtOAc and water. The organic layer was separated and washed with water and brine. After drying over sodium sulfate, the solution was concentrated, and the residue was purified by column chromatography on an ISCO® chromatography system (SiO₂ column: hexanes/EtOAc gradient; 0-100% EtOAc) to afford the title compound as a foam. The product was dissolved in a water and acetonitrile mixture and lyophilized to obtain pure product I-25 as white solid (78 mg, 44% yield). ¹H NMR (300 MHz, CDCl₃): δ 11.63 (br s, 1H), 8.22 (m, 2H), 7.61 (s, 1H), 7.36-7.40 (m, 2H), 6.19 (br s, 1H), 5.27 (m, 1H), 2.14 (s, 3H), 1.59 (d, J=6.9 Hz, 3H). LCMS (method 3): Rt=3.65 min, m/z=358.1, 360.1 [M+H]⁺.

Example 44—(S)—N-(2-((1-(6-Chloro-2-oxo-1,2-dihydroquinolin-3-yl)ethyl)amino)pyrmidin-4-yl)-N-neopentylacetamide (I-26)

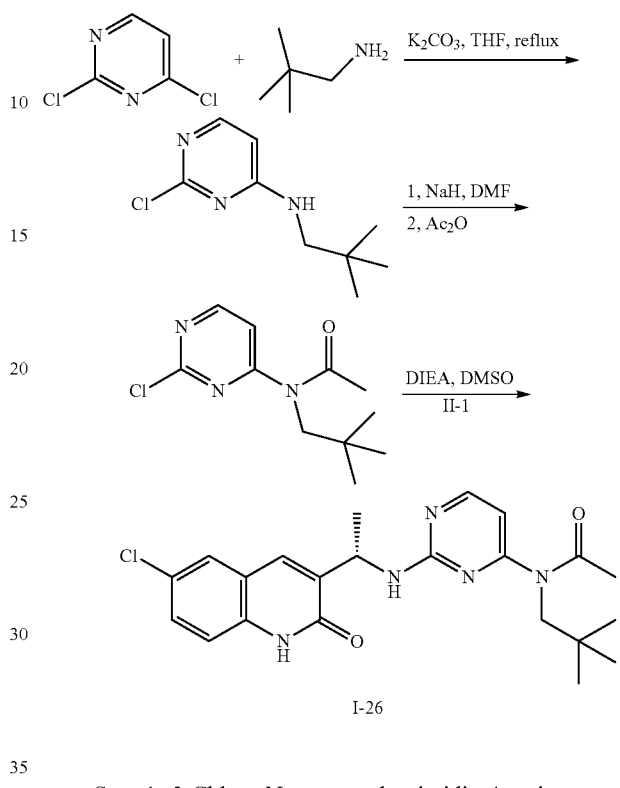

Step-1: 2-Chloro-N-neopentylpyrimidin-4-amine

A mixture of 2,4-dichloropyrimidine (3.00 g, 20.1 mmol), neopentylamine (3.1 mL, 26.2 mmol) and potassium carbonate (30.2 mmol) in THF (50 mL) was heated to reflux for 6 hours. TLC showed the product and unreacted pyrimidine. The reaction was then cooled to room temperature, filtered and concentrated to dryness. The residue was purified by column chromatography on an ISCO® chromatography system (SiO₂ column: Hex/EtOAc gradient; 0 to 60% EtOAc) to afford the title compound as white solid (2.41 g, 60% yield). ¹H NMR (300 MHz, CDCl₃): δ ppm 8.02 (br s, 1H), 6.25 (d, J=6.0 Hz, 1H), 5.31 (br s, 1H), 302 (br s, 2H), 0.98 (s, 9H).

Step-2: N-(2-Chloropyrimidin-4-yl)-N-neopentylacetamide

At 0° C., 60% NaH in oil (120 mg, 3 mmol) was added into a solution of 2-chloro-N-neopentylpyrimidin-4-amine (500 mg, 2.50 mmol) in DMF (10 mL). After stirring for 10 minutes, acetic anhydride (0.47 mL, 5.0 mmol) was added, and the mixture was stirred at room temperature overnight. Water was then added, and the mixture was extracted with EtOAc. The organic layer was separated and washed with water and brine. After drying over sodium sulfate, the solution was concentrated and purified by column chromatography on an ISCO® chromatography system (SiO₂ column: hexanes/EtOAc gradient; 0-40% EtOAc) to afford the title compound (466 mg, 77% yield). ¹H NMR (300 MHz, CDCl₃): δ ppm 8.51 (d, J=5.5 Hz, 1H), 7.42 (d, J=5.5 Hz, 1H), 3.98 (s, 2H), 2.31 (s, 3H), 0.84 (s, 9H).

Step-3: (S)—N-(2-((1-(6-chloro-2-oxo-1,2-dihydro-quinolin-3-yl)ethyl)amino)pyrimidin-4-yl)-N-neopentylacetamide (I-26)

In a sealed tube, a mixture of N-(2-chloropyrimidin-4-yl)-N-neopentylacetamide (120 mg, 0.5 mmol), (S)-3-(1-aminoethyl)-6-chloroquinolin-2(1H)-one hydrochloride II-1 (65 mg, 0.25 mmol) and diisopropylethylamine (0.13 mL, 0.75 mmol) in EtOH (2 mL) was heated to 130° C. for 2 hours. Once MS and TLC showed completion of reaction, the reaction mixture was cooled to room temperature and diluted with EtOAc and water. The layers were separated, and the organic layer was washed with brine and dried over sodium sulfate. After concentration, the resulting residue was purified by column chromatography on an ISCO® chromatography system (SiO$_2$ Column: hexanes/EtOAc gradient; 0-100% EtOAc) to afford the title compound as pale yellow solid (24 mg, 22% yield). $^1$H NMR (300 MHz, CDCl$_3$): δ ppm 11.32 (br s, 1H), 8.23 (d, J=5.2 Hz, 1H), 7.66 (s, 1H), 7.48 (d, J=1.9 Hz, 1H), 7.42 (dd, J=8.5, 2.2 Hz, 1H), 6.44 (d, J=5.2 Hz, 1H), 6.14 (d, J=7.7 Hz, 1H), 5.27 (m, 1H), 3.80-3.65 (m, 2H), 2.11 (s, 3H), 1.64 (d, J=7.1 Hz, 3H), 0.65 (s, 9H). LCMS (method 3): Rt 4.56 min, m/z 428.2, 430.2 [M+H]$^+$.

Example 45—(S)—N-(2-((1-(6-chloro-2-oxo-1,2-dihydroquinolin-3-yl)ethyl)amino)pyrimidin-4-yl)-2-(tetrahydro-2H-pyran-4-yl)acetamide (I-27)

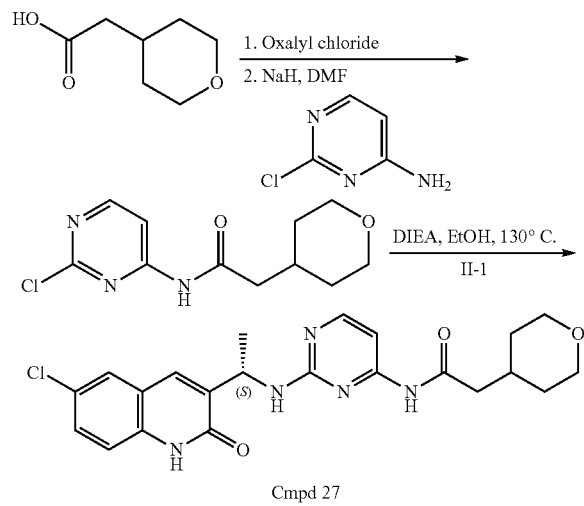

Cmpd 27

Step-1: 2-(Tetrahydro-2H-pyran-4-yl)acetylchloride

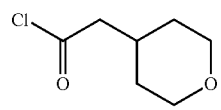

To an ice-cold solution of 2-(tetrahydro-2H-pyran-4-yl) acetic acid (150 mg, 1.0 mmol) in 3 mL of CH$_2$Cl$_2$ was added oxalyl chloride (0.11 mL, 1.2 mmol) followed by addition of one drop of DMF. The reaction mixture was allowed to warm to a room temperature over 4 hours, then concentrated to dryness under reduced pressure and kept on a high vacuum line for an hour. The crude mixture was used in the next step without further purification.

Step-2: N-(2-chloropyrimidin-4-yl)-2-(tetrahydro-2H-pyran-4-yl)acetamide

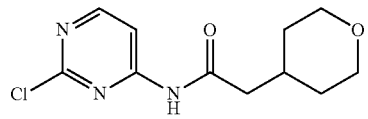 [SMILES: O=C(CC1CCOCC1)Nc1ccnc(Cl)n1]

To an ice-cold solution of 2-chloropyrimidin-4-amine (112 mg, 0.86 mmol) in 3 mL of DMF was added 60% NaH in oil (70 mg, 1.7 mmol), and the reaction mixture was stirred at 0° C. for 30 minutes. A solution of crude 2-(tetrahydro-2H-pyran-4-yl)acetylchloride in DMF was added dropwise to the reaction mixture. The solution was allowed to warm to room temperature overnight. The reaction was then quenched with NaHCO$_3$ (saturated aqueous solution) and extracted with EtOAc. The organic layer was dried over Na$_2$SO$_4$, filtered and concentrated to dryness under reduced pressure. The crude was purified by column chromatography using an ISCO® chromatography system (12 g normal phase (SiO$_2$) column, eluted with an EtOAc/hexanes gradient) to afford the title compound (108 mg, 40% yield for 2 steps).

Step-3: (S)—N-(2-((1-(6-Chloro-2-oxo-1,2-dihydro-quinolin-3-yl)ethyl)amino)pyrimidin-4-yl)-2-(tetrahydro-2H-pyran-4-yl)acetamide (I-27)

A mixture containing N-(2-chloropyrimidin-4-yl)-2-(tetrahydro-2H-pyran-4-yl)acetamide (104 mg, 0.41 mmol), (S)-3-(1-aminoethyl)-6-chloroquinolin-2(1H)-one hydrochloride II-1 (104 mg, 0.41 mmol) and DIEA (0.145 mL, 0.82 mmol) in 2 mL of anhydrous EtOH (200 proof) was microwaved at 140° C. for 4 hours. The reaction mixture was concentrated to dryness under reduced pressure and purified by column chromatography on an ISCO® chromatography system using 12 g normal phase (SiO$_2$) column and eluted with an EtOAc/CH$_2$Cl$_2$ gradient to afford the title compound 27 (50 mg, 28% yield). 1H NMR (300 MHz, DMSO-d$_6$): δ ppm 11.97 (s, 1H), 10.21 (s, 1H), 8.12 (d, J=5.5 Hz, 1H), 7.75 (s, 1H), 7.73 (d, J=2.46 Hz, 1H), 7.48 (dd, J=8.79, 2.46 Hz, 1H), 7.32 (d, J=8.79 Hz), 7.25 (d, J=5.8 Hz, 1H), overlapped with br singlet 7-25-7.35 (br s, 1H), 5.20 (quintet, 1H), 3.75-3.85 (m, 2H), 3.20-3.35 (m, 2H), 2.31 (m, 2H), 1.85-2.0 (m, 1H), 1.45-1.60 (m, 2H), 1.41 (d, J=6.9 Hz, 3H), 1.1-1.3 (m, 2H). LCMS (Method 3): Rt 4.25 min; m/z 442.2/444.2 (Cl1-pattern) [M+H]$^+$.

Example 46—(S)—N-(2-((1-(6-chloro-2-oxo-1,2-dihydroquinolin-3-yl)ethyl)amino)pyrimidin-4-yl)-N-cyclopropylacetamide (I-28)

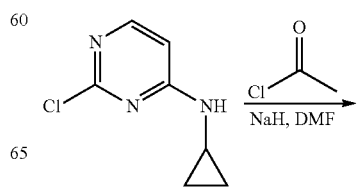

135

-continued

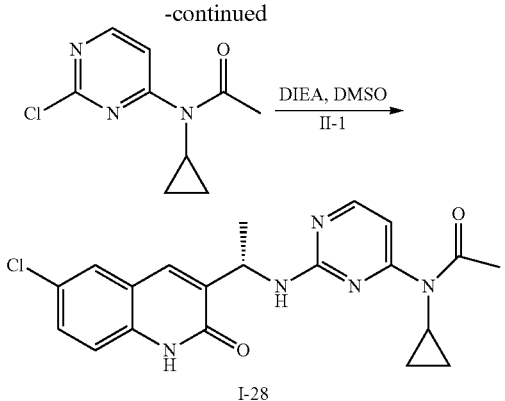

Step-1:
N-(2-Chloropyrimidin-4-yl)-N-cyclopropylacetamide

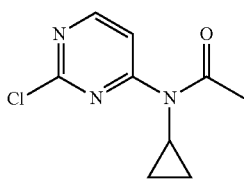

In a dried 3-neck round bottom flask, a solution of 2-chloro-N-cyclopropylpyrimidin-4-amine (see Example 9, 410 mg, 2.4 mmol, 1 equivalent) in 5 mL of DMF was cooled to 0° C. and then treated portionwise with NaH (60 wt % in oil, 116 mg, 2.9 mmol, 1.2 equivalents). After stirring at room temperature for 15 minutes, the solution was cooled to 0° C., and acetyl chloride (210 mg, 2.6 mmol, 1.1 equivalents) was added. The reaction was stirred overnight at room temperature, and then quenched with water and an aqueous solution of NaHCO₃. Extraction with EtOAc (2×) followed by flash silica gel chromatography with toluene/EtOAc (85/15) provided the title compound (310 mg, 44% yield) as a colorless thick liquid.

Step-2: (S)—N-(2-((1-(6-Chloro-2-oxo-1,2-dihydroquinolin-3-yl)ethyl)amino)pyrimidin-4-yl)-N-cyclopropylacetamide (I-28)

A mixture of N-(2-chloropyrimidin-4-yl)-N-cyclopropylacetamide (100 mg, 0.48 mmol, 1.2 equivalents), (S)-3-(1-aminoethyl)-6-chloroquinolin-2(1H)-one hydrochloride II-1 (92 mg, 0.36 mmol, 1 equivalent) and DIEA (93 mg, 0.72 mmol, 2 equivalents) in 2.5 mL of EtOH was heated in microwave at 130° C. for 2 hours. Following removal of the solvent by rotary evaporation, the crude residue was purified by silica gel chromatography (EtOAc/hexane, 85/15). The pure fractions were combined and lyophilized from ACN/water to provide the title compound (9.5 mg) as a white solid. ¹H NMR (300 MHz, CDCl₃): δ ppm 11.35 (br s, 1H), 8.14 (d, J=5.76 Hz, 1H), 7.71 (s, 1H), 7.51 (d, J=2.19 Hz, 1H) 7.40 (dd, J=2.19, 8.79 Hz, 1H), 7.25 (d, 1H), 6.80 (br s, 1H), 5.32 (m, 1H), 2.87 (m, 1H), 2.31 (s, 3H), 1.61 (d, 3H), 1.02 (m, 1H), 0.87 (m, 1H), 0.56 (m, 1H), 0.46 (m, 1H). LCMS (Method 3), Rt 3.65 min., m/z 398 [M+H]⁺.

136

Example 47—(S)—N-(2-((1-(6-Chloro-2-oxo-1,2-dihydroquinolin-3-yl)ethyl)amino) pyrimidin-4-yl)-2-methoxyacetamide (I-32)

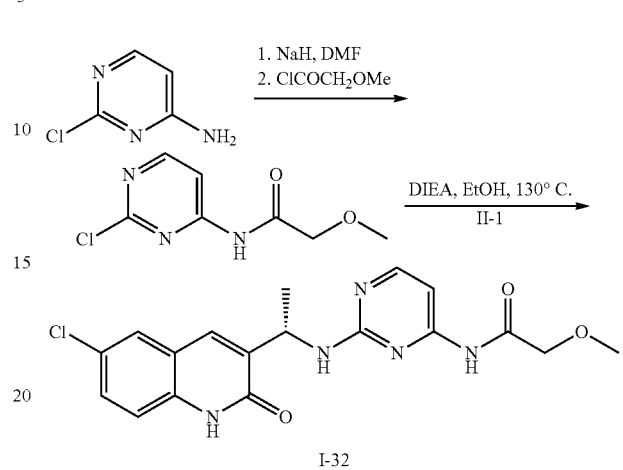

Step-1:
N-(2-Chloropyrimidin-4-yl)-2-methoxyacetamide

To an ice-cold solution of 2-chloropyrimidin-4-amine (410 mg, 3.2 mmol) in 6 mL of DMF was added 60% NaH in oil (152 mg, 3.8 mmol) and the reaction mixture was stirred at 0° C. for 30 minutes. Neat 2-methoxyacetyl chloride (0.38 mL, 0.42 mmol) was then added dropwise and the reaction was allowed to warm to a room temperature overnight. The reaction was quenched with NaHCO₃ (saturated aqueous solution) and then extracted with EtOAc. The organic layer was dried over Na₂SO₄, filtered and concentrated to dryness under reduced pressure. The crude product was purified by column chromatography on an ISCO® chromatography system using 40 g normal phase (SiO₂) column with a gradient elution of EtOAc in CH₂Cl₂ to obtain the title compound (210 mg, 33% yield).

Step-2: (S)—N-(2-((1-(6-Chloro-2-oxo-1,2-dihydroquinolin-3-yl)ethyl)amino)pyrimidin-4-yl)-2-methoxyacetamide (I-32)

A mixture containing N-(2-chloropyrimidin-4-yl)-2-methoxyacetamide (150 mg, 0.75 mmol), (S)-3-(1-aminoethyl)-6-chloroquinolin-2(1H)-one hydrochloride II-1 (150 mg, 0.58 mmol) and DIEA (0.2 mL, 1.2 mmol) in 2.5 mL of anhydrous EtOH (200 proof) was microwaved at 130° C. for 2 hours and 30 minutes. The reaction mixture was concentrated to dryness under reduced pressure and purified twice by column chromatography on an ISCO® chromatography system using 12 g normal phase (SiO₂) "gold" column with a gradient elution of EtOAc in CH₂Cl₂, to afford 25 mg (11% yield) of the title compound 32. ¹H NMR (300 MHz, CDCl₃): δ ppm 11.47 (s, 1H), 8.54 (s, 1H), 8.21 (m, 1H), 7.68 (s, 1H), 7.51 (m, 1H), 7.40-7.45 (m, 2H), 7.20-7.30 (m, 1H, overlapping with CDCl₃ signal), 6.02 (d, J=8.25 Hz, 1H), 5.30 (quintet, 1H), 3.97 (s, 2H), 3.46 (s, 3H), 1.50 (m, 3H overlapping with water signal). LCMS (Method 3), Rt 4.04 min. m/z 388.1 [M+H]⁺.

TABLE 5
The examples listed in Table 5 were prepared using methods similar to those described for the preparation of I-22-I-28 and I-32.
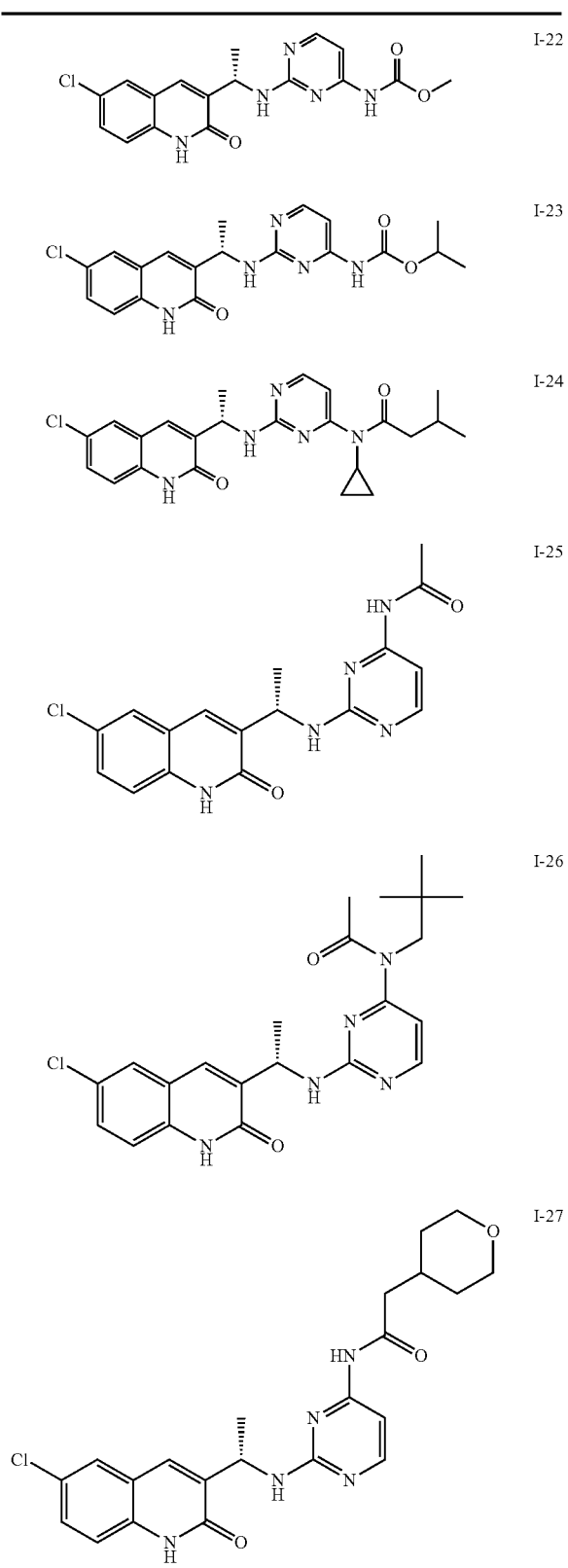
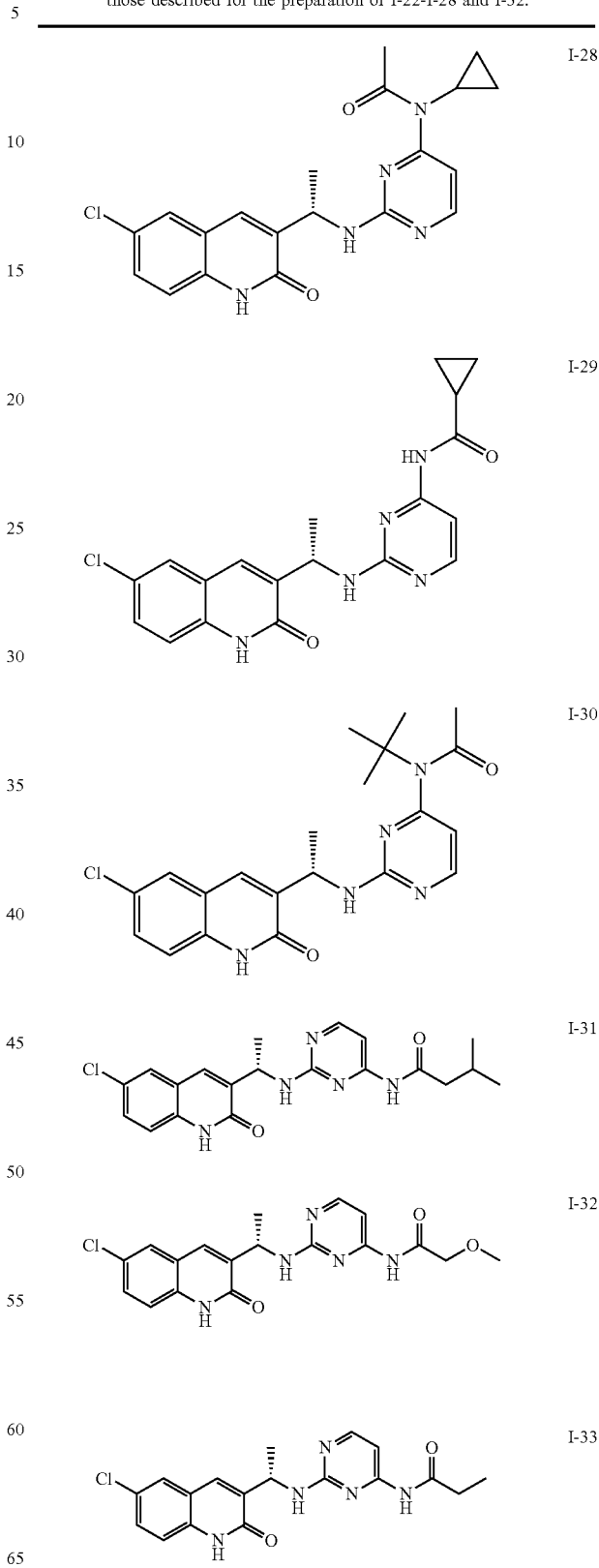

TABLE 5-continued

The examples listed in Table 5 were prepared using methods similar to those described for the preparation of I-22-I-28 and I-32.

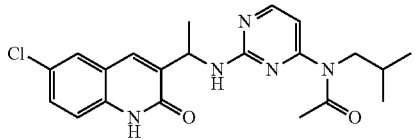 [SMILES: CC(=O)N(CC(C)C)c1ccnc(NC(C)c2cc3cc(Cl)ccc3[nH]c2=O)n1]
I-34

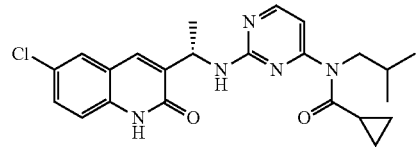 [SMILES: CC(C)CN(C(=O)C1CC1)c1ccnc(N[C@@H](C)c2cc3cc(Cl)ccc3[nH]c2=O)n1]
I-35

TABLE 6

LCMS signal and NMR chemical shifts for each compounds listed in Table 5.

| Cmpds No | LCMS$^a$ | $^1$H NMR (300 MHz) δ ppm |
|---|---|---|
| I-22 | m/z: 373.9739 [M + H]$^+$ Rt (min): 0.96 | $^1$H NMR (300 MHz, DMSO-d$_6$): δ ppm 11.94 (s, 1 H), 10.09 (s, 1 H), 8.08 (br d, J = 5.86 Hz, 1 H), 7.69-7.74 (m, 2 H), 7.46 (dd, J = 8.94, 2.49 Hz, 1 H), 7.27 (d, J = 9.09 Hz, 1 H), 7.00 (d, J = 5.57 Hz, 1 H), 5.08-5.19 (m, 1 H), 3.63 (s, 3 H), 1.37 (d, J = 6.74 Hz, 3 H) |
| I-23 | m/z: 402.05 [M + H]$^+$ Rt (min): 1.19 | |
| I-24 | m/z: 440.18 [M + H]$^+$ Rt (min): 1.42 | $^1$H-NMR (300 MHz, CDCl$_3$): δ ppm 10.55 (br s, 1 H), 7.79 (m, 2 H), 7.57 (br s, 1 H), 7.41 (br dd, 1 H), 7.31 (br d, 1 H), 7.18 (br d, 1 H), 5.55 (m, 1 H), 2.80 (m, 1 H), 2.64 (t, 2 H), 2.16 (m, 1 H), 1.62 (d, 3 H), 1.24 (m, 1 H), 1.02 (m, 1 H), 0.92 (dd, 6 H), 0.62 (m, 1 H), 0.48 (m, 1 H). |
| I-25 | m/z: 358.0807 [M + H]$^+$ Rt (min): 0.95 | $^1$H NMR (300 MHz, CDCl$_3$): δ ppm 11.63 (br s, 1 H), 8.22 (m, 2 H), 7.61 (s, 1 H), 7.36-7.40 (m, 2 H), 6.19 (br s, 1 H), 5.27 (m, 1 H), 2.14 (s, 3 H), 1.59 (d, J = 6.9 Hz, 3 H). |
| I-26 | m/z: 428.11 [M + H]$^+$ Rt (min): 1.34 | $^1$H NMR (300 MHz, CDCl$_3$): δ ppm 11.32 (br s, 1 H), 8.23 (d, J = 5.2 Hz, 1 H), 7.66 (s, 1 H), 7.48 (d, J = 1.9 Hz, 1 H), 7.42 (dd, J = 8.5, 2.2 Hz, 1 H), 6.44 (d, J = 5.2 Hz, 1 H), 6.14 (d, J = 7.7 Hz, 1 H), 5.27 (m, 1 H), 3.80-3.66 (m, 2 H), 2.11 (s, 3 H), 1.64 (d, J = 7.1 Hz, 3 H), 0.65 (s, 9 H). |
| I-27 | m/z: 442.05 [M + H]$^+$ Rt (min): 1.059 | $^1$H NMR (300 MHz, DMSO-d$_6$): δ ppm 11.97 (s, 1 H), 10.21 (s, 1 H), 8.12 (d, J = 5.5 Hz, 1 H), 7.75 (s, 1 H), 7.73 (d, J = 2.46 Hz, 1 H), 7.48 (dd, J = 8.79, 2.46 Hz, 1 H), 7.32 (d, J = 8.79 Hz, 1 H), 7.25 (d, J = 5.8 Hz, 1 H), overlapped with br singlet 7.25-7.35 (br s, 1 H), 5.20 (quintet, 1 H), 3.75-3.85 (m, 2 H), 3.20-3.35 (m, 2 H), 2.31 (m, 2 H), 1.85-2.0 (m, 1 H), 1.45-1.60 (m, 2 H), 1.41 (d, J = 6.9 Hz, 3 H), 1.1-1.3 (m, 2 H). |
| I-28 | m/z: 398.07 [M + H]$^+$ Rt (min): 1.12 | $^1$H-NMR(300 MHz, CDCl$_3$): δ ppm 11.35 (br s, 1 H), 8.14 (d, J = 5.76 Hz, 1 H), 7.71 (s, 1 H), 7.51 (d, J = 2.19 Hz, 1 H) 7.40 (dd, J = 2.19, 8.79 Hz, 1 H), 7.25 (d, 1 H), 6.80 (br s, 1 H), 5.32 (m, 1 H), 2.87 (m, 1 H), 2.31 (s, 3 H), 1.61 (d, 3 H), 1.02 (m, 1 H), 0.87 (m, 1 H), 0.56 (m, 1 H), 0.46 (m, 1 H). |
| I-29 | m/z: 383.99 [M + H]$^+$ Rt (min): 1.07 | $^1$H NMR (300 MHz, DMSO-d$_6$): δ ppm 11.97 (s, 1 H), 10.53 (s, 1 H), 8.12 (d, J = 5.22 Hz, 1 H), 7.75 (s, 1 H), 7.73 (d, J = 2.46 Hz, 1 H), 7.48 (dd, $_1$ = 8.79, 2.46 Hz, 1 H), 7.30 (d, J = 8.79 Hz, 1 H) overlapping with br singlet 7.25-7.35 (br s, 1 H), 7.20 (d, J = 5.49 Hz, 1 H), 5.20 (quintet, 1 H), 2.10 (quintet, 1 H), 1.40 (d, J = 6.6 Hz, 3 H), 0.75-0.85 (m, 4 H) |
| I-30 | m/z: 414.09 [M + H]$^+$ Rt (min): 1.29 | $^1$H NMR (300 MHz, CDCl$_3$): δ ppm 11.27 (br s, 1 H), 8.31 (d, J = 5.1 Hz, 1 H), 7.66 (s, 1 H), 7.50 (m, 1 H), 7.45 (m, 1 H), 7.27-7.24 (m, 1 H), 6.36 (d, J = 5.0 Hz, 1 H), 6.27 (m, 1 H), 5.25 (br s, 1 H), 1.69-1.57 (m, 6 H), 1.33 (s, 9 H). |
| I-31 | m/z: 400.13 [M + H]$^+$ Rt (min): 1.2473 | $^1$H NMR (300 MHz, CDCl$_3$): δ ppm 11.13 (br s, 1 H), 8.21 (d, J = 5.5 Hz, 1 H), 7.82 (m, 1 H), 7.62 (m, 1 H), 7.45-7.41 (m, 2 H), 7.25-7.19 (m, 1 H), 6.00 (br s, 1 H), 5.28 (m, 1 H), 2.20-2.16 (m, 3 H), 1.60-1.58 (m, 6 H), 0.95 (d, J = 6.1 Hz, 6 H). |

TABLE 6-continued

LCMS signal and NMR chemical shifts for each compounds listed in Table 5.

| Cmpds No | LCMS[a] | $^1$H NMR (300 MHz) δ ppm |
|---|---|---|
| I-32 | m/z: 388.06 [M + H]$^+$ Rt (min): 1.0414 | $^1$H NMR (300 MHz, CDCl$_3$): δ ppm 11.54 (br s, 1 H), 8.5 (s, 1 H), 8.21-8.23 (m, 1 H), 7.68 (m, 1 H), 7.51 (m, 1 H), 7.40-7.42 (m, 2 H), 7.25 (m, 1 H), 6.00 (br s, 1 H), 5.31 (m, 1 H), 4.00 (m, 2 H), 3.46 (m, 3 H), 1.61 (m, 3 H). |
| I-33 | m/z: 372.12 [M + H]$^+$ Rt (min): 1.03 | $^1$H NMR (300 MHz, DMSO-d$_6$): δ ppm 11.97 (s, 1 H), 10.16 (s, 1 H), 8.12 (d, J = 5.22 Hz, 1 H), 7.75 (s, 1 H), 7.73 (d, J = 2.46 Hz, 1 H), 7.48 (dd, J = 8.79, 2.46 Hz, 1 H), 7.30 (d, J = 8.79, 1 H) overlapping with br singlet 7.2-7.3 (br s, 1 H), 7.25 (d, J = 5.5 Hz, 1 H), 5.20 (quintet, 1 H), 2.40 (q, 2 H), 1.40 (d, J = 6.9, 3 H), 1.00 (t, J = 7.4 Hz, 3 H). |
| I-34 | m/z: 414.26 [M + H]$^+$ Rt (min): 1.27 | |
| I-35 | m/z: 440.24 [M + H]$^+$ Rt (min): 1.45 | |

[a]LCMS (method 4)

Example 48—(S)-2-((1-(6-Chloro-2-oxo-1,2-dihydroquinolin-3-yl)ethyl)amino)-4-methoxypyrimidine-5-carbonitrile (I-36)

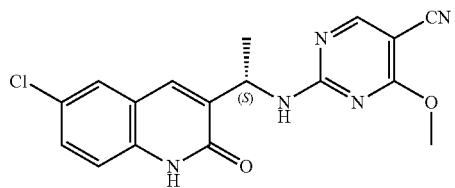

To a solution of 2-chloro-4-methoxypyrimidine-5-carbonitrile (65.4 mg, 0.386 mmol) and (S)-3-(1-aminoethyl)-6-chloroquinolin-2(1H)-one hydrochloride II-1 (100 mg, 0.386 mmol) in DMSO (0.60 mL) was added DIEA (0.135 mL, 0.772 mmol). The solution was stirred at 110° C. for 4 hours. Once LCMS analysis indicated that most starting material was consumed, the mixture was diluted with DCM and washed with water (2×) and brine (1×). The organic extract was dried over Na$_2$SO$_4$, filtered, and evaporated under reduced pressure. The crude material was purified by column chromatography on Biotage® chromatography system (eluted with 0-80% EtOAc in hexanes) to provide the title compound 36 (34.1 mg, >95% HPLC pure @ 220 nm, 26% yield). $^1$H NMR (300 MHz, DMSO-d$_6$, at 120° C.): δ ppm 11.65 (br s, 1H), 8.42 (s, 1H), 8.20 (br s, 1H), 7.79 (s, 1H), 7.68 (s, 1H), 7.45 (d, J=8.8 Hz, 1H), 7.33 (d, J=8.8 Hz, 1H), 5.32 (m, 1H), 3.94 (s, 3H), 1.50 (d, J=6.3 Hz, 3H). LCMS (Method 1): Rt: 2.31 min; m/z: Calculated for C$_{17}$H$_{14}$ClN$_5$O$_2$: 355.78; found: 356.00 [M+H]$^+$.

Example 49—(S)-2-((1-(6-Chloro-2-oxo-1,2-dihydroquinolin-3-yl)ethyl)amino)-4-methylpyrimidine-5-carbonitrile (I-39)

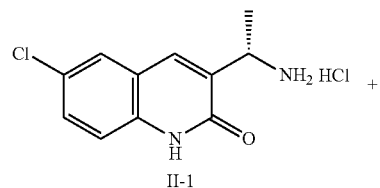

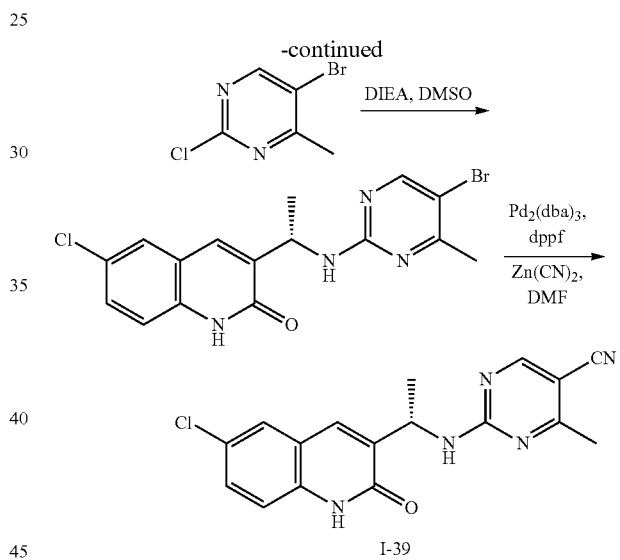

Step-1: (S)-3-(1-((5-bromo-4-methylpyrimidin-2-yl)amino)ethyl)-6-chloroquinolin-2(1H)-one A mixture of 5-bromo-2-chloro-4-methylpyrimidine (440 mg, 2.122 mmol) and (S)-3-(1-aminoethyl)-6-chloroquinolin-2(1H)-one hydrochloride (500 mg, 1.930 mmol) was dissolved in DMSO (3 mL) and DIEA (5.79 mmol, 748 mg, 1 mL) and the solution was stirred at 110° C. for 12 hours. Once LCMS indicated most of the starting material was consumed, the mixture was cooled to room temperature and stirred for 2 days. The solution was then diluted with water and extracted with DCM (2×). The extracts were dried (Na$_2$SO$_4$), filtered, and evaporated under reduced pressure. The crude material was purified by silica gel chromatography on a Biotage® chromatography system (eluted with 0-80% EtOAc/Hexanes) on 50 g column to afford (S)-3-(1-((5-bromo-4-methylpyrimidin-2-yl)amino)ethyl)-6-chloroquinolin-2(1H)-one (635 mg, 84% yield). $^1$H NMR (300 MHz, DMSO-d$_6$): δ ppm 11.94 (s, 1H), 8.13-8.29 (m, 1H), 7.66-7.88 (m, 2H), 7.46 (dd, J=8.79, 2.35 Hz, 1H), 7.20-7.32 (m, 1H), 5.08 (br s, 1H), 2.17-2.37 (m, 3H), 1.25-1.46 (m, 3H). LCMS (Method 1): Rt 2.59 min, m/z 395.84 [M+H]+.

Step-2: (S)-2-((1-(6-chloro-2-oxo-1,2-dihydroquinolin-3-yl)ethyl)amino)-4-methyl pyrimidine-5-carbonitrile (I-39)

A mixture of Pd$_2$(dba)$_3$ (11.63 mg, 0.013 mmol), dppf (14.0 mg, 0.025 mmol), (S)-3-(1-((5-bromo-4-methylpyrimidin-2-yl)amino)ethyl)-6-chloroquinolin-2(1H)-one (635 mg, 1.613 mmol) and dicyanozinc (379 mg, 3.23 mmol in DMF, 30 mL) was purged with nitrogen for 10 minutes. The mixture was then heated to 120° C. overnight. Once LCMS showed 50% conversion, the volatiles were removed under vacuum. Water was added to the resulting residue, and solids were removed by filtration. The crude material was purified by silica gel chromatography on a Biotage® chromatography system (25 g column eluted with 10-100% EtOAc/Hexanes) afforded ((S)-2-((1-(6-chloro-2-oxo-1,2-dihydroquinolin-3-yl)ethyl)amino)-4-methylpyrimidine-5-carbonitrile (517 mg, 94% yield)$^1$H NMR (300 MHz, DMSO-d$_6$): δ ppm 11.98 (s, 1H), 8.46-8.74 (m, 2H), 7.67-7.89 (m, 2H), 7.18-7.53 (m, 2H), 5.08-5.42 (m, 1H), 2.14-2.45 (m, 3H), 1.25-1.50 (m, 3H). LCMS (Method 1): Rt 2.35 min, m/z 340.96[M+H]+.

Example 50—(S)-2-((1-(6-Chloro-2-oxo-1,2-dihydroquinolin-3-yl)ethyl)amino)-4-cyclopropylpyrimidine-5-carbonitrile (I-40)

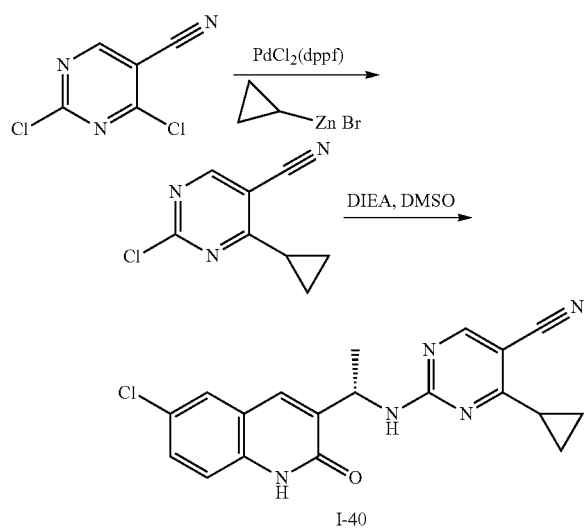

Step-1:
2-chloro-4-cyclopropylpyrimidine-5-carbonitrile

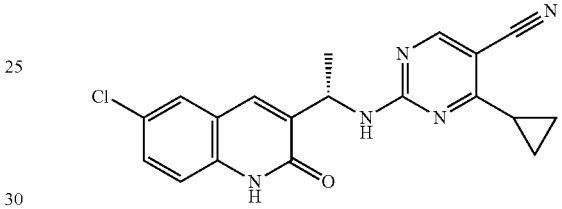

A mixture of 2,4-dichloropyrimidine-5-carbonitrile (600 mg, 3.45 mmol), PdCl2(dppf) (126 mg, 0.172 mmol) in THF (15 mL) was purged with N2 for 10 minutes. To the deoxygenated solution was added cyclopropylzinc (II) bromide (13.79 mL, 6.90 mmol). The mixture was heated to reflux overnight. The reaction mixture was cooled and diluted with ethyl acetate then was washed with water, dried and concentrated. The crude material was purified by chromatography on a Biotage® using a 25 g silica gel column eluted with 0-25% EtOAc/Hexanes to afford 2-chloro-4-cyclopropylpyrimidine-5-carbonitrile (34 mg, 5.5%). 1H NMR (300 MHz, CHLOROFORM-d) δ ppm 8.59 (s, 1H), 2.21-2.47 (m, 1H), 1.29-1.45 (m, 3H), 0.58-0.92 (m, 1H). LCMS (Method 1): Rt 2.00 min, m/z 180.97[M+H]+.

Step-2: (S)-2-((1-(6-Chloro-2-oxo-1,2-dihydroquinolin-3-yl)ethyl)amino)-4-cyclopropylpyrimidine-5-carbonitrile A mixture of 2-chloro-4-cyclopropylpyrimidine-5-carbonitrile (35 mg, 0.195 mmol) and (S)-3-(1-aminoethyl)-6-chloroquinolin-2(1H)-one hydrochloride (50.5 mg, 0.195 mmol) was dissolved in DMSO (1 mL) and DIEA (50.4 mg, 0.390 mmol) and the solution was stirred at 110° C. for 12 hours. Once LCMS indicated most starting material was consumed, the mixture was cooled to room temperature and stirred 2 days. The solution was diluted with water and extracted with DCM (2x). The extracts were then dried (Na$_2$SO$_4$), filtered, and evaporated under reduced pressure. The crude material was purified by HPLC to afford (S)-2-((1-(6-chloro-2-oxo-1,2-dihydroquinolin-3-yl)ethyl)amino)-4-cyclopropylpyrimidine-5-carbonitrile I-40 (12 mg, 16.8% yield). $^1$H NMR (300 MHz, DMSO-d$_6$): δ ppm 11.96 (br s, 1H), 8.34-8.56 (m, 1H), 7.55-7.79 (m, 2H), 7.44 (dt, J=8.79, 2.20 Hz, 1H), 7.25 (d, J=8.79 Hz, 1H), 4.95-5.17 (m, 1H), 1.84-2.19 (m, 1H), 1.34 (d, J=7.04 Hz, 3H), 0.96-1.20 (m, 2H), 0.47-0.93 (m, 2H). LCMS (Method 1): Rt 2.51 min, m/z 366.92 [M+H]+.

Example 51—(S)-2-((1-(6-chloro-1-methyl-2-oxo-1,2-dihydroquinolin-3-yl)ethyl)amino)-4-methoxypyrimidine-5-carbonitrile (I-41)

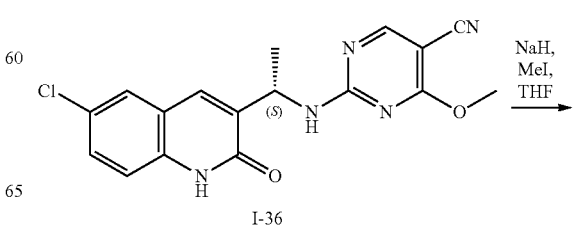

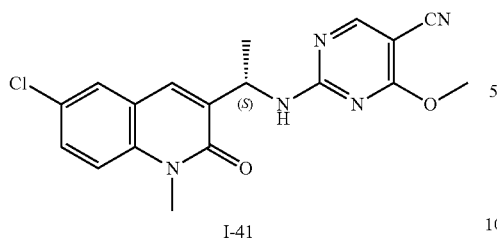

I-41

To a solution of (S)-2-((1-(6-chloro-2-oxo-1,2-dihydroquinolin-3-yl)ethyl)amino)-4-methoxypyrimidine-5-carbonitrile (I-36) (118 mg, 0.33 mmol) in THF (6 ml) was added sodium hydride (60%, 13.3 mg, 0.33 mmol) at ice cold temperature. The resultant mixture was stirred at 0° C. for 1 h. Methyl iodide (0.042 ml, 0.66 mmol) was added to the reaction and stirred at ice cold temperature for 1 h. The reaction was allowed to warm up to room temperature and stirred overnight. Saturated ammonium chloride solution was added to the reaction and extracted with ethyl acetate. The organic extract was dried over $Na_2SO_4$, filtered, and evaporated under reduced pressure. The crude material was purified on ISCO ($SiO_2$:0-50% ethyl acetate in hexanes) to give the title compound I-41 (90 mg, 74%). $^1$H NMR (300 MHz, DMSO-$d_6$, at 120° C.): δ 8.40 (s, 1H), 8.12 (br s, 1H), 7.81 (s, 1H), 7.73 (s, 1H), 7.65-7.44 (m, 2H), 5.50-5.25 (m, 1H), 3.93 (s, 3H), 3.66 (s, 3H), 1.51 (d, J=6.6 Hz, 3H). LCMS (Method 3): Rt 5.46 min, m/z 370.1 (M+H)$^+$.

TABLE 7

The Compounds listed in Table 7 were prepared using methods similar to those described for the preparation of I-36 and I-39-I-41.

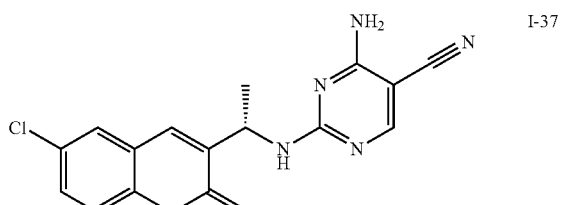

I-36

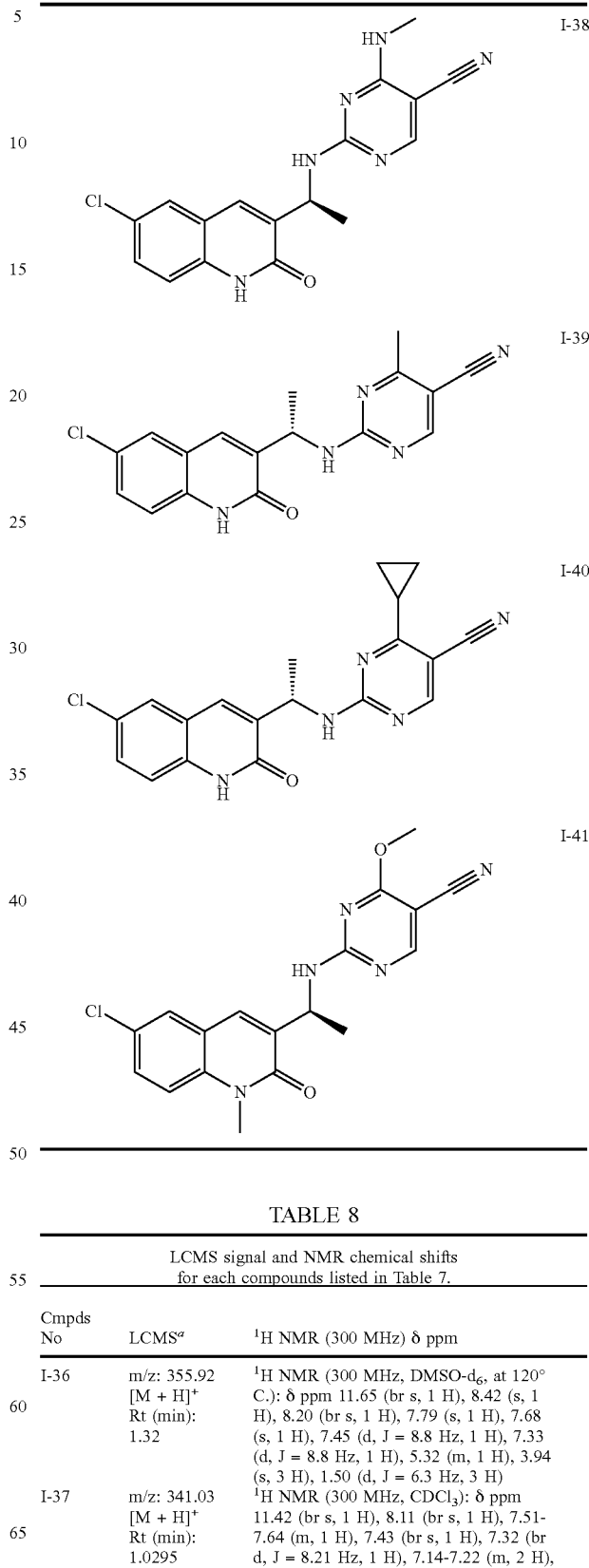

TABLE 8

LCMS signal and NMR chemical shifts for each compounds listed in Table 7.

| Cmpds No | LCMS$^a$ | $^1$H NMR (300 MHz) δ ppm |
|---|---|---|
| I-36 | m/z: 355.92 [M + H]$^+$ Rt (min): 1.32 | $^1$H NMR (300 MHz, DMSO-$d_6$, at 120° C.): δ ppm 11.65 (br s, 1 H), 8.42 (s, 1 H), 8.20 (br s, 1 H), 7.79 (s, 1 H), 7.68 (s, 1 H), 7.45 (d, J = 8.8 Hz, 1 H), 7.33 (d, J = 8.8 Hz, 1 H), 5.32 (m, 1 H), 3.94 (s, 3 H), 1.50 (d, J = 6.3 Hz, 3 H) |
| I-37 | m/z: 341.03 [M + H]$^+$ Rt (min): 1.0295 | $^1$H NMR (300 MHz, CDCl$_3$): δ ppm 11.42 (br s, 1 H), 8.11 (br s, 1 H), 7.51-7.64 (m, 1 H), 7.43 (br s, 1 H), 7.32 (br d, J = 8.21 Hz, 1 H), 7.14-7.22 (m, 2 H), |

TABLE 8-continued

LCMS signal and NMR chemical shifts
for each compounds listed in Table 7.

| Cmpds No | LCMS[a] | $^1$H NMR (300 MHz) δ ppm |
|---|---|---|
| I-38 | m/z: 354.07 [M + H]+ Rt (min): 1.37 | 6.58-6.82 (m, 1 H), 5.14-5.39 (m, 2 H), 1.53 (br d, J = 6.45 Hz, 3 H). $^1$H NMR (300 MHz, CDCl$_3$): δ ppm 11.60 (br s, 1 H), 7.57 (s, 1 H), 7.43 (s, 1 H), 7.34-7.41 (m, 1 H), 7.27 (dd, J = 8.65, 3.08 Hz, 2 H), 5.90 (br d, J = 7.04 Hz, 1 H), 5.58 (d, J = 8.21 Hz, 1 H), 5.33-5.46 (m, 1 H), 2.77 (d, J = 4.69 Hz, 3 H), 1.53 (br d, J = 7.04 Hz, 3 H). |
| I-39 | m/z: 339.95 [M + H]+ Rt (min): 1.32 | $^1$H NMR (300 MHz, DMSO-d$_6$): δ ppm 12.40 (br s, 1 H), 8.38 (s, 1 H)7.68 (s. 1 H), 7.52 (s, 1 H), 7.43 (dd, J = 2.6 Hz, J = 8.5 Hz, 1 H), 7.32 (d, J = 8.48 Hz, 1 H), 7.33 (d, J = 8.8 Hz, 1 H), 5.32 (m, 1 H), 3.94 (s, 3 H), 1.50 (d, J = 6.3 Hz, 3 H) |
| I-40 | m/z: 366.02 [M + H]+ Rt (min): 1.42 | $^1$H NMR (300 MHz, DMSO-d$_6$): δ ppm 11.96 (br s, 1 H), 8.36-8.48 (m, 2 H), 7.68 (m, 1 H), 7.61 (s, 1 H), 7.42 (m, 1 H), 7.25 (d, J = 8.7 Hz, 1 H), 5.01-5.16 (m, 1 H), 1.94-2.00 (m, 1 H), 1.5 (d, J = 7.03 Hz, 3 H), 0.52-1.20 (m, 4 H). |
| I-41 | m/z: 370.1[b] [M + H]+ Rt (min): 5.47 | $^1$H NMR (300 MHz, DMSO-d$_6$, at 120° C.): δ 8.40 (s, 1 H), 8.12 (br s, 1 H), 7.81 (s, 1 H), 7.73 (s, 1 H), 7.65-7.44 (m, 2 H), 5.50-5.25 (m, 1 H), 3.93 (s, 3 H), 3.66 (s, 3 H), 1.51 (d, J = 6.6 Hz, 3 H). |

[a]LCMS (method 4)

Example 52—(S)-3-(2-(((S)-1-(6-Chloro-2-oxo-1,2-dihydroquinolin-3-yl) ethyl) amino) pyrimidin-4-yl)-4-isopropyloxazolidin-2-one (I-42)

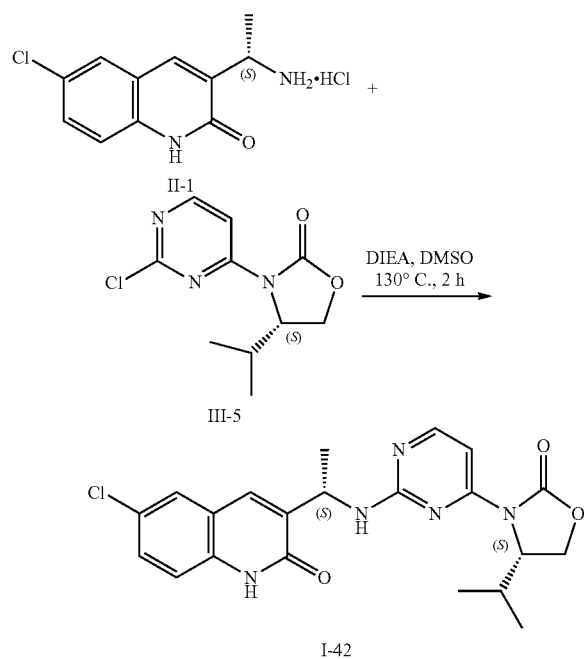

To a mixture of (S)-3-(1-aminoethyl)-6-chloroquinolin-2(1H)-one hydrochloride II-1 (95 mg, 0.367 mmol) and (S)-3-(2-chloropyrimidin-4-yl)-4-isopropyloxazolidin-2-one III-5 (177 mg, 0.734 mmol) in DMSO (2 mL) was added DIEA (126 µL, 0.734 mmol) at room temperature. The resulting mixture was heated to 130° C. for 2 hours. After TLC and LCMS showed completion of reaction, the mixture was cooled to room temperature and diluted with EtOAc (30 mL). The organic layer washed with water (3×20 mL), dried over anhydrous Na$_2$SO$_4$, filtered and evaporated to dryness. The resulting residue was purified by column chromatography on an ISCO® chromatography system (SiO$_2$ column: eluted with hexanes/EtOAc; 0-100% EtOAc) to afford the title compound I-42 as an off-white solid (25 mg, 16% yield). $^1$H NMR (300 MHz, DMSO-d$_6$): δ ppm 11.97 (br s, 1H), 8.23 (d, J=6.0 Hz, 1H), 7.75 (d, J=2.2 Hz, 1H), 7.60 (br s, 1H), 7.49 (d, J=2.2 Hz, 1H), 7.45 (d, J=2.2 Hz, 1H), 7.31 (d, J=8.8 Hz, 1H), 7.24 (d, J=5.8 Hz, 1H), 4.90-5.05 (m, 1H), 4.21-4.44 (m, 3H), 1.60-1.75 (m, 1H), 1.41 (d, J=6.8 Hz, 3H), 0.25-0.95 (m, 6H). LCMS (Method 3): Rt 4.32 min, m/z 428.1 [M+H]+.

Example 53—(S)-3-(2-(((R)-1-(6-Chloro-2-oxo-1,2-dihydroquinolin-3-yl)ethyl)amino) pyrimidin-4-yl)-4-isopropyloxazolidin-2-one (I-43)

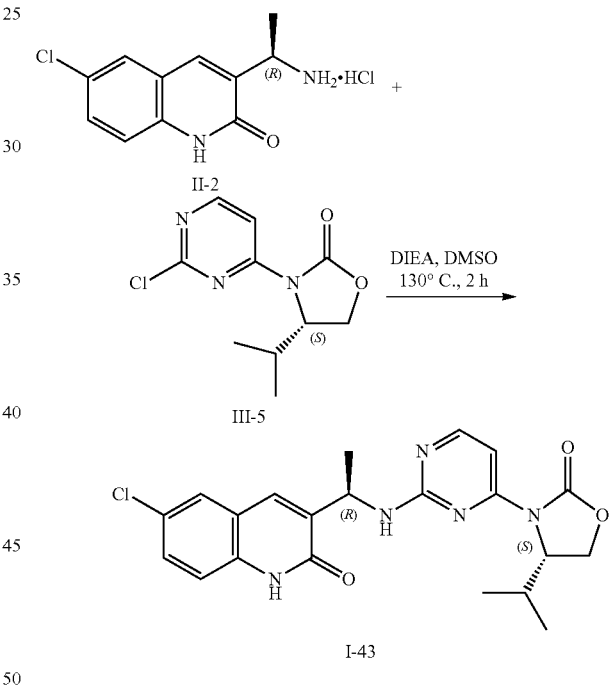

To a mixture of II-2 (93 mg, 0.359 mmol) and III-5 (173 mg, 0.719 mmol) in DMSO (2 mL), was added DIEA (123 L, 0.719 mmol) at room temperature. The resulting mixture was then heated at 130° C. for 3 hours. Once TLC and MS showed completion of reaction, the reaction mixture was cooled to room temperature and diluted with EtOAc (30 mL). The organic layer was washed with water (3×20 mL), dried over anhydrous Na$_2$SO$_4$, filtered, and evaporated to dryness. The resulting residue was purified by column chromatography on an ISCO® chromatography system (Gold column, SiO$_2$: Hex/EtOAc gradient, 0-100% EtOAc) to afford the title compound 43 as a white solid (38 mg, 25% yield). $^1$H NMR (300 MHz, DMSO-d$_6$): δ ppm 11.95 (br s, 1H), 8.19 (d, J=5.5 Hz, 1H), 7.74 (d, J=2.5 Hz, 2H), 7.49 (dd, J=8.5, 2.2 Hz, 1H), 7.30 (d, J=2.2 Hz, 1H), 7.30 (d, J=8.8 Hz, 1H), 7.24 (d, J=5.5 Hz, 1H), 4.95-5.15 (m, 1H), 4.21-4.40 (m, 3H), 1.39 (J=6.6 Hz, 3H), 0.93 (d, J=7.1 Hz, 3H), 0.76 (d, J=6.8 Hz, 3H). LCMS (Method 3): Rt 4.53 min, m/z 428.1 [M+H]+.

Example 54—(S)-3-(2-((1-(6-Chloro-2-oxo-1,2-dihydroquinolin-3-yl)ethyl)amino) pyrimidin-4-yl)oxazolidin-2-one (I-44)

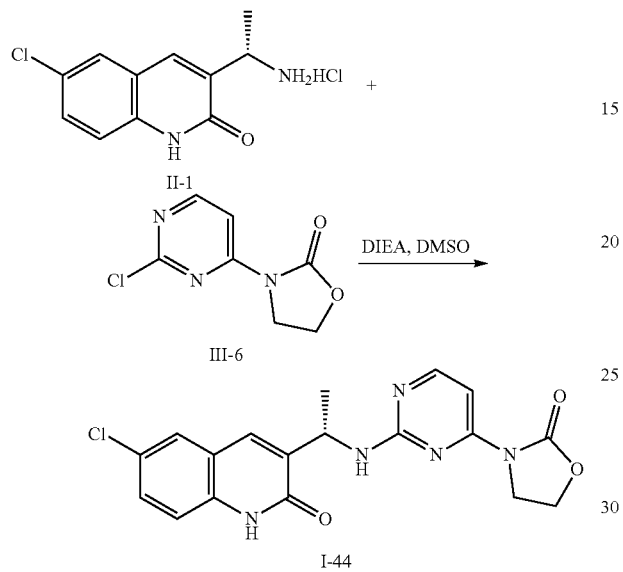

In a sealed tube, a mixture of 3-(2-chloropyrimidin-4-yl)oxazolidin-2-one III-6 (1.54 g, 7.72 mmol), (S)-3-(1-aminoethyl)-6-chloroquinolin-2(1H)-one hydrochloride II-1 (1.00 g, 3.86 mmol) and diisopropylethylamine (2.0 mL, 11.58 mmol) in DMSO (9 mL) was heated to 130° C. for 30 minutes. Once MS and TLC showed formation of product, the reaction mixture was cooled to room temperature and diluted with EtOAc and water. After the separation of the layers, the organic layer was washed with brine, dried over sodium sulfate and concentrated. The resulting residue was purified by column chromatography on an ISCO® chromatography system (SiO2 column: eluted with CH2Cl2/EtOAc gradient; 20%-100% DCM) to afford the title compound I-44 as a white solid (660 mg, 44% yield). 1H NMR (300 MHz, DMSO-d6): δ ppm 11.94 (br s, 1H), 8.13 (br s, 1H), 7.75 (s, 1H), 7.73 (d, J=2.0 Hz, 1H), 7.64 (br s, 1H), 7.40 (dd, J=8.8, 2.5 Hz, 1H), 7.29 (d, J=8.8 Hz, 1H), 7.20 (d, J=4.9 Hz, 1H), 5.17 (m, 1H), 4.41 (br s, 2H), 4.09 (br s, 2H), 1.39 (d, J=7.1 Hz, 3H). LCMS (Method 3): Rt 4.49 min, m/z 386.1, 388.1 [M+H]+.

Example 55—(S)-3-(2-(((6-Chloro-2-oxo-1,2-dihydroquinolin-3-yl)methyl)amino) pyrimidin-4-yl)-4-isopropyloxazolidin-2-one (I-46)

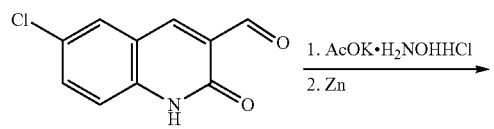

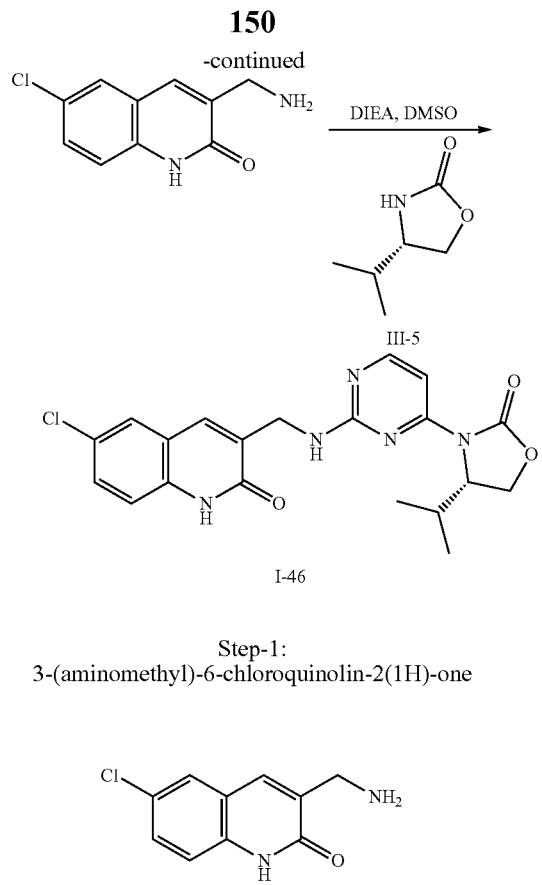

Step-1: 3-(aminomethyl)-6-chloroquinolin-2(1H)-one

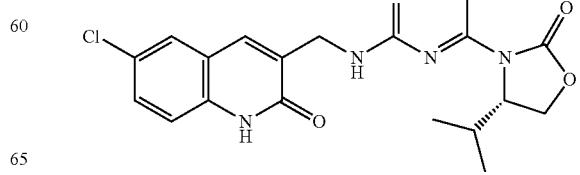

To a solution of potassium acetate (0.709 g, 7.22 mmol), 6-chloro-2-oxo-1,2-dihydroquinoline-3-carbaldehyde (1 g, 4.82 mmol) in 10 mL of water and 30 mL of MeOH was added hydroxylamine hydrochloride (0.502 g, 7.22 mmol). The mixture was stirred at room temperature overnight. The reaction was diluted with EtOAc, washed with a saturated aqueous solution of sodium bicarbonate, dried and concentrated to afford crude product. To the crude was added 40 mL of AcOH and zinc (15.75 g, 241 mmol) over a 3 hour period. The mixture was stirred at room temperature overnight, filtered, and concentrated to remove AcOH. The residue was partitioned between EtOAc and 2 M NaOH. The organic layer was separated, dried and concentrated. The crude was purified by silica gel chromatography on a Biotage® to afford 3-(aminomethyl)-6-chloroquinolin-2(1H)-one (220 mg, 21.9%). 1H NMR (300 MHz, DMSO-d6) δ ppm 8.11-8.23 (m, 1H), 7.96-8.09 (m, 1H), 7.69-7.80 (m, 1H), 7.45-7.59 (m, 1H), 3.79-4.04 (m, 2H). LCMS (Method 1): Rt 1.13 min, m/z 209.94[M+H]+.

Step-2: (S)-3-(2-(((6-Chloro-2-oxo-1,2-dihydroquinolin-3-yl)methyl)amino)pyrimidin-4-yl)-4-isopropyloxazolidin-2-one To a solution of DIEA (0.173 mL, 0.993 mmol), 3-(aminomethyl)-6-chloroquinolin-2(1H)-one (62.2 mg, 0.298 mmol), in DMSO (1 mL) was added (S)-3-(2-chloropyrimidin-4-yl)-4-isopropyloxazolidin-2-one III-5 (60 mg, 0.248 mmol). The mixture was stirred at 125° C. for 3 hours then was cooled to room temperature, and diluted with EtOAc. The mixture was washed with water, saturated aqueous sodium bicarbonate solution, and brine. The organic layer was separated, dried and concentrated. The crude was purified by chromatography on a Biotage® using a 25 g column eluted with 0-100% EtOAc/Hexanes to afford (S)-3-(2-(((6-chloro-2-oxo-1,2-dihydroquinolin-3-yl)methyl)amino)pyrimidin-4-yl)-4-isopropyloxazolidin-2-one (50 mg, 48.7%). $^1$H NMR (300 MHz, CDCl3): δ 11.76 (br. s, 1H), 8.16 (d, J=5.86 Hz, 1H), 7.60 (s, 1H), 7.42-7.48 (m, 2H), 7.20-7.38 (m, 2H), 4.50-4.61 (m, 3H), 4.12-4.25 (m, 2H), 2.30-2.40 (m, 1H), 0.70 (m, 6H). LCMS (Method 1): Rt 1.17 min, m/z 414.07 [M+H]$^+$.

TABLE 9

The Compounds listed in Table 9 were prepared using methods similar to those described for the preparation of I-42-I-44 and I-46.

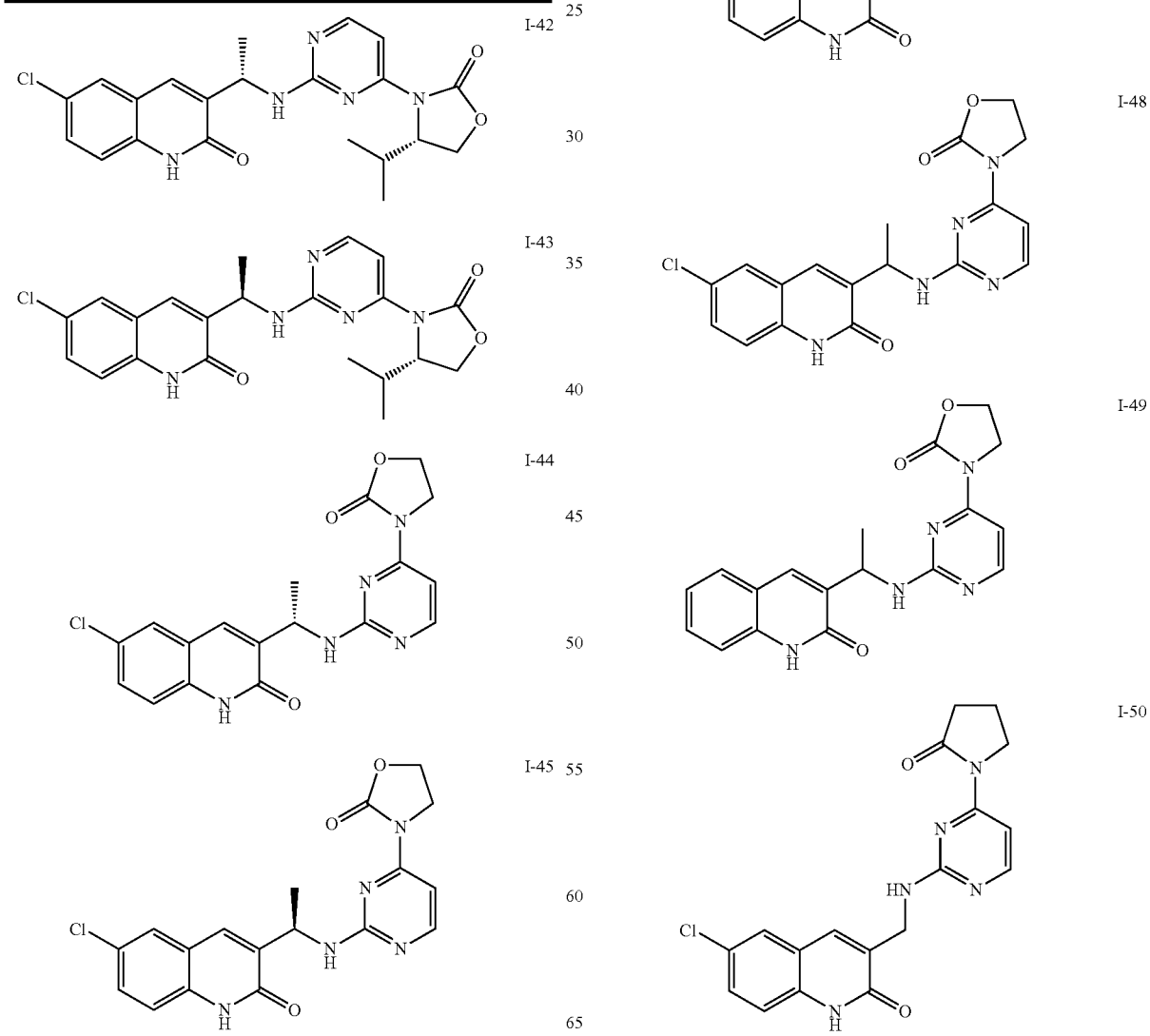

TABLE 10

LCMS signal and NMR chemical shifts for each compounds listed in Table 9.

| Cmpds No | LCMS[a] | $^1$H NMR (300 MHz) δ ppm |
|---|---|---|
| I-42 | m/z: 428.15 [M + H]$^+$ Rt (min): 1.21 | $^1$H NMR (300 MHz, DMSO-d$_6$): δ ppm 11.97 (br s, 1 H), 8.23 (d, J = 6.0 Hz, 1 H), 7.75 (d, J = 2.2 Hz, 1 H), 7.60 (br s, 1 H), 7.49 (d, J = 2.2 Hz, 1 H), 7.45 (d, J = 2.2 Hz, 1 H), 7.31 (d, J = 8.8 Hz, 1 H), 7.24 (d, J = 5.8 Hz, 1 H), 4.90-5.05 (m, 1 H), 4.21-4.44 (m, 3 H), 1.60-1.75 (m, 1 H), 1.41 (d, J = 6.8 Hz, 3 H), 0.25-0.95 (m, 6 H). |
| I-43 | m/z: 428.12 [M + H]$^+$ Rt (min): 1.27 | $^1$H NMR (300 MHz, DMSO-d$_6$): δ ppm 11.95 (br s, 1 H), 8.19 (d, J = 5.5 Hz, 1 H), 7.74 (d, J = 2.5 Hz, 2 H), 7.49 (dd, J = 8.5, 2.2 Hz, 1 H), 7.30 (d, J = 2.2 Hz, 1 H), 7.30 (d, J = 8.8 Hz, 1 H), 7.24 (d, J = 5.5 Hz, 1 H), 4.95-5.15 (m, 1 H), 4.21-4.40 (m, 3 H), 1.39 (J = 6.6 Hz, 3 H), 0.93 (d, J = 7.1 Hz, 3 H), 0.76 (d, J = 6.8 Hz, 3 H). |
| I-44 | m/z: 386.11 [M + H]$^+$ Rt (min): 1.04 | $^1$H NMR (300 MHz, DMSO-d$_6$): δ ppm 11.91 (br s, 1 H), 8.12 (s, 1 H), 7.73 (s, 1 H), 7.769 (s, 1 H), 7.60 (br, 1 H), 7.45 (d, J = 8.79 Hz, 1 H), 7.28 (d, J = 8.8 Hz, 1 H), 7.18 (s, 1 H), 5.14 (m, 1 H), 4.37 (m, 2 H), 3.20-3.60 (m, 2 H).1.37 (d, J = 6.74 Hz, 3 H). |
| I-45 | m/z: 386.17 [M + H]$^+$ Rt (min): 1.05 | |
| I-46 | m/z: 414.07 [M + H]$^+$ Rt (min): 1.17 | $^1$H NMR (300 MHz, CDCl$_3$): δ ppm 11.76 (br s, 1 H), 8.16 (d, J = 5.86 Hz, 1 H), 7.60 (s, 1 H), 7.42-7.48 (m, 2 H), 7.20-7.38 (m, 2 H), 4.50-4.61 (m, 3 H), 4.12-4.25 (m, 2 H), 2.30-2.40 (m, 1 H), 0.70 (m, 6 H). |
| I-47 | m/z: 372.03 [M + H]+ Rt (min): 0.96 | $^1$H NMR (300 MHz, DMSO-d$_6$): δ ppm 11.97 (br s, 1 H), 8.15 (d, J = 5.86 Hz, 1 H), 7.78 (s, 1 H), 7.64 (s, 1 H), 7.44-7.48 (m, 2 H), 7.29 (s, 1 H), 7.24-7.29 (m, 2 H), 4.32-4.34 (m, 4 H), 3.90-4.10 (m, 2 H). |
| I-48 | m/z: 386.07 [M + H]$^+$ Rt (min): 1.01 | |
| I-49 | m/z: 352.02 [M + H]$^+$ Rt (min): 0.85 | |
| I-50 | m/z: 370.1093 [M + H]$^+$ Rt (min): 1.01 | $^1$H NMR (300 MHz, DMSO-d$_6$): δ ppm 11.97 (br s, 1 H), 8.12 (s, 1 H), 7.75 (s, 1 H), 7.63 (s, 1 H), 7.43-7.46 (m, 2 H), 7.27 (d, J = 8.8 Hz, 1 H), 4.32 (m, 2 H), 3.54-3.62 (m, 1 H), 3.20-3.40 (m, 2 H), 1.80-2.00 (m., 3 H) |

[a]LCMS (method 4)

Example 56—(S)-6-Chloro-3-(1-((4-(2-methyl-1H-pyrrol-1-yl)pyrimidin-2-yl)amino) ethyl) quinolin-2(1H)-one (I-51)

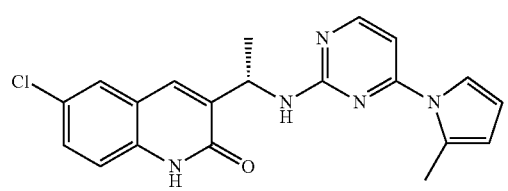 [SMILES: Cc1cccn1-c1ccnc(N[C@@H](C)c2cc3cc(Cl)ccc3[nH]c2=O)n1]

To a suspension of 2-chloro-4-(2-methyl-1H-pyrrol-1-yl)pyrimidine III-7 (167 mg, 0.868 mmol) and (S)-3-(1-aminoethyl)-6-chloroquinolin-2(1H)-one hydrochloride II-1 (150 mg, 0.578 mmol) in EtOH (2 mL) was added DIEA (0.2 mL, 1.157 mmol) and the suspension was heated to 145° C. for 4.5 hours in microwave reactor. After cooling to room temperature, the reaction mixture was poured into a mixture of EtOAc (20 mL) and water (20 mL). The organic layer was separated, and the aqueous layer was extracted with EtOAc (10 mL). The combined extracts were washed with brine (10 mL), dried over anhydrous Na$_2$SO$_4$, filtered, and evaporated. The residue was purified by column chromatography on silica gel (eluted with 0-10% MeOH in DCM) to afford the title compound as an off-white solid 1-51 (154 mg, 70% yield). $^1$H NMR (300 MHz, DMSO-d$_6$): δ ppm 11.97 (s, 1H), 8.29 (s, 1H), 7.89-7.68 (m, 3H), 7.46 (dd, J=8.8, 2.2 Hz, 1H), 7.28 (d, J=8.8 Hz, 1H), 7.24 (s, 1H), 6.72 (d, J=5.5 Hz, 1H), 6.07 (br s, 1H), 5.92 (br s, 1H), 5.14 (br s, 1H), 2.24 (s, 3H), 1.41 (d, J=6.9 Hz, 3H). LCMS (method 3): Rt 4.72 min, m/z 380.1 [M+H]$^+$.

Example 57—(S)-6-Chloro-3-(1-((4-(4,5-dimethyl-1H-imidazol-1-yl)pyrimidin-2-yl)amino) ethyl)quinolin-2(1H)-one (I-53)

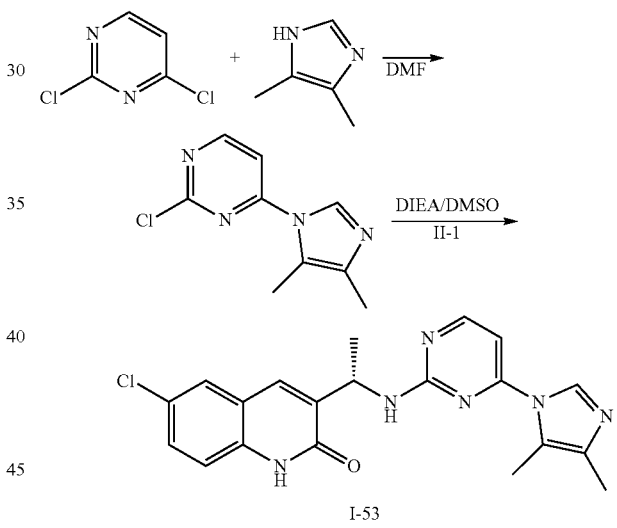

Step-1: 4-chloro-2-(4,5-dimethyl-1H-imidazol-1-yl)pyrimidine

A solution of 2,4-dichloropyrimidine (0.4 g, 2.68 mmol) and 4,5-dimethyl-1H-imidazole (0.516 g, 5.37 mmol) in DMF (5.37 mL) was heated to 45° C. for 3 hours. LCMS showed complete conversion. Water was added (120 mL) and a precipitate was filtered off. Both the filtrate and the precipitate contained product. The water phase was concentrated under reduced pressure and combined with the precipitate. The crude material was purified on SiO$_2$ (25 g SNAP® column, 0% EtOAc/hexanes for 5 minutes then 0-50% EtOAc/hexanes for 20 minutes, then 50% EtOAc/hexanes for 10 minutes and finally the column was washed with 10% MeOH/DCM for 10 minutes). The title compound 4-chloro-2-(4,5-dimethyl-1H-imidazol-1-yl)pyrimidine (0.358 g, 1.716 mmol, 63.92% yield) was isolated and used in the next step without further purification.

Step-2: (S)-6-chloro-3-(1-((4-(4,5-dimethyl-1H-imidazol-1-yl)pyrimidin-2-yl)amino)ethyl) quinolin-2(1H)-one A mixture of (S)-3-(1-aminoethyl)-6-chloroquinolin-2 (1H)-one (0.1 g, 0.449 mmol), 2-chloro-4-(4,5-dimethyl-1H-imidazol-1-yl)pyrimidine (0.094 g, 0.449 mmol) and DIEA (0.471 mL, 2.69 mmol) in DMSO (2.99 mL) was heated to 130° C. for 5 hours. Water (15 mL) was added and an off white solid was filtered off and washed once with water (5 mL). The crude material was purified by column chromatography on SiO₂ (25 g SNAP® column, eluted with 0% MeOH/DCM for 5 minutes, 0-5% MeOH/DCM for 25 minutes, and 5-10% MeOH/DCM for 10 minutes) to afford (S)-6-Chloro-3-(1-((4-(4,5-dimethyl-1H-imidazol-1-yl)pyrimidin-2-yl)amino)ethyl) quinolin-2(1H)-one Compound 1-53 (0.0309 g, 0.078 mmol, 17.43% yield). ¹H NMR (300 MHz, DMSO-d₆): δ ppm 11.97 (s, 1H), 8.24-8.42 (m, 1H), 7.93-8.20 (m, 2H), 7.73 (d, J=2.64 Hz, 2H), 7.45 (dd, J=8.79, 2.35 Hz, 1H), 7.27 (d, J=8.79 Hz, 1H), 6.79 (d, J=5.57 Hz, 1H), 5.02-5.25 (m, 1H), 1.92-2.21 (m, 6H), 1.40 (d, J=6.74 Hz, 3H).

Example 58—(S)-6-Chloro-3-(1-((4-(5-methylisoxazol-4-yl)pyrimidin-2-yl)amino) ethyl)quinolin-2(1H)-one (I-58)

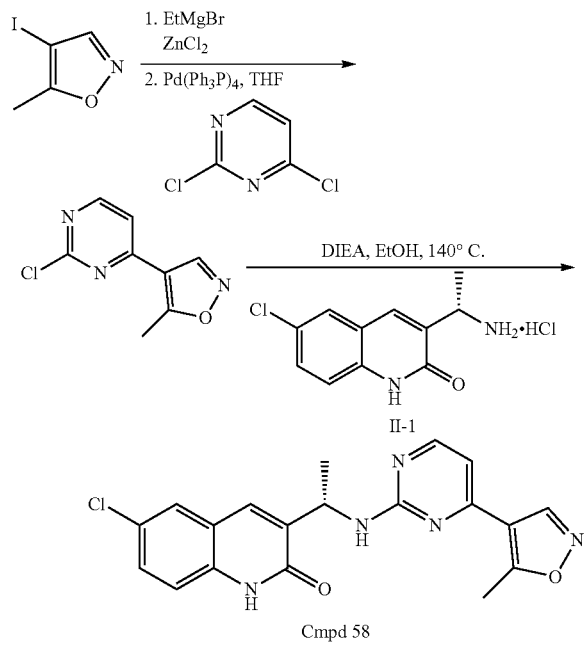

Step-1:
4-(2-Chloropyrimidin-4-yl)-5-methylisoxazole

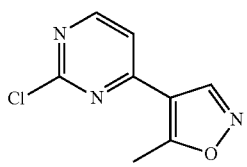

A solution of ethyl magnesium bromide (EtMgBr) (0.57 mL, 1.72 mmol, 3M in ether) was added to a suspension of 4-iodo-5-methylisoxazole (300 mg, 1.44 mmol) in THF (6 mL) under an atmosphere of nitrogen at room temperature. After stirring for ~90 minutes, a solution of ZnCl₂ (3.44 mL, 1.72 mmol, 0.5M in THF) was added dropwise and the reaction mixture was stirred at room temperature for an additional 90 minutes. The reaction mixture was then flushed with argon and 2,4-dichloropyrimidine (215 mg, 1.44 mmol) and Pd(Ph₃P)₄ (100 mg, 0.09 mmol) were added. After stirring for 18 hours at reflux, the reaction mixture was cooled to room temperature, diluted with CH₂Cl₂ and treated with EDTA (aqueous saturated solution). After the layers were separated, the pH of the aqueous layer was adjusted to pH ~8 and then extracted with CH₂Cl₂. The combined organic layers were dried over Na₂SO₄, filtered and concentrated to dryness under reduced pressure. The crude product was purified by column chromatography on an ISCO® chromatography system using a 40 g normal phase (SiO₂) column and the product was eluted with a hexanes/EtOAc to afford the title compound (150 mg, 55% yield).

Step-2: (S)-6-Chloro-3-(1-((4-(5-methylisoxazol-4-yl)pyrimidin-2-yl)amino)ethyl)quinolin-2(1H)-one

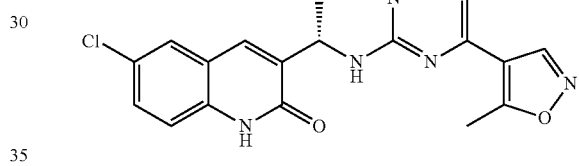

A mixture containing 4-(2-chloropyrimidin-4-yl)-5-methylisoxazole (150 mg, 0.77 mmol), (S)-3-(1-aminoethyl)-6-chloroquinolin-2(1H)-one hydrochloride II-1 (209 mg, 0.81 mmol) and DIEA (0.27 mL, 1.6 mmol) in 2.5 mL of anhydrous EtOH was heated in the microwave at 140° C. for 4 hours. The reaction mixture was concentrated to dryness under reduced pressure and purified by column chromatography on an ISCO® chromatography system using 12 g normal phase (SiO₂) and "gold" columns with a gradient elution of EtOAc in CH₂Cl₂, followed by trituration of slightly impure material with Et₂O/MeOH to provide the title compound I-58 (55 mg, 19% yield). 1H NMR (300 MHz, DMSO-d₆): δ ppm 11.82 (br s 1H), 9.02 (s, 1H), 8.05 (s, 1H), 7.80 (s, 1H), 7.76 (s, 1H), 7.48 (d, J=9.06 Hz, 1H), 7.33 (d, J=9.06 Hz, 1H), 6.25 (s, 1H), 5.18 (m, 1H), 2.24 (s, 3H), 1.48 (d, J=6.33 Hz, 3H); LCMS (Method 3): Rt 4.99 min. m/z 382.1/384.1 (Cl1-pattern) [M+H]⁺. m.p.=291-292° C.

Example 59—(S)-6-chloro-3-(1-((4-(5-methyl-1H-tetrazol-1-yl)pyrimidin-2-yl)amino)ethyl)quinolin-2(1H)-one (I-59)

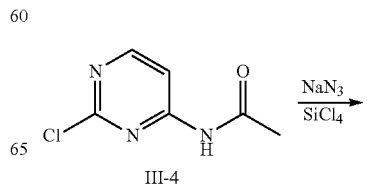

-continued

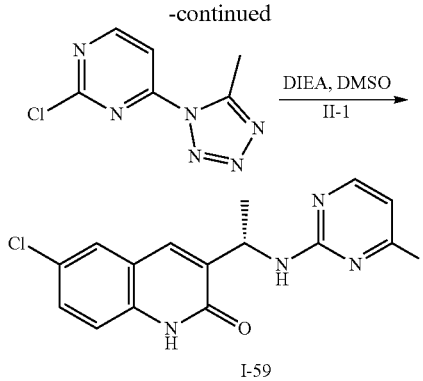

Step-1: 2-chloro-4-(5-methyl-1H-tetrazol-1-yl)pyrimidine

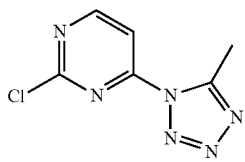

A mixture of perchlorosilane (856 mg, 5.04 mmol), N-(2-chloropyrimidin-4-yl)acetamide (150 mg, 0.874 mmol), sodium azide (1000 mg, 15.38 mmol) in 20 ml of CH$_3$CN was stirred at RT for over weekend. Once LC/Mass showed the reaction was complete, the mixture was poured into ice cold saturated Na$_2$CO$_3$ solution, Added EtOAc, extracted with EtOAc twice, dried and concentrated to afford 2-chloro-4-(5-methyl-1H-tetrazol-1-yl)pyrimidine (150 mg, 87%). 1H NMR (300 MHz, CDCl$_3$) δ ppm 8.82 (d, J=5.57 Hz, 1H), 7.90-8.12 (m, 1H), 2.97 (s, 3H). LCMS (Method 1): Rt 1.57 min, m/z 197.93 [M+H]+.

Step-2: (S)-6-chloro-3-(1-((4-(5-methyl-1H-tetrazol-1-yl)pyrimidin-2-yl)amino)ethyl) quinolin-2(1H)-one

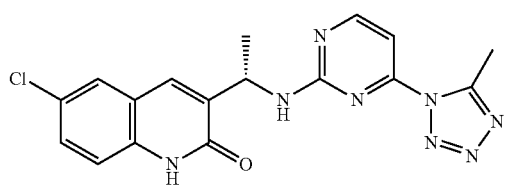 [SMILES: Cc1nnnn1-c1ccnc(N[C@@H](C)c2cc3cc(Cl)ccc3[nH]c2=O)n1]

A mixture of DIEA (0.267 ml, 1.526 mmol), (S)-3-(1-aminoethyl)-6-chloroquinolin-2(1H)-one (170 mg, 0.763 mmol), and 2-chloro-4-(5-methyl-1H-tetrazol-1-yl)pyrimidine (150 mg, 0.763 mmol) in DMSO (2 ml) was heated to 110° C. for overnight, added EtOAc, washed with water, dried and concentrated. The biotage purification with 0-5& MeOH/DCM on a 25 g column) afforded (S)-6-chloro-3-(1-((4-(5-methyl-1H-tetrazol-1-yl)pyrimidin-2-yl)amino)ethyl) quinolin-2(1H)-one (22 mg, 28.4%). 1H NMR (300 MHz, DMSO-d6): δ 12.03 (br. s, 1H), 8.58 (s 1H), 8.41 (s, 1H), 7.74 (s, 1H), 7.45 (d, J=8.5 Hz, 1H), 7.25 (d, J=8.51 Hz, 1H), 7.11 (d, J=5.28 Hz, 1H), 5.20 (m, 1H), 3.13 (s, 3H) 1.42 (d, J=6.44 Hz, 3H).

Example 60—(S)-6-Chloro-3-(1-((4-(1-(2,2,2-trifluoroethyl)-1H-imidazol-5-yl)pyrimidin-2-yl)amino)ethyl)quinolin-2(1H)-one (I-60)

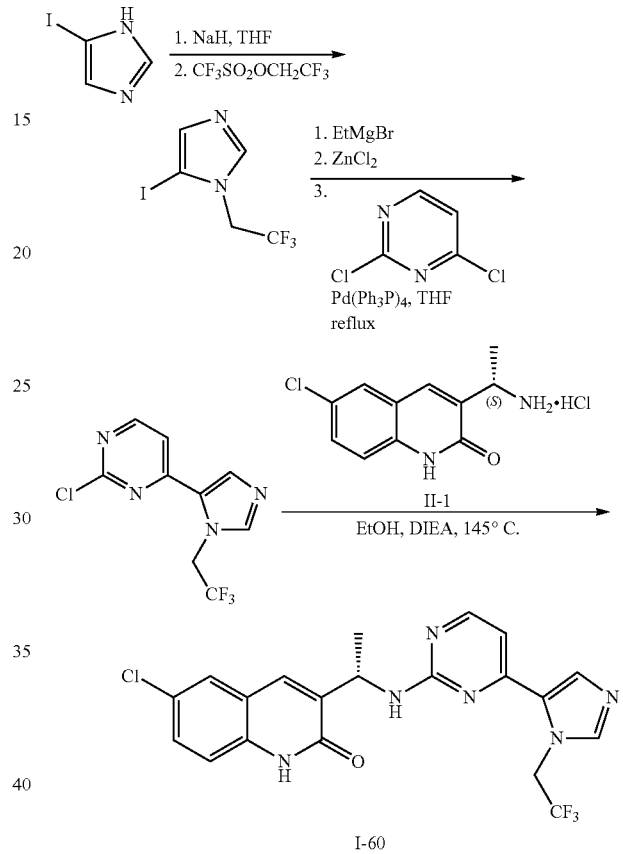

Step-1: 5-Iodo-1-(2,2,2-trifluoroethyl)-1H-imidazole

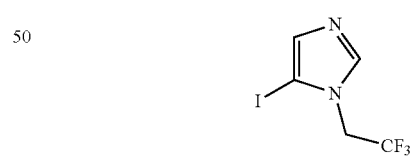

To an ice cold solution of 5-iodo-1H-imidazole (1.87 g, 9.6 mmol) in 20 mL of THF was added 60% NaH in oil (1.15 g, 28.7 mmol) in portions. After stirring at room temperature for 30 minutes, the reaction mixture was cooled to 0° C., and 2,2,2-trifluoroethyl trifluoromethanesulfonate (4.45 g, 19.2 mmol) in 4 mL of THF was added dropwise. The suspension was stirred at room temperature for 2 hours (TLC indicated completion of reaction) and was then quenched with cold water and extracted several times with EtOAc. Organic phases were combined, washed with brine, dried over Na$_2$SO$_4$, filtered and concentrated to dryness under reduced pressure. The crude mixture was purified twice by column chromatography on an ISCO® chromatography system using 80 g and 40 g normal phase columns (SiO₂) with a gradient elution of hexanes in EtOAc to afford 220 mg (~8% yield) of the pure isomer 5-iodo-1-(2,2,2-trifluoroethyl)-1H-imidazole.

Step-2: 2-Chloro-4-(1-(2,2,2-trifluoroethyl)-1H-imidazol-5-yl)pyrimidine

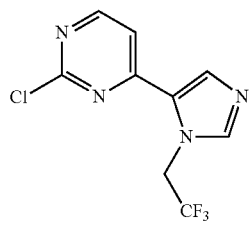 [SMILES: FC(F)(F)Cn1cncc1-c1ccnc(Cl)n1]

A solution of ethyl magnesium bromide (EtMgBr) (0.35 mL, 1.04 mmol, 3M in ether) was added to a suspension of 5-iodo-1-(2,2,2-trifluoroethyl)-1H-imidazole (200 mg, 0.80 mmol) in THF (3 mL) under atmosphere of nitrogen at room temperature. After stirring at room temperature for ~90 minutes, a solution of ZnCl₂ (2.23 mL, 1.2 mmol, 0.5M in THF) was added dropwise, and the reaction mixture was stirred at room temperature for an additional 90 minutes. The reaction mixture was the flushed with argon and 2,4-dichloropyrimidine (119 mg, 0.80 mmol) was added followed by the addition of Pd(Ph₃P)₄ (55 mg, 0.05 mmol). After stirring for 15 hours at reflux, the reaction mixture was cooled to the room temperature, diluted with CH₂Cl₂ and treated with EDTA (aqueous saturated solution). After the layers were separated, the pH of the aqueous layer was adjusted to pH ~8 and was then extracted again with CH₂Cl₂. The combined organic layers were dried over Na₂SO₄, filtered and concentrated to dryness under reduced pressure. The crude mixture was purified by column chromatography on an ISCO® chromatography system using a 12 g normal phase column (SiO₂) with a gradient elution of CH₂Cl₂ in EtOAc to afford the title compound (100 mg 48% yield).

Step-3: (S)-6-Chloro-3-(1-((4-(1-(2,2,2-trifluoroethyl)-1H-imidazol-5-yl)pyrimidin-2-yl)amino) ethyl)quinolin-2(1H)-one (I-60)

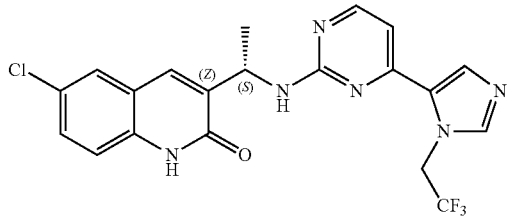

A mixture containing 2-chloro-4-(1-(2,2,2-trifluoroethyl)-1H-imidazol-5-yl)pyrimidine (100 mg, 0.38 mmol), (S)-3-(1-aminoethyl)-6-chloroquinolin-2(1H)-one hydrochloride II-1 (120 mg, 0.46 mmol) and DIEA (0.16 mL, 0.76 mmol) in 2 mL of anhydrous EtOH was heated in a microwave to 145° C. for 4 hours and 30 minutes. The reaction mixture was then concentrated to dryness under reduced pressure and purified by column chromatography on an ISCO® chromatography system using a 12 g normal phase (SiO₂) "gold" column with a gradient elution of EtOAc in CH₂Cl₂ followed by a gradient elution of MeOH in EtOAc to afford 124 mg (73% yield) of the title compound I-60. ¹H NMR (300 MHz, DMSO-d₆, 80° C. (v. broad signals at room temperature)): δ ppm 11.8 (br s, 1H), 8.26 (m, 1H), 7.90 (m, 1H), 7.78 (m, 1H), 7.6-7.7 (m, 2H), 7.4-7.5 (m, 2H), 7.25-7.35 (m, 1H), 6.88-6.96 (m, 1H), 5.5-5.7 (m, 2H), 5.23 (m, 1H), 1.48 (m, 3H). LCMS (Method 3): Rt 4.25 min. m/z 349.1 [M+H]⁺. mp: 156-157° C.

Example 61—(S)-3-(1-(4,5'-bipyrimidin-2-ylamino) ethyl)-6-chloroquinolin-2(1H)-one (I-62)

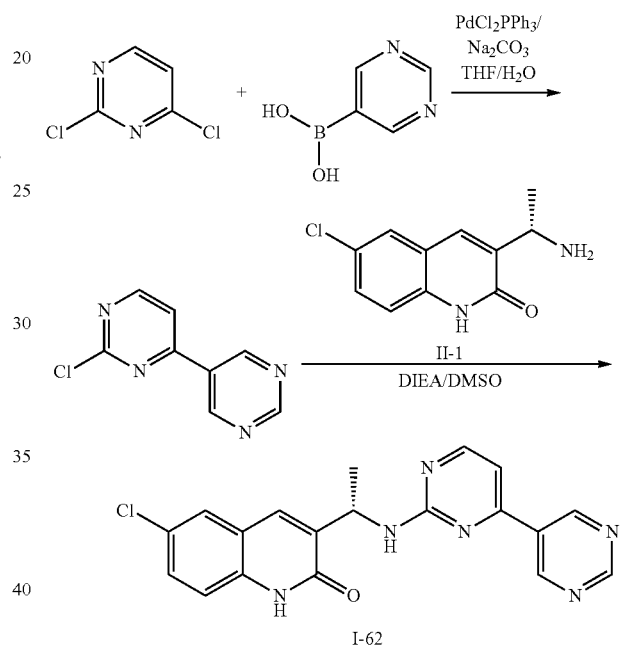

Step-1: 2-chloro-4,5'-bipyrimidine

To a solution of 2,4-dichloropyrimidine (0.5 g, 3.36 mmol) and pyrimidin-5-ylboronic acid (0.416 g, 3.36 mmol) in a mixture of THF (4.20 mL) and water (1.30 mL) was added bis(triphenylphosphine)palladium(II) chloride (0.141 g, 0.201 mmol) and Na₂CO₃ (1.067 g, 10.07 mmol). The reaction mixture was refluxed for 16 hours, and then water (15 mL) was added. The aqueous phase was extracted with EtOAc (3×15 mL) and the combined organic phases were washed with brine (15 mL). The organic phase was dried over MgSO4, and the volatiles were removed under reduced pressure. The crude material was purified on SiO₂ (25 SNAP® column, eluted with 0-75% EtOAc/hexanes for 30 minutes then 75-100% EtOAc/hexanes for 5 minutes). The title compound 2-chloro-4,5'-bipyrimidine (0.267 g, 1.386 mmol, 41.3% yield) was isolated and used in the next step without further purification.

Step-2: (S)-3-(1-(4,5'-bipyrimidin-2-ylamino)ethyl)-6-chloroquinolin-2(1H)-one

A solution of (S)-3-(1-aminoethyl)-6-chloroquinolin-2 (1H)-one hydrochloride II-1 (0.075 g, 0.289 mmol) and DIEA (0.303 mL, 1.737 mmol) in DMSO (2.067 mL) was heated to 120° C. for 3 hours. The reaction was then cooled to room temperature and stirred for 16 hours. Water (15 mL) was added, and the resulting precipitate was filtered off and washed with water (2×5 mL). The precipitate was purified by column chromatography on SiO$_2$ (10 g SNAP® column, with gradient elution, DCM for 5 minutes, 0-5% MeOH/DCM for 20 minutes, 5-15% MeOH/DCM for 5 minutes, and 15-20% for 15 minutes) to afford (S)-3-(1-(4,5'-bipyrimidin-2-yl amino)ethyl)-6-chloroquinolin-2(1H)-one 1-62 (0.029 g, 0.077 mmol, 26.5% yield). $^1$H NMR (300 MHz, DMSO-d$_6$): δ ppm 11.99 (br s, 1H), 9.18-9.49 (m, 3H), 8.42 (br s, 1H), 7.92 (br s, 1H), 7.65-7.84 (m, 2H), 7.44 (dd, J=8.79, 2.05 Hz, 1H), 7.22-7.35 (m, 2H), 5.31 (br s, 1H), 1.42 (d, J=7.04 Hz, 3H).

Example 62—(S)-6-chloro-3-(1-((4-(imidazo[1,2-a]pyridin-3-yl)pyrimidin-2-yl)amino)ethyl)quinolin-2(1H)-one (I-63)

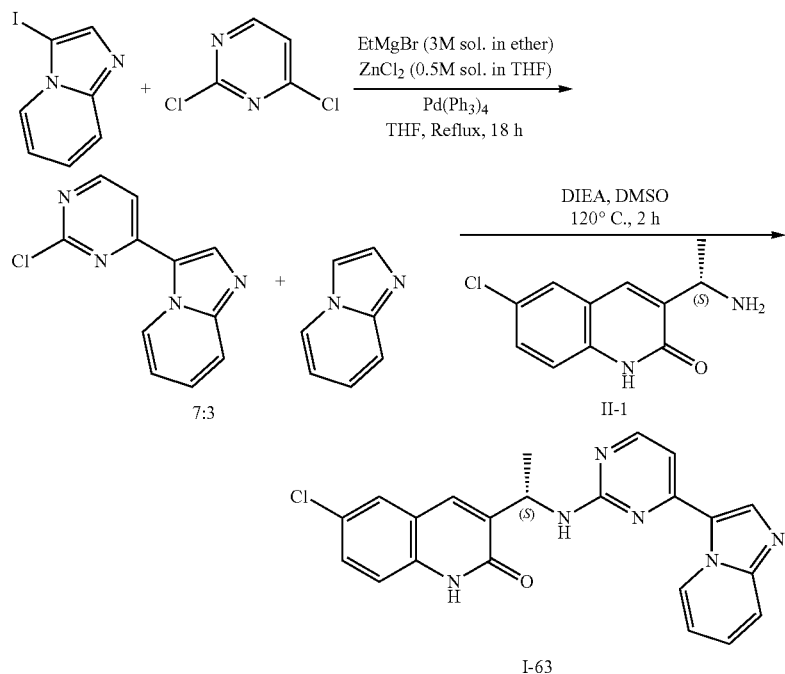

Step-1: 3-(2-chloropyrimidin-4-yl)imidazo[1,2-a]pyridine

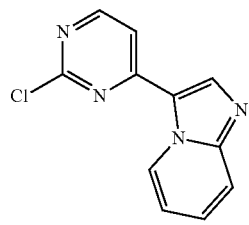 [SMILES: Clc1nccc(-c2cnc3ccccn23)n1]

Ethylmagnesium bromide (EtMgBr) (3M solution in ether, 1.36 mL, 4.92 mmol) was slowly added to a suspension of 3-iodoimidazo[1,2-a]pyridine (1.0 g, 4.1 mmol) in 15 mL of THF. The resulting mixture was stirred at room temperature for 1.5 hours. Zinc chloride (0.5 M solution in THF, 8.2 mL, 4.92 mmol) was then added and the reaction was stirred at room temperature for 1.5 hours. The reaction was purged with nitrogen gas and then 2,4-dichloropyrimidine (0.61 g, 4.1 mmol) and Pd(PPh$_3$)$_4$ (0.235 g, 0.2 mmol) were added. The resulting mixture was heated to reflux for 18 hours under an atmosphere of nitrogen. The reaction was cooled and filtered through Celite®, rinsing the filter cake with ethyl acetate. The filtrate was concentrated, and the resulting residue was taken into dichloromethane and washed with water. The organic layer was dried over Na$_2$SO$_4$, filtered, and evaporated under reduced pressure. The crude material was purified by column chromatography on an ISCO® chromatography system (SiO$_2$ column: eluted 0-100% ethyl acetate/hexanes gradient) to afford 325 mg of a mixture containing 3-(2-chloropyrimidin-4-yl)imidazo[1,2-a]pyridine and imidazo[1,2-a]pyridine in a ~7:3 ratio. This product was used in the next step without further purification.

Step-2: (S)-6-chloro-3-(1-((4-(imidazo[1,2-a]pyridin-3-yl)pyrimidin-2-yl)amino) ethyl) quinolin-2(1H)-one (I-63)

To a mixture of 3-(2-chloropyrimidin-4-yl)imidazo[1,2-a]pyridine and imidazo[1,2-a]pyridine (123 mg; 7:3 ratio) in DMSO was added (S)-3-(1-aminoethyl)-6-chloroquinolin-2(1H)-one hydrochloride (II-1) (200 mg, 0.77 mmol) followed by DIEA (0.435 mL, 2.5 mmol). The resulting mixture was heated in a microwave to 1200 for 2 hours. The reaction was cooled to room temperature and diluted with ethyl acetate, and washed with water (2×) and brine. The organic extract was then dried over Na$_2$SO$_4$, filtered, and evaporated under reduced pressure. The crude material was purified by column chromatography on an ISCO® chromatography system (SiO$_2$ column: eluted with 0-5% methanol in ethyl acetate gradient) to afford the title compound I-63 (90 mg, 58% yield). $^1$H NMR (300 MHz, DMSO-d$_6$, at 90° C.): δ ppm 11.74 (br s, 1H), 9.87 (d, J=8.2 Hz, 1H), 8.40 (s, 1H), 8.26 (d, J=5.5 Hz, 1H), 7.83 (s, 1H), 7.76-7.62 (m, 2H), 7.50-7.28 (m, 4H), 7.18-7.00 (m, 2H), 5.40-5.26 (m, 1H), 1.52 (d, J=6.8 Hz, 3H). LCMS (Method 3): Rt 3.80 min, m/z 417.1 [M+H].

Example 63—(S)-6-chloro-3-(1-((4-(1-isopropyl-1H-imidazol-5-yl)pyrimidin-2-yl)amino)ethyl) quinolin-2(1H)-one (I-64)

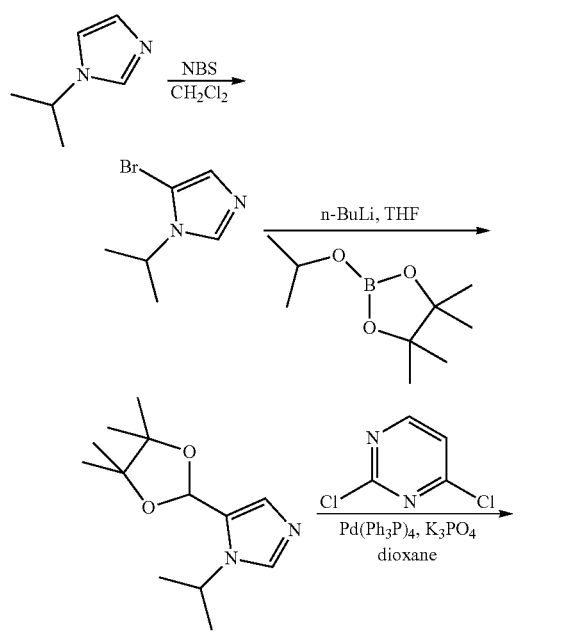

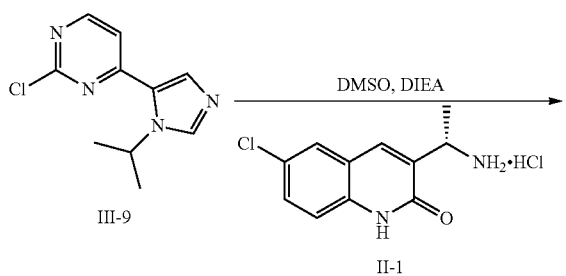

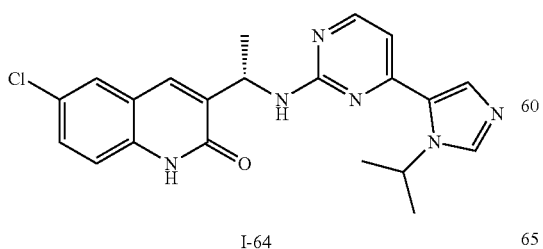

I-64

Step-1: 5-Bromo-1-isopropyl-1H-imidazole

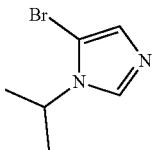

To a solution of 1-isopropyl-1H-imidazole (11.0 g, 0.1 mol) in CH$_2$Cl$_2$ (200 mL) was added NBS (17.8 g, 0.1 mol) portionwise, and the resulting reaction mixture was heated to reflux for 4 hours. The reaction mixture was then cooled to room temperature and quenched by addition of saturated aqueous NaHCO$_3$ solution (100 mL). The organic layer was separated, and the aqueous layer was extracted with CH$_2$Cl$_2$ (50 mL×3). The combined organic layers were dried (Na$_2$SO$_4$), concentrated, and purified by column chromatography using an ISCO® chromatography system with hexane/ethyl acetate to afford 5-bromo-1-isopropyl-1H-imidazole as a colorless liquid (4.32 g, 23% yield). $^1$H NMR (300 MHz, CDCl$_3$): δ ppm 7.61 (s, 1H), 7.90 (s, 1H), 7.00 (s, 1H), 4.41 (m, 1H), 1.49 (d, J=6.60 Hz, 6H). LCMS (Method 3): Rt 3.22 min, m/z 189.0 [M+H]$^+$.

Step-2: 1-Isopropyl-5-(4,4,5,5-tetramethyl-1,3,2-dioxaborolan-2-yl)-1H-imidazole

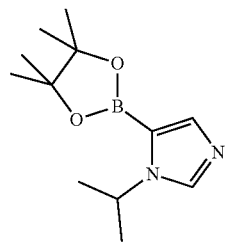 [SMILES: CC(C)n1cncc1B1OC(C)(C)C(C)(C)O1]

To a solution of 5-bromo-1-isopropyl-1H-imidazole (2 g, 10.6 mmol) in anhydrous THF (100 mL) at −78° C. was added dropwise n-BuLi (2.5M solution in hexane, 6.36 mL, 16 mmol) and the resulting reaction mixture was stirred at −78° C. for 1 hour. 2-isopropoxy-4,4,5,5-tetramethyl-1,3,2-dioxaborolane (4 g, 21.2 mmol) was then added in one portion and the reaction mixture was stirred at −78° C. for 1 hour and then warmed up to room temperature for 2 hours. The reaction mixture was then quenched with saturated NH$_4$Cl (100 mL). The organic layer was separated, and the aqueous layer was extracted with ethyl acetate (50 mL×3). The combined organic layers were dried (Na$_2$SO$_4$), concentrated, and passed through a pad of silica gel to afford a crude mixture of the title compound which was used in the next step without further purification (3.95 g).

Step-3: 2-Chloro-4-(1-isopropyl-1H-imidazol-5-yl)pyrimidine, III-9

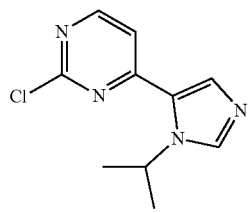

To a mixture of 2,4-dichloropyrimidine (1.49 g, 10 mmol) and crude 1-isopropyl-5-(4,4,5,5-tetramethyl-1,3,2-dioxaborolan-2-yl)-1H-imidazole 3 (2.36 g, 10 mmol) in 1,4-dioxane (50 mL) was added K$_3$PO$_4$ (6.26 g, 30 mmol), Pd(PPh$_3$)$_4$(578 mg, 0.5 mmol) and water (1 mL). The reaction mixture was then heated to reflux overnight. The solvents were evaporated and water (100 mL) and ethyl acetate (50 mL) were added to the resulting residue. The organic layer was separated and the aqueous layer was extracted with ethyl acetate (50 mL×3). The combined organic layers were dried (Na$_2$SO$_4$), concentrated, and purified by silica gel chromatography on an ISCO® chromatography system eluted with a hexanes/ethyl acetate gradient to afford impure III-9 (810 mg). This was used in the next step without further purification.

Step-4: (S)-6-Chloro-3-(1-((4-(1-isopropyl-1H-imidazol-5-yl)pyrimidin-2-yl)amino) ethyl) quinolin-2(1H)-one (I-64)

To a mixture of (5)-3-(1-aminoethyl)-6-chloroquinolin-2(1H)-one hydrochloride II-1 (750 mg, 2.9 mmol) and 2-chloro-4-(1-isopropyl-1H-imidazol-5-yl)pyrimidine (650 mg, 2.9 mmol) in DMSO (50 mL) was added DIEA (1 mL, 5.8 mmol) at room temperature and the resulting mixture was heated to 130° C. for 2 hours. The mixture was then cooled to room temperature and diluted with EtOAc (200 mL). The organic layer washed with water (3×100 mL), dried over anhydrous Na$_2$SO$_4$, and concentrated. The resulting residue was purified by column chromatography on an ISCO® chromatography system (SiO$_2$ column) eluted with CH$_2$Cl$_2$/MeOH (0-10% MeOH) and then further purified by prep TLC with CH$_2$Cl$_2$/MeOH (9:1) to afford the title compound I-64 as a white solid (13 mg, 1% yield). $^1$H NMR (300 MHz, DMSO-d$_6$): δ ppm 8.23 (d, J=6.57 Hz, 1H), 7.90 (s, 1H), 7.81 (s, 1H), 7.59 (d, J=3.33 Hz, 1H), 7.56 (s, 1H), 7.21 (dd, J=8.46, 3.33 Hz, 1H), 7.31 (d, J=8.46 Hz, 1H), 6.91 (d, J=4.32 Hz, 1H), 5.50 (br s, 1H), 5.22 (m, 1H), 1.55 (d, J=6.87 Hz, 3H), 1.48 (d, J=6.87 Hz, 3H), 1.01 (m, 3H). LCMS (Method 3): Rt 3.74 min, m/z 409.1 [M+H]$^+$.

Example 64—(S)-6-Chloro-3-(1-((4-(2-(triflouromethyl)-1H-pyrrol-1-yl)pyrimidin-2-yl)amino)ethyl)quinolin-2(1H)-one (I-65)

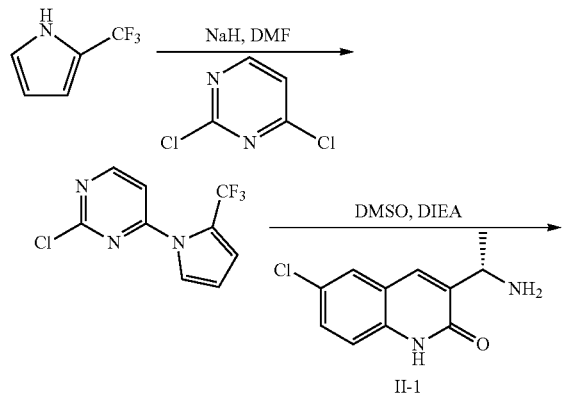

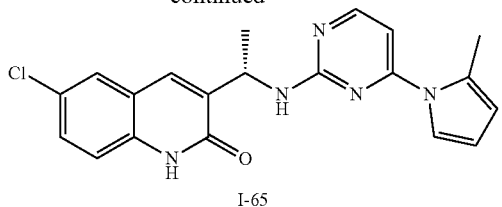

I-65

Step-1: 2-Chloro-4-(2-(trifluoromethyl)-1H-pyrrol-1-yl)pyrimidine

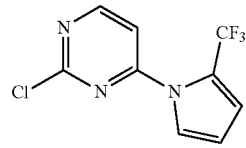 [SMILES: FC(F)(F)c1cccn1-c1ccnc(Cl)n1]

In a dried 3-neck round bottom flask, a solution of 2-trifluoromethyl pyrrole (540 mg, 4 mmol, 1 equivalent) in 10 mL anhydrous DMF was cooled to −78° C. Sodium hydride (NaH) (60 wt. % in oil, 160 mg, 4 mmol, 1 equivalent) was added in one portion and the resulting mixture was then stirred in a 0° C. bath for 20 minutes. After cooling again to −78° C., a solution of 2,4-dichloropyrimidine in 4 mL DMF was added. The cooling bath was removed, and the reaction was stirred at room temperature for 2 hours. Water was added followed by extraction with EtOAc. The combined organic phases were dried, filtered and concentrated. Purification by column chromatography on 30 g of silica gel (hexane/EtOAc, 9/1) provided the title compound (290 mg, 29% yield) as a white waxy solid.

Step-2: (S)-6-Chloro-3-(1-((4-(2-(triflouromethyl)-1H-pyrrol-1-yl)pyrimidin-2-yl)amino) ethyl) quinolin-2(1H)-one (I-65)

A mixture of 2-chloro-4-(2-(trifluoromethyl)-1H-pyrrol-1-yl)pyrimidine 2 (135 mg, 0.55 mmol, 1 equivalent), (S)-3-(1-aminoethyl)-6-chloroquinolin-2(1H)-one hydrochloride II-1 (110 mg, 0.5 mmol, 1 equivalent) and DIEA (129 mg, 1.0 mmol, 2 equivalents) in 0.3 mL EtOH was heated in a microwave to 150° C. for 45 minutes. After evaporation of the solvent, the resulting foam was purified by column chromatography on 7 g of silica gel using a gradient of 0-10% MeOH in DCM to provide 106 mg I-65 as a white solid. $^1$H NMR (300 MHz, d$_6$-DMSO at 90° C.): δ ppm 11.68 (br s, 1H), 8.40 (d, J 5.22, 1H), 7.78 (br s, 1H), 7.66 (d, J 2.19, 1 H), 7.55 (m, 1H), 7.43 (dd, J 2.19, 8.79, 2H), 7.31 (d, J 8.79, 1H), 6.88 (m, 1H), 6.74 (d, J=5.49, 1H), 6.36 (m, 1H), 5.27 (m, 1H), 1.47 (d, J=6.87, 1H). LC/MS (Method 3): Rt 5.3 min., m/z 434 [M+H]$^+$.

Example 65—(S)-6-chloro-3-(1-((4-(1-methyl-1H-1,2,3-triazol-5-yl)pyrimidin-2-yl)amino)ethyl)quinolin-2(1H)-one (I-66)

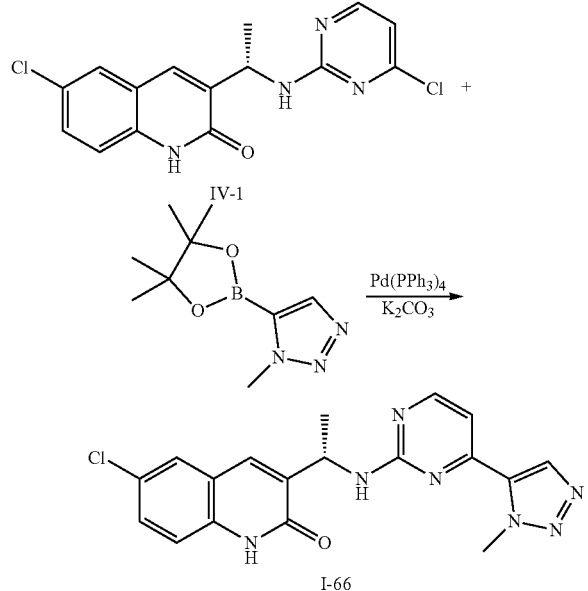

To a 20 ml of reaction tube was added (S)-6-chloro-3-(1-((4-chloropyrimidin-2-yl)amino)ethyl)quinolin-2(1H)-one IV-1 (60 mg, 0.179 mmol) $K_2CO_3$ (99 mg, 0.716 mmol) Pd(Ph$_3$P)$_4$ (10.34 mg, 8.95 μmol), and 1-methyl-5-(4,4,5,5-tetramethyl-1,3,2-dioxaborolan-2-yl)-1H-1,2,3-triazole (41.2 mg, 0.197 mmol) followed by water (1 ml) and DME (4.000 ml). The resulting mixture was bubbled with $N_2$ for 10 min. and heated to 100° C. overnight. The reaction mixture was then cooled to room temperature and EtOAc was added. The reaction mixture was washed with brine, dried and concentrated. The crude mixture was purified by HPLC chromatography to afford (S)-6-chloro-3-(1-((4-(1-methyl-1H-1,2,3-triazol-5-yl)pyrimidin-2-yl)amino)ethyl)quinolin-2(1H)-one (1.1 mg, >90% HPLC pure, 1.7% yield). $^1$H NMR (300 MHz, DMSO-d$_6$): δ ppm 12.01 (br s, 1H), 8.45 (br d, J=4.40 Hz, 1H), 7.80 (br s, 3H), 7.71 (d, J=2.35 Hz, 1H), 7.46 (dd, J=8.79, 2.35 Hz, 1H), 7.03 (d, J=4.98 Hz, 1H), 5.28 (br s, 1H), 4.10 (q, J=5.28 Hz, 1H), 1.41 (d, J=6.74 Hz, 3H).

Example 66—(S)-6-Chloro-3-(1-((4-(1-methyl-1H-pyrazol-5-yl)pyrimidin-2-yl)amino)ethyl)quinolin-2(1H)-one (I-67)

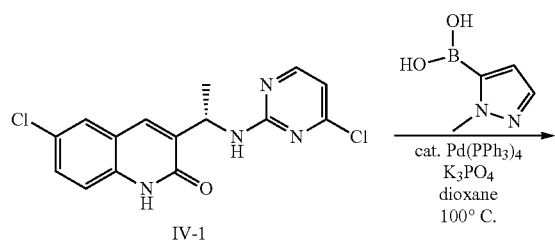

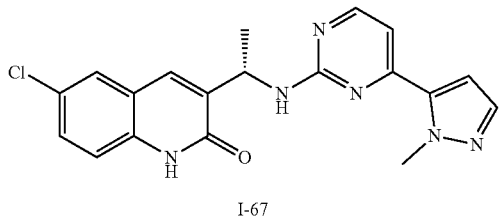

A 2 mL reaction vial was charged with a 0.2M 1,4-dioxane solution containing (S)-3-(1-((4-bromopyrimidin-2-yl)amino)ethyl)-6-chloroquinolin-2(1H)-one IV-1 (100 μL, 20 μmol) and (1-methyl-1H-pyrazol-5-yl)boronic acid (150 μL, 30 μmol, 1.5 equivalents). To the mixture was added 1M aqueous potassium phosphate tribasic solution (75 μL, 75 μmol, 3.75 equivalents). Nitrogen gas was then bubbled through the mixture for 3-5 seconds before a 0.01M solution of palladium tetrakis in 1,4-dioxane (50 μL, 0.5 μmol) was added. Nitrogen gas was passed through the mixture once more before the vial was sealed and heated to 100° C. overnight. LCMS analysis confirmed the presence of the cross-coupled product. The mixture was then diluted with brine (500 μL) and extracted with ethyl acetate (2×500 μL). The organic layers were placed onto a 0.5 gram ion exchange column (benzenesulfonic acid on silica). The column was flushed with ethyl acetate (3 mL) and the title compound was eluted with 3 mL of a 10:1:1 solution of ethyl acetate/methanol/triethylamine. The eluent containing crude product was concentrated under a stream of nitrogen at 50° C. The resulting residue was dissolved in DMSO (500 μL), and purified by mass-triggered preparatory HPLC to afford the title compound (3.8 mg, 50% yield). LCMS (Method 4) Rt 1.18 min, m/z 381.04 [M+H]$^+$.

TABLE 11

The compounds listed in Table 11 were prepared using the same method described for the preparation of I-67.

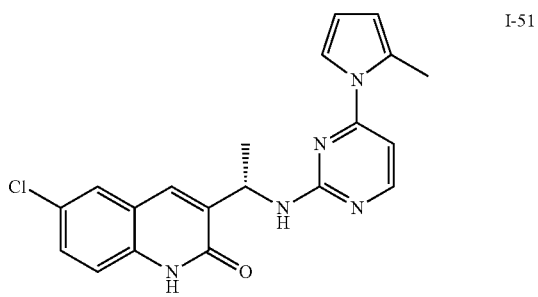

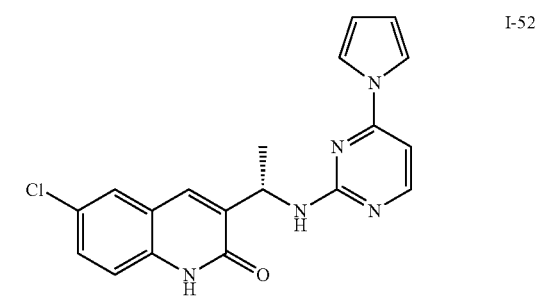

TABLE 11-continued
The compounds listed in Table 11 were prepared using the same method described for the preparation of I-67.
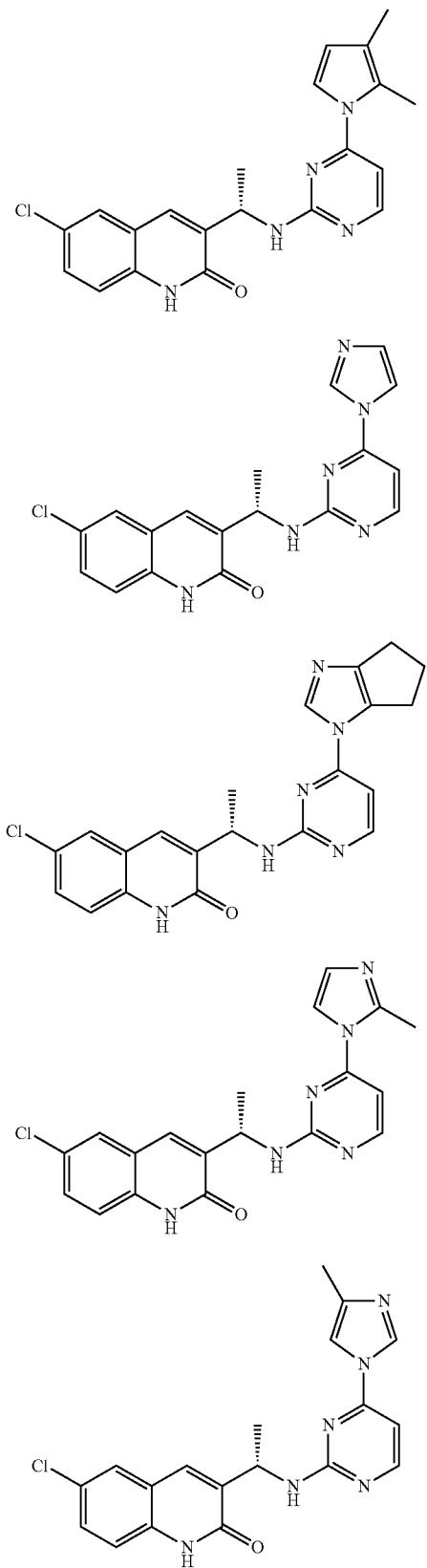
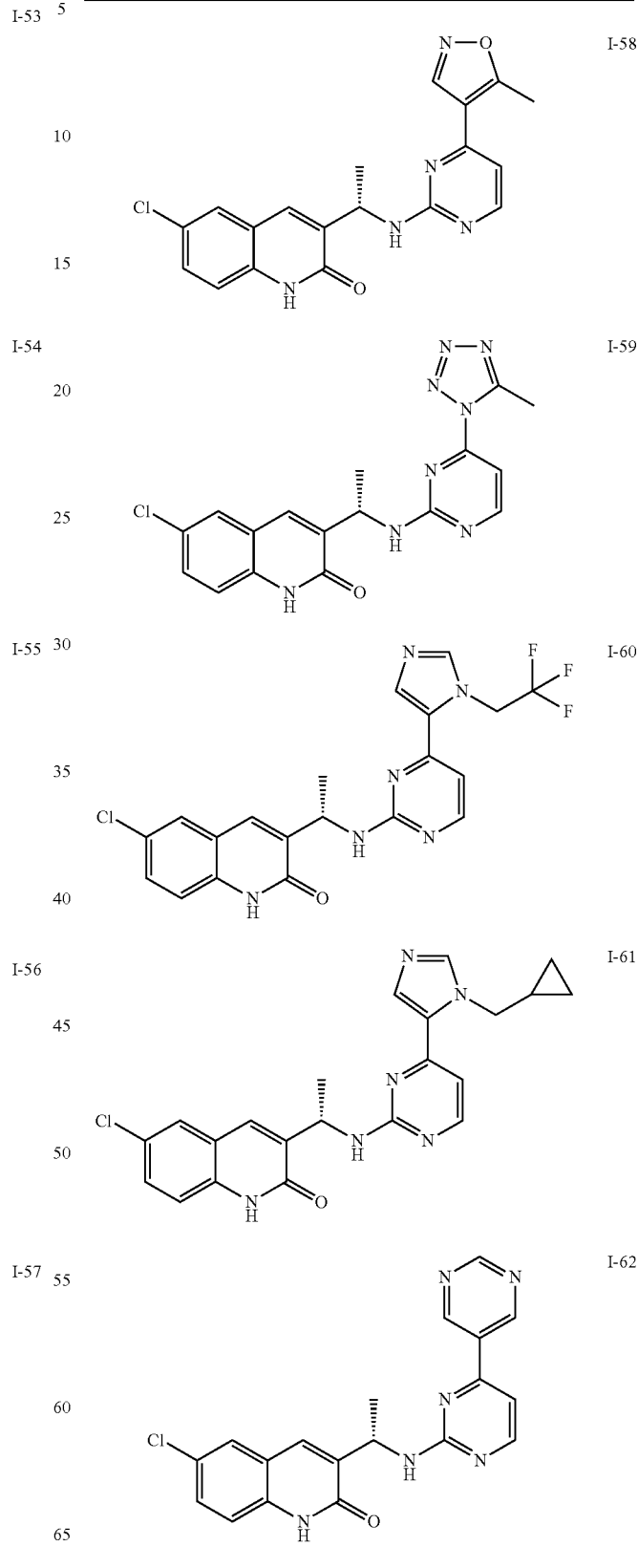

TABLE 11-continued
The compounds listed in Table 11 were prepared using the same method described for the preparation of I-67.
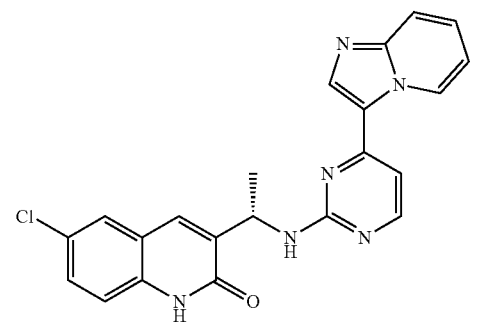 [SMILES: C[C@H](Nc1nccc(-c2cnc3ccccn23)n1)c1cc2cc(Cl)ccc2[nH]c1=O]
I-63
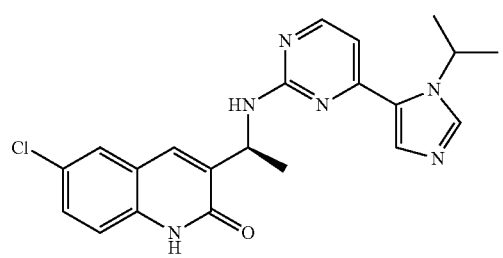 [SMILES: CC(C)n1cncc1-c1ccnc(N[C@@H](C)c2cc3cc(Cl)ccc3[nH]c2=O)n1]
I-64
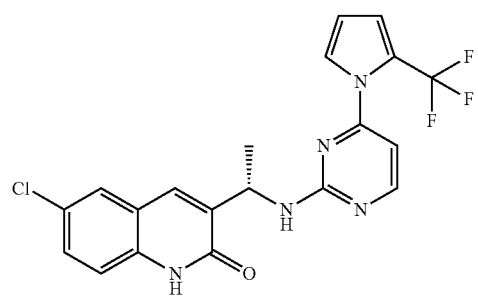 [SMILES: C[C@H](Nc1nccc(-n2cccc2C(F)(F)F)n1)c1cc2cc(Cl)ccc2[nH]c1=O]
I-65
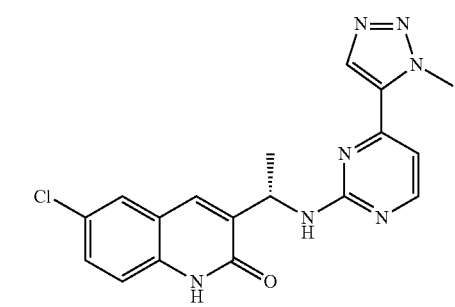
I-66
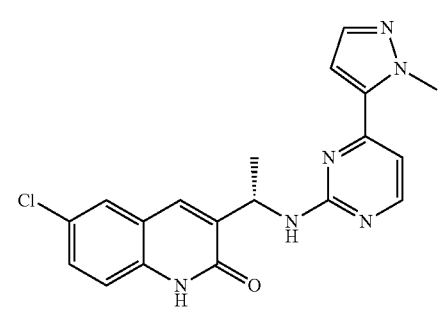 [SMILES: C[C@H](Nc1nccc(-c2ccnn2C)n1)c1cc2cc(Cl)ccc2[nH]c1=O]
I-67
TABLE 11-continued
The compounds listed in Table 11 were prepared using the same method described for the preparation of I-67.
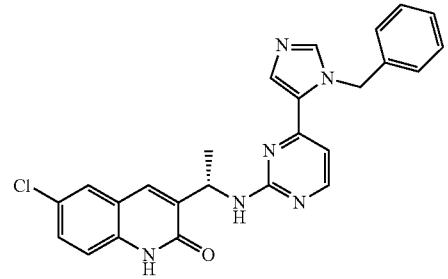 [SMILES: C[C@H](Nc1nccc(-c2cncn2Cc2ccccc2)n1)c1cc2cc(Cl)ccc2[nH]c1=O]
I-68
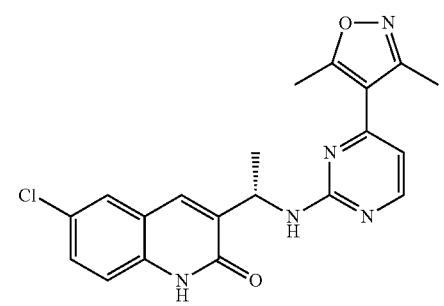 [SMILES: Cc1noc(C)c1-c1ccnc(N[C@@H](C)c2cc3cc(Cl)ccc3[nH]c2=O)n1]
I-69
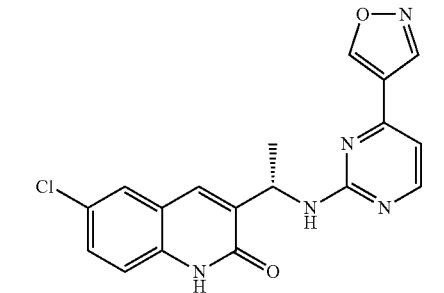
I-70
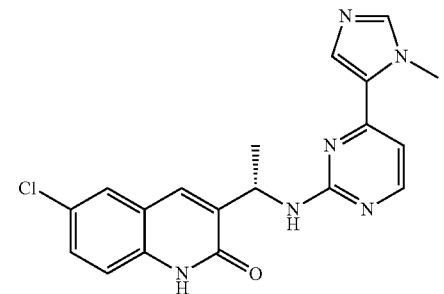 [SMILES: C[C@H](Nc1nccc(-c2cncn2C)n1)c1cc2cc(Cl)ccc2[nH]c1=O]
I-71
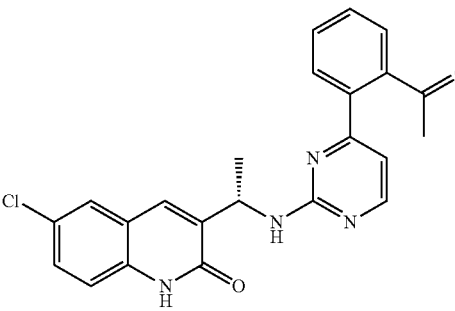
I-72

TABLE 11-continued
The compounds listed in Table 11 were prepared using the same method described for the preparation of I-67.
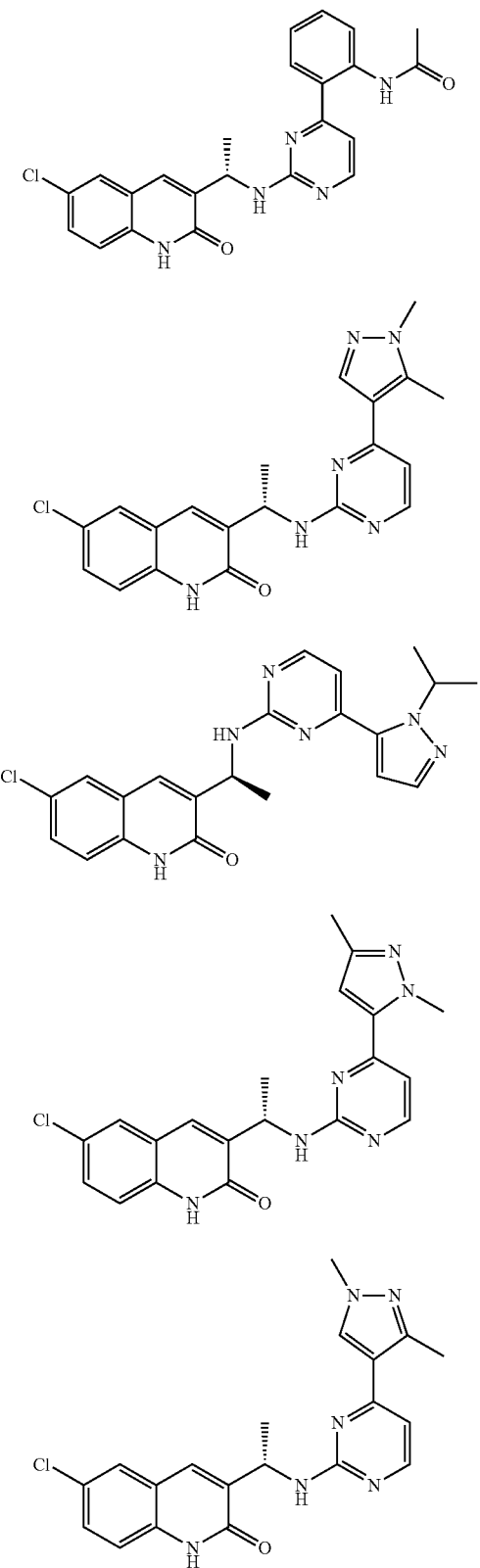
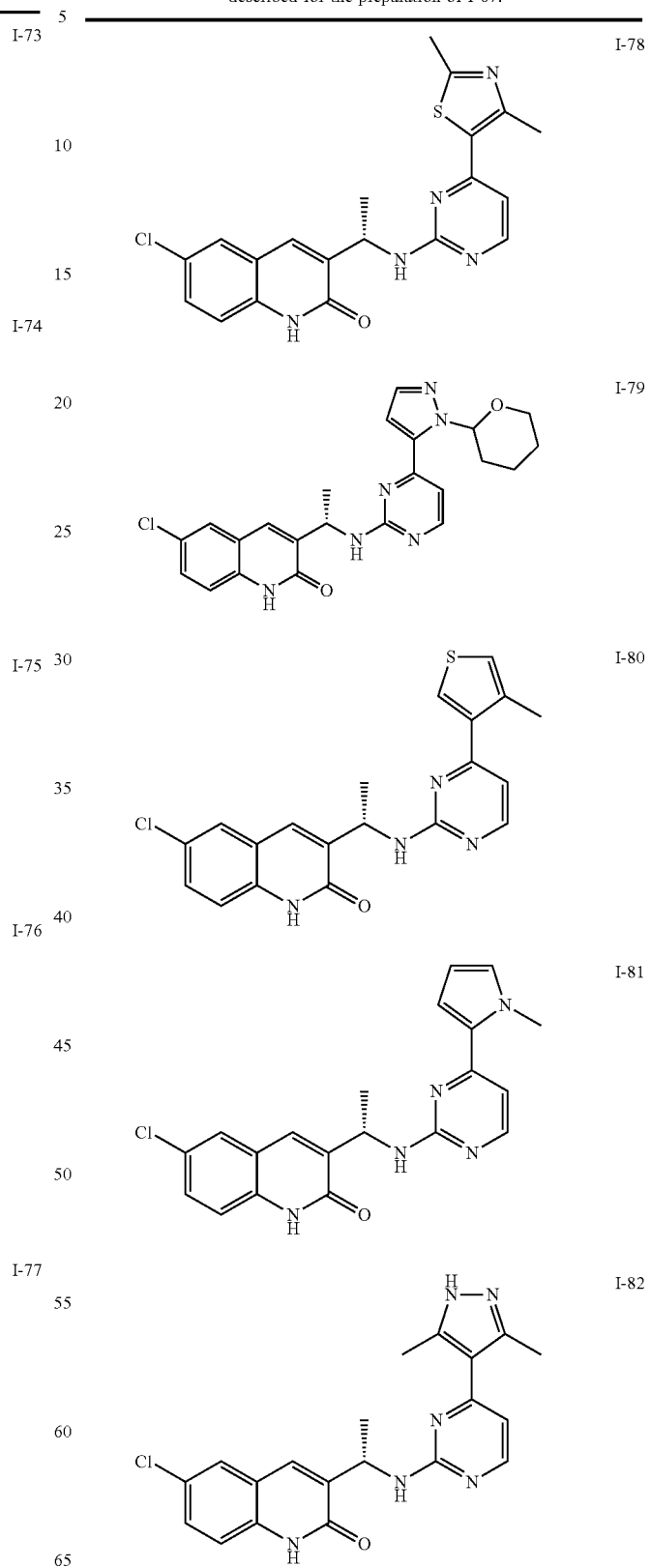

TABLE 11-continued
The compounds listed in Table 11 were prepared using the same method described for the preparation of I-67.
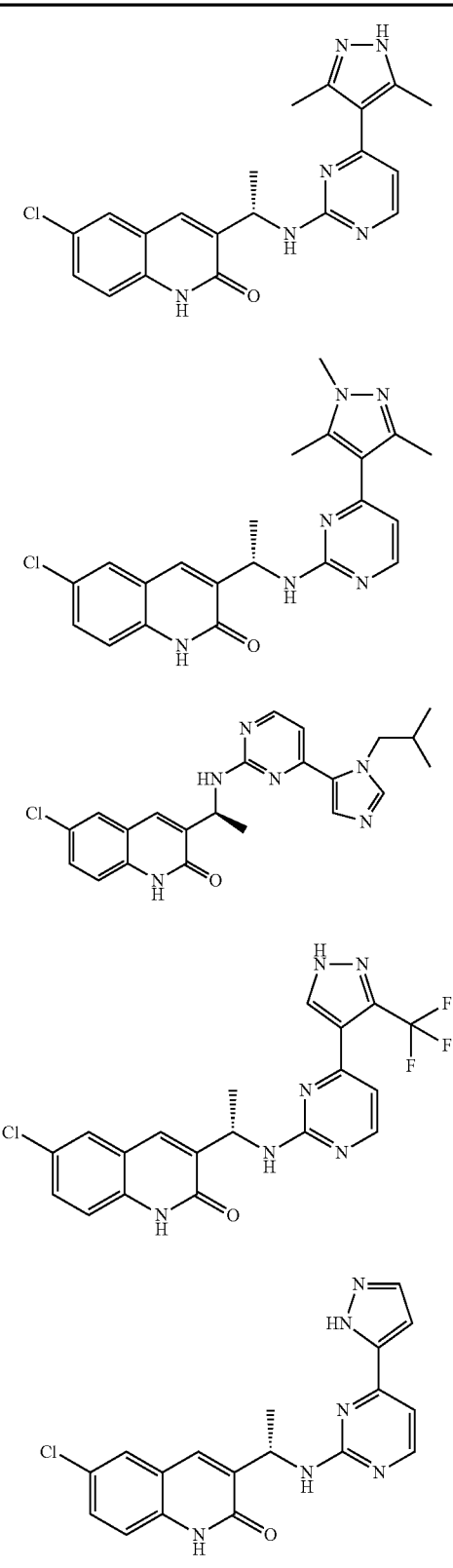
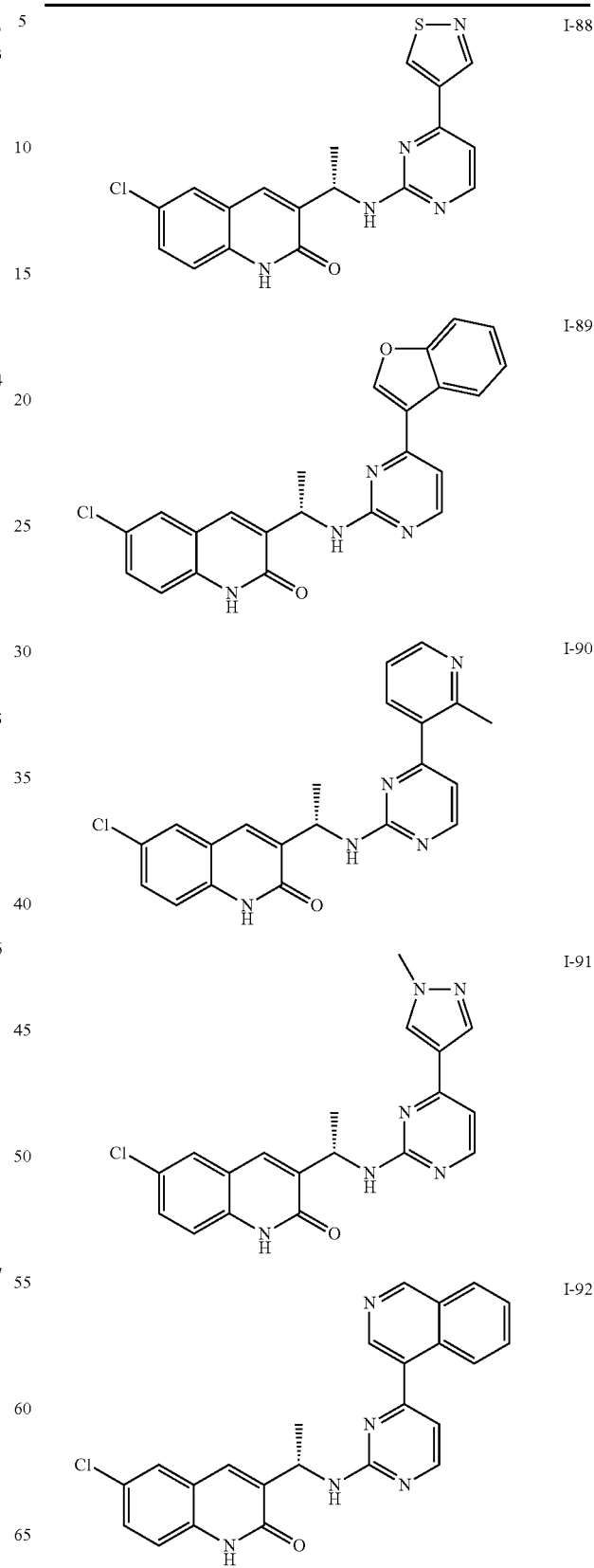

TABLE 11-continued
The compounds listed in Table 11 were prepared using the same method described for the preparation of I-67.
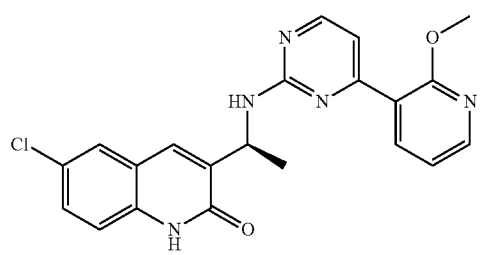 [SMILES: COc1ncccc1-c1ccnc(N[C@@H](C)c2cc3cc(Cl)ccc3[nH]c2=O)n1]
I-93
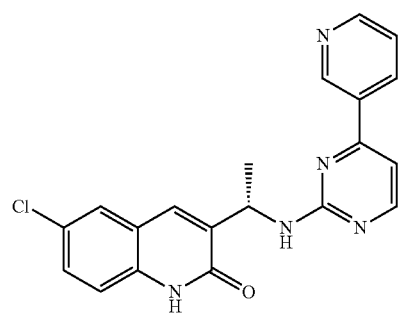 [SMILES: C[C@H](Nc1nccc(-c2cccnc2)n1)c1cc2cc(Cl)ccc2[nH]c1=O]
I-94
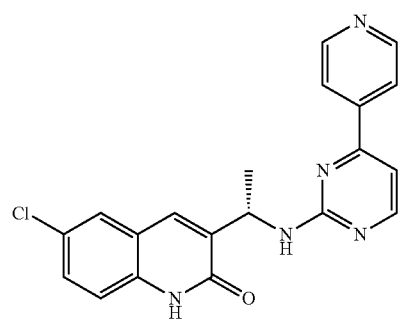 [SMILES: C[C@H](Nc1nccc(-c2ccncc2)n1)c1cc2cc(Cl)ccc2[nH]c1=O]
I-95
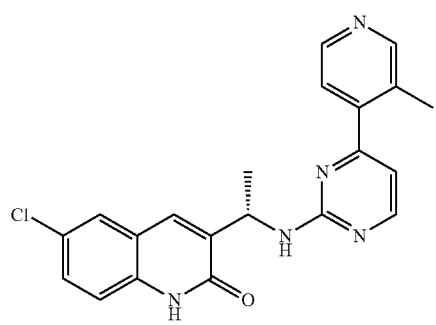 [SMILES: Cc1cnccc1-c1ccnc(N[C@@H](C)c2cc3cc(Cl)ccc3[nH]c2=O)n1]
I-96
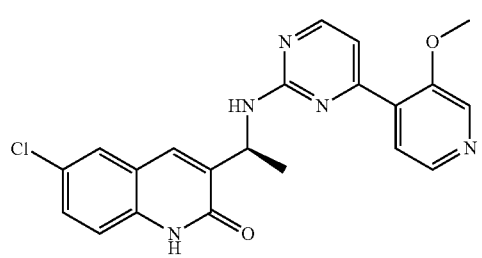 [SMILES: COc1cnccc1-c1ccnc(N[C@@H](C)c2cc3cc(Cl)ccc3[nH]c2=O)n1]
I-97
TABLE 11-continued
The compounds listed in Table 11 were prepared using the same method described for the preparation of I-67.
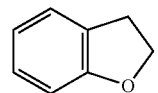
I-98
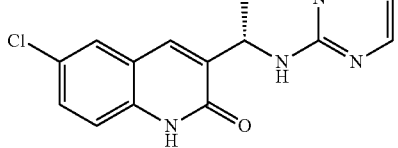
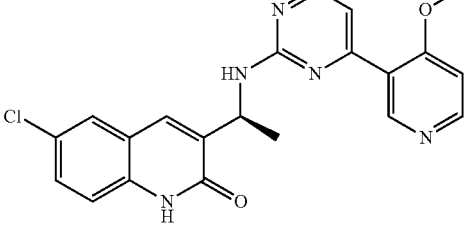
I-99
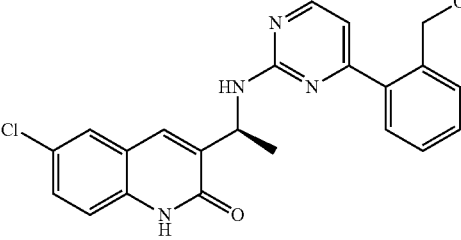
I-100
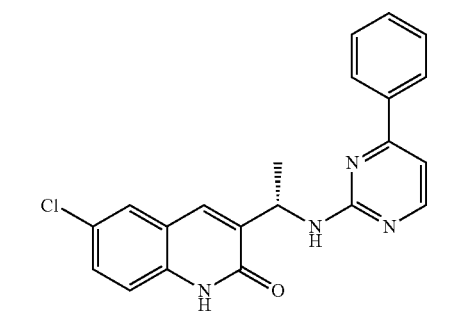 [SMILES: C[C@H](Nc1nccc(-c2ccccc2)n1)c1cc2cc(Cl)ccc2[nH]c1=O]
I-101
I-102

TABLE 11-continued

The compounds listed in Table 11 were prepared using the same method described for the preparation of I-67.

I-103

TABLE 12

LCMS signal and NMR chemical shifts for each compounds listed in Table 11.

| Cmpds No | LCMS<sup>a</sup> | ¹H NMR (300 MHz) δ ppm |
|---|---|---|
| I-51 | m/z: 380.04 [M + H]⁺ Rt (min): 1.46 | ¹H NMR (300 MHz, DMSO-d₆): δ ppm 11.97 (s, 1 H), 8.29 (s, 1 H), 7.89-7.68 (m, 3 H), 7.46 (dd, J = 8.8, 2.2 Hz, 1 H), 7.28 (d, J = 8.8 Hz, 1 H), 7.24 (s, 1 H), 6.72 (d, J = 5.5 Hz, 1 H), 6.07 (br s, 1 H), 5.92 (br s, 1 H), 5.14 (br s, 1 H), 2.24 (s, 3 H), 1.41 (d, J = 6.9 Hz, 3 H). |
| I-52 | m/z: 366.08 [M + H]⁺ Rt (min): 1.41 | ¹H NMR (300 MHz, CDCl₃): δ ppm 11.26 (br s, 1 H), 8.22 (d, J = 5.5 Hz, 1 H), 7.71 (s, 1 H), 7.49 (d, J = 2.2 Hz, 1 H), 7.45 (t, J = 2.2 Hz, 2 H), 7.40 (dd, J = 8.8 Hz, 2.1 Hz, 1 H), 7.18 (d, J = 8.5 Hz, 1 H), 6.50 (d, J = 5.5 Hz, 1 H), 6.26 (br s, 2 H), 6.14 (d, J = 8.0 Hz, 1 H), 5.42 (m, 1 H), 1.65 (d, J = 6.9 Hz, 3 H). |
| I-53 | m/z: 395.06 [M + H]⁺ Rt (min): 0.95 | ¹H NMR (300 MHz, DMSO-d₆): δ ppm 11.97 (s, 1 H), 8.24-8.40 (m, 1 H), 7.93-8.20 (m, 2 H), 7.73 (d, J = 2.64 Hz, 2 H), 7.45 (dd, J = 8.79, 2.35 Hz, 1 H), 7.27 (d, J = 8.79 Hz, 1 H), 6.79 (d, J = 5.57 Hz, 1 H), 5.02-5.25 (m, 1 H), 1.92-2.21 (m, 6 H), 1.40 (d, J = 6.74 Hz, 3 H). |
| I-54 | m/z: 367.11 [M + H]⁺ Rt (min): 0.97 | ¹H NMR (300 MHz, DMSO-d₆): δ ppm 12.02 (br s, 1 H), 8.24-8.68 (m, 2 H), 7.61-8.24 (m, 4 H), 7.20-7.61 (m, 2 H), 6.88-7.20 (m, 2 H), 5.21 (br s, 1 H), 1.04-1.54 (m, 3 H). |
| I-55 | m/z: 407.08 [M + H]⁺ Rt (min): 1.03 | ¹H NMR (300 MHz, DMSO-d₆): δ ppm 12.04 (br s, 1 H), 8.17-8.41 (m, 2 H), 7.93-8.03 (m, J = 15.39 Hz, 1 H), 7.62-7.78 (m, 2 H), 7.45 (dd, J = 8.79, 2.35 Hz, 1 H), 7.26 (d, J = 8.79 Hz, 1 H), 6.78 (d, J = 4.98 Hz, 1 H), 5.03-5.25 (m, 1 H), 2.80-3.10 (m, 2 H), 2.53-2.73 (m, 2 H), 2.20-2.39 (m, 2 H), 1.34-1.47 (m, 3 H). |
| I-56 | m/z: 381.00 [M + H]⁺ Rt (min): 0.9 | ¹H NMR (300 MHz, DMSO-d₆): δ ppm 11.94-12.10 (m, 1 H), 8.25-8.45 (m, 1 H), 7.82-8.13 (m, 1 H), 7.66-7.78 (m, 2 H), 7.51-7.66 (m, 1 H), 7.42 (dd, J = 8.79, 2.05 Hz, 1 H), 7.26 (d, J = 8.79 Hz, 1 H), 6.69-6.96 (m, 2 H), 5.05-5.27 (m, 1 H), 2.30-2.75 (m, 3 H), 1.36-1.47 (m, 3 H) |
| I-57 | m/z: 381.03 [M + H]⁺ Rt (min): 0.95 | ¹H NMR (300 MHz, CDCl₃): δ ppm 10.00 (br s, 1 H), 8.47 (br s, 1 H), 7.80 (br s, 1 H), 7.62 (br s, 1 H), 7.47 (s, 1 H), 7.33 (br s, 3 H), 7.04 (br s, 1 H), 5.44 (br s, 1 H), 2.40 (s, 3 H), 1.57 (br d, J = 5.86 Hz, 3 H). |
| I-58 | m/z: 382.03 [M + H]⁺ Rt (min): 1.19 | ¹H NMR (300 MHz, DMSO-d₆): δ ppm 11.82 (br s, 1 H), 9.02 (s, 1 H), 8.05 (s, 1 H), 7.80 (s, 1 H), 7.76 (s, 1 H), 7.48 (d, J = 9.06 Hz, 1 H), 7.33 (d, J = 9.06 Hz, 1 H), 6.25 (s, 1 H), 5.18 (m, 1 H), 2.24 (s, 3 H), 1.48 (d, J = 6.33 Hz, 3 H). |
| I-59 | m/z: 383.07 [M + H]⁺ Rt (min): 1.17 | ¹H NMR (300 MHz, DMSO-d₆): δ ppm 12.03 (br s, 1 H), 8.58 (s 1 H), 8.41 (s, 1 H), 7.74 (s, 1 H), 7.45 (d, J = 8.5 Hz, 1 H), 7.25 (d, J = 8.51 Hz, 1 H), 7.11 (d, J = 5.28 Hz, 1 H), 5.20 (m, 1 H), 3.13 (s, 3 H) 1.42 (d, J = 6.44 Hz, 3 H). |
| I-60 | m/z: 449.07 [M + H]⁺ Rt (min): 1.17 | ¹H NMR (300 MHz, DMSO-d₆, 80° C. (v. broad signals at RT): δ ppm 11.8 (br s, 1 H), 8.26 (m, 1 H), 7.90 (m, 1 H), 7.78 (m, 1 H), 7.6-7.7 (m, 2 H), 7.4-7.5 (m, 2 H), 7.25-7.35 (m, 1 H), 6.88-6.96 (m, 1 H), 5.5-5.7 (m, 2 H), 5.23 (m, 1 H), 1.48 (m, 3 H). |
| I-61 | m/z: 421. 11 [M + H]⁺ Rt (min): 0.98 | ¹H NMR (300 MHz, DMSO-d₆, 80° C.): δ ppm 11.74 (br s, 1 H), 8.23 (d, J = 5.22 Hz, 1 H), 7.78 (d, J = 3.27 Hz, 1 H), 7.66 (d, J = 2.46 Hz, 1 H), 7.58 (s, 1 H), 7.45 (dd, J = 8.79, 2.46 Hz, 1 H), 7.24-7.35 (m, 2 H), 6.89 (d, J = 5.22 Hz, 1 H), 5.26 (quintet, 1 H), 4.23-4.36 (m, 2 H), 1.47 (d, J = 6.87 Hz, 3 H), 1.06 (m, 1 H), 0.20-0.35 (m, 4 H). |
| I-62 | m/z: 379.13 [M + H]⁺ Rt (min): 1.09 | ¹H NMR (300 MHz, DMSO-d₆): δ ppm 11.99 (br s, 1 H), 9.18-9.49 (m, 3 H), 8.42 (br s, 1 H), 7.92 (br s, 1 H), 7.65-7.84 (m, 2 H), 7.44 (dd, J = 8.79, 2.05 Hz, 1 H), 7.22-7.35 (m, 2 H), 5.31 (br s, 1 H), 1.42 (d, J = 7.04 Hz, 3 H). |
| I-63 | m/z: 417.03 [M + H]⁺ Rt (min): 1 | ¹H NMR (300 MHz, DMSO-d₆, at 90° C.): δ ppm 11.74 (br s, 1 H), 9.87 (d, J = 8.2 Hz, 1 H), 8.40 (s, 1 H), 8.26 (d, J = 5.5 Hz, 1 H), 7.83 (s, 1 H), 7.76-7.62 (m, 2 H), 7.50-7.28 (m, 4 H), 7.18-7.00 (m, 2 H), 5.40-5.26 (m, 1 H), 1.52 (d, J = 6.8 Hz, 3 H). |
| I-64 | m/z: 409.08 [M + H]⁺ Rt (min): 0.94 | ¹H NMR (300 MHz, DMSO-d₆): δ ppm 8.23 (d, J = 6.57 Hz, 1 H), 7.90 (s, 1 H), 7.81 (s, 1 H), 7.59 (d, J = 3.33 Hz, 1 H), 7.56 (s, 1 H), 7.21 (dd, J = 8.46, 3.33 Hz, 1 H), 7.31 (d, J = 8.46 Hz, 1 H), 6.91 (d, J = 4.32 Hz, 1 H), 5.50 (br s, 1 H), 5.22 (m, 1 H), 1.55 (d, J = 6.87 Hz, 3 H), 1.48 (d, J = 6.87 Hz, 3 H), 1.01 (m, 3 H). |
| I-65 | m/z: 299.11 [M + H]⁺ Rt (min): 1.44 | ¹H-NMR(300 MHz, DMSO-d₆, at 90° C.): δ ppm 11.68 (br s, 1 H), 8.40 (d, J = 5.22 Hz, 1 H), 7.78 (br s, 1 H), 7.66 (d, J = 2.19 Hz, 1 H), 7.55 (m, 1 H), 7.43 (dd, J = 2.19, 8.79 Hz, 2 H), 7.31 (d, J = 8.79 Hz, 1 H), 6.88 (m, 1 H), 6.74 (d, J = 5.49 Hz, 1 H), 6.36 (m, 1 H), 5.27 (m, 1 H), 1.47 (d, J = 6.87 Hz, 1 H). |
| I-66 | m/z: 382.13 [M + H]⁺ Rt (min): 1.61 | ¹H NMR (300 MHz, DMSO-d₆): δ ppm 12.01 (br s, 1 H), 8.45 (br d, J = 4.40 Hz, 1 H), 7.80 (br s, 3 H), 7.71 (d, J = 2.35 Hz, 1 H), 7.46 (dd, J = 8.79, 2.35 Hz, 1 H), 7.03 (d, J = 4.98 Hz, 1 H), 5.28 (br s, 1 H), 4.10 (q, J = 5.28 Hz, 1 H), 1.41 (d, J = 6.74 Hz, 3 H). |

TABLE 12-continued

LCMS signal and NMR chemical shifts for each compounds listed in Table 11.

| Cmpds No | LCMS[a] | ¹H NMR (300 MHz) δ ppm |
|---|---|---|
| I-67 | m/z: 381.04 [M + H]⁺ Rt (min): 1.17 | |
| I-68 | m/z: 457.14 [M + H]⁺ Rt (min): 1.12 | |
| I-69 | m/z: 396.02 [M + H]⁺ Rt (min): 1.3 | |
| I-70 | m/z: 368.01 [M + H]⁺ Rt (min): 1.01 | |
| I-71 | m/z: 381.12 [M + H]⁺ Rt (min): 0.93 | |
| I-72 | m/z: 419.12 [M + H]⁺ Rt (min): 1.49 | |
| I-73 | m/z: 434.10 [M + H]⁺ Rt (min): 1.42 | |
| I-74 | m/z: 395.01 [M + H]⁺ Rt (min): 1 | |
| I-75 | m/z: 409.07 [M + H]⁺ Rt (min): 1.32 | |
| I-76 | m/z: 395.06 [M + H]⁺ Rt (min): 1.24 | |
| I-77 | m/z: 395.04 [M + H]⁺ Rt (min): 0.99 | |
| I-78 | m/z: 412.02 [M + H]⁺ Rt (min): 1.26 | |
| I-79 | m/z: 451.05 [M + H]⁺ Rt (min): 1.33 | |
| I-80 | m/z: 397.00 [M + H]⁺ Rt (min): 1.49 | |
| I-81 | m/z: 380.04 [M + H]⁺ Rt (min): 1.16 | |
| I-82 | m/z: 395.06 [M + H]⁺ Rt (min): 0.95 | |
| I-83 | m/z: 381.05 [M + H]⁺ Rt (min): 0.91 | |
| I-84 | m/z: 409.08 [M + H]⁺ Rt (min): 1.04 | |
| I-85 | m/z: 423.09 [M + H]⁺ Rt (min): 1.44 | |
| I-86 | m/z: 435.03 [M + H]⁺ Rt (min): 1.24 | |
| I-87 | m/z: 367.12 [M + H]⁺ Rt (min): 1.06 | |
| I-88 | m/z: 384.05 [M + H]⁺ Rt (min): 1.26 | |
| I-89 | m/z: 417.09 [M + H]⁺ Rt (min): 1.55 | |
| I-90 | m/z: 392.07 [M + H]⁺ Rt (min): 1 | |
| I-91 | m/z: 381.02 [M + H]⁺ Rt (min): 1.02 | |
| I-92 | m/z: 428.06 [M + H]⁺ Rt (min): 1.29 | |
| I-93 | m/z: 408.06 [M + H]⁺ Rt (min): 1.43 | |
| I-94 | m/z: 378.03 [M + H]⁺ Rt (min): 1.13 | |
| I-95 | m/z: 378.03 [M + H]⁺ Rt (min): 1.08 | |
| I-96 | m/z: 392.18 [M + H]⁺ Rt (min): 1.1 | |
| I-97 | m/z: 408.18 [M + H]⁺ Rt (min): 1.19 | |
| I-98 | m/z: 419.19 [M + H]⁺ Rt (min): 1.55 | |
| I-99 | m/z: 408.18 [M + H]⁺ Rt (min): 0.97 | |
| I-100 | m/z: 421.07 [M + H]⁺ Rt (min): 1.49 | |
| I-101 | m/z: 377.06 [M + H]⁺ Rt (min): 1.52 | |
| I-102 | m/z: 407.08 [M + H]⁺ Rt (min): 1.5 | |

TABLE 12-continued

LCMS signal and NMR chemical shifts for each compounds listed in Table 11.

| Cmpds No | LCMS[a] | $^1$H NMR (300 MHz) δ ppm |
|---|---|---|
| I-103 | m/z: 392.85 [M + H]$^+$ Rt (min): 1.58 | $^1$H NMR (300 MHz, CDCl$_3$): δ ppm 12.02 (br s, 1 H), 8.17 (s, 1 H), 7.67 (s, 1 H), 7.51 (s, 1 H), 7.44 (d, J = 6.45 Hz, 1 H), 7.31 (d, J = 9 Hz, 1 H), 6.08 (d, J = 8.21 Hz, 1 H), 5.28 (m, 1 H), 2.404 (s, 3 H), 1.62(d, J = 6.74 Hz, 3 H). |

[a]LCMS (method 4)

Example 67—6-chloro-3-((S)-1-(4-((S)-3-isopropyl-morpholino)pyrimidin-2-ylamino)ethyl) quinolin-2(1H)-one (I-104)

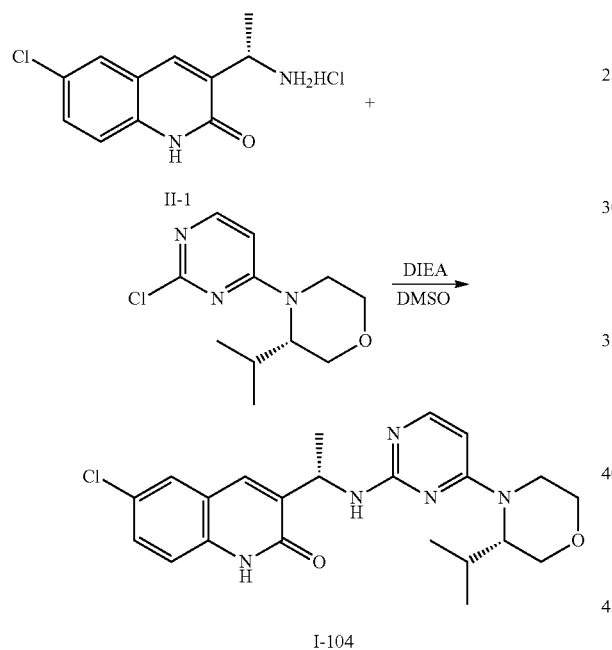

I-104

A mixture of (S)-4-(2-chloropyrimidin-4-yl)-3-isopropylmorpholine (70.0 mg, 0.289 mmol) and (S)-3-(1-aminoethyl)-6-chloroquinolin-2(1H)-one hydrochloride II-1 (50 mg, 0.193 mmol) was treated with DMSO (1 ml) and DIEA (74.8 mg, 0.101 ml, 0.579 mmol) and the resulting solution was stirred at 110° C. for 12 hours. LC-MS indicated most of the starting material was consumed. The mixture was then cooled to RT and stirred for 2 days. Water was added and the reaction mixture was extracted with EtOAc The combined extracts were dried (Na$_2$SO$_4$), filtered, and evaporated under reduced pressure. The crude material was purified by silica gel chromatography on a Biotage® chromatography system to afford 6-chloro-3-((S)-1-(4-((S)-3-isopropylmorpholino) pyrimidin-2-ylamino) ethyl)quinolin-2(1H)-one (17.1 mg, 20.7% yield). $^1$H NMR (300 MHz, CDCl$_3$): δ ppm 10.50 (br s, 1H), 7.81 (d, J 6.158 Hz, 1H), 7.68 (s, 1H), 7.48 (s, 1H), 7.40 (d, J 8.79 Hz, 1H), 7.16 (d, J 8.51 Hz, 1H), 5.80 (br, 1H), 5.77 (d, J 6.45 Hz, 1H), 5.27 (m, 1H), 3.92 (d, J 12.31 Hz, 2H), 3.79 (d, J 8.5 Hz, 2H), 3.30-3.40 (m, 2H), 3.02-3.20 (m, 1H), 1.50-1.65 (m, 1H), 1.54 (d, J=7.04, 3H). 1.25 (br s, 3H), 0.95 (br s, 3H).

Example 68—(S)-6-Chloro-3-(1-((4-(methylsulfonyl)pyrimidin-2-yl)amino)ethyl)quinolin-2(1H)-one (I-105)

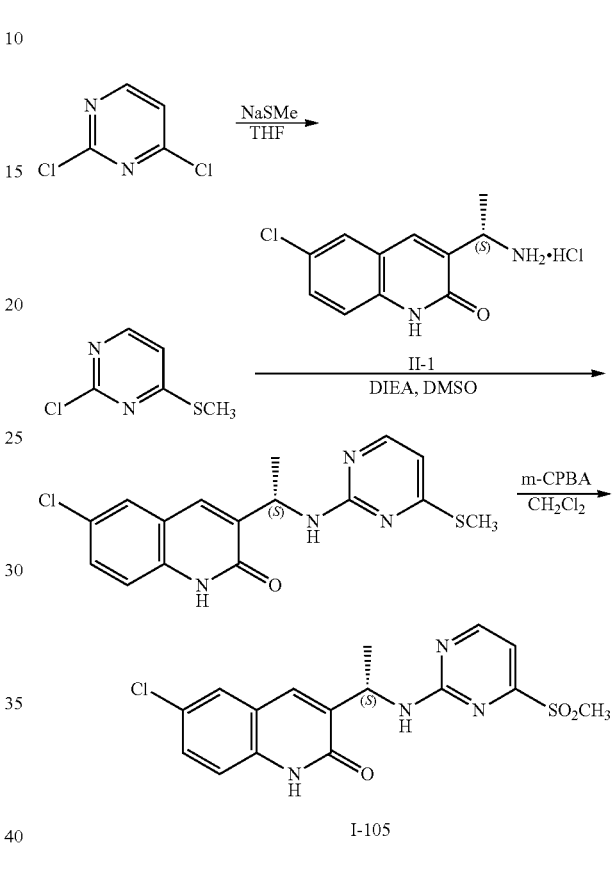

I-105

Step-1: 2-Chloro-4-(methylthio)pyrimidine

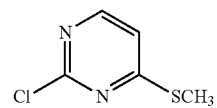

To a solution of 2,4-dichloropyrimidine (1 g, 6.71 mmol) in THF (12 mL) was added sodium thiomethoxide (565 mg, 8.05 mmol) and the resulting suspension was stirred at ambient temperature overnight. After TLC and MS showed completion of reaction, the mixture was quenched with water, extracted with EtOAc (2×25 mL), dried over anhydrous Na$_2$SO$_4$, filtered and evaporated to dryness. The resulting residue was purified by column chromatography on an ISCO® chromatography system (SiO$_2$ column: hexanes/EtOAc 0 to 20% gradient elution) to afford the title compound as yellow solid (348 g, 33% yield).

Step-2: (S)-6-Chloro-3-(1-((4-(methylthio)pyrimidin-2-yl)amino)ethyl)quinolin-2(1H)-one

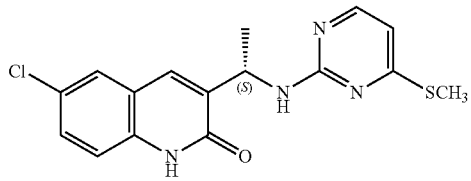

A mixture of (S)-3-(1-aminoethyl)-6-chloroquinolin-2 (1H)-one hydrochloride II-1 (1.0 g, 3.85 mmol), 2-chloro-4-(methylthio)pyrimidine (1.24 g, 7.71 mmol) and DIEA (1.32 mL, 7.71 mmol) in DMSO (10 mL) was heated at 130° C. for 1.5 hours. After TLC and MS showed completion of reaction, the mixture was cooled to room temperature and poured onto crushed ice. The mixture was then extracted with EtOAc (3×25 mL), dried over anhydrous Na$_2$SO$_4$, filtered and evaporated to dryness. The resulting residue was purified by column chromatography on an ISCO® chromatography system (SiO$_2$ column: hexanes/EtOAc 0 to 100% gradient elution) to obtain the title compound (770 mg, 58% yield).

Step-3: (S)-6-Chloro-3-(1-((4-(methylsulfonyl)pyrimidin-2-yl)amino)ethyl)quinolin-2(1)-one (I-105)

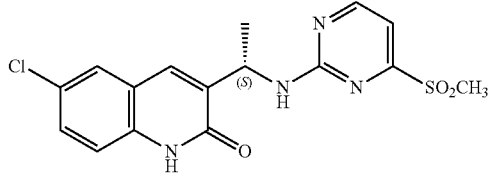

To a mixture of (S)-6-chloro-3-(1-((4-(methylthio)pyrimidin-2-yl)amino)ethyl)quinolin-2(1H)-one 3 (768 mg, 2.21 mmol) in CH$_2$Cl$_2$ (40 mL) at 0° C. was added m-CPBA (~75%, 1.12 g, 4.87 mmol). The ice bath was removed and the mixture was then stirred at room temperature for 2.5 hours. After TLC and MS showed completion of reaction, the mixture was filtered and rinsed with CH$_2$Cl$_2$ (10 mL). The organic layer was washed with saturated NaHCO$_3$ (10 mL) and 10% NaHSO$_3$ (10 mL), dried over anhydrous Na$_2$SO$_4$, filtered and evaporated to dryness. The resulting residue was purified by column chromatography on an ISCO® chromatography system (SiO$_2$ column: hexanes/EtOAc 0 to 100% gradient elution) to afford I-105 as white solid (460 mg, 55% yield). $^1$H NMR (300 MHz, DMSO-d$_6$): δ ppm 11.99 (br s, 1H), 8.65-8.45 (br m, 2H), 7.75 (m, 2H), 7.49 (d, J=8.8 Hz, 1H), 7.30 (d, J=8.8 Hz, 1H), 7.05 (m, 1H), 5.22-5.19 (m, 1H), 3.28 (d, 3H), 1.43 (d, J=6.9 Hz, 3H). LCMS (method 3): Rt 5.92 min, m/z 379 [M+H]$^+$.

Example 69—(S)-2-((1-(6-chloro-2-oxo-1,2-dihydroquinolin-3-yl)ethyl)amino)pyrimidine-4-carboxamide (I-114)

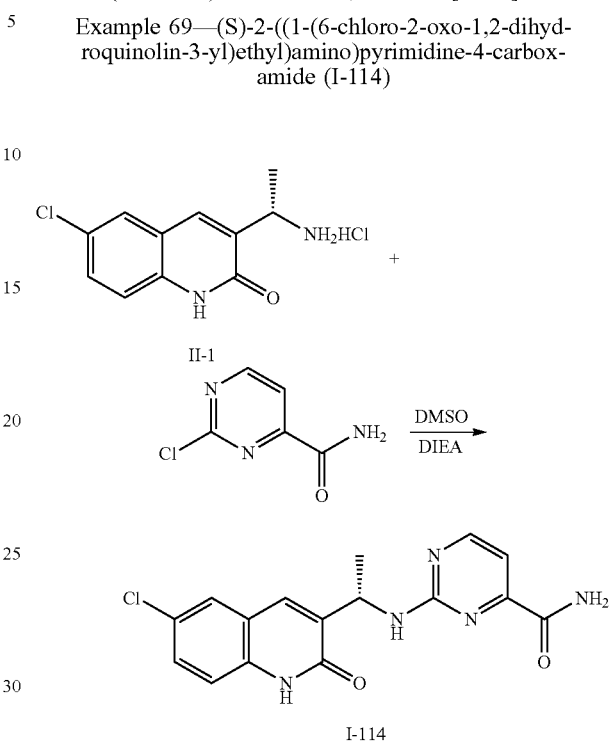

A mixture of DIEA (0.111 ml, 0.635 mmol), (S)-3-(1-aminoethyl)-6-chloroquinolin-2(1H)-one II-1 (70.7 mg, 0.317 mmol), and 2-chloropyrimidine-4-carboxamide (50 mg, 0.317 mmol) in DMSO (2 ml) was heated to 110° C. for overnight, added EtOAc, washed with water, dried and concentrated. The biotage purification with 0-5% MeOH/DCM on a 25 g column afforded (S)-2-((1-(6-chloro-2-oxo-1,2-dihydroquinolin-3-yl)ethyl)amino)pyrimidine-4-carboxamide I-114 (49 mg, 44.9%). 1H NMR (300 MHz, DMSO-d6): δ 11.02 (br s, 1H), 8.45 (d, J=4.7 Hz, 1H), 8.00 (br, 1H), 7.79 (br, 2H), 7.72 (s, 1H), 7.47 (d, J=8.79 Hz, 1H), 7.28 (d, J=8.8 Hz, 1H), 7.02 (d, J=4.69 Hz, 1H), 5.29 (m, 1H), 1.41 (d, J=7.04 Hz, 3H).

Example 70—(S)-6-chloro-3-(1-((4-((1,1-dioxidoisothiazolidin-2-yl)methyl)pyrimidin-2-yl)amino)ethyl) quinolin-2(1H)-one (I-119)

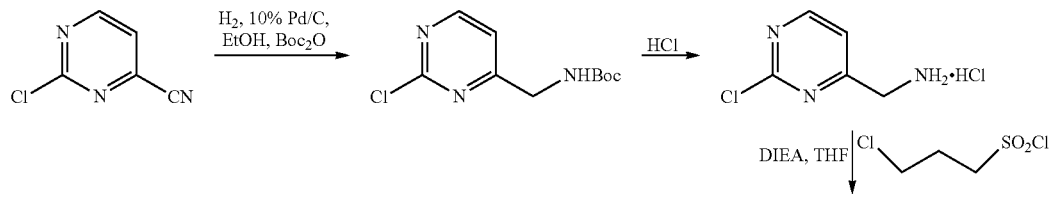

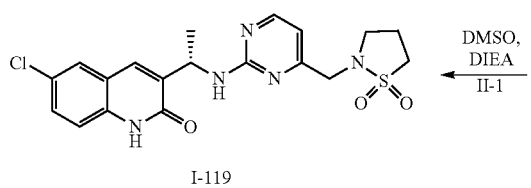 

I-119

Step-1: tert-Butyl ((2-chloropyrimidin-4-yl)methyl)carbamate

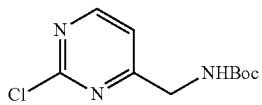 [SMILES: CC(C)(C)OC(=O)NCc1ccnc(Cl)n1]

A mixture of 2-chloropyrimidin-4-carbonitrile (1.00 g, 7.1 mmol, 1 equivalent), Boc$_2$O (2.92 g, 13.4 mmol, 1.9 equivalents) and 180 mg 10% Pd/C in 100 mL EtOH was stirred under an atmosphere of hydrogen for 2 hours at 1 atmosphere. The catalyst was filtered off, and the filtrate was purified by column chromatography on 60 g of silica gel (eluted with hexane/EtOAc, 7/3) to provide 0.52 g of the title compound (30% yield) as a waxy yellow solid.

Step-2: (2-Chloropyrimidin-4-yl)methanamine hydrochloride

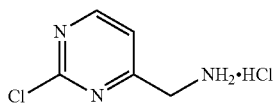

To a solution of tert-butyl ((2-chloropyrimidin-4-yl)methyl)carbamate (0.52 g, 2.4 mmol, 1 equivalent) in 6 mL THF was added 3 mL 4N HCl in 1,4-dioxane (12 mmol, 5 equivalents). After stirring overnight at room temperature, ether was added and a solid precipitated from solution. The solid obtained was filtered and rinsed with ethyl ether to afford 0.30 g (100%) of the title compound as the hydrochloride salt.

Step-3: 3-Chloro-N-((2-chloropyrimidin-4-yl)methyl)propane-1-sulfonamide

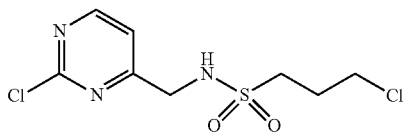 [SMILES: O=S(=O)(CCCCl)NCc1ccnc(Cl)n1]

A suspension of (2-chloropyrimidin-4-yl)methanamine hydrochloride (300 mg, 2.1 mmol, 1 equivalent) in 10 mL DCM was cooled to 0° C. and treated with DIEA (570 mg, 4.4 mmol, 2.1 equivalents) followed by 3-chloro-propane sulfonyl chloride (437 mg, 2.5 mmol, 1.2 equivalents). After stirring for 60 minutes at room temperature, the reaction was poured into water and extracted with EtOAc. The extract was washed with brine, dried over Na$_2$SO$_4$ and purified by column chromatography on 15 g of silica gel (eluted with DCM/1% EtOH) to provide the title compound (258 mg, 43% yield) as a dark gold resin.

Step-4: 2-((2-Chloropyrimidin-4-yl)methyl)isothiazolidine 1,1-dioxide

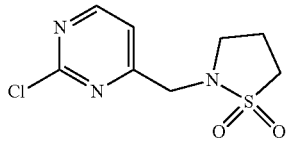 [SMILES: O=S1(=O)CCCN1Cc1ccnc(Cl)n1]

A solution of 3-chloro-N-((2-chloropyrimidin-4-yl)methyl)propane-1-sulfonamide (210 mg, 0.74 mmol, 1 equivalent) in 6.5 mL DMF was cooled to 0° C., treated with NaH (60 wt % in oil, 41 mg, 1.02 mmol, 1.35 equivalents) and stirred at room temperature overnight. After quenching with water, brine was added, and the reaction mixture was extracted with EtOAc (×2). After drying over Na$_2$SO$_4$, the extract was purified by column chromatography on 4 g of silica gel (eluted with hexane/EtOAc, 75/25) to provide the title compound (56 mg, 43% yield) as a gold resin.

Step-5: (S)-6-Chloro-3-(1-((4-((1,1-dioxidoisothiazolidin-2-yl)methyl)pyrimidin-2-yl)amino)ethyl)quinolin-2(1H)-one (I-119)

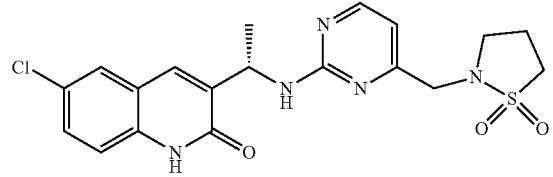 [SMILES: C[C@H](Nc1nccc(CN2CCCS2(=O)=O)n1)c1cc2cc(Cl)ccc2[nH]c1=O]

A mixture of 2-((2-chloropyrimidin-4-yl)methyl)isothiazolidine 1,1-dioxide (56 mg, 0.23 mmol, 1 equivalent), (S)-3-(1-aminoethyl)-6-chloroquinolin-2(1H)-one hydrochloride II-1 (60 mg, 0.23 mmol, 1 equivalent) and DIEA (74 mg, 0.58 mmol, 2.5 equivalents) in 0.5 mL of DMSO was heated in a sealed tube to 130° C. for 90 minutes. The reaction was then poured into water and extracted with EtOAc (×2). After drying over Na$_2$SO$_4$, the extract was purified by column chromatography on 4 g of silica gel (eluted with EtOAc/EtOH, 98/2), and the purest fractions obtained were triturated with EtOAc/Et$_2$O (1/1) to provide I-119 (14 mg, 14% yield) as an off-white solid. $^1$H-NMR (300 MHz, CDCl$_3$): δ ppm 11.35 (br s, 1H), 8.23 (d, J 4.95 Hz, 1H), 7.69 (s, 1H), 7.51 (d, J 2.19 Hz, 1H), 7.40 (dd, J 2.22, 8.79 Hz, 1H), 7.23 (m, 1H) 6.64 (d, J 4.95 Hz, 1H), 6.05 (br d, J 7.95 Hz, 1H), 5.30 (m, 1H), 4.05 (s, 2H), 3.22 (t, 2H), 3.13 (t, 2H), 2.28 (m, 2H), 1.61 (d, J 6.87 Hz, 3H). LCMS (Method 3): Rt 8.5 min., m/z 434 [M+H]$^+$.

Example 71—(S)-6-Chloro-3-(1-(4-(isobutylsulfonylmethyl)pyrimidin-2-ylamino)ethyl)quinolin-2(1H)-one (I-121)

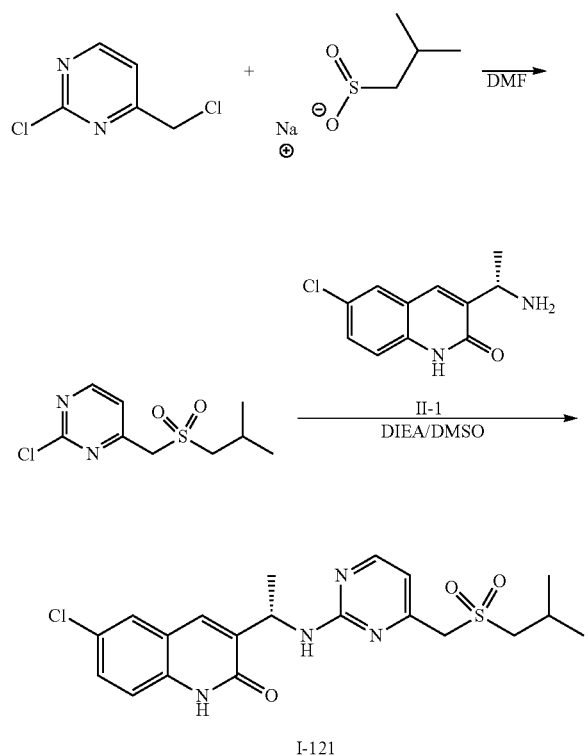

Step-1: 2-Chloro-4-((isobutylsulfonyl)methyl)pyrimidine

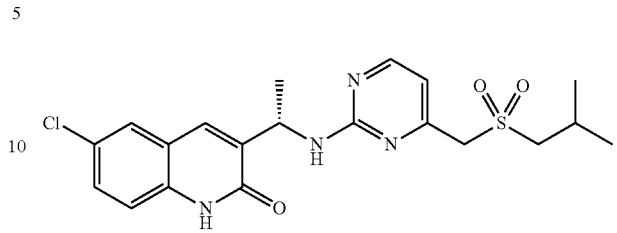

Sodium 2-methylpropane-1-sulfinate (0.265 g, 1.840 mmol) was added in one portion to a solution of 2-chloro-4-(chloromethyl)pyrimidine (0.25 g, 1.534 mmol) in DMF (4 mL). The reaction mixture was stirred at room temperature for 16 hours. Water (30 mL) was then added to the reaction mixture and the aqueous phase was extracted with EtOAc (3×30 mL). The combined organic extracts were dried over MgSO$_4$ and the volatiles were removed under reduced pressure. The crude material was purified by column chromatography on SiO$_2$ (25 g SNAP® column, 0% EtOAc/hexanes for 5 minutes, 0-30% EtOAc/hexanes for 30 minutes, and 30-50% EtOAc/hexanes for 5 minutes) to afford 2-Chloro-4-(isobutylsulfonylmethyl) pyrimidine (0.268 g, 1.077 mmol, 70.3% yield).

Step-2: (S)-6-Chloro-3-(1-((4-((isobutylsulfonyl)methyl)pyrimidin-2-yl)amino)ethyl) quinolin-2(1H)-one A solution of (S)-3-(1-aminoethyl)-6-chloroquinolin-2(1H)-one hydrochloride II-1 (0.1 g, 0.386 mmol), 2-chloro-4-(isobutylsulfonylmethyl)pyrimidine (0.096 g, 0.386 mmol) and DIEA (0.404 mL, 2.315 mmol) in DMSO (2.76 mL) was heated to 120° C. for 16 hours. Water (20 mL) was added to the reaction mixture, and the aqueous phase was extracted with EtOAc (3×30 mL). The combined organic extracts were dried over MgSO$_4$, and the volatiles were removed under reduced pressure. The crude material was purified by column chromatography on SiO$_2$ (10 g SNAP® column, 0% MeOH/DCM for 5 minutes, 0-15% MeOH/DCM for 30 minutes, and 15% MeOH/DCM for 10 minutes) to afford (S)-6-chloro-3-(1-(4-(isobutylsulfonyl methyl)pyrimidin-2-ylamino)ethyl)quinolin-2(1H)-one (0.074 g, 0.170 mmol, 44.1% yield) as an orange oil. $^1$H NMR (300 MHz, DMSO-d$_6$): δ ppm 11.96 (s, 1H), 8.28 (br s, 1H), 7.65-7.80 (m, 3H), 7.45 (dd, J=8.79, 2.35 Hz, 1H), 7.27 (d, J=8.79 Hz, 1H), 6.65 (d, J=4.69 Hz, 1H), 5.17 (quin, J=7.11 Hz, 1H), 4.26-4.44 (m, 2H), 2.63-3.22 (m, 2H), 2.00-2.36 (m, 1H), 1.39 (d, J=7.04 Hz, 3H), 0.64-1.11 (m, 6H).

Example 72—6-Chloro-3-((1S)-1-((4-((tetrahydrofuran-3-yl)amino)pyrimidin-2-yl)amino)ethyl) quinolin-2(1H)-one (I-122)

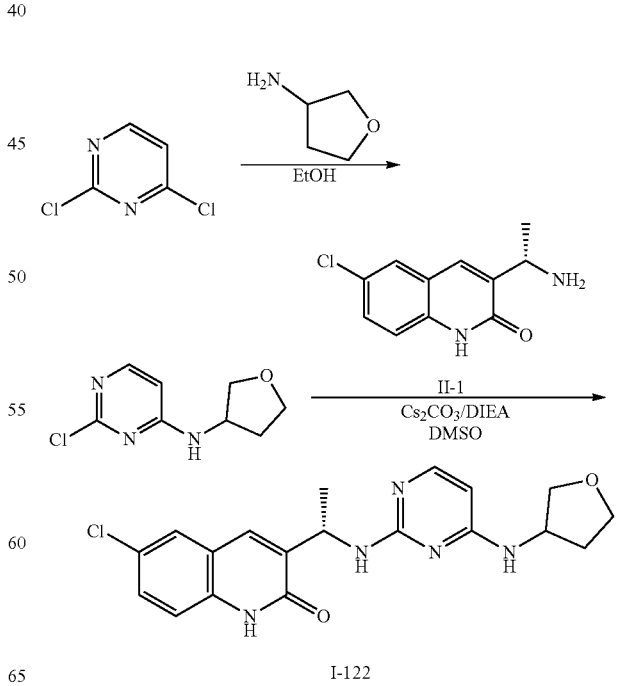

Step-1: 2-Chloro-N-(tetrahydrofuran-3-yl)pyrimidin-4-amine

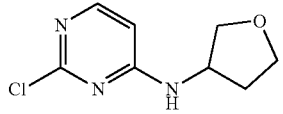 [SMILES: Clc1nccc(NC2CCOC2)n1]

To a solution of 2,4-dichloropyrimidine (0.428 g, 2.87 mmol) in EtOH (28.7 mL) was added tetrahydrofuran-3-amine (0.25 g, 2.87 mmol). The solution was stirred at 45° C. for 16 hours and then concentrated under vacuum. The crude product was purified by SiO$_2$ column chromatography (25 g SNAP® column, 0% MeOH/DCM for 5 minutes, 0-5% MeOH/DCM for 25 minutes, and 5-10% MeOH/DCM for 15 minutes) to afford 2-chloro-N-(tetrahydrofuran-3-yl)pyrimidin-4-amine (0.141 g, 0.706 mmol, 24.61% yield).

Step-2: 6-Chloro-3-((1S)-1-((4-((tetrahydrofuran-3-yl)amino)pyrimidin-2-yl)amino)ethyl) quinolin-2(1H)-one (I-122)

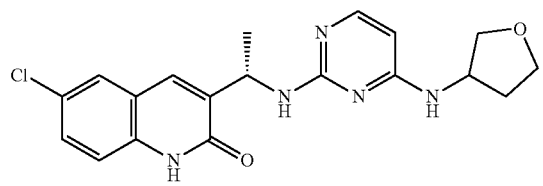 [SMILES: C[C@H](Nc1nccc(NC2CCOC2)n1)c1cc2cc(Cl)ccc2[nH]c1=O]

A solution of (S)-3-(1-aminoethyl)-6-chloroquinolin-2 (1H)-one hydrochloride II-1 (0.183 g, 0.706 mmol), 2-chloro-N-(tetrahydrofuran-3-yl)pyrimidin-4-amine (0.141 g, 0.706 mmol) and DIEA (0.740 mL, 4.24 mmol) in DMSO (4.71 mL) was heated to 130° C. for 1 hour. Cs$_2$CO$_3$ (0.460 g, 1.413 mmol) was then added and the temperature was increased to 155° C. for 3 hours. Water (25 mL) was added, and the resulting precipitate was filtered off and dried under reduced pressure. The crude material was purified by SiO$_2$ column chromatography (25 g SNAP® column, 0% MeOH/DCM for 5 minutes, 0-5% MeOH/DCM for 25 minutes, 5-10% MeOH/DCM for 15 minutes, and 10-15% MeOH/DCM for 15 minutes) to afford 6-chloro-3-((1S)-1-((4-((tetrahydrofuran-3-yl)amino)pyrimidin-2-yl)amino)ethyl)quinolin-2(1H)-one I-122 (0.0439 g, 0.114 mmol, 16.11% yield). $^1$H NMR (300 MHz, DMSO-d$_6$): δ ppm 11.87 (s, 1H), 7.60-7.67 (m, 2H), 7.55 (br d, J=4.98 Hz, 1H), 7.40 (dd, J=8.65, 2.49 Hz, 1H), 7.22 (d, J=8.79 Hz, 1H), 6.74-7.14 (m, 1H), 5.65 (d, J=5.86 Hz, 1H), 5.04 (br t, J=6.74 Hz, 1H), 3.35-3.85 (m, 5H), 1.95-2.13 (m, 1H), 1.59-1.73 (m, 1H), 1.28 (d, J=6.74 Hz, 3H).

Example 73—(S)-6-Chloro-3-(1-((4-(2-oxoimidazolidin-1-yl)pyrimidin-2-yl)amino)ethyl)quinolin-2(1H)-one (I-123)

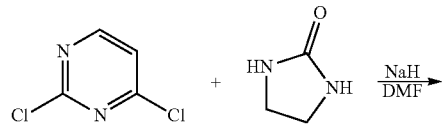

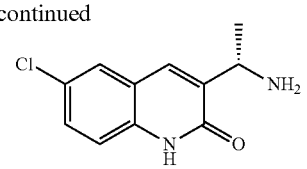

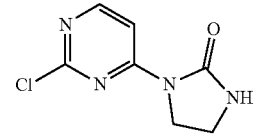 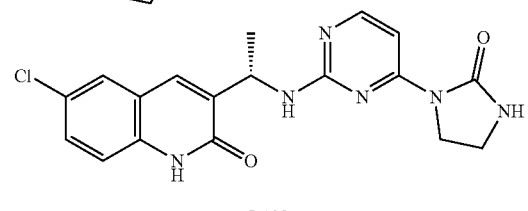

Step-1: 1-(2-Chloropyrimidin-4-yl)imidazolidin-2-one

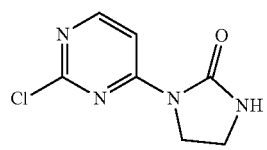 [SMILES: O=C1NCCN1c1ccnc(Cl)n1]

To a solution of imidazolidin-2-one (1.445 g, 16.78 mmol) in DMF (6.71 mL) at 0° C. was added 60% NaH in oil (0.671 g, 16.78 mmol). The reaction mixture was stirred at room temperature for 30 minutes and then 2,4-dichloropyrimidine (0.5 g, 3.36 mmol) was added. The reaction mixture was stirred at room temperature for 1 hour. Water (20 mL) was added, and the aqueous phase was extracted with EtOAc (3×30 mL). The combined organic extracts were washed with brine (30 mL), dried over MgSO$_4$ and evaporated under reduced pressure. The solid was treated with DCM (2 mL) and filtered to afford 50% pure 1-(2-chloropyrimidin-4-yl)imidazolidin-2-one (0.087 g, 0.438 mmol, 13.05% yield) as a white solid. This material was used in the next step without further purification.

Step-2: (S)-6-Chloro-3-(1-((4-(2-oxoimidazolidin-1-yl)pyrimidin-2-yl)amino)ethyl)quinolin-2(1H)-one (I-123)

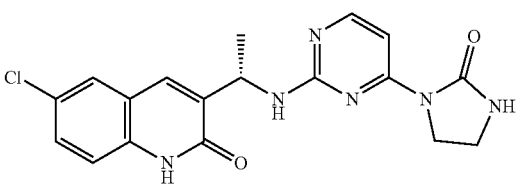 [SMILES: C[C@H](Nc1nccc(N2CCNC2=O)n1)c1cc2cc(Cl)ccc2[nH]c1=O]

A mixture of (S)-3-(1-aminoethyl)-6-chloroquinolin-2 (1H)-one hydrochloride II-1 (0.117 g, 0.453 mmol), 1-(2-chloropyrimidin-4-yl)imidazolidin-2-one (0.09 g, 0.453 mmol) and DIEA (0.475 mL, 2.72 mmol) in DMSO (3.02 mL) was heated to 120° C. for 16 hours. Water (10 mL) was added and an off white solid formed. The solid was collected by filtration and washed once with water (5 mL). The crude material was purified by SiO₂ column chromatography 2 (25 g SNAP® column, 0% MeOH/DCM for 5 minutes, 0-5% MeOH/DCM for 25 minutes, and 5-10% MeOH/DCM for 10 minutes) to afford (S)-6-Chloro-3-(1-((4-(2-oxoimidazolidin-1-yl)pyrimidin-2-yl)amino) ethyl) quinolin-2(1H)-one 1-123 (0.0115 g, 0.030 mmol, 6.59% yield) ¹H NMR (300 MHz, DMSO-d₆): δ ppm 11.93 (s, 1H), 7.9-7.98 (m, 1H), 7.67-7.74 (m, 2H), 7.45 (dd, J=8.79, 2.35 Hz, 1H), 7.16-7.41 (m, 5H), 5.06-5.21 (m, 1H), 3.89 (br s, 2H), 3.2-3.41 (m, 2H), 1.35 (d, J=7.04 Hz, 3H).

Example 74—(S)-1-(2-((1-(6-chloro-2-oxo-1,2-dihydroquinolin-3-yl)ethyl)amino)pyrimidin-4-yl)-1,3,3-trimethylurea (I-125)

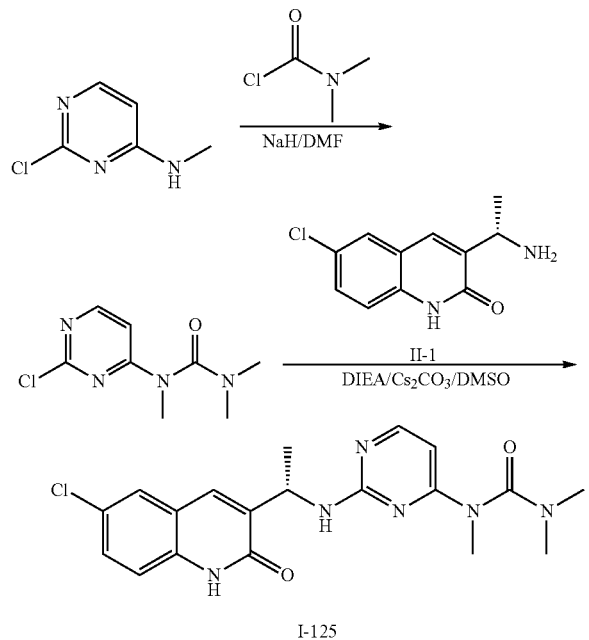

Step-1: 1-(2-Chloropyrimidin-4-yl)-1,3,3-trimethylurea

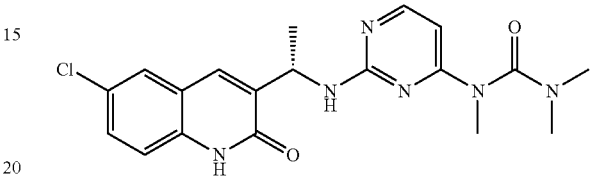

To a solution of 2-chloro-N-methylpyrimidin-4-amine (0.25 g, 1.741 mmol) in DMF (17.41 mL) at 0° C. was added 60% NaH in oil (0.139 g, 3.48 mmol). The reaction mixture was stirred at 0° C. for 30 minutes and dimethylcarbamic chloride (0.160 mL, 1.741 mmol) was then added. The reaction was allowed to warm to room temperature and was stirred at room temperature for 1 hour. The reaction mixture was then poured on ice/water (50 mL) and extracted with EtOAc (3×20 mL). The combined organic phases were dried over MgSO₄, and the volatiles were removed under reduced pressure. The crude material was purified by SiO₂ column chromatography (50 g SNAP® column, 0% MeOH/DCM for 5 minutes, 0-5% MeOH/DCM for 25 minutes, and 5-10% MeOH/DCM for 10 minutes to afford 1-(2-chloropyrimidin-4-yl)-1,3,3-trimethylurea.

Step-2: (S)-1-(2-((1-(6-Chloro-2-oxo-1,2-dihydroquinolin-3-yl)ethyl)amino)pyrimidin-4-yl)-1,3,3-trimethylurea (I-125)

A solution of (S)-3-(1-aminoethyl)-6-chloroquinolin-2(1H)-one hydrochloride II-1 (0.241 g, 0.932 mmol), 1-(2-chloropyrimidin-4-yl)-1,3,3-trimethylurea (0.2 g, 0.932 mmol) and DIEA (0.976 mL, 5.59 mmol) in DMSO (6.21 mL) was heated to 125° C. for 6 hours. Cs₂CO₃ (0.607 g, 1.863 mmol) was then added to the reaction mixture and the temperature was increased to 150° C. for 2 hours. Water (25 mL) was added, and the resulting precipitate was filtered off and dried under reduced pressure. The crude material was purified by SiO₂ column chromatography (25 g SNAP® column, 0% MeOH/DCM for 5 minutes, 0-5% MeOH/DCM for 25 minutes, and 5-10% MeOH/DCM for 15 minutes) to afford (S)-1-(2-((1-(6-chloro-2-oxo-1,2-dihydroquinolin-3-yl)ethyl)amino)pyrimidin-4-yl)-1,3,3-trimethylurea (0.0456 g, 0.114 mmol, 12.21% yield). ¹H NMR (300 MHz, DMSO-d₆): δ ppm 11.92-11.97 (m, 1H), 7.85-7.97 (m, 1H), 7.67-7.74 (m, 2H), 7.41-7.49 (m, 1H), 7.27 (d, J=8.79 Hz, 2H), 5.91-5.97 (m, 1H), 4.97-5.17 (m, 1H), 2.55-3.17 (m, 9H), 1.30-1.39 (m, 3H).

Example 75—(S)-3-(2-((1-(6-chloro-2-oxo-1,2-dihydroquinolin-3-yl)ethyl)amino)pyrimidin-4-yl)-1,1-dimethylurea (I-126)

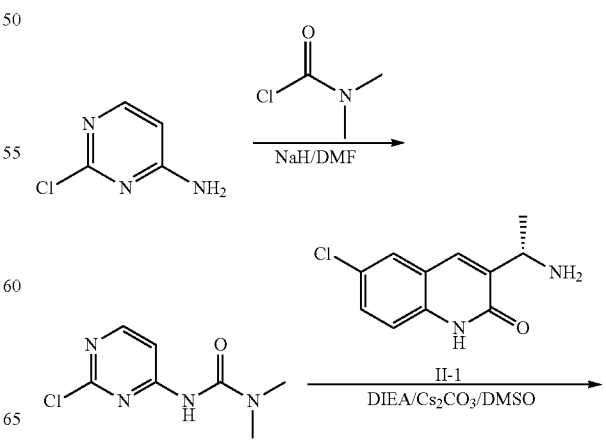

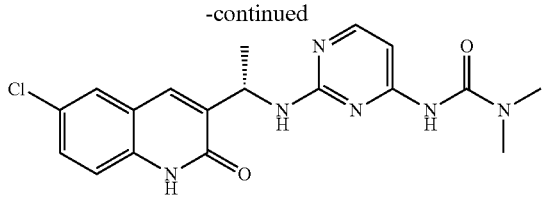

I-126

Step-1:
3-(2-Chloropyrimidin-4-yl)-1,1-dimethylurea

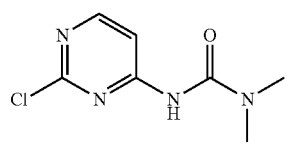

To a solution of 2-chloropyrimidin-4-amine (0.250 g, 1.930 mmol) in DMF (19.30 mL) at 0° C. was added 60% NaH (0.154 g, 3.86 mmol). The reaction mixture was stirred at 0° C. for 30 minutes, then dimethylcarbamic chloride (0.177 mL, 1.930 mmol) was added. The reaction was allowed to reach room temperature and was stirred at room temperature for 1 hour. The reaction was poured on ice/water (50 mL), and the product was extracted into EtOAc (3×20 mL). The combined organic phases were dried over MgSO$_4$, and the volatiles were removed under reduced pressure. 3-(2-Chloropyrimidin-4-yl)-1,1-dimethylurea (0.248 g, 1.236 mmol, 64.1% yield) was isolated and used in the next step without further purification.

Step-2: (S)-3-(2-((1-(6-Chloro-2-oxo-1,2-dihydroquinolin-3-yl)ethyl)amino)pyrimidin-4-yl)-1,1-dimethylurea (I-126)

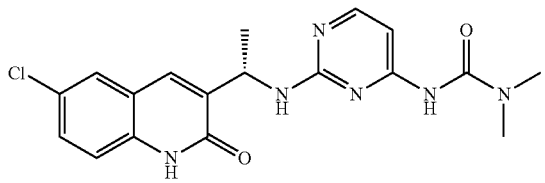 [SMILES: C[C@H](Nc1nccc(NC(=O)N(C)C)n1)c1cc2cc(Cl)ccc2[nH]c1=O]

A mixture of (S)-3-(1-aminoethyl)-6-chloroquinolin-2 (1H)-one hydrochloride II-1 (0.1 g, 0.386 mmol), 3-(2-chloropyrimidin-4-yl)-1,1-dimethylurea (0.077 g, 0.386 mmol) and DIEA (0.404 mL, 2.315 mmol) in DMSO (2.57 mL) was heated to 130° C. for 1 hour. Water (20 mL) was added and an off white solid precipitated out of solution. The resulting solid was filtered off and washed once with water (5 mL). The crude material was purified by SiO$_2$ column chromatography (25 g SNAP® column, 0% MeOH/DCM for 5 minutes, 0-10% MeOH/DCM for 25 minutes, and 10% MeOH/DCM for 10 minutes) to afford (S)-3-(2-((1-(6-chloro-2-oxo-1,2-dihydroquinolin-3-yl)ethyl)amino)pyrimidin-4-yl)-1,1-dimethylurea (0.0686 g, 0.177 mmol, 46.0% yield). $^1$H NMR (300 MHz, DMSO-d$_6$): δ ppm 11.94-12.00 (m, 1H), 9.42-9.49 (m, 1H), 9.01-9.11 (m, 1H), 7.99-8.05 (m, 1H), 7.81-7.87 (m, 1H), 7.75-7.81 (m, 1H), 7.44-7.52 (m, 1H), 7.23-7.33 (m, 1H), 6.26-6.36 (m, 1H), 4.86-5.01 (m, 1H), 3.06 (s, 6H), 1.41 (d, J=7.04 Hz, 3H).

Example 76—(S)-6-Chloro-3-(1-((4-(oxazol-2-ylamino)pyrimidin-2-yl)amino)ethyl)quinolin-2 (1H)-one (I-127)

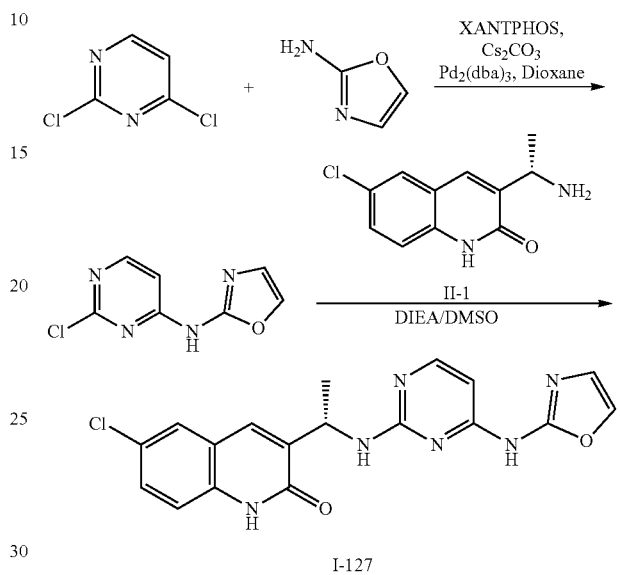

I-127

Step-1: N-(2-chloropyrimidin-4-yl)oxazol-2-amine

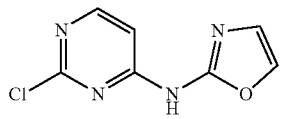 [SMILES: Clc1nccc(Nc2ncco2)n1]

A mixture of Xantphos (0.194 g, 0.336 mmol), Cs$_2$CO$_3$ (1.094 g, 3.36 mmol), Pd$_2$(dba)$_3$ (0.154 g, 0.168 mmol), 2,4-dichloropyrimidine (0.5 g, 3.36 mmol), and oxazol-2-amine (0.282 g, 3.36 mmol) in 1,4-dioxane (11.19 mL) was heated to 100° C. for 3 hours. The reaction was filtered to remove the solid, and the solid was rinsed with DCM (3×5 mL). The volatiles were removed under reduced pressure and the crude material was purified by SiO$_2$ column chromatography (50 g SNAP® column, 0% EtOAc in hexanes for 5 minutes, then 0-100% EtOAc in hexanes for 30 minutes) to afford N-(2-Chloropyrimidin-4-yl)oxazol-2-amine (0.1 g, 0.509 mmol, 15.16% yield).

Step-2: (S)-6-Chloro-3-(1-((4-(oxazol-2-ylamino)pyrimidin-2-yl)amino)ethyl)quinolin-2(1H)-one (I-127)

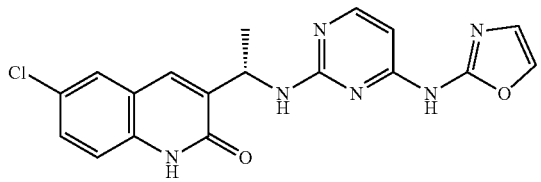 [SMILES: C[C@H](Nc1nccc(Nc2ncco2)n1)c1cc2cc(Cl)ccc2[nH]c1=O]

A solution of (S)-3-(1-aminoethyl)-6-chloroquinolin-2 (1H)-one II-1 (0.113 g, 0.509 mmol), N-(2-chloropyrimidin-4-yl)oxazol-2-amine (0.1 g, 0.509 mmol) and DIEA (0.533 mL, 3.05 mmol) in DMSO (3.39 mL) was heated to 120° C. for 16 hours. Water (25 mL) was then added and the resulting precipitate was filtered off and dried under reduced pressure. The crude material was purified by SiO₂ column chromatography (25 g SNAP® column, 0% MeOH/DCM for 5 minutes, 0-10% MeOH/DCM for 25 minutes, and 10% MeOH/DCM for 10 minutes). The product containing fractions were concentrated under reduced pressure, and the residue was dissolved in EtOAc (2 mL) and hexane (5 mL) was added. The resulting precipitate was filtered to afford (S)-6-Chloro-3-(1-((4-(oxazol-2-ylamino)pyrimidin-2-yl) amino)ethyl) quinolin-2(1H)-one, 1-127 (0.012 g, 0.031 mmol, 6.16% yield). ¹H NMR (300 MHz, DMSO-d₆): δ ppm 11.94 (s, 1H), 10.63 (s, 1H), 8.00-8.10 (m, 1H), 7.72 (br d, J=6.45 Hz, 3H), 7.46 (br d, J=8.50 Hz, 1H), 7.27 (br d, J=8.79 Hz, 2H), 7.09 (d, J=5.86 Hz, 1H), 7.02 (s, 1H), 5.10-5.22 (m, 1H), 1.35-1.43 (m, 3H).

Example 77—(S)-2-(2-((1-(6-chloro-2-oxo-1,2-dihydroquinolin-3-yl)ethyl)amino)pyrimidin-4-yl) acetamide (I-130)

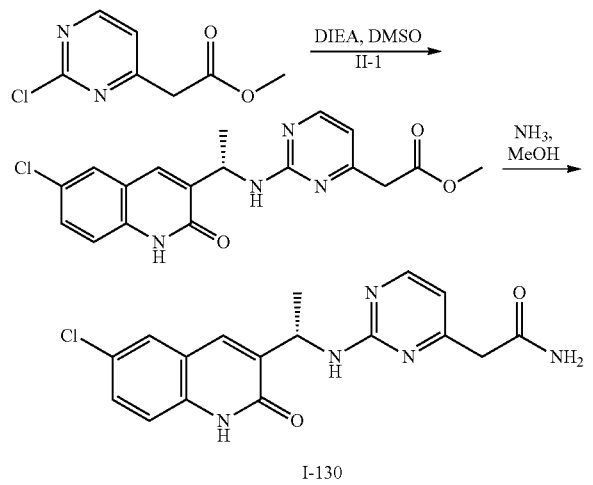

Step-1: methyl (S)-2-(2-((1-(6-chloro-2-oxo-1,2-dihydroquinolin-3-yl)ethyl)amino) pyrimidin-4-yl) acetate

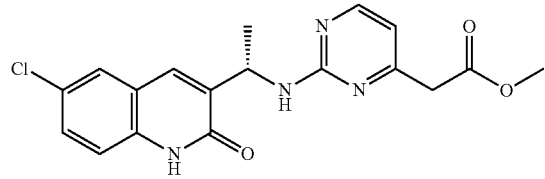 [SMILES: COC(=O)Cc1ccnc(N[C@@H](C)c2cc3cc(Cl)ccc3[nH]c2=O)n1]

A mixture of DIEA (0.314 ml, 1.796 mmol), (S)-3-(1-aminoethyl)-6-chloroquinolin-2(1H)-one (200 mg, 0.898 mmol), and ethyl 2-(2-chloropyrimidin-4-yl)acetate (180 mg, 0.898 mmol) in DMSO (2 ml) was heated to 110° C. for overnight. The reaction mixture was treated with EtOAc, washed with water, dried, and concentrated. The crude material was purified by silica gel chromatography on a Biotage® chromatography system on a 25 g column eluted with 0-5% MeOH/DCM to afford methyl (S)-2-(2-((1-(6-chloro-2-oxo-1,2-dihydroquinolin-3-yl)ethyl)amino)pyrimidin-4-yl)acetate (83 mg, 23% yield). ¹H NMR (300 MHz, CDCl₃): δ ppm 12.02 (br s, 1H), 8.19 (d, J=4.98 Hz, 1H), 7.68 (s, 1H), 7.50-7.50 (m, 1H), 7.35-7.46 (m, 1H), 7.28-7.36 (m, 1H), 6.52 (d, J=4.98 Hz, 1H), 6.11 (br d, J=8.21 Hz, 1H), 5.31-5.42 (m, 1H), 5.29 (s, 3H), 3.56 (s, 2H), 1.62 (d, J=7.04 Hz, 3H). LCMS (Method 1): Rt 2.33 min, m/z 387.94 [M+H]⁺.

Step-2: (S)-2-(2-((1-(6-chloro-2-oxo-1,2-dihydroquinolin-3-yl)ethyl)amino)pyrimidin-4-yl)acetamide

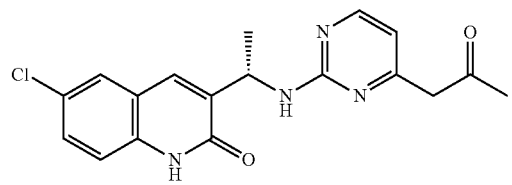 [SMILES: CC(=O)Cc1ccnc(N[C@@H](C)c2cc3cc(Cl)ccc3[nH]c2=O)n1]

A mixture of ammonia (4 ml, 7N in MeOH, 28 mmol) and (S)-ethyl 2-(2-((1-(6-chloro-2-oxo-1,2-dihydroquinolin-3-yl)ethyl)amino)pyrimidin-4-yl)acetate (40 mg, 0.103 mmol) was stirred at 40° C. for overnight. The reaction was concentrated purified on a Gilson® reverse phase HPLC to afford(S)-2-(2-((1-(6-chloro-2-oxo-1,2-dihydroquinolin-3-yl)ethyl)amino)pyrimidin-4-yl)acetamide (2.2 mg, 5.9% yield).

Example 78—(S)-6-Chloro-3-(1-(4-(methylsulfonylmethyl)pyrimidin-2-ylamino)ethyl) quinolin-2(1H)-one (I-134)

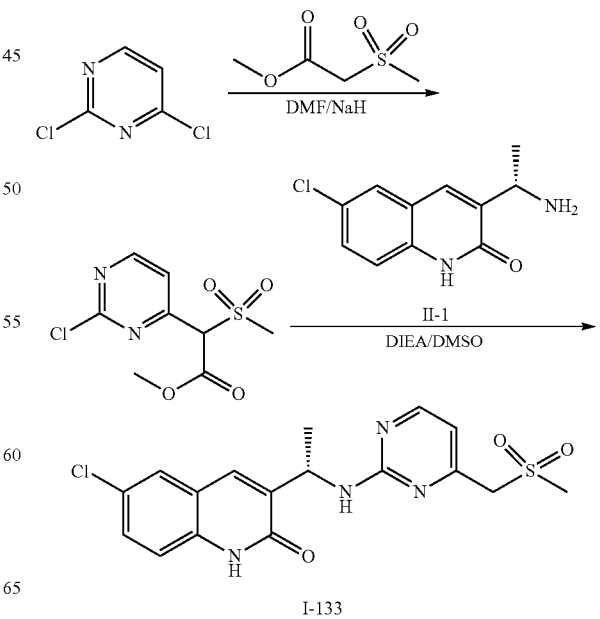

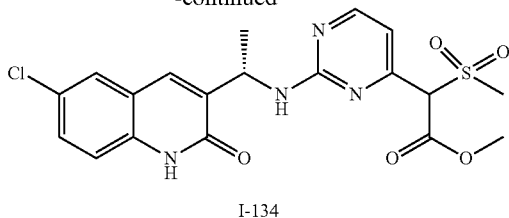

I-134

Step-1: Methyl 2-(2-chloropyrimidin-4-yl)-2-(methylsulfonyl)acetate

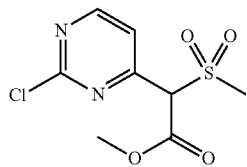 [SMILES: COC(=O)C(c1ccnc(Cl)n1)S(C)(=O)=O]

To a solution of methyl 2-(methylsulfonyl)acetate (3 g, 19.71 mmol) in DMF (25.3 mL) at 0° C. was added 60% sodium hydride (NaH) in oil (1.577 g, 39.4 mmol). The reaction mixture was stirred at room temperature for 5 minutes (until bubbling ceased) and 2,4-dichloropyrimidine (2.94 g, 19.71 mmol) was then added. The reaction mixture was stirred at room temperature for 16 hours. The reaction mixture was poured into 2M aqueous HCl solution (20 mL), and the aqueous phase was extracted with EtOAc (3×20 mL). The combined organic extracts were dried over MgSO$_4$. The crude material was purified by SiO$_2$ column chromatography (50 g SNAP® column, 0% EtOAc/hexanes for 5 minutes, 0-50% EtOAc/hexanes for 30 minutes, and then 50-75% EtOAc/hexanes for 5 minutes) to afford methyl 2-(2-chloropyrimidin-4-yl)-2-(methylsulfonyl)acetate (1.58 g, 5.97 mmol, 30.3% yield).

Step-2: (S)-6-chloro-3-(1-(4-(methylsulfonylmethyl)pyrimidin-2-ylamino)ethyl)quinolin-2(1H)-one

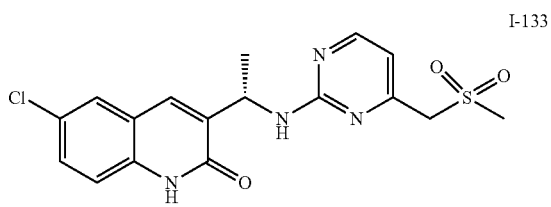

I-133

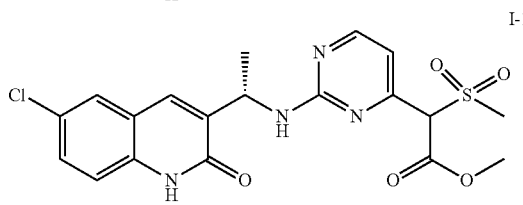

I-134

A solution of (S)-3-(1-aminoethyl)-6-chloroquinolin-2(1H)-one II-1 (0.210 g, 0.945 mmol), methyl 2-(2-chloropyrimidin-4-yl)-2-(methylsulfonyl)acetate (0.25 g, 0.945 mmol) and DIEA (0.990 mL, 5.67 mmol) in DMSO (6.75 mL) was heated to 120° C. for 16 hours. Water (15 mL) was then added, and the resulting precipitate was filtered off and washed with water (2×5 mL). The precipitate was dried under reduced pressure and purified by SiO$_2$ column chromatography (25 g SNAP® column, eluted with 0-75% EtOAc/hexanes for 30 minutes, and then 75-100% EtOAc/hexanes for 5 minutes). The title compound was further purified on a Gilson® reverse phase HPLC (20 mL/minute, 10 minute gradient 15-85% CH$_3$CN, 0.01% HCO$_2$H on an XTerra Prep MS C18 OBD 5 M, 19×100 mm column) to afford methyl 2-(2-((S)-1-(6-chloro-2-oxo-1,2-dihydroquinolin-3-yl)ethylamino)pyrimidin-4-yl)-2-(methylsulfonyl)acetate (0.0117 g, 0.026 mmol, 2.75% yield).

The Gilson® reverse phase column was further washed with EtOAc for 10 minutes to collect (S)-6-chloro-3-(1-(4-(methylsulfonylmethyl)pyrimidin-2-ylamino)ethyl)quinolin-2(1H)-one. This material was further purified on a Gilson reverse phase HPLC (20 mL/minute, 10 minute gradient 15-85% CH$_3$CN, 0.01% HCO$_2$H on an XTerra Prep MS C18 OBD 5 M, 19×100 mm column) to afford (S)-6-chloro-3-(1-(4-(methylsulfonylmethyl)pyrimidin-2-ylamino)ethyl)quinolin-2(1H)-one, I-134 (0.0122 g, 0.031 mmol, 3.29% yield).

I-133: $^1$H NMR (300 MHz, DMSO-d$_6$): δ ppm 11.95 (s, 1H), 8.16-8.38 (m, 1H), 7.60-7.80 (m, 3H), 7.39-7.50 (m, 1H), 7.21-7.31 (m, 1H), 6.59-6.70 (m, 1H), 5.08-5.21 (m, 1H), 4.29-4.44 (m, 2H), 2.74-3.22 (m, 3H), 1.38 (d, J=6.74 Hz, 3H).

Example 79—6-Chloro-3-((1S)-1-((4-(1-(methylsulfonyl)ethyl)pyrimidin-2-yl)amino)ethyl) quinolin-2(1H)-one (I-135)

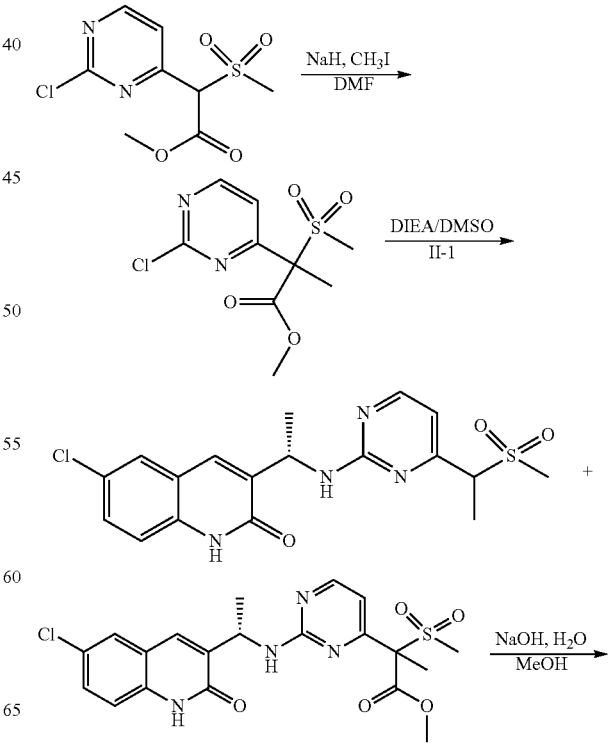

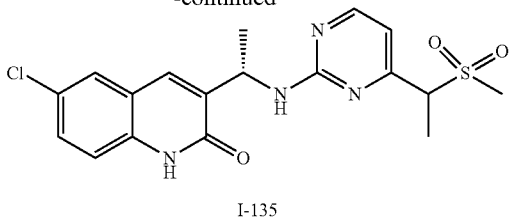

I-135

Step-1: Methyl 2-(2-chloropyrimidin-4-yl)-2-(methylsulfonyl)propanoate

To a solution of methyl 2-(2-chloropyrimidin-4-yl)-2-(methylsulfonyl)acetate (0.14 g, 0.529 mmol) in DMF (5.29 mL) at room temperature was added 60% NaH in oil (0.025 g, 0.635 mmol). The reaction mixture was stirred at room temperature for 10 minutes before iodomethane (0.049 mL, 0.793 mmol) was added. The reaction mixture was then stirred at room temperature for 1 hour. Water (20 mL) was added, and the aqueous phase was extracted with EtOAc (3×20 mL). The combined organic phases were washed with brine and dried over MgSO$_4$. The volatiles were removed under reduced pressure, and the resulting residue was purified by SiO$_2$ column chromatography (25 g SNAP® column, 0-75% EtOAc/hexanes for 30 minutes and then 75-100% EtOAc/hexanes for 5 minutes) to afford methyl 2-(2-chloropyrimidin-4-yl)-2-(methylsulfonyl) propanoate (0.077 g, 0.276 mmol, 52.2% yield).

Step-2: 6-Chloro-3-((1S)-1-((4-(1-(methylsulfonyl)ethyl)pyrimidin-2-yl)amino)ethyl) quinolin-2(1H)-one and methyl 2-(2-(((S)-1-(6-chloro-2-oxo-1,2-dihydroquinolin-3-yl)ethyl)amino)pyrimidin-4-yl)-2-(methylsulfonyl)propanoate A solution of (S)-3-(1-aminoethyl)-6-chloroquinolin-2(1H)-one hydrochloride II-1 (0.072 g, 0.276 mmol), methyl 2-(2-chloropyrimidin-4-yl)-2-(methyl sulfonyl)propanoate (0.077 g, 0.276 mmol) and DIEA (0.290 mL, 1.658 mmol) in DMSO (6.75 mL) was heated to 120° C. for 16 hours. Water (15 mL) was added, and the resulting precipitate was filtered off and washed with water (2×5 mL). This precipitate consisted of a mixture of 6-chloro-3-((1S)-1-(4-(1-(methylsulfonyl)ethyl)pyrimidin-2-ylamino)ethyl)quinolin-2(1H)-one (0.056 g, 0.138 mmol, 50.0% yield) and methyl 2-(2-((S)-1-(6-chloro-2-oxo-1,2-dihydroquinolin-3-yl)ethylamino) pyrimidin-4-yl)-2-(methylsulfonyl) propanoate (0.064 g, 0.138 mmol, 50.0% yield). The mixture was used in the next step without further purification.

Step-3: 6-Chloro-3-((1S)-1-((4-(1-(methylsulfonyl)ethyl)pyrimidin-2-yl)amino)ethyl) quinolin-2(1H)-one To a suspension of 6-chloro-3-((1S)-1-(4-(1-(methylsulfonyl)ethyl)pyrimidin-2-ylamino) ethyl)quinolin-2(1H)-one (0.057 g, 0.138 mmol) and methyl 2-(2-((S)-1-(6-chloro-2-oxo-1,2-dihydroquinolin-3-yl)ethylamino)pyrimidin-4-yl)-2-(methyl sulfonyl)propanoate (0.065 g, 0.138 mmol) in methanol (1.493 mL) was added an aqueous solution of NaOH (0.373 mL, 0.017 g, 0.420 mmol). The reaction mixture was stirred at 60° C. for 1 hour. The reaction mixture was neutralized with 2M aqueous HCl solution, and a brown precipitate was filtered off. The aqueous phase was extracted with EtOAc (3×15 mL) and the combined extracts were dried over MgSO$_4$. The crude mixture was further purified by reverse phase HPLC to yield the title compound. $^1$H NMR (300 MHz, DMSO-d$_6$): δ ppm 11.96 (br s, 1H), 8.26 (br s, 1H), 7.65-7.95 (m, 3H), 7.46 (br dd, J=8.79, 2.35 Hz, 1H), 7.06-7.36 (m, 1H), 6.65 (br d, J=5.28 Hz, 1H), 5.05-5.20 (m, 1H), 4.20-4.40 (m, 1H), 1.07-1.43 (m, 9H).

Example 80—(S)-6-Chloro-3-(1-(4-(1-(methylsulfonyl)cyclopropyl)pyrimidin-2-ylamino)ethyl)quinolin-2(1H)-one (I-136)

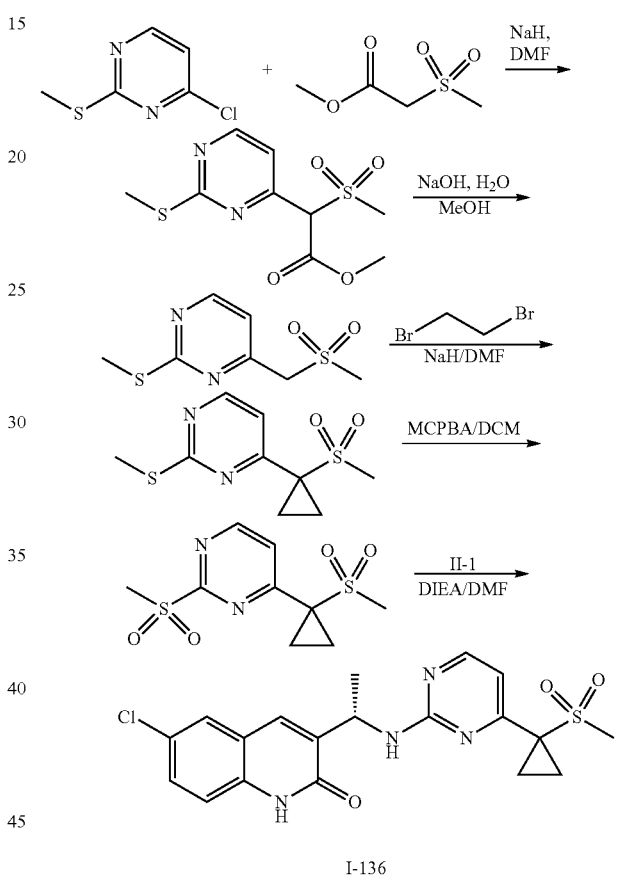

I-136

Step-1: Methyl 2-(methylsulfonyl)-2-(2-(methylthio)pyrimidin-4-yl)acetate

To a solution of methyl 2-(methylsulfonyl)acetate (3 g, 19.71 mmol) in DMF (25.3 mL) at 0° C. was added 60% sodium hydride (1.577 g, 39.4 mmol). The reaction mixture was stirred at room temperature for 5 minutes (until bubbling had ceased) and 4-chloro-2-(methylthio)pyrimidine (3.17 g, 19.71 mmol) was then added. The reaction mixture was stirred at room temperature for 16 hours and then neutralized with 2M aqueous HCl solution to pH 7 and extracted with EtOAc (3×20 mL). The combined extracts were dried over MgSO$_4$, filtered and concentrated under reduced pressure. The crude material was purified by SiO$_2$ column chromatography (50 g SNAP® column, 0% EtOAc/hexanes for 5 minutes, 0-50% EtOAc/hexanes for 30 minutes, and 50-75% EtOAc/hexanes for 5 minutes) to afford methyl 2-(methylsulfonyl)-2-(2-(methylthio)pyrimidin-4-yl)acetate (0.486 g, 1.759 mmol, 8.92% yield).

Step-2: 4-(Methylsulfonylmethyl)-2-(methylthio)pyrimidine

To a solution of methyl 2-(methylsulfonyl)-2-(2-(methylthio)pyrimidin-4-yl)acetate (0.475 g, 1.719 mmol) in MeOH (18.34 mL) was added a solution of NaOH (0.206 g, 5.16 mmol) in water (4.58 mL). The homogenous solution was stirred at 45° C. for 1 hour and then at 55° C. for 3 hours. 4-(Methylsulfonylmethyl)-2-(methylthio) pyrimidine (0.275 g, 1.260 mmol, 73.3% yield) was isolated and used in the next step without further purification.

Step-3: 4-(1-(Methylsulfonyl)cyclopropyl)-2-(methylthio)pyrimidine

To a solution of 4-(methylsulfonylmethyl)-2-(methylthio) pyrimidine (0.215 g, 0.985 mmol) in DMF (6.52 mL) at room temperature was added 60% NaH in oil (0.158 g, 3.94 mmol) the reaction was stirred at room temperature for 10 minutes. A solution of 1,2-dibromoethane (0.339 mL, 3.94 mmol) in DMF (1 mL) was then added dropwise and the reaction was stirred at room temperature for 2 hours. Additional NaH (0.079 g, 1.970 mmol) and 1,2-dibromoethane (0.170 mL, 1.970 mmol) were added, and the reaction mixture was stirred for another 2 hours. Water (20 mL) was added to the reaction mixture, and the reaction mixture was extracted with EtOAc (3×20 mL). The combined organic phases were dried over MgSO$_4$, and the volatiles were removed under reduced pressure. The crude material was purified by SiO$_2$ column chromatography (25 g SNAP® column, 0% EtOAc/hexanes for 5 minutes, 0-30% EtOAc/hexanes for 30 minutes, and then 30-50% EtOAc/hexanes for 5 minutes) to afford 4-(1-(methylsulfonyl)cyclopropyl)-2-(methylthio)pyrimidine (0.162 g, 0.663 mmol, 67.3% yield) as a white solid.

Step-4: 2-(Methylsulfonyl)-4-(1-(methylsulfonyl)cyclopropyl)pyrimidine

To a solution of 4-(1-(methyl sulfonyl)cyclopropyl)-2-(methylthio)pyrimidine (0.162 g, 0.663 mmol) in DCM (50 mL) at room temperature was added m-CPBA (0.343 g, 1.492 mmol) the resulting reaction mixture was stirred for 3 hours at room temperature. The reaction mixture was then washed with saturated aqueous Na$_2$S$_2$O$_3$ solution (50 mL), saturated aqueous Na$_2$CO$_3$ solution (50 mL) and brine (50 mL). The organic layer was dried over MgSO$_4$ and the volatiles were removed under reduced pressure to afford 2-(methylsulfonyl)-4-(1-(methylsulfonyl)cyclopropyl)pyrimidine (0.173 g, 0.626 mmol, 94% yield) which was used in the next step without further purification.

Step-5: (S)-6-chloro-3-(1-(4-(1-(methylsulfonyl)cyclopropyl)pyrimidin-2-ylamino)ethyl) quinolin-2(1H)-one (I-136)

A solution of 2-(methylsulfonyl)-4-(1-(methylsulfonyl)cyclopropyl)pyrimidine (0.085 g, 0.308 mmol), (S)-3-(1-aminoethyl)-6-chloroquinolin-2(1H)-one hydrochloride II-1 (0.080 g, 0.308 mmol) and DIEA (0.322 mL, 1.846 mmol) in DMF (1.538 mL) was heated to 100° C. for 16 hours. Water (30 mL) was then added to the reaction mixture, and the resulting precipitate was filtered off. The crude material was purified by SiO$_2$ column chromatography (10 g SNAP® column, 0% EtOAc/hexanes for 5 minutes, 0-50% EtOAc/hexanes for 30 minutes, and then 50-75% EtOAc/hexanes for 5 minutes) to afford (S)-6-chloro-3-(1-(4-(1-(methyl sulfonyl)cyclopropyl)pyrimidin-2-ylamino)ethyl) quinolin-2(1H)-one, I-136 (0.015 g, 0.036 mmol, 11.64% yield).

Example 81—(S)—N-((2-((1-(6-chloro-2-oxo-1,2-dihydroquinolin-3-yl)ethyl)amino)pyrimidin-4-yl)methyl)-N-cyclopropylacetamide (I-137)

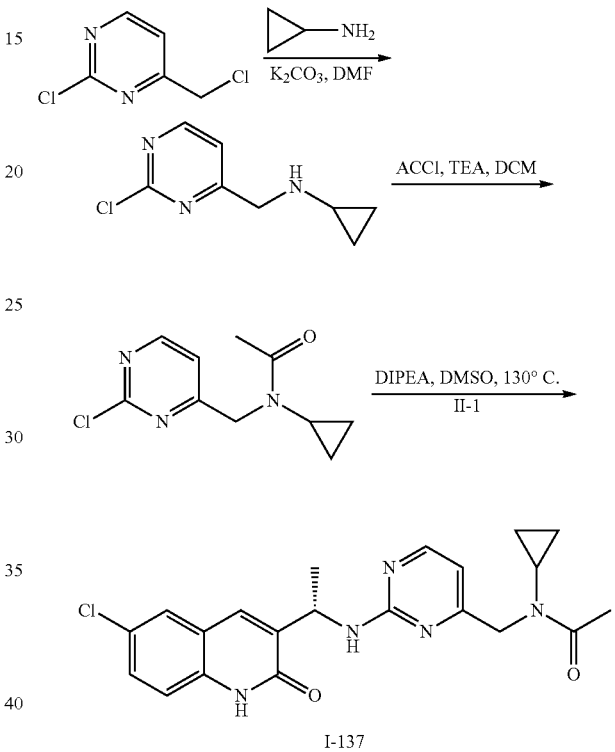

I-137

Step-1: N-((2-chloropyrimidin-4-yl)methyl)cyclopropanamine

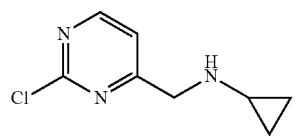 [SMILES: Clc1nccc(CNC2CC2)n1]

A mixture of 2-chloro-4-(chloromethyl)pyrimidine (500 mg, 3.07 mmol, 1 equivalent) and K$_2$CO$_3$ (506 mg, 3.66 mmol, 1.2 eq.) in 4.5 mL DMF was treated with cyclopropylamine (173 mg, 3.03 mmol, 1 eq.) and stirred at room temperature. After 5 hours, the reaction mixture was poured into water and extracted with EtOAc (×2). After washing with brine and drying over Na$_2$SO$_4$, the combined extracts were purified by column chromatography on 15 g of silica gel (EtOAc/hexane, 65/35) to provide the title compound (235 mg, 41% yield) as a thick gold liquid.

Step-2: N-((2-Chloropyrimidin-4-yl)methyl)-N-cyclopropylacetamide

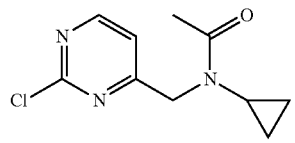

A solution of N-((2-chloropyrimidin-4-yl)methyl)cyclopropanamine (235 mg, 1.28 mmol, 1 equivalent) in 5 mL DCM at 0° C. was treated with TEA (196 mg, 1.92 mmol, 1.5 eq.) followed by acetyl chloride (110 mg, 1.4 mmol, 1.1 equivalents). After stirring for 2 hours at room temperature, the reaction mixture was poured into water and extracted with EtOAc (×2). After washing with brine and drying over $Na_2SO_4$, the extracts were purified by column chromatography on 6.5 g of silica gel (100% EtOAc) to provide the title compound (230 mg, 80% yield) as a thick gold liquid.

Step-3: (S)—N-((2-((1-(6-Chloro-2-oxo-1,2-dihydroquinolin-3-yl)ethyl)amino)pyrimidin-4-yl)methyl)-N-cyclopropylacetamide (I-137)

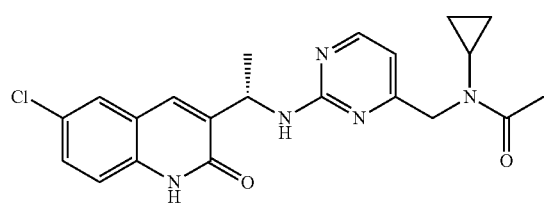 [SMILES: CC(=O)N(Cc1ccnc(N[C@@H](C)c2cc3cc(Cl)ccc3[nH]c2=O)n1)C1CC1]

A mixture of N-((2-chloropyrimidin-4-yl)methyl)-N-cyclopropylacetamide (180 mg, 0.80 mmol, 1.5 equivalents), (S)-3-(1-aminoethyl)-6-chloroquinolin-2(1H)-one hydrochloride II-1 (140 mg, 0.54 mmol, 1 eq.) and DIEA (141 mg, 1.1 mmol, 2 equivalents) in 2 mL DMSO was heated in a sealed tube to 130° C. for 2 hours. The reaction was then poured into water and extracted with EtOAc (×2). After washing with brine and drying over $Na_2SO_4$, the extracts were chromatographed on 20 g of silica gel using an EtOAc to EtOAc/EtOH (90/10) gradient elution, and the pure fractions were lyophilized from ACN/water to provide 57 mg (25%) of an off-white solid. 1H NMR (300 MHz, $CDCl_3$): δ ppm 11.93 (br s, 1H), 8.15 (d, J 5.22 Hz, 1H), 7.67 (s, 1H), 7.49 (d, J=2.22 Hz, 1H), 7.39 (dd, J=2.22, 8.49 Hz, 1H), 7.27 (d, J=8.52 Hz, 1H) 6.36 (d, J=4.95 Hz, 1H), 6.00 (br d, J=7.95 Hz, 1H), 5.30 (m, 1H), 4.41 (s, 2H), 2.73 (m, 1H), 2.22 (s, 3H), 1.60 (d, J=6.87 Hz, 3H), 0.72 (m, 4H). LC/MS (Method 3): Rt 4.05 min., m/z 412 [M+H]+.

TABLE 13

The compounds listed in Table 13 were prepared using methods similar to those described for the preparation of I-105, I-111, I-114, I-116, I-119, I-121-I-127, I-133, and I-135-I-137.

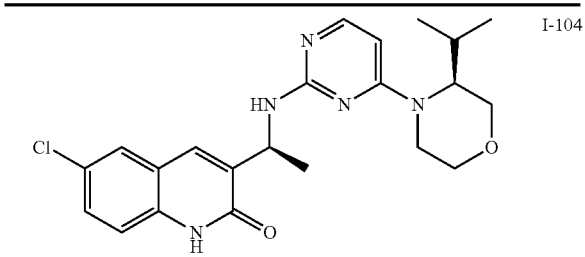

I-104

TABLE 13-continued

The compounds listed in Table 13 were prepared using methods similar to those described for the preparation of I-105, I-111, I-114, I-116, I-119, I-121-I-127, I-133, and I-135-I-137.

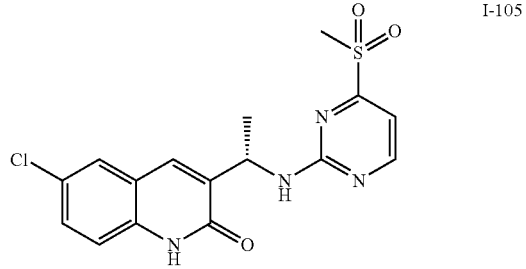

I-105

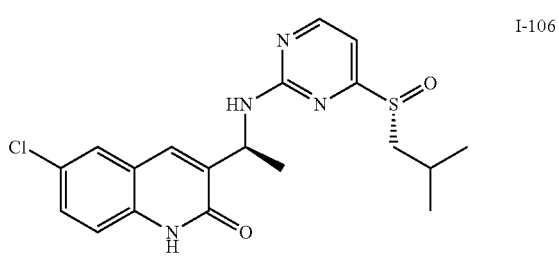

I-106

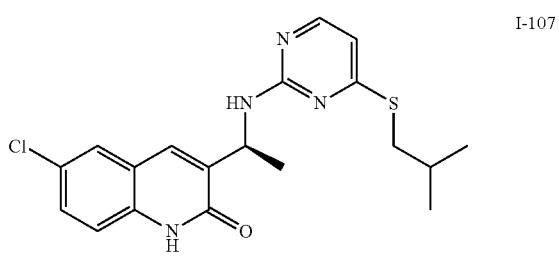

I-107

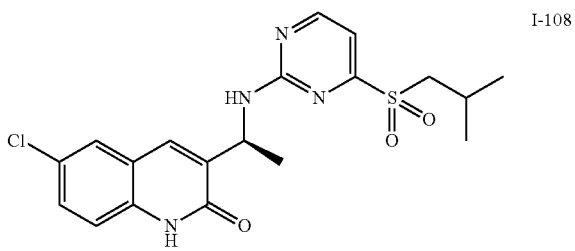

I-108

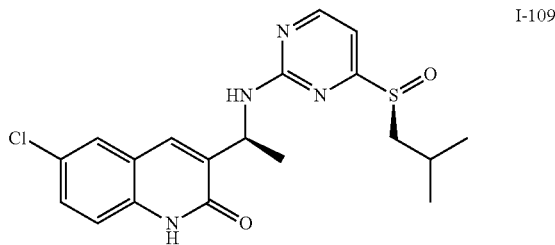

I-109

TABLE 13-continued
The compounds listed in Table 13 were prepared using methods similar to those described for the preparation of I-105, I-111, I-114, I-116, I-119, I-121-I-127, I-133, and I-135-I-137.
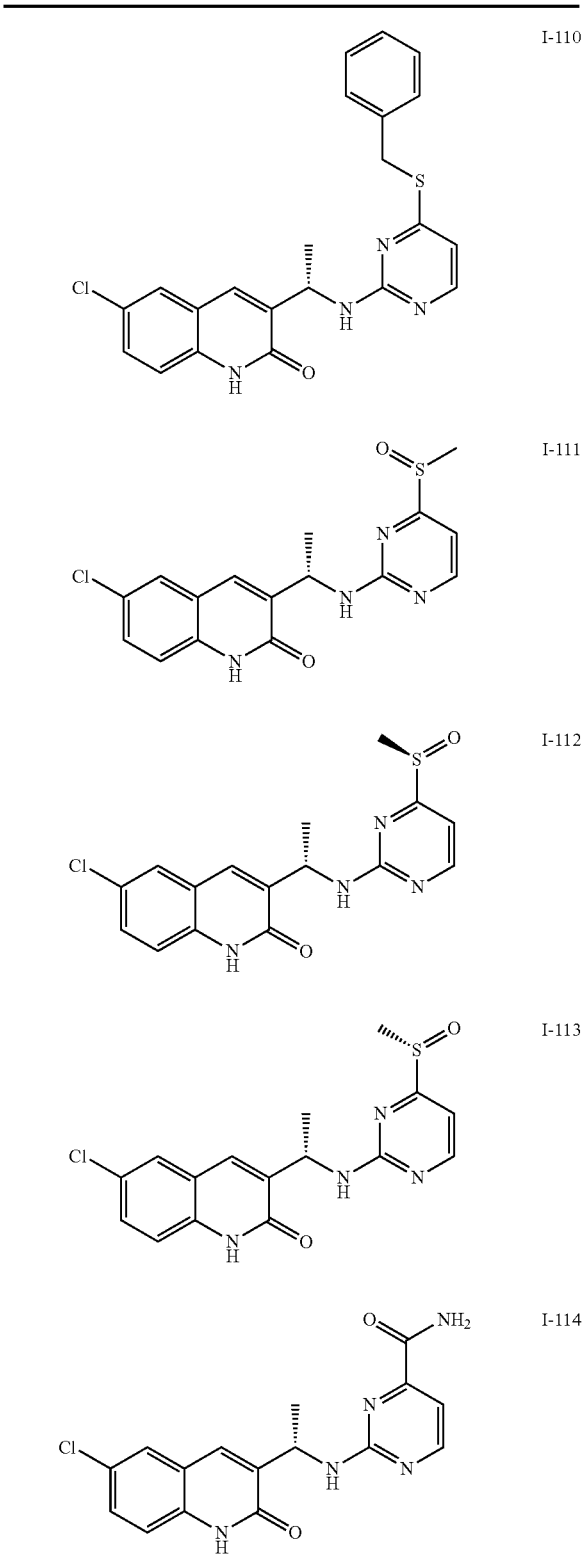
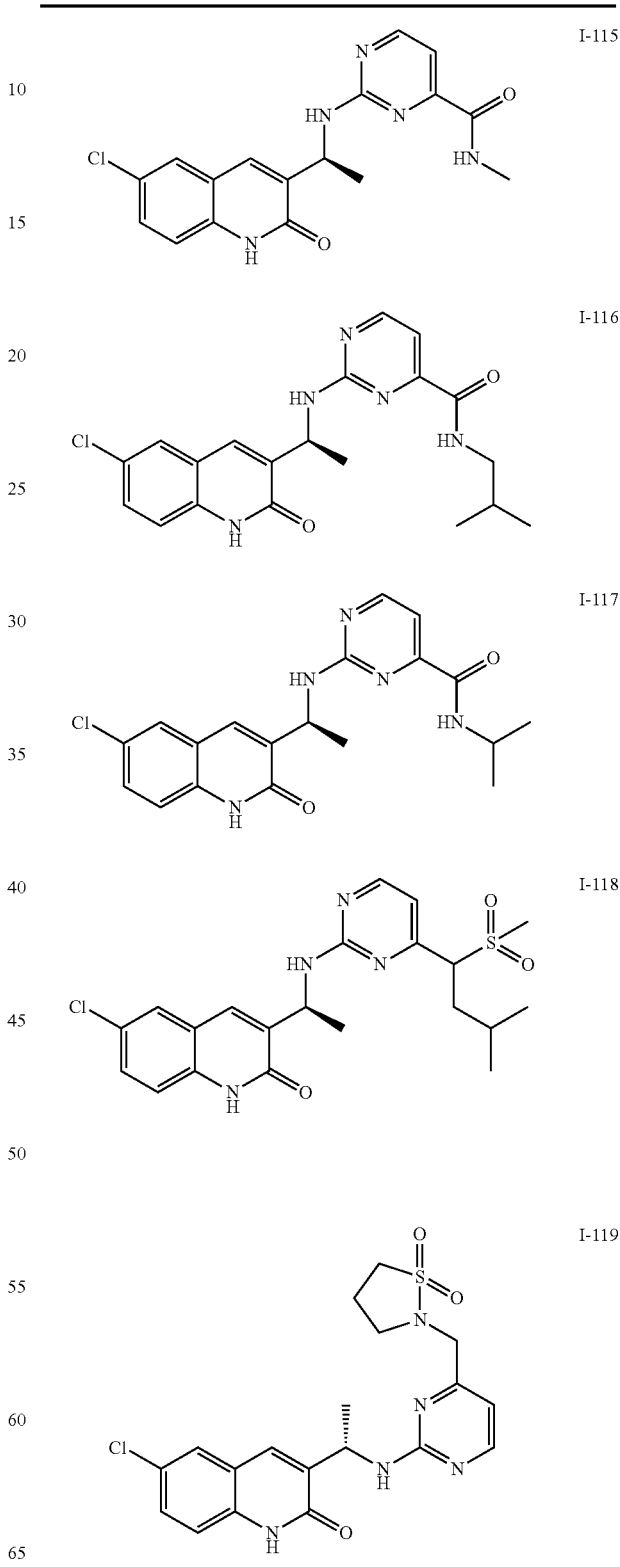

TABLE 13-continued
The compounds listed in Table 13 were prepared using methods similar to those described for the preparation of I-105, I-111, I-114, I-116, I-119, I-121-I-127, I-133, and I-135-I-137.
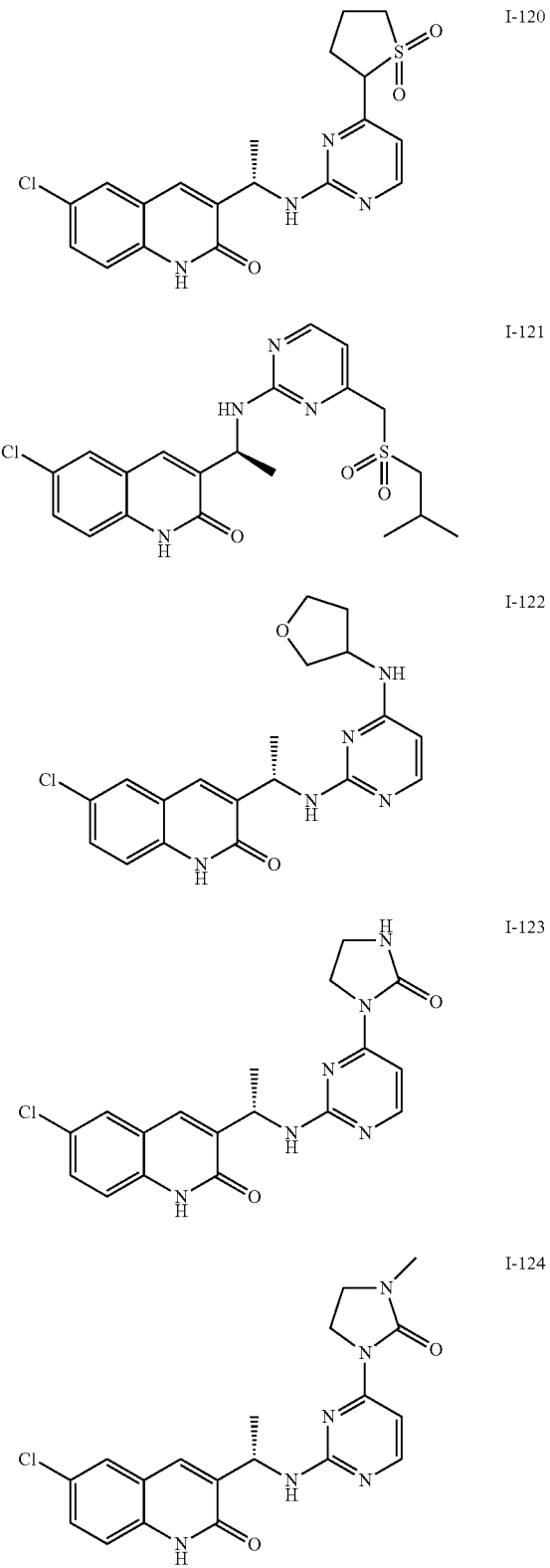
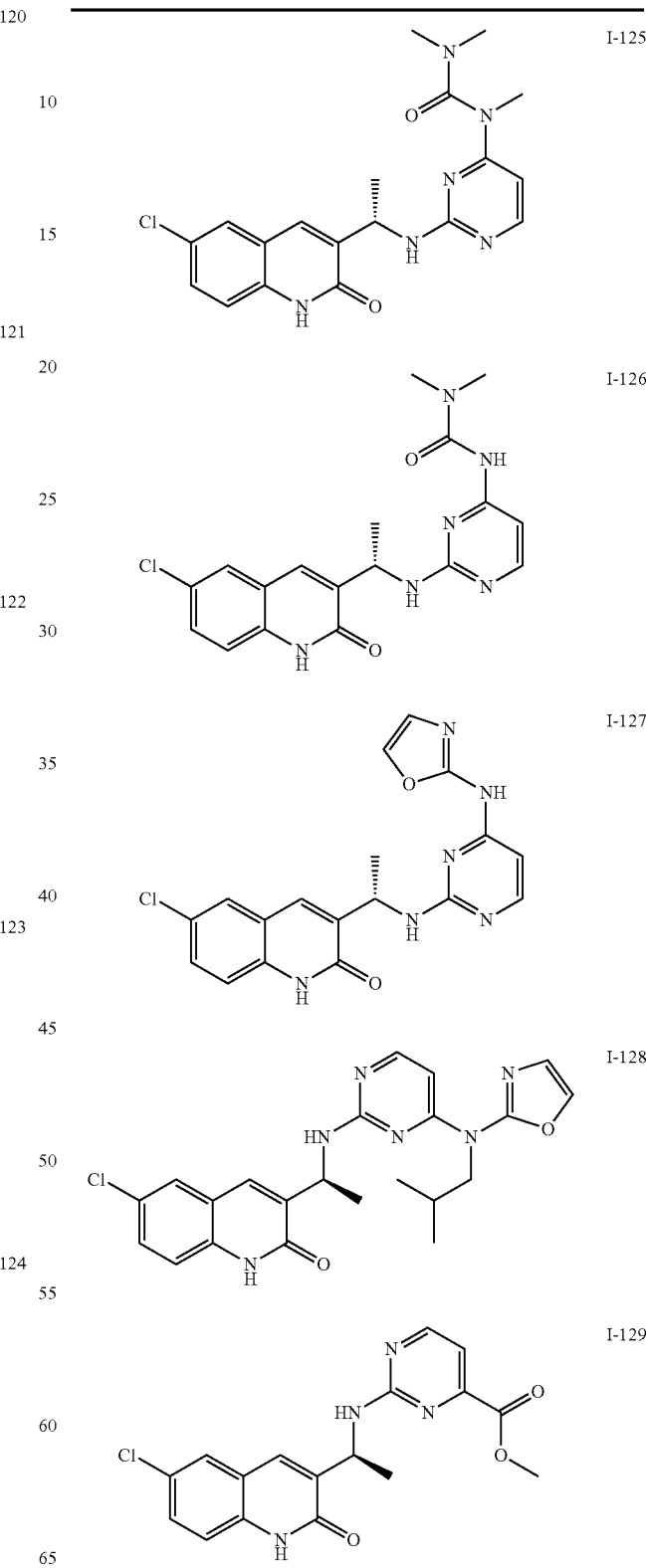

TABLE 13-continued
The compounds listed in Table 13 were prepared using methods similar to those described for the preparation of I-105, I-111, I-114, I-116, I-119, I-121-I-127, I-133, and I-135-I-137.
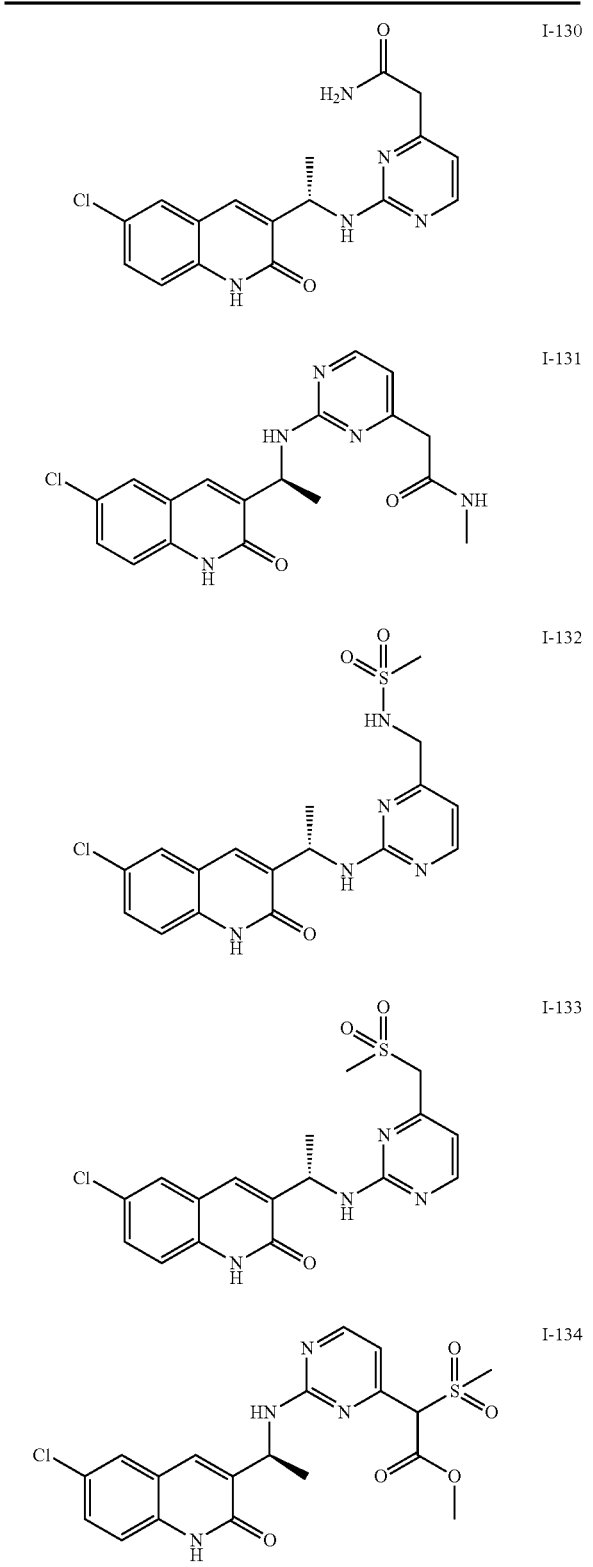

TABLE 13-continued

The compounds listed in Table 13 were prepared using methods similar to those described for the preparation of I-105, I-111, I-114, I-116, I-119, I-121-I-127, I-133, and I-135-I-137.

I-140

TABLE 14

LCMS signal and NMR chemical shifts for each compound listed in Table 13.

| Cmpds No | LCMS[a] | ¹H NMR (300 MHz) δ ppm |
|---|---|---|
| I-104 | m/z: 428.19 [M + H]⁺ Rt (min): 1.04 | ¹H NMR (300 MHz, CDCl$_3$): δ ppm 10.50 (br s, 1 H), 7.81 (d, J = 6.158 Hz, 1H), 7.68 (s, 1H), 7.48 (s, 1 H), 7.40 (d, J = 8.79 Hz, 1 H), 7.16 (d, J = 8.51 Hz, 1 H), 5.80 (br, 1 H), 5.77 (d, J = 6.45 Hz, 1 H), 5.27 (m, 1 H), 3.92 (d, J = 12.31 Hz, 1 H), 3.79 (d, J = 8.5 Hz, 1 H), 3.30-3.40 (m, 2 H), 3.02-3.20 (m, 1 H), 2.20-2.40 (m, 1 H), 1.54 (m, 4 H), 1.30 (br s, 3 H), 0.89 (br s, 3 H). |
| I-105 | m/z: 378.95 [M + H]⁺ Rt (min): 1.11 | ¹H NMR (300 MHz, CDCl$_3$): δ ppm 12.39 (br s, 1 H), 8.57 (d, J = 5.28 Hz, 1 H), 7.75 (s, 1 H), 7.55 (s, 1 H), 7.32-7.40 (m, 2 H), 7.14 (d, J = 4.69 Hz, 1 H), 5.35 (m, 1 H), 3.12 (s, 3 H), 1.68 (d, J = 7.04 Hz, 3 H). |
| I-106 | m/z: 405.05 [M + H]⁺ Rt (min): 1.18 | ¹H NMR (300 MHz, CDCl$_3$): δ ppm 11.75 (br s, 1 H), 7.90 (d, J = 5.27 Hz, 1 H), 7.67 (s, 1 H), 7.49 (s, 1 H), 7.427 (d, J = 8.8 Hz, 1 H), 7.29 (s, 1 H), 6.41 (d, J = 5.28 Hz, 1 H), 6.00 (d, J = 7.92 Hz, 1 H) 5.34 (m, 1 H), 2.94 (d, J = 6.74 Hz, 2 H), 1.81 (m, 1 H), 1.62 (d, J = 7.03 Hz, 3 H), 1.21 (m, 6 H). |
| I-107 | m/z: 389.11 [M + H]⁺ Rt (min): 1.72 | ¹H NMR (300 MHz, CDCl$_3$): δ ppm 12.68 (br s, 1 H), 7.91 (d, J = 5.28 Hz, 1 H), 7.69 (s, 1 H), 7.48 (s, 1 H), 7.37 (s, 1 H), 6.42 (d, J = 5.28 Hz, 1 H), 6.21 (br, 1 H), 5.37 (m, 1 H), 2.94 (m, 1 H), 1.82(m, 2 H), 1.27 (d, J = 6.75 Hz, 3 H), 0.93 (m, 6H). |
| I-108 | m/z: 421.04 [M + H]⁺ Rt (min): 1.36 | ¹H NMR (300 MHz, CDCl$_3$): δ ppm 12.06 (br s, 1 H), 8.54 (d, J = 8.5 Hz, 1 H), 8.32(d, J = 6.16 Hz, 1 H), 7.67 (s, 1 H), 7.47 (s, 1 H), 7.44 (m, 1 H), 7.33 (d, J = 8.8 Hz, 1 H), 5.292 (m, 1 H), 3.10 (m, 2H), 1.67 (d, J = 7.03 Hz, 3 H), 0.95 (d, J = 6.75 Hz, 3 H), 0.88 (d, J = 6.74 Hz, 3 H). |
| I-109 | m/z: 405.05 [M + H]⁺ Rt (min): 1.24 | ¹H NMR (300 MHz, CDCl$_3$): δ ppm 11.75 (br s, 1 H), 7.90 (d, J = 5.27 Hz, 1 H), 7.67 (s, 1 H), 7.49 (s, 1 H), 7.42 (d, J = 8.8 Hz, 1 H), 7.29 (s, 1 H), 6.41 (d, J = 5.28 Hz, 1 H), 6.00 (d, J = 7.92 Hz, 1 H) 5.34 (m, 1 H), 2.94 (d, J = 6.74 Hz, 2 H), 1.81 (m, 1 H), 1.62(d, J = 7.03 Hz, 3 H), 1.21 (m, 6 H). |
| I-110 | m/z: 422.95 [M + H]⁺ Rt (min): 1.65 | ¹H NMR (300 MHz, DMSO-d$_6$): δ ppm 11.92 (br s, 1 H), 7.94 (s, 1 H), 7.72 (m, 3 H), 7.47 (m, 1 H), 7.20-7.40 (m, 2 H), 7.68-7.20 (m, 3 H), 7.65 (d, J = 5.28 Hz, 1 H), 5.22 (m, 1 H), 4.34 (m, 1 H), 3.41 (m, 1H), 1.39 (d, J = 6.74 Hz, 1H). |
| I-111 | m/z: 363.03 [M + H]⁺ Rt (min): 0.98 | ¹H NMR (300 MHz, DMSO-d$_6$): δ ppm 11.96 (br s, 1 H), 8.53 (br, 1 H), 8.24 (br, 1 H), 7.72 (s, 1 H), 7.43-7.54 (m, 1 H), 7.26 (d, J = 8.84 Hz, 1 H), 7.09 (d, J = 4.98 Hz, 1 H), 5.12 (m, 1 H), 2.68 (s, 3 H), 1.38 (d, J = 6.74 Hz, 3 H). |

TABLE 14-continued

LCMS signal and NMR chemical shifts for each compound listed in Table 13.

| Cmpds No | LCMS[a] | ¹H NMR (300 MHz) δ ppm |
|---|---|---|
| I-112 | m/z: 363 [M + H]⁺ Rt (min): 0.99 | ¹H NMR (300 MHz, CDCl$_3$): δ ppm 11.50 (br s, 1 H), 8.49 (d, J = 4.98 Hz, 1 H), 7.68 (d, J = 4.99 Hz, 1 H), 7.52 (m, 1 H), 7.42-7.46 (m, 1 H), 7.29 (s, 1 H), 7.20 (d, J = 3.52 Hz, 1 H), 6.46 (br, 1 H), 5.30 (m, 1 H), 2.84 (s, 3 H), 1.65 (d, J = 7.04 Hz, 3H). |
| I-113 | m/z: 363.02 [M + H]⁺ Rt (min): 0.99 | ¹H NMR (300 MHz, DMSO-d$_6$): δ ppm 11.49 (br s, 1 H), 8.48 (d, J = 4.7 Hz, 1 H), 7.68 (d, J = 4.99 Hz, 1 H), 7.46 (d, J = 8.8 Hz, 1 H), 7.32 (s, 1 H), 7.18 (d, J = 8.21 Hz, 1 H), 6.66 (m, 1 H), 5.30 (m, 1 H), 2.71 (s, 3 H), 1.64 (d, J = 7.04 Hz, 3 H). |
| I-114 | m/z: 343.97 [M + H]⁺ Rt (min): 0.98 | ¹H NMR (300 MHz, DMSO-d$_6$): δ ppm 11.02 (br s, 1 H), 8.45 (d, J = 4.7 Hz, 1 H), 8.00 (br 1 H), 7.79 (br, 2 H), 7.72 (s, 1 H), 7.47 (d, J = 8.79 Hz, 1 H), 7.28 (d, J = 8.8 Hz, 1 H), 7.02 (d, J = 4.69 Hz, 1 H), 5.29 (m, 1 H), 1.41 (d, J = 7.04 Hz, 3 H). |
| I-115 | m/z: 358.08 [M + H]⁺ Rt (min): 1.04 | ¹H NMR (300 MHz, CDCl$_3$): δ ppm 11.05 (br s, 1 H), 8.47 (d, J = 4.99 Hz, 1 H), 7.95 (br, 1 H), 7.73 (s, 1 H), 7.52 (s, 1 H), 7.42 (d, J = 8.79 Hz, 1 H), 7.32 (d, J = 4.98 Hz, 1 H), 6.17 (s, 1 H) 5.43 (m, 1 H), 2.94 (d, J = 4.98 Hz, 3 H), 1.64 (d, J = 6.74 Hz, 3 H). |
| I-116 | m/z: 400.13 [M + H]⁺ Rt (min): 1.31 | ¹H NMR (300 MHz, DMSO-d$_6$): δ ppm 11.93 (br. s, 1 H), 8.47 (d, J = 4.69 Hz, 1 H), 8.30 (br, 1 H), 8.04 (br, 1 H), 7.80 (s, 1 H), 7.70 (s, 1 H), 7.44 (d, J = 8.8 Hz, 1 H), 7.28 (d, J = 9.09 Hz, 1 H), 7.02 (d, J = 4.1 Hz, 1 H) 5.23 (m, 1 H), 3.07 (m, 2 H), 1.81 (m, 1 H) 1.41 (d, J = 7.04 Hz, 3 H), 0.83 (m, 6 H). |
| I-117 | m/z: 386.10 [M + H]⁺ Rt (min): 1.21 | ¹H NMR (300 MHz, DMSO-d$_6$): δ ppm 11.92 (br s, 1 H), 8.45 (s, 1 H), 8.07 (br, 1 H), 7.79 (s, 1 H), 7.70 (s, 1 H), 7.45 (d, J = 8.8 Hz, 1 H), 7.31 (d, J = 9.09 Hz, 1 H), 7.01 (s, 1 H) 5.23 (m, 1 H), 3.99 (m, 1 H), 1.40 (d, J = 7.03 Hz, 3 H), 1.19 (d, J = 6.45 Hz, 3 H), 1.12(m, 3 H). |
| I-118 | m/z: 449.17 [M + H]⁺ Rt (min): 1.33 | |
| I-119 | m/z: 434.05 [M + H]⁺ Rt (min): 1.09 | ¹H-NMR(300 MHz, CDCl$_3$): δ ppm 11.35 (br s, 1 H), 8.23 (d, J = 4.95 Hz, 1 H), 7.69 (s, 1 H), 7.51 (d, J = 2.19 Hz, 1 H), 7.40 (dd, J = 2.22, 8.79 Hz, 1 H), 7.23 (m, 1 H), 6.64 (d, J = 4.95 Hz, 1 H), 6.05 (br d, J = 7.95 Hz, 1 H), 5.30 (m, 1 H), 4.05 (s, 2 H), 3.22 (t, 2 H), 3.13 (t, 2 H), 2.28 (m, 2 H), 1.61 (d, J = 6.87 Hz, 3 H). |
| I-120 | m/z: 419.01 [M + H]⁺ Rt (min): 1.1 | |
| I-121 | m/z: 435.09 [M + H]⁺ Rt (min): 1.38 | ¹H NMR (300 MHz, DMSO-d$_6$): δ ppm 11.96 (s, 1 H), 8.28 (br s, 1 H), 7.65-7.80 (m, 3 H), 7.45 (dd, J = 8.79, 2.35 Hz, 1 H), 7.27 (d, J = 8.79 Hz, 1 H), 6.65 (d, J = 4.69 Hz, 1 H), 5.17 (quin, J = 7.11 Hz, 1 H), 4.26-4.44 (m, 2 H), 2.63-3.22 (m, 2 H), 2.00-2.36 (m, 1 H), 1.39 (d, J = 7.04 Hz, 3 H), 0.64-1.11 (m, 6 H). |
| I-122 | m/z: 386.04 [M + H]⁺ Rt (min): 0.8 | ¹H NMR (300 MHz, DMSO-d$_6$): δ ppm 11.87 (s, 1 H), 7.60-7.67 (m, 2 H), 7.55 (br d, J = 4.98 Hz, 1 H), 7.40 (dd, J = 8.65, 2.49 Hz, 1 H), 7.22 (d, J = 8.79 Hz, 1 H), 6.74-7.14 (m, 1 H), 5.65 (d, J = 5.86 Hz, 1 H), 5.04 (br t, J = 6.74 Hz, 1 H), 3.35-3.85 (m, 5 H), 1.95-2.13 (m, 1 H), 1.59-1.73 (m, 1H), 1.28 (d, J = 6.74 Hz, 3 H). |
| I-123 | m/z: 384.99 [M + H]⁺ Rt (min): 0.85 | ¹H NMR (300 MHz, DMSO-d$_6$): δ ppm 11.93 (s, 1 H), 7.90-7.98 (m, 1 H), 7.67-7.74 (m, 2 H), 7.45 (dd, J = 8.79, 2.35 Hz, 1 H), 7.16-7.41 (m, 5 H), 5.06-5.21 (m, 1 H), 3.89 (br s, 2 H), 3.24-3.41 (m, 2H), 1.35 (d, J = 7.04 Hz, 3 H). |

TABLE 14-continued

LCMS signal and NMR chemical shifts for each compound listed in Table 13.

| Cmpds No | LCMS[a] | ¹H NMR (300 MHz) δ ppm |
|---|---|---|
| I-124 | m/z: 399.03 [M + H]+ Rt (min): 0.9 | ¹H NMR (300 MHz, DMSO-d₆): δ ppm 11.92 (s, 1 H), 7.96 (br d, J = 4.69 Hz, 1 H), 7.71 (d, J = 3.52 Hz, 2H), 7.45 (dd, J = 8.79, 2.35 Hz, 1 H), 7.22-7.82 (m 3H) 5.07-5.19 (m 1H) 3.33-3.95 (m, 2 H), 2.65-2.80 (m, 2 H), 1.36 (d, J = 6.74 Hz, 3 H). |
| I-125 | m/z: 401.07 [M + H]+ Rt (min): 0.83 | ¹H NMR (300 MHz, DMSO-d₆): δ ppm 11.92-11.97 (m, 1 H), 7.85-7.97 (m, 1 H), 7.67-7.74 (m, 2 H), 7.41-7.49 (m, 1 H), 7.27 (d, J = 8.79 Hz, 2 H), 5.91-5.97 (m, 1 H), 4.97-5.17 (m, 1 H), 2.55-3.17 (m, 9 H), 1.30-1.39 (m, 3 H). |
| I-126 | m/z: 387.07 [M + H]+ Rt (min): 0.97 | ¹H NMR (300 MHz, DMSO-d₆): δ ppm 11.94-12.00 (m, 1 H), 9.42-9.49 (m, 1 H), 9.01-9.11 (m, 1 H), 7.99-8.05 (m, 1 H), 7.81-7.87 (m, 1 H), 7.75-7.81 (m, 1 H), 7.44-7.52 (m, 1 H), 7.23-7.33 (m, 1 H), 6.26-6.36 (m, 1 H), 4.86-5.01 (m, 1 H), 3.06 (s, 6 H), 1.41 (d, J = 7.04 Hz, 3 H). |
| I-127 | m/z: 383.06 [M + H]+ Rt (min): 0.88 | ¹H NMR (300 MHz, DMSO-d₆): δ ppm 11.94 (s, 1 H), 10.63 (s, 1 H), 8.00-8.10 (m, 1 H), 7.72 (br d, J = 6.45 Hz, 3 H), 7.46 (br d, J = 8.50 Hz, 1 H), 7.27 (br d, J = 8.79 Hz, 2 H), 7.09 (d, J = 5.86 Hz, 1 H), 7.02 (s, 1 H), 5.10-5.22 (m, 1 H), 1.35-1.43 (m, 3 H). |
| I-128 | m/z: 439.09 [M + H]+ Rt (min): 1.2 | |
| I-129 | m/z: 358.99 [M + H]+ Rt (min): 1.21 | ¹H NMR (300 MHz, CDCl₃): δ ppm 12.60 (br s, 1 H), 8.46 (d, J = 4.78 Hz, 1 H), 7.71 (s, 1 H), 7.50 (s, 1 H), 7.42 (d, J = 8.79 Hz, 1 H), 7.32 (s, 1 H), 7.18 (d, J = 4.99 Hz, 1 H), 6.32 (br, 1 H), 5.29 (m, 1 H), 3.97(s, 3 H), 1.64 (d, J = 7.04 Hz, 3 H). |
| I-130 | m/z: 358 [M + H]+ Rt (min): 0.89 | ¹H NMR (300 MHz, CDCl₃): δ ppm 11.85 (br. s, 1 H), 8.16 (d, J = 5.87 Hz, 1 H), 7.69 (s, 1 H), 7.60 (d, J = 6.45 Hz, 1 H), 7.48 (s, 1 H), 7.40 (d, J = 8.51 Hz, 1 H), 6.05 (d, J = 7.62 Hz, 1 H), 5.30 (m, 1 H), 3.98 (m, 1 H), 3.82 (m, 1 H), 2.53 (m, 2 H), 1.96 (m, 2 H), 1.62 (d, J = 6.74 Hz, 3 H). |
| I-131 | m/z: 372.00 [M + H]+ Rt (min): 0.93 | ¹H NMR (300 MHz, CD₃OD): δ ppm 8.15 (d, J = 4.98 Hz, 1 H), 7.81 (s, 1 H), 7.60 (s, 1 H), 7.50 (d, J = 8.79 Hz, 1 H), 7.30 (d, J = 8.79 Hz, 1 H), 6.50 (d, J = 5.27 Hz, 1 H), 5.28 (m, 1 H), 3.44 (s, 2 H), 2.66 (s, 3 H), 1.53 (d, J = 7.04 Hz, 3 H). |
| I-132 | m/z: 408.02 [M + H]+ Rt (min): 1.03 | ¹H-NMR(300 MHz, CDCl₃) δ ppm: 10.40 (broad s, 0.6H), 8.19 (d, J = 4.95, 1H), 7.71 (s, 1H), 7.51 (d, J = 2.19, 1 H) 7.39 (dd, J = 2.22, 8.52, 1H), 7.17 (d, J = 8.52, 1H), 6.44 (d, J = 4.92, 1H), 6.04 (broad s, 1.4H), 5.35 (m, 1H), 4.19 (d, J = 4.92, 2H), 2.87 (s, 3H), 1.59 (d, J = 6.87, 3H) |
| I-133 | m/z: 393.08 [M + H]+ Rt (min): 1.05 | ¹H NMR (300 MHz, DMSO-d₆): δ ppm 11.95 (s, 1 H), 8.16-8.38 (m, 1 H), 7.60-7.80 (m, 3 H), 7.39-7.50 (m, 1 H), 7.21-7.31 (m, 1 H), 6.59-6.70 (m, 1 H), 5.08-5.21 (m, 1 H), 4.29-4.44 (m, 2 H), 2.74-3.22 (m, 3 H), 1.38 (d, J = 6.74 Hz, 3 H). |
| I-134 | m/z: 451.06 [M + H]+ Rt (min): 1.13 | |
| I-135 | m/z: 407.09 [M + H]+ Rt (min): 1.09 | ¹H NMR (300 MHz, DMSO-d₆): δ ppm 11.96 (br s, 1 H), 8.26 (br s, 1 H), 7.65-7.95 (m, 3 H), 7.46 (br dd, J = 8.79, 2.35 Hz, 1 H), 7.06-7.36 (m, 1 H), 6.65 (br d, J = 5.28 Hz, 1 H), 5.05-5.20(m, 1 H), 4.20-4.40 (m, 1 H), 1.07-1.43 (m, 9 H). |
| I-136 | m/z: 419.06 [M + H]+ Rt (min): 1.25 | |
| I-137 | m/z: 411.98 [M + H]+ Rt (min): 1.14 | ¹H-NMR(300 MHz, CDCl₃): δ ppm 11.93 (br s, 1.0 H), 8.15 (d, J = 5.22 Hz, 1 H), 7.67 (s, 1 H), 7.49 (d, J = 2.22 Hz, 1 H), 7.39 (dd, J = 2.22, 8.49 Hz, 1 H), 7.27 (d, J = 8.52 Hz, 1 H), 6.36 (d, J = 4.95 Hz, 1 H), 6.00 (br d, J = 7.95 Hz, 1 H), 5.30 (m, 1 H), 4.41 (s, 2 H), 2.73 (m, 1 H), 2.22 (s, 3 H), 1.60 (d, J = 6.87 Hz, 3 H), 0.72 (m, 4H). |
| I-138 | m/z: 384.08 [M + H]+ Rt (min): 1.14 | ¹H NMR (300 MHz, CDCl₃): δ ppm 11.85 (br s, 1 H), 8.16 (d, J = 5.87 Hz, 1 H), 7.69 (s, 1 H), 7.61 (d, J = 3.22 Hz, 1 H), 7.49 (s, 1 H), 7.40 (d, J = 8.51 Hz, 1 H), 7.28 (s, 1 H), 6.05 (d, J = 7.62 Hz, 1 H), 5.31 (m, 1 H), 3.90-4.02 (m, 1 H), 3.70-3.90 (m, 1 H), 2.42-2.56 (m, 2 H), 1.90-2.00 (m, 2 H), 1.60 (d, J = 6.74 Hz, 3 H). |
| I-139 | m/z: 315.95 [M + H]+ Rt (min): 0.8 | |
| I-140 | m/z: 400.12 [M + H]+ Rt (min): 0.86 | |

[a]LCMS (method 4)

Example 82—(R)-2-((1-(6-chloro-7-fluoro-2-oxo-1,2-dihydroquinolin-3-yl)ethyl)amino)-4-methoxypyrimidine-5-carbonitrile (I-141)

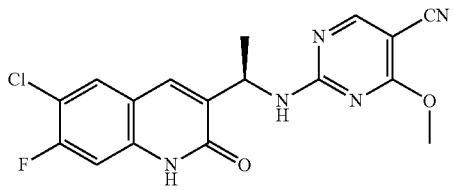 [SMILES: COc1nc(N[C@H](C)c2cc3cc(Cl)c(F)cc3[nH]c2=O)ncc1C#N]

A mixture of 2-chloro-4-methoxypyrimidine-5-carbonitrile (37.6 mg, 0.222 mmol) and (R)-3-(1-aminoethyl)-6-chloro-7-fluoroquinolin-2(1H)-one hydrochloride II-3b (55.0 mg, 0.198 mmol) was dissolved in DMSO (1.3 mL) and DIEA (105 μL, 0.601 mmol). The solution was stirred at 110° C. for 40 minutes. Water (20 mL) was added and the reaction mixture was extracted with DCM (2×15 mL). The combined extracts were dried (Na₂SO₄) and filtered. Silica gel was then added, and the solvent was evaporated under reduced pressure. The material was purified by column chromatography on a Biotage® MPLC chromatography system (10 g silica gel column, eluted with 0 to 50% EtOAc in hexanes). The material obtained was slurried in MeCN (2 mL) and water (1 mL), frozen, and lyophilized to provide (R)-2-((1-(6-chloro-7-fluoro-2-oxo-1,2-dihydroquinolin-3-yl)ethyl)amino)-4-methoxy pyrimidine-5-carbonitrile I-141 (42.6 mg, 0.114 mmol, 57.4% yield) as a white solid. ¹H NMR (300 MHz, DMSO-d₆): δ ppm 12.03 (br s, 1H), 8.57-8.80 (m, 1H), 8.49 (d, J=6.16 Hz, 1H), 7.98 (d, J=7.92 Hz, 1H), 7.74 (d, J=9.38 Hz, 1H), 7.20 (d, J=10.55 Hz, 1H), 5.13-5.29 (m, 1H), 3.77-4.01 (m, 3H), 1.37-1.48 (m, 3H). LCMS: m/z 374 [M+H]+.

Example 83—(S)-2-((1-(6-Chloro-7-methoxy-2-oxo-1,2-dihydroquinolin-3-yl)ethyl)amino)-4-methoxypyrimidine-5-carbonitrile (I-143)

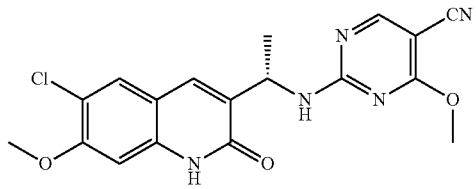 [SMILES: COc1cc2[nH]c(=O)c([C@H](C)Nc3ncc(C#N)c(OC)n3)cc2cc1Cl]

A mixture of 2-chloro-4-methoxypyrimidine-5-carbonitrile (45.9 mg, 0.271 mmol) and (S)-3-(1-aminoethyl)-6-chloro-7-methoxyquinolin-2(1H)-one hydrochloride II-4a (70.1 mg, 0.242 mmol) was dissolved in DMSO (1.6 mL) and DIEA (127 µl, 0.727 mmol). The solution was stirred at 110° C. for 45 minutes. Water (20 mL) was added and the reaction mixture was extracted with DCM (2×15 mL). The extracts were dried (Na$_2$SO$_4$) and filtered. Silica gel was then added, and the solvent was evaporated under reduced pressure. The material was purified by column chromatography on a Biotage® MPLC chromatography system (10 g silica gel column, eluted with 0 to 100% EtOAc in hexanes, with isocratic elution when peaks eluted). The product fractions were washed with water (40 mL), dried (Na$_2$SO$_4$), filtered, and evaporated under reduced pressure. The material was treated with MeCN (0.8 mL) and water (0.4 mL) to provide a thick slurry. The mixture was then frozen on a dry ice/acetone bath, then lyophilized to provide (S)-2-((1-(6-chloro-7-methoxy-2-oxo-1,2-dihydroquinolin-3-yl)ethyl) amino)-4-methoxypyrimidine-5-carbonitrile I-143 (70.3 mg, 0.182 mmol, 75% yield, HPLC purity 100% at 220 nm) as a white solid. $^1$H NMR (300 MHz, DMSO-d$_6$): δ ppm 11.83 (s, 1H), 8.50-8.74 (m, 1H), 8.48 (d, J=1.76 Hz, 1H), 7.77 (s, 1H), 7.68 (d, J=7.04 Hz, 1H), 6.94 (s, 1H), 5.15-5.29 (m, 1H), 3.78-4.00 (m, 3H), 3.88 (s, 3H), 1.36-1.46 (m, 3H). LCMS: m/z 386 [M+H]$^+$.

Example 84—(R)-2-((1-(6-Chloro-7-methoxy-2-oxo-1,2-dihydroquinolin-3-yl)ethyl)amino)-4-methoxypyrimidine-5-carbonitrile (I-144)

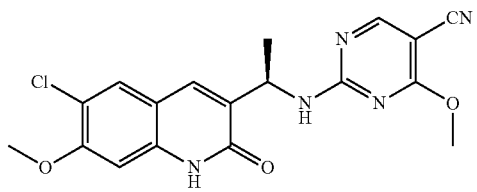 [SMILES: COc1cc2[nH]c(=O)c([C@@H](C)Nc3ncc(C#N)c(OC)n3)cc2cc1Cl]

A mixture of 2-chloro-4-methoxypyrimidine-5-carbonitrile (45.4 mg, 0.268 mmol) and (R)-3-(1-aminoethyl)-6-chloro-7-methoxyquinolin-2(1H)-one hydrochloride II-4b (69.7 mg, 0.241 mmol) was dissolved in DMSO (1.6 mL) and DIEA (127 µl, 0.727 mmol). The solution was stirred at 110° C. for 45 minutes. Water (20 mL) was added and the reaction mixture was extracted with DCM (2×15 mL). The extracts were dried (Na$_2$SO$_4$) and filtered. Silica gel was then added, and the solvent was evaporated under reduced pressure. The material was purified by column chromatography on a Biotage® MPLC chromatography system (using a 10 g silica gel column eluted with 0 to 100% EtOAc in hexanes, with isocratic elution when peaks eluted). The product fractions were washed with water (40 mL), then dried (Na$_2$SO$_4$), filtered, and evaporated. The material was treated with MeCN (0.8 mL) and water (0.4 mL) to provide a thick slurry. The mixture was then frozen on a dry ice/acetone bath, then lyophilized to provide (R)-2-((1-(6-chloro-7-methoxy-2-oxo-1,2-dihydroquinolin-3-yl)ethyl) amino)-4-methoxy pyrimidine-5-carbonitrile I-144 (73.2 mg, 0.190 mmol, 79% yield, HPLC purity 100% at 220 nm) as a white solid. $^1$H NMR (300 MHz, DMSO-d$_6$): δ ppm 11.83 (s, 1H), 8.50-8.74 (m, 1H), 8.48 (d, J=1.47 Hz, 1H), 7.77 (s, 1H), 7.68 (d, J=7.04 Hz, 1H), 6.94 (s, 1H), 5.14-5.30 (m, 1H), 3.77-4.02 (m, 3H), 3.88 (s, 3H), 1.42 (t, J=6.45 Hz, 3H). LCMS: m/z 386 [M+H]$^+$.

Example 85—(S)-2-((1-(6-Chloro-2-oxo-7-(pyridin-2-ylmethoxy)-1,2-dihydroquinolin-3-yl)ethyl) amino)-4-methoxypyrimidine-5-carbonitrile (I-151) and (S)-2-((1-(6-chloro-2-oxo-7-(pyridin-2-ylmethoxy)-1,2-dihydroquinolin-3-yl)ethyl)amino)-4-hydroxypyrimidine-5-carbonitrile (I-152)

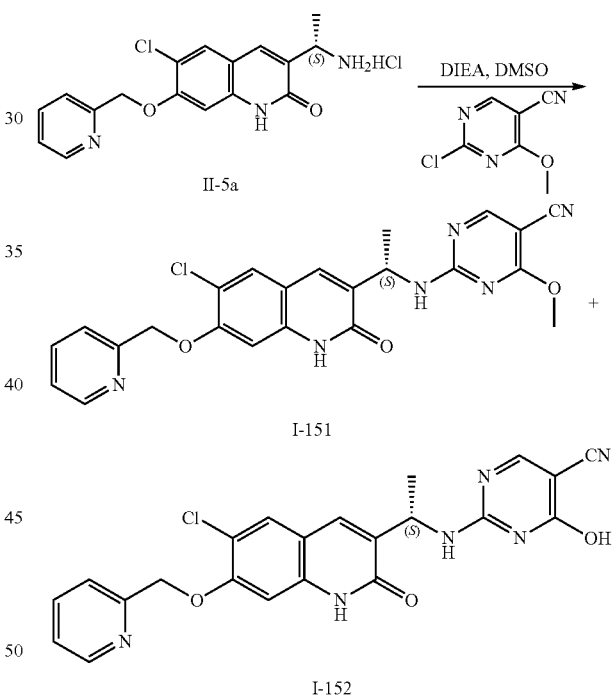

To a solution of 2-chloro-4-methoxypyrimidine-5-carbonitrile (9.72 mg, 0.057 mmol) and (S)-3-(1-aminoethyl)-6-chloro-7-(pyridin-2-ylmethoxy)quinolin-2(1H)-one hydrochloride II-5a (21 mg, 0.057 mmol) in DMSO (0.4 mL) was added DIEA (0.060 mL, 0.344 mmol). The solution was stirred at 110° C. for 5 hours. Once LCMS indicated most of the starting material was consumed, the mixture was cooled to 40° C. and a stream nitrogen gas was blown into the mixture for 2 days. De-methylated by-product (~23%) was also observed by LCMS. The mixture was then diluted with DCM and washed with water (2×) and brine (×1). The organic extracts were dried (Na$_2$SO$_4$), filtered, and evaporated under reduced pressure. The crude material (35 mg) was purified by reversed phase HPLC to yield two products:

(S)-2-((1-(6-Chloro-2-oxo-7-(pyridin-2-ylmethoxy)-1,2-dihydroquinolin-3-yl)ethyl)amino)-4-methoxypyrimidine-5-carbonitrile (I-151)

(6.2 mg, 23.4% yield), $^1$H NMR (300 MHz, CDCl$_3$): δ ppm 11.50 (br s, 1H), 10.80 (br s, 1H), 8.47-8.59 (m, 1H), 8.12-8.26 (m, 1H), 7.64-7.75 (m, 1H), 7.45-7.59 (m, 3H), 7.19-7.26 (m, 1H), 6.76-6.89 (m, 1H), 5.33 (d, J=12.3 Hz, 2H), 5.12-5.27 (m, 1H), 3.77-3.97 (m, 3H), 1.49-1.69 (m, 3H). LCMS (Method 1): Rt 2.52 min, m/z 462.87 [M+H]$^+$.

(S)-2-((1-(6-chloro-2-oxo-7-(pyridin-2-ylmethoxy)-1,2-dihydroquinolin-3-yl)ethyl)amino)-4-hydroxypyrimidine-5-carbonitrile (I-152)

(2.7 mg, 10.5% yield), LC/MS (Method 1): Rt 2.52 min, m/z 448.3987 [M+H]$^+$.

Example 86—(S)-methyl (2-((1-(6-Vhloro-2-oxo-7-(pyridin-2-ylmethoxy)-1,2-dihydroquinolin-3-yl)ethyl) amino)pyrimidin-4-yl)carbamate title compound as a yellow solid (890 mg, 62% yield). The compound was used in the next step without further purification.

Step-2: (S)-methyl (2-((1-(6-Chloro-2-oxo-7-(pyridin-2-ylmethoxy)-1,2-dihydroquinolin-3-yl)ethyl)amino) pyrimidin-4-yl)carbamate (I-154)

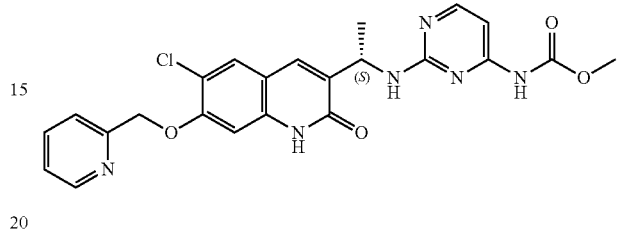

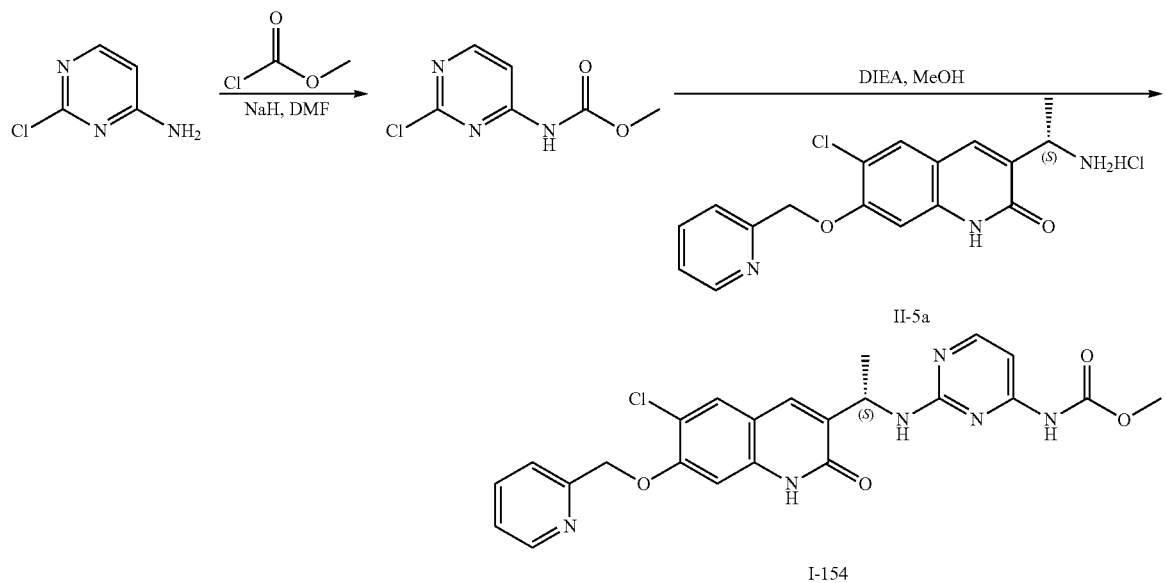

Step-1: Methyl (2-chloropyrimidin-4-yl)carbamate

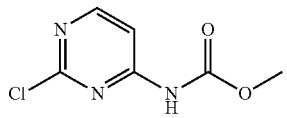

To a solution of 2-chloropyrimidin-4-amine (1 g, 7.71 mmol) in DMF (10 mL) was added sodium hydride (60% in paraffin oil, 620 mg, 15.43 mmol). The resulting suspension was stirred at ambient temperature for 20 minutes. To this mixture was added methyl carbonochloridate (0.9 mL, 11.57 mmol), and the mixture was then stirred at room temperature overnight. Once TLC and MS showed completion of reaction, the mixture was poured on to crushed ice, the resulting solid was filtered, washed with water and dried to afford the A mixture of II-5a (100 mg, 0.22 mmol), methyl (2-chloropyrimidin-4-yl)carbamate (64 mg, 0.34 mmol) and DIEA (76 μL, 0.44 mmol) in MeOH (3 mL) was heated at 120° C. for 2 hours. Once TLC and MS showed completion of reaction, the mixture was diluted with CH$_2$Cl$_2$ (25 mL) and water. The organic layer was separated, dried over anhydrous Na$_2$SO$_4$, filtered and evaporated to dryness. The resulting residue was purified by column chromatography on an ISCO® chromatography system (SiO$_2$ column: MeOHCH$_2$Cl$_2$ 0 to 5% gradient elution) to obtain the title compound I-154 (9 mg, 8° % yield). $^1$H NMR (300 MHz, DMSO-d$_6$): δ ppm 11.78 (br s, 1H), 10.08 (br s, 1H), 8.61 (d, J=4.1 Hz, 1H), 8.1 (d, J=5.5 Hz, 1H), 7.90-7.82 (m, 1H), 7.78 (s, 1H), 7.69 (s, 1H), 7.56 (d, J:=7.6 Hz, 1H), 7.39-7.34 (mi, 1H), 7.19 (br, s, 1H), 7.02-7.00 (m, 2H), 5.28 (s, 2H), 5.15-5.11 (m, 1H), 3.65 (s, 3H), 1.39 (d, J=6.9 Hz, 3H). LCMS (method 3): Rt 7.79 min, m/z 481.1 [M+H]$^+$.

Example 87—(S)-2-((1-(7-Chloro-3-oxo-3,4-dihydroquinoxalin-2-yl)ethyl)amino)-4-methoxy pyrimidine-5-carbonitrile (I-156)

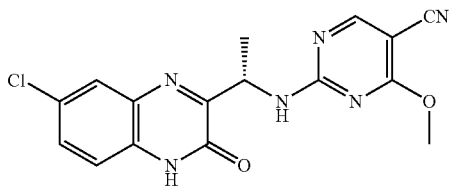 [SMILES: COc1nc(N[C@@H](C)c2nc3cc(Cl)ccc3[nH]c2=O)ncc1C#N]

To a solution of intermediate II-7b (35 mg, 0.1 mmol) in EtOH (10 mL), was added 2-chloro-4-methoxypyrimidine-5-carbonitrile (26 mg, 0.16 mmol) and DIEA (0.5 mL). The reaction mixture was heated to 70° C. and stirred for 4 hours. The reaction mixture was then cooled to room temperature, concentrated under vacuum and purified by column chromatography on an ISCO® chromatography system with hexanes to EtOAc as eluent to afford I-156 (31 mg, 87%) as a white solid. $^1$H NMR (300 MHz, DMSO-$d_6$, 120° C.): δ ppm 12.20 (br, s, 1H), 8.42 (s, 1H), 7.92 (br s, 1H), 7.74 (d, J=2.19 Hz, 1H), 7.53 (dd, J=8.52, 2.19 Hz, 1H), 7.31 (d, J=8.52 Hz, 1H), 5.22 (m, 1H), 3.94 (s, 3H), 1.53 (d, J=6.87 Hz, 3H). LCMS (Method 3): Rt 5.28 min, m/z 356.1 [M+H]$^+$.

Example 88—(S)-2-((1-(6-chloro-2-oxo-1,2-dihydro-1,8-naphthyridin-3-yl)ethyl)amino)-4-methoxy pyrimidine-5-carbonitrile (I-155)

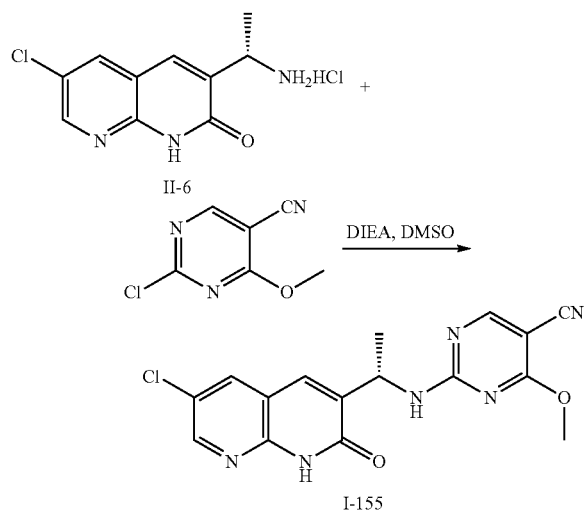

A mixture of (S)-3-(1-aminoethyl)-6-chloro-1,8-naphthyridin-2(1H)-one, HCl, II-6 (49 mg, 0.188 mmol), DIEA (0.099 ml, 0.565 mmol), and 2-chloro-4-methoxypyrimidine-5-carbonitrile (41.5 mg, 0.245 mmol) in DMSO (1 ml) was heated to 110° C. for 3 hours, Once crude LC/Mass completion of reaction, the reaction mixture was cooled room temperature, 15 ml water was added and the resulting mixture was filtered. The crude solid was then purified by HPLC on a Waters HPLC chromatography system using a long method to afford (S)-2-((1-(6-chloro-2-oxo-1,2-dihydro-1,8-naphthyridin-3-yl)ethyl)amino)-4-methoxypyrimidine-5-carbonitrile (18.2 mg, 27.1% yield). $^1$H NMR (300 MHz, DMSO-$d_6$): δ ppm 12.39 (br s, 1H), 8.76 (br d, J=7.33 Hz, 0.5H), 8.59 (br d, J=7.62 Hz, 0.5H), 8.35-8.49 (m, 2H), 8.07-8.27 (m, 1H), 7.69 (d, J=5.86 Hz, 1H), 5.04-5.31 (m, 1H), 3.64-4.01 (m, 3H), 1.09-1.52 (m, 3H).

Example 89—2-(((S)-1-(6-chloro-2-oxo-7-((R)-1-(pyridin-2-yl)ethoxy)-1,2-dihydroquinolin-3-yl)ethyl)amino)-4-methoxypyrimidine-5-carbonitrile (I-158)

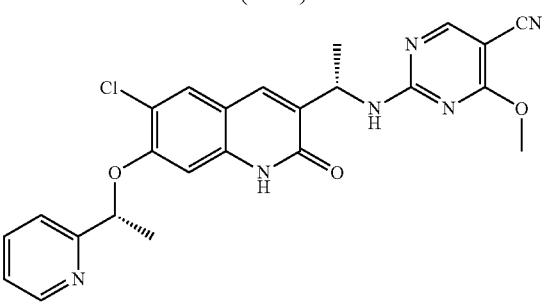

A mixture of 2-chloro-4-methoxypyrimidine-5-carbonitrile (22.0 mg, 0.130 mmol) and 3-((S)-1-aminoethyl)-6-chloro-7-((R)-1-(pyridin-2-yl)ethoxy)quinolin-2(1H)-one hydrochloride II-8 (43.2 mg, 0.114 mmol) was dissolved in DMSO (0.8 mL) and DIEA (60 μL, 0.344 mmol) the resulting solution was stirred at 110° C. for 40 minutes. Water (20 mL) was then added and the reaction mixture was extracted with DCM (2×15 mL). The combined extracts were washed with water (2×20 mL), dried (Na$_2$SO$_4$) and filtered, silica gel was added, and the solvent was evaporated under reduced pressure. The material was purified by column chromatography on a Biotage® MPLC chromatography system (using a 10 g silica gel column eluted with 0 to 4.4% MeOH in hexanes). The product fractions were evaporated and then combined with material from a previous batch. The material was dissolved in MeCN (0.8 mL), treated with water (0.4 mL), frozen on a dry ice/acetone bath and lyophilized to provide 2-(((S)-1-(6-chloro-2-oxo-7-((R)-1-(pyridin-2-yl)ethoxy)-1,2-dihydroquinolin-3-yl)ethyl)amino)-4-methoxypyrimidine-5-carbonitrile I-158 (41.5 mg, 0.087 mmol, 38% yield for the combined runs, HPLC purity 100% at 220 nm) as a white solid. $^1$H NMR (300 MHz, DMSO-$d_6$): δ ppm 11.64-11.71 (m, 1H), 8.49-8.71 (m, 2H), 8.45-8.48 (m, 1H), 7.75-7.85 (m, 2H), 7.63 (d, J=9.09 Hz, 1H), 7.37-7.43 (m, 1H), 7.28-7.36 (m, 1H), 6.85 (s, 1H), 5.51 (q, J=6.16 Hz, 1H), 5.11-5.24 (m, 1H), 3.77-4.00 (m, 3H), 1.66 (d, J=6.45 Hz, 3H), 1.31-1.43 (m, 3H). LCMS: m/z 477 [M+H]$^+$.

Example 90—(S)-2-((1-(6-chloro-7-(Cyclopropylmethoxy)-2-oxo-1,2-dihydroquinolin-3-yl)ethyl)amino)-4-methoxypyrimidine-5-carbonitrile (I-159)

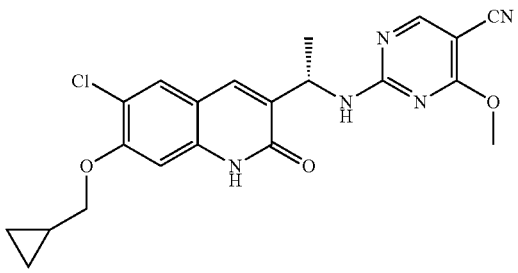 [SMILES: COc1nc(N[C@@H](C)c2cc3cc(Cl)c(OCC4CC4)cc3[nH]c2=O)ncc1C#N]

A mixture of 2-chloro-4-methoxypyrimidine-5-carbonitrile (40.9 mg, 0.241 mmol) and (S)-3-(1-aminoethyl)-6-chloro-7-(cyclopropylmethoxy)quinolin-2(1H)-one hydrochloride II-9 (70.8 mg, 0.215 mmol) was dissolved in DMSO (1.5 mL) and DIEA (114 μL, 0.653 mmol) the resulting solution was stirred at 110° C. for 40 minutes. Water (40 mL) was then added and the reaction mixture was extracted with DCM (2×20 mL). The combined extracts were washed with water (2×20 mL), dried (Na$_2$SO$_4$) and filtered. Silica gel was then added, and the solvent was evaporated under reduced pressure. The material was purified by column chromatography on a Biotage® MPLC chromatography system (using a 10 g silica gel column eluted with 0 to 65% EtOAc in hexanes). The purified product was dissolved in MeCN (2 mL), treated with water (1 mL), frozen on a dry ice/acetone bath, and lyophilized to provide (S)-2-((1-(6-chloro-7-(cyclopropylmethoxy)-2-oxo-1,2-dihydroquinolin-3-yl)ethyl)amino)-4-methoxypyrimidine-5-carbonitrile I-159 (63.2 mg, 0.148 mmol, 69.0% yield, HPLC purity 100% at 220 nm) as a white solid. $^1$H NMR (300 MHz, DMSO-d$_6$): δ ppm 11.73-11.81 (m, 1H), 8.51-8.74 (m, 1H), 8.48 (d, J=2.05 Hz, 1H), 7.76 (s, 1H), 7.67 (d, J=7.62 Hz, 1H), 6.91 (s, 1H), 5.15-5.28 (m, 1H), 3.79-4.01 (m, 3H), 3.92 (d, J=6.74 Hz, 2H), 1.36-1.46 (m, 3H), 1.21-1.30 (m, 1H), 0.56-0.65 (m, 2H), 0.35-0.44 (m, 2H). LCMS: m/z 426 [M+H]$^+$.

Example 91—(S)—N-(2-((1-(6-Chloro-8-fluoro-2-oxo-1,2-dihydroquinolin-3-yl)ethyl)amino)pyrimidin-4-yl)acetamide (I-160)

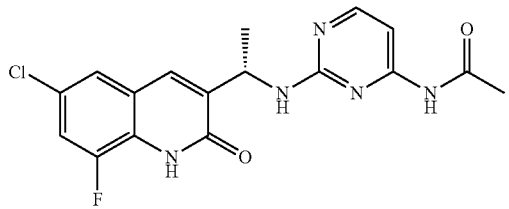 [SMILES: CC(=O)Nc1ccnc(N[C@@H](C)c2cc3cc(Cl)cc(F)c3[nH]c2=O)n1]

A solution of (S)-3-(1-aminoethyl)-6-chloro-8-fluoroquinolin-2(1H)-one hydrochloride II-11 (111.2 mg, 0.401 mmol) and N-(2-chloropyrimidin-4-yl)acetamide III-4 (75.4 mg, 0.439 mmol) in DMSO (2.4 mL) was treated with DIEA (207 μL, 1.185 mmol) and stirred at 110° C. for six hours. The sample was then pipetted onto water (40 mL), and the resulting precipitate was extracted with EtOAc (2×20 mL). The combined organic extracts were washed with water (20 mL), treated with silica gel, and evaporated under reduced pressure. The material was purified by column chromatography on a Biotage® MPLC chromatography system (10 g silica gel column) and eluted with 0 to 73% EtOAc in hexanes, with isocratic elution when peaks eluted. The product fractions were combined, washed with water (2×30 mL), and evaporated under reduced pressure. The residue was dissolved in MeCN (2 mL) and water (1 mL), frozen (dry ice/acetone bath), and lyophilized to provide (S)—N-(2-((1-(6-chloro-8-fluoro-2-oxo-1,2-dihydroquinolin-3-yl)ethyl)amino)pyrimidin-4-yl)acetamide I-160 (24.3 mg, 0.065 mmol, 16.12% yield, HPLC purity 100% at 220 nm) as a light orange solid. $^1$H NMR (300 MHz, DMSO-d$_6$): δ ppm 12.00 (br s, 1H), 10.23 (s, 1H), 8.13 (br d, J=5.57 Hz, 1H), 7.78 (s, 1H), 7.62 (br s, 1H), 7.57 (dd, J=10.55, 2.05 Hz, 1H), 7.14-7.45 (m, 2H), 5.19 (quin, J=7.11 Hz, 1H), 2.06 (s, 3H), 1.41 (d, J=6.74 Hz, 3H). LCMS: m/z 376 [M+H]$^+$.

Example 92—(S)-2-((1-(6-Chloro-8-fluoro-2-oxo-1,2-dihydroquinolin-3-yl)ethyl)amino)-4-methoxypyrimidine-5-carbonitrile (I-161)

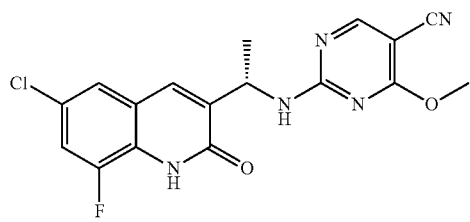 [SMILES: COc1nc(N[C@@H](C)c2cc3cc(Cl)cc(F)c3[nH]c2=O)ncc1C#N]

A solution of (S)-3-(1-aminoethyl)-6-chloro-8-fluoroquinolin-2(1H)-one hydrochloride II-11 (90.6 mg, 0.327 mmol) and 2-chloro-4-methoxypyrimidine-5-carbonitrile (63.7 mg, 0.376 mmol) in DMSO (2.0 mL) was treated with DIEA (172 μl, 0.985 mmol) and stirred at 110° C. for 50 minutes. The sample was poured into water (40 mL), and the resulting precipitate was extracted with DCM (2×20 mL). The combined extracts were washed with water (30 mL), and the aqueous layer was back-extracted with EtOAc (20 mL). The DCM and EtOAc extracts were combined, dried (MgSO$_4$), and filtered. Silica gel was then added and the sample was evaporated under reduced pressure. The material was purified by column chromatography on a Biotage® MPLC chromatography system (using a 10 g silica gel column eluted with 0 to 45% EtOAc in hexanes, with isocratic elution when peaks eluted). The product fractions were combined, washed with water (2×30 mL), and evaporated under reduced pressure. The residue was dissolved in MeCN (2 mL) and water (1 mL), frozen (using a dry ice/acetone bath), and lyophilized to provide (S)-2-((1-(6-chloro-8-fluoro-2-oxo-1,2-dihydroquinolin-3-yl)ethyl) amino)-4-methoxypyrimidine-5-carbonitrile I-161 (68.1 mg, 0.182 mmol, 55.7% yield, HPLC purity 100% at 220 nm) as a pale yellow solid. $^1$H NMR (300 MHz, DMSO-d$_6$): δ ppm 12.07 (s, 1H), 8.60-8.85 (m, 1H), 8.49 (d, J=7.33 Hz, 1H), 7.77 (d, J=7.92 Hz, 1H), 7.65 (br s, 1H), 7.54-7.62 (m, 1H), 5.16-5.30 (m, 1H), 3.77-4.01 (m, 3H), 1.38-1.49 (m, 3H). LCMS: m/z 374 [M+H]$^+$.

Example 93—6-Chloro-3-(((4,6-dimethoxypyrimidin-2-yl)amino)methyl)quinolin-2(1H)-one (I-163)

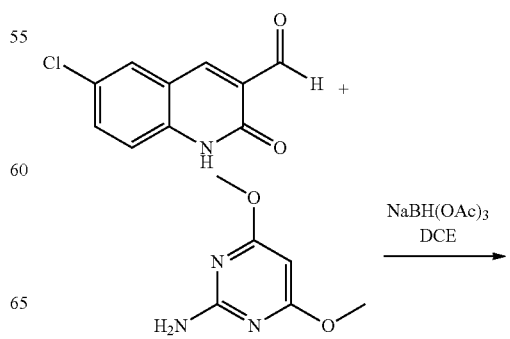

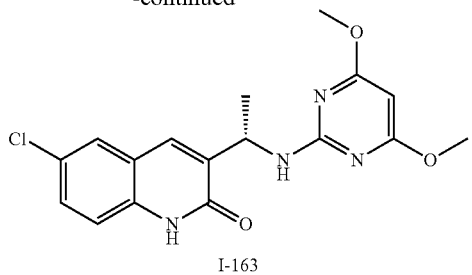

I-163

6-Chloro-2-oxo-1,2-dihydroquinoline-3-carbaldehyde (6.21 mg, 30 μmol) was added as a solid to a 0.2M solution of 4,6-dimethoxypyrimidin-2-amine in DMA (165 μL, 33 μmol). Additional 1,2-dichloroethane (150 mL) was then added, and the mixture was agitated at room temperature for 5 minutes. The resulting mixture was treated with a 0.2M suspension of sodium triacetoxyborohydride in DCE (300 μL, 60 μmol) and was agitated overnight at room temperature. Once LCMS analysis confirmed the presence of reductive amination product, the mixture was partitioned between ethyl acetate (500 μL) and saturated aqueous sodium bicarbonate solution (500 μL). The organic layer was transferred and the aqueous layer was then extracted once more with fresh ethyl acetate (500 μL). The organic layers were combined and concentrated under reduced pressure with heat (50° C.). The crude residue was dissolved in DMSO (500 μL) and purified by mass-triggered preparatory HPLC to afford the title compound (1.3 mg, 13% yield). LCMS (Method 4, ESI): Rt 1.36 min, m/z 347.02 [M+H]$^+$.

TABLE 15

The compounds listed in Table 15 were prepared using methods similar to those described for the preparation of I-141, I-143, I-144, I-151, I-154-I-156, and I-158-I-163.

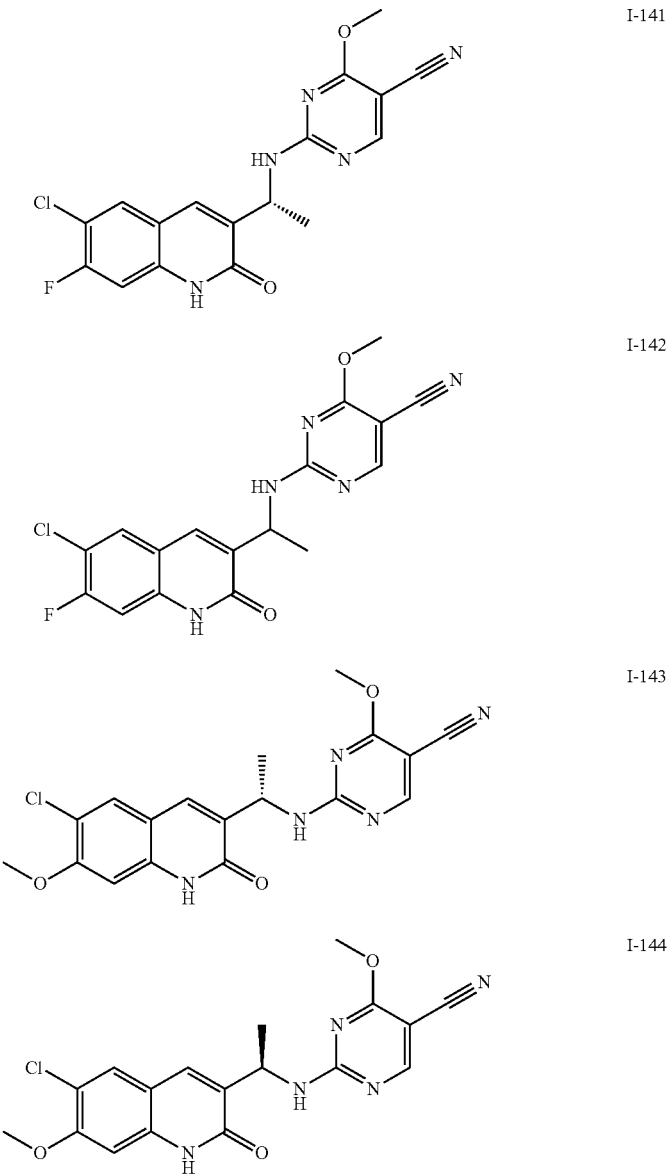

TABLE 15-continued
The compounds listed in Table 15 were prepared using methods similar to those described for the preparation of I-141, I-143, I-144, I-151, I-154-I-156, and I-158-I-163.
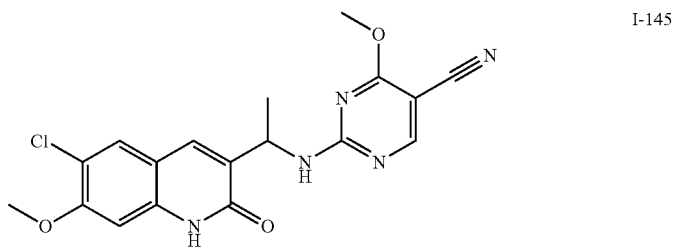
I-145
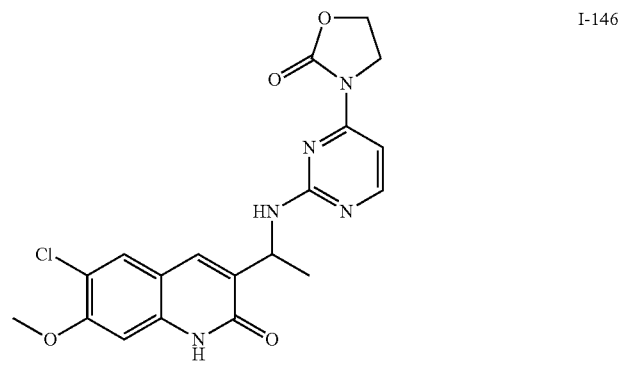
I-146
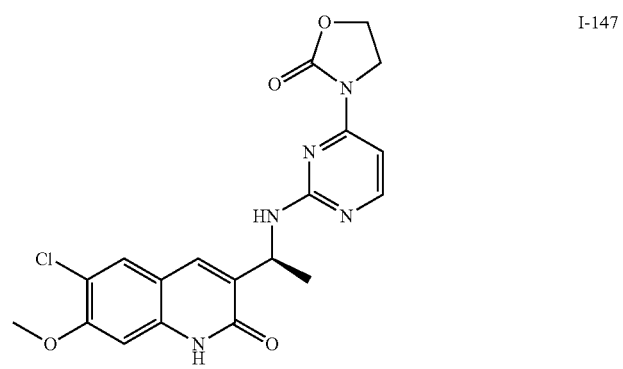
I-147
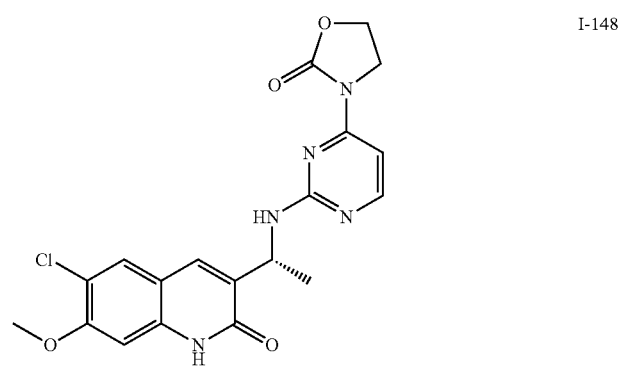
I-148

TABLE 15-continued
The compounds listed in Table 15 were prepared using methods similar to those described for the preparation of I-141, I-143, I-144, I-151, I-154-I-156, and I-158-I-163.
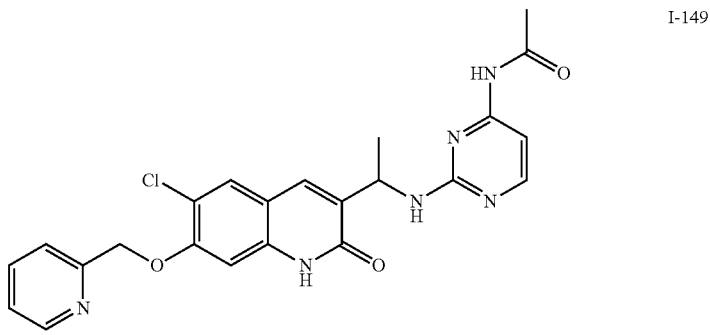
I-149
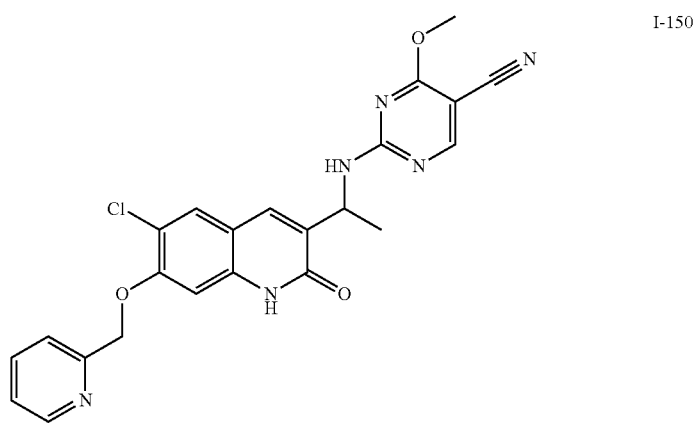
I-150
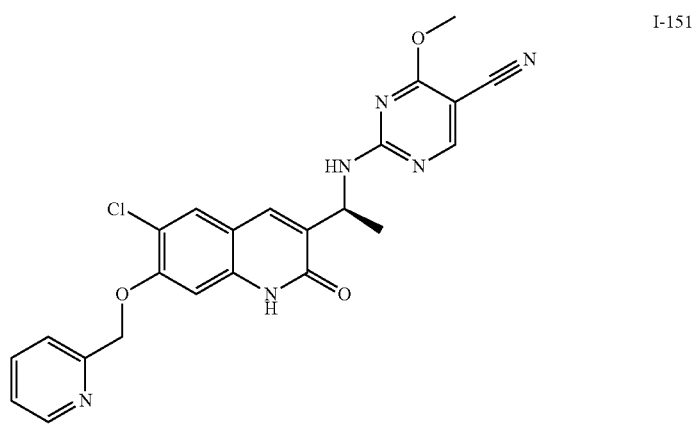
I-151
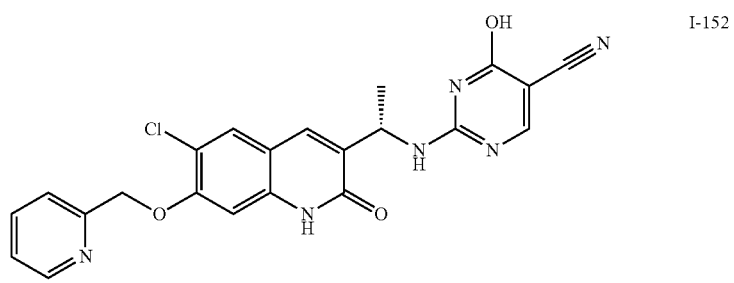
I-152

TABLE 15-continued
The compounds listed in Table 15 were prepared using methods similar to those described for the preparation of I-141, I-143, I-144, I-151, I-154-I-156, and I-158-I-163.
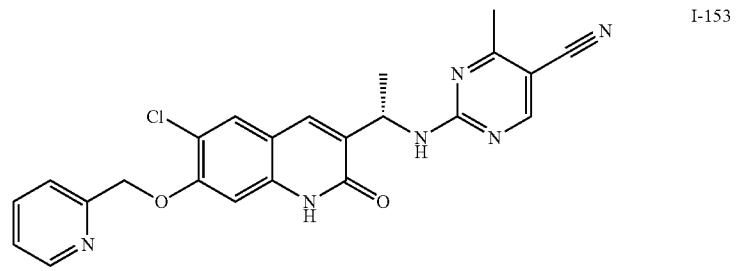
I-153
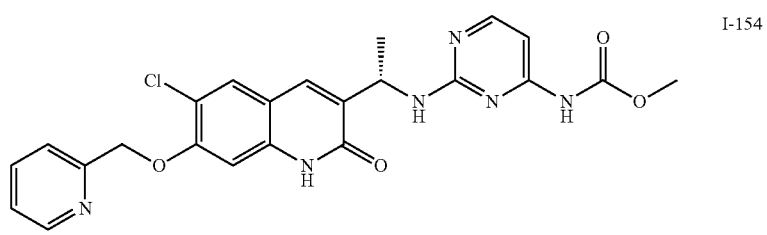
I-154
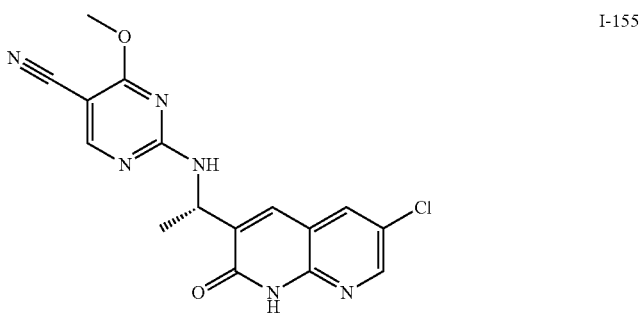
I-155
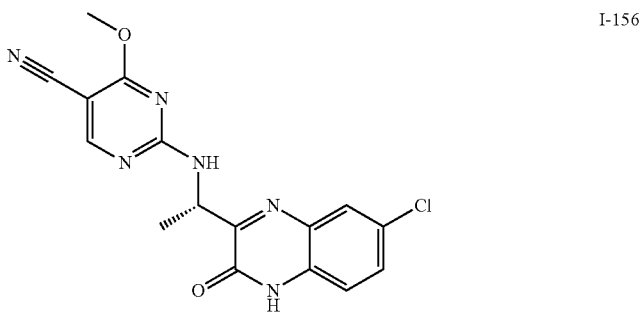
I-156
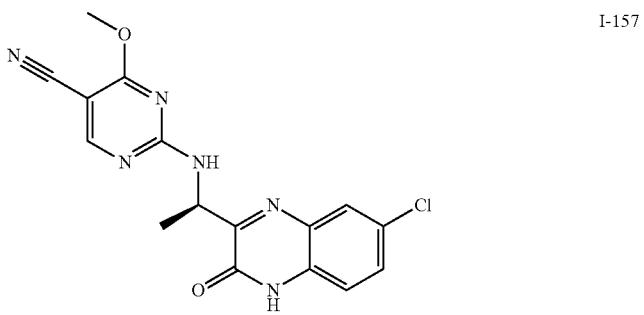
I-157

TABLE 15-continued
The compounds listed in Table 15 were prepared using methods similar to those described for the preparation of I-141, I-143, I-144, I-151, I-154-I-156, and I-158-I-163.
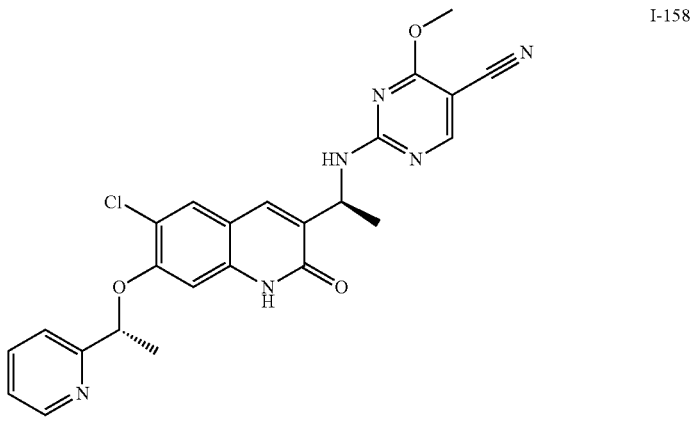
I-158
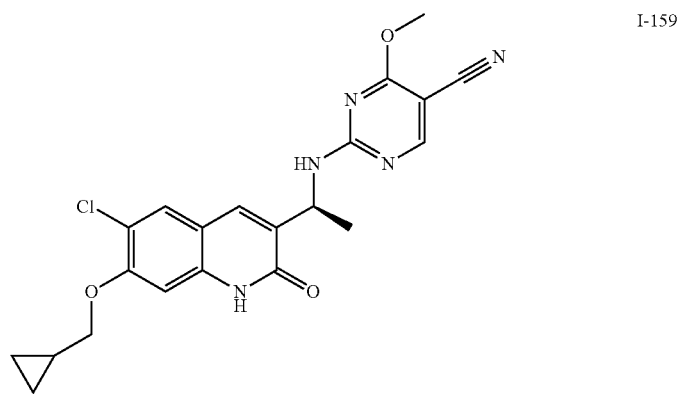
I-159
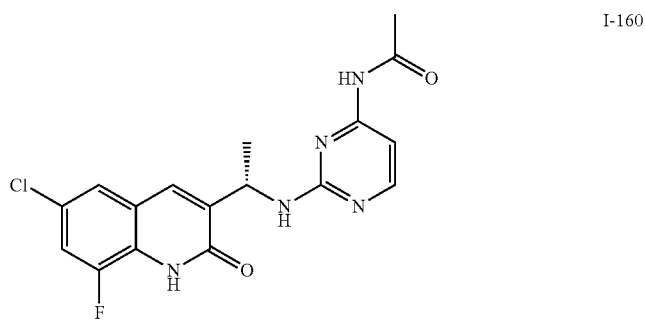
I-160
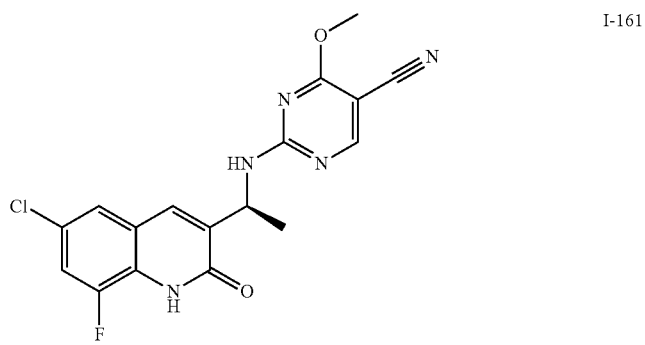
I-161

TABLE 15-continued

The compounds listed in Table 15 were prepared using methods similar to those described for the preparation of I-141, I-143, I-144, I-151, I-154-I-156, and I-158-I-163.

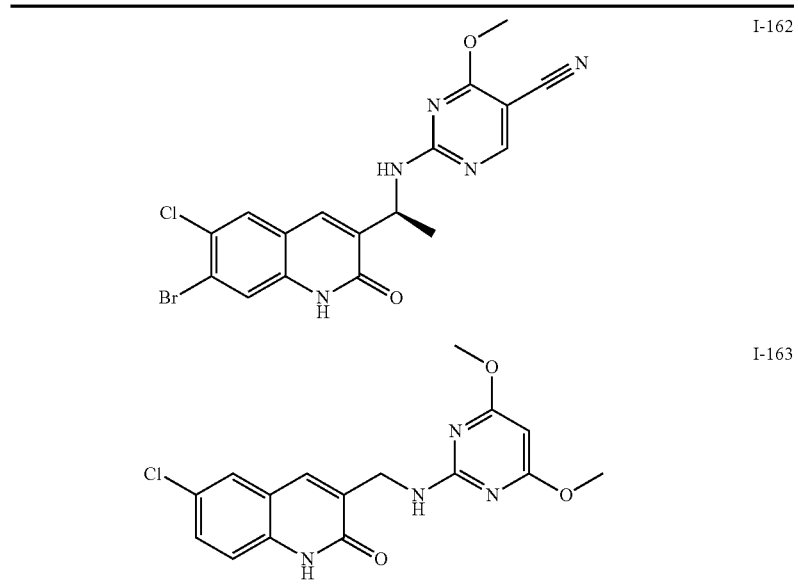

I-162

I-163

TABLE 16

LCMS signal and NMR chemical shifts for each compounds listed in Table 15.

| Cmpds No | LCMS[a] | $^1$H NMR (300 MHz) δ ppm |
|---|---|---|
| I-141 | m/z: 374.07 [M + H]$^+$ Rt (min): 1.56 | $^1$H NMR (300 MHz, DMSO-d$_6$): δ ppm 12.03 (br s, 1 H), 8.57-8.80 (m, 1 H), 8.49 (d, J = 6.16 Hz, 1 H), 7.98 (d, J = 7.92 Hz, 1 H), 7.74 (d, J = 9.38 Hz, 1 H), 7.20 (d, J = 10.55 Hz, 1H), 5.13-5.29 (m, 1 H), 3.77-4.01 (m, 3 H), 1.37-1.48 (m, 3 H). |
| I-142 | m/z: 374.00 [M + H]$^+$ Rt (min): 1.33 | $^1$H NMR (300 MHz, DMSO-d$_6$): δ ppm 12.05 (s, 1 H), 8.58-8.82 (m, 1 H), 8.49 (d, J = 6.16 Hz, 1 H), 7.98 (d, J = 7.92 Hz, 1 H), 7.74 (d, J = 9.67 Hz, 1 H), 7.19 (d, J = 10.26 Hz, 1 H), 5.11-5.30 (m, 1 H), 3.76-4.02 (m, 3 H), 1.36-1.48 (m, 3 H). |
| I-143 | m/z: 386.10 [M + H]$^+$ Rt (min): 1.36 | $^1$H NMR (300 MHz, DMSO-d$_6$): δ ppm 11.83 (s, 1 H), 8.50-8.74 (m, 1 H), 8.48 (d, J = 1.76 Hz, 1 H), 7.77 (s, 1 H), 7.68 (d, J = 7.04 Hz, 1 H), 6.94 (s, 1 H), 5.15-5.29 (m, 1 H), 3.78-4.00 (m, 3 H), 3.88 (s, 3 H), 1.41 (t, J = 6.45 Hz, 3 H). |
| I-144 | m/z: 386.16 [M + H]$^+$ Rt (min): 1.36 | $^1$H NMR (300 MHz, DMSO-d$_6$): δ ppm 11.83 (s, 1 H), 8.50-8.74 (m, 1 H), 8.48 (d, J = 1.47 Hz, 1 H), 7.77 (s, 1 H), 7.68 (d, J = 7.04 Hz, 1 H), 6.94 (s, 1 H), 5.14-5.30 (m, 1 H), 3.77-4.02 (m, 3 H), 3.88 (s, 3 H), 1.42 (t, J = 6.45 Hz, 3 H). |
| I-145 | m/z: 386.03 [M + H]$^+$ Rt (min): 1.29 | $^1$H NMR (300 MHz, DMSO-d$_6$): δ ppm 11.80-11.89 (m, 1 H), 8.52-8.76 (m, 1 H), 8.48 (d, J = 2.05 Hz, 1 H), 7.77 (s, 1 H), 7.68 (d, J = 7.33 Hz, 1 H), 6.94 (s, 1 H), 5.14-5.29 (m, 1 H), 3.79-4.00 (m, 3 H), 3.88 (s, 3 H), 1.36-1.47 (m, 3 H). |
| I-146 | m/z: 416.06 [M + H]$^+$ Rt (min): 1.06 | |
| I-147 | m/z: 415.99 [M + H]$^+$ Rt (min): 1.03 | |
| I-148 | m/z: 415.99 [M + H]$^+$ Rt (min): 1.03 | |
| I-149 | m/z: 465.13 [M + H]$^+$ Rt (min): 1.04 | $^1$H NMR (300 MHz, DMSO-d$_6$): δ ppm 11.80 (s, 1 H), 10.23 (s, 1 H), 8.57-8.64 (m, 1 H), 8.12 (d, J = 5.28 Hz, 1 H), 7.88 (td, J = 7.77, 1.76 Hz, 1 H), 7.79 (s, 1 H), 7.69 (s, 1 H), 7.55 (d, J = 7.92 Hz, 1 H), 7.34-7.42 (m, 1 H), 7.20 (d, J = 5.57 Hz, 1 H), 7.03 (s, 1 H), 5.29 (s, 2 H), 5.16 (quin, J = 7.18 Hz, 1 H), 2.06 (s, 3 H), 1.39 (d, J = 6.74 Hz, 3 H). |
| I-150 | m/z: 463.09 [M + H]$^+$ Rt (min): 1.3292 | $^1$H NMR (300 MHz, CDCl$_3$): δ ppm 11.29-11.83 (m, 1 H), 8.52 (br d, J = 4.98 Hz, 1 H), 8.13-8.24 (m, 1 H), 7.65-7.74 (m, 1 H), 7.53-7.60 (m, 2 H), 7.50 (d, J = 9.67 Hz, 1 H), 7.19-7.34 (m, 1 H), 6.82-6.92 (m, 2 H), 5.33 (br d, J = 4.10 Hz, 2 H), 5.11-5.27 (m, 1 H), 3.79-3.94 (m, 3 H), 1.55-1.63 (m, 3 H). |
| I-151 | m/z: 463.10 [M + H]$^+$ Rt (min): 1.35 | $^1$H NMR (300 MHz, CDCl$_3$): δ ppm 11.50 (br s, 1 H), 10.80 (br s, 1 H), 8.47-8.59 (m, 1 H), 8.12-8.26 (m, 1 H), 7.64-7.75 (m, 1 H), 7.45-7.59 (m, 3 H), 7.19-7.26 (m, 1 H), 6.76-6.89 (m, 1 H), 5.33 (d, J = 12.3 Hz, 2 H), 5.12-5.27 (m, 1 H), 3.77-3.97 (m, 3 H), 1.49-1.69 (m, 3 H). |
| I-152 | m/z: 449.02 [M + H]$^+$ Rt (min): 1.14 | |

TABLE 16-continued

LCMS signal and NMR chemical shifts for each compounds listed in Table 15.

| Cmpds No | LCMS[a] | $^1$H NMR (300 MHz) δ ppm |
|---|---|---|
| I-153 | m/z: 447.18 [M + H]$^+$ Rt (min): 1.37 | $^1$H NMR (300 MHz, DMSO-d$_6$ at 120° C.): δ 11.41 (br s, 1H), 8.63-8.49 (m, 2H), 8.01-7.81 (m, 2H), 7.73-7.59 (m, 2H), 7.57 (d, J = 7.9 Hz, 1H), 7.36-7.32 (m, 1H), 7.11 (s, 1H), 5.31-5.27 (m, 3H), 2.42 (s, 3H), 1.48 (d, J = 6.9 Hz, 3H) |
| I-154 | m/z: 481.18 [M + H]$^+$ Rt (min): 1.59 | $^1$H NMR (300 MHz, DMSO-d$_6$): δ ppm 11.78 (br s, 1 H), 10.08 (br s, 1 H), 8.61 (d, J = 4.1 Hz, 1 H), 8.1 (d, J = 5.5 Hz, 1 H), 7.90-7.82 (m, 1 H), 7.78 (s, 1 H), 7.69 (s, 1 H), 7.56 ( d, J = 7.6 Hz, 1 H), 7.39-7.34 (m, 1 H), 7.19 (br s, 1 H), 7.02-7.00 (m, 2 H), 5.28 (s, 2 H), 5.15-5.11 (m, 1 H), 3.65 (s, 3 H), 1.39 (d, J = 6.9 Hz, 3 H). |
| I-155 | m/z: 357.11 [M + H]$^+$ Rt (min): 1.22 | $^1$H NMR (300 MHz, DMSO-d$_6$): δ ppm 12.39 (br s, 1 H), 8.76 (br d, J = 7.33 Hz, 0.5 H), 8.59 (br d, J = 7.62 Hz, 0.5 H), 8.35-8.49 (m, 2 H), 8.07-8.27 (m, 1 H), 7.69 (d, J = 5.86 Hz, 1 H), 5.04-5.31 (m, 1 H), 3.64-4.01 (m, 3 H), 1.09-1.52 (m, 3 H). |
| I-156 | m/z: 395.25 [M + H]$^+$ Rt (min): 0.82 | $^1$H NMR (300 MHz, DMSO-d$_6$ 120° C.): δ ppm 12.20 (br, s, 1 H), 8.42 (s, 1 H), 7.92 (br s, 1 H), 7.74 (d, J = 2.19 Hz, 1 H), 7.53 (dd, J = 8.52, 2.19 Hz, 1 H), 7.31 (d, J = 8.52 Hz, 1 H), 5.22 (m, 1 H), 3.94 (s, 3 H), 1.53 (d, J = 6.87 Hz, 3 H). |
| I-157 | m/z: 357.11 [M + H]$^+$ Rt (min): 1.78 | $^1$H NMR (300 MHz, DMSO-d$_6$ 120° C.): δ ppm 12.20 (br, s, 1 H), 8.42 (s, 1 H), 7.92 (br, s, 1 H), 7.74 (d, J = 2.19 Hz, 1 H), 7.53 (dd, J = 8.52, 2.19 Hz, 1 H), 7.31 (d, J = 8.52 Hz, 1H), 5.22 (m, 1 H), 3.94 (s, 3 H), 1.53 (d, J = 6.87 Hz, 3 H). |
| I-158 | m/z: 477.25 [M + H]$^+$ Rt (min): 1.44 | $^1$H NMR (300 MHz, DMSO-d$_6$): δ ppm 11.64-11.71 (m, 1 H), 8.49-8.71 (m, 2 H), 8.45-8.48 (m, 1 H), 7.75-7.85 (m, 2 H), 7.63 (d, J = 9.09 Hz, 1 H), 7.37-7.43 (m, 1 H), 7.28--7.36 (m, 1 H), 6.85 (s, 1 H), 5.51 (q, J = 6.16 Hz, 1 H), 5.11-5.24 (m, 1 H), 3.77-4.00 (m, 3H), 1.66 (d, J = 6.45 Hz, 3 H), 1.31-1.43 (m, 3 H). |
| I-159 | m/z: 426.19 [M + H]$^+$ Rt (min): 1.52 | $^1$H NMR (300 MHz, DMSO-d$_6$): δ ppm 11.73-11.81 (m, 1 H), 8.51-8.74 (m, 1 H), 8.48 (d, J = 2.05 Hz, 1 H), 7.76 (s, 1 H), 7.67 (d, J = 7.62 Hz, 1 H), 6.91 (s, 1 H), 5.15-5.28 (m, 1 H), 3.79-4.01 (m, 3 H), 3.92 (d, J = 6.74 Hz, 2 H), 1.36-1.46 (m, 3 H), 1.21-1.30 (m, 1 H), 0.56-0.65 (m, 2 H), 0.35-0.44 (m, 2 H). |
| I-160 | m/z: 376.26 [M + H]$^+$ Rt (min): 0.97 | $^1$H NMR (300 MHz, DMSO-d$_6$): δ ppm 12.00 (br s, 1 H), 10.23 (s, 1 H), 8.13 (br d, J = 5.57 Hz, 1 H), 7.78 (s, 1 H), 7.62 (br s, 1 H), 7.57 (dd, J-10.55, 2.05 Hz, 1 H), 7.14-7.45 (m, 2 H), 5.19 (quin, J = 7.11 Hz, 1 H), 2.06 (s, 3 H), 1.41 (d, J = 6.74 Hz, 3 H). |
| I-161 | m/z: 374.2 [M + H]$^+$ Rt (min): 1.33 | $^1$H NMR (300 MHz, DMSO-d$_6$): δ ppm 12.07 (s, 1 H), 8.60-8.85 (m, 1 H), 8.49 (d, J = 7.33 Hz, 1 H), 7.77 (d, J = 7.92 Hz, 1 H), 7.65 (br s, 1 H), 7.54-7.62 (m, 1 H), 5.16-5.30 (m, 1 H), 3.77-4.01 (m, 3 H), 1.38-1.49 (m, 3 H). |
| I-162 | m/z: 433.99 [M + H]$^+$ Rt (min): 1.5 | $^1$H NMR (300 MHz, DMSO-d$_6$): δ ppm 12.39 (br s, 1 H), 8.75 (d, J = 7.04 Hz, 1 H), 8.60 (d, J = 7.62 Hz, 1 H), 8.43 (m, 2 H), 8.424 (m, 1 H), 7.68 (d, J = 5.86 Hz, 1 H), 5.32 (m, 1 H), 3.92-3.73 (m, 3 H), 1.50 (m, 3 H). |
| I-163 | m/z: 347.0174 [M + H]$^+$ Rt (min): 1.36 | |

[a]LCMS (method 4)

Example 94—N-isopropyl-N-(2-(((2-oxo-1,2-dihydroquinolin-3-yl)methyl)amino) pyrimidin-4-yl)methanesulfonamide (I-164)

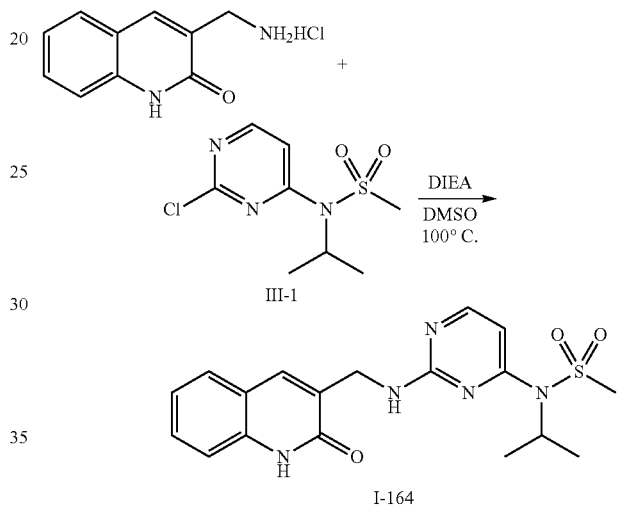

A 0.2M solution of 3-(aminomethyl)quinolin-2(1H)-one hydrochloride in 9:1 DMA/N,N-diisopropylethylamine (v/v) (165 μL, 33 μmol) was combined with a 0.2M DMSO solution of N-(2-chloropyrimidin-4-yl)-N-isopropylmethanesulfonamide III-1 (150 μL, 30 μmol) in a 2.0 mL reaction vial. An additional volume of N,N-diisopropylethylamine (20 μL, 115 μmol) was added, and the vial was sealed and heated to 100° C. with agitation for 18-24 hours. The reaction mixture was concentrated under reduced pressure with heat (50° C.) to drive off volatiles, and the remaining crude DMSO solution containing the product was purified by mass-triggered preparatory HPLC to yield the title compound (8.6 mg, 74% yield). LCMS (Method 4): Rt 1.11 min, m/z 388.11 [M+H]+.

TABLE 17

The compounds listed in Table 17 were prepared using the same method as described for the preparation of I-164.

TABLE 17-continued

The compounds listed in Table 17 were prepared using the same method as described for the preparation of I-164.

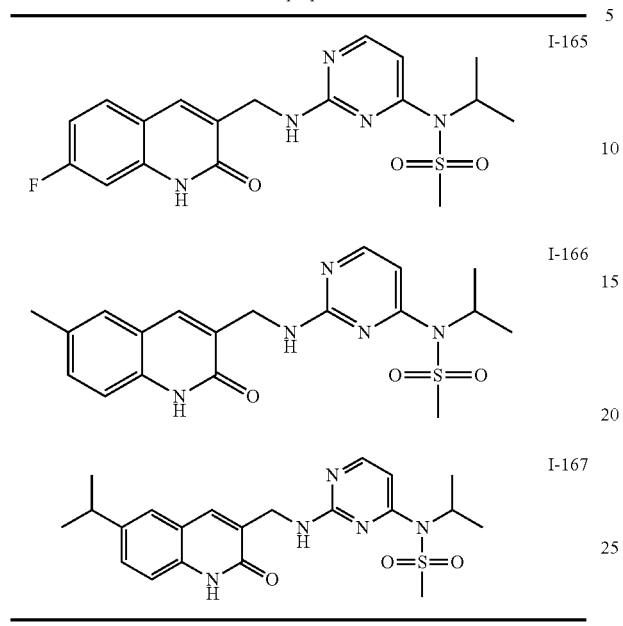

TABLE 18

LCMS signal and chemical name for each compounds listed in Table 17

| Cmpds No | LCMS[a] |
|---|---|
| I-164 | m/z: 388.11 [M + H]+ Rt (min): 1.11 |
| I-165 | m/z: 406.20 [M + H]+ Rt (min): 1.11 |
| I-166 | m/z: 402.10 [M + H]+ Rt (min): 1.22 |
| I-167 | m/z: 440.18 [M + H]+ Rt (min): 1.42 |

[a]LCMS (method 4)

Example 95—2-((1-(6-Chloro-2-oxo-1,2-dihydroquinolin-3-yl)cyclopropyl)amino)-4-methoxypyrimidine-5-carbonitrile (I-169)

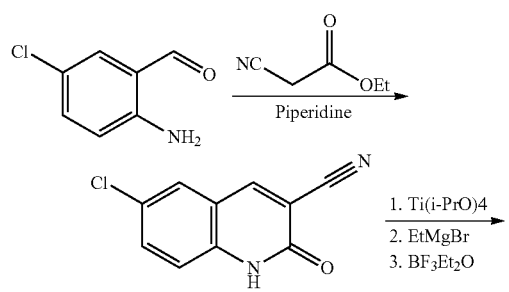

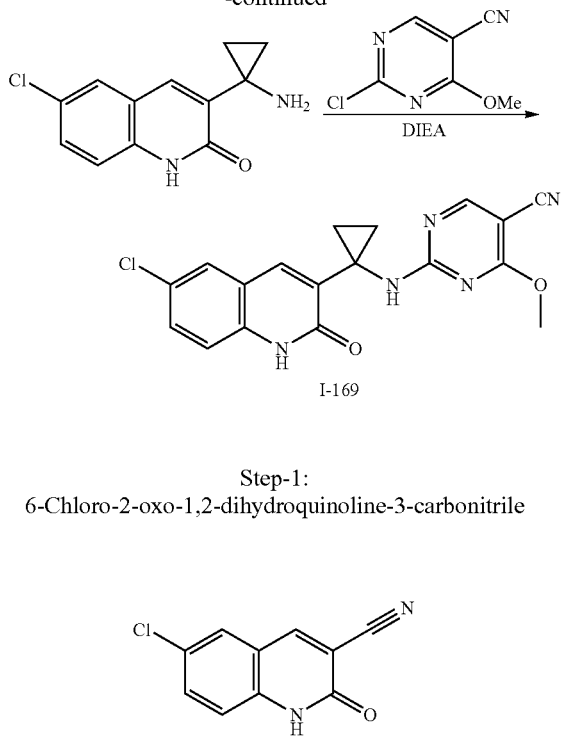

Step-1: 6-Chloro-2-oxo-1,2-dihydroquinoline-3-carbonitrile

A mixture of piperidine (0.022 g, 0.257 mmol), 2-amino-5-chlorobenzaldehyde (2 g, 12.85 mmol), and ethyl 2-cyanoacetate (1.454 g, 12.85 mmol) in EtOH (30 mL) was stirred at room temperature for 30 minutes and then at reflux for 2 hours. The mixture was cooled to room temperature, filtered and washed with EtOH. The collected solids were dried to afford 6-chloro-2-oxo-1,2-dihydroquinoline-3-carbonitrile (1.84 g, 70% yield). $^1$H NMR (300 MHz, DMSO-$d_6$): δ ppm 12.43-12.68 (br s, 1H), 8.50-8.78 (s, 1H), 7.54-7.96 (m, 1H), 7.33 (d, J=9.09 Hz, 1H); LCMS (Method 1): Rt 1.87 min, m/z=205.95[M+H]+.

Step-2: 3-(1-Aminocyclopropyl)-6-chloroquinolin-2(1H)-one

To a solution of 6-chloro-2-oxo-1,2-dihydroquinoline-3-carbonitrile (800 mg, 3.91 mmol) in THF (15 mL) at −78° C. was added titanium (IV) isopropoxide (Ti(O$^i$Pr)$_4$) (1.333 g, 1.375 mL, 4.69 mmol), After 10 minutes of stirring, ethyl magnesium bromide (EtMgBr) (1824 mg, 3N, 5 mL, 13.68 mmol) in ether was added. The solution was stirred at −78° C. for 30 minutes, then warmed up to room temperature and was followed by the addition of BF$_3$.OEt$_2$ (1.942 g, 1.734 mL, 13.68 mmol). The resulting solution was stirred at room temperature for two hours and then an aqueous solution of NH$_4$Cl was added to quench the reaction. The reaction mixture was treated with 1 N aqueous NaOH solution to adjust to pH=11-12, extracted with EtOAc, dried, and concentrated. The crude product was then purified by column chromatography on a Biotage® chromatography system to afford 3-(1-aminocyclopropyl)-6-chloroquinolin-2(1H)-one (140 mg, 15.26% yield). $^1$H NMR (300 MHz, CDCl$_3$): δ ppm 12.53 (br s, 1H), 7.64-7.83 (m, 1H), 7.55-7.61 (m, 1H), 7.35-7.47 (m, 1H), 3.03-3.21 (m, 1H), 1.29-1.37 (m, 1H), 1.08-1.25 (m, 1H), 0.83-0.99 (m, 1H). LCMS (Method 1): Rt 2.11 min, m/z 235.99 [M+H]$^+$.

Step-3: 2-((1-(6-Chloro-2-oxo-1,2-dihydroquinolin-3-yl)cyclopropyl)amino)-4-methoxy pyrimidine-5-carbonitrile (I-169)

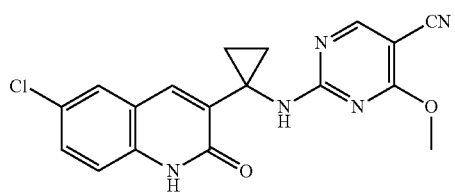 [SMILES: COc1nc(NC2(c3cc4cc(Cl)ccc4[nH]c3=O)CC2)ncc1C#N]

A mixture of DIEA (0.096 mL, 0.548 mmol), 3-(1-aminocyclopropyl)-6-chloroquinolin-2(1H)-one (42.9 mg, 0.183 mmol), and 2-chloro-4-methoxypyrimidine-5-carbonitrile (31 mg, 0.183 mmol) in DMSO (1 mL) was stirred at 100° C. overnight. The mixture was then diluted with EtOAc, washed with water, dried and concentrated. HPLC purification afforded 4 mg of 2-((1-(6-chloro-2-oxo-1,2-dihydroquinolin-3-yl)cyclopropyl)amino)-4-methoxypyrimidine-5-carbonitrile with minor impurities (6%). LCMS (Method 1): Rt 2.49 min, m/z 368.93[M+H]$^+$.

Example 96—2-((1-(6-chloro-7-((3,3-difluorocyclobutyl)methoxy)-2-oxo-1,2-dihydroquinolin-3-yl)ethyl)amino)-4-methoxypyrimidine-5-carbonitrile (I-172)

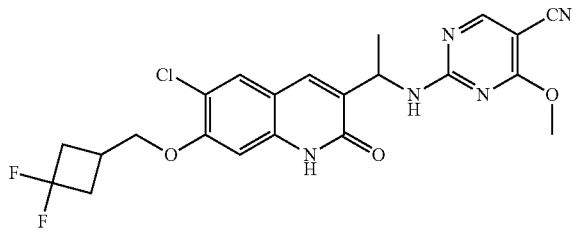 [SMILES: COc1nc(NC(C)c2cc3cc(Cl)c(OCC4CC(F)(F)C4)cc3[nH]c2=O)ncc1C#N]

A solution of 3-(1-aminoethyl)-6-chloro-7-((3,3-difluorocyclobutyl)methoxy) quinolin-2(1H)-one hydrochloride (30.1 mg, 0.079 mmol) and 2-chloro-4-methoxypyrimidine-5-carbonitrile (15.2 mg, 0.090 mmol) in DMSO (0.50 ml) was treated with DIEA (41.6 µl, 0.238 mmol) and stirred at 110° C. for 30 minutes. The sample was then allowed to cool, poured into water (20 mL) and the resulting precipitate was extracted with DCM (2×10 mL). The combined extracts were dried (Na$_2$SO$_4$) and filtered. Silica gel was added, and the mixture was evaporated under reduced pressure. The material was purified by column chromatography on a Biotage MPLC chromatography system (using a 10 g silica gel column eluted with 0 to 88% EtOAc in hexanes, with isocratic elution when peaks eluted) to provide 2-((1-(6-chloro-7-((3,3-difluorocyclobutyl)methoxy)-2-oxo-1,2-dihydroquinolin-3-yl)ethyl)amino)-4-methoxy pyrimidine-5-carbonitrile (28.1 mg, 0.059 mmol, 74.4% yield) as a pale orange solid. $^1$H NMR (300 MHz, DMSO-d$_6$): δ ppm 11.82 (br s, 1H), 8.51-8.75 (m, 1H), 8.48 (d, J=2.05 Hz, 1H), 7.78 (s, 1H), 7.68 (d, J=7.62 Hz, 1H), 6.93 (s, 1H), 5.13-5.29 (m, 1H), 4.13 (d, J=4.69 Hz, 2H), 3.78-4.00 (m, 3H), 2.53-2.80 (m, 4H), 1.35-1.47 (m, 3H). LCMS (Method1): m/z 476 [M+H]$^+$

TABLE 19

The compounds listed in Table 19 were prepared using methods similar to those described for the preparation of I-169.

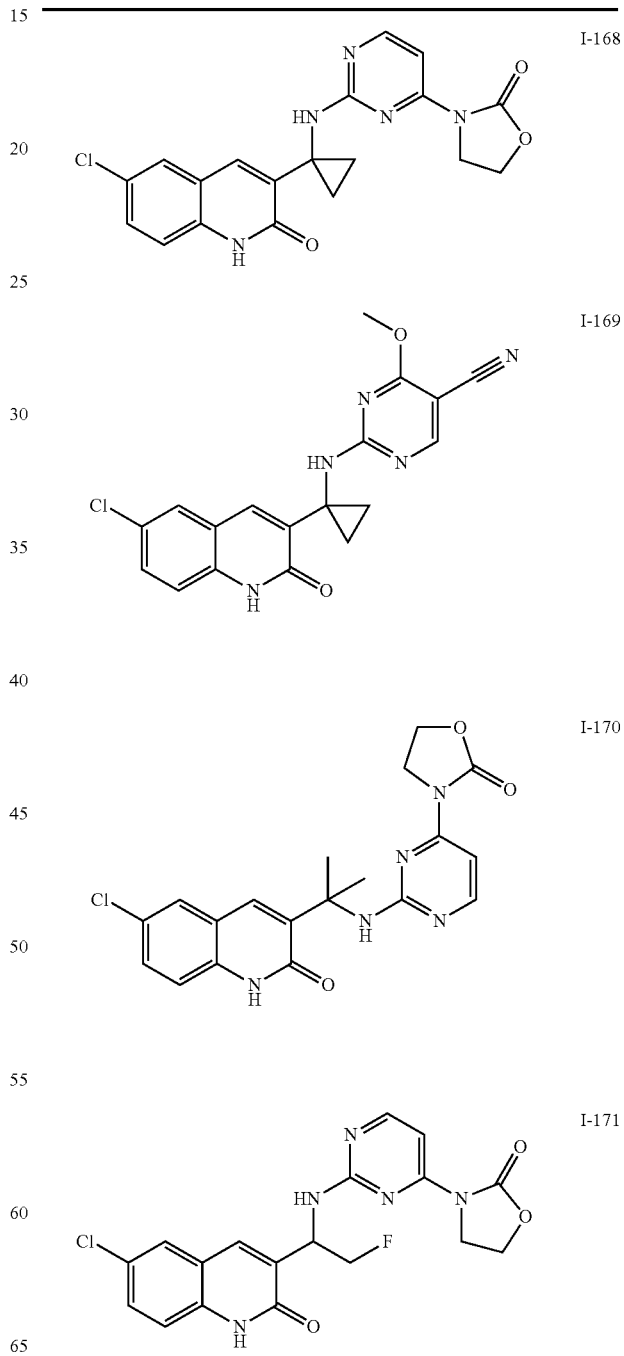

TABLE 19-continued

The compounds listed in Table 19 were prepared using methods similar to those described for the preparation of I-169.

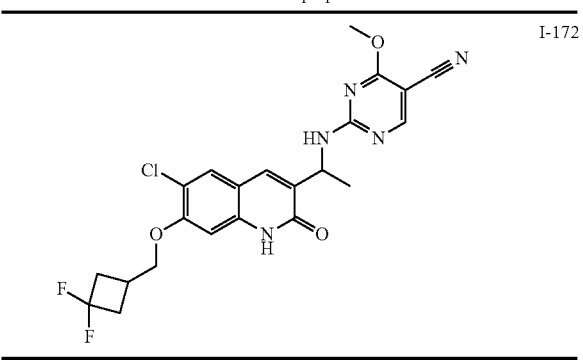

I-172

TABLE 20

LCMS signal and NMR chemical shifts for each compounds listed in Table 19

| Cmpds No | LCMS[a] | $^1$H NMR (300 MHz) δ ppm |
|---|---|---|
| I-168 | m/z: 398.03 [M + H]$^+$ Rt (min): 1.09 | |
| I-169 | m/z: 368.03 [M + H]$^+$ Rt (min): 1.35 | |
| I-170 | m/z: 400.11 [M + H]$^+$ Rt (min): 1.11 | $^1$H NMR (300 MHz, CDCl$_3$): δ ppm 11.11 (br s 1 H), 8.08 (d, J = 5.77 Hz, 1 H), 7.72 (s, 1 H), 7.50 (s, 1 H), 7.30-7.41 (m, 2 H), 5.96 (s, 1 H), 4.24-4.32 (m, 2 H), 3.83-3.85 (m, 2 H) 3.12 (s, 3 H), 1.61 (s, 6 H) |
| I-171 | m/z: 402.00 [M + H]$^+$ Rt (min): 0.87 | |
| I-172 | m/z: 476.23 (M + H)$^+$ Rt (min): 1.58 | $^1$H NMR (300 MHz, DMSO-d$_6$): δ ppm 11.82 (br s, 1 H), 8.51-8.75 (m, 1 H), 8.48 (d, J = 2.05 Hz, 1 H), 7.78 (s, 1 H), 7.68 (d, J = 7.62 Hz, 1 H), 6.93 (s, 1 H), 5.13-5.29 (m, 1 H), 4.13 (d, J = 4.69 Hz, 2 H), 3.78-4.00 (m, 3 H), 2.53-2.80 (m, 4 H), 1.35-1.47 (m, 3 H) |

[a]LCMS (method 4)

Example 97—(S)-6-chloro-3-(1-((4-(1-isopropyl-1H-imidazol-5-yl)pyrimidin-2-yl)amino)ethyl)-1-methylquinolin-2(1H)-one (I-173)

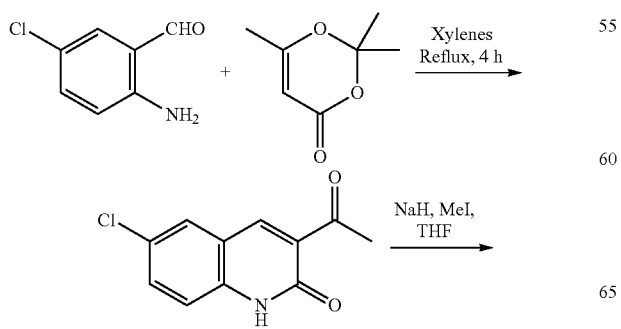

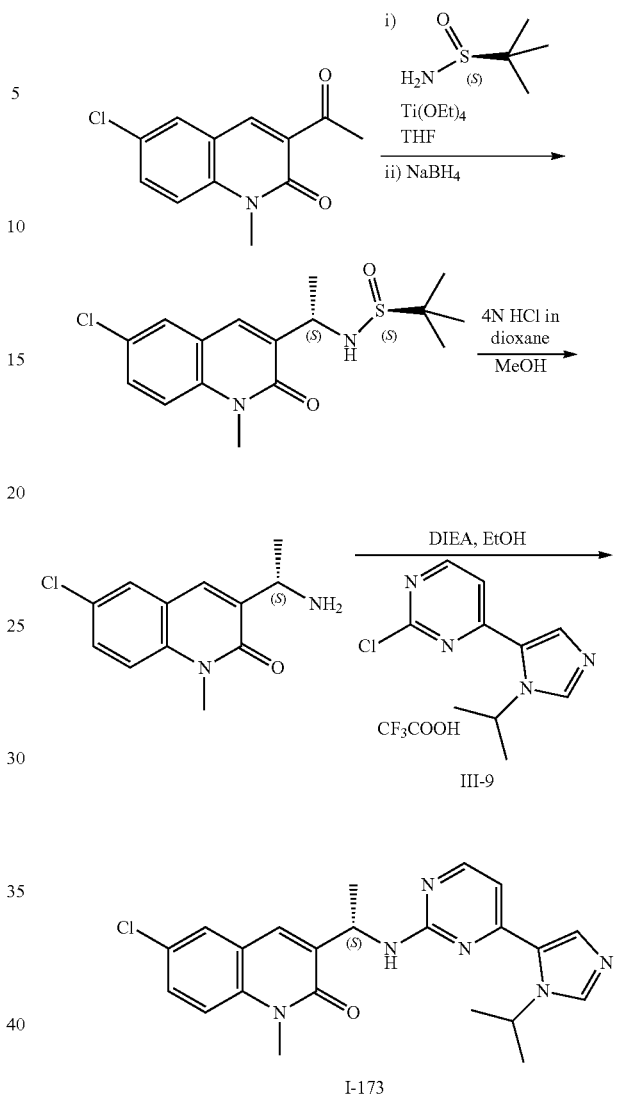

Step-1: 3-Acetyl-6-chloroquinolin-2(1H)-one

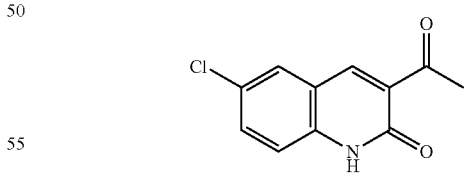

The mixture of 2-amino-5-chlorobenzaldehyde (12.8 g, 82.2 mmol), and 2,2,6-trimethyl-4H-1,3-dioxin-4-one (17.5 g, 123 mmol) in xylene (100 ml) was heated to reflux for 4 hours. The reaction was cooled to room temperature and the solid precipitated was filtered, washed with xylenes, and dried to give the title compound (1.8 g, 10%). $^1$H NMR (300 MHz, DMSO-d$_6$): δ 12.24 (s, 1H), 8.43 (s, 1H), 8.02 (d, J=2.1 Hz, 1H), 7.65 (dd, J=8.88 and 2.1, Hz 1H), 7.34 (d, J=8.8 Hz, 1H), 2.61 (s, 3H).

Step-2: 3-Acetyl-6-chloro-1-methylquinolin-2(1H)-one

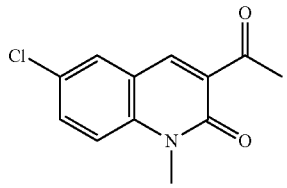 [SMILES: CC(=O)c1cc2cc(Cl)ccc2n(C)c1=O]

Sodium hydride (60%, 20 mg, 0.5 mmol) was added to a solution of 3-acetyl-6-chloroquinolin-2(1H)-one (110 mg, 0.5 mmol) in THF (10 ml) at ice cold temperature. The resultant mixture was stirred at ice cold temperature for 1 h. Methyl iodide (142 mg, 1.0 mmol) was added to the reaction and stirred at ice cold temperature for 1 h. The reaction was allowed to come to room temperature and stirred overnight. Saturated ammonium chloride solution was added to the reaction and extracted with dichloromethane. The organic extract was washed with water, dried over $Na_2SO_4$, filtered, and evaporated under reduced pressure. The crude material was purified on ISCO ($SiO_2$:0-50% ethyl acetate in hexanes) to give the title compound (101 mg, 86.4%). $^1$H NMR (300 MHz, $CDCl_3$): δ 8.28 (s, 1H), 7.69-7.57 (m, 2H), 7.31 (d, J=9.0 Hz, 1H), 3.74 (s, 3H), 2.75 (s, 3H). LCMS (Method 3): m/z=236.1 $(M+H)^+$.

Step-3: (S)—N—((S)-1-(6-Chloro-1-methyl-2-oxo-1,2-dihydroquinolin-3-yl)ethyl)-2-methyl propane-2-sulfinamide

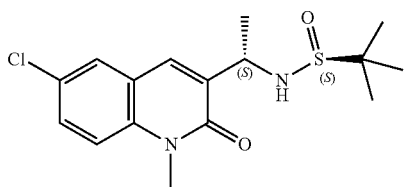

The mixture of tetraethoxytitanium (570 mg, 2.5 mmol), (S)-2-methylpropane-2-sulfinamide (181 mg, 1.5 mmol), and 3-acetyl-6-chloro-1-methylquinolin-2(1H)-one (235 mg, 1.0 mmol) in THF (20 ml) was heated to reflux overnight. The reaction was allowed to cool to room temperature and further cooled to −60° C. using dry ice acetone bath. Sodium borohydride (190 mg, 5.0 mmol) was added to the reaction. The reaction was slowly warmed to room temperature and stirred overnight. Methanol was added to destroy excess sodium borohydride, diluted with water, and extracted with ethyl acetate. The organic extract was washed with water, dried over $Na_2SO_4$, filtered, and evaporated under reduced pressure. The crude material was purified on ISCO ($SiO_2$:0-100% ethyl acetate in hexanes followed by 0-5% methanol in ethyl acetate) to give the title compound (175 mg, 51.5%). $^1$H NMR (300 MHz, $CDCl_3$): δ 7.21-7.560 (m, 4H), 5.12 (d, J=12.0 Hz, 1H), 4.48-4.34 (m, 1H), 3.69 (s, 3H), 1.56 (d, 3H). LCMS (Method 4): m/z 341.1 (M+H)+.

Step-4: (S)-3-(1-aminoethyl)-6-chloro-1-methylquinolin-2(1H)-one hydrochloride

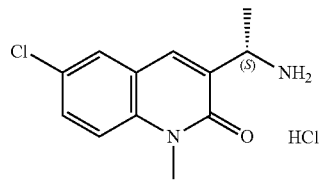

To a mixture of (S)—N—((S)-1-(6-chloro-1-methyl-2-oxo-1,2-dihydroquinolin-3-yl)ethyl)-2-methylpropane-2-sulfinamide (100 mg, 0.29 mmol) in MeOH (3 mL), was added 4N HCl in dioxane (2.0 mL) at 0° C. The resultant mixture was stirred at 0° C. for 2.5 h. After the completion of the reaction, the solvents were evaporated to dryness and the residue was triturated with ether to give the title compound (80 mg, 100%) as white solid. $^1$H NMR (300 MHz, DMSO-$d_6$): δ 8.27 (br s, 3H), 8.08 (s, 1H), 7.92 (d, J=2.2 Hz, 1H), 7.80-7.62 (m, 2H), 4.52-4.38 (m, 1H), 3.69 (s, 3H), 1.53 (d, J=6.9 Hz, 3H). LCMS (Method 3): m/z 237.1 $(M+H)^+$.

Step 5: (S)-6-chloro-3-(1-((4-(1-isopropyl-1H-imidazol-5-yl)pyrimidin-2-yl)amino)ethyl)-1-methylquinolin-2(1H)-one (I-173)

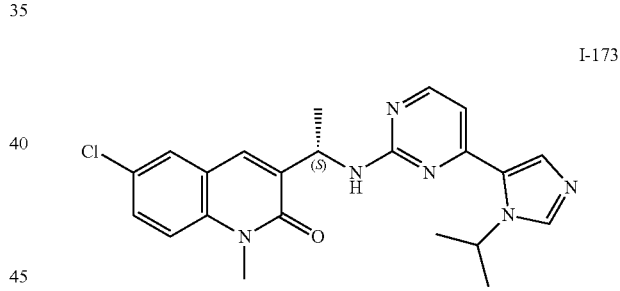

I-173

To a mixture of (S)-3-(1-aminoethyl)-6-chloro-1-methylquinolin-2(1H)-one hydrochloride (60 mg, 0.15 mmol) and 2-chloro-4-(1-isopropyl-1H-imidazol-5-yl)pyrimidine trifluoroacetic acid salt III-9 (96 mg, 0.30 mmol) in ethanol (5 ml) was added DIEA (0.267 ml, 1.5 mmol. The resulting mixture was heated in microwave oven at 1800 for 6 hours. The reaction was cooled to room temperature and concentrated under reduced pressure. The residue was dissolved in ethyl acetate, and washed with water (2×) and brine. The organic extract was dried over $Na_2SO_4$, filtered, and evaporated under reduced pressure. The crude material was purified on ISCO ($SiO_2$: 0-5% methanol in ethyl acetate) to give the title compound I-173 (42 mg, 65.4%). $^1$H NMR (300 MHz, DMSO-$d_6$ at 120° C.): δ 8.30-7.40 (m, 7H), 7.15-6.80 (m, 2H), 5.60-5.10 (m, 2H), 3.69 (s, 3H), 1.60-1.30 (two doublets, 6H), 1.18 (d, J=6.6 Hz, 3H). LCMS (Method 3): Rt 6.95 min, m/z 423.2 (M+H)+.

Example 98—(S)-2-((1-(6-chloro-7-isopropoxy-2-oxo-1,2-dihydroquinolin-3-yl)ethyl)amino)-4-methoxypyrimidine-5-carbonitrile (I-175)

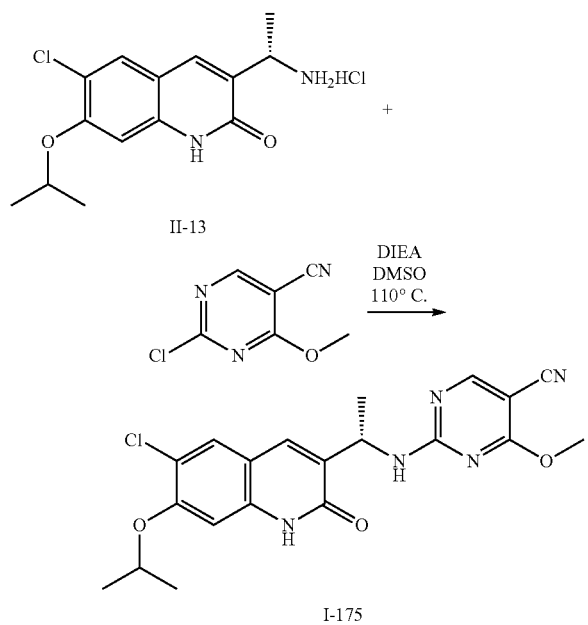

A solution of (S)-3-(1-aminoethyl)-6-chloro-7-isopropoxyquinolin-2(1H)-one hydrochloride (75.2 mg, 0.237 mmol) II-13 and 2-chloro-4-methoxypyrimidine-5-carbonitrile (43.9 mg, 0.259 mmol) in DMSO (1.7 ml) was treated with DIEA (124 µl, 0.710 mmol) and stirred at 110° C. for 35 minutes. The sample was allowed to cool, then was pipetted onto water (20 mL). The resulting precipitate was extracted with DCM (2×20 mL), and the combined extracts were washed with water (2×20 mL), dried (Na$_2$SO$_4$), filtered, treated with silica gel, and evaporated under reduced pressure. The material was chromatographed by Biotage MPLC (10 g silica gel column, 0 to 65% EtOAc in hexanes, with isocratic elution when peaks eluted). The material thus obtained was slurried in MeCN (2 mL) and water (1 mL), frozen (dry ice/acetone bath), and lyopholyzed, but NMR indicated the sample still had MeCN. The sample was sonicated in EtOH (5 mL) for 15 minutes, and then the solvent was evaporated. The residue was slurried in water (5 mL), frozen (dry ice/acetone bath), and lyopholyzed to provide the title compound I-175 (56.7 mg, 0.137 mmol, 57.8% yield) as a white solid. $^1$H NMR (300 MHz, DMSO-d$_6$): δ ppm 11.67-11.78 (m, 1H), 8.51-8.76 (m, 1H), 8.48 (d, J=2.64 Hz, 1H), 7.76 (s, 1H), 7.66 (d, J=8.79 Hz, 1H), 6.97 (s, 1H), 5.13-5.29 (m, 1H), 4.52-4.67 (m, 1H), 3.78-4.01 (m, 3H), 1.37-1.46 (m, 3H), 1.34 (d, J=6.16 Hz, 6H). LCMS (Method 1): Rt 2.55 min, m/z 414.0 [M+H]$^+$.

Example 99—(S)-2-((1-(6-chloro-7-cyclopropyl-2-oxo-1,2-dihydroquinolin-3-yl)ethyl)amino)-4-methoxypyrimidine-5-carbonitrile (I-176)

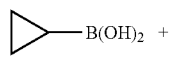

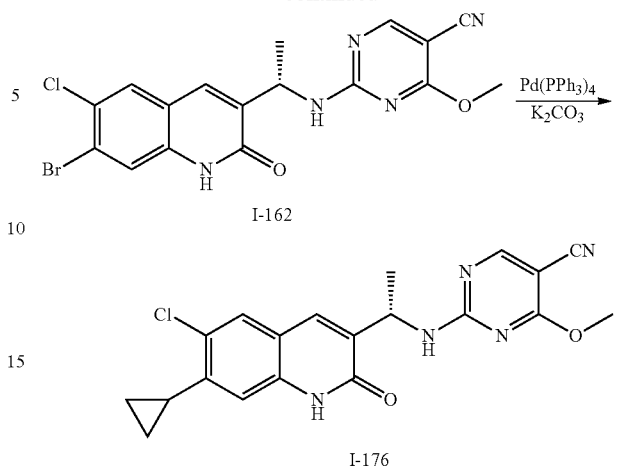

The mixture of Pd(PPh$_3$)$_4$ (11.96 mg, 10.35 µmol), K$_2$CO$_3$ (57.2 mg, 0.414 mmol), (S)-2-((1-(7-bromo-6-chloro-2-oxo-1,2-dihydroquinolin-3-yl)ethyl)amino)-4-methoxypyrimidine-5-carbonitrile 162 (90 mg, 0.207 mmol) and cyclopropylboronic acid (26.7 mg, 0.311 mmol) in water (1.5 ml) and 1,4-dioxane (30.0 ml) was bubbled with N$_2$ for 10 min. The resulting mixture was refluxing for overnight, and then treated with EtOAc, washed with brine twice, dried and concentrated. The crude was purified by reversed phase preparative HPLC to afford (S)-2-((1-(6-chloro-7-cyclopropyl-2-oxo-1,2-dihydroquinolin-3-yl)ethyl)amino)-4-methoxypyrimidine-5-carbonitrile (6 mg, 9.8%). $^1$H NMR (300 MHz, METHANOL-d$_4$) δ ppm 8.15-8.34 (m, 1H), 7.68 (br d, J=11.73 Hz, 1H), 7.54 (s, 1H), 6.84 (s, 1H), 5.12-5.38 (m, 1H), 3.71-3.97 (m, 3H), 2.08-2.33 (m, 1H), 1.44 (br d, J=6.16 Hz, 2H), 0.94-1.06 (m, 1H), 0.65 (br d, J=4.40 Hz, 1H). LCMS (Method 1): Rt 2.57 min, m/z 396.03 [M+H]+.

Example 100—(S)—4-methoxy-2-((1-(2-oxo-1,2-dihydro-1,5-naphthyridin-3-yl)ethyl) amino)pyrimidine-5-carbonitrile (I-177)

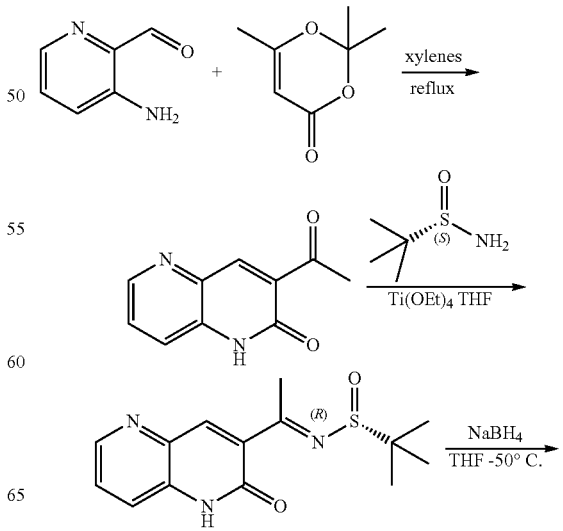

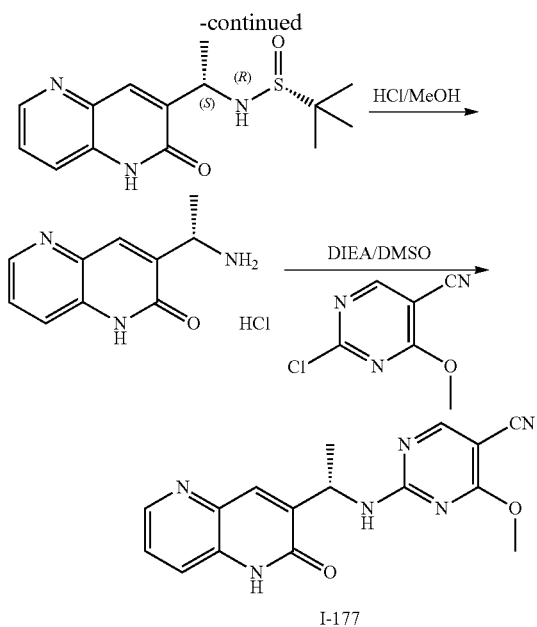

Step-1: 3-acetyl-1,5-naphthyridin-2(1H)-one

The mixture of 3-aminopicolinaldehyde (1 g, 8.19 mmol), and 2,2,6-trimethyl-4H-1,3-dioxin-4-one (1.746 g, 12.28 mmol) in Xylene (30 ml) was heated to reflux for 3 hours, cooled to RT, filtered and washed with xylene twice to afford 3-acetyl-1,5-naphthyridin-2(1H)-one (1 g, 65%). $^1$H NMR (300 MHz, DMSO-d$_6$) δ ppm 8.44-8.60 (m, 1H), 8.25 (s, 1H), 7.70 (d, J=1.47 Hz, 1H), 7.59 (dd, J=8.50, 4.40 Hz, 1H), 2.60 (s, 3H). LCMS (Method 1): Rt 1.05 min, m/z 189.10 [M+H]$^+$.

Step-2&3: (S)-2-methyl-N—((S)-1-(2-oxo-1,2-dihydro-1,5-naphthyridin-3-yl)ethyl)propane-2-sulfinamide The mixture of tetraethoxytitanium (3.03 g, 13.28 mmol), (S)-2-methylpropane-2-sulfinamide (0.966 g, 7.97 mmol) and 3-acetyl-1,5-naphthyridin-2(1H)-one (1 g, 5.31 mmol) in THF (150 ml) was heated to 80° C. overnight, first cooled to RT and then cooled to −60° C. To this cooled mixture was added NaBH$_4$ (1.005 g, 26.6 mmol). The mixture was slowly warmed up to RT and stirred for overnight, MeOH was added to destroy excess NaBH$_4$, then water was added. The mixture was extracted with EtOAc twice, dried over sodium sulfate, and concentrated under reduced pressure. The Biotage purification on a 100 g column first with 0-20% i-PrOH/Hexanes, then with 0-10% of MeOH in EtOAc afforded (S)-2-methyl-N—((S)-1-(2-oxo-1,2-dihydro-1,5-naphthyridin-3-yl)ethyl)propane-2-sulfinamide (140 mg, 9%). The product is very low UV active. $^1$H NMR (300 MHz, CDCl$_3$-d) δ ppm 11.31 (br s, 1H), 8.02-8.25 (m, 1H), 7.57 (s, 1H), 7.32-7.49 (m, 1H), 6.84-7.18 (m, 1H), 6.04 (d, J=9.67 Hz, 1H), 4.37 (br dd, J=9.53, 6.89 Hz, 1H), 1.58 (d, J=6.74 Hz, 3H), 1.35 (s, 9H). LCMS (Method 1): Rt 1.60 min, m/z 294.11 [M+H]$^+$.

Step-4: (S)-3-(1-aminoethyl)-1,5-naphthyridin-2 (1H)-one hydrochloride

To a solution of (S)-2-methyl-N—((S)-1-(2-oxo-1,2-dihydro-1,5-naphthyridin-3-yl)ethyl)propane-2-sulfinamide (140 mg, 0.477 mmol) in methanol (5 ml) was added HCl (2 ml, 4 N in dioxane, 8.00 mmol). The mixture was stirred at room temperature for overnight, then ether (6 ml) was added. The mixture was filtered, washed with ether twice and dried to afford 65 mg of (S)-3-(1-aminoethyl)-1,8-naphthyridin-2(1H)-one, HCl (60%). $^1$H NMR (300 MHz, DMSO-d$_6$) δ ppm 12.38 (br s, 1H), 8.35-8.71 (m, 1H), 8.14 (s, 1H), 7.69-8.02 (m, 1H), 7.57 (dd, J=8.35, 4.54 Hz, 1H), 1.51 (d, J=6.74 Hz, 3H). LCMS (Method 1): Rt 0.47, m/z 190.12 [M+H]$^+$.

Step-5: (S)—4-methoxy-2-((1-(2-oxo-1,2-dihydro-1,5-naphthyridin-3-yl)ethyl) amino)pyrimidine-5-carbonitrile (I-177)

The mixture of DIEA (0.151 ml, 0.864 mmol), (S)-3-(1-aminoethyl)-1,5-naphthyridin-2(1H)-one, HCl (65 mg, 0.288 mmol), and 2-chloro-4-methoxypyrimidine-5-carbonitrile (58.6 mg, 0.346 mmol) in DMSO (1 ml) was heated to 110° C. for two hour. The mixture was cooled to room temperature. LC/MS analysis showed the reaction was completed. The reaction mixture was treated with water, and then filtered. The Biotage purification with 0-10% MeOH/DCM on a 25 g column afforded (S)-4-methoxy-2-((1-(2-oxo-1,2-dihydro-1,5-naphthyridin-3-yl) amino)pyrimidine-5-carbonitrile 177 (33 mg, 35.5%). $^1$H NMR (300

MHz, DMSO-d$_6$) δ ppm 11.99 (br d, J=4.69 Hz, 2H), 8.68-9.12 (m, 1H), 8.35-8.52 (m, 1H), 7.81 (d, J=7.33 Hz, 1H), 7.64 (br d, J 8.21 Hz, 1H), 7.45 (dd, J 8.50, 4.40 Hz, 1H), 5.29 (br dd, J 14.07, 6.74 Hz, 1H), 3.63-4.09 (m, 3H), 1.24-1.65 (m, 3H). LCMS (Method 1): Rt 1.76, m/z 323.11 [M+H]$^+$.

Example 101—(S)-2-((1-(6-chloro-2-oxo-1,2-dihydroquinolin-3-yl)ethyl)amino)-6-oxo-1,6-dihydropyrimidine-5-carbonitrile (I-178)

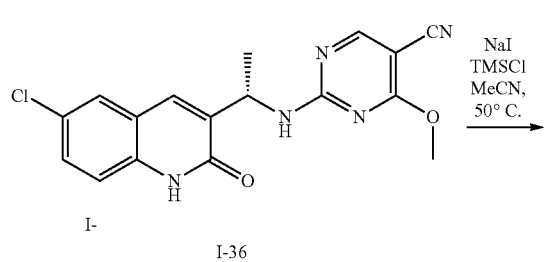

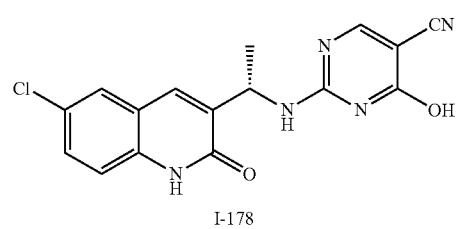

A mixture of (S)-2-((1-(6-chloro-2-oxo-1,2-dihydroquinolin-3-yl)ethyl)amino)-4-methoxypyrimidine-5-carbonitrile (69.9 mg, 0.196 mmol) (I-36) and sodium iodide (89.4 mg, 0.596 mmol) in MeCN (2.2 ml) was treated with TMSCl (0.11 mL, 0.861 mmol) and stirred at room temperature 4 hours, then at 50° C. overnight. LCMS indicated the reaction had gone to completion. The mixture was diluted with a few mL MeOH and DCM, treated with silica gel, and evaporated under reduced pressure. The material was chromatographed by Biotage MPLC (10 g silica gel column, 0 to 5% MeOH in DCM, with isocratic elution at 2.4%). The material thus obtained was reabsorbed onto silica gel and rechromatographed by Biotage MPLC (10 g silica gel column, 0 to 100% EtOAc in hexanes followed by 0 to 5.7% MeOH in EtOAc, with isocratic elution when peaks came off). The material thus obtained was sonicated in EtOH and water (5 mL each). The EtOH was evaporated under reduced pressure, and the remaining aqueous suspension was frozen (dry ice/acetone bath) and lyophilized to provide the title compound (43.3 mg, 0.127 mmol, 64.5% yield, HPLC purity 100% at 220 nm) as a white solid. $^1$H NMR (300 MHz, DMSO-d$_6$): δ ppm 12.11 (s, 1H), 11.71 (br s, 1H), 8.23 (s, 1H), 8.07 (br s, 1H), 7.85 (s, 1H), 7.79 (s, 1H), 7.53 (dd, J=8.79, 2.35 Hz, 1H), 7.32 (d, J=8.79 Hz, 1H), 5.12-5.30 (m, 1H), 1.46 (d, J=7.04 Hz, 3H). LCMS (Method 1): Rt 2.13 min., m/z 342.0 [M+H]$^+$.

Example 102—(S)—N-(2-((1-(6-chloro-7-fluoro-2-oxo-1,2-dihydroquinolin-3-yl)ethyl)amino) pyrimidin-4-yl)acetamide (I-179)

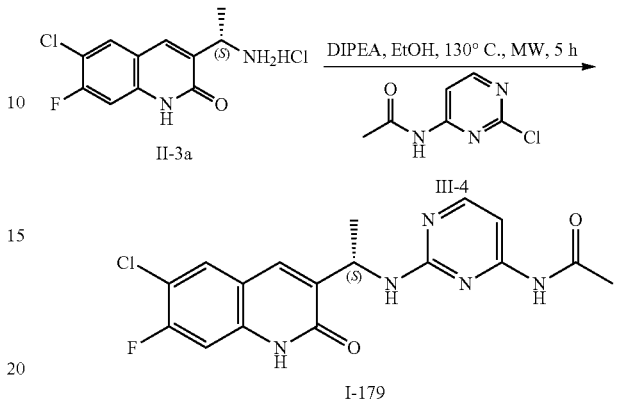

A mixture of (S)-3-(1-aminoethyl)-6-chloro-7-fluoroquinolin-2(1H)-one Hydrochloride II-3a (150 mg, 0.54 mmol), N-(2-chloropyrimidin-4-yl)acetamide III-4 (185 mg, 1.08 mmol) and DIPEA (282 µL, 1.62 mmol) in ethanol (3 mL) was irradiated under microwaves at 130° C. for 5 h. After TLC and MS showed completed reaction, the mixture was concentrated. The residue was purified by ISCO (SiO$_2$: hexanes/EtOAc 0 to 100%) followed by trituration with CH$_2$Cl$_2$-hexanes to give the title compound 179 (58 mg, 29%) as white solid. $^1$H NMR (300 MHz, DMSO-d$_6$): δ 12.01 (s, 1H-), 10.22 (s, 1H), 8.12 (d, J=5.2 1-Hz, 1H-), 7.95 (d, J=8.0 Hz, 1H), 7.74 (s, 1H), 7.30 (bs, 1H), 7.22-7.18 (m, 2H), 5.16 (m, 1H), 2.06 (s, 3H), 1.40 (d, J=6.9 Hz, 3H). LCMS (Method 3): Rt 3.93 min, m/z 376.8[M+H]$^+$.

Example 103—(S)—N-(2-((1-(6-chloro-7-fluoro-2-oxo-1,2-dihydroquinolin-3-yl)ethyl)amino) pyrimidin-4-yl)cyclopropanecarboxamide (I-180)

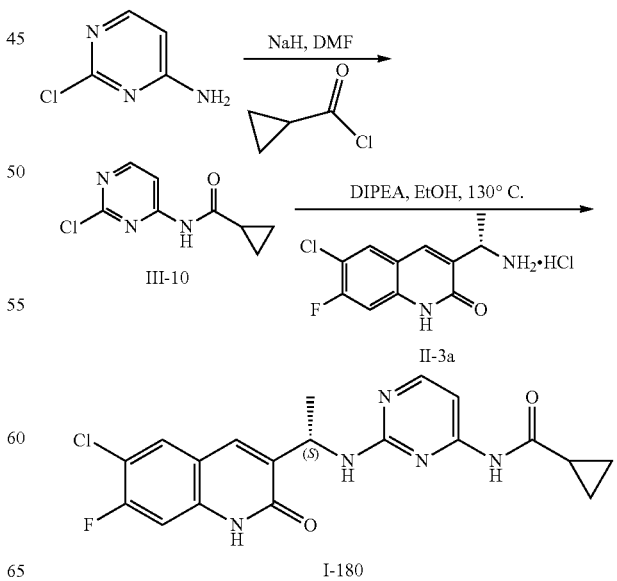

Step-1: N-(2-chloropyrimidin-4-yl)cyclopropanecarboxamide (III-10)

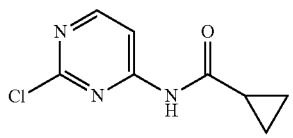 [SMILES: O=C(Nc1ccnc(Cl)n1)C1CC1]

To an ice-cold solution of 2-chloropyrimidin-4-amine (400 mg, 3.1 mmol) in 6 mL of DMF was added NaH (148 mg, 3.7 mmol) and the reaction mixture was stirred at 0° C. for 30-40 min. Neat cyclopropanecarbonyl chloride (0.36 mL, 0.40 mmol) was added dropwise to the reaction mixture which was allowed to warm to room temperature overnight. The reaction was quenched with NaHCO$_3$ (satu.) followed by extraction with EtOAc. Organic layer was dried over Na$_2$SO$_4$, filtered and concentrated to dryness under reduced pressure. The crude was purified by ISCO, using 40 g normal phase column with a gradient elution of EtOAc in CH$_2$Cl$_2$ providing 250 mg (41% yield) of the title compound III-10. $^1$H NMR (300 MHz, DMSO-d$_6$) δ ppm 11.57 (s, 1H), 8.52 (d, J=5.86 Hz, 1H), 7.99 (d, J=5.57 Hz, 1H), 1.96 (m, 1H), 0.81-1.04 (m, 4H). LCMS (Method 1): Rt 1.92 min, m/z 198.06 [M+H]$^+$.

Step-2: (S)—N-(2-(((1-(6-chloro-7-fluoro-2-oxo-1,2-dihydroquinolin-3-yl)ethyl)amino) pyrimidin-4-yl)cyclopropanecarboxamide (I-180)

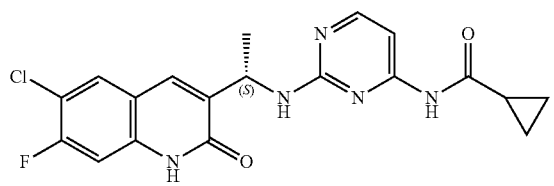

A mixture of (S)-3-(1-aminoethyl)-6-chloro-7-fluoroquinolin-2(1H)-one hydrochloride II-3a (150 mg, 0.54 mmol), N-(2-chloropyrimidin-4-yl)cyclopropanecarboxamide (III-10) (213 mg, 1.08 mmol) and DIPEA (282 µL, 1.62 mmol) in ethanol (3 mL) was irradiated under microwaves at 130° C. for 5 h. After TLC and MS showed completed reaction, the mixture was concentrated. The residue was purified by ISCO (SiO$_2$: hexanes/EtOAc 0 to 100%) followed by trituration with CH$_2$Cl$_2$-hexanes to give the title compound I-180 (110 mg, 51%) as a white solid. $^1$H NMR (300 MHz, DMSO-d$_6$): δ 12.02 (s, 1H), 10.53 (s, 1H), 8.11 (d, J=5.2 Hz, 1H), 7.95 (d, J=8.0 Hz, 1H), 7.75 (s, 1H), 7.30 (bs, 1H), 7.22-7.18 (m, 2H), 5.18 (m, 1H), 2.05 (m, 1H), 1.40 (d, J=6.6 Hz, 3H), 0.86-0.78 (m, 4H). LCMS (Method 3): Rt 4.32 min, m/z 402.1 [M+H]$^+$.

Example 104—(S)-6-chloro-3-(1-((4-(5-cyclopropyl-1H-tetrazol-1-yl)pyrimidin-2-yl)amino) ethyl) quinolin-2(1H)-one (I-183)

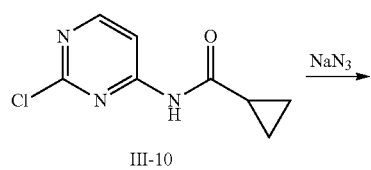

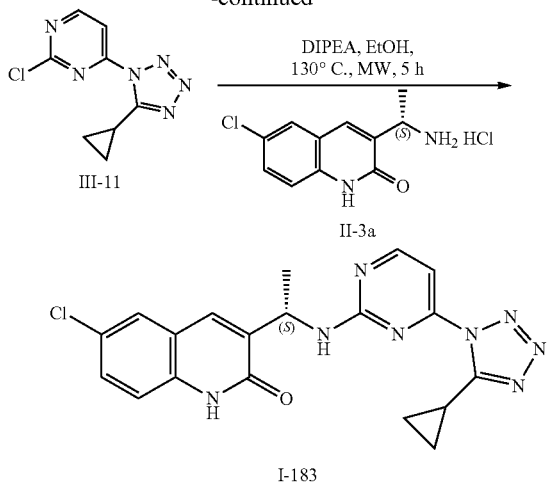

Step-1: 2-chloro-4-(5-cyclopropyl-1H-tetrazol-1-yl)pyrimidine (III-11)

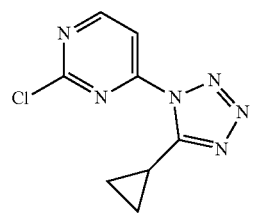 [SMILES: Clc1nccc(-n2nnnc2C2CC2)n1]

A mixture of perchlorosilane (4.35 ml, 37.9 mmol), N-(2-chloropyrimidin-4-yl) cyclopropanecarboxamide III-10 (1.07 g, 5.41 mmol), sodium azide (7.04 g, 108 mmol) in 80 ml of CH$_3$CN was stirred and reflux overnight. LCMS showed the reaction was completed. The mixture was poured into ice cold saturated Na$_2$CO$_3$ solution, then extracted with EtOAc twice, dried and concentrated. The biotage purification of the crude with 0 to 70% EtOAc/Hexanes on a 50 g column afforded 166 mg of pure 2-chloro-4-(5-cyclopropyl-1H-tetrazol-1-yl)pyrimidine (13.8%). $^1$H NMR (300 MHz, DMSO-d$_6$) δ ppm 9.04 (d, J=5.57 Hz, 1H), 8.13 (d, J=5.57 Hz, 1H), 2.83-2.97 (m, 1H), 1.24-1.52 (m, 2H), 0.94-1.24 (m, 2H). LCMS (Method 1): Rt 1.86 min, m/z 223.07[M+H]$^+$.

Step-2: (S)-6-chloro-3-(1-((4-(5-cyclopropyl-1H-tetrazol-1-yl)pyrimidin-2-yl)amino) ethyl) quinolin-2(1H)-one (I-183)

The mixture of DIEA (0.377 ml, 2.156 mmol), (S)-3-(1-aminoethyl)-6-chloro-1,8-naphthyridin-2(1H)-one, HCl (187 mg, 0.719 mmol), and 2-chloro-4-(5-cyclopropyl-1H-tetrazol-1-yl)pyrimidine (160 mg, 0.719 mmol) in DMSO (2 ml) was heated to 110° C. for overnight. LCMS showed the reaction was completed. To the mixture was added EtOAc, then washed with water, dried and concentrated. The biotage purification of the crude with 0-5% MeOH/DCM (a 25 g column) afforded 126 mg of the desired product with impurities. Further purification by reversed phase preparative HPLC afforded (S)-6-chloro-3-(1-((4-(5-cyclopropyl-1H-tetrazol-1-yl) pyrimidin-2-yl)amino)ethyl)-1,8-naphthyridin-2(1H)-one (66 mg, 42.3%). $^1$H NMR (300 MHz, DMSO-$d_6$) δ ppm 12.49 (br, 1H), 8.63 (br d, J=4.98 Hz, 1H), 8.40-8.54 (m, 2H), 8.32 (d, J=2.35 Hz, 1H), 7.78 (s, 1H), 7.15 (d, J=5.28 Hz, 1H), 4.89-5.21 (m, 1H), 2.68-2.94 (m, 1H), 1.44 (br d, J=6.74 Hz, 3H), 1.23 (m, 1H), 1.05-1.18 (m, 1H), 0.86-1.00 (m, 1H), 0.68-0.89 (m, 1H). LCMS (Method 1): Rt 2.27 min, m/z 409.99 M+H]$^+$.

TABLE 21

The compounds listed in Table 21 were prepared using the same method described for the preparation of I-173, I-175, and I-177-I-183.

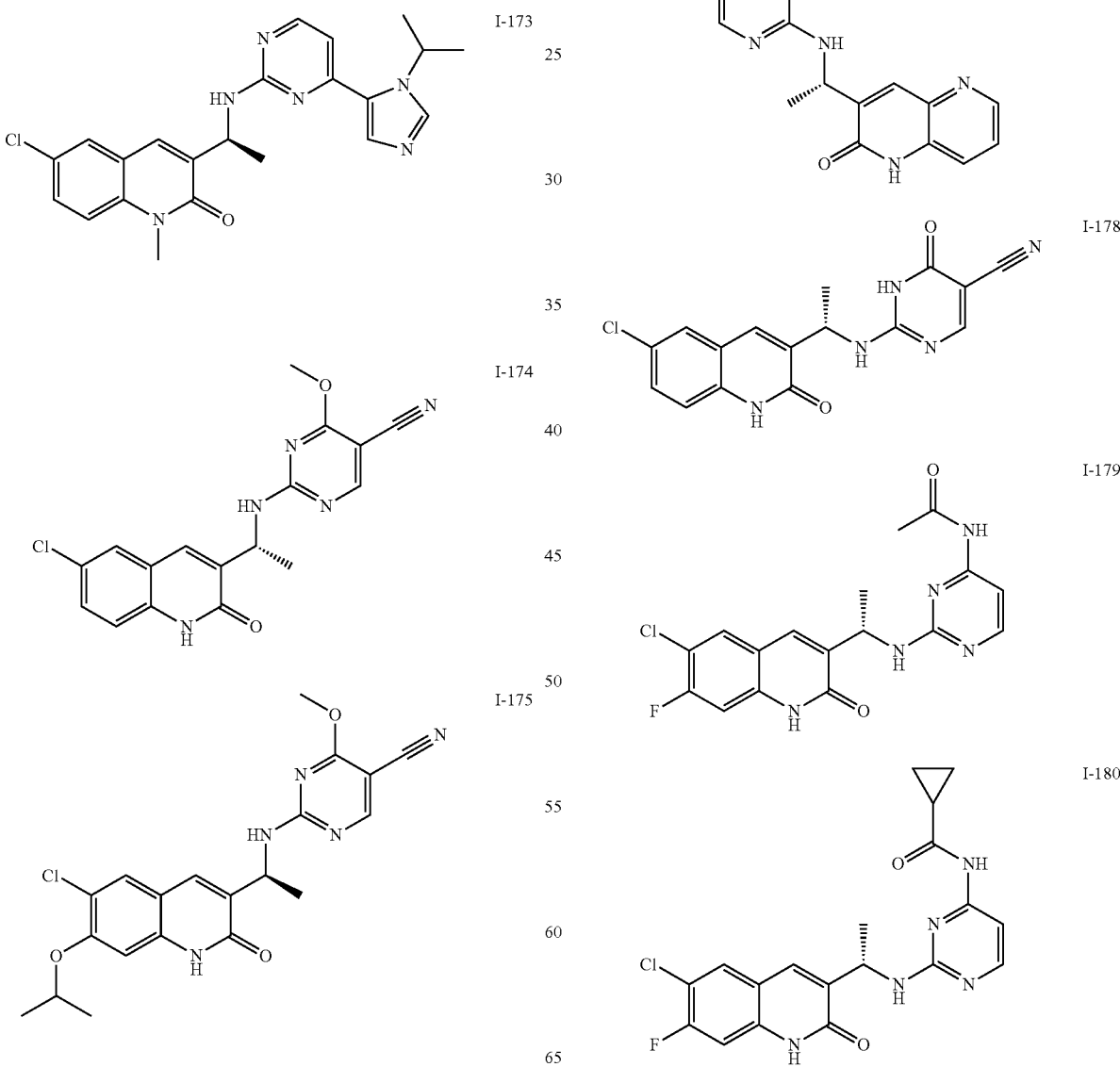

TABLE 21-continued

The compounds listed in Table 21 were prepared using the same method described for the preparation of I-173, I-175, and I-177-I-183.

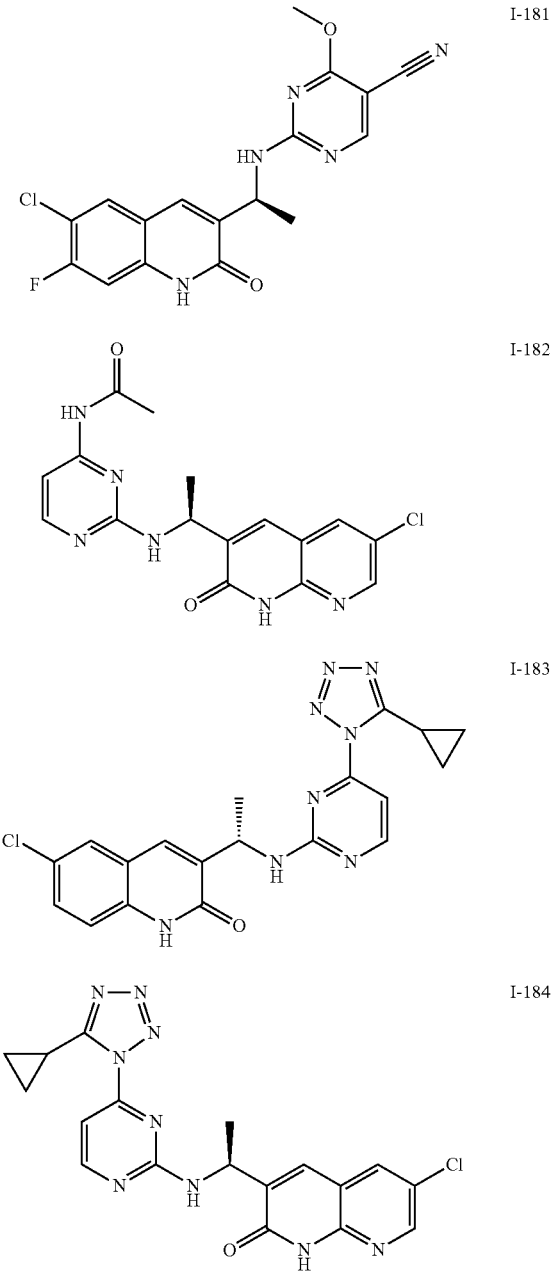

I-181

I-182

I-183

I-184

TABLE 22

LCMS signal and NMR chemical shifts for each compounds listed in Table 21

| Cmpds No | LCMS$^a$ | $^1$H NMR (300 MHz) δ ppm |
|---|---|---|
| I-173 | m/z: 423.27 (M + H)$^+$ Rt (min): 1.07 | $^1$H NMR (300 MHz, DMSO-d$_6$ at 120° C.): δ 8.30-7.40 (m, 7 H), 7.15-6.80 (m, 2 H), 5.60-5.10 (m, 2 H), 3.69 (s, 3 H), 1.60-1.30 (two doublets, 6 H), 1.18 (d, J = 6.6 Hz, 3 H) |

TABLE 22-continued

LCMS signal and NMR chemical shifts for each compounds listed in Table 21

| Cmpds No | LCMS$^a$ | $^1$H NMR (300 MHz) δ ppm |
|---|---|---|
| I-174 | m/z: 356.19 (M + H)$^+$ Rt (min): 1.27 | $^1$H NMR (300 MHz, CDCl$_3$-d) δ ppm 10.56-11.02(m, 1 H), 8.23 (br d, J = 4.98 Hz, 1 H), 7.60 (br d, J = 7.04 Hz, 1 H), 7.49 (s, 1 H), 7.39 (dd, J = 8.79, 2.05 Hz, 1 H), 6.60-6.91 (m, 1 H), 5.16-5.43 (m, 1 H), 3.89 (d, J = 2.05 Hz, 3 H), 1.59 (d, J = 7.04 Hz, 3 H). |
| I-175 | m/z: 414.23 (M + H)$^+$ Rt (min): 1.51 | $^1$H NMR (300 MHz, DMSO-d$_6$): δ ppm 11.67-11.78 (m, 1 H), 8.51-8.76 (m, 1 H), 8.48 (d, J = 2.64 Hz, 1 H), 7.76 (s, 1 H), 7.66 (d, J = 8.79 Hz, 1 H), 6.97 (s, 1 H), 5.13-5.29 (m, 1 H), 4.52-4.67 (m, 1 H), 3.78-4.01 (m, 3 H), 1.37-1.46 (m, 3 H), 1.34 (d, J = 6.16 Hz, 6 H). |
| I-176 | m/z: 396.22 (M + H)$^+$ Rt (min): 1.51 | $^1$H NMR (300 MHz, METHANOL-d$_4$) δ ppm 8.15-8.34 (m, 1 H), 7.68 (br d, J = 11.73 Hz, 1 H), 7.54 (s, 1 H), 6.84 (s, 1 H), 5.12-5.38 (m, 1 H), 3.71-3.97 (m, 3 H), 2.08-2.33 (m, 1 H), 1.44 (br d, J = 6.16 Hz, 2H), 0.94-1.06 (m, 1 H), 0.65 (br d, J = 4.40 Hz, 1H). |
| I-177 | m/z: 323.20 (M + H)$^+$ Rt (min): 0.83 | $^1$H NMR (300 MHz, DMSO-d$_6$) δ ppm 11.99 (br d, J = 4.69 Hz, 2 H), 8.68-9.12 (m, 1 H), 8.35-8.52 (m, 1 H), 7.81 (d, J = 7.33 Hz, 1 H), 7.64 (br d, J = 8.21 Hz, 1 H), 7.45 (dd, J = 8.50, 4.40 Hz, 1 H), 5.29 (br dd, J = 14.07, 6.74 Hz, 1 H), 3.63-4.09 (m, 3 H), 1.24-1.65 (m, 3 H). |
| I-178 | m/z: 342.16 (M + H)$^+$ Rt (min): 1.04 | $^1$H NMR (300 MHz, DMSO-d$_6$): δ ppm 12.11 (s, 1 H), 11.71 (br s, 1 H), 8.23 (s, 1 H), 8.07 (br s, 1 H), 7.85 (s, 1 H), 7.79 (s, 1 H), 7.53 (dd, J = 8.79, 2.35 Hz, 1 H), 7.32 (d, J = 8.79 Hz, 1 H), 5.12-5.30 (m, 1 H), 1.46 (d, J = 7.04 Hz, 3 H). |
| I-179 | m/z: 376.17 (M + H)+ Rt (min): 1.45 | $^1$H NMR (300 MHz, DMSO-d$_6$): δ 12.01 (s, 1H), 10.22 (s, 1H), 8.12 (d, J = 5.2 Hz, 1H), 7.95 (d, J = 8.0 Hz, 1H), 7.74 (s, 1H), 7.30 (bs, 1H), 7.22-7.18 (m, 2H), 5.16 (m, 1H), 2.06 (s, 3H), 1.40 (d, J = 6.9 Hz, 3H) |
| I-180 | m/z: 402.21 (M + H)+ Rt (min): 1.13 | $^1$H NMR (300 MHz, DMSO-d$_6$): δ 12.02 (s, 1H), 10.53 (s, 1H), 8.11 (d, J = 5.2 Hz, 1H), 7.95 (d, J = 8.0 Hz, 1H), 7.75 (s, 1H), 7.30 (bs, 1H), 7.22-7.18 (m, 2H), 5.18 (m, 1H), 2.05 (m, 1H), 1.40 (d, J = 6.6 Hz, 3H), 0.86-0.78 (m, 4H). |
| I-181 | m/z: 374.16 (M + H)+ Rt (min): 1.31 | $^1$H NMR (300 MHz, DMSO-d$_6$): δ ppm 12.04 (br s, 1 H), 8.60-8.77 (m, 1 H), 8.49 (d, J = 6.51 Hz, 1 H), 7.98 (d, J = 7.95 Hz, 1 H), 7.74 (d, J = 9.63 Hz, 1 H), 7.20 (d, J = 10.20 Hz, 1 H), 5.17-5.22 (m, 1 H), 3.80-3.99 (m, 3 H), 1.40-1.44 (m, 3 H). |
| I-182 | m/z: 359.19 (M + H)+ Rt (min): 0.79 | 1H NMR (300 MHz, DMSO-d$_6$): δ ppm 12.42 (br s, 1 H), 10.22 (s, 1 H), 8.50 (d, J = 2.46 Hz, 1 H), 8.29 (d, J = 2.49 Hz, 1 H), 8.13 (d, J = 5.22 Hz, 1 H), 7.75 (s, 1H), 7.20 (d, J = 5.49 Hz, 1 H), 5.16-5.21 (m, 1 H), 2.06 (s, 3 H), 1.41 (d, J = 5.49 Hz, 3 H). |
| I-183 | m/z: 409.16 (M + H)+ Rt (min): 1.27 | $^1$H NMR (300 MHz, DMSO-d$_6$) δ ppm 12.13 (br s, 1 H), 8.66-8.88 (m, 1 H), 8.39-8.61 (m, 1 H), 7.74-7.92 (m, 2 H), 7.51-7.62 (m, 1 H), 7.38 (s, 1 H), 7.14-7.28 (m, 1 H), 4.97-5.26 (m, 1 H), 2.72-2.98 (m, 1 H), 1.50 (br d, J = 6.74 Hz, 3 H), 1.26-1.36 (m, 1 H), 0.98-1.19 (m, 2 H), 0.65-0.85 (m, 1 H). |

TABLE 22-continued

LCMS signal and NMR chemical shifts for each compounds listed in Table 21

| Cmpds No | LCMS[a] | $^1$H NMR (300 MHz) δ ppm |
|---|---|---|
| I-184 | m/z: 410.20 (M + H)+ Rt (min): 1.15 | $^1$H NMR (300 MHz, DMSO-$d_6$) δ ppm 12.49 (br, 1 H), 8.63 (br d, J = 4.98 Hz, 1 H), 8.40-8.54 (m, 2 H), 8.32 (d, J = 2.35 Hz, 1 H), 7.78 (s, 1 H), 7.15 (d, J = 5.28 Hz, 1 H), 4.89-5.21 (m, 1 H), ), 2.68-2.94 (m, 1 H), 1.44 (br d, J = 6.74 Hz, 3 H), 1.23 (m, 1 H), 1.05-1.18 (m, 1 H), 0.86-1.00 (m, 1 H), 0.68-0.89 (m, 1 H). |

[a]LCMS (method 4);

Example 105—IDH1-R132H and IDH1-R132C Enzymatic Assay

Assays were performed in a 384-well black plate. An aliquot of 250 nL of compound was incubated with 10 µL of 30 nM IDH1-R132H or 10 nM IDH1-R132C recombinant protein in assay buffer (50 mM Tris pH=7.5, 150 mM NaCl, 5 mM $MgCl_2$, 0.1% (w/v) Bovine Serum Albumin, and 0.01% Triton X-100) in each well at 25° C. for 15 minutes. After the plate was centrifuged briefly, an aliquot of 10 µL of 2 mM α-ketoglutarate and 20 µM NADPH solution prepared in assay buffer was then added to each well and the reaction was maintained at 25° C. for 45 minutes. An aliquot of 10 µL of diaphorase solution (0.15 U/mL diaphorase and 30 M Resazurin in assay buffer) was added to each well. The plate was maintained at 25° C. for 15 minutes and then read on a plate reader with excitation and emission wavelengths at 535 nm and 590 nm, respectively. The $IC_{50}$ of a given compound was calculated by fitting the dose response curve of inhibition of NADPH consumption at a given concentration with the four parameter logistic equation.

Example 106—Cellular 2-HG assay using HCT116 mutant IDH1 cells

HCT116 isogenic IDH1-R132H and IDH1-R132C mutant cells were cultured in growth media (McCoy's 5 A, 10% fetal bovine serum, 1× antibiotic-antimycotic solution and 0.3 mg/mL G418) in 5% $CO_2$ in an incubator at 37° C. To prepare the assay, cells were trypsinized and resuspended in assay media (McCoy's 5 A with no L-glutamine, 10% fetal bovine serum, 1× antibiotic-antimycotic solution and 0.3 mg/mL G418). An aliquot of 10,000 cells/100 µL was transferred to each well of a clear 96-well tissue culture plate. The cells were incubated in 5% $CO_2$ at 37° C. in an incubator overnight to allow for proper cell attachment. An aliquot of 50 µL of compound containing assay media were then added to each well and the assay plate was kept in 5% $CO_2$ at 37° C. in an incubator for 24 hours. The media was then removed from each well and 150 µL of a methanol/water mixture (80/20 v/v) was added to each well. The plates were kept at −80° C. freezer overnight to allow for complete cell lysis. An aliquot of 125 µL of extracted supernatant was analyzed by RapidFire high-throughout-mass spectrometry (Agilent) to determine the cellular 2-HG level. The $IC_{50}$ of a given compound was calculated by fitting the dose response curve of cellular 2-HG inhibition at a given concentration with the four parameter logistic equation.

TABLE 23

Results of the illustrative compounds of Formula (I) in IDH1-R132H, IDH1-R132C, IDH1-MS-HTC116-R132H, and IDH1-MS-HTC116-R132C assays.

| Cmpd No | Enzyme IDH1 R132H $IC_{50}$ (Range) | Enzyme IDH1 R132C IC50 (Range) | HCT116 IDH1 R132H IC50 (Range) | HCT116 IDH1 R132C IC50 (Range) |
|---|---|---|---|---|
| I-1 | ++++ | | | |
| I-2 | ++++ | ++++ | | |
| I-3 | +++ | +++ | | |
| I-4 | ++++ | ++++ | | |
| I-5 | ++++ | +++ | | |
| I-6 | +++ | | | |
| I-7 | +++ | ++ | | |
| I-8 | ++++ | ++++ | | |
| I-9 | ++ | | | |
| I-10 | ++++ | +++ | | |
| I-11 | ++++ | ++++ | | |
| I-12 | +++ | ++ | +++ | +++ |
| I-13 | ++++ | | | |
| I-14 | +++ | ++ | | |
| I-15 | +++ | +++ | | |
| I-16 | +++ | ++ | | |
| I-17 | + | | | |
| I-18 | ++ | | | |
| I-19 | ++ | | | |
| I-20 | +++ | +++ | +++ | +++ |
| I-21 | +++ | ++ | | |
| I-22 | ++++ | +++ | ++++ | ++++ |
| I-23 | ++ | | +++ | +++ |
| I-24 | +++ | | | |
| I-25 | ++++ | ++++ | ++++ | ++++ |
| I-26 | ++++ | | | |
| I-27 | +++ | | | |
| I-28 | +++ | | | |
| I-29 | ++++ | ++++ | +++ | +++ |
| I-30 | ++ | | | |
| I-31 | +++ | | | |
| I-32 | ++++ | | | |
| I-33 | ++++ | ++++ | ++++ | +++ |
| I-34 | +++ | | | |
| I-35 | +++ | ++ | | |
| I-36 | ++++ | +++ | ++++ | +++ |
| I-37 | +++ | | +++ | ++ |
| I-38 | + | ++ | | |
| I-39 | ++++ | +++ | +++ | +++ |
| I-40 | ++++ | | ++ | +++ |
| I-41 | ++ | ++ | | |
| I-42 | ++++ | ++++ | | ++++ |
| I-43 | + | | | |
| I-44 | ++++ | ++++ | ++++ | +++ |
| I-45 | ++ | ++ | | |
| I-46 | ++++ | ++++ | | |
| I-47 | +++ | +++ | +++ | ++ |
| I-48 | ++++ | +++ | | |
| I-49 | +++ | | | |
| I-50 | +++ | | | |
| I-51 | ++++ | +++ | +++ | +++ |
| I-52 | +++ | | | |
| I-53 | ++++ | | | |
| I-54 | +++ | ++ | ++ | ++ |
| I-55 | +++ | +++ | +++ | +++ |
| I-56 | ++ | | | |
| I-57 | +++ | | | |
| I-58 | ++++ | ++ | ++ | ++ |
| I-59 | ++++ | +++ | +++ | +++ |
| I-60 | ++++ | +++ | ++++ | +++ |
| I-61 | ++++ | ++++ | +++ | +++ |
| I-62 | ++ | | | |
| I-63 | ++++ | ++++ | +++ | ++ |
| I-64 | ++++ | +++ | +++ | +++ |
| I-65 | +++ | ++ | +++ | ++ |
| I-66 | +++ | ++ | +++ | +++ |
| I-67 | +++ | | | |
| I-68 | ++++ | ++++ | ++++ | +++ |
| I-69 | ++ | | | |
| I-70 | ++ | | | |

TABLE 23-continued

Results of the illustrative compounds of Formula (I) in IDH1-R132H, IDH1-R132C, IDH1-MS-HTC116-R132H, and IDH1-MS-HTC116-R132C assays.

| Cmpd No | Enzyme IDH1 R132H IC$_{50}$ (Range) | Enzyme IDH1 R132C IC50 (Range) | HCT116 IDH1 R132H IC50 (Range) | HCT116 IDH1 R132C IC50 (Range) |
|---|---|---|---|---|
| I-71 | ++++ | +++ | ++++ | ++++ |
| I-72 | ++ | | | |
| I-73 | ++ | | | |
| I-74 | +++ | | +++ | +++ |
| I-75 | ++++ | +++ | +++ | ++ |
| I-76 | ++ | | | |
| I-77 | ++ | | | |
| I-78 | ++ | | | |
| I-79 | ++++ | | ++ | ++ |
| I-80 | ++++ | | +++ | +++ |
| I-81 | ++++ | | +++ | +++ |
| I-82 | ++ | | | |
| I-83 | +++ | ++ | ++ | +++ |
| I-84 | ++ | + | | |
| I-85 | +++ | +++ | +++ | +++ |
| I-86 | ++ | + | | |
| I-87 | +++ | ++ | +++ | ++ |
| I-88 | ++++ | +++ | +++ | ++ |
| I-89 | ++ | ++ | | |
| I-90 | +++ | ++ | ++ | ++ |
| I-91 | +++ | ++ | | |
| I-92 | +++ | +++ | +++ | ++ |
| I-93 | ++ | + | | |
| I-94 | +++ | +++ | ++++ | ++ |
| I-95 | +++ | +++ | +++ | ++ |
| I-96 | ++++ | +++ | ++++ | +++ |
| I-97 | ++ | ++ | | |
| I-98 | + | + | | |
| I-99 | +++ | +++ | | |
| I-100 | +++ | ++ | | |
| I-101 | ++++ | +++ | +++ | +++ |
| I-102 | ++ | ++ | | |
| I-103 | +++ | | | |
| I-104 | +++ | ++ | | |
| I-105 | +++ | | | |
| I-106 | ++ | | | |
| I-107 | ++ | | | |
| I-108 | +++ | | | |
| I-109 | ++++ | | | |
| I-110 | ++ | | | |
| I-111 | ++++ | +++ | | |
| I-112 | +++ | ++ | +++ | ++ |
| I-113 | ++++ | +++ | ++++ | +++ |
| I-114 | ++++ | +++ | +++ | +++ |
| I-115 | +++ | +++ | +++ | +++ |
| I-116 | +++ | +++ | +++ | ++ |
| I-117 | +++ | ++ | | |
| I-118 | +++ | | | |
| I-119 | +++ | | | |
| I-120 | +++ | | | |
| I-121 | +++ | +++ | | |
| I-122 | ++ | | | |
| I-123 | ++++ | +++ | +++ | +++ |
| I-124 | +++ | | +++ | +++ |
| I-125 | ++ | | | |
| I-126 | + | | | |
| I-127 | +++ | | | |
| I-128 | +++ | | | |
| I-129 | +++ | ++ | ++ | ++ |
| I-130 | +++ | | | |
| I-131 | +++ | | | |
| I-132 | ++ | | | |
| I-133 | +++ | ++ | | |
| I-134 | ++ | + | | |
| I-135 | ++ | + | | |
| I-136 | +++ | | | |
| I-137 | ++ | | | |
| I-138 | ++++ | +++ | | |
| I-139 | ++ | | | |
| I-140 | + | | | |
| I-141 | + | + | | |
| I-142 | ++++ | +++ | ++++ | +++ |
| I-143 | ++++ | ++++ | ++++ | ++++ |
| I-144 | +++ | ++ | | |
| I-145 | ++++ | ++++ | ++++ | +++ |
| I-146 | ++++ | +++ | ++++ | +++ |
| I-147 | ++++ | | ++++ | ++++ |
| I-148 | + | | | |
| I-149 | ++++ | ++++ | ++++ | ++++ |
| I-150 | ++++ | ++++ | | |
| I-151 | ++++ | ++++ | ++++ | ++++ |
| I-152 | ++++ | ++ | +++ | ++ |
| I-153 | ++++ | ++++ | | ++++ |
| I-154 | ++++ | ++++ | ++++ | ++++ |
| I-155 | ++++ | ++ | +++ | ++ |
| I-156 | ++++ | +++ | ++++ | +++ |
| I-157 | +++ | ++ | ++++ | +++ |
| I-158 | ++++ | ++++ | ++++ | +++ |
| I-159 | ++++ | ++++ | ++++ | ++++ |
| I-160 | ++++ | ++++ | ++++ | ++++ |
| I-161 | ++++ | +++ | ++++ | +++ |
| I-162 | ++++ | +++ | ++++ | +++ |
| I-163 | ++ | | | |
| I-164 | + | | | |
| I-165 | ++ | | | |
| I-166 | ++ | | | |
| I-167 | +++ | | | |
| I-168 | +++ | ++ | | |
| I-169 | +++ | ++ | | |
| I-170 | +++ | | +++ | ++ |
| I-171 | + | | | |
| I-172 | ++++ | +++ | | |
| I-173 | ++++ | ++++ | | |
| I-174 | ++ | ++ | | |
| I-175 | ++++ | ++++ | | |
| I-176 | ++++ | +++ | | |
| I-177 | ++ | + | | |
| I-178 | ++++ | ++ | | |
| I-179 | ++++ | ++++ | ++++ | ++++ |
| I-180 | +++ | +++ | +++ | +++ |
| I-181 | ++++ | +++ | +++ | +++ |
| I-182 | ++++ | +++ | +++ | +++ |
| I-183 | ++++ | ++++ | ++++ | +++ |
| I-184 | +++ | +++ | +++ | +++ |

++++indicates an IC$_{50}$ of less than about 0.1 μM,
+++indicates an IC$_{50}$ between about 0.1 μM and about 1 μM,
++indicates an IC$_{50}$ between about 1 μM and about 10 μM, and
+indicates an IC$_{50}$ greater than 10 μM.

EQUIVALENTS

Those skilled in the art will recognize, or be able to ascertain, using no more than routine experimentation, numerous equivalents to the specific embodiments described specifically herein. Such equivalents are intended to be encompassed in the scope of the following claims.

The invention claimed is:

1. The compound 2-{[(1S)-1-(6-chloro-2-oxo-1,2-dihydroquinolin-3-yl)ethyl]amino}-4-methoxypyrimidine-5-carbonitrile, or a pharmaceutically acceptable salt thereof.

2. A pharmaceutical composition comprising the compound:
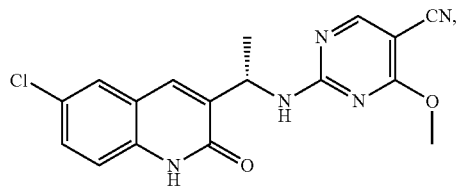 [SMILES: COc1nc(N[C@@H](C)c2cc3cc(Cl)ccc3[nH]c2=O)ncc1C#N]
or a pharmaceutically acceptable salt thereof.
* * * * *